United States Patent
Hanna et al.

(10) Patent No.: US 10,920,192 B2
(45) Date of Patent: Feb. 16, 2021

(54) ISOLATED NAIVE PLURIPOTENT STEM CELLS AND METHODS OF GENERATING SAME

(71) Applicant: Yeda Research and Development Co. Ltd., Rehovot (IL)

(72) Inventors: Yaqub Hanna, Tel-Aviv (IL); Noa Novershtern, Rehovot (IL); Yoach Rais, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/259,997

(22) Filed: Apr. 23, 2014

(65) Prior Publication Data

US 2014/0315301 A1   Oct. 23, 2014

Related U.S. Application Data

(60) Provisional application No. 61/932,935, filed on Jan. 29, 2014, provisional application No. 61/878,769, filed on Sep. 17, 2013, provisional application No. 61/814,920, filed on Apr. 23, 2013.

(51) Int. Cl.
*C12N 5/0735* (2010.01)
*C12N 5/074* (2010.01)

(52) U.S. Cl.
CPC .......... *C12N 5/0611* (2013.01); *C12N 5/0606* (2013.01); *C12N 5/0696* (2013.01); *C12N 2501/115* (2013.01); *C12N 2501/15* (2013.01); *C12N 2501/155* (2013.01); *C12N 2501/235* (2013.01); *C12N 2501/2306* (2013.01); *C12N 2501/42* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/727* (2013.01); *C12N 2501/999* (2013.01)

(58) Field of Classification Search
CPC ............ C12N 2506/02; C12N 15/1136; C12N 15/1138; C12N 2310/14; C12N 2310/3513; C12N 2501/41; C12N 15/113; C12N 2310/141; C12N 2501/125; C12N 2501/15; C12N 2501/155; C12N 2501/23; C12N 2501/235; A61K 2039/53; A61K 39/0011; A61K 51/1051; A61K 51/1054; A61K 51/1057; A61K 51/106; A61K 51/1072; A61K 2039/505; A61K 2300/00; A61K 38/00; A61K 2039/545; A61K 35/16; A61K 38/36; A61K 38/484
See application file for complete search history.

(56) References Cited

U.S. PATENT DOCUMENTS

| 6,090,622 A | 7/2000 | Gearhart et al. |
| 2011/0076678 A1 | 3/2011 | Jaenisch et al. |
| 2013/0273649 A1 | 10/2013 | Wu et al. |
| 2017/0275593 A1 | 9/2017 | Hanna et al. |

FOREIGN PATENT DOCUMENTS

| CN | 102317442 | 1/2012 |
| GB | 2436737 | 10/2007 |
| WO | WO 98/43679 | 10/1998 |
| WO | WO 2009/101084 | 8/2009 |
| WO | WO 2010/077955 | 7/2010 |
| WO | WO 2014/174470 | 10/2014 |
| WO | WO 2016/016894 | 2/2016 |
| WO | WO 2016/079146 | 5/2016 |

OTHER PUBLICATIONS

Ludwig et al. Derivation of human embryonic stem cells in defined conditions. Nature Biotechnology, 2006, vol. 24, 185-187.*
Yoshida et al. Hypoxia Enhances the Generation of Induced Pluripotent Stem Cells. Cell Stem Cell, 2009, vol. 5, pp. 237-241.*
Ezashi et al. Low O2 tensions and the prevention of differentiation of hES cells. PNAS, 2005, vol. 102, pp. 4783-4788.*
Ludwig et al. Derivation of human embryonic stem cells in defined conditions. Nature Biotechnology, 2006, vol. 24, 185-187, supplementary material p. 1.*
Lai et al. Cancer biology and NuRD: a multifaceted chromatin remodelling complex. Nature Reviews, 2011, vol. 11, pp. 588-596.*
Kaji et al. The NuRD component Mbd3 is required for pluripotency of embryonic stem cells. Nature Cell Biology, 2006, vol. 8, pp. 285-292.*
Huangfu et al. Induction of pluripotent stem cells from primary human fibroblasts with only Oct4 and Sox2. Nature Biotechnology, 2008, pp. 1-7, doi:10.1038/nbt.*
Zhu et al. Mbd3, a Component of NuRD/Mi-2 Complex, Helps Maintain Pluripotency of Mouse Embryonic Stem Cells by Repressing Trophectoderm Differentiation. PLoS One, 2009, vol. 4(11), pp. 7684-7694.*
Larsen et al.The chromatin-remodeling factor CHD4 coordinates signaling and repair after DNA damage. J. Cell Biol., 2010, vol. 190, pp. 731-740.*

(Continued)

*Primary Examiner* — Anoop K Singh

(57) ABSTRACT

Provided is an isolated human naive pluripotent stem cell (PSC), wherein: (i) when the naive PSC is a female PSC, then said naive female PSC has two unmethylated alleles of an X-inactive specific transcript (XIST) gene; and (ii) when said naive PSC is a male PSC, then said naive male PSC has an unmethylated allele of said XIST gene. Also provided is a culture medium which comprises an ERK1/2 inhibitor, a GSK3beta inhibitor, a p38 inhibitor, a JNK inhibitor, a STAT3 activator and at least one agent selected from the group consisting of: bFGF, TGFbeta 1, a PKC inhibitor, a ROCK inhibitor and a NOTCH inhibitor; or at least agent selected from the group consisting of: a TGFR inhibitor, a FGFR inhibitor, a PKC inhibitor, a ROCK inhibitor and a NOTCH inhibitor.

32 Claims, 160 Drawing Sheets
(147 of 160 Drawing Sheet(s) Filed in Color)
Specification includes a Sequence Listing.

(56) References Cited

OTHER PUBLICATIONS

Gnanapragasam et al. p66α-MBD2 coiled-coil interaction and recruitment of Mi-2 are critical for globin gene silencing by the MBD2-NuRD complex. PNAS, 2011, vol. 108, pp. 7487-7492.*
Genetics Home Reference. National Library of Medicine, Apr. 28, 2015, http://ghr.nlm.nih.gov/handbook/basics/gene.*
Vasques et al. XIST Repression in the Absence of DNMT1 and DNMT3B. DNA Research, 2005, vol. 12, 373-378.*
Genetics Home Reference. What is a Gene? National LIbrary of Medicine, Apr. 28, 2015, http://ghr.nlm.nih.gov/handbook/basics/gene.*
de Vooght et al. Management of Gene Promoter Mutations in Molecular Diagnostics. Clinical Chemistry, 2009, vol. 55, pp. 4698-4708.*
Gerstein et al. What is a gene, post-ENCODE? History and updated definition. Genome Research, 2007, vol. 17, pp. 669-681.*
Hanna et al., Supporting Information, PNAS, 2010, vol. 107, pp. 1-10.*
ThermoFisher Scientific, Technical Resources, 12634, Advanced D-MEM/F-12, 2016, pp. 1-3.*
Hanna et al PNAS, 2010, 107, 9222-9227.*
Gafni et al Nature, 2013, 282-286.*
Huang et al Cell Research (2009) 19:1127-1138.*
Theunissen Cell, 2014, 15, 471-487.*
Ware et al PNAS, 2014, 4484-4489.*
Tsuneyoshi et al Cell, 2013, 153. 281-283.*
Betschinger et al (Cell, 2013, 153. 335-347.*
Fang et al Cell Stem cell, 15, 4, 488-497 (Year: 2014).*
Ang et al. "Wdr5 Mediates Self-Renewal and Reprogramming Via the Embryonic Stem Cell Core Transcriptional Network", Cell, 145: 183-197, Apr. 15, 2011.
De Los Angeles et al. "Accessing Naive Human Pluripotency", Current Opinion in Genetics & Development, 22: 272-282, 2012.
Hanna "The STATs on Naive iPSC Reprogramming", Cell Stem Cell, 7: 274-276, Sep. 3, 2010.
Hanna et al. "Direct Cell Reprogramming is a Stochastic Process Amenable to Acceleration", Nature, 462(7273): 595-601, Dec. 3, 2009.
Hanna et al. "Human Embryonic Stem Cells With Biological and Epigenetic Characteristics Similar to Those of Mouse ESCs", Proc. Natl. Acad. Sci. USA, PNAS, 107(20): 9222-9227, May 18, 2010.
Hanna et al. "Metastable Pluripotent States in NOD Mouse Derived ES Cells", Cell Stem Cell, 4(6): 513-524, Jun. 5, 2009.
Hanna et al. "Pluripotency and Cellular Reprogramming: Facts, Hypotheses, Unresolved Issues", Cell, 143: 508-525, Nov. 12, 2010.
Kawakami et al. "XIST Unmethylated DNA Fragments in Male-Derived Plasma as a Tumour Marker for Testicular Cancer", The Lancet, 363: 40-42, Jan. 3, 2004.
Lengner et al. "Derivation of Pre-X Inactivation Human Embryonic Stem Cells Under Physiological Oxygen Concentrations", Cell, 141: 872-883, May 2010.
Luo et al. "NuRD Blocks ReprogAramming of Mouse Somatic Cells Into Pluripotent Stem Cells", Stem Cells, p. 1-18, Epub Ahead of Print, Mar. 26, 2013.
Mansour et al. "The H3K27 Demethylase Utx Regulates Somatic and Germ Cell Epigenetic Reprogramming", Nature, 488: 409413, Aug. 16, 2012.
Okamoto et al. "Eutherian Mammals Use Diverse Strategies to Initiate X-Chromosome Inactivation During Development", Nature, 472: 370-374, Apr. 21, 2011.
Onder et al. "Chromatin-Modifying Enzymes as Modulators of Reprogramming", Nature, 483: 598-602, Mar. 29, 2012.
Orkin et al. "Chromatin Connections to Pluripotency and Cellular Reprogramming", Cell, 145: 835-850, Jun. 10, 2011.
Polo et al. "A Molecular Roadmap of Reprogramming Somatic Cells Into iPS Cells", Cell, 151: 1617-1632, Dec. 21, 2012.
Takahashi et al. "Induction of Pluripotent Stem Cells From Mouse Embryonic and Adult Fibroblast Cultures by Defined Factors", Cell, 126: 663-676, Aug. 25, 2006.
Tesar et al. "New Cell Lines From Mouse Epiblast Share Defining Features With Human Embryonic Stem Cells", Nature, 448: 196-199, Jul. 12, 2007.
Tomoda et al. "Derivation Conditions Impact X-Inactivation Status in Female Human Induced Pluripotent Stem Cells", Cell Stem Cell, 11: 91-99, Jul. 6, 2012.
Xu et al. "Proliferation Rate of Somatic Cells Affects Reprogramming Efficiency", The Journal of Biological Chemistry, 288(14): 9767-9778, Apr. 5, 2013.
Zhou et al. "Generation of Induced Pluripotent Stem Cells Using Recombinant Proteins", Cell Stem Cell, 4(5): 381-384, May 8, 2009.
Kim et al. "Modulation of Beta-Catenin Function Maintains Mouse Epiblast Stem Cell and Human Embryonic Stem Cell Self-Renewal", Nature Communications, 4(2403): 1-11, Aug. 29, 2013.
Li el al. "Calcineurin-NFAT Signaling Critically Regulates Early Lineage Specification in Mouse Embryonic Stem Cells and Embryos", Cell Stem Cell, 8: 46-58, Jan. 7, 2011.
Shimizu et al. "Dual Inhibition of Src and GSK3 Maintains Mouse Embryonic Stem Cells, Whose Differentiation Is Mechanically Regulated by Scr Signalling", Stem Cells, 30: 1394-1404, 2012.
Bermejo-Alvarez et al. "Solving the 'X' in Embryos and Stem Cells", Stem Cells and Development, XP055128368, 21(8): 1215-1224, May 20, 2012.
Gafni et al. "Derivation of Novel Human Ground State Naive Pluripotent Stem Cells", Nature, XP055128176, 504(7479): 282-286, Dec. 12, 2013.
Ware et al. "Derivation of Naive Human Embryonic Stem Cells", Proc. Natl. Acad. Sci. USA, PNAS, XP002727154, 111(12): 4484-4489, Mar. 25, 2014.
Zhang et al. "Small Molecules, Big Roles—The Chemical Manipulation of Stem Cell Fate and Somatic Cell Reprogramming", Journal of Cell Science, XP055112620, 125(23): 5609-5620, Dec. 1, 2012.
International Search Report and the Written Opinion dated Oct. 7, 2014 From the International Searching Authority Re. Application No. PCT/IB2014/060954.
Ahn et al. "Production of Human CD59-Transgenic Pigs by Embryonic Germ Cell Nuclear Transfer", Biochemical and Biophysical Research Communications, XP027356570, 400(4): 667-672, Available Online Sep. 8, 2010.
Eguizabal et al. "Generation of Primordial Germ Cells From Pluripotent Stem Cells", Differentiation, XP026601254, 78(2-3): 116-123, Sep. 1, 2009. Fig.1, 2.
Hayashi et al. "Reconstitution of the Mouse Germ Cell Specification Pathway in Culture by Pluripotent Stem Cells", Cell, XP028383021, 146(4): 519-532, Aug. 19, 2011. p. 531, Fig.6.
Park et al. "Derivation of Primordial Germ Cells From Human Embryonic and Induced Pluripotent Stem Cells Is Significantly Improved by Coculture With Human Fetal Gonadal Cells", Stem Cells, XP002730074, 27(4): 783-795, 2009.
Ying et al. "Induction of Primordial Germ Cells From Pluripotent Epiblast", Reviews in Stem and Progenitor Cells, The Scientific World Journal, XP009097195, 2: 801-810, Mar. 26, 2002.
International Search Report and the Written Opinion dated Jan. 12, 2016 From the International Searching Authority Re. Application No. PCT/IL2015/050785.
Medvedev et al. "Epigenetics of Pluripotent Cells", Acta Naturae, XP055236451, 4(4): 28-46, Oct. 2012. Abstract, p. 34, r-h Col., Para 2, p. 40, 1-h Col., Para 1.
Office Action dated Apr. 13, 2016 From the Israel Patent Office Re. Application No. 241930.
Communication Relating to the Results of the Partial International Search dated Nov. 11, 2015 From the International Searching Authority Re. Application No. PCT/IL2015/050785.
International Preliminary Report on Patentability dated Nov. 5, 2015 From the International Bureau of WIPO Re. Application No. PCT/IB2015/060954.
Hao et al. "WNT/Beta-Catenin Pathway Up-Regulates Stat3 and Converges on LIF to Prevent Differentiation of Mouse Embryonic Stem Cells", Developmental Biology, XP027332417, 290(1): 81-91, Available Online Dec. 5, 2005. Abstract, p. 86, Fig.2, p. 89, 1-h Col., Para 1, Fig.5.

(56) References Cited

OTHER PUBLICATIONS

Lin et al. "Toward Directed Reprogramming Through Exogenous Factors", Current Opinion in Genetics & Development, XP055224607, 23(5): 519-525, Available Online Aug. 8, 2013. Abstract, p. 519, r-h Col., Para 4—p. 520, 1-h Col., Para 1, Fig.1.
Van der Jeught et al. "Application of Small Molecules Favoring Naive Pluripotency During Human Embryonic Stem Cell Derivation", Cellular Reprogramming, XP055224755, 17(3): 170-180, Jun. 2015. Abstract, p. 174, r-h Col., Para 3.
Claveria et al. "Myc-Driven Endogenous Cell Competition in the Early Mammalian Embryo", Nature, 500(7460): 39-44, Aug. 1, 2013.
Dejosez et al. "Safeguards for Cell Cooperation in Mouse Embryogenesis Shown by Genome-Wide Cheater Screen", Science, 341: 1511-1514, Sep. 27, 2013.
International Preliminary Report on Patentability dated Feb. 9, 2017 From the International Bureau of WIPO Re. Application No. PCT/IL2015/050785. (11 Pages).
Communication Pursuant to Article 94(3) EPC dated Oct. 25, 2016 From the European Patent Office Re. Application No. 14727237.1. (5 Pages).
Communication Pursuant to Article 94(3) EPC dated Oct. 26, 2017 From the European Patent Office Re. Application No. 14727237.1. (4 Pages).
Notice of Reasons for Refusal dated Mar. 27, 2018 From the Japan Patent Office Re. Application No. 2016-509588 and its Translation Into English. (7 Pages).
Notification of Office Action and Search Report dated Apr. 17, 2018 From the State Intellectual Property Office of the People's Republic of China Re. Application No. 201480035892.7 and Its Translation Into English. (38 Pages).
Bendall et al. "IGF and FGF Cooperatively Establish the Regulatory Stem Cell Niche of Pluripotent Human Cells in Vitro", Nature, 448(7157): 1015-1023, Aug. 30, 2007.
Cerdan et al. "Novel Roles for Notch, Wnt and Hedgehog in Hematopoiesis Derived From Human Pluripotent Stem Cells", The International Journal of Developmental Biology, 54(6-7): 955-964, Published Online Mar. 15, 2010.
Dutta et al. "Self-Renewal Versus Lineage Commitment of Embryonic Stem Cells: Protein Kinase C Signaling Shifts the Balance", Stem Cells, 29(4): 618-628, Published Online Feb. 3, 2011.
Gauthaman et al. "Effect of ROCK Inhibitor Y-27632 on Normal and Variant Human Embryonic Stem Cells (hESCs) In Vitro: Its Benefits in hESC Expansion", Stem Cell Reviews and Reports, 6(1): 86-95, Published Online Dec. 15, 2009.
Katoh "Network of WNT and Other Reguatlory Signaling Cascades in Pluripotent Stem Cells and Cancer Stem Cells", Current Pharmaceutical Biotechnology, 12(2): 160-170, Feb. 1, 2011.
Ludwig et al. "Feeder-Independent Culture of Human Embryonic Stem Cells", Nature Methods, 3(8): 637-646, Aug. 2006.
Song et al. "Formation of Mouse Chimeras From Early Embryonic Pluripotent Stem Cell", Acta Genetica Sinica, 20(6): 499-503, 1993. English Abstract.
Xu et al. "C-Jun NH2-Terminal Kinase Is Required for Lineage-Specific Differentiation But Not Stem Cell Self-Renewal", Molecular and Cellular Biology, 3096): 1329-1340, May 30, 2010.
Zhou et al. "Two Vital Transcriptional Factors Oct-4 and Nanog to Keep the Pluripotency and Self-Renewal of Stem Cells and Related Regulation Network", Hereditas, 30(5): 529-536, May 2008. English Abstract.
Restriction Official Action dated Jul. 2, 2018 From the US Patent and Trademark Office Re. U.S. Appl. No. 15/500,163. (8 pages).
Communication Pursuant to Article 94(3) EPC dated Jul. 24, 2018 From the European Patent Office Re. Application No. 14727237.1. (4 Pages)

Declaration Yaqub Hanna Under 37 CFR 1.132 Dated Jan. 23, 2017 in the U.S. Patent and Trademark Office Re. U.S. Appl. No. 14/259,997.
Daheron et al. "LIF/STAT3 Signaling Fails to Maintain Self-Renewal of Human Embryonic Stem Cells", Stem Cells 22(5): 770-778, Sep. 2004.
Hanna. "Curriculum Vitae for Jacob H. Hanna," 18 pages, Apr. 2017.
Humphrey et al. "Maintenance of Pluripotency in Human Embryonic Stem Cells Is STAT3 Independent", Stem Cells, 22(4): 522-530, Jul. 2004.
Kee et al. "Human DAZL, DAZ and BOULE Genes Modulate Primordial Germ Cell and Haploid Gamete Formation", Nature, 462(7270): 222-225, Nov. 12, 2009.
Liu et al. "Generation of Induced Pluripotent Stem Cells from Adult Rhesus Monkey Fibroblasts", Cell Stem Cell, 3(6), 587-590, Dec. 4, 2008.
Mitalipov et al. "Isolation and Characterization of Novel Rhesus Monkey Embryonic Stem Cell Lines", Stem Cells, 24(10): 2177-2186, Oct. 2006.
Silva et al. "X-chromosome Inactivation and Epigenetic Fluidity in Human Embryonic Stem Cells", Proceedings of the National Academy of Sciences 105(12): 4820-4825, Mar. 25, 2008.
Thomson et al. "Embryonic Stem Cell Lines Derived from Human Blastocysts", Science, 282: 1145-1147, Nov. 6, 1998.
Thomson et al. "Isolation of a Primate Embryonic Stem Cell Line," Proceedings of the National Academy of Sciences of the United States of America, 92: 7844-7848, 1995.
Thomson et al. "Pluripotent Cell Lines Derived from Common Marmoset (*Callithrix jacchus*) Blastocysts," Biology of Reproduction 55: 254-259, 1996.
Verfaillie et al. "Stem Cells: Hype and Reality", American Society of Hematology Education Program Book, 2002(1): 369-391, 2002.
Xu et al. "NANOG Is a Direct Target of TGFbeta/Activin-Mediated SMAD Signaling in Human ESCs", Cell Stem Cell 3(2): 196-206, Aug. 7, 2008.
Communication Pursuant to Article 94(3) EPC dated Jun. 5, 2019 From the European Patent Office Re. Application No. 15759548.9 (6 Pages).
Office Action dated May 23, 2019 From the Israel Patent Office Re. Application No. 241930 and Its Translation Into English. (7 Pages).
Office Action dated Mar. 28, 2019 From the Israel Patent Office Re. Application No. 250340 and Its Translation Into English. (6 Pages).
Official Action dated Jul. 25, 2019 From the US Patent and Trademark Office Re. U.S. Appl. No. 15/500,163. (25 pages).
Official Action dated Jan. 8, 2019 From the US Patent and Trademark Office Re. U.S. Appl. No. 15/500,163. (45 pages).
Rajendran et al. "Inhibition of Protein Kinase C Signaling Maintains Rat Embryonic Stem Cell Pluripotency", Journal of Biological Chemistry 288(34): 24351-24362, Aug. 23, 2013.
Takao et al. "Beta-Catenin Up-Regulates Nanog Expression Through Interaction With Oct-3/4 in Embryonic Stem Cells", Biochemical and Biophysical Research Communications, 353(3): 699-705, Available Online Dec. 20, 2006.
Communication Pursuant to Article 94(3) EPC dated Mar. 19, 2020 From the European Patent Office Re. Application No. 15759548.9 (5 Pages).
Official Action dated Mar. 20, 2020 from the US Patent and Trademark Office Re. U.S. Appl. No. 15/500,163. (26 pages).
Dutta "Signaling Pathways Dictating Pluripotency in Embryonic Stem Cells", The International Journal of Developmental Biology, XP055224613, 57(9-10): 667-675, Nov. 4, 2013.
Final Official Action dated Sep. 24, 2020 from the US Patent and Trademark Office Re. U.S. Appl. No. 15/500,163. (25 pages).
Griffin et al. "RAPGEF5 Regulates Nuclear Translocation of b-Catenin", Developmental Cell 44: 1-13, 2018.

\* cited by examiner

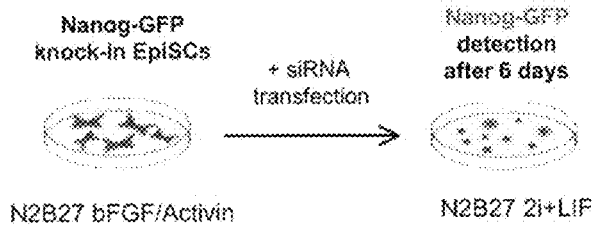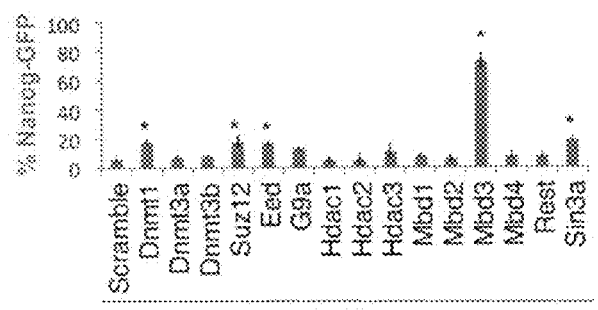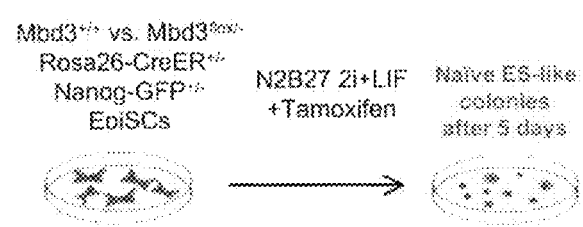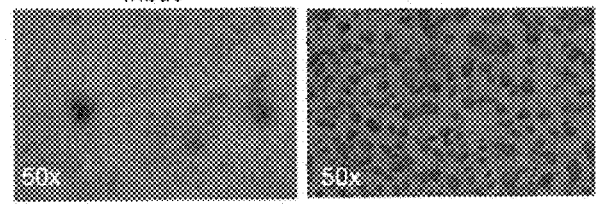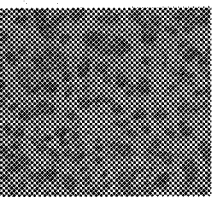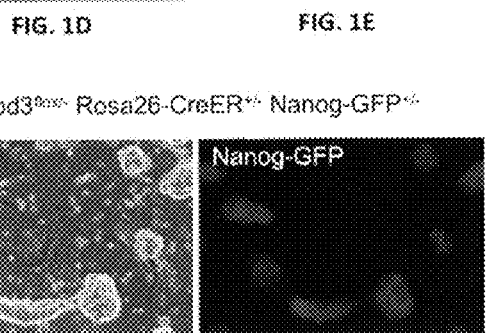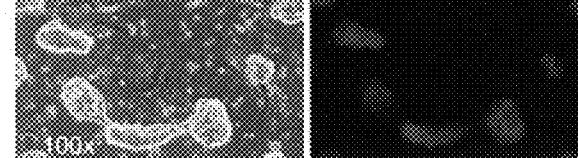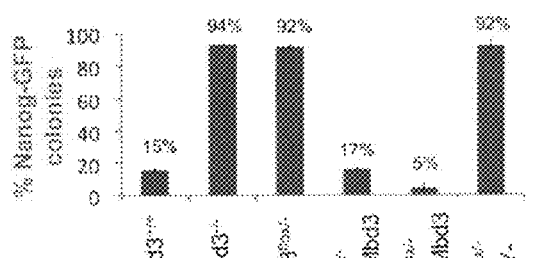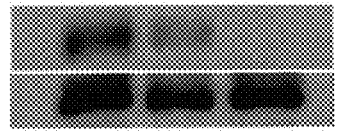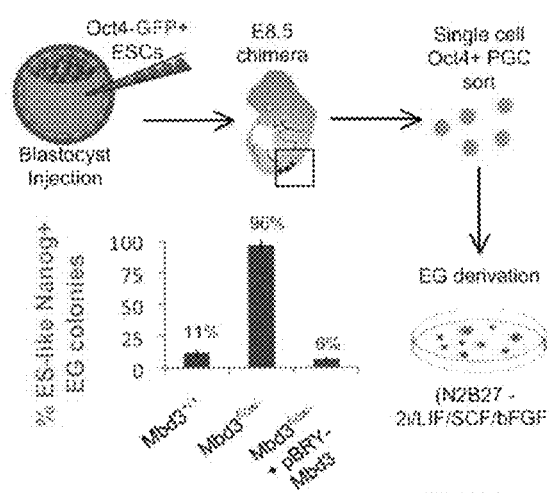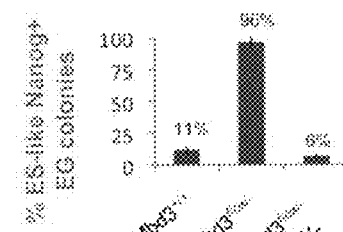

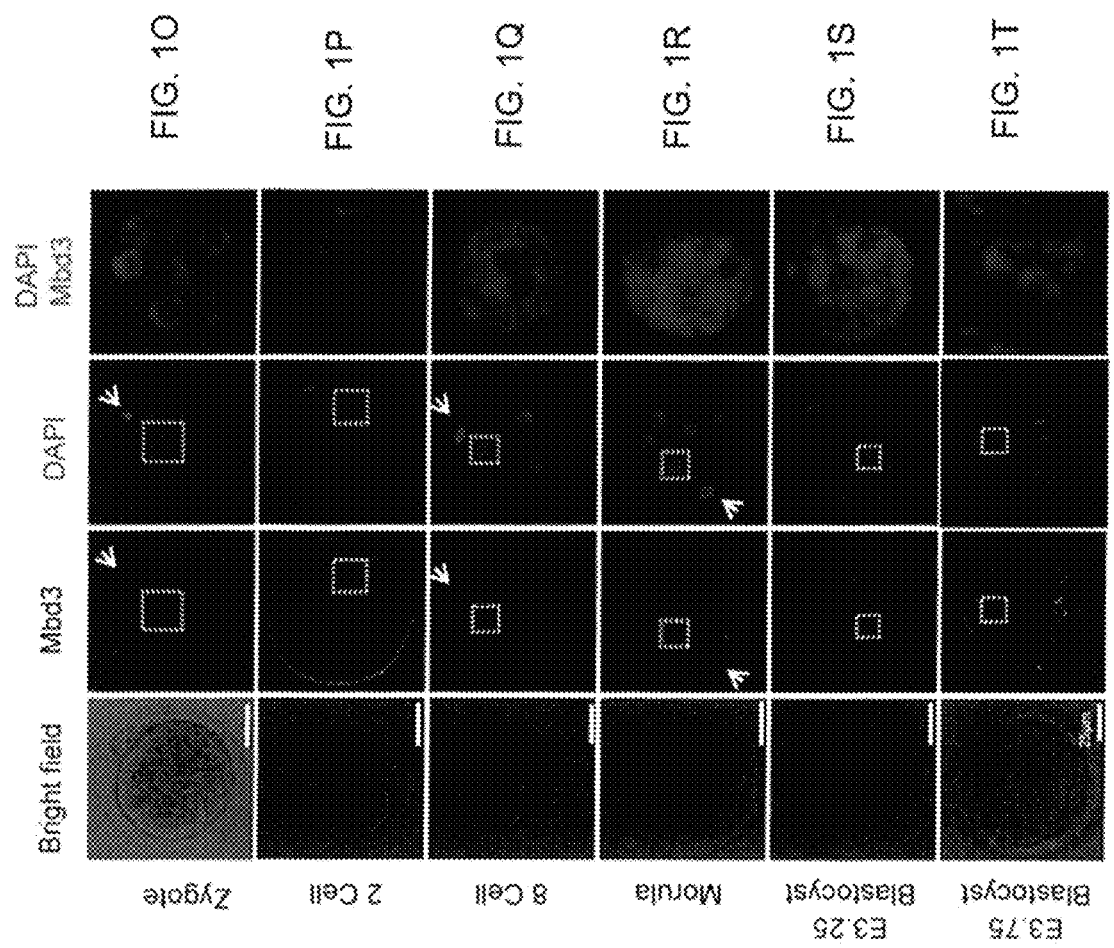

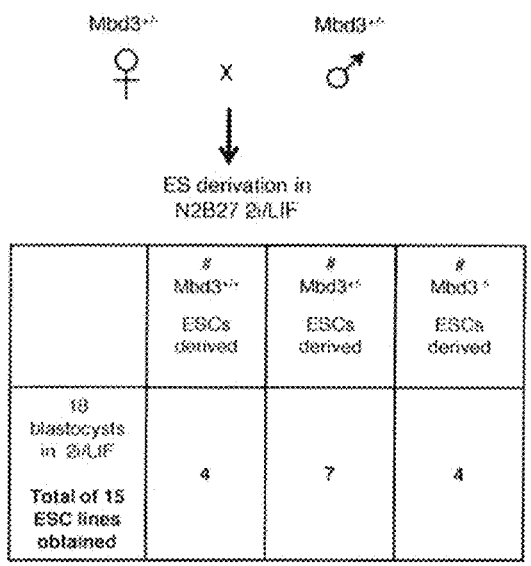
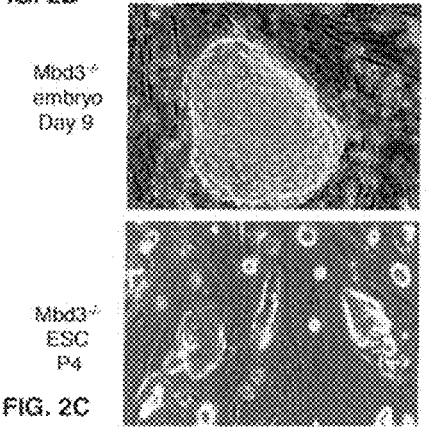
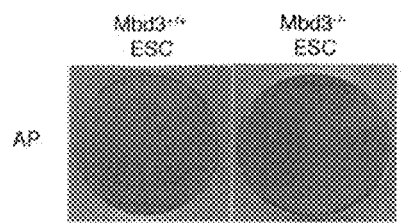
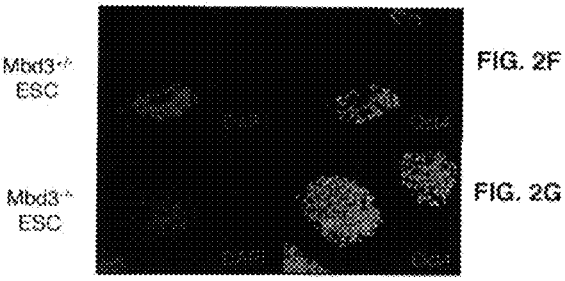
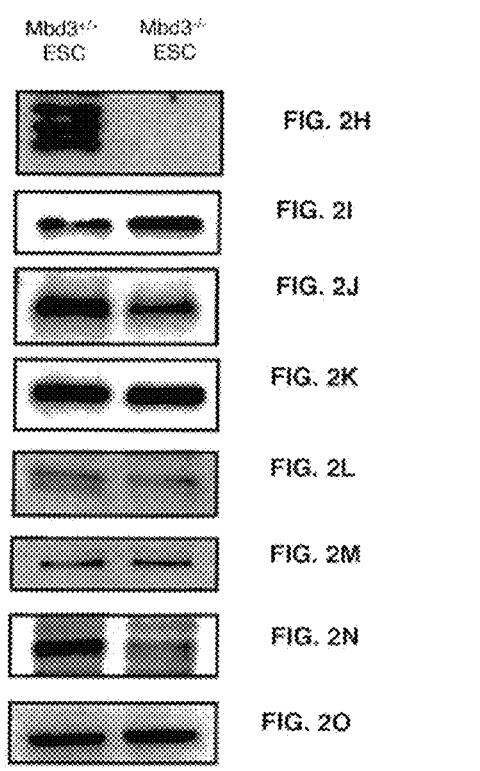

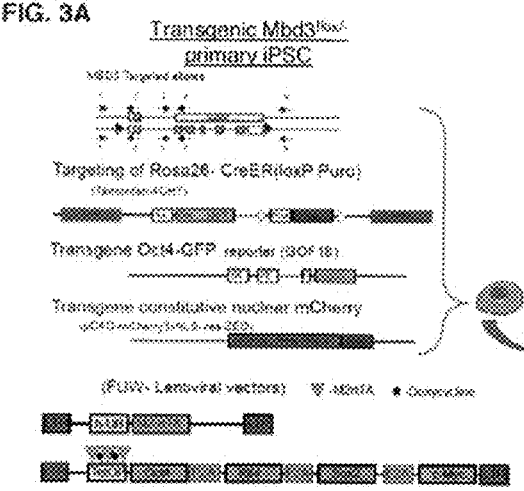
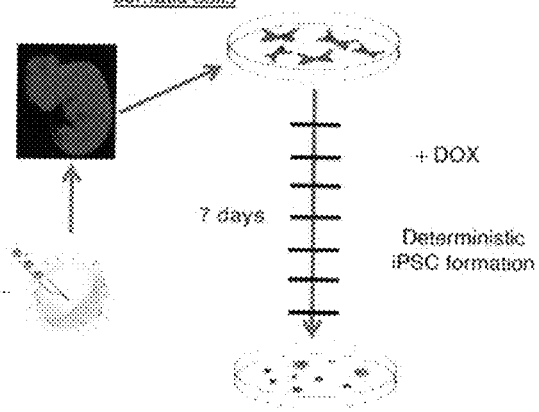
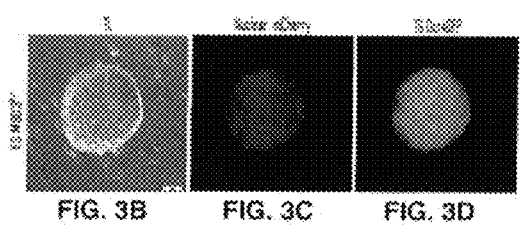
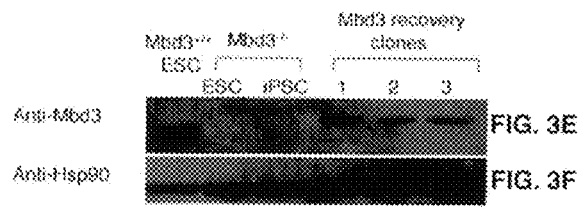
FIG. 3A, FIG. 3B, FIG. 3C, FIG. 3D, FIG. 3E, FIG. 3F

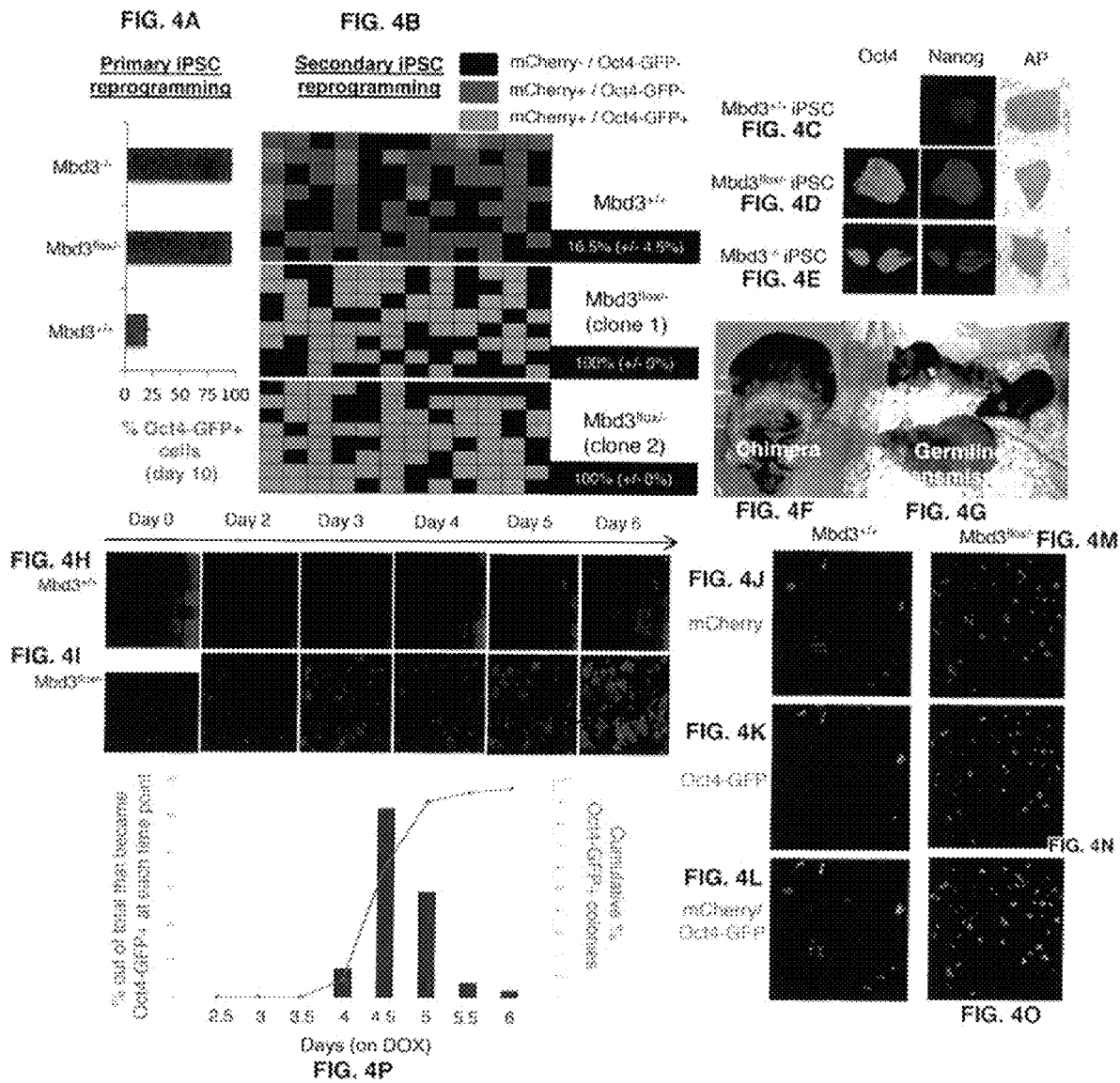

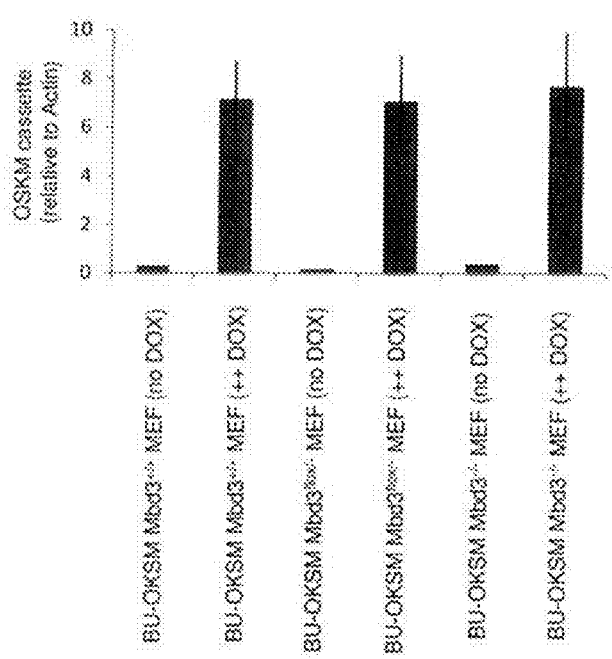
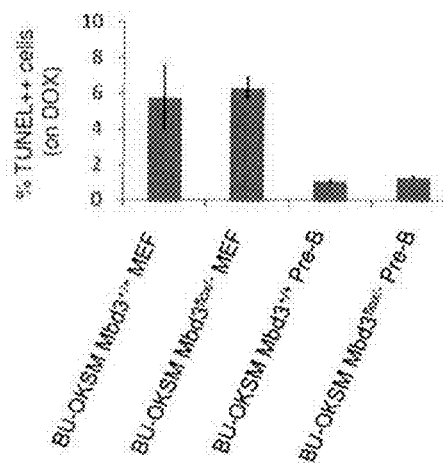

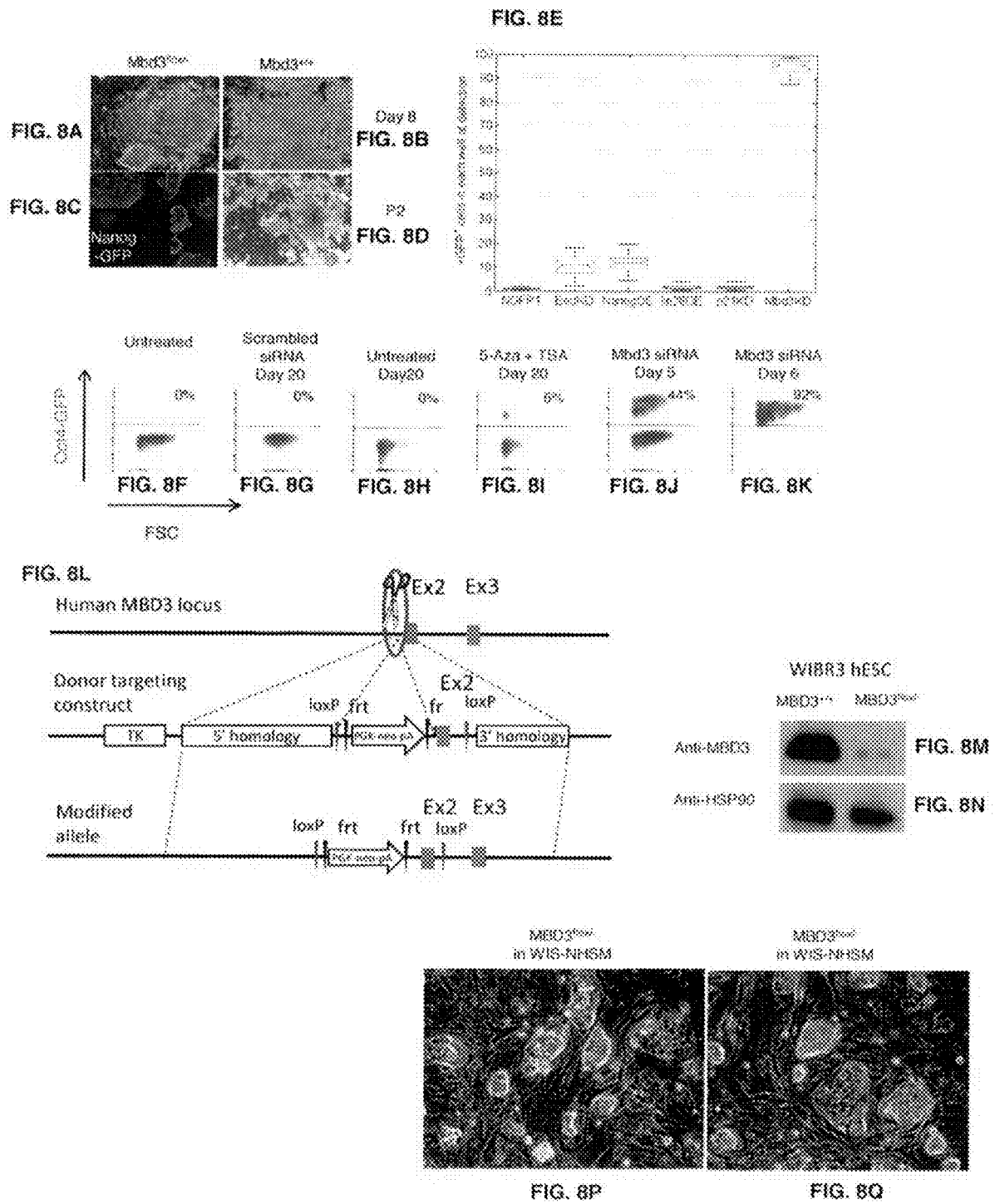

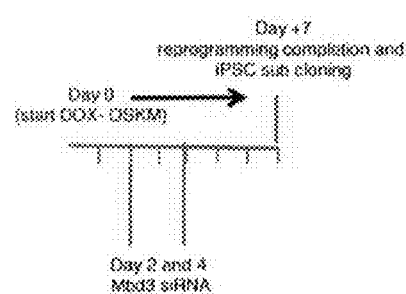
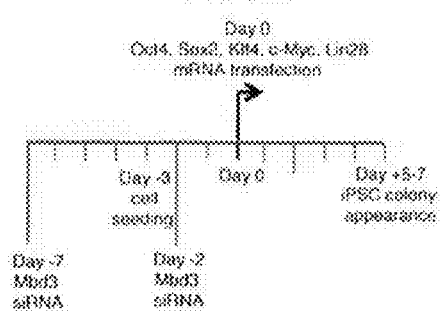
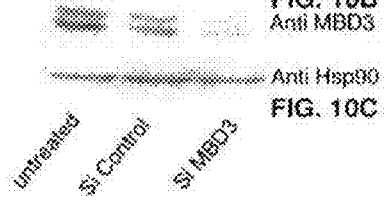
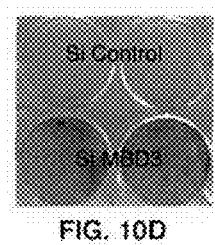
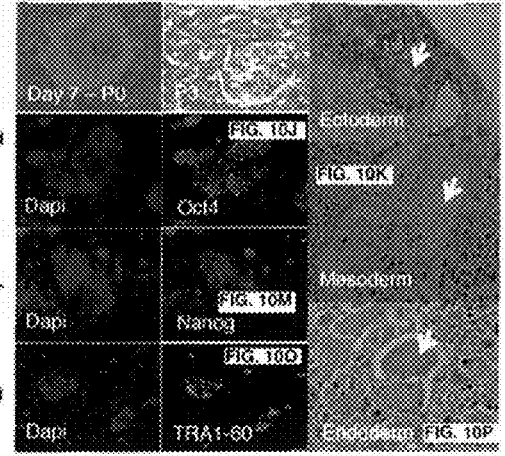

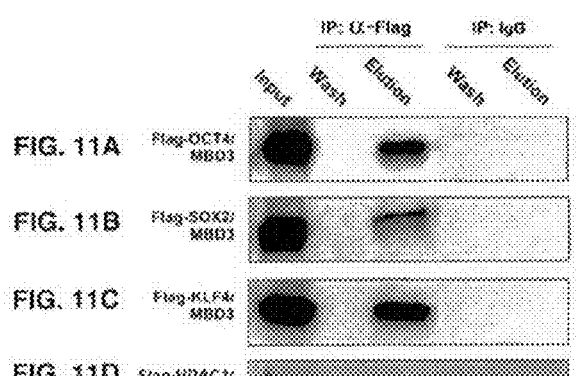
FIG. 11A
FIG. 11B
FIG. 11C
FIG. 11D
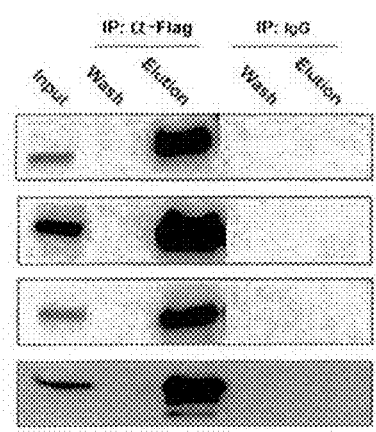
FIG. 11E
FIG. 11F
FIG. 11G
FIG. 11H
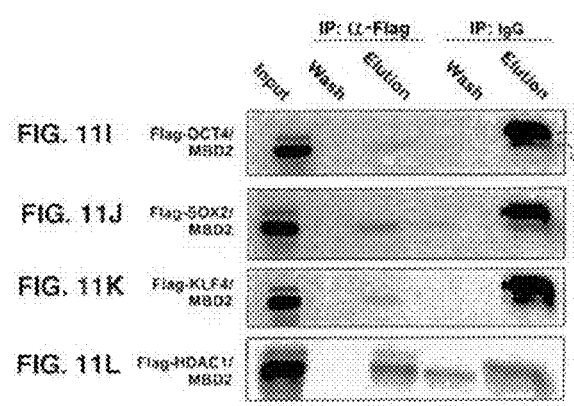
FIG. 11I
FIG. 11J
FIG. 11K
FIG. 11L
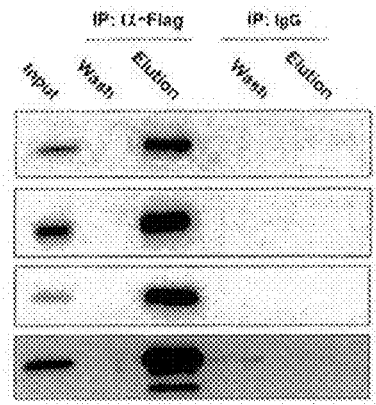
FIG. 11M
FIG. 11N
FIG. 11O
FIG. 11P

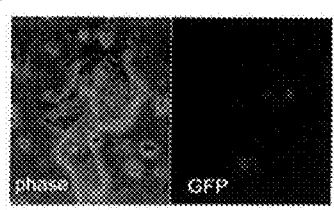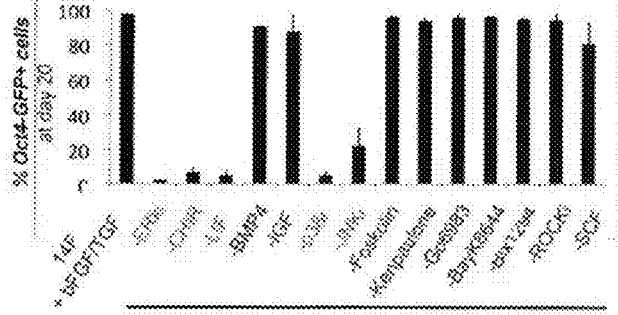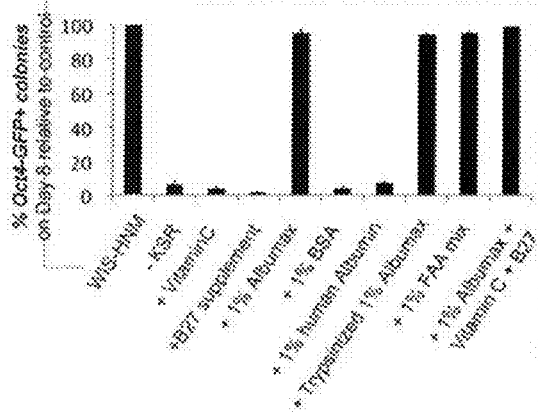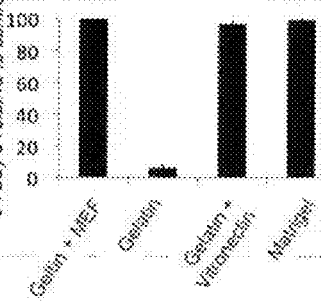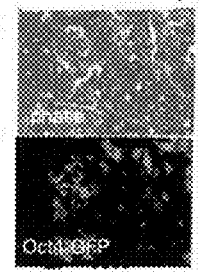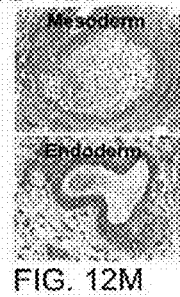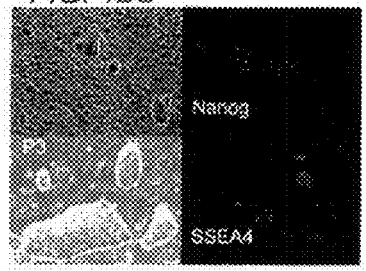

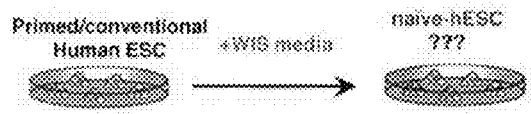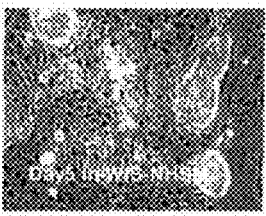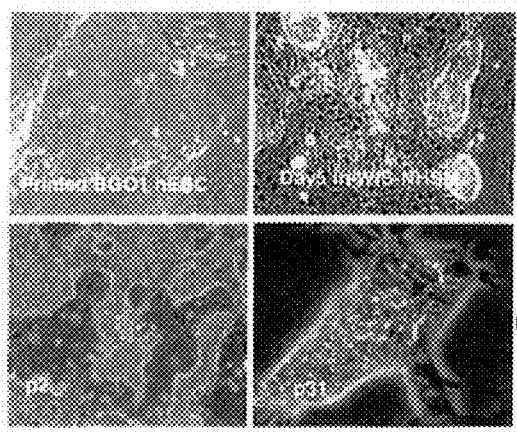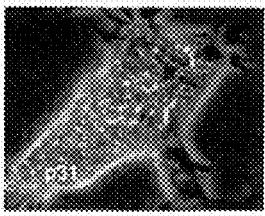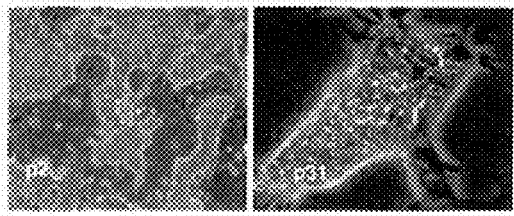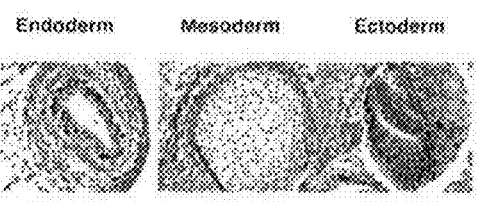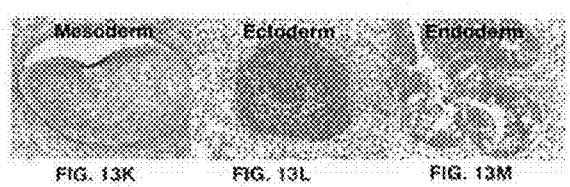

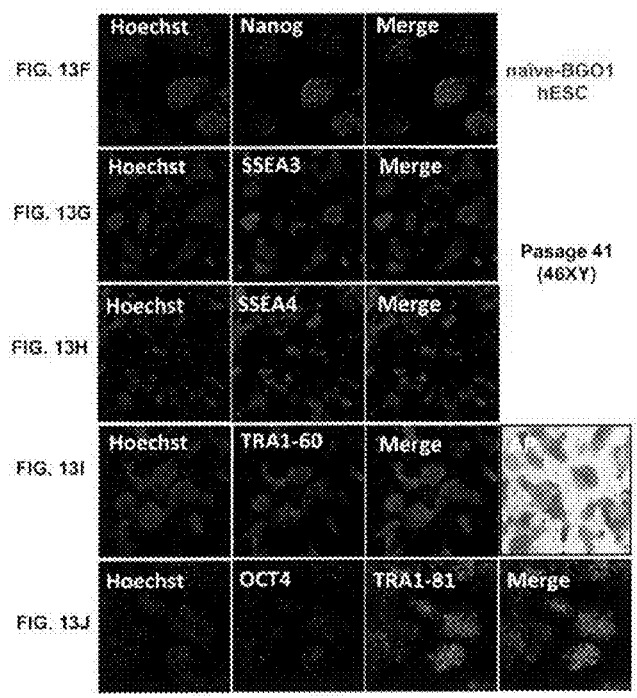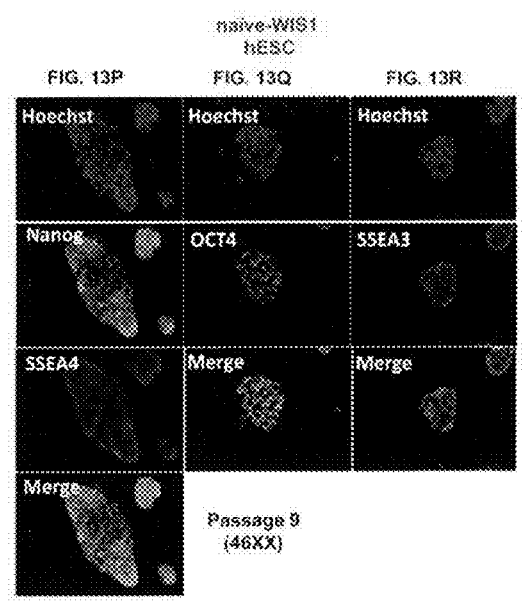

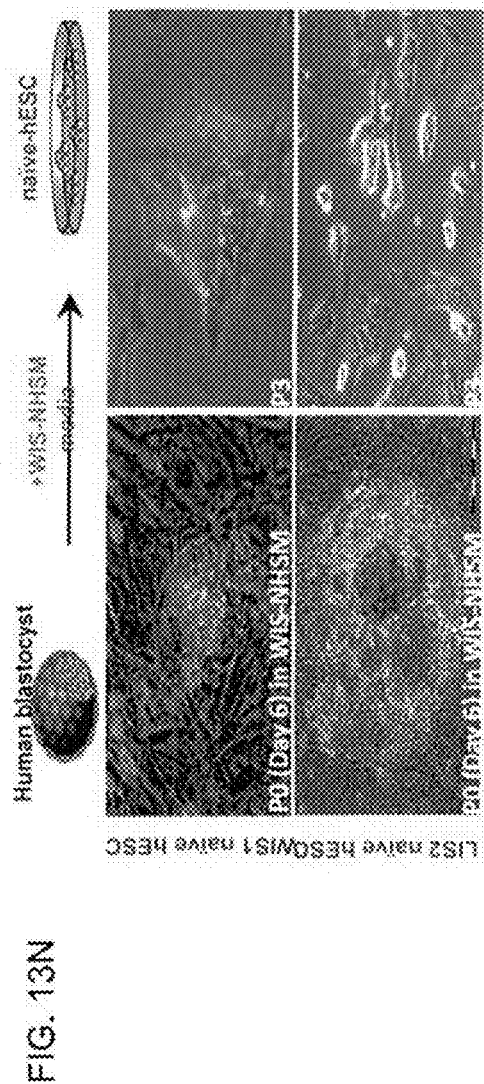
FIG. 13N
FIG. 13O
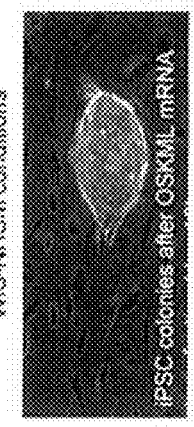
FIG. 13V

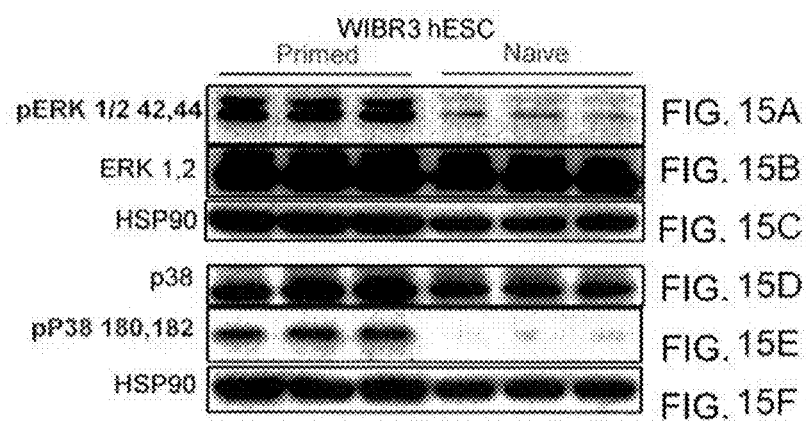
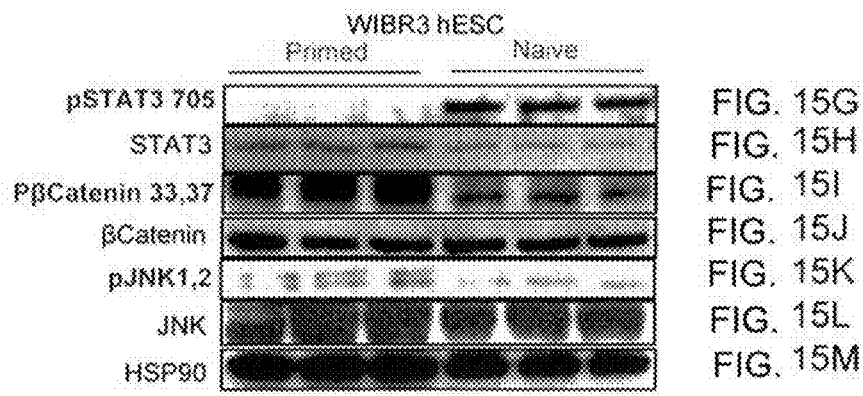

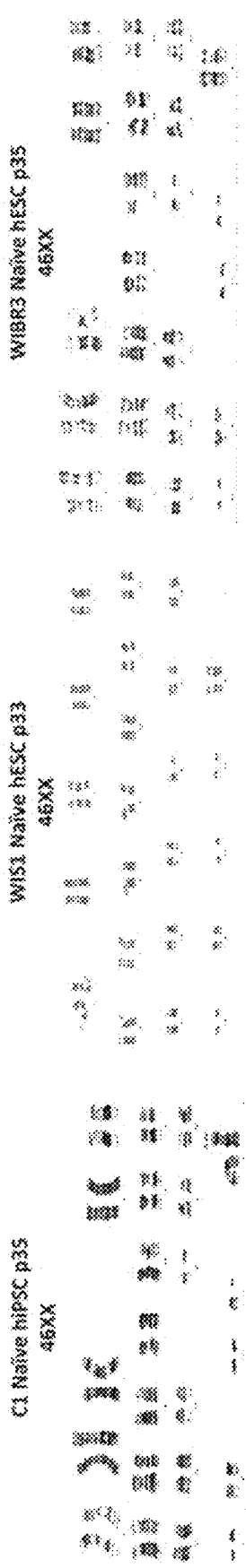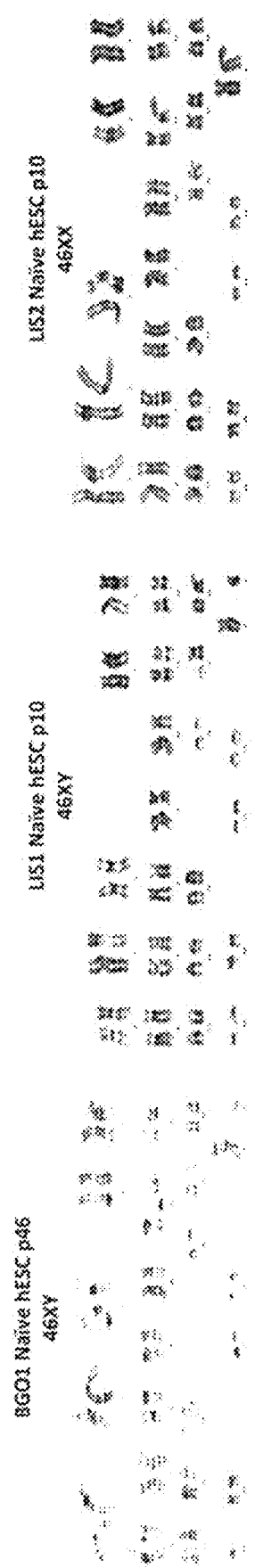
FIG. 15P
FIG. 15S
FIG. 15O
FIG. 15R
FIG. 15N
FIG. 15Q

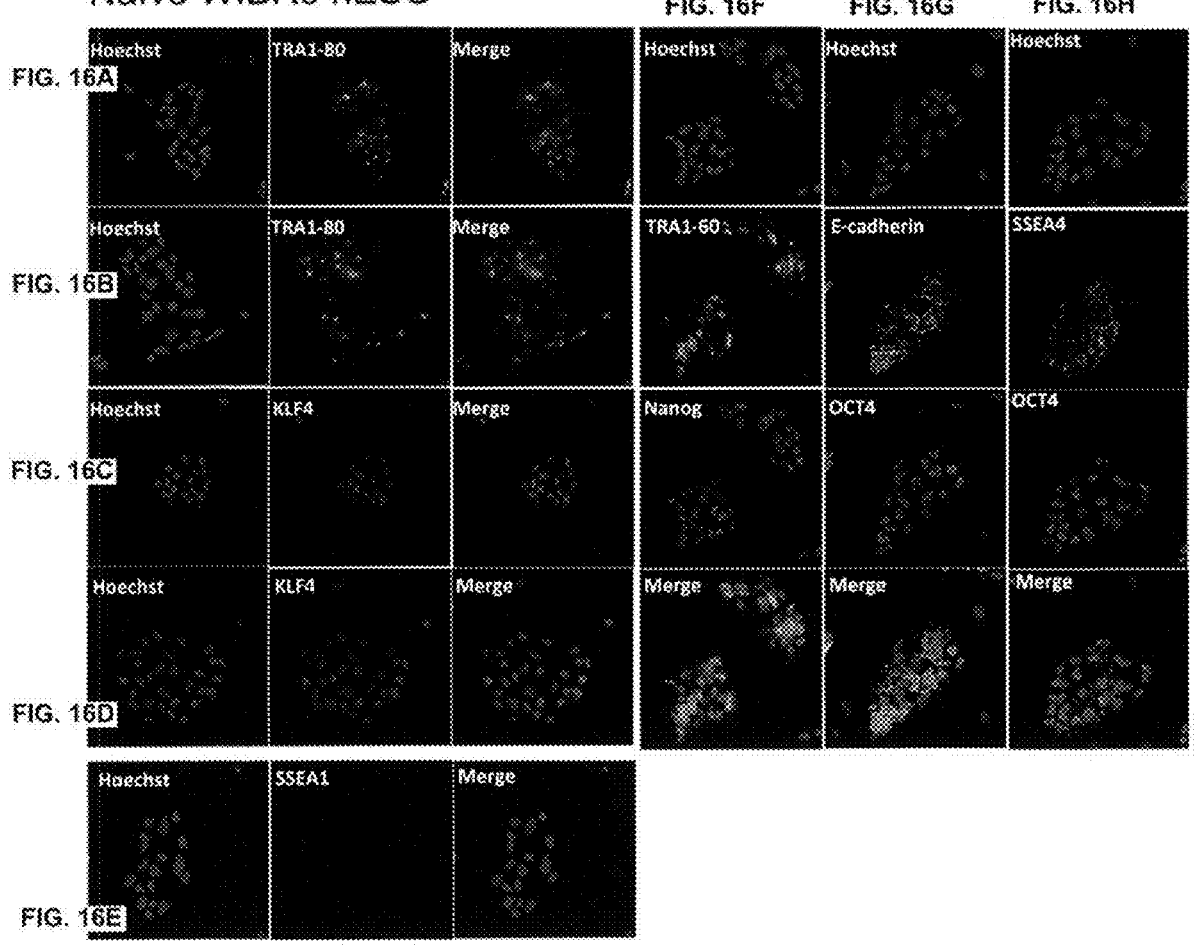

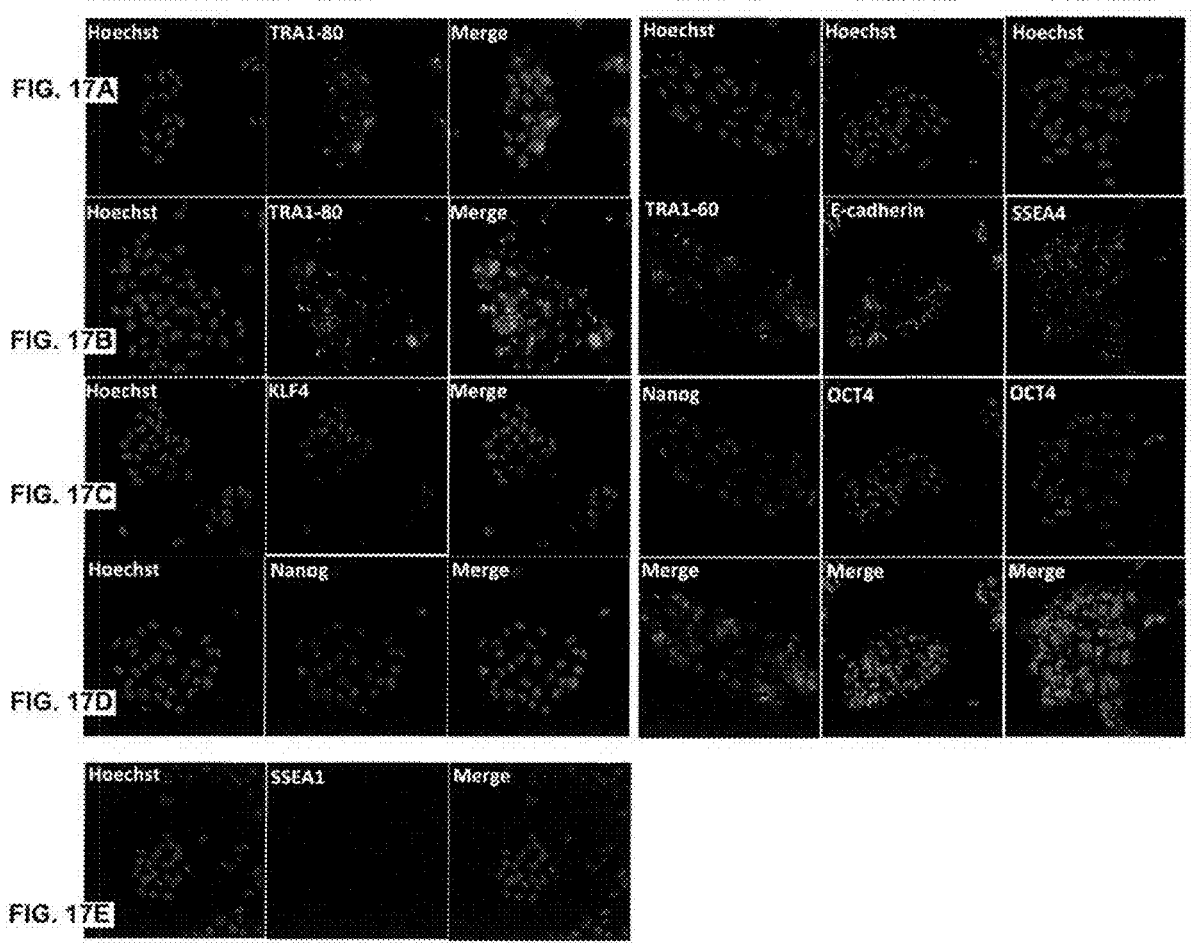

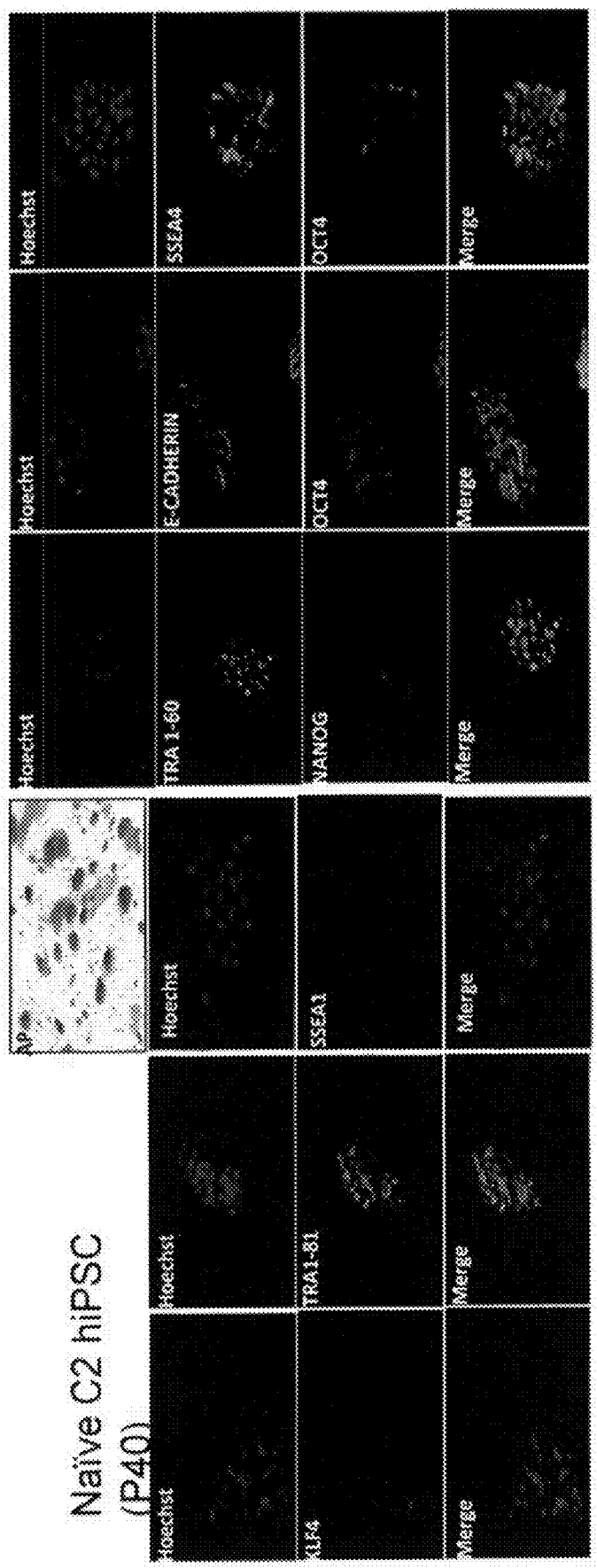

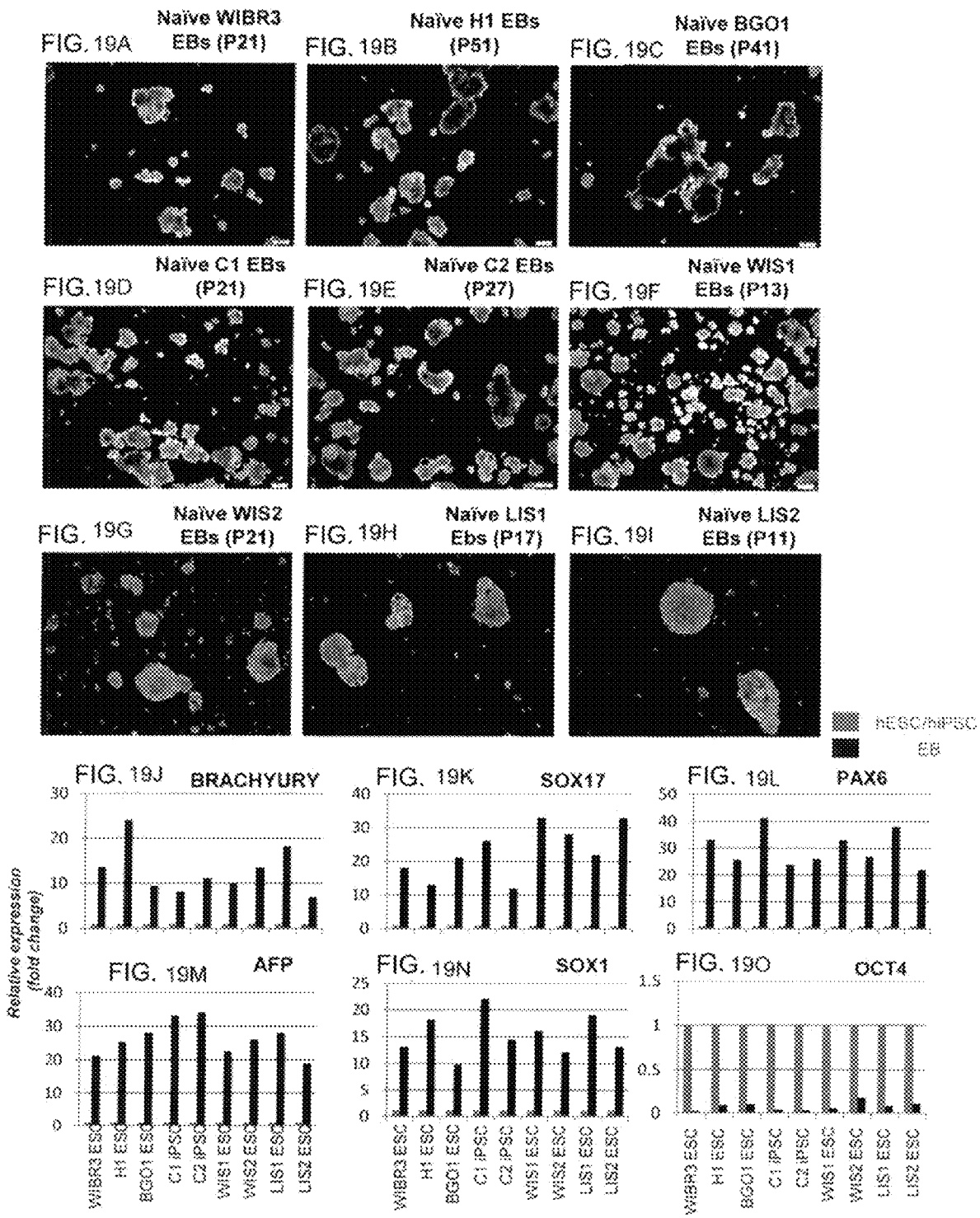

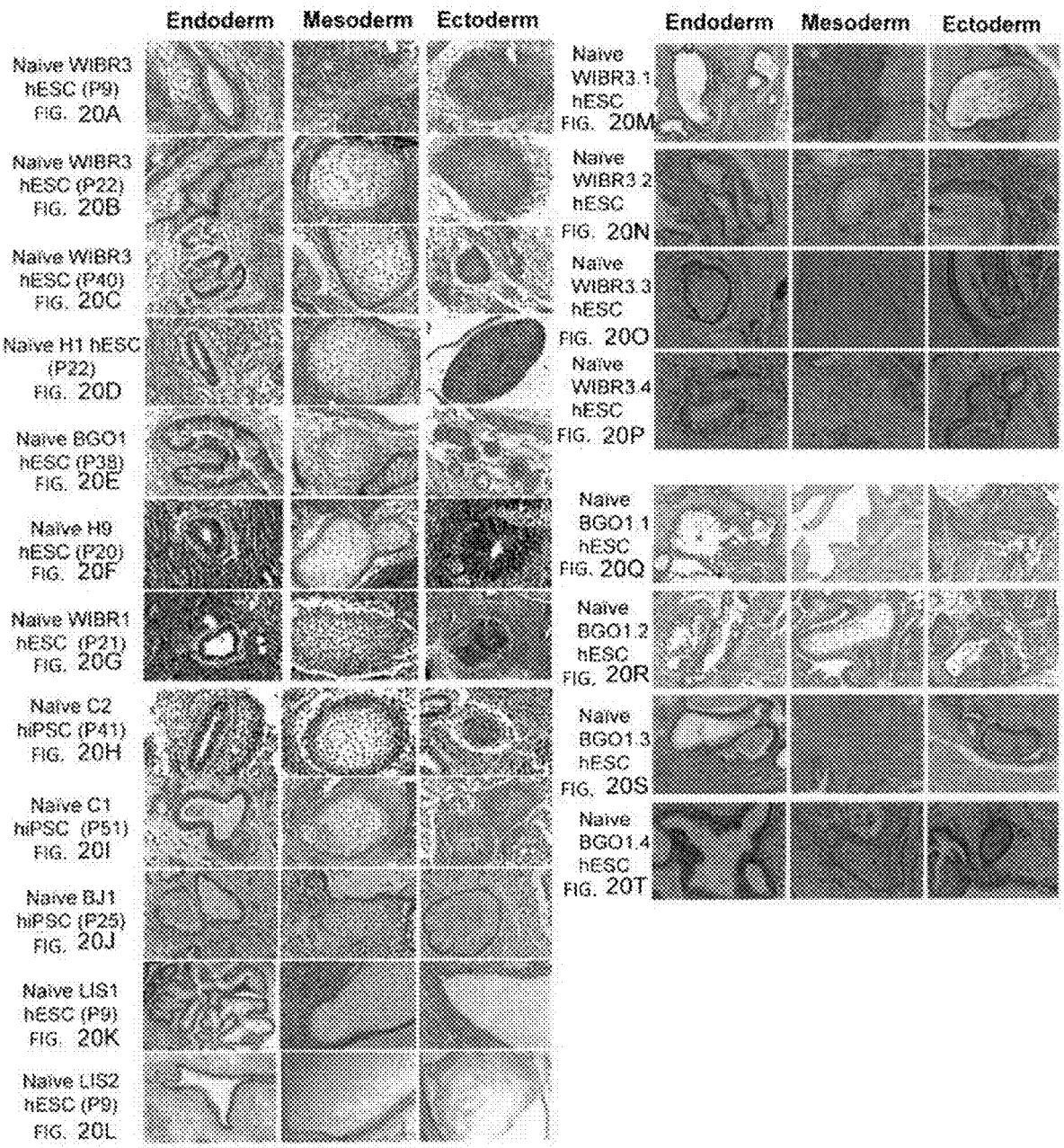

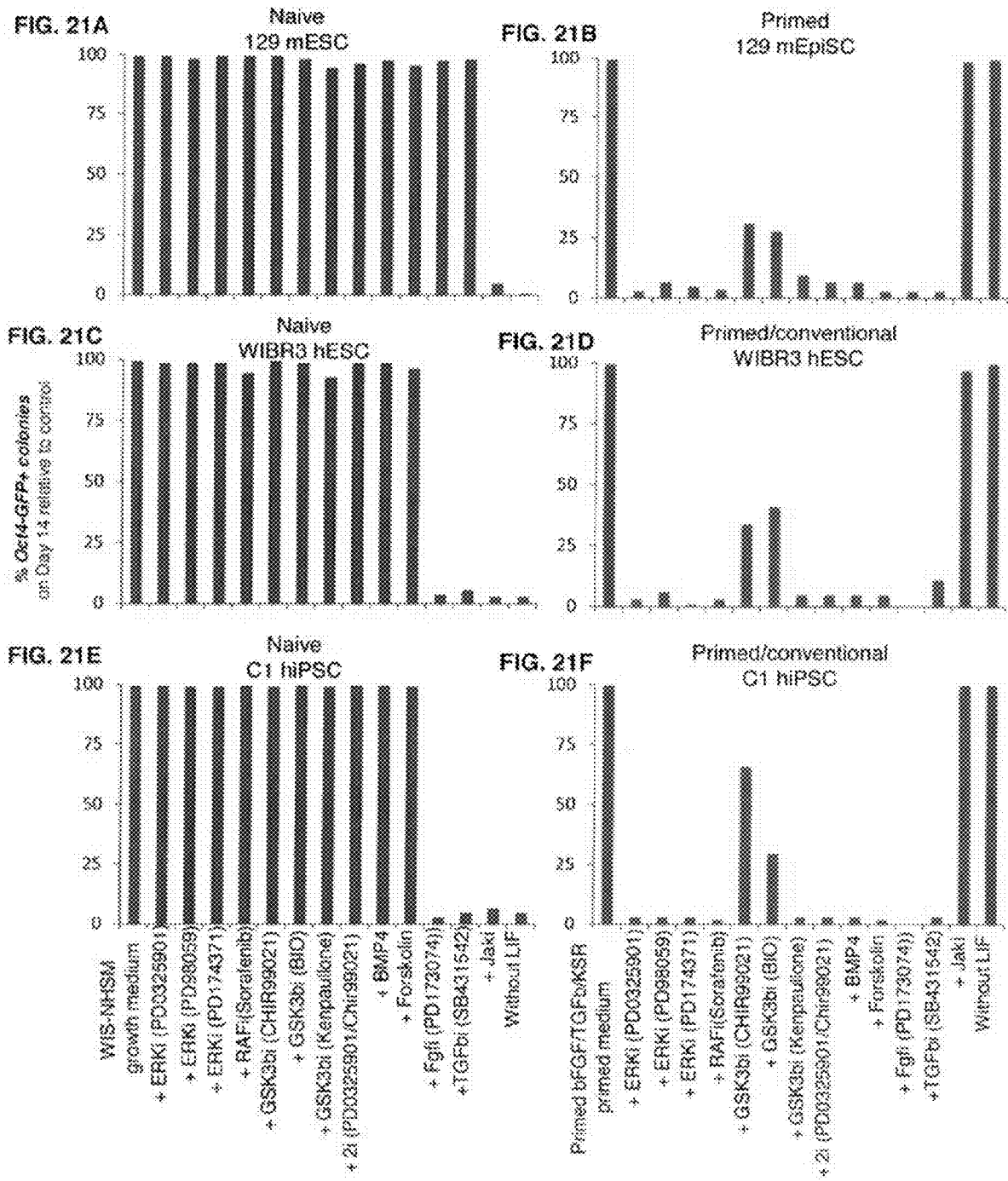

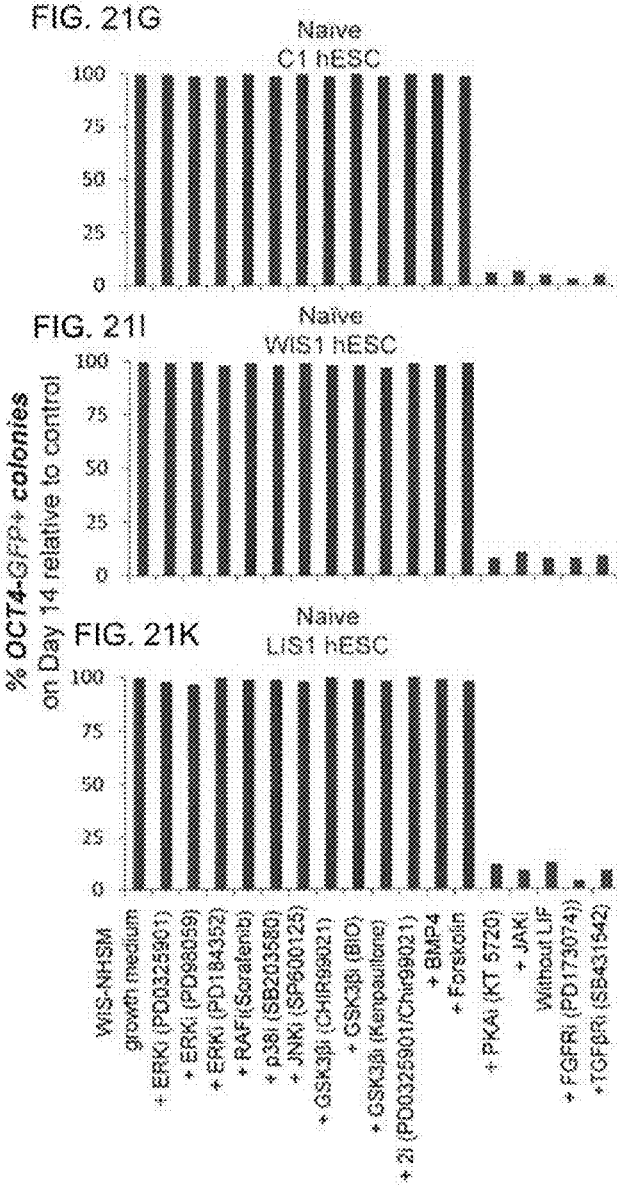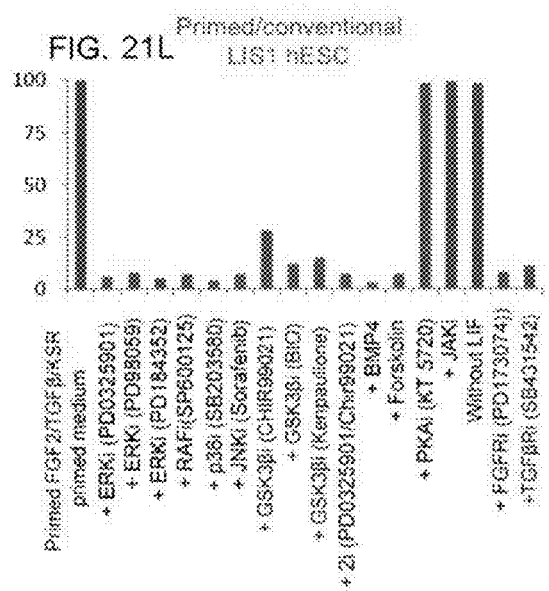

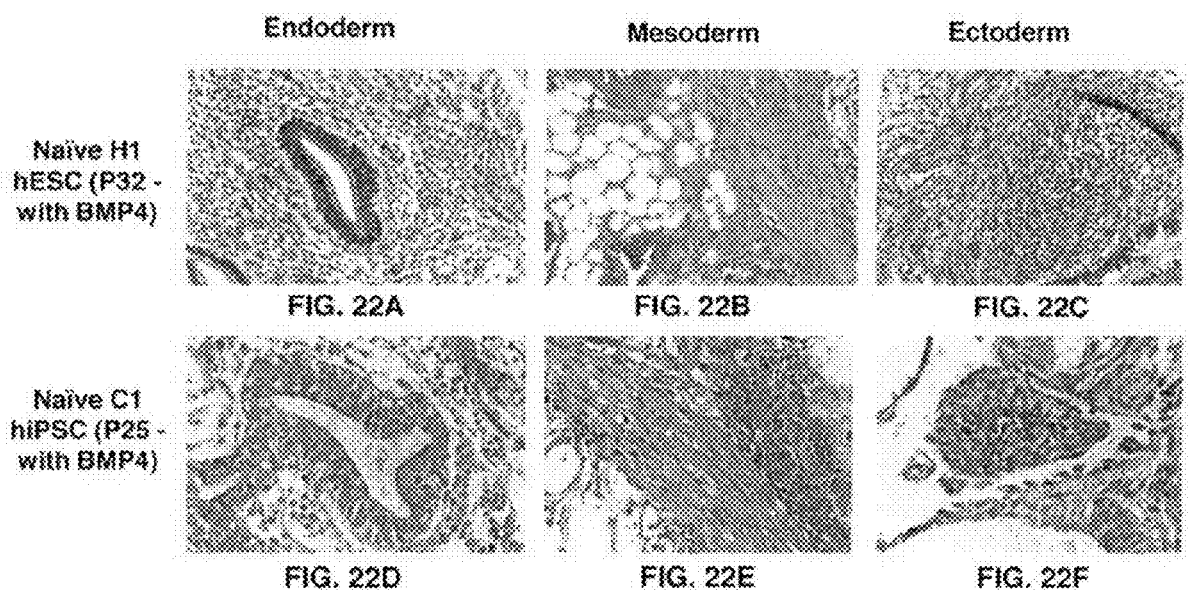
FIG. 22A  FIG. 22B  FIG. 22C
FIG. 22D  FIG. 22E  FIG. 22F
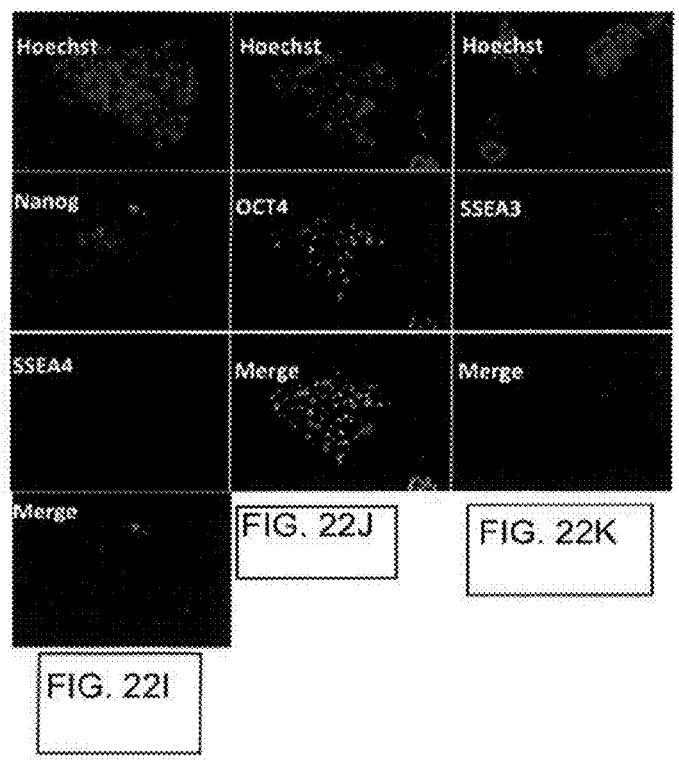
FIG. 22I  FIG. 22J  FIG. 22K

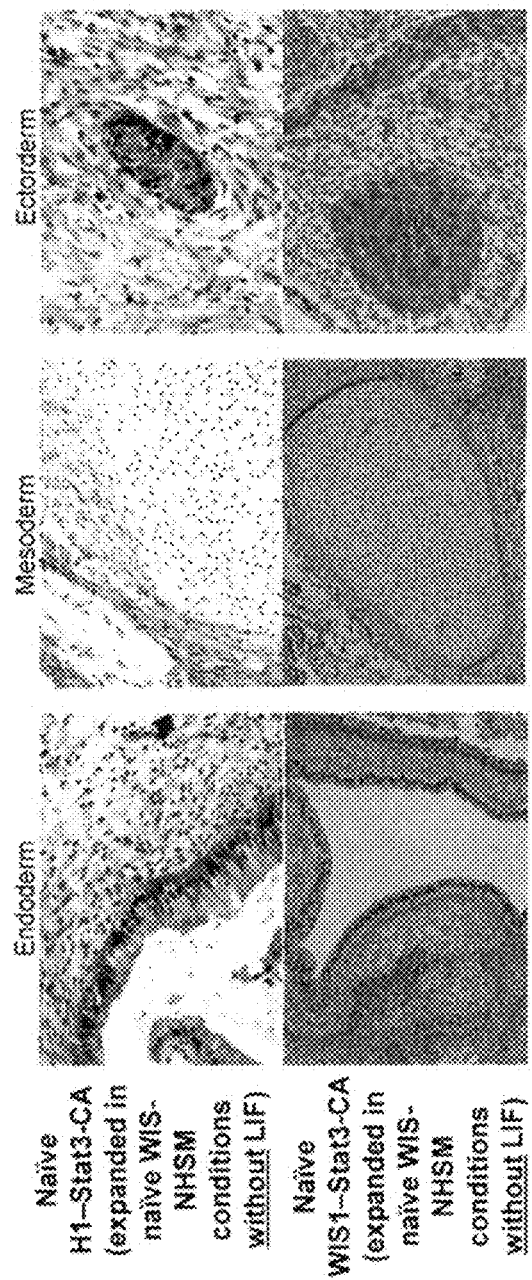

FIG. 24A
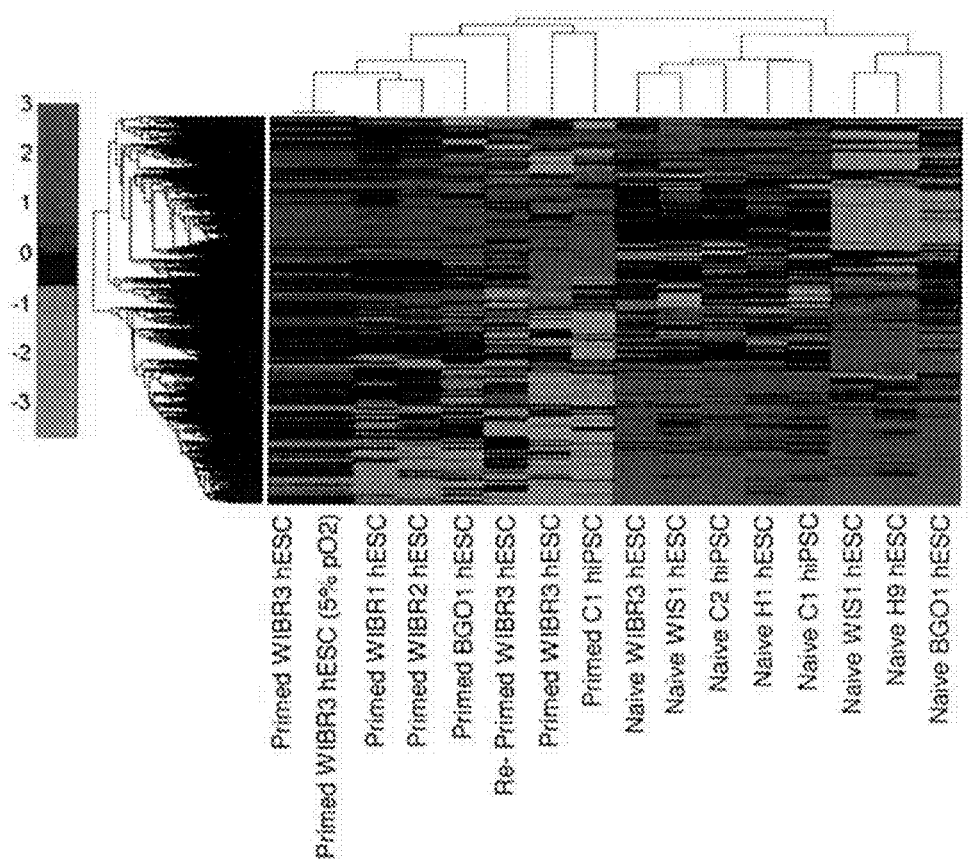
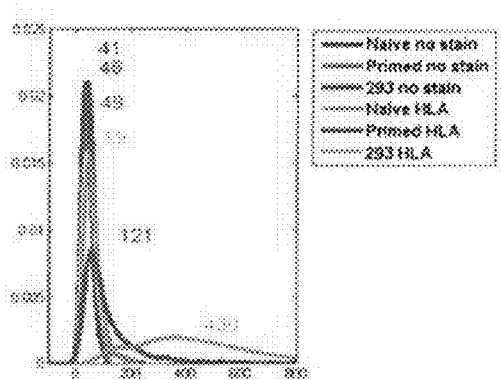
FIG. 24B
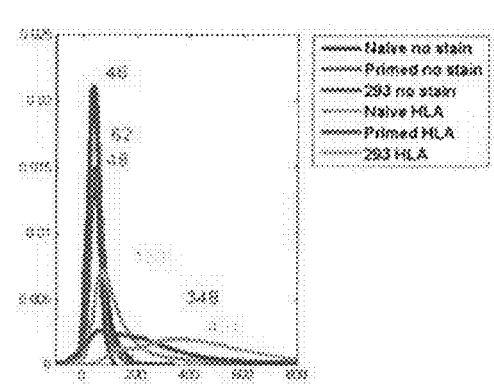
FIG. 24C

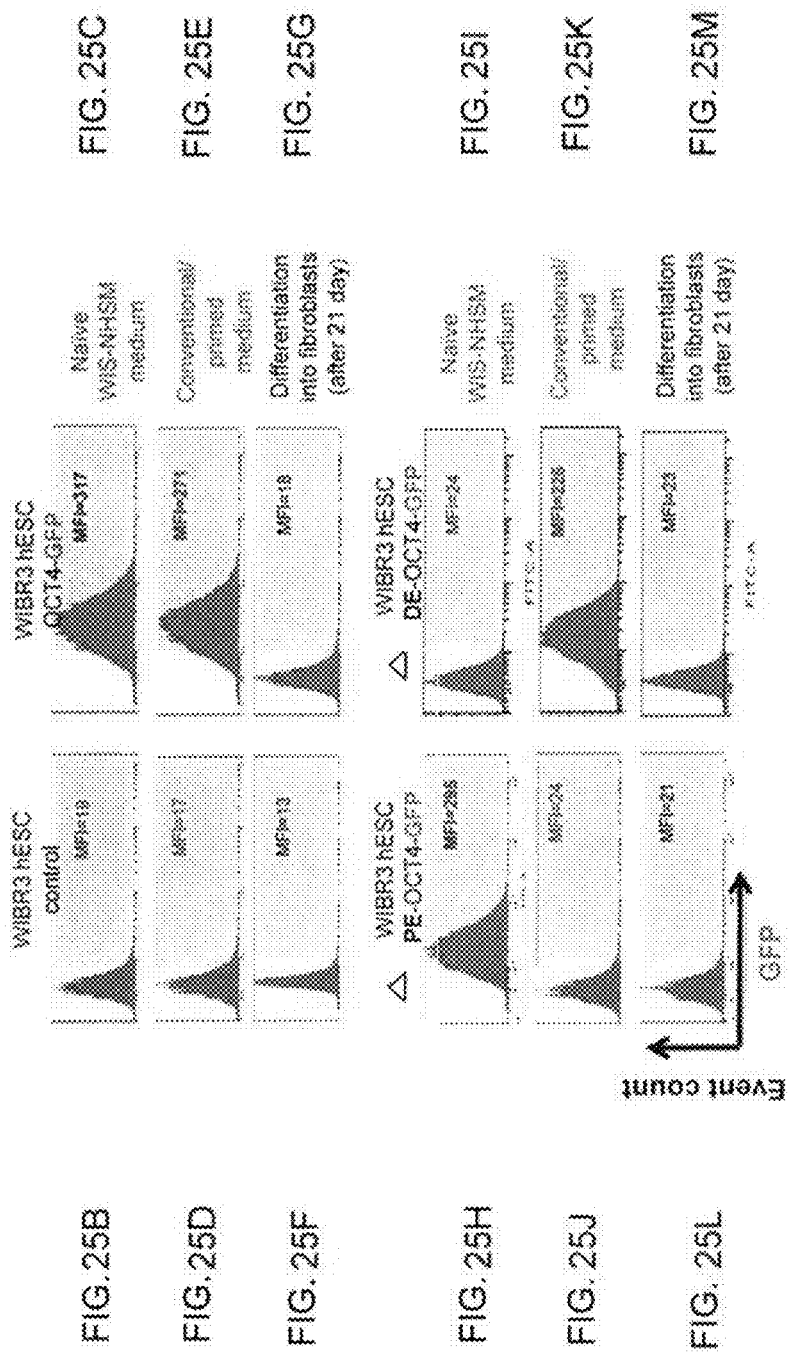

Loading human naive GFP+ iPSC cells

Injection into mouse morula

Bright field | EGFP | Merge

Day of Inj.

1 day after Inj.

XIST promoter CpG islands

GGGTAAATTTTGAACCAACCAAATCACAAAGATGTCCGGCTTTCAATCTTCTAGG
CCACGCCTCTTATGCTCTCTCCGCCCTCAGCCCCCCCTTCAGTTCTTAAAGCGCTG
CAATTCCCTGCTGCAGCCATATTTCTTACTCTCTCGGGGCTGGAAGCTTCCTGACT
GAAGATCTGTTCTAGAAAGAACCCCAAGTGCAGAGA (SEQ ID NO:70)

FIG. 27

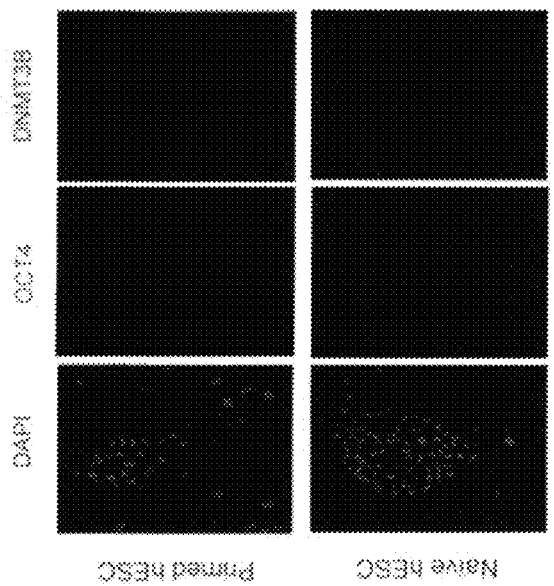
FIG. 29A
FIG. 29B
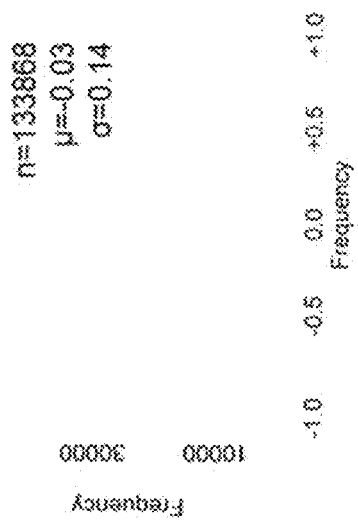
FIG. 29C
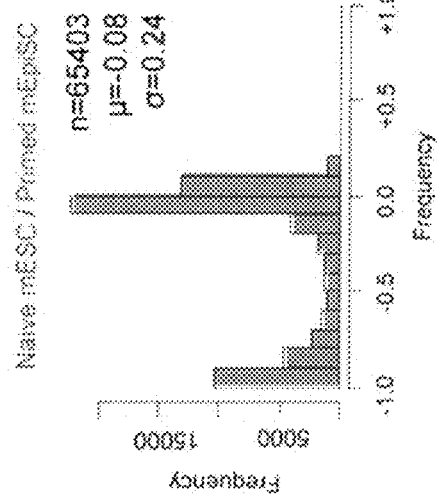
FIG. 29D

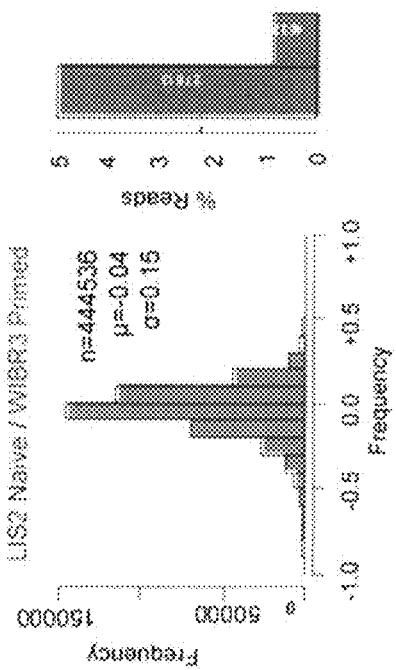
FIG. 30D
FIG. 30E
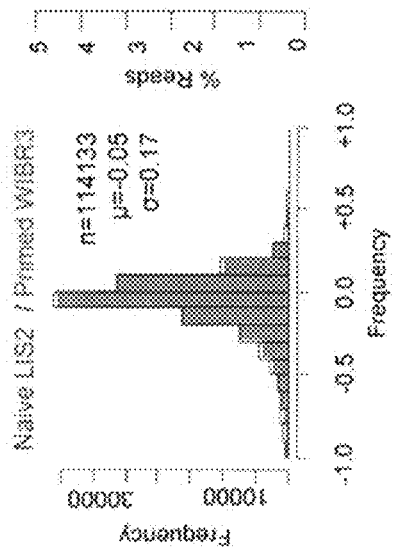
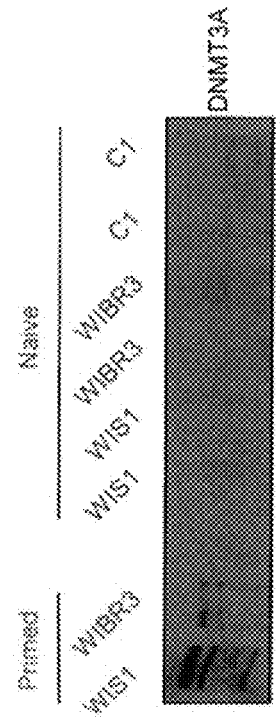
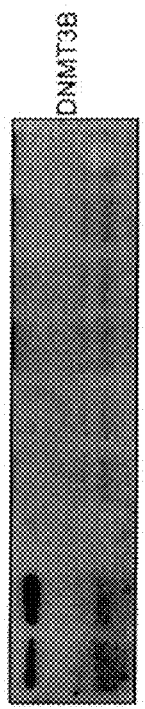
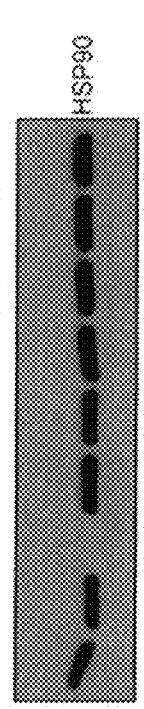
FIG. 30A
FIG. 30B
FIG. 30C

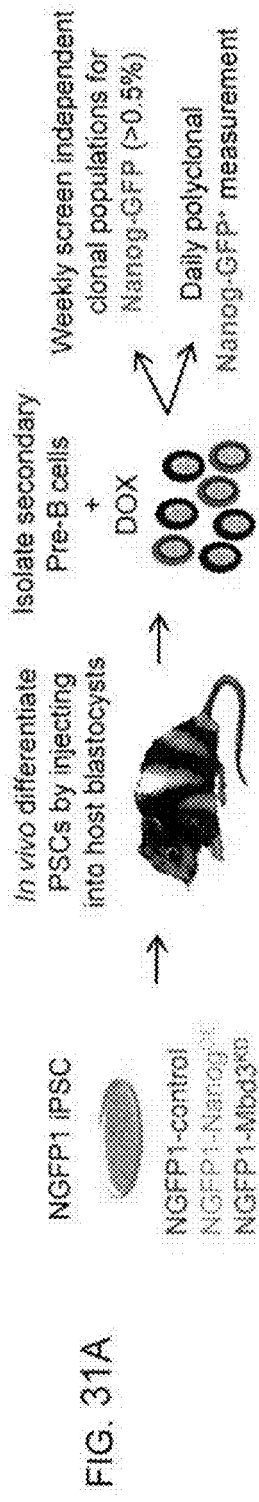
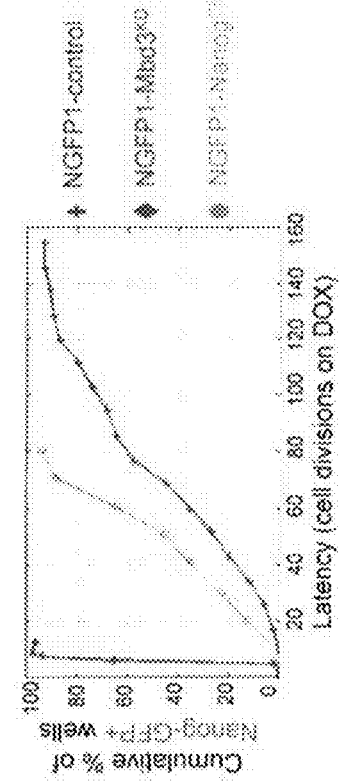
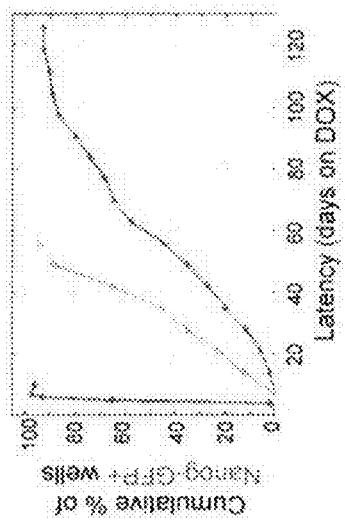
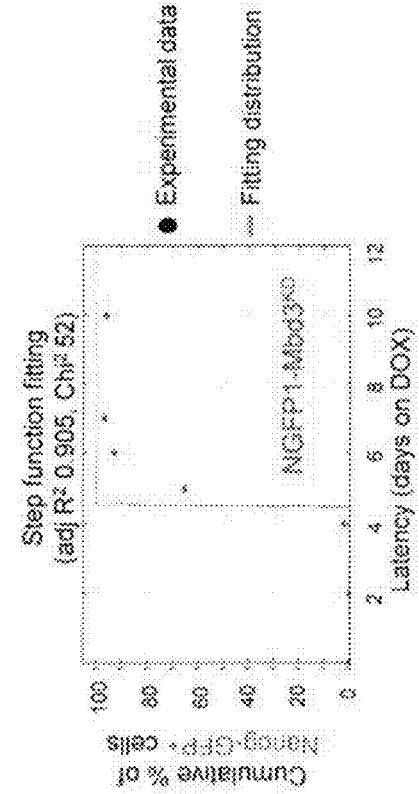
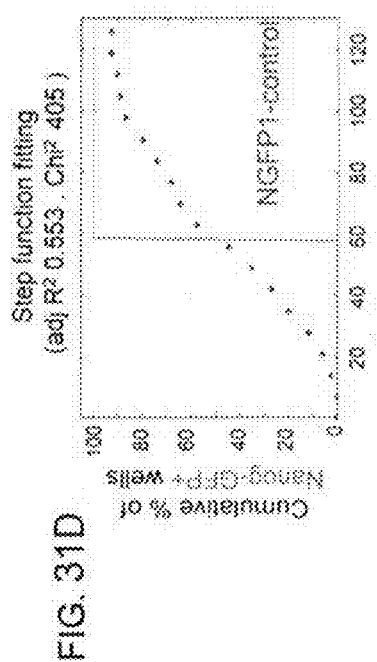
FIG. 31A
FIG. 31B
FIG. 31C
FIG. 31D
FIG. 31E

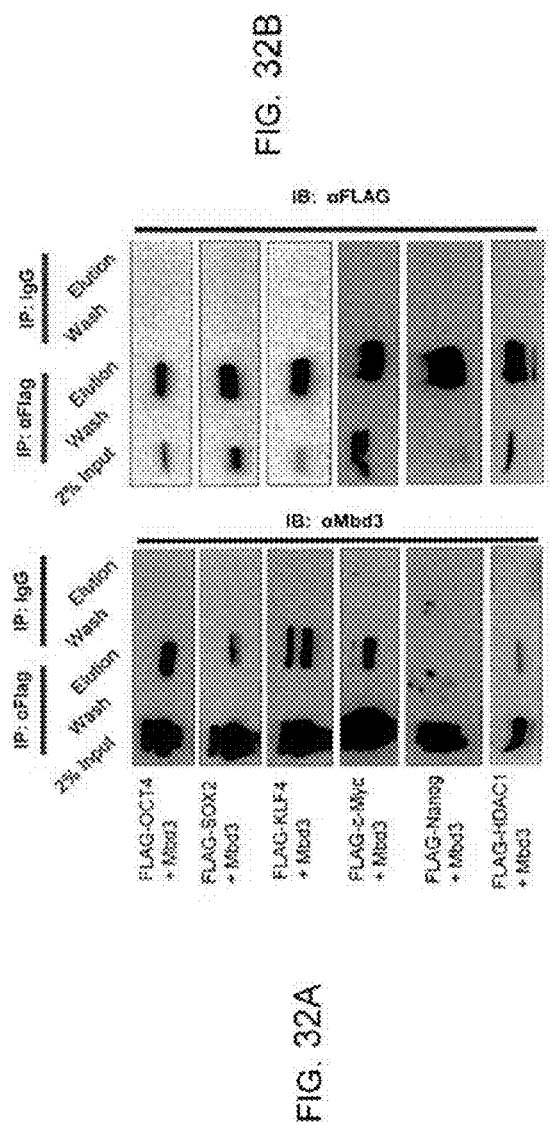
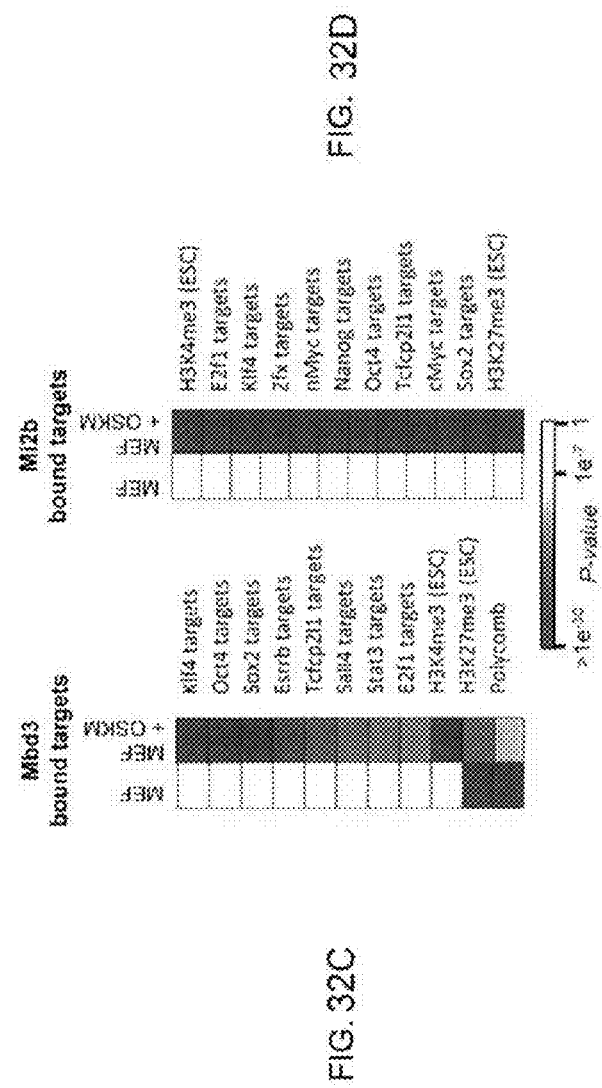
FIG. 32A
FIG. 32B
FIG. 32C
FIG. 32D

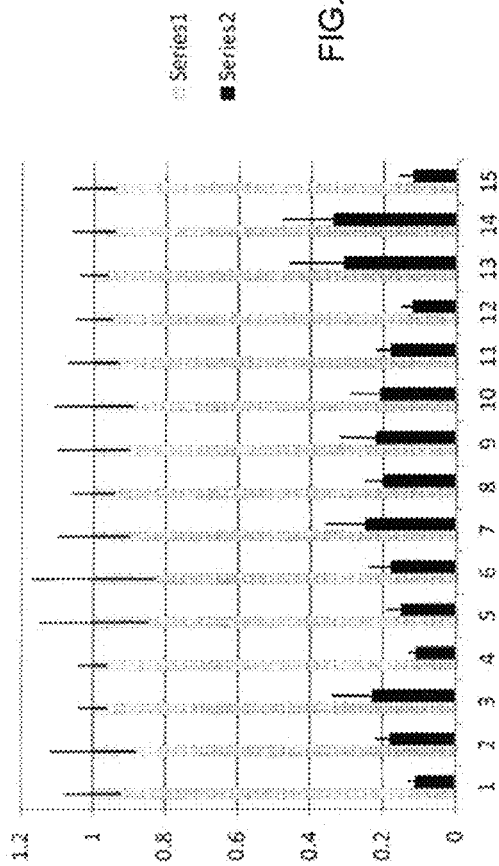
FIG. 33A
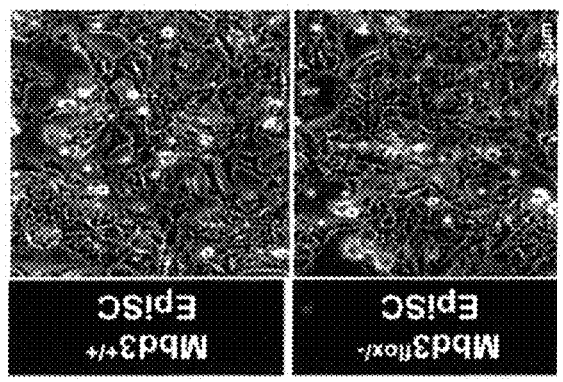
FIG. 33B
FIG. 33C

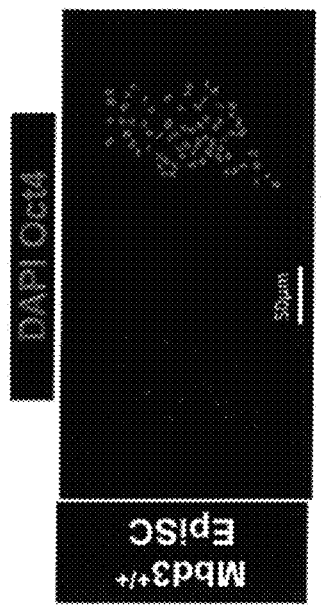
FIG. 33D
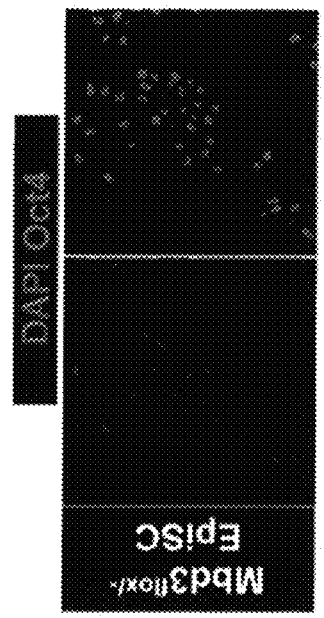
FIG. 33E
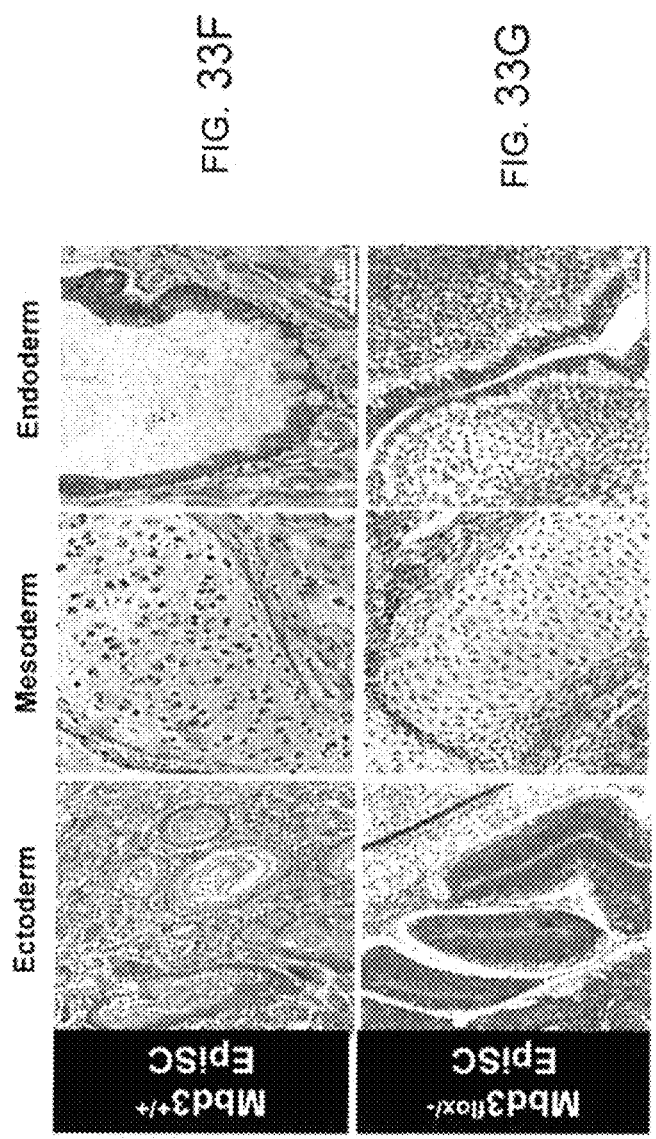
FIG. 33F
FIG. 33G

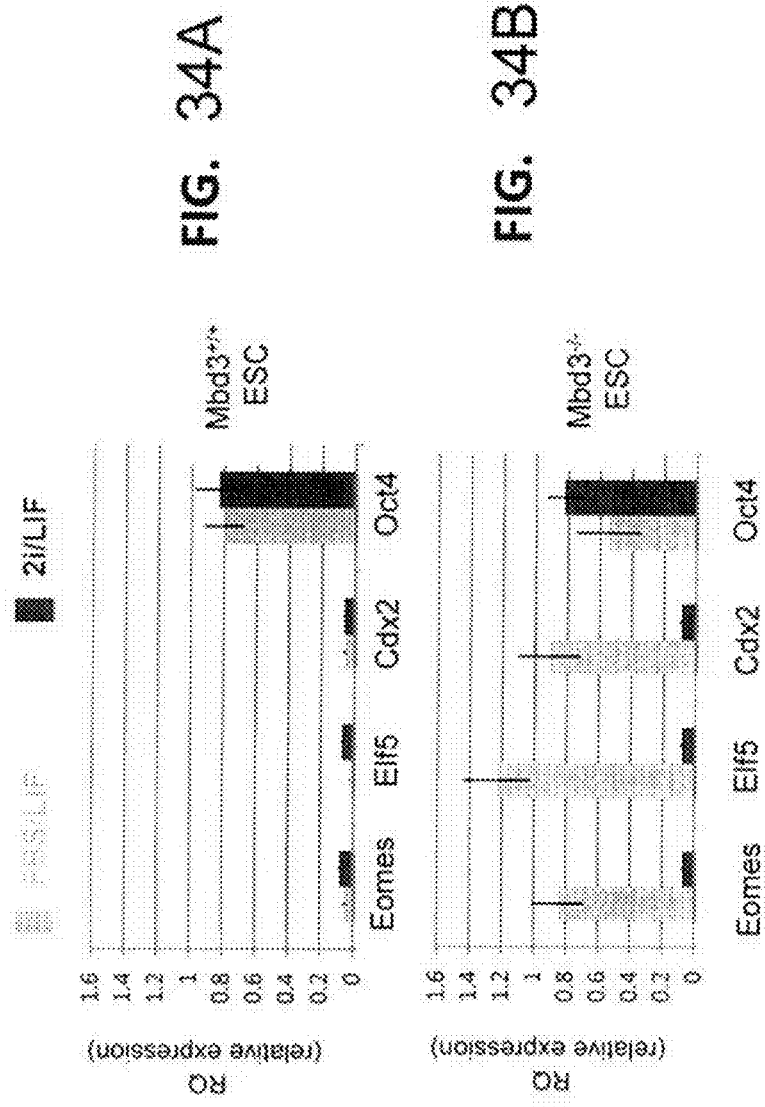

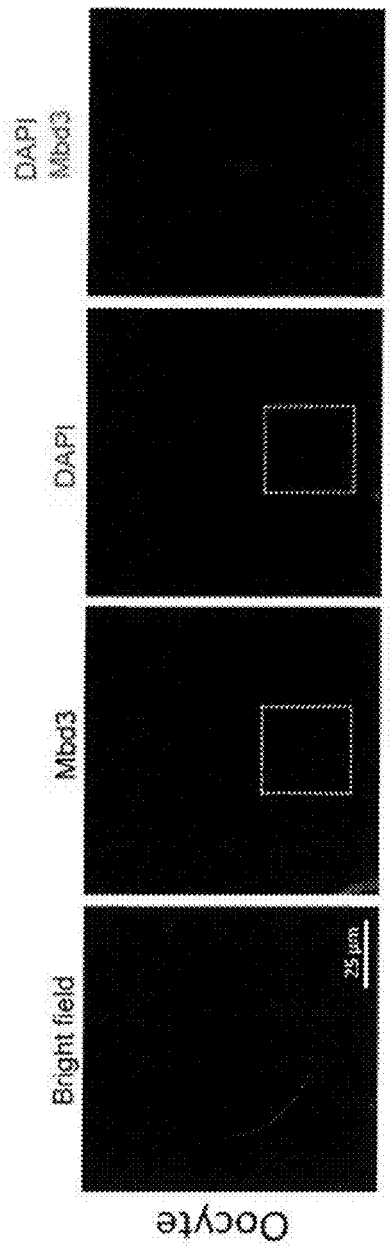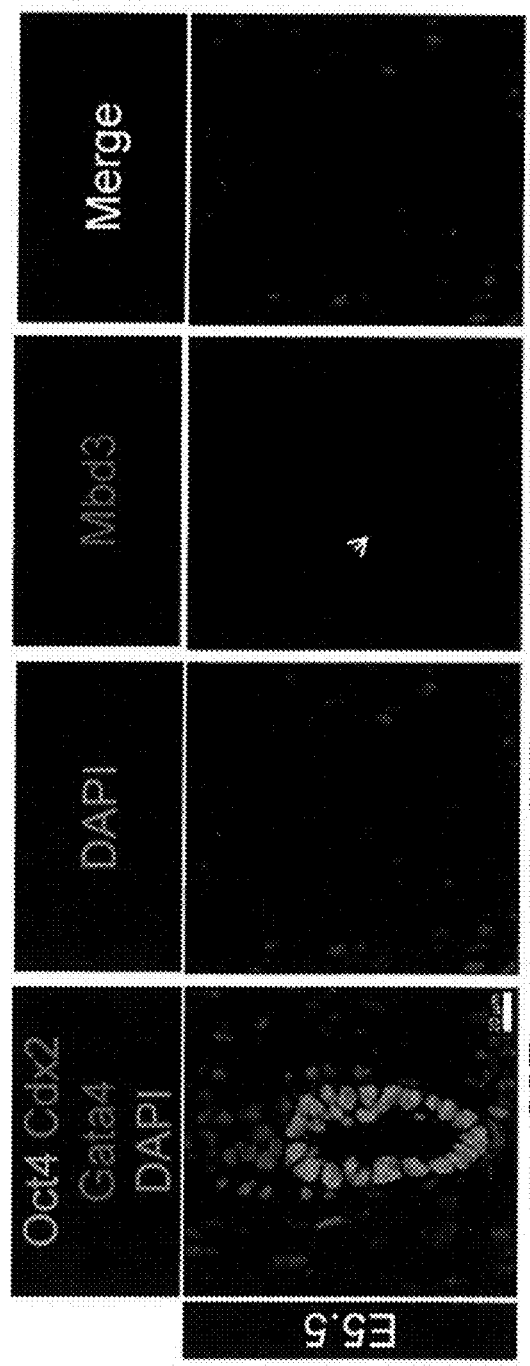

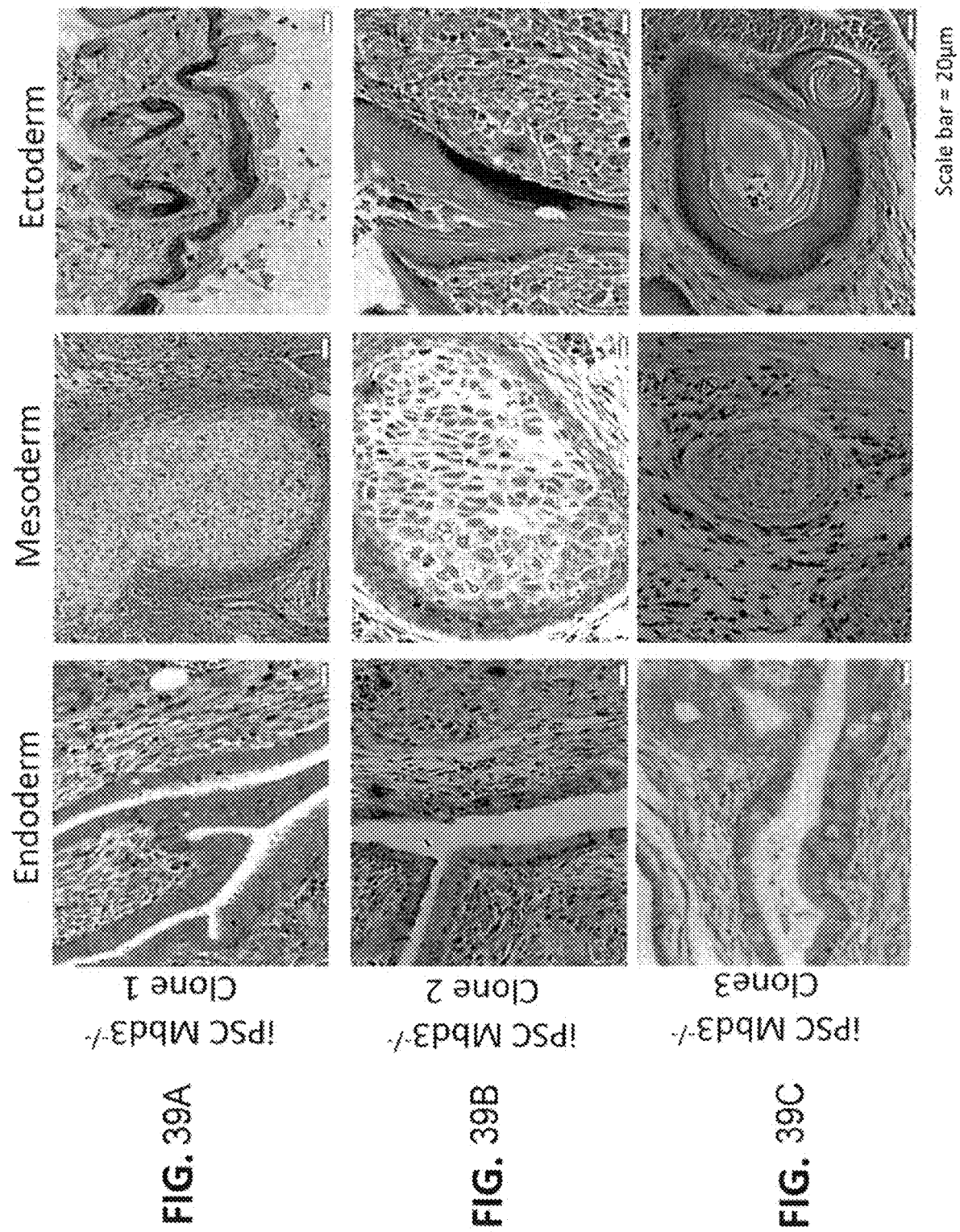

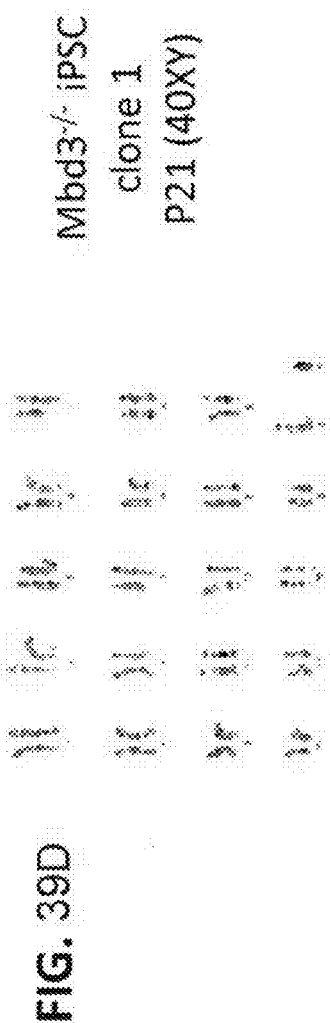
FIG. 39D
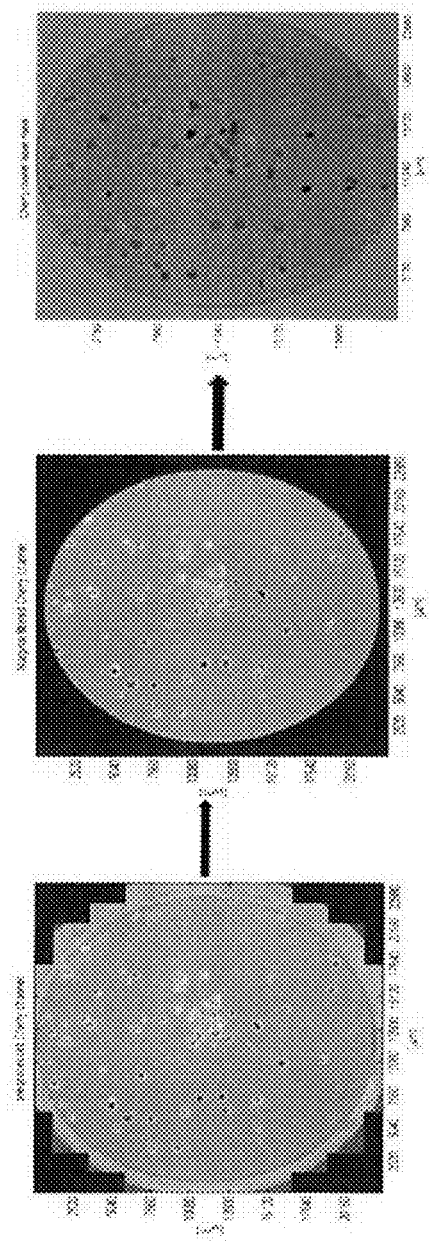
FIG. 40A
FIG. 40B
FIG. 40C

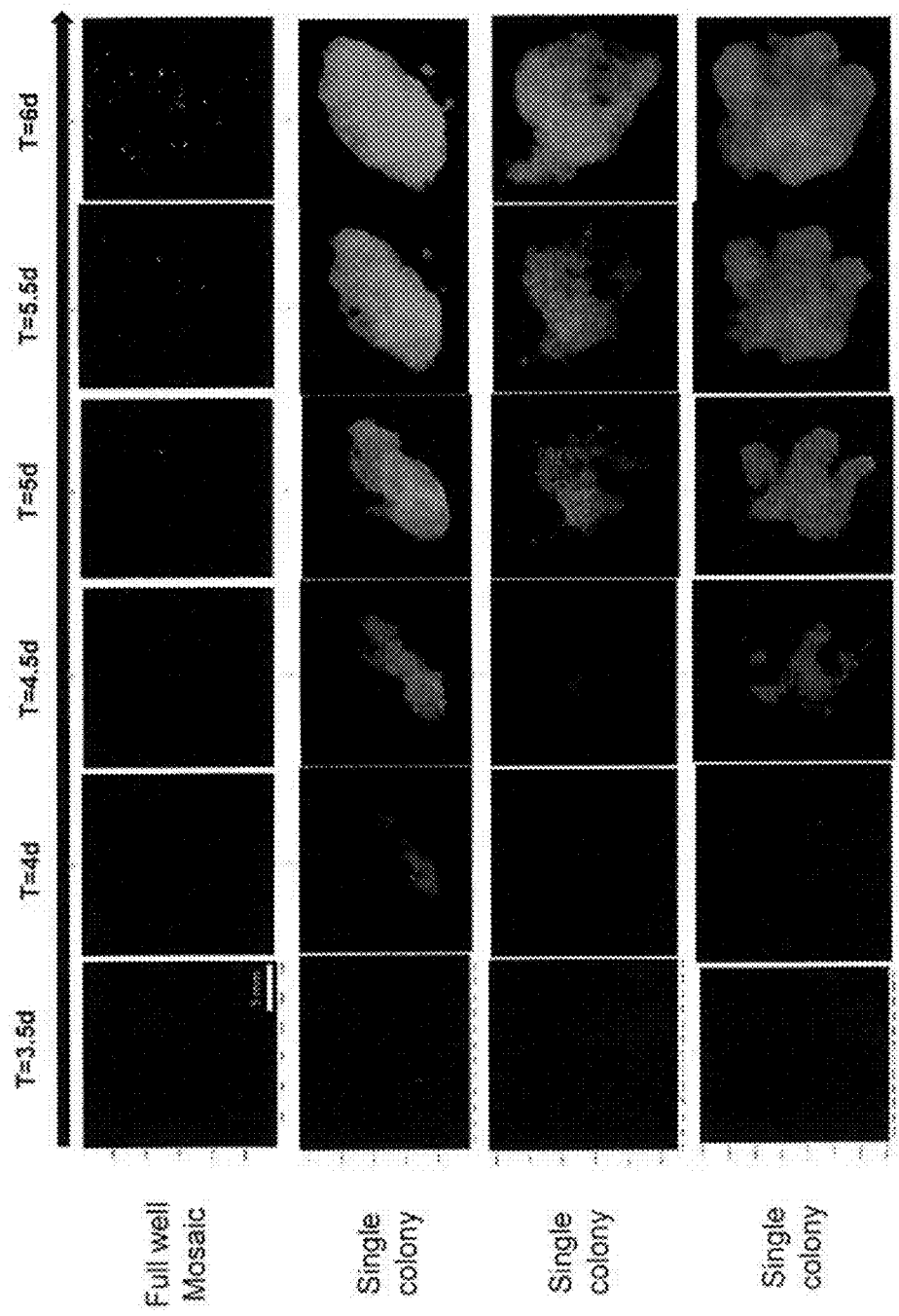

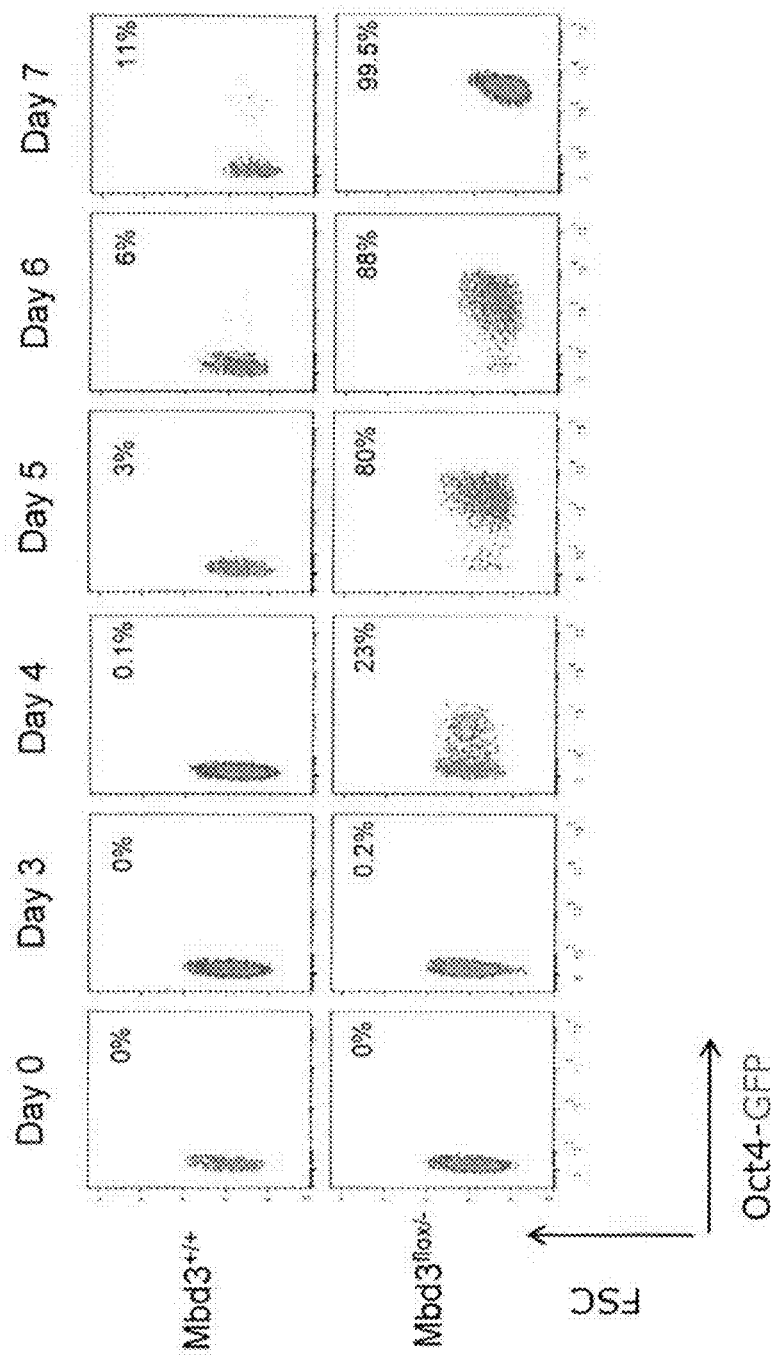

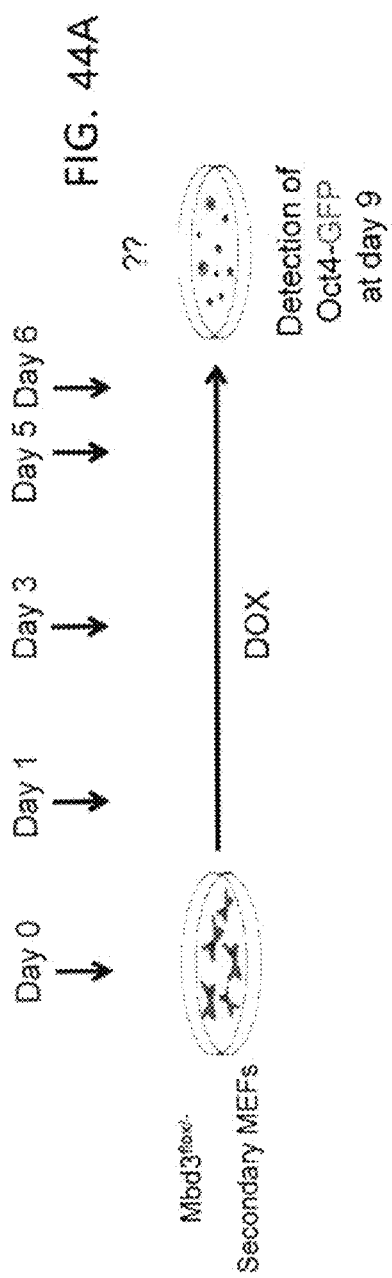
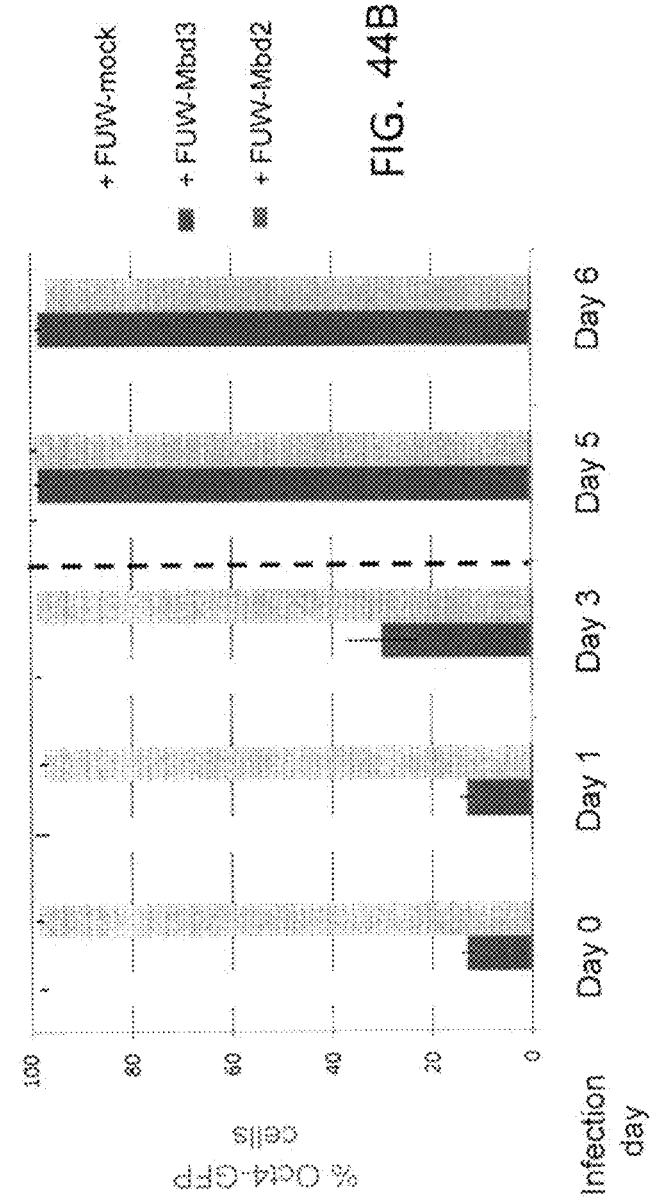
FIG. 44A
FIG. 44B

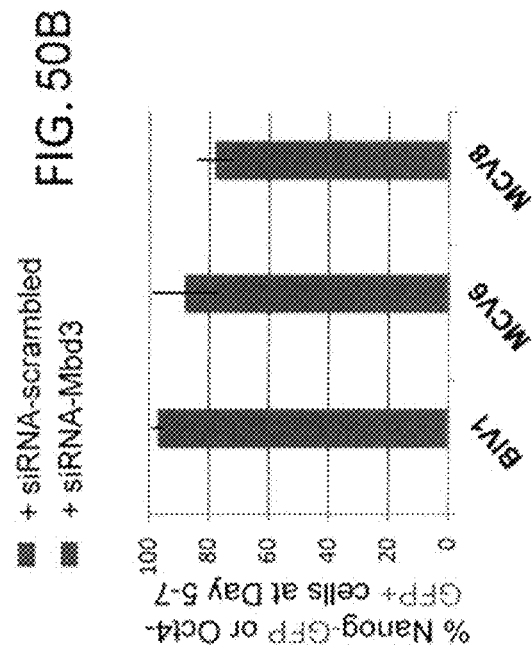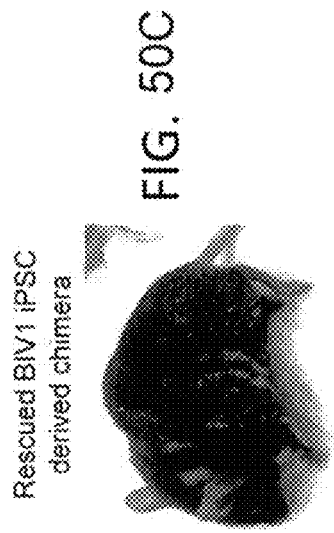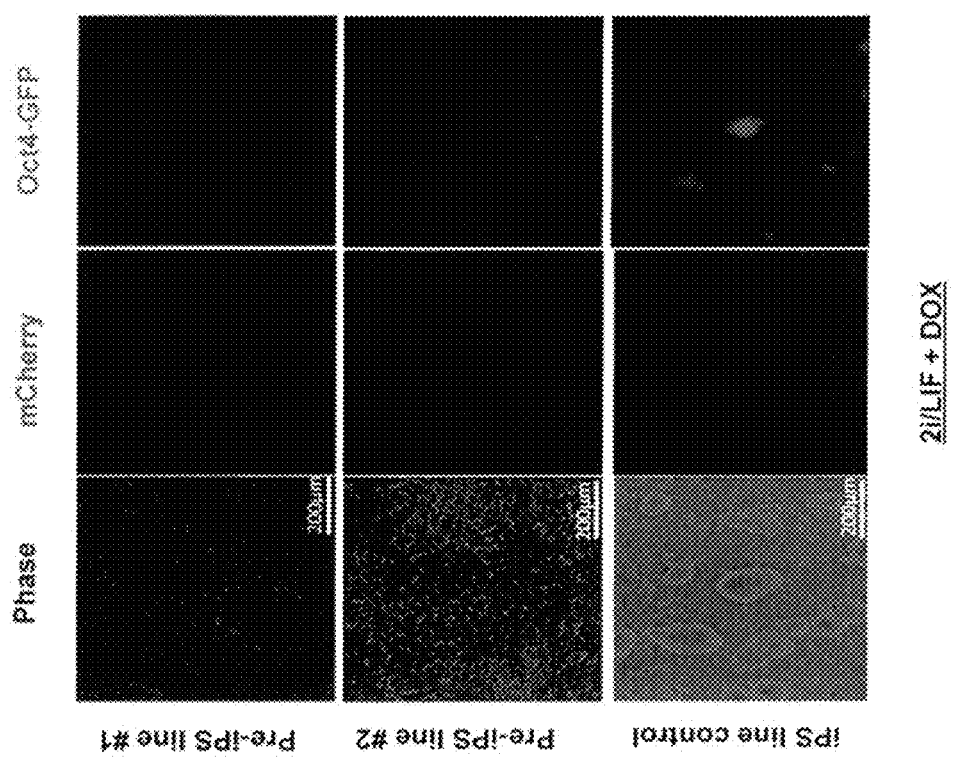
FIG. 50B
FIG. 50C
FIG. 50A

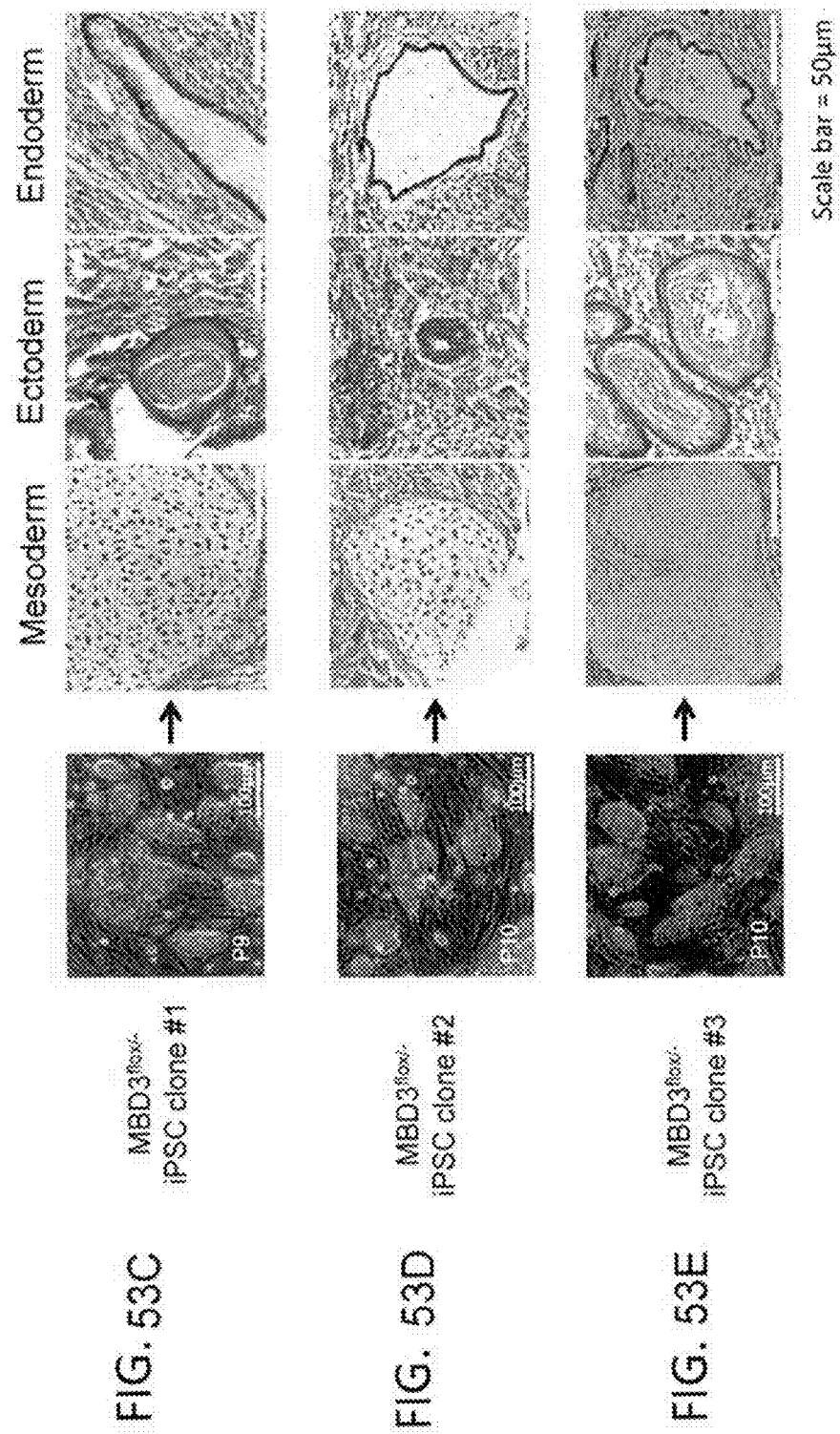

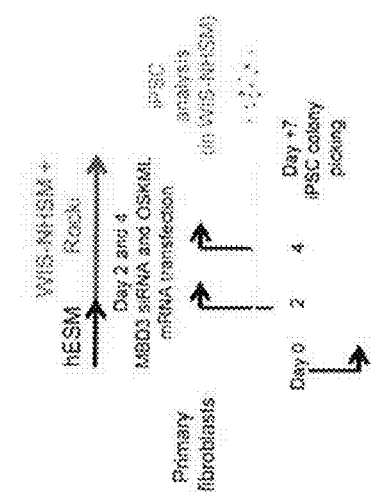
FIG. 54A
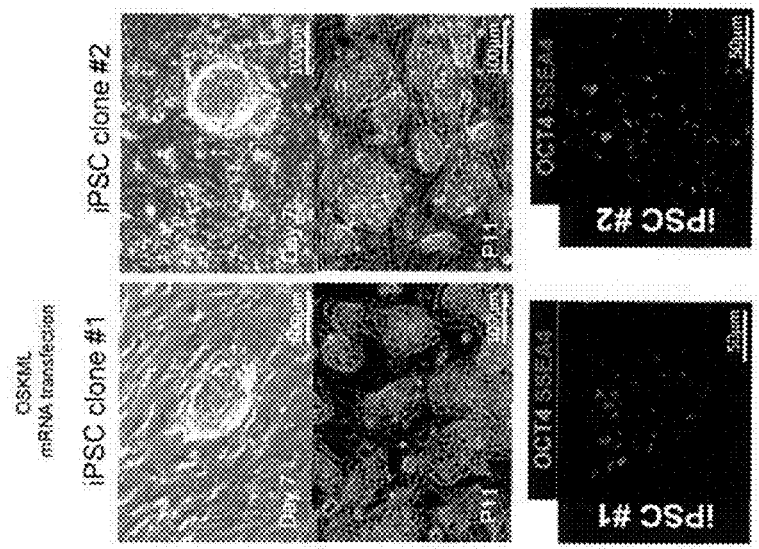
FIG. 54C
FIG. 54D
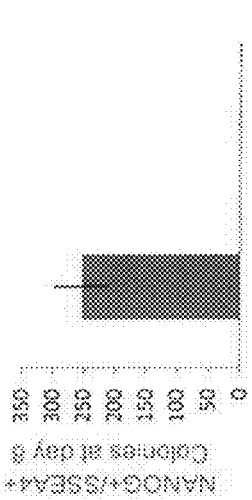
FIG. 54B
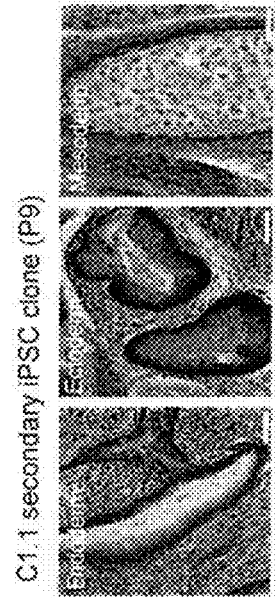
FIG. 54G
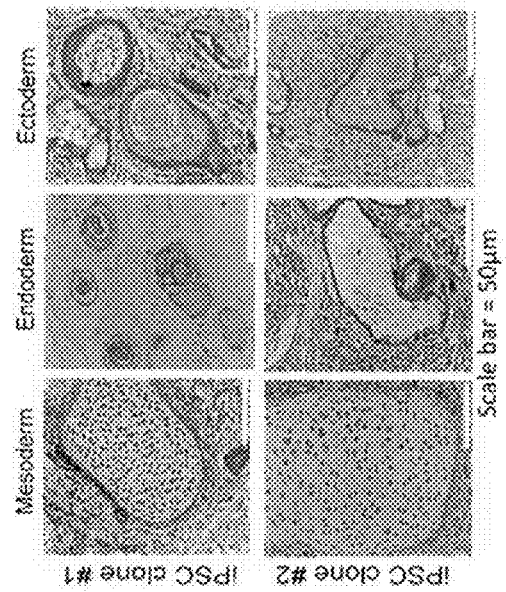
FIG. 54E
FIG. 54F

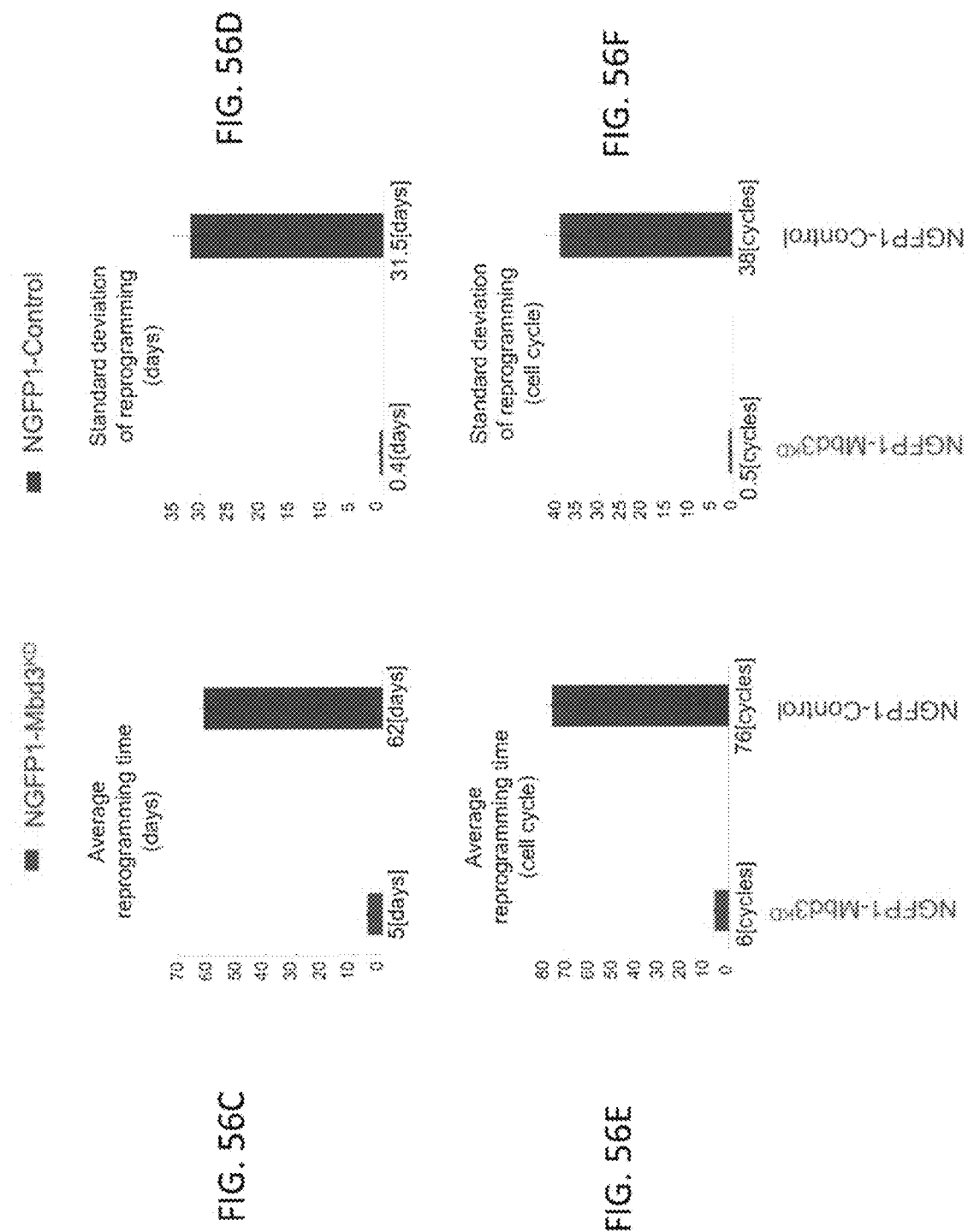

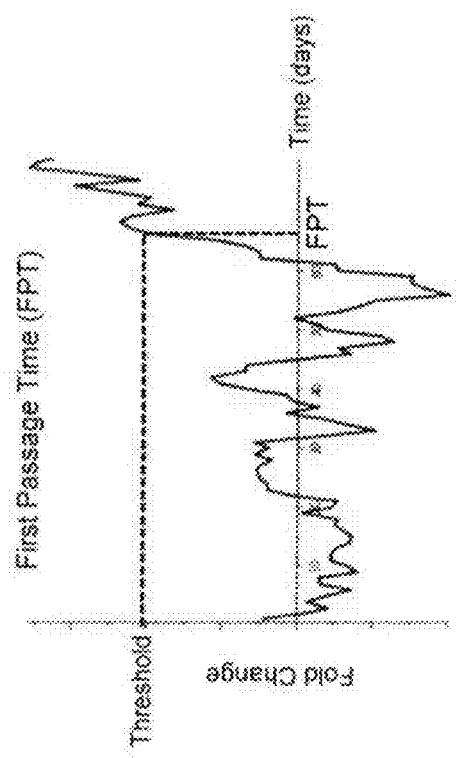
FIG. 57C
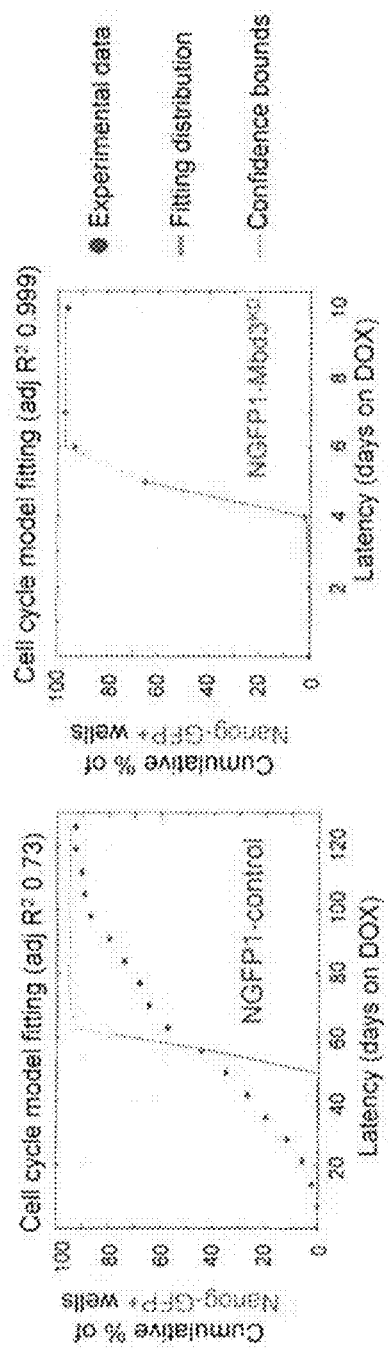
FIG. 57E
FIG. 57D

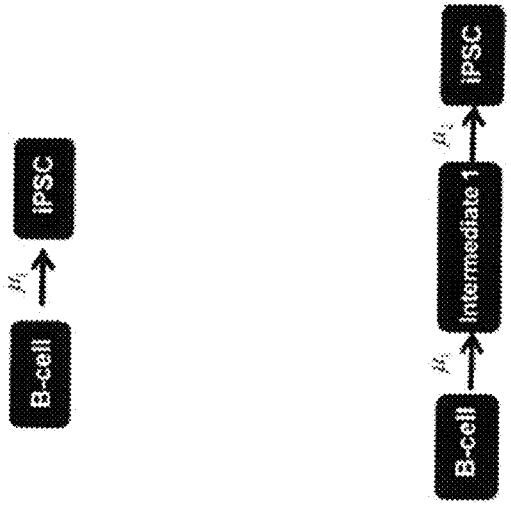
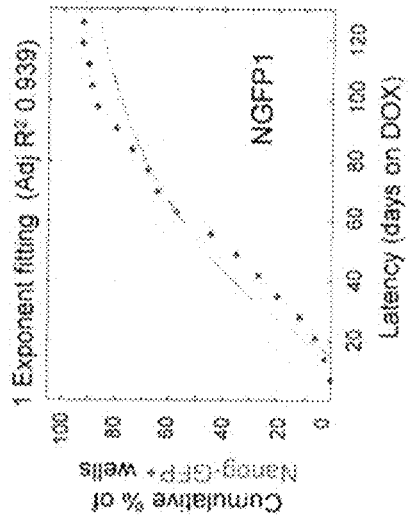
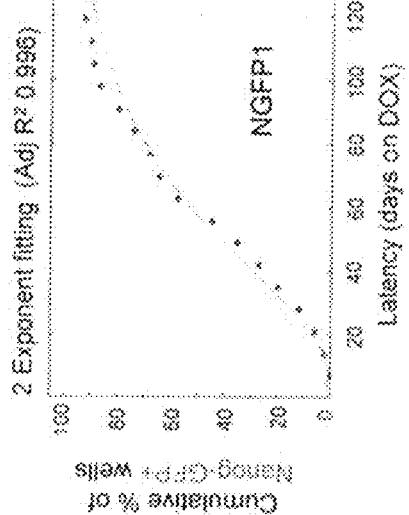
FIG. 58A
FIG. 58B

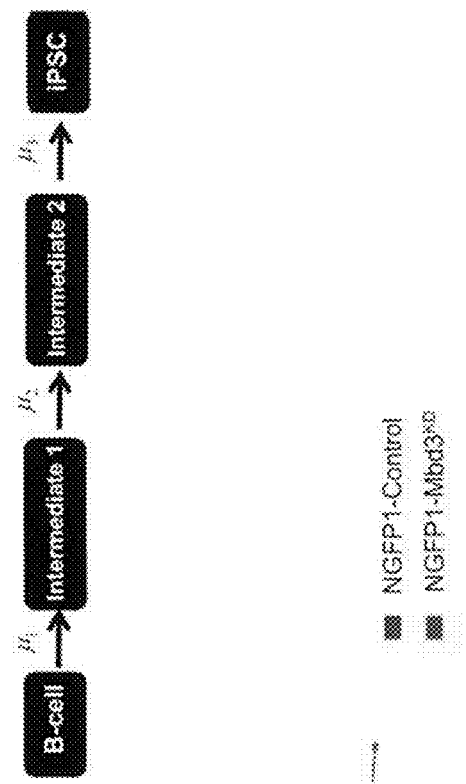
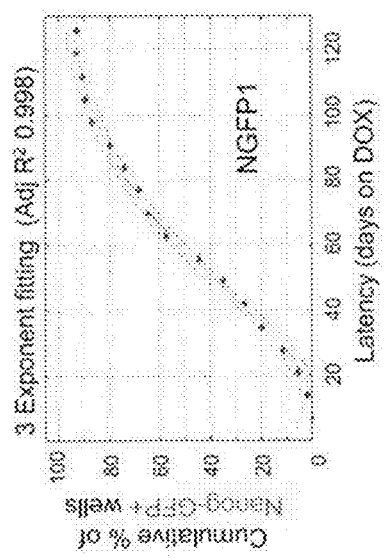
FIG. 58C
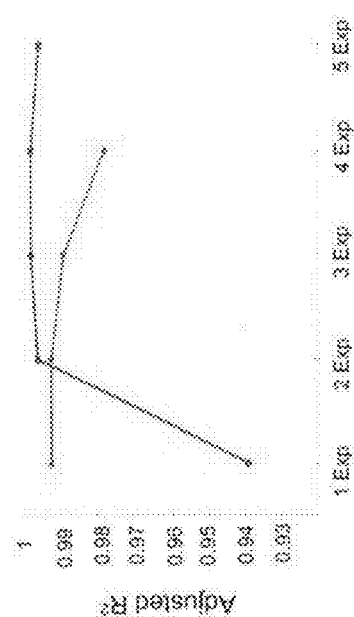
FIG. 58D

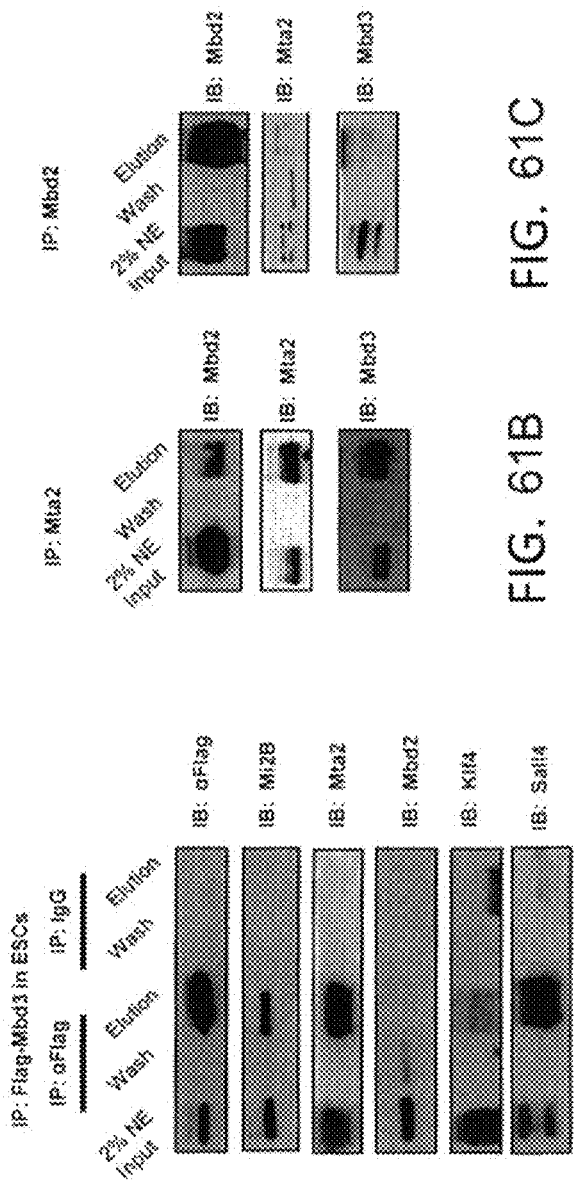

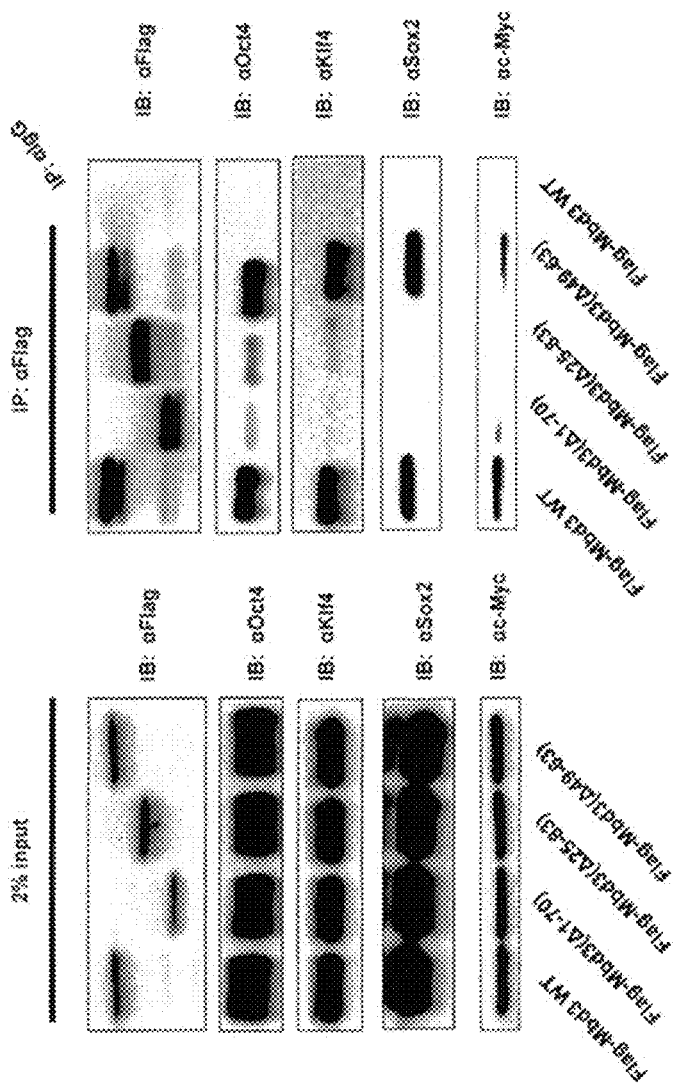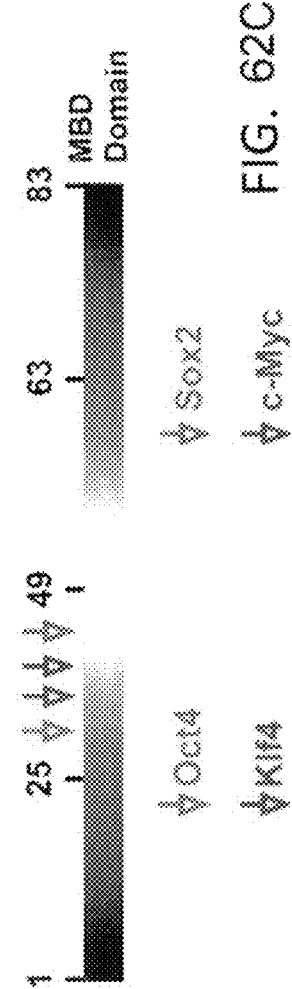

Motifs in Mbd3 bound regions following OSKM induction

| Factor | Z score | P-value |
|---|---|---|
| Smad2/3 | -20.7289 | 1.00E-30 |
| Pou5f1 | -20.646 | 1.00E-30 |
| Klf1 | -18.7681 | 1.00E-30 |
| Sox2 | -18.1417 | 1.00E-30 |
| Klf4 | -18.0815 | 1.00E-30 |
| Klf7 | -14.6281 | 1.00E-30 |
| Rxra | -8.8792 | 3.37E-19 |
| Zfp281 | -7.90E+00 | 1.35E-15 |
| Nr2f2 | -7.6746 | 8.30E-15 |
| Rara | -7.2955 | 1.49E-13 |
| Sox11 | -7.1281 | 5.09E-13 |
| Nr5a2 | -6.7859 | 5.77E-12 |
| Nr1d2 | -6.6024 | 2.02E-11 |
| Sox30 | -5.1197 | 1.53E-07 |
| Rela | -4.7827 | 8.65E-07 |
| Ctcf | -4.7463 | 0.000001036 |
| Zic3 | -4.6215 | 1.9045E-06 |
| Zfp423 | -4.6082 | 2.0304E-06 |
| LMO2,Lmo2 | -4.03E+00 | 0.000028302 |
| Egr2 | -3.8483 | 0.000059459 |
| Sox15 | -3.7769 | 0.000079394 |
| Zfp740 | -3.7689 | 0.000081987 |
| Tcfap2a | -3.7374 | 0.000092951 |
| Tcfap2c | -3.5205 | 0.00021537 |
| Ppara | -3.39E+00 | 0.00034913 |
| Sox12 | -3.2536 | 0.00056986 |
| Tcfap2b | -3.2505 | 0.00057604 |
| Zfp161 | -5.6591 | 7.61E-09 |
| Zscan10 | -3.6055 | 0.00015575 |
| Zfp161 | -3.1773 | 0.00074322 |

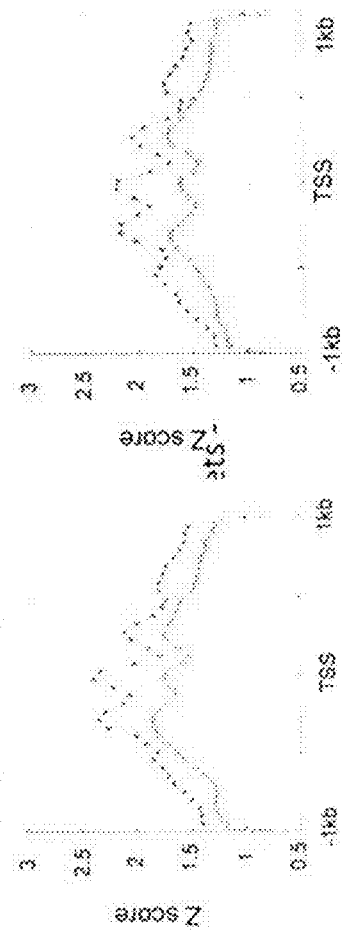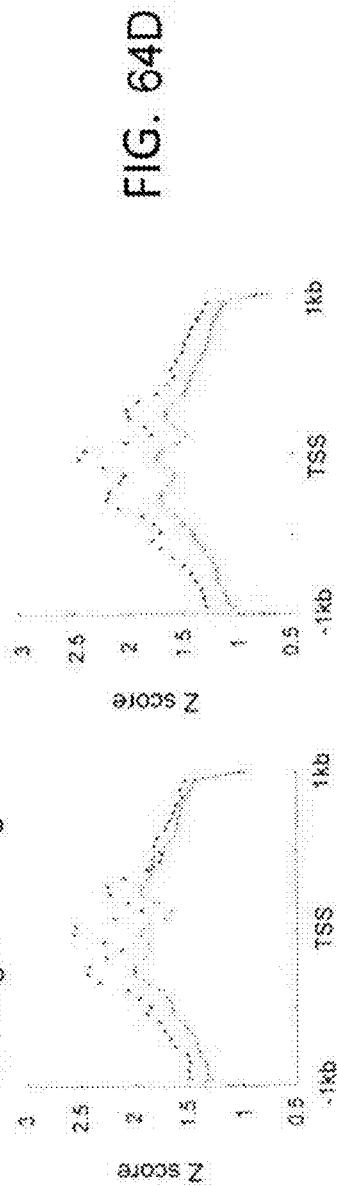

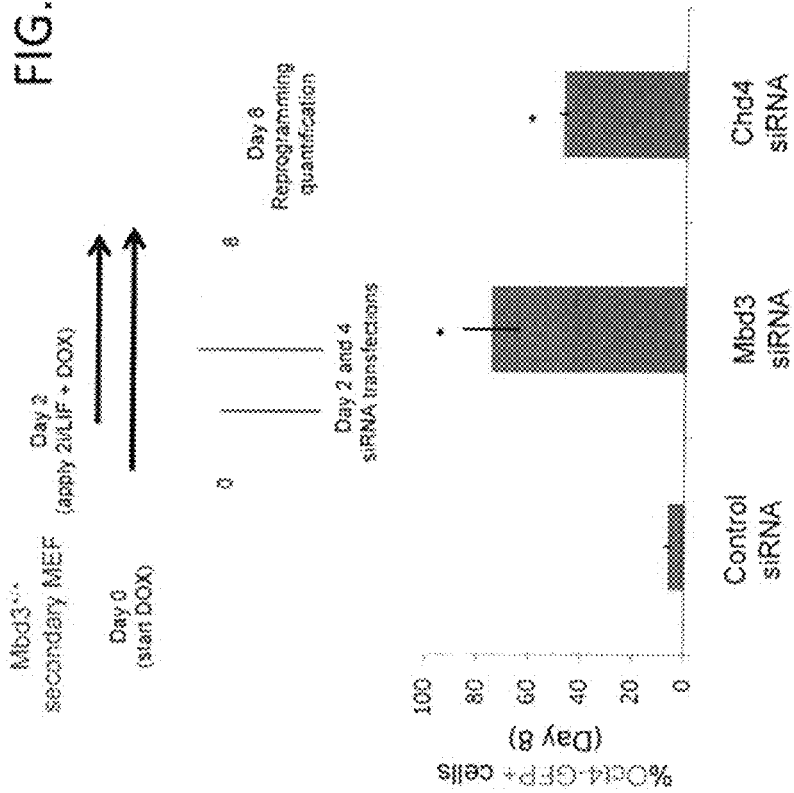
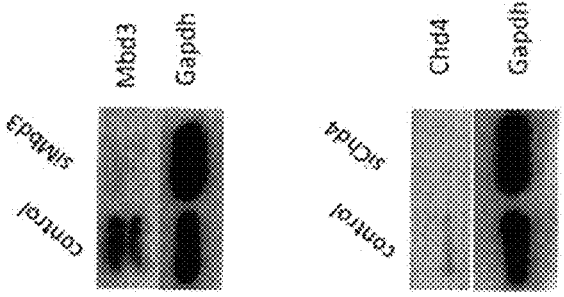
FIG. 64G
FIG. 64H
FIG. 64E
FIG. 64F

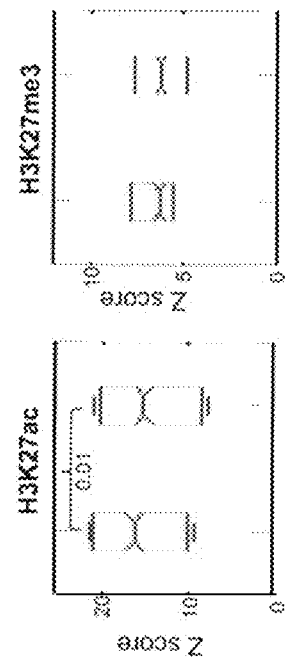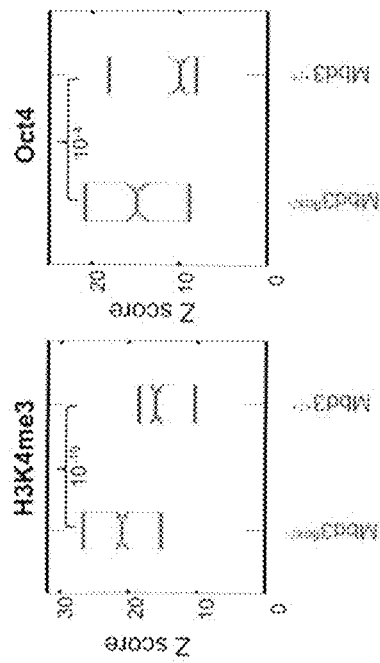

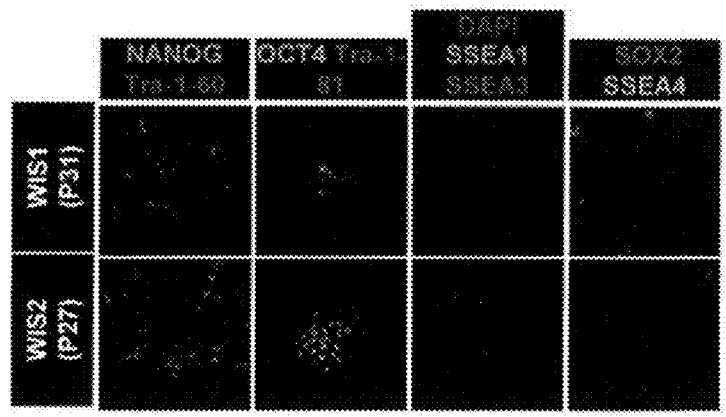
FIG. 68A
FIG. 68B
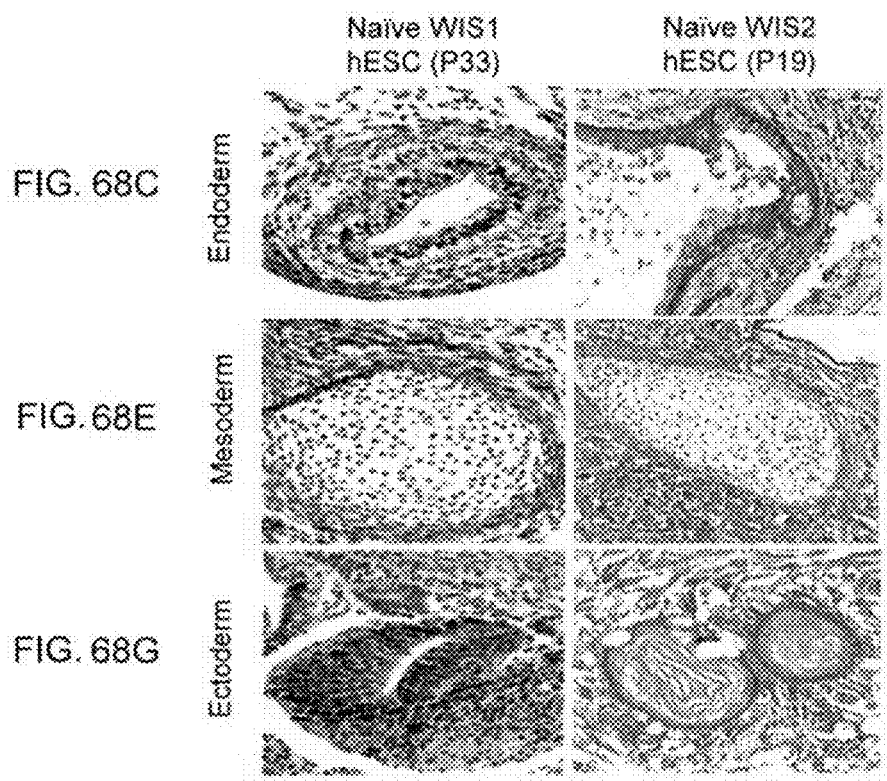
FIG. 68C
FIG. 68D
FIG. 68E
FIG. 68F
FIG. 68G
FIG. 68H

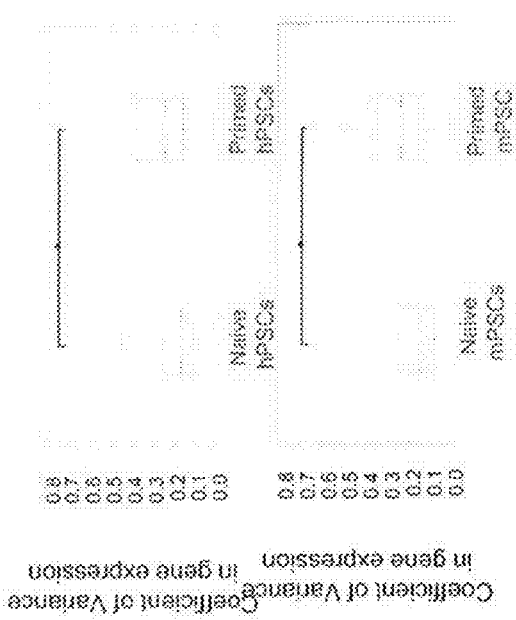
FIG. 69C
FIG. 69D
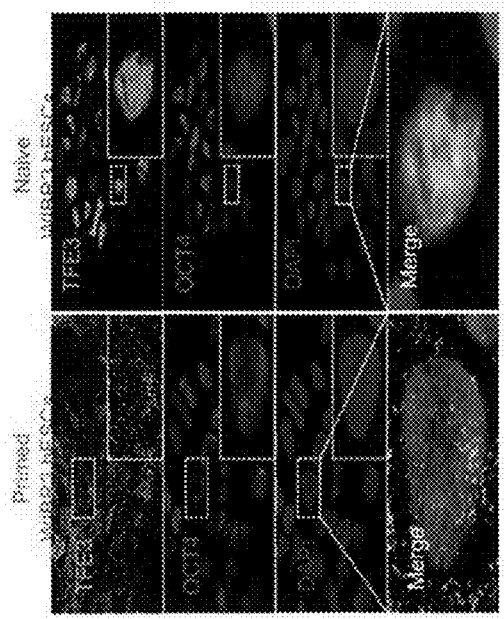
FIG. 69E
FIG. 69F

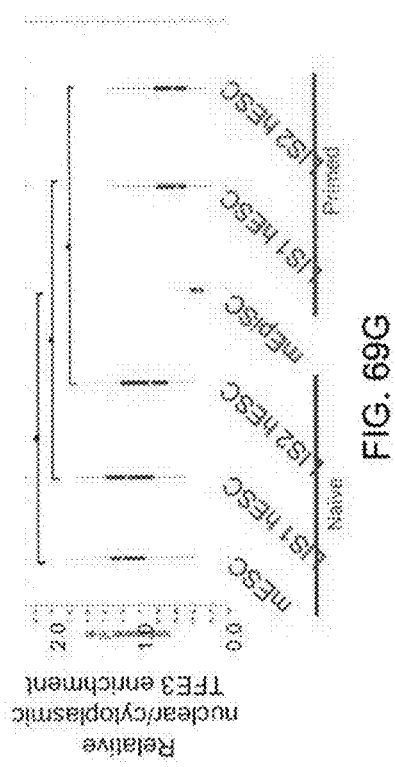
FIG. 69G
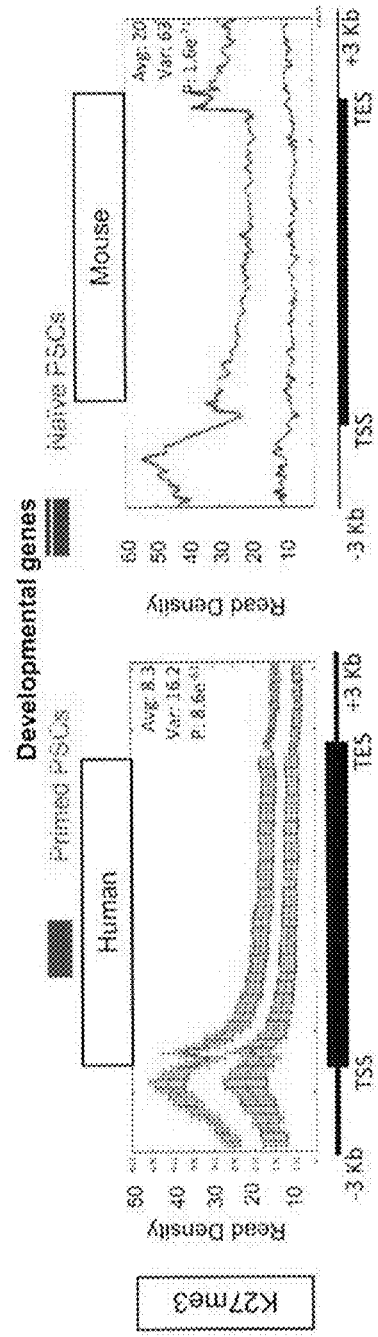
FIG. 70B
FIG. 70A

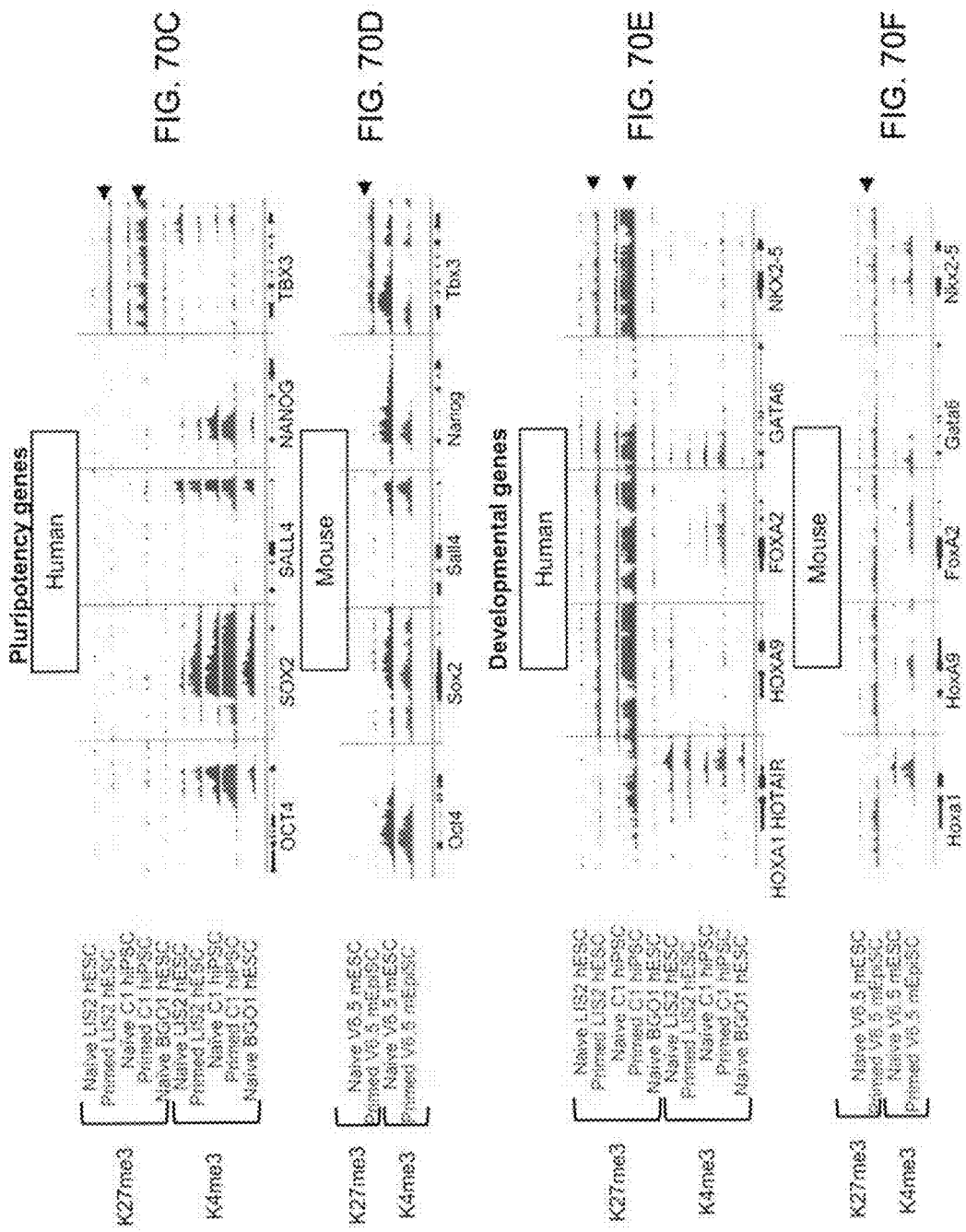

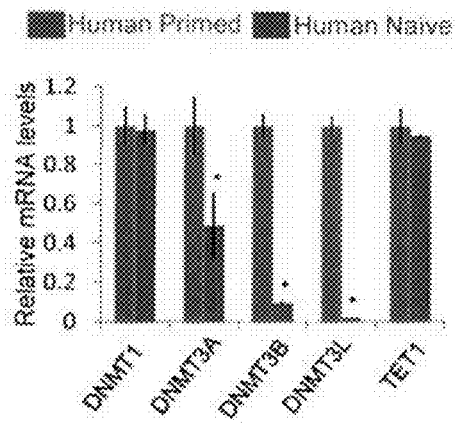
FIG. 70G
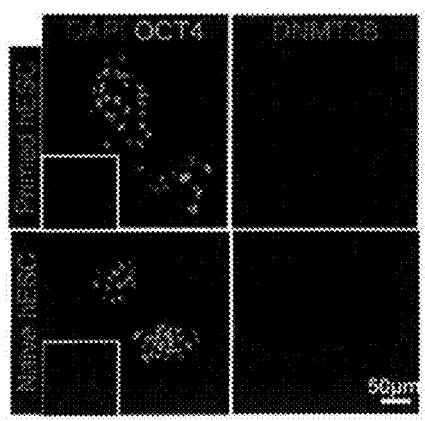
FIG. 70H
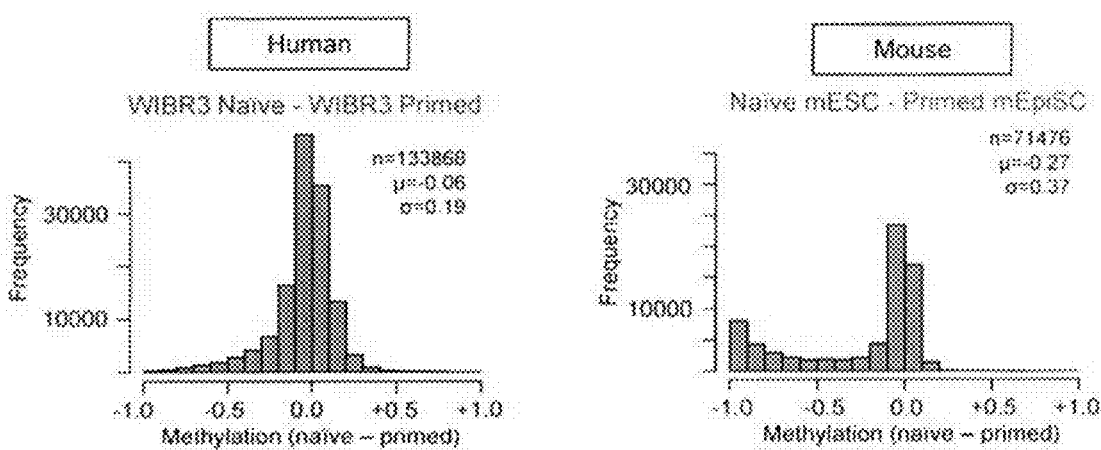
FIG. 70I
FIG. 70J

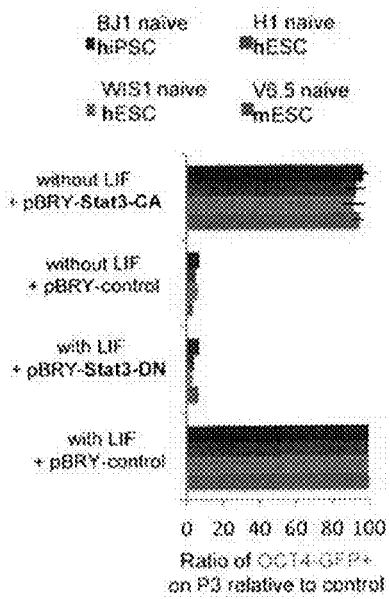
FIG. 71A
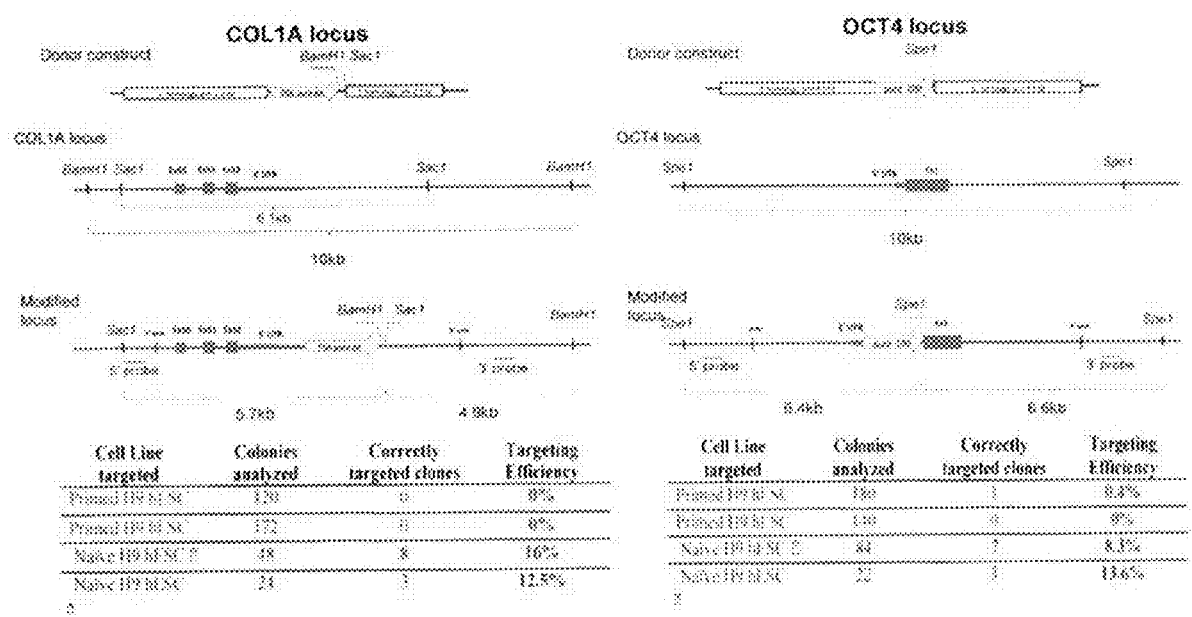
FIG. 71B
FIG. 71C

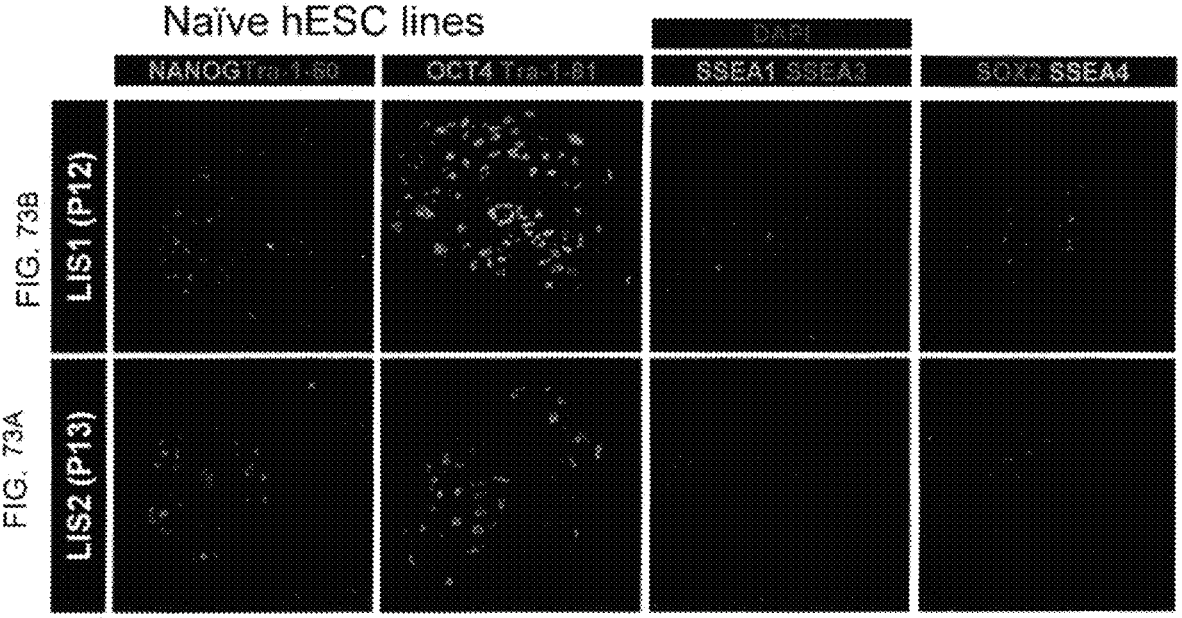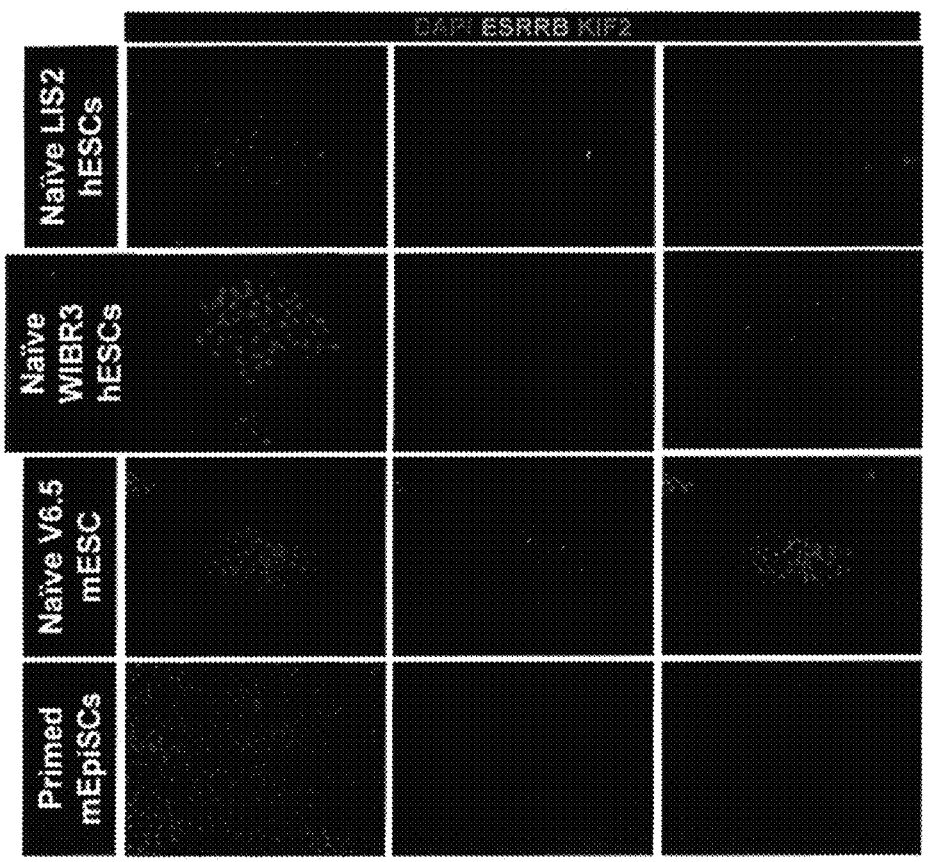

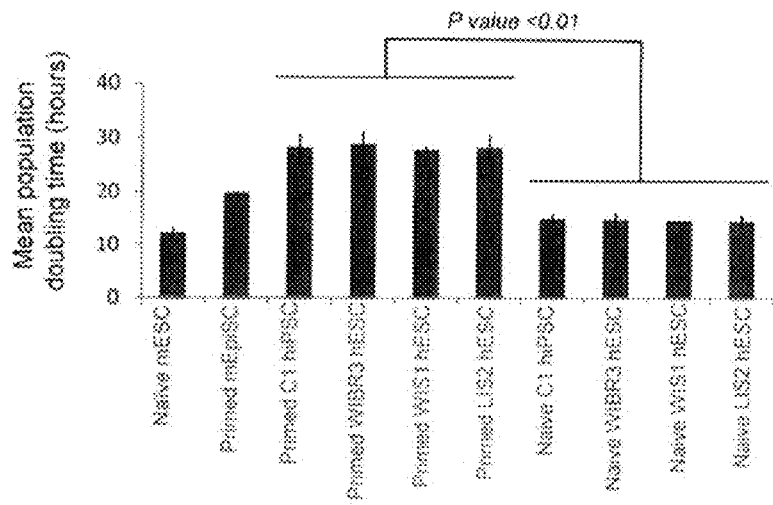
FIG. 74A
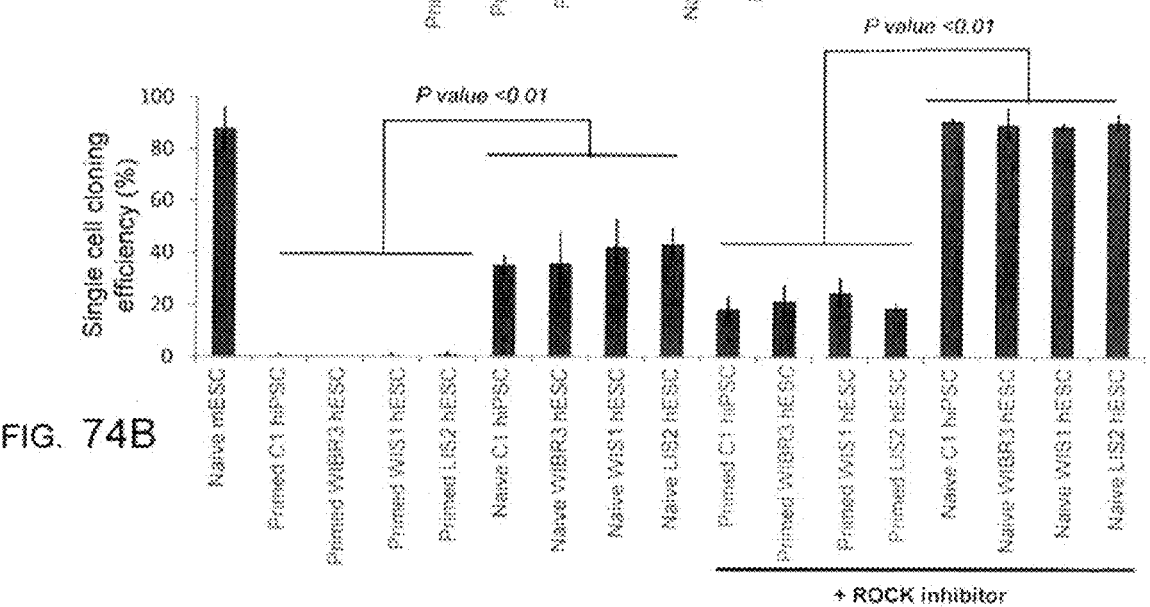
FIG. 74B
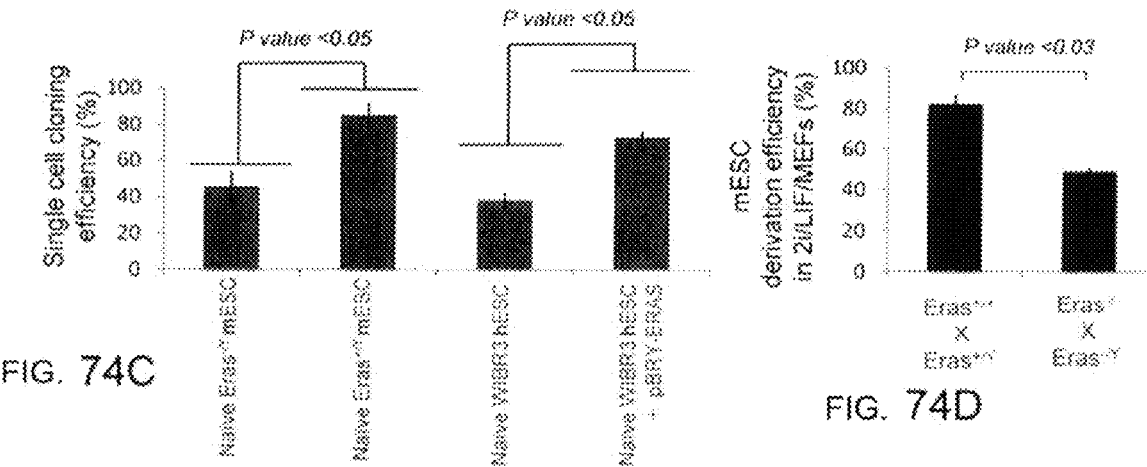
FIG. 74C
FIG. 74D

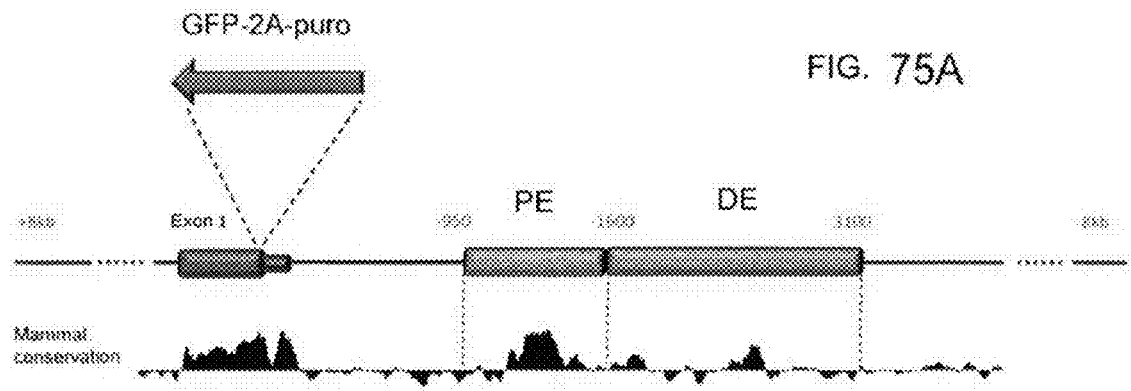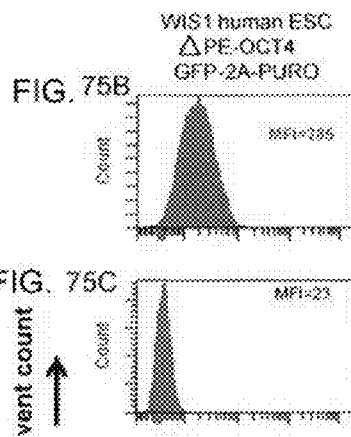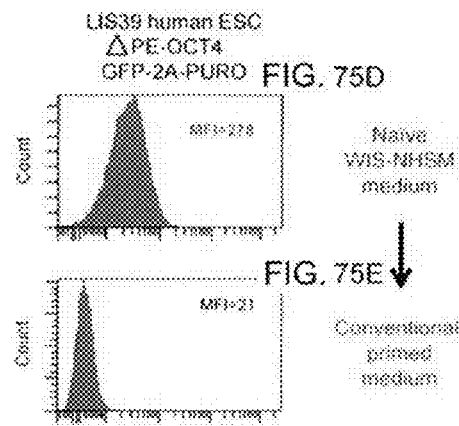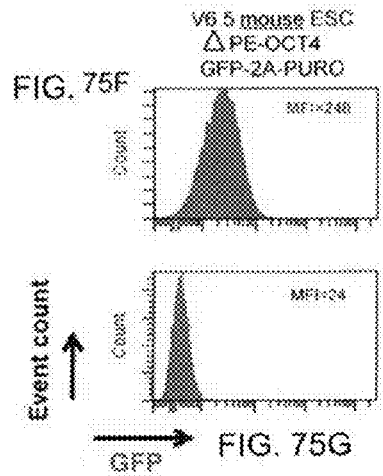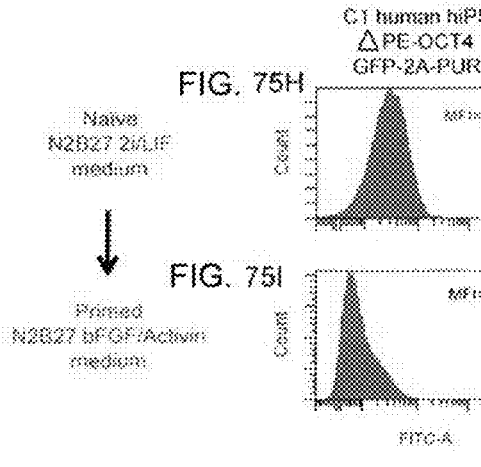

FIG. 80A
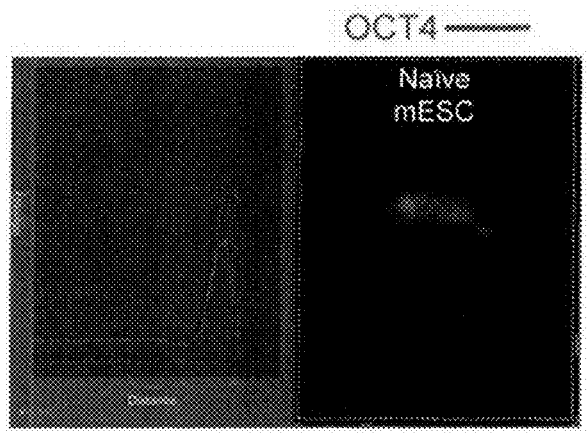
FIG. 80B
FIG. 80C
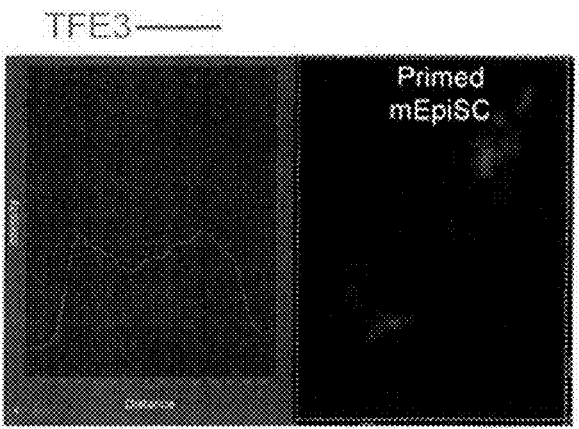
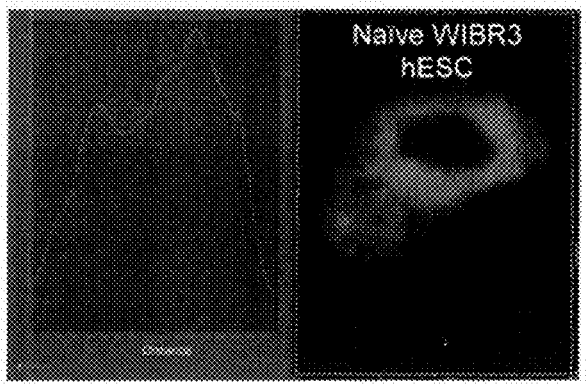
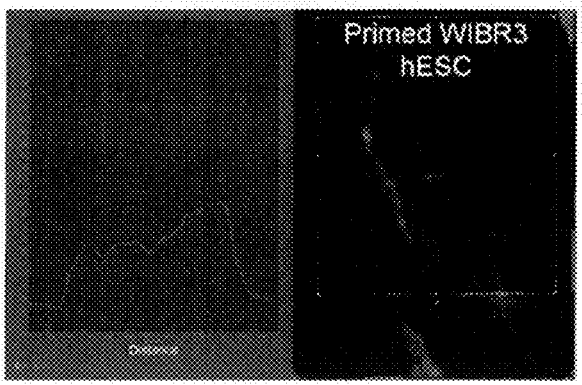
FIG. 80D

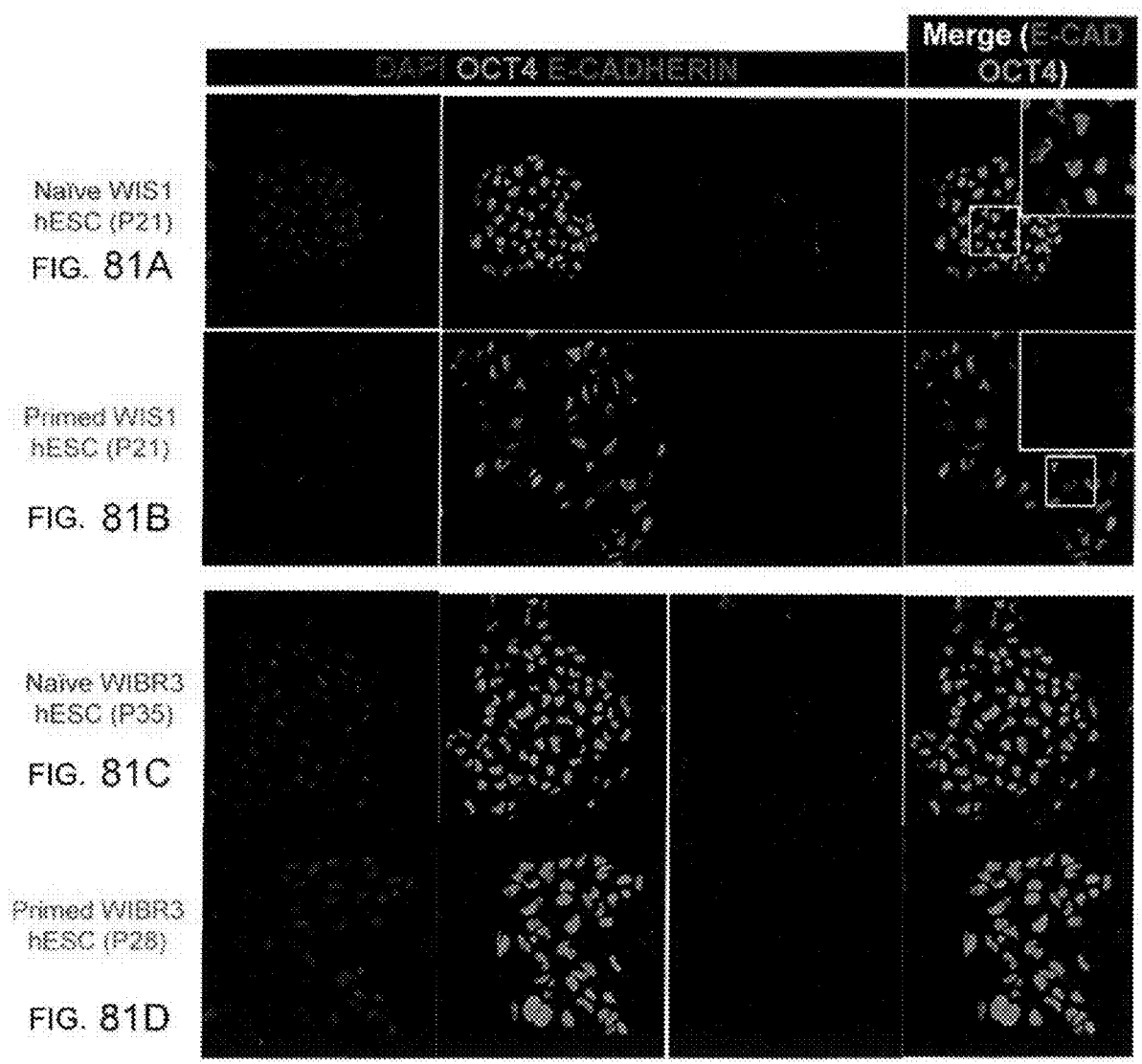
FIG. 81A Naive WIS1 hESC (P21)
FIG. 81B Primed WIS1 hESC (P21)
FIG. 81C Naive WIBR3 hESC (P35)
FIG. 81D Primed WIBR3 hESC (P28)

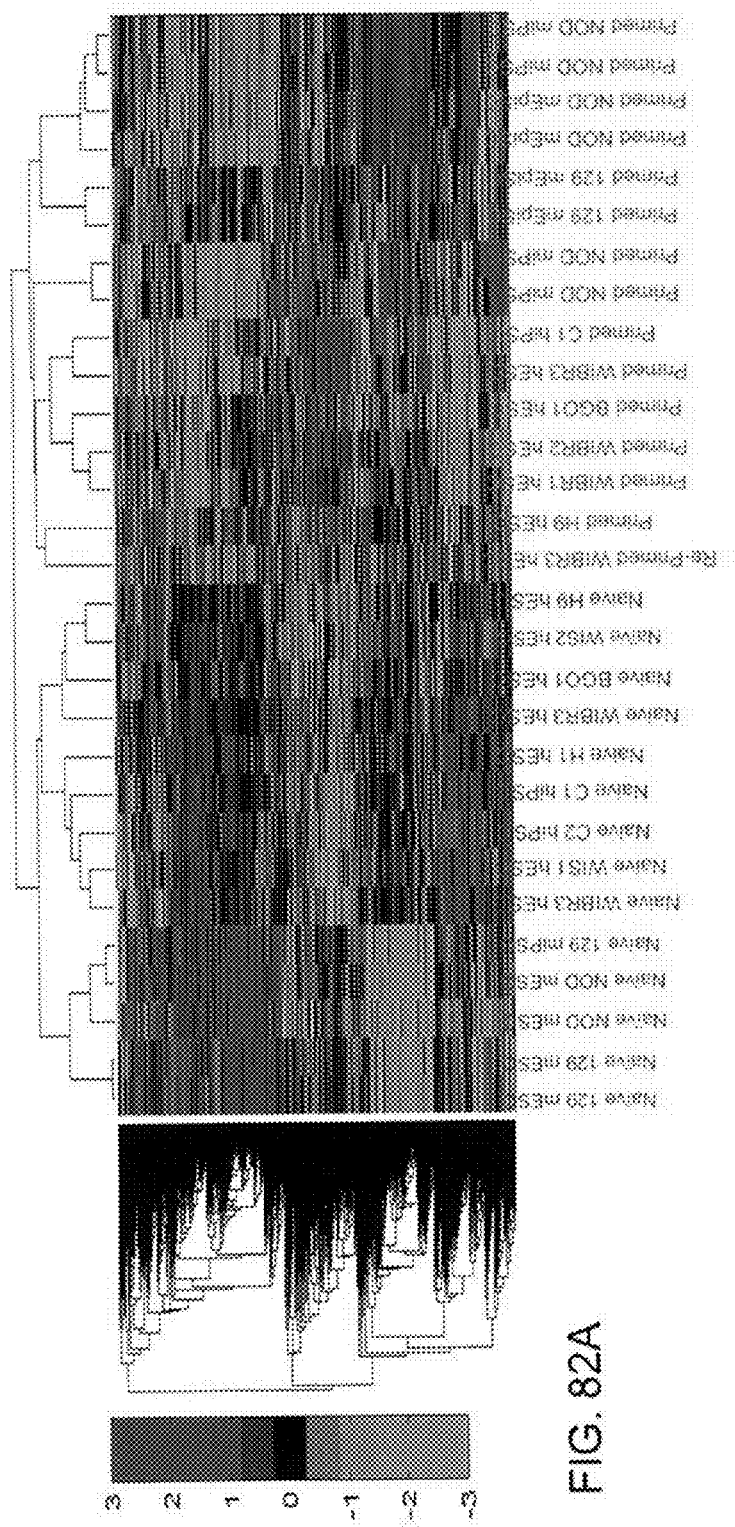
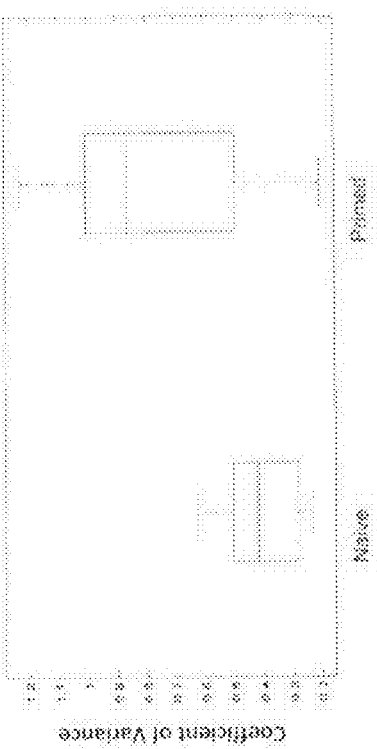
FIG. 82A
FIG. 82B

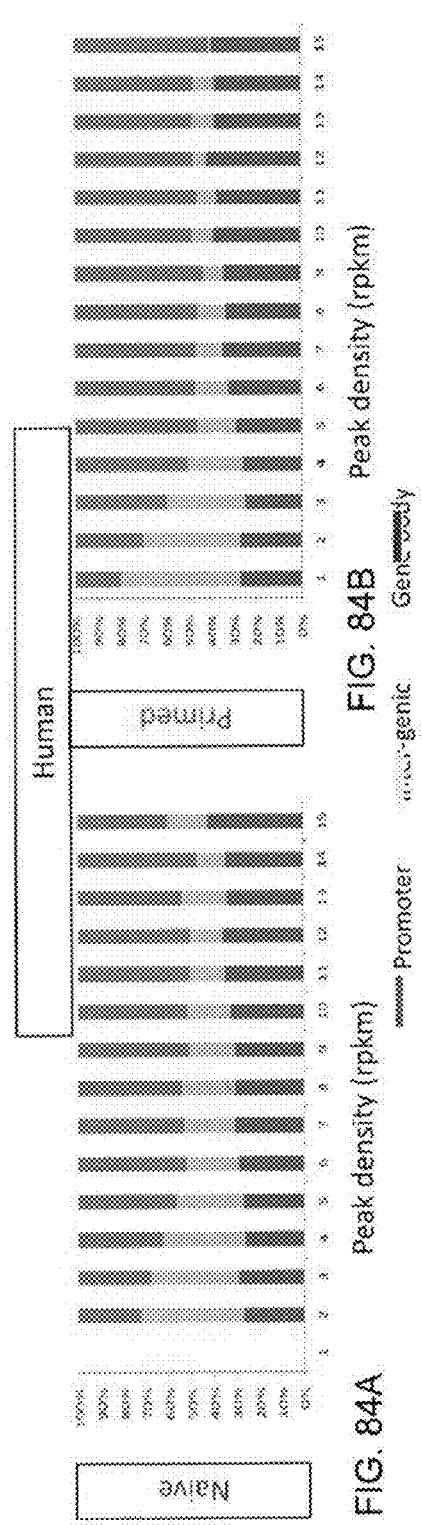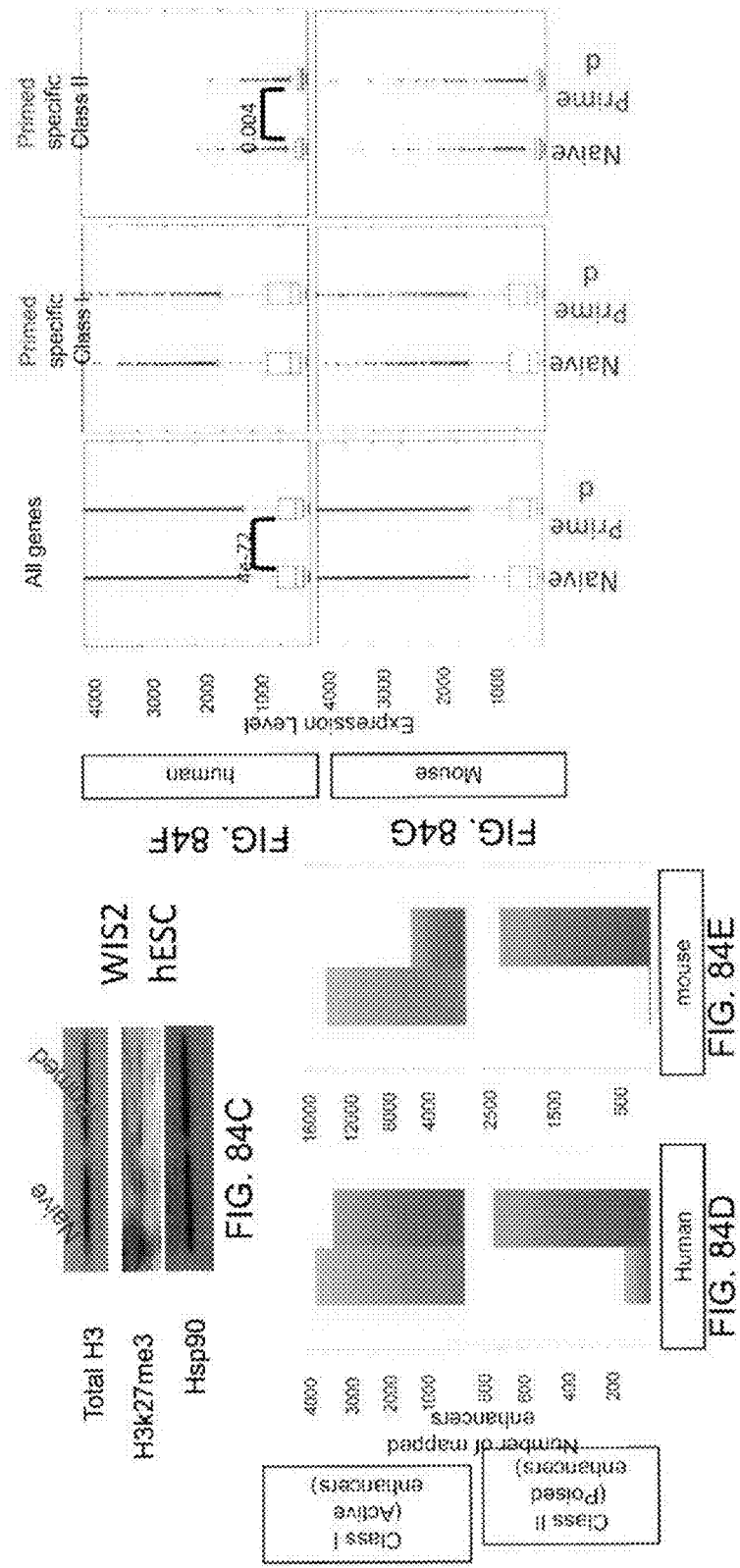

FIG. 85A

Condition 1: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)

Condition 7: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)
+BMPi (LDN-193189 0.5μM)

Condition 8: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)
+NOTCHi (DBZ 2μM)

Condition 9: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)
+BMPi (LDN-193189 0.5μM)
+NOTCHi (DBZ 2μM)

Condition 10: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)
+ BMPi (LDN-193189 0.5μM)
+ NOTCHi (DBZ 2μM)
+ IGFII (20ng/ml)

Condition 11: WIS-NHSM

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
ROCKi (Y27632 5μM)
+ BMPi (LDN-193189 0.5μM)
+ NOTCHi (DBZ 2μM)
+ SHHi (RU-SKI-43 5μM)

Condition 12: WIS-NHSM
(TGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFRi (SB432541 2μM)
ROCKi (Y27632 5μM)
+ BMPi (LDN-193189 0.5μM)
+ NOTCHi (DBZ 2μM)

Condition 13: WIS-NHSM
(FGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFβ1 (2 ng/ml)
FGFRi (PD173471 0.1μM)
ROCKi (Y27632 5μM)
+ BMPi (LDN-193189 0.5μM)
+ NOTCHi (DBZ 2μM)
+ IGFII (20ng/ml)
+ SCF 10ng/ml

Condition 14: WIS-NHSM
(TGFR+FGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
FGFRi (PD173471 0.1μM)
TGFRi (SB432541 2μM)
ROCKi (Y27632 5μM)
+ BMPi (LDN-193189 0.5μM)
+ NOTCHi (DBZ 2μM)
+ IGFII (20ng/ml)
+ SCF 10ng/ml

Condition 15: WIS-NHSM
(TGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
FGF2 (16 ng/ml)
TGFRi (SB432541 2μM)
ROCKi (Y27632 5μM)
+ BMPi (LDN-193189 0.5μM)
+ NOTCHi (DBZ 2μM)
+ SHHi (RU-SKI-43 5μM)

Condition 16: WIS-NHSM
(FGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
TGFβ1 (2 ng/ml)
FGFRi (PD173471 0.1μM)
ROCKi (Y27632 5μM)
+ BMPi (LDN-193189 0.5μM)
+ NOTCHi (DBZ 2μM)
+ IGFII (20ng/ml)
+ SCF 10ng/ml
+ SHHi (RU-SKI-43 5μM)

Condition 17: WIS-NHSM
(TGFR+FGFR pathway inhibition)

LIF (20ng/ml)
ERK1/2i (PD0325901 1μM)
GSK3βi (CHIR99021 3μM)
JNKi (SP600125 5μM)
P38i (BIRB796 2μM)
FGFRi (PD173471 0.1μM)
TGFRi (SB432541 2μM)
ROCKi (Y27632 5μM)
+ BMPi (LDN-193189 0.5μM)
+ NOTCHi (DBZ 2μM)
+ IGFII (20ng/ml)
+ SCF 10ng/ml
+ SHHi (RU-SKI-43 5μM)

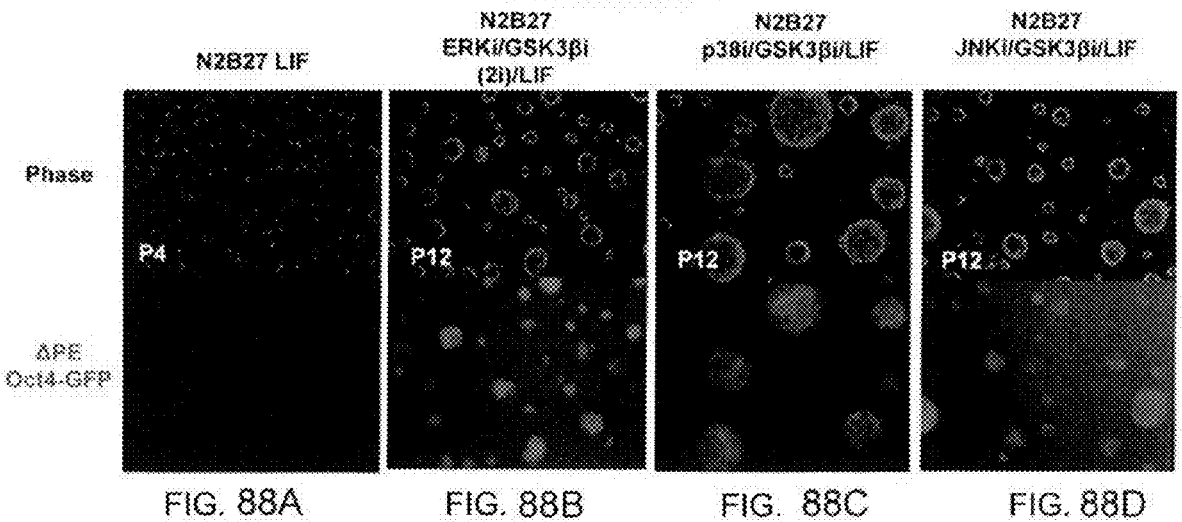
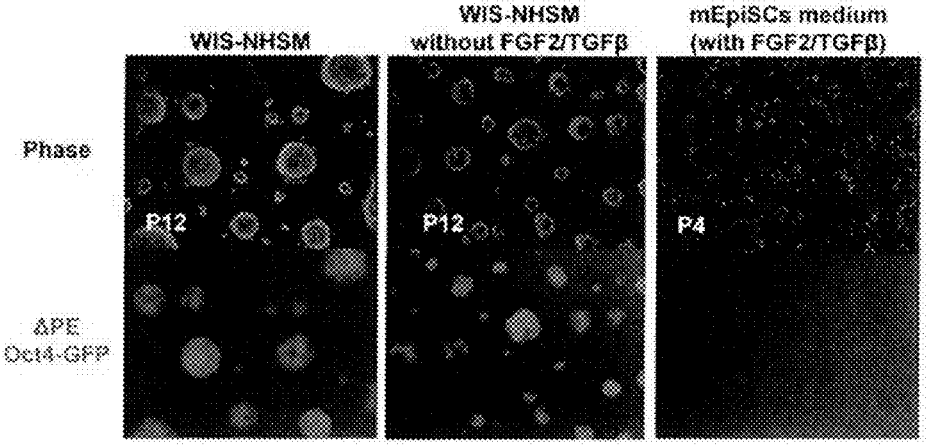
FIG. 88A  FIG. 88B  FIG. 88C  FIG. 88D  FIG. 88E  FIG. 88F  FIG. 88G  FIG. 88H  FIG. 88I  FIG. 88J FIG. 89A
| Medium | Injected embryos | Recipient females | Dead fetuses and pups | Pups born alive | Fostered pups |
|---|---|---|---|---|---|
| N2B27 2i/LIF | 150 | 7 | 1 | 9 | 7 |
| N2B27 p38i/GSK3βi, LIF | 160 | 8 | 3 | 6 | 4 |
| N2B27 JNKi/GSK3βi, LIF | 145 | 7 | 1 | 10 | 6 |
| WIS-NHSM | 150 | 7 | 2 | 12 | 7 |
| WIS-NHSM (without FGF2/TGFβ) | 135 | 6 | 3 | 8 | 4 |
V6.5 ESC in WIS-NHSM
FIG. 89B
V6.5 ESC in WIS-NHSM (without FGF2/TGFβ)
FIG. 89C

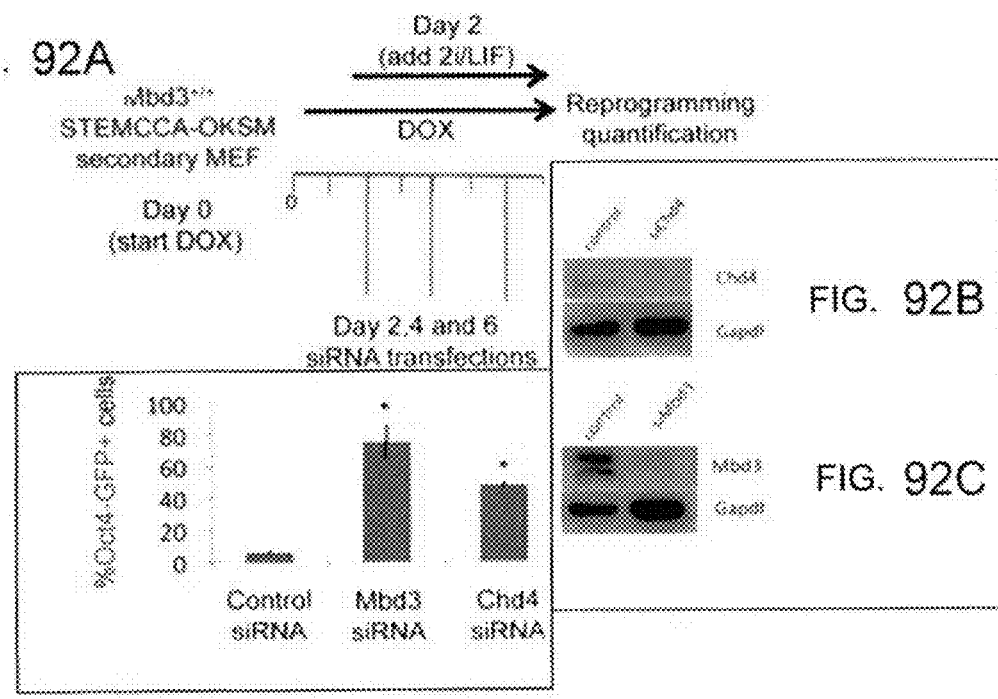
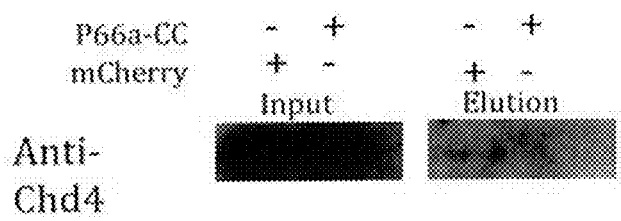

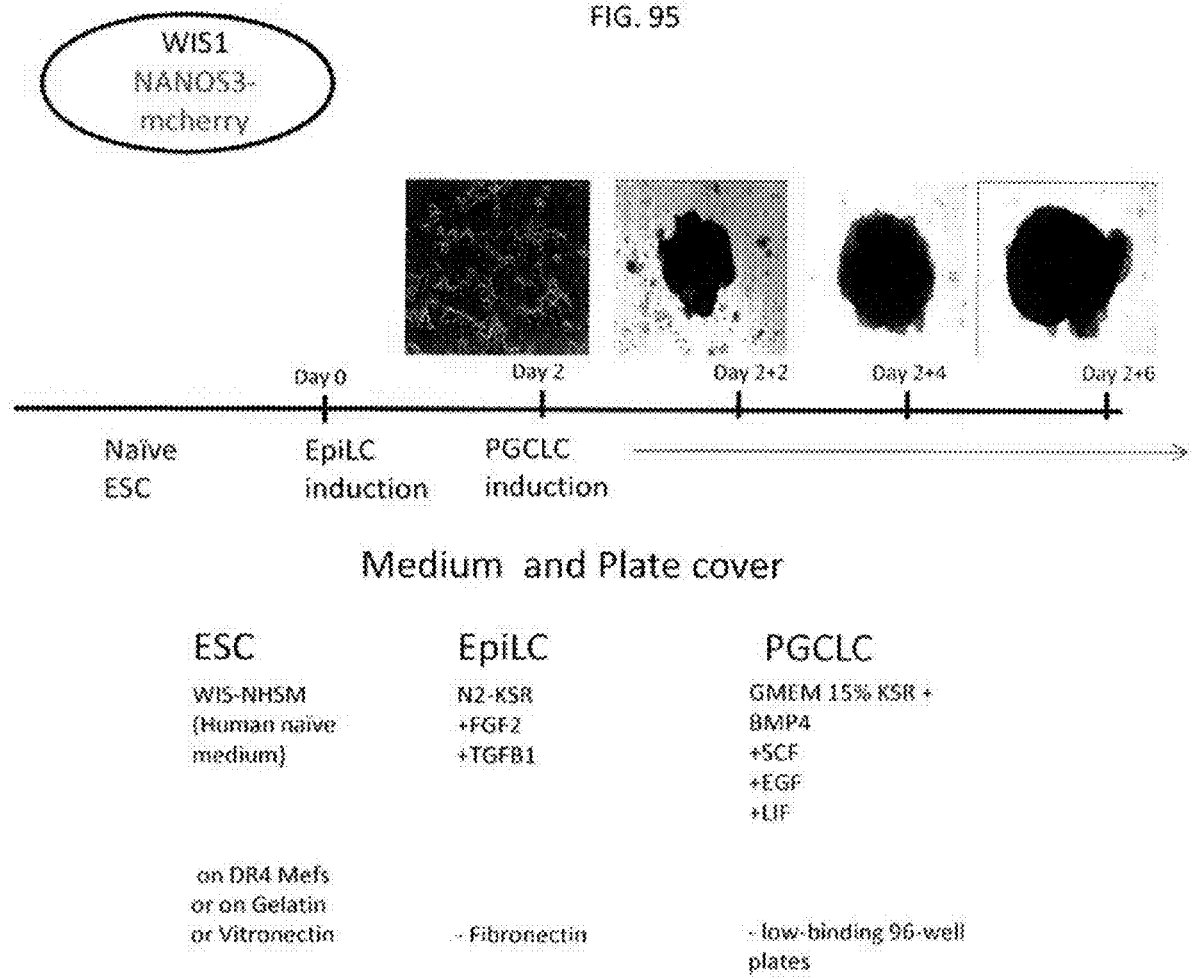

FIG. 96A
Human ESC differentiation to PGC – Nanos3-cherry
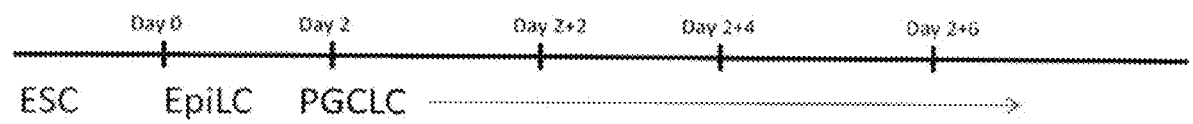
FIG. 96B  
Naïve ESC
FIG. 96C  
Primed EpiLC
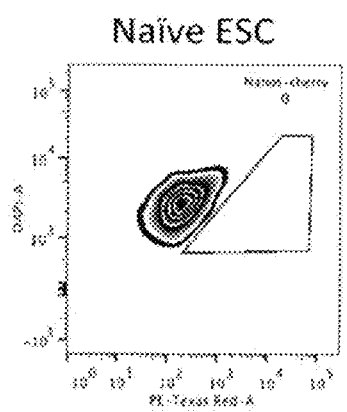
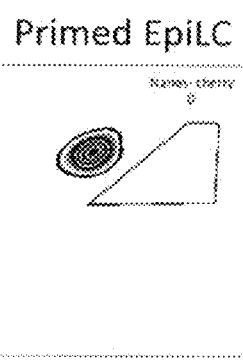
Day 2+2  
FIG. 96D
Day 2+4  
FIG. 96E
Day 2+6  
FIG. 96F
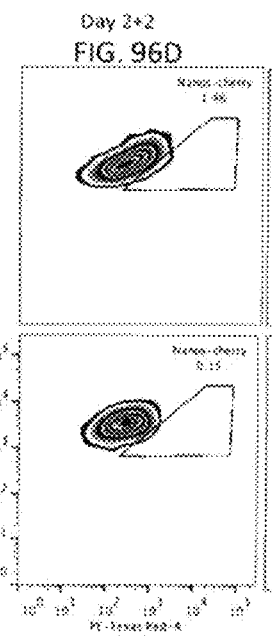
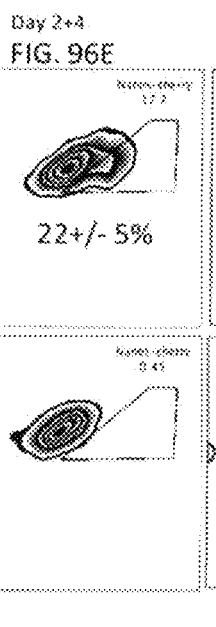
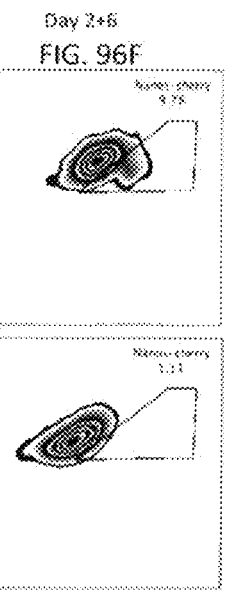
22+/- 5%
FIG. 96G   FIG. 96H   FIG. 96I

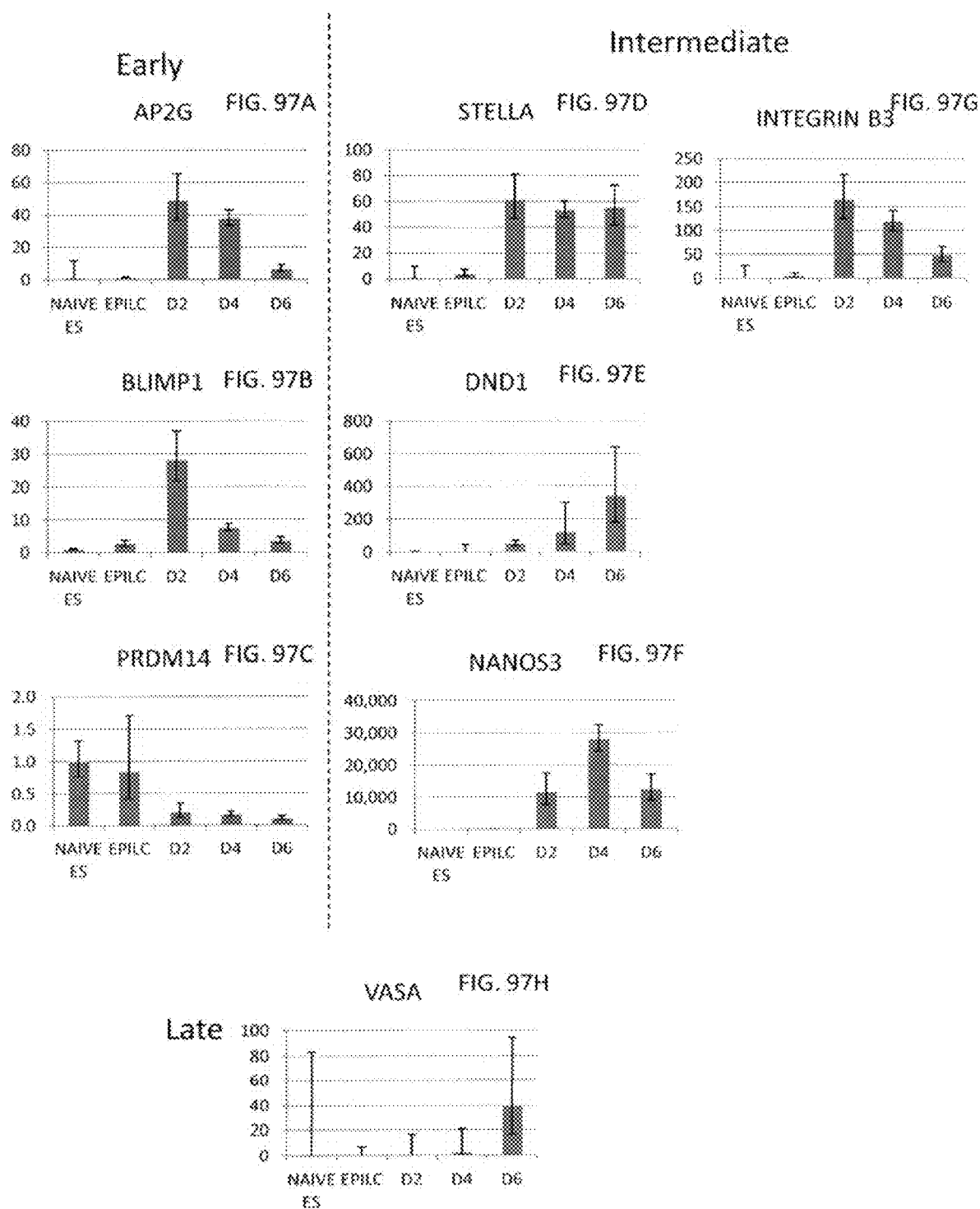

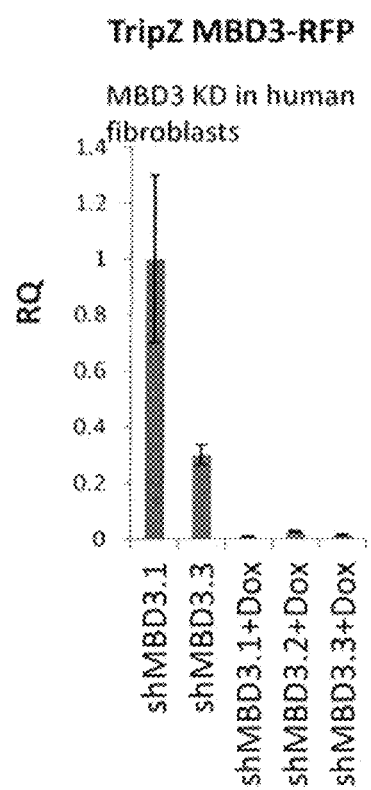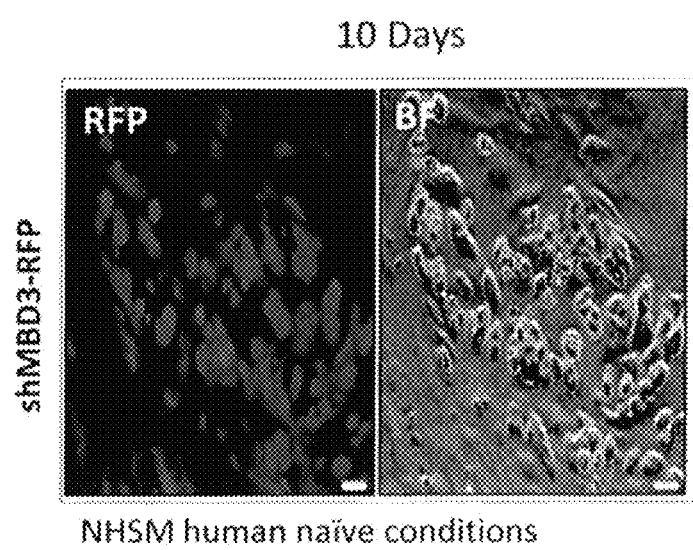
FIG. 99A
FIG. 99B   FIG. 99C

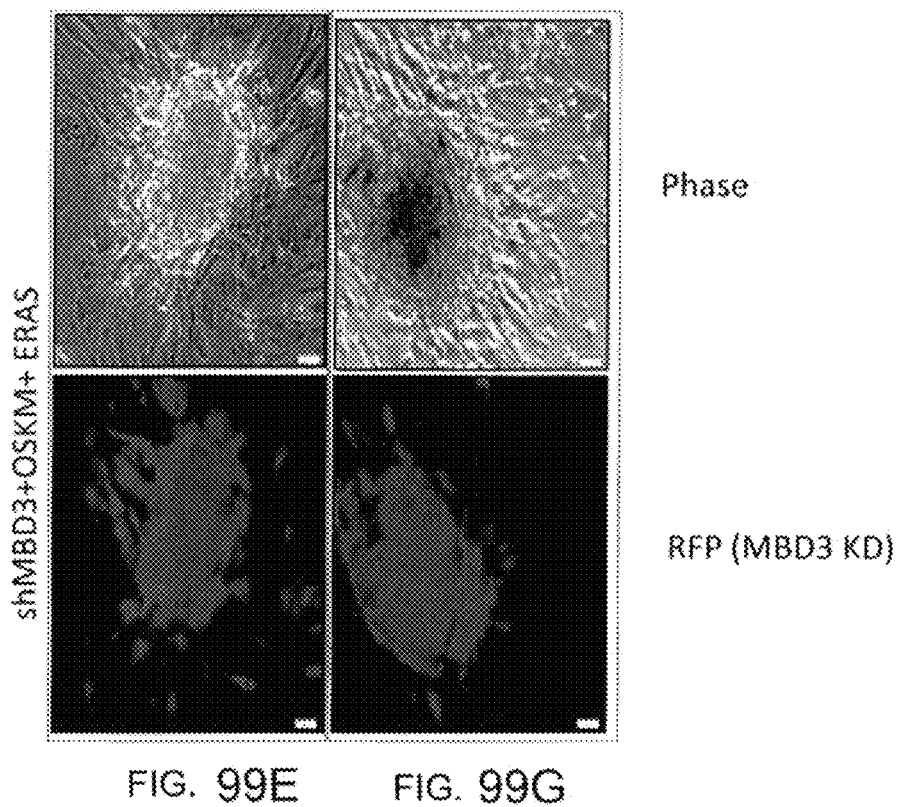

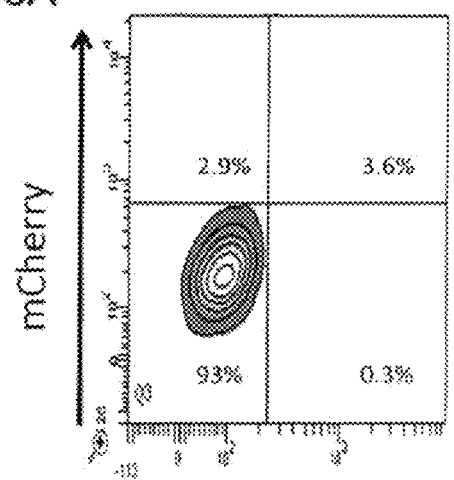
FIG. 106A Naïve human ESC
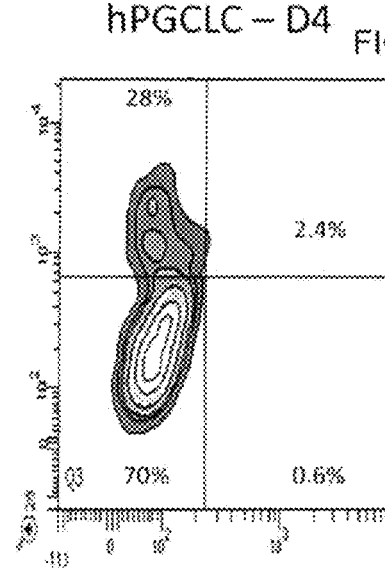
FIG. 106C hPGCLC – D4
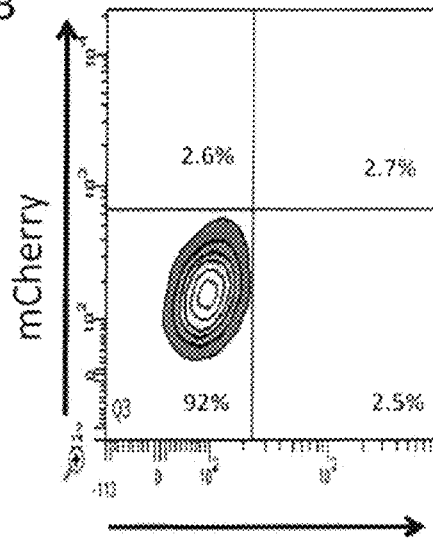
FIG. 106B
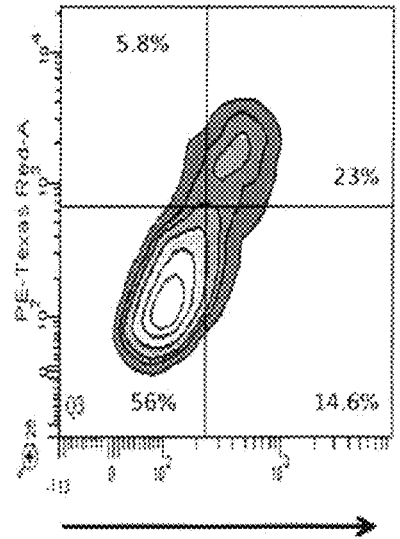
FIG. 106D

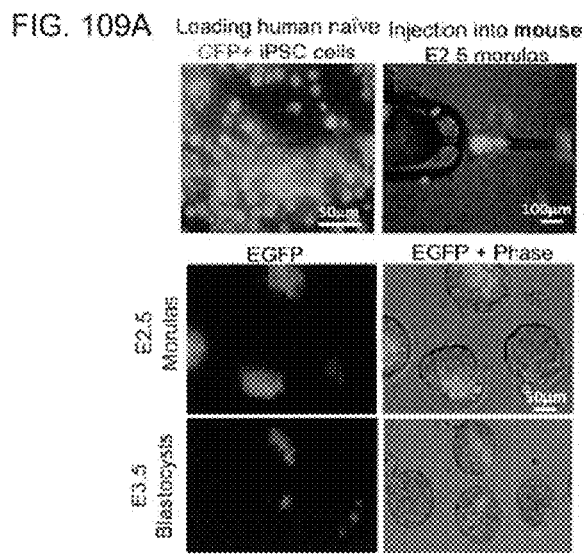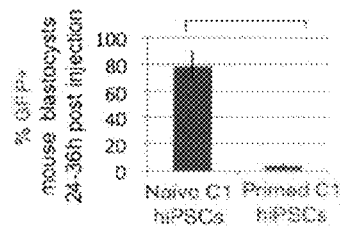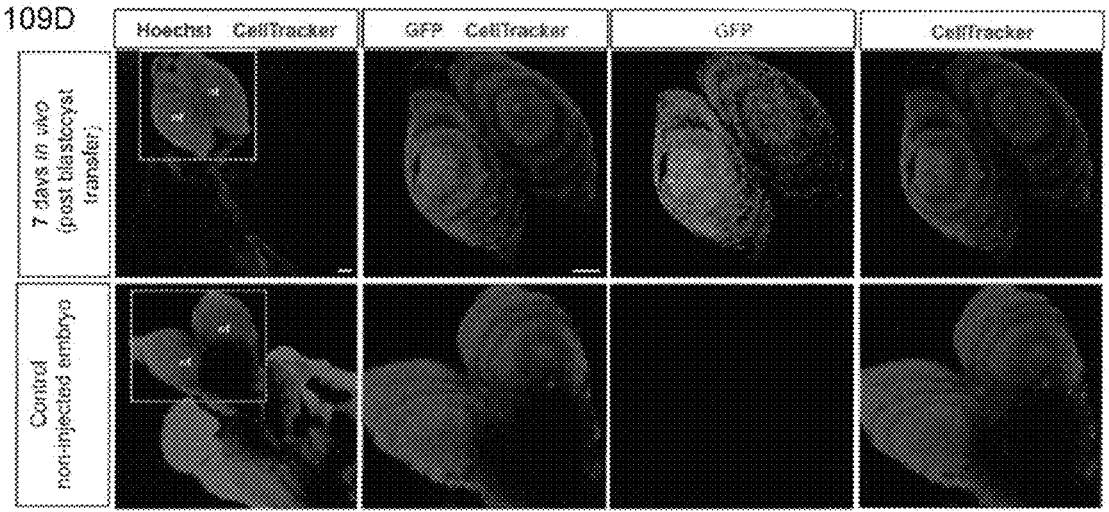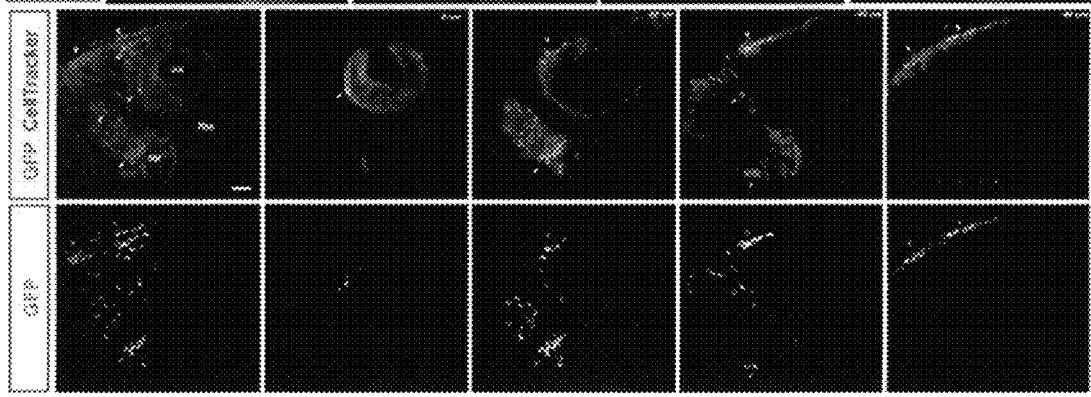

SEQUENCE LISTING

<160> NUMBER OF SEQ ID NOS: 123

<210> SEQ ID NO 1
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 1
ggtaccggat actcaggcca ggcccagaaa                30

```
<210> SEQ ID NO 2
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 2
ctcgagtcca cagacctctg gcact                                           25

<210> SEQ ID NO 3
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 3
ggtacccatt gagtccaaat cctctttact aggtg                                35

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4
ctcgagctga ggctcatgct gctgg                                           25

<210> SEQ ID NO 5
<211> LENGTH: 605
<212> TYPE: PRT
<213> ORGANISM: Homo sapiens

<400> SEQUENCE: 5
```

Met Ala Glu Asp Trp Leu Asp Cys Pro Ala Leu Gly Pro Gly Trp Lys
1               5                   10                  15

Arg Arg Glu Val Phe Arg Lys Ser Gly Ala Thr Cys Gly Arg Ser Asp
            20                  25                  30

Thr Tyr Tyr Gln Ser Pro Thr Gly Asp Arg Ile Arg Ser Lys Val Glu
        35                  40                  45

Leu Thr Arg Tyr Leu Gly Pro Ala Cys Asp Leu Thr Leu Phe Asp Phe
    50                  55                  60

Lys Gln Gly Ile Leu Cys Tyr Pro Ala Pro Lys Ala His Pro Val Ala
65                  70                  75                  80

Val Ala Ser Lys Lys Arg Lys Lys Pro Ser Arg Pro Ala Lys Thr Arg
                85                  90                  95

Lys Arg Gln Val Gly Pro Gln Ser Gly Glu Val Arg Lys Glu Ala Pro
            100                 105                 110

Arg Asp Glu Thr Lys Ala Asp Thr Asp Thr Ala Pro Ala Ser Phe Pro
        115                 120                 125

Ala Pro Gly Cys Cys Glu Asn Cys Gly Ile Ser Phe Ser Gly Asp Gly
    130                 135                 140

Thr Gln Arg Gln Arg Leu Lys Thr Leu Cys Lys Asp Cys Arg Ala Gln
145                 150                 155                 160

Arg Ile Ala Phe Asn Arg Glu Gln Arg Met Phe Lys Arg Val Gly Cys
                165                 170                 175

Gly Glu Cys Ala Ala Cys Gln Val Thr Glu Asp Cys Gly Ala Cys Ser
            180                 185                 190

```
Thr Cys Leu Leu Gln Leu Pro His Asp Val Ala Ser Gly Leu Phe Cys
            195                 200                 205

Lys Cys Glu Arg Arg Arg Cys Leu Arg Ile Val Glu Arg Ser Arg Gly
210                 215                 220

Cys Gly Val Cys Arg Gly Cys Gln Thr Gln Glu Asp Cys Gly His Cys
225                 230                 235                 240

Pro Ile Cys Leu Arg Pro Arg Pro Gly Leu Arg Arg Gln Trp Lys
                245                 250                 255

Cys Val Gln Arg Arg Cys Leu Arg Gly Lys His Ala Arg Arg Lys Gly
                260                 265                 270

Gly Cys Asp Ser Lys Met Ala Ala Arg Arg Pro Gly Ala Gln Pro
                275                 280                 285

Leu Pro Pro Pro Pro Ser Gln Ser Pro Glu Pro Thr Glu Pro His
290                 295                 300

Pro Arg Ala Leu Ala Pro Ser Pro Ala Glu Phe Ile Tyr Tyr Cys
305                 310                 315                 320

Val Asp Glu Asp Glu Leu Gln Pro Tyr Thr Asn Arg Arg Gln Asn Arg
                325                 330                 335

Lys Cys Gly Ala Cys Ala Ala Cys Leu Arg Arg Met Asp Cys Gly Arg
                340                 345                 350

Cys Asp Phe Cys Cys Asp Lys Pro Lys Phe Gly Gly Ser Asn Gln Lys
                355                 360                 365

Arg Gln Lys Cys Arg Trp Arg Gln Cys Leu Gln Phe Ala Met Lys Arg
                370                 375                 380

Leu Leu Pro Ser Val Trp Ser Glu Ser Glu Asp Gly Ala Gly Ser Pro
385                 390                 395                 400

Pro Pro Tyr Arg Arg Arg Lys Arg Pro Ser Ser Ala Arg Arg His His
                405                 410                 415

Leu Gly Pro Thr Leu Lys Pro Thr Leu Ala Thr Arg Thr Ala Gln Pro
                420                 425                 430

Asp His Thr Gln Ala Pro Thr Lys Gln Glu Ala Gly Gly Gly Phe Val
            435                 440                 445

Leu Pro Pro Pro Gly Thr Asp Leu Val Phe Leu Arg Glu Gly Ala Ser
450                 455                 460

Ser Pro Val Gln Val Pro Gly Pro Val Ala Ser Thr Glu Ala Leu
465                 470                 475                 480

Leu Gln Glu Ala Gln Cys Ser Gly Leu Ser Trp Val Val Ala Leu Pro
            485                 490                 495

Gln Val Lys Gln Glu Lys Ala Asp Thr Gln Asp Glu Trp Thr Pro Gly
            500                 505                 510

Thr Ala Val Leu Thr Ser Pro Val Leu Val Pro Gly Cys Pro Ser Lys
            515                 520                 525

Ala Val Asp Pro Gly Leu Pro Ser Val Lys Gln Glu Pro Pro Asp Pro
530                 535                 540

Glu Glu Asp Lys Glu Glu Asn Lys Asp Asp Ser Ala Ser Lys Leu Ala
545                 550                 555                 560

Pro Glu Glu Glu Ala Gly Gly Ala Gly Thr Pro Val Ile Thr Glu Ile
                565                 570                 575

Phe Ser Leu Gly Gly Thr Arg Phe Arg Asp Thr Ala Val Trp Leu Pro
                580                 585                 590

Arg Ser Lys Asp Leu Lys Lys Pro Gly Ala Arg Lys Gln
                595                 600                 605
```

<210> SEQ ID NO 6
<211> LENGTH: 411
<212> TYPE: PRT
<213> ORGANISM: Homo sapiens

<400> SEQUENCE: 6

Met Arg Ala His Pro Gly Gly Gly Arg Cys Cys Pro Glu Gln Glu Glu
1               5                   10                  15

Gly Glu Ser Ala Ala Gly Gly Ser Gly Ala Gly Gly Asp Ser Ala Ile
            20                  25                  30

Glu Gln Gly Gly Gln Gly Ser Ala Leu Ala Pro Ser Pro Val Ser Gly
        35                  40                  45

Val Arg Arg Glu Gly Ala Arg Gly Gly Arg Gly Arg Gly Arg Trp
50                  55                  60

Lys Gln Ala Gly Arg Gly Gly Val Cys Gly Arg Gly Arg Gly Arg
65                  70                  75                  80

Gly Arg Gly Arg Gly Arg Gly Arg Gly Arg Gly Arg Gly Arg
                85                  90                  95

Pro Pro Ser Gly Gly Ser Gly Leu Gly Gly Asp Gly Gly Gly Cys Gly
            100                 105                 110

Gly Gly Gly Ser Gly Gly Gly Ala Pro Arg Arg Glu Pro Val Pro
            115                 120                 125

Phe Pro Ser Gly Ser Ala Gly Pro Gly Pro Arg Gly Pro Arg Ala Thr
130                 135                 140

Glu Ser Gly Lys Arg Met Asp Cys Pro Ala Leu Pro Pro Gly Trp Lys
145                 150                 155                 160

Lys Glu Glu Val Ile Arg Lys Ser Gly Leu Ser Ala Gly Lys Ser Asp
                165                 170                 175

Val Tyr Tyr Phe Ser Pro Ser Gly Lys Lys Phe Arg Ser Lys Pro Gln
            180                 185                 190

Leu Ala Arg Tyr Leu Gly Asn Thr Val Asp Leu Ser Ser Phe Asp Phe
        195                 200                 205

Arg Thr Gly Lys Met Met Pro Ser Lys Leu Gln Lys Asn Lys Gln Arg
210                 215                 220

Leu Arg Asn Asp Pro Leu Asn Gln Asn Lys Gly Lys Pro Asp Leu Asn
225                 230                 235                 240

Thr Thr Leu Pro Ile Arg Gln Thr Ala Ser Ile Phe Lys Gln Pro Val
                245                 250                 255

Thr Lys Val Thr Asn His Pro Ser Asn Lys Val Lys Ser Asp Pro Gln
            260                 265                 270

Arg Met Asn Glu Gln Pro Arg Gln Leu Phe Trp Glu Lys Arg Leu Gln
        275                 280                 285

Gly Leu Ser Ala Ser Asp Val Thr Glu Gln Ile Ile Lys Thr Met Glu
290                 295                 300

Leu Pro Lys Gly Leu Gln Gly Val Gly Pro Gly Ser Asn Asp Glu Thr
305                 310                 315                 320

Leu Leu Ser Ala Val Ala Ser Ala Leu His Thr Ser Ser Ala Pro Ile
                325                 330                 335

Thr Gly Gln Val Ser Ala Ala Val Glu Lys Asn Pro Ala Val Trp Leu
            340                 345                 350

Asn Thr Ser Gln Pro Leu Cys Lys Ala Phe Ile Val Thr Asp Glu Asp
        355                 360                 365

Ile Arg Lys Gln Glu Glu Arg Val Gln Gln Val Arg Lys Lys Leu Glu
370                 375                 380

```
Glu Ala Leu Met Ala Asp Ile Leu Ser Arg Ala Ala Asp Thr Glu
385                 390                 395                 400

Met Asp Ile Glu Met Asp Ser Gly Asp Glu Ala
            405                 410

<210> SEQ ID NO 7
<211> LENGTH: 291
<212> TYPE: PRT
<213> ORGANISM: Homo sapiens

<400> SEQUENCE: 7

Met Glu Arg Lys Arg Trp Glu Cys Pro Ala Leu Pro Gln Gly Trp Glu
1               5                   10                  15

Arg Glu Glu Val Pro Arg Arg Ser Gly Leu Ser Ala Gly His Arg Asp
            20                  25                  30

Val Phe Tyr Tyr Ser Pro Ser Gly Lys Lys Phe Arg Ser Lys Pro Gln
        35                  40                  45

Leu Ala Arg Tyr Leu Gly Gly Ser Met Asp Leu Ser Thr Phe Asp Phe
    50                  55                  60

Arg Thr Gly Lys Met Leu Met Ser Lys Met Asn Lys Ser Arg Gln Arg
65                  70                  75                  80

Val Arg Tyr Asp Ser Ser Asn Gln Val Lys Gly Lys Pro Asp Leu Asn
                85                  90                  95

Thr Ala Leu Pro Val Arg Gln Thr Ala Ser Ile Phe Lys Gln Pro Val
            100                 105                 110

Thr Lys Ile Thr Asn His Pro Ser Asn Lys Val Lys Ser Asp Pro Gln
        115                 120                 125

Lys Ala Val Asp Gln Pro Arg Gln Leu Phe Trp Glu Lys Lys Leu Ser
    130                 135                 140

Gly Leu Asn Ala Phe Asp Ile Ala Glu Glu Leu Val Lys Thr Met Asp
145                 150                 155                 160

Leu Pro Lys Gly Leu Gln Gly Val Gly Pro Gly Cys Thr Asp Glu Thr
                165                 170                 175

Leu Leu Ser Ala Ile Ala Ser Ala Leu His Thr Ser Thr Met Pro Ile
            180                 185                 190

Thr Gly Gln Leu Ser Ala Ala Val Glu Lys Asn Pro Gly Val Trp Leu
        195                 200                 205

Asn Thr Thr Gln Pro Leu Cys Lys Ala Phe Met Val Thr Asp Glu Asp
    210                 215                 220

Ile Arg Lys Gln Glu Glu Leu Val Gln Val Arg Lys Arg Leu Glu
225                 230                 235                 240

Glu Ala Leu Met Ala Asp Met Leu Ala His Val Glu Glu Leu Ala Arg
                245                 250                 255

Asp Gly Glu Ala Pro Leu Asp Lys Ala Cys Ala Glu Asp Asp Glu
            260                 265                 270

Glu Asp Glu Glu Glu Glu Glu Glu Pro Asp Pro Asp Pro Glu Met
        275                 280                 285

Glu His Val
    290

<210> SEQ ID NO 8
<211> LENGTH: 580
<212> TYPE: PRT
<213> ORGANISM: Homo sapiens

<400> SEQUENCE: 8
```

```
Met Gly Thr Thr Gly Leu Glu Ser Leu Ser Leu Gly Asp Arg Gly Ala
1               5                   10                  15
Ala Pro Thr Val Thr Ser Ser Glu Arg Leu Val Pro Asp Pro Pro Asn
            20                  25                  30
Asp Leu Arg Lys Glu Asp Val Ala Met Glu Leu Glu Arg Val Gly Glu
            35                  40                  45
Asp Glu Glu Gln Met Met Ile Lys Arg Ser Ser Glu Cys Asn Pro Leu
50                      55                  60
Leu Gln Glu Pro Ile Ala Ser Ala Gln Phe Gly Ala Thr Ala Gly Thr
65                  70                  75                  80
Glu Cys Arg Lys Ser Val Pro Cys Gly Trp Glu Arg Val Val Lys Gln
                85                  90                  95
Arg Leu Phe Gly Lys Thr Ala Gly Arg Phe Asp Val Tyr Phe Ile Ser
                100                 105                 110
Pro Gln Gly Leu Lys Phe Arg Ser Lys Ser Ser Leu Ala Asn Tyr Leu
                115                 120                 125
His Lys Asn Gly Glu Thr Ser Leu Lys Pro Glu Asp Phe Asp Phe Thr
                130                 135                 140
Val Leu Ser Lys Arg Gly Ile Lys Ser Arg Tyr Lys Asp Cys Ser Met
145                 150                 155                 160
Ala Ala Leu Thr Ser His Leu Gln Asn Gln Ser Asn Asn Ser Asn Trp
                165                 170                 175
Asn Leu Arg Thr Arg Ser Lys Cys Lys Lys Asp Val Phe Met Pro Pro
                180                 185                 190
Ser Ser Ser Ser Glu Leu Gln Glu Ser Arg Gly Leu Ser Asn Phe Thr
                195                 200                 205
Ser Thr His Leu Leu Leu Lys Glu Asp Glu Gly Val Asp Asp Val Asn
                210                 215                 220
Phe Arg Lys Val Arg Lys Pro Lys Gly Lys Val Thr Ile Leu Lys Gly
225                 230                 235                 240
Ile Pro Ile Lys Lys Thr Lys Lys Gly Cys Arg Lys Ser Cys Ser Gly
                245                 250                 255
Phe Val Gln Ser Asp Ser Lys Arg Glu Ser Val Cys Asn Lys Ala Asp
                260                 265                 270
Ala Glu Ser Glu Pro Val Ala Gln Lys Ser Gln Leu Asp Arg Thr Val
                275                 280                 285
Cys Ile Ser Asp Ala Gly Ala Cys Gly Glu Thr Leu Ser Val Thr Ser
                290                 295                 300
Glu Glu Asn Ser Leu Val Lys Lys Lys Glu Arg Ser Leu Ser Ser Gly
305                 310                 315                 320
Ser Asn Phe Cys Ser Glu Gln Lys Thr Ser Gly Ile Ile Asn Lys Phe
                325                 330                 335
Cys Ser Ala Lys Asp Ser Glu His Asn Glu Lys Tyr Glu Asp Thr Phe
                340                 345                 350
Leu Glu Ser Glu Glu Ile Gly Thr Lys Val Glu Val Val Glu Arg Lys
                355                 360                 365
Glu His Leu His Thr Asp Ile Leu Lys Arg Gly Ser Glu Met Asp Asn
                370                 375                 380
Asn Cys Ser Pro Thr Arg Lys Asp Phe Thr Gly Glu Lys Ile Phe Gln
385                 390                 395                 400
Glu Asp Thr Ile Pro Arg Thr Gln Ile Glu Arg Arg Lys Thr Ser Leu
                405                 410                 415
Tyr Phe Ser Ser Lys Tyr Asn Lys Glu Ala Leu Ser Pro Pro Arg Arg
```

-continued

```
                420             425             430
Lys Ala Phe Lys Lys Trp Thr Pro Pro Arg Ser Pro Phe Asn Leu Val
            435                 440                 445

Gln Glu Thr Leu Phe His Asp Pro Trp Lys Leu Leu Ile Ala Thr Ile
        450                 455                 460

Phe Leu Asn Arg Thr Ser Gly Lys Met Ala Ile Pro Val Leu Trp Lys
465                 470                 475                 480

Phe Leu Glu Lys Tyr Pro Ser Ala Glu Val Ala Arg Thr Ala Asp Trp
                485                 490                 495

Arg Asp Val Ser Glu Leu Leu Lys Pro Leu Gly Leu Tyr Asp Leu Arg
            500                 505                 510

Ala Lys Thr Ile Val Lys Phe Ser Asp Glu Tyr Leu Thr Lys Gln Trp
        515                 520                 525

Lys Tyr Pro Ile Glu Leu His Gly Ile Gly Lys Tyr Gly Asn Asp Ser
            530                 535                 540

Tyr Arg Ile Phe Cys Val Asn Glu Trp Lys Gln Val His Pro Glu Asp
545                 550                 555                 560

His Lys Leu Asn Lys Tyr His Asp Trp Leu Trp Glu Asn His Glu Lys
                565                 570                 575

Leu Ser Leu Ser
            580
```

<210> SEQ ID NO 9
<211> LENGTH: 360
<212> TYPE: PRT
<213> ORGANISM: Homo sapiens

<400> SEQUENCE: 9

```
Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205
```

-continued

```
Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
                275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
                340                 345                 350

Leu Gly Ser Pro Met His Ser Asn
        355                 360

<210> SEQ ID NO 10
<211> LENGTH: 317
<212> TYPE: PRT
<213> ORGANISM: Homo sapiens

<400> SEQUENCE: 10

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220
```

```
Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Val Val Thr
            245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315
```

<210> SEQ ID NO 11
<211> LENGTH: 1912
<212> TYPE: PRT
<213> ORGANISM: Homo sapiens

<400> SEQUENCE: 11

```
Met Ala Ser Gly Leu Gly Ser Pro Ser Pro Cys Ser Ala Gly Ser Glu
1               5                   10                  15

Glu Glu Asp Met Asp Ala Leu Leu Asn Asn Ser Leu Pro Pro Pro His
            20                  25                  30

Pro Glu Asn Glu Glu Asp Pro Glu Asp Leu Ser Glu Thr Glu Thr
            35                  40                  45

Pro Lys Leu Lys Lys Lys Lys Pro Lys Lys Pro Arg Asp Pro Lys
50                  55                  60

Ile Pro Lys Ser Lys Arg Gln Lys Lys Glu Arg Met Leu Leu Cys Arg
65                  70                  75                  80

Gln Leu Gly Asp Ser Ser Gly Glu Gly Pro Glu Phe Val Glu Glu Glu
                85                  90                  95

Glu Glu Val Ala Leu Arg Ser Asp Ser Glu Gly Ser Asp Tyr Thr Pro
            100                 105                 110

Gly Lys Lys Lys Lys Lys Lys Leu Gly Pro Lys Lys Glu Lys Lys Ser
            115                 120                 125

Lys Ser Lys Arg Lys Glu Glu Glu Glu Glu Asp Asp Asp Asp
130                 135                 140

Ser Lys Glu Pro Lys Ser Ser Ala Gln Leu Leu Glu Asp Trp Gly Met
145                 150                 155                 160

Glu Asp Ile Asp His Val Phe Ser Glu Glu Asp Tyr Arg Thr Leu Thr
                165                 170                 175

Asn Tyr Lys Ala Phe Ser Gln Phe Val Arg Pro Leu Ile Ala Ala Lys
            180                 185                 190

Asn Pro Lys Ile Ala Val Ser Lys Met Met Met Val Leu Gly Ala Lys
            195                 200                 205

Trp Arg Glu Phe Ser Thr Asn Asn Pro Phe Lys Gly Ser Ser Gly Ala
            210                 215                 220

Ser Val Ala Ala Ala Ala Ala Ala Val Ala Val Val Glu Ser Met
225                 230                 235                 240

Val Thr Ala Thr Glu Val Ala Pro Pro Pro Val Glu Val Pro
            245                 250                 255

Ile Arg Lys Ala Lys Thr Lys Glu Gly Lys Gly Pro Asn Ala Arg Arg
            260                 265                 270

Lys Pro Lys Gly Ser Pro Arg Val Pro Asp Ala Lys Lys Pro Lys Pro
```

-continued

```
            275                 280                 285
Lys Lys Val Ala Pro Leu Lys Ile Lys Leu Gly Gly Phe Gly Ser Lys
    290                 295                 300
Arg Lys Arg Ser Ser Ser Glu Asp Asp Leu Asp Val Glu Ser Asp
305                 310                 315                 320
Phe Asp Asp Ala Ser Ile Asn Ser Tyr Ser Val Ser Asp Gly Ser Thr
                325                 330                 335
Ser Arg Ser Ser Arg Ser Arg Lys Lys Leu Arg Thr Thr Lys Lys Lys
                340                 345                 350
Lys Lys Gly Glu Glu Val Thr Ala Val Asp Gly Tyr Glu Thr Asp
        355                 360                 365
His Gln Asp Tyr Cys Glu Val Cys Gln Gln Gly Gly Glu Ile Ile Leu
        370                 375                 380
Cys Asp Thr Cys Pro Arg Ala Tyr His Met Val Cys Leu Asp Pro Asp
385                 390                 395                 400
Met Glu Lys Ala Pro Glu Gly Lys Trp Ser Cys Pro His Cys Glu Lys
                405                 410                 415
Glu Gly Ile Gln Trp Glu Ala Lys Glu Asp Asn Ser Glu Gly Glu Glu
                420                 425                 430
Ile Leu Glu Glu Val Gly Gly Asp Leu Glu Glu Asp Asp His His
            435                 440                 445
Met Glu Phe Cys Arg Val Cys Lys Asp Gly Gly Glu Leu Leu Cys Cys
    450                 455                 460
Asp Thr Cys Pro Ser Ser Tyr His Ile His Cys Leu Asn Pro Pro Leu
465                 470                 475                 480
Pro Glu Ile Pro Asn Gly Glu Trp Leu Cys Pro Arg Cys Thr Cys Pro
                485                 490                 495
Ala Leu Lys Gly Lys Val Gln Lys Ile Leu Ile Trp Lys Trp Gly Gln
                500                 505                 510
Pro Pro Ser Pro Thr Pro Val Pro Arg Pro Pro Asp Ala Asp Pro Asn
            515                 520                 525
Thr Pro Ser Pro Lys Pro Leu Glu Gly Arg Pro Glu Arg Gln Phe Phe
    530                 535                 540
Val Lys Trp Gln Gly Met Ser Tyr Trp His Cys Ser Trp Val Ser Glu
545                 550                 555                 560
Leu Gln Leu Glu Leu His Cys Gln Val Met Phe Arg Asn Tyr Gln Arg
                565                 570                 575
Lys Asn Asp Met Asp Glu Pro Pro Ser Gly Asp Phe Gly Gly Asp Glu
                580                 585                 590
Glu Lys Ser Arg Lys Arg Lys Asn Lys Asp Pro Lys Phe Ala Glu Met
                595                 600                 605
Glu Glu Arg Phe Tyr Arg Tyr Gly Ile Lys Pro Glu Trp Met Met Ile
            610                 615                 620
His Arg Ile Leu Asn His Ser Val Asp Lys Lys Gly His Val His Tyr
625                 630                 635                 640
Leu Ile Lys Trp Arg Asp Leu Pro Tyr Asp Gln Ala Ser Trp Glu Ser
                645                 650                 655
Glu Asp Val Glu Ile Gln Asp Tyr Asp Leu Phe Lys Gln Ser Tyr Trp
                660                 665                 670
Asn His Arg Glu Leu Met Arg Gly Glu Glu Gly Arg Pro Gly Lys Lys
            675                 680                 685
Leu Lys Lys Val Lys Leu Arg Lys Leu Glu Arg Pro Pro Glu Thr Pro
        690                 695                 700
```

```
Thr Val Asp Pro Thr Val Lys Tyr Glu Arg Gln Pro Glu Tyr Leu Asp
705                 710                 715                 720

Ala Thr Gly Gly Thr Leu His Pro Tyr Gln Met Glu Gly Leu Asn Trp
            725                 730                 735

Leu Arg Phe Ser Trp Ala Gln Gly Thr Asp Thr Ile Leu Ala Asp Glu
        740                 745                 750

Met Gly Leu Gly Lys Thr Val Gln Thr Ala Val Phe Leu Tyr Ser Leu
    755                 760                 765

Tyr Lys Glu Gly His Ser Lys Gly Pro Phe Leu Val Ser Ala Pro Leu
770                 775                 780

Ser Thr Ile Ile Asn Trp Glu Arg Glu Phe Glu Met Trp Ala Pro Asp
785                 790                 795                 800

Met Tyr Val Val Thr Tyr Val Gly Asp Lys Asp Ser Arg Ala Ile Ile
                805                 810                 815

Arg Glu Asn Glu Phe Ser Phe Glu Asp Asn Ala Ile Arg Gly Gly Lys
            820                 825                 830

Lys Ala Ser Arg Met Lys Lys Glu Ala Ser Val Lys Phe His Val Leu
        835                 840                 845

Leu Thr Ser Tyr Glu Leu Ile Thr Ile Asp Met Ala Ile Leu Gly Ser
    850                 855                 860

Ile Asp Trp Ala Cys Leu Ile Val Asp Glu Ala His Arg Leu Lys Asn
865                 870                 875                 880

Asn Gln Ser Lys Phe Phe Arg Val Leu Asn Gly Tyr Ser Leu Gln His
                885                 890                 895

Lys Leu Leu Leu Thr Gly Thr Pro Leu Gln Asn Asn Leu Glu Glu Leu
            900                 905                 910

Phe His Leu Leu Asn Phe Leu Thr Pro Glu Arg Phe His Asn Leu Glu
        915                 920                 925

Gly Phe Leu Glu Glu Phe Ala Asp Ile Ala Lys Glu Asp Gln Ile Lys
    930                 935                 940

Lys Leu His Asp Met Leu Gly Pro His Met Leu Arg Arg Leu Lys Ala
945                 950                 955                 960

Asp Val Phe Lys Asn Met Pro Ser Lys Thr Glu Leu Ile Val Arg Val
                965                 970                 975

Glu Leu Ser Pro Met Gln Lys Lys Tyr Tyr Lys Tyr Ile Leu Thr Arg
            980                 985                 990

Asn Phe Glu Ala Leu Asn Ala Arg Gly Gly Gly Asn Gln Val Ser Leu
        995                 1000                1005

Leu Asn Val Val Met Asp Leu Lys Lys Cys Cys Asn His Pro Tyr
    1010                1015                1020

Leu Phe Pro Val Ala Ala Met Glu Ala Pro Lys Met Pro Asn Gly
    1025                1030                1035

Met Tyr Asp Gly Ser Ala Leu Ile Arg Ala Ser Gly Lys Leu Leu
    1040                1045                1050

Leu Leu Gln Lys Met Leu Lys Asn Leu Lys Glu Gly Gly His Arg
    1055                1060                1065

Val Leu Ile Phe Ser Gln Met Thr Lys Met Leu Asp Leu Leu Glu
    1070                1075                1080

Asp Phe Leu Glu His Glu Gly Tyr Lys Tyr Glu Arg Ile Asp Gly
    1085                1090                1095

Gly Ile Thr Gly Asn Met Arg Gln Glu Ala Ile Asp Arg Phe Asn
    1100                1105                1110
```

-continued

```
Ala Pro Gly Ala Gln Gln Phe Cys Phe Leu Leu Ser Thr Arg Ala
    1115                1120                1125

Gly Gly Leu Gly Ile Asn Leu Ala Thr Ala Asp Thr Val Ile Ile
    1130                1135                1140

Tyr Asp Ser Asp Trp Asn Pro His Asn Asp Ile Gln Ala Phe Ser
    1145                1150                1155

Arg Ala His Arg Ile Gly Gln Asn Lys Lys Val Met Ile Tyr Arg
    1160                1165                1170

Phe Val Thr Arg Ala Ser Val Glu Glu Arg Ile Thr Gln Val Ala
    1175                1180                1185

Lys Lys Lys Met Met Leu Thr His Leu Val Val Arg Pro Gly Leu
    1190                1195                1200

Gly Ser Lys Thr Gly Ser Met Ser Lys Gln Glu Leu Asp Asp Ile
    1205                1210                1215

Leu Lys Phe Gly Thr Glu Glu Leu Phe Lys Asp Glu Ala Thr Asp
    1220                1225                1230

Gly Gly Gly Asp Asn Lys Glu Gly Glu Asp Ser Ser Val Ile His
    1235                1240                1245

Tyr Asp Asp Lys Ala Ile Glu Arg Leu Leu Asp Arg Asn Gln Asp
    1250                1255                1260

Glu Thr Glu Asp Thr Glu Leu Gln Gly Met Asn Glu Tyr Leu Ser
    1265                1270                1275

Ser Phe Lys Val Ala Gln Tyr Val Val Arg Glu Glu Met Gly
    1280                1285                1290

Glu Glu Glu Glu Val Glu Arg Glu Ile Ile Lys Gln Glu Glu Ser
    1295                1300                1305

Val Asp Pro Asp Tyr Trp Glu Lys Leu Leu Arg His His Tyr Glu
    1310                1315                1320

Gln Gln Gln Glu Asp Leu Ala Arg Asn Leu Gly Lys Gly Lys Arg
    1325                1330                1335

Ile Arg Lys Gln Val Asn Tyr Asn Asp Gly Ser Gln Glu Asp Arg
    1340                1345                1350

Asp Trp Gln Asp Asp Gln Ser Asp Asn Gln Ser Asp Tyr Ser Val
    1355                1360                1365

Ala Ser Glu Glu Gly Asp Glu Asp Phe Asp Glu Arg Ser Glu Ala
    1370                1375                1380

Pro Arg Arg Pro Ser Arg Lys Gly Leu Arg Asn Asp Lys Asp Lys
    1385                1390                1395

Pro Leu Pro Pro Leu Leu Ala Arg Val Gly Gly Asn Ile Glu Val
    1400                1405                1410

Leu Gly Phe Asn Ala Arg Gln Arg Lys Ala Phe Leu Asn Ala Ile
    1415                1420                1425

Met Arg Tyr Gly Met Pro Pro Gln Asp Ala Phe Thr Thr Gln Trp
    1430                1435                1440

Leu Val Arg Asp Leu Arg Gly Lys Ser Glu Lys Glu Phe Lys Ala
    1445                1450                1455

Tyr Val Ser Leu Phe Met Arg His Leu Cys Glu Pro Gly Ala Asp
    1460                1465                1470

Gly Ala Glu Thr Phe Ala Asp Gly Val Pro Arg Glu Gly Leu Ser
    1475                1480                1485

Arg Gln His Val Leu Thr Arg Ile Gly Val Met Ser Leu Ile Arg
    1490                1495                1500

Lys Lys Val Gln Glu Phe Glu His Val Asn Gly Arg Trp Ser Met
```

```
              1505                1510                1515

Pro Glu Leu Ala Glu Val Glu Glu Asn Lys Lys Met Ser Gln Pro
        1520                1525                1530

Gly Ser Pro Ser Pro Lys Thr Pro Thr Pro Ser Thr Pro Gly Asp
        1535                1540                1545

Thr Gln Pro Asn Thr Pro Ala Pro Val Pro Pro Ala Glu Asp Gly
        1550                1555                1560

Ile Lys Ile Glu Glu Asn Ser Leu Lys Glu Glu Ser Ile Glu
        1565                1570                1575

Gly Glu Lys Glu Val Lys Ser Thr Ala Pro Glu Thr Ala Ile Glu
        1580                1585                1590

Cys Thr Gln Ala Pro Ala Pro Ala Ser Glu Asp Glu Lys Val Val
        1595                1600                1605

Val Glu Pro Pro Glu Gly Glu Glu Lys Val Glu Lys Ala Glu Val
        1610                1615                1620

Lys Glu Arg Thr Glu Glu Pro Met Glu Thr Glu Pro Lys Gly Ala
        1625                1630                1635

Ala Asp Val Glu Lys Val Glu Glu Lys Ser Ala Ile Asp Leu Thr
        1640                1645                1650

Pro Ile Val Val Glu Asp Lys Glu Glu Lys Lys Glu Glu Glu
        1655                1660                1665

Lys Lys Glu Val Met Leu Gln Asn Gly Glu Thr Pro Lys Asp Leu
        1670                1675                1680

Asn Asp Glu Lys Gln Lys Lys Asn Ile Lys Gln Arg Phe Met Phe
        1685                1690                1695

Asn Ile Ala Asp Gly Gly Phe Thr Glu Leu His Ser Leu Trp Gln
        1700                1705                1710

Asn Glu Glu Arg Ala Ala Thr Val Thr Lys Lys Thr Tyr Glu Ile
        1715                1720                1725

Trp His Arg Arg His Asp Tyr Trp Leu Leu Ala Gly Ile Ile Asn
        1730                1735                1740

His Gly Tyr Ala Arg Trp Gln Asp Ile Gln Asn Asp Pro Arg Tyr
        1745                1750                1755

Ala Ile Leu Asn Glu Pro Phe Lys Gly Glu Met Asn Arg Gly Asn
        1760                1765                1770

Phe Leu Glu Ile Lys Asn Lys Phe Leu Ala Arg Arg Phe Lys Leu
        1775                1780                1785

Leu Glu Gln Ala Leu Val Ile Glu Glu Gln Leu Arg Arg Ala Ala
        1790                1795                1800

Tyr Leu Asn Met Ser Glu Asp Pro Ser His Pro Ser Met Ala Leu
        1805                1810                1815

Asn Thr Arg Phe Ala Glu Val Glu Cys Leu Ala Glu Ser His Gln
        1820                1825                1830

His Leu Ser Lys Glu Ser Met Ala Gly Asn Lys Pro Ala Asn Ala
        1835                1840                1845

Val Leu His Lys Val Leu Lys Gln Leu Glu Glu Leu Leu Ser Asp
        1850                1855                1860

Met Lys Ala Asp Val Thr Arg Leu Pro Ala Thr Ile Ala Arg Ile
        1865                1870                1875

Pro Pro Val Ala Val Arg Leu Gln Met Ser Glu Arg Asn Ile Leu
        1880                1885                1890

Ser Arg Leu Ala Asn Arg Ala Pro Glu Pro Thr Pro Gln Gln Val
        1895                1900                1905
```

Ala Gln Gln Gln
    1910

<210> SEQ ID NO 12
<211> LENGTH: 305
<212> TYPE: PRT
<213> ORGANISM: Homo sapiens

<400> SEQUENCE: 12

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 13
<211> LENGTH: 424
<212> TYPE: PRT
<213> ORGANISM: Homo sapiens

<400> SEQUENCE: 13

```
Met Ala Asp Lys Glu Ala Phe Asp Asp Ala Val Glu Arg Val Ile
1               5                   10                  15

Asn Glu Glu Tyr Lys Ile Trp Lys Lys Asn Thr Pro Phe Leu Tyr Asp
                20                  25                  30

Leu Val Met Thr His Ala Leu Glu Trp Pro Ser Leu Thr Ala Gln Trp
            35                  40                  45

Leu Pro Asp Val Thr Arg Pro Glu Gly Lys Asp Phe Ser Ile His Arg
    50                  55                  60

Leu Val Leu Gly Thr His Thr Ser Asp Glu Gln Asn His Leu Val Ile
65              70                  75                  80

Ala Ser Val Gln Leu Pro Asn Asp Ala Gln Phe Asp Ala Ser His
                85                  90                  95

Tyr Asp Ser Glu Lys Gly Glu Phe Gly Gly Phe Gly Ser Val Ser Gly
                100                 105                 110

Lys Ile Glu Ile Glu Ile Lys Ile Asn His Glu Gly Glu Val Asn Arg
        115                 120                 125

Ala Arg Tyr Met Pro Gln Asn Pro Cys Ile Ile Ala Thr Lys Thr Pro
    130                 135                 140

Ser Ser Asp Val Leu Val Phe Asp Tyr Thr Lys His Pro Ser Lys Pro
145                 150                 155                 160

Asp Pro Ser Gly Glu Cys Asn Pro Asp Leu Arg Leu Arg Gly His Gln
                165                 170                 175

Lys Glu Gly Tyr Gly Leu Ser Trp Asn Pro Asn Leu Ser Gly His Leu
                180                 185                 190

Leu Ser Ala Ser Asp Asp His Thr Ile Cys Leu Trp Asp Ile Ser Ala
        195                 200                 205

Val Pro Lys Glu Gly Lys Val Val Asp Ala Lys Thr Ile Phe Thr Gly
    210                 215                 220

His Thr Ala Val Val Glu Asp Val Ser Trp His Leu Leu His Glu Ser
225                 230                 235                 240

Leu Phe Gly Ser Val Ala Asp Asp Gln Lys Leu Met Ile Trp Asp Thr
                245                 250                 255

Arg Ser Asn Asn Thr Ser Lys Pro Ser His Ser Val Asp Ala His Thr
            260                 265                 270

Ala Glu Val Asn Cys Leu Ser Phe Asn Pro Tyr Ser Glu Phe Ile Leu
        275                 280                 285

Ala Thr Gly Ser Ala Asp Lys Thr Val Ala Leu Trp Asp Leu Arg Asn
    290                 295                 300

Leu Lys Leu Lys Leu His Ser Phe Glu Ser His Lys Asp Glu Ile Phe
305                 310                 315                 320

Gln Val Gln Trp Ser Pro His Asn Glu Thr Ile Leu Ala Ser Ser Gly
                325                 330                 335

Thr Asp Arg Arg Leu Asn Val Trp Asp Leu Ser Lys Ile Gly Glu Glu
            340                 345                 350

Gln Ser Pro Glu Asp Ala Glu Asp Gly Pro Pro Glu Leu Leu Phe Ile
        355                 360                 365

His Gly Gly His Thr Ala Lys Ile Ser Asp Phe Ser Trp Asn Pro Asn
    370                 375                 380

Glu Pro Trp Val Ile Cys Ser Val Ser Glu Asp Asn Ile Met Gln Val
385                 390                 395                 400

Trp Gln Met Ala Glu Asn Ile Tyr Asn Asp Gly Asp Pro Glu Gly Ser
                405                 410                 415
```

Val Asp Pro Glu Gly Gln Gly Ser
            420

<210> SEQ ID NO 14
<211> LENGTH: 1792
<212> TYPE: PRT
<213> ORGANISM: Homo sapiens

<400> SEQUENCE: 14

Met Ser Cys Val His Tyr Lys Phe Ser Ser Lys Leu Asn Tyr Asp Thr
1               5                   10                  15

Val Thr Phe Asp Gly Leu His Ile Ser Leu Cys Asp Leu Lys Lys Gln
            20                  25                  30

Ile Met Gly Arg Glu Lys Leu Lys Ala Ala Asp Cys Asp Leu Gln Ile
        35                  40                  45

Thr Asn Ala Gln Thr Lys Glu Glu Tyr Thr Asp Asn Ala Leu Ile
    50                  55                  60

Pro Lys Asn Ser Ser Val Ile Val Arg Arg Ile Pro Ile Gly Gly Val
65                  70                  75                  80

Lys Ser Thr Ser Lys Thr Tyr Val Ile Ser Arg Thr Glu Pro Ala Met
                85                  90                  95

Ala Thr Thr Lys Ala Ile Asp Asp Ser Ser Ala Ser Ile Ser Leu Ala
            100                 105                 110

Gln Leu Thr Lys Thr Ala Asn Leu Ala Glu Ala Asn Ala Ser Glu Glu
        115                 120                 125

Asp Lys Ile Lys Ala Met Met Ser Gln Ser Gly His Glu Tyr Asp Pro
    130                 135                 140

Ile Asn Tyr Met Lys Lys Pro Leu Gly Pro Pro Pro Ser Tyr Thr
145                 150                 155                 160

Cys Phe Arg Cys Gly Lys Pro Gly His Tyr Ile Lys Asn Cys Pro Thr
                165                 170                 175

Asn Gly Asp Lys Asn Phe Glu Ser Gly Pro Arg Ile Lys Lys Ser Thr
            180                 185                 190

Gly Ile Pro Arg Ser Phe Met Met Glu Val Lys Asp Pro Asn Met Lys
        195                 200                 205

Gly Ala Met Leu Thr Asn Thr Gly Lys Tyr Ala Ile Pro Thr Ile Asp
    210                 215                 220

Ala Glu Ala Tyr Ala Ile Gly Lys Lys Glu Lys Pro Pro Phe Leu Pro
225                 230                 235                 240

Glu Glu Pro Ser Ser Ser Glu Glu Asp Asp Pro Ile Pro Asp Glu
                245                 250                 255

Leu Leu Cys Leu Ile Cys Lys Asp Ile Met Thr Asp Ala Val Val Ile
            260                 265                 270

Pro Cys Cys Gly Asn Ser Tyr Cys Asp Glu Cys Ile Arg Thr Ala Leu
        275                 280                 285

Leu Glu Ser Asp Glu His Thr Cys Pro Thr Cys His Gln Asn Asp Val
    290                 295                 300

Ser Pro Asp Ala Leu Ile Ala Asn Lys Phe Leu Arg Gln Ala Val Asn
305                 310                 315                 320

Asn Phe Lys Asn Glu Thr Gly Tyr Thr Lys Arg Leu Arg Lys Gln Leu
                325                 330                 335

Pro Pro Pro Pro Pro Ile Pro Pro Arg Pro Leu Ile Gln Arg
            340                 345                 350

Asn Leu Gln Pro Leu Met Arg Ser Pro Ile Ser Arg Gln Gln Asp Pro
        355                 360                 365

```
Leu Met Ile Pro Val Thr Ser Ser Thr His Pro Ala Pro Ser Ile
    370             375             380
Ser Ser Leu Thr Ser Asn Gln Ser Ser Leu Ala Pro Pro Val Ser Gly
385             390             395             400
Asn Pro Ser Ser Ala Pro Ala Pro Val Pro Asp Ile Thr Ala Thr Val
            405             410             415
Ser Ile Ser Val His Ser Glu Lys Ser Asp Gly Pro Phe Arg Asp Ser
            420             425             430
Asp Asn Lys Ile Leu Pro Ala Ala Leu Ala Ser Glu His Ser Lys
        435             440             445
Gly Thr Ser Ser Ile Ala Ile Thr Ala Leu Met Glu Glu Lys Gly Tyr
    450             455             460
Gln Val Pro Val Leu Gly Thr Pro Ser Leu Leu Gly Gln Ser Leu Leu
465             470             475             480
His Gly Gln Leu Ile Pro Thr Thr Gly Pro Val Arg Ile Asn Thr Ala
            485             490             495
Arg Pro Gly Gly Gly Arg Pro Gly Trp Glu His Ser Asn Lys Leu Gly
            500             505             510
Tyr Leu Val Ser Pro Pro Gln Gln Ile Arg Arg Gly Glu Arg Ser Cys
    515             520             525
Tyr Arg Ser Ile Asn Arg Gly Arg His His Ser Glu Arg Ser Gln Arg
    530             535             540
Thr Gln Gly Pro Ser Leu Pro Ala Thr Pro Val Phe Val Pro Val Pro
545             550             555             560
Pro Pro Pro Leu Tyr Pro Pro Pro His Thr Leu Pro Leu Pro Pro
            565             570             575
Gly Val Pro Pro Pro Gln Phe Ser Pro Gln Phe Pro Gly Gln Pro
        580             585             590
Pro Pro Ala Gly Tyr Ser Val Pro Pro Gly Phe Pro Ala Pro
        595             600             605
Ala Asn Leu Ser Thr Pro Trp Val Ser Ser Gly Val Gln Thr Ala His
        610             615             620
Ser Asn Thr Ile Pro Thr Thr Gln Ala Pro Pro Leu Ser Arg Glu Glu
625             630             635             640
Phe Tyr Arg Glu Gln Arg Arg Leu Lys Glu Glu Glu Lys Lys Lys Ser
            645             650             655
Lys Leu Asp Glu Phe Thr Asn Asp Phe Ala Lys Glu Leu Met Glu Tyr
            660             665             670
Lys Lys Ile Gln Lys Glu Arg Arg Ser Phe Ser Arg Ser Lys Ser
        675             680             685
Pro Tyr Ser Gly Ser Ser Tyr Ser Arg Ser Ser Tyr Thr Tyr Ser Lys
            690             695             700
Ser Arg Ser Gly Ser Thr Arg Ser Arg Ser Tyr Ser Arg Ser Phe Ser
705             710             715             720
Arg Ser His Ser Arg Ser Tyr Ser Arg Ser Pro Tyr Pro Arg Arg
            725             730             735
Gly Arg Gly Lys Ser Arg Asn Tyr Arg Ser Arg Ser Arg Ser His Gly
            740             745             750
Tyr His Arg Ser Arg Ser Arg Ser Pro Pro Tyr Arg Arg Tyr His Ser
        755             760             765
Arg Ser Arg Ser Pro Gln Ala Phe Arg Gly Gln Ser Pro Asn Lys Arg
        770             775             780
```

```
Asn Val Pro Gln Gly Glu Thr Glu Arg Glu Tyr Phe Asn Arg Tyr Arg
785                 790                 795                 800

Glu Val Pro Pro Pro Tyr Asp Met Lys Ala Tyr Tyr Gly Arg Ser Val
            805                 810                 815

Asp Phe Arg Asp Pro Phe Glu Lys Glu Arg Tyr Arg Glu Trp Glu Arg
        820                 825                 830

Lys Tyr Arg Glu Trp Tyr Glu Lys Tyr Tyr Lys Gly Tyr Ala Ala Gly
    835                 840                 845

Ala Gln Pro Arg Pro Ser Ala Asn Arg Glu Asn Phe Ser Pro Glu Arg
    850                 855                 860

Phe Leu Pro Leu Asn Ile Arg Asn Ser Pro Phe Thr Arg Gly Arg Arg
865                 870                 875                 880

Glu Asp Tyr Val Gly Gly Gln Ser His Arg Ser Arg Asn Ile Gly Ser
            885                 890                 895

Asn Tyr Pro Glu Lys Leu Ser Ala Arg Asp Gly His Asn Gln Lys Asp
        900                 905                 910

Asn Thr Lys Ser Lys Glu Lys Glu Ser Glu Asn Ala Pro Gly Asp Gly
    915                 920                 925

Lys Gly Asn Lys His Lys Lys His Arg Lys Arg Arg Lys Gly Glu Glu
    930                 935                 940

Ser Glu Gly Phe Leu Asn Pro Glu Leu Leu Glu Thr Ser Arg Lys Ser
945                 950                 955                 960

Arg Glu Pro Thr Gly Val Glu Glu Asn Lys Thr Asp Ser Leu Phe Val
            965                 970                 975

Leu Pro Ser Arg Asp Asp Ala Thr Pro Val Arg Asp Glu Pro Met Asp
        980                 985                 990

Ala Glu Ser Ile Thr Phe Lys Ser  Val Ser Glu Lys Asp  Lys Arg Glu
        995                 1000                1005

Arg Asp  Lys Pro Lys Ala Lys  Gly Asp Lys Thr  Lys Arg Lys Asn
    1010            1015                1020

Asp Gly  Ser Ala Val Ser Lys  Lys Glu Asn Ile Val  Lys Pro Ala
    1025            1030                1035

Lys Gly  Pro Gln Glu Lys Val  Asp Gly Glu Arg Glu  Arg Ser Pro
    1040            1045                1050

Arg Ser  Glu Pro Pro Ile Lys  Lys Ala Lys Glu Glu  Thr Pro Lys
    1055            1060                1065

Thr Asp  Asn Thr Lys Ser Ser  Ser Ser Ser Gln Lys  Asp Glu Lys
    1070            1075                1080

Ile Thr  Gly Thr Pro Arg Lys  Ala His Ser Lys Ser  Ala Lys Glu
    1085            1090                1095

His Gln  Glu Thr Lys Pro Val  Lys Glu Glu Lys Val  Lys Lys Asp
    1100            1105                1110

Tyr Ser  Lys Asp Val Lys Ser  Glu Lys Leu Thr Thr  Lys Glu Glu
    1115            1120                1125

Lys Ala  Lys Lys Pro Asn Glu  Lys Asn Lys Pro Leu  Asp Asn Lys
    1130            1135                1140

Gly Glu  Lys Arg Lys Arg Lys  Thr Glu Glu Lys Gly  Val Asp Lys
    1145            1150                1155

Asp Phe  Glu Ser Ser Ser Met  Lys Ile Ser Lys Leu  Glu Val Thr
    1160            1165                1170

Glu Ile  Val Lys Pro Ser Pro  Lys Arg Lys Met Glu  Pro Asp Thr
    1175            1180                1185

Glu Lys  Met Asp Arg Thr Pro  Glu Lys Asp Lys Ile  Ser Leu Ser
```

```
                1190                1195                1200
Ala Pro Ala Lys Lys Ile Lys Leu Asn Arg Glu Thr Gly Lys Lys
        1205                1210                1215
Ile Gly Ser Thr Glu Asn Ile Ser Asn Thr Lys Glu Pro Ser Glu
        1220                1225                1230
Lys Leu Glu Ser Thr Ser Ser Lys Val Lys Gln Glu Lys Val Lys
        1235                1240                1245
Gly Lys Val Arg Arg Lys Val Thr Gly Thr Glu Gly Ser Ser Ser
        1250                1255                1260
Thr Leu Val Asp Tyr Thr Ser Thr Ser Ser Thr Gly Gly Ser Pro
        1265                1270                1275
Val Arg Lys Ser Glu Glu Lys Thr Asp Thr Lys Arg Thr Val Ile
        1280                1285                1290
Lys Thr Met Glu Glu Tyr Asn Asn Asp Asn Thr Ala Pro Ala Glu
        1295                1300                1305
Asp Val Ile Ile Met Ile Gln Val Pro Gln Ser Lys Trp Asp Lys
        1310                1315                1320
Asp Asp Phe Glu Ser Glu Glu Asp Val Lys Ser Thr Gln Pro
        1325                1330                1335
Ile Ser Ser Val Gly Lys Pro Ala Ser Val Ile Lys Asn Val Ser
        1340                1345                1350
Thr Lys Pro Ser Asn Ile Val Lys Tyr Pro Glu Lys Glu Ser Glu
        1355                1360                1365
Pro Ser Glu Lys Ile Gln Lys Phe Thr Lys Asp Val Ser His Glu
        1370                1375                1380
Ile Ile Gln His Glu Val Lys Ser Ser Lys Asn Ser Ala Ser Ser
        1385                1390                1395
Glu Lys Gly Lys Thr Lys Asp Arg Asp Tyr Ser Val Leu Glu Lys
        1400                1405                1410
Glu Asn Pro Glu Lys Arg Lys Asn Ser Thr Gln Pro Glu Lys Glu
        1415                1420                1425
Ser Asn Leu Asp Arg Leu Asn Glu Gln Gly Asn Phe Lys Ser Leu
        1430                1435                1440
Ser Gln Ser Ser Lys Glu Ala Arg Thr Ser Asp Lys His Asp Ser
        1445                1450                1455
Thr Arg Ala Ser Ser Asn Lys Asp Phe Thr Pro Asn Arg Asp Lys
        1460                1465                1470
Lys Thr Asp Tyr Asp Thr Arg Glu Tyr Ser Ser Ser Lys Arg Arg
        1475                1480                1485
Asp Glu Lys Asn Glu Leu Thr Arg Arg Lys Asp Ser Pro Ser Arg
        1490                1495                1500
Asn Lys Asp Ser Ala Ser Gly Gln Lys Asn Lys Pro Arg Glu Glu
        1505                1510                1515
Arg Asp Leu Pro Lys Lys Gly Thr Gly Asp Ser Lys Lys Ser Asn
        1520                1525                1530
Ser Ser Pro Ser Arg Asp Arg Lys Pro His Asp His Lys Ala Thr
        1535                1540                1545
Tyr Asp Thr Lys Arg Pro Asn Glu Glu Thr Lys Ser Val Asp Lys
        1550                1555                1560
Asn Pro Cys Lys Asp Arg Glu Lys His Val Leu Glu Ala Arg Asn
        1565                1570                1575
Asn Lys Glu Ser Ser Gly Asn Lys Leu Leu Tyr Ile Leu Asn Pro
        1580                1585                1590
```

Pro Glu Thr Gln Val Glu Lys Glu Gln Ile Thr Gly Gln Ile Asp
   1595                1600                1605

Lys Ser Thr Val Lys Pro Lys Pro Gln Leu Ser His Ser Ser Arg
   1610                1615                1620

Leu Ser Ser Asp Leu Thr Arg Glu Thr Asp Glu Ala Ala Phe Glu
   1625                1630                1635

Pro Asp Tyr Asn Glu Ser Ser Glu Ser Asn Val Ser Val Lys
   1640                1645                1650

Glu Glu Glu Ser Ser Gly Asn Ile Ser Lys Asp Leu Lys Asp Lys
   1655                1660                1665

Ile Val Glu Lys Ala Lys Glu Ser Leu Asp Thr Ala Ala Val Val
   1670                1675                1680

Gln Val Gly Ile Ser Arg Asn Gln Ser His Ser Ser Pro Ser Val
   1685                1690                1695

Ser Pro Ser Arg Ser His Ser Pro Ser Gly Ser Gln Thr Arg Ser
   1700                1705                1710

His Ser Ser Ser Ala Ser Ser Ala Glu Ser Gln Asp Ser Lys Lys
   1715                1720                1725

Lys Lys Lys Lys Lys Glu Lys Lys Lys His Lys Lys His Lys Lys
   1730                1735                1740

His Lys Lys His Lys Lys His Ala Gly Thr Glu Val Glu Leu Glu
   1745                1750                1755

Lys Ser Gln Lys His Lys Lys Lys Lys Lys Ser Lys Lys Asn
   1760                1765                1770

Lys Asp Lys Glu Lys Glu Lys Glu Lys Asp Asp Gln Lys Val Lys
   1775                1780                1785

Ser Val Thr Val
   1790

<210> SEQ ID NO 15
<211> LENGTH: 469
<212> TYPE: PRT
<213> ORGANISM: Homo sapiens

<400> SEQUENCE: 15

Met Ala Ala Glu Ala Gly Val Val Gly Ala Gly Ala Ser Pro Asp Gly
1               5                   10                  15

Asp Trp Arg Asp Gln Ala Cys Gly Leu Leu His Val His Leu Ser
                20                  25                  30

Ser Arg Leu Gly Arg Ala Ala Pro Val Arg Thr Gly Arg His Leu Arg
            35                  40                  45

Thr Val Phe Glu Asp Thr Val Glu Glu Arg Val Ile Asn Glu Glu Tyr
        50                  55                  60

Lys Ile Trp Lys Lys Asn Thr Pro Phe Leu Tyr Asp Leu Val Met Thr
65                  70                  75                  80

His Ala Leu Gln Trp Pro Ser Leu Thr Val Gln Trp Leu Pro Glu Val
                85                  90                  95

Thr Lys Pro Glu Gly Lys Asp Tyr Ala Leu His Trp Leu Val Leu Gly
                100                 105                 110

Thr His Thr Ser Asp Glu Gln Asn His Leu Val Val Ala Arg Val His
            115                 120                 125

Ile Pro Asn Asp Asp Ala Gln Phe Asp Ala Ser His Cys Asp Ser Asp
        130                 135                 140

Lys Gly Glu Phe Gly Gly Phe Gly Ser Val Thr Gly Lys Ile Glu Cys

```
            145                 150                 155                 160
Glu Ile Lys Ile Asn His Glu Gly Glu Val Asn Arg Ala Arg Tyr Met
                165                 170                 175
Pro Gln Asn Pro His Ile Ile Ala Thr Lys Thr Pro Ser Ser Asp Val
                180                 185                 190
Leu Val Phe Asp Tyr Thr Lys His Pro Ala Lys Pro Asp Pro Ser Gly
                195                 200                 205
Glu Cys Asn Pro Asp Leu Arg Leu Arg Gly His Gln Lys Glu Gly Tyr
            210                 215                 220
Gly Leu Ser Trp Asn Ser Asn Leu Ser Gly His Leu Leu Ser Ala Ser
225                 230                 235                 240
Asp Asp His Thr Val Cys Leu Trp Asp Ile Asn Ala Gly Pro Lys Glu
                245                 250                 255
Gly Lys Ile Val Asp Ala Lys Ala Ile Phe Thr Gly His Ser Ala Val
                260                 265                 270
Val Glu Asp Val Ala Trp His Leu Leu His Glu Ser Leu Phe Gly Ser
                275                 280                 285
Val Ala Asp Asp Gln Lys Leu Met Ile Trp Asp Thr Arg Ser Asn Thr
            290                 295                 300
Thr Ser Lys Pro Ser His Leu Val Asp Ala His Thr Ala Glu Val Asn
305                 310                 315                 320
Cys Leu Ser Phe Asn Pro Tyr Ser Glu Phe Ile Leu Ala Thr Gly Ser
                325                 330                 335
Ala Asp Lys Thr Val Ala Leu Trp Asp Leu Arg Asn Leu Lys Leu Lys
                340                 345                 350
Leu His Thr Phe Glu Ser His Lys Asp Glu Ile Phe Gln Val His Trp
                355                 360                 365
Ser Pro His Asn Glu Thr Ile Leu Ala Ser Ser Gly Thr Asp Arg Arg
            370                 375                 380
Leu Asn Val Trp Asp Leu Ser Lys Ile Gly Glu Glu Gln Ser Ala Glu
385                 390                 395                 400
Asp Ala Glu Asp Gly Pro Pro Glu Leu Leu Phe Ile His Gly Gly His
                405                 410                 415
Thr Ala Lys Ile Ser Asp Phe Ser Trp Asn Pro Asn Glu Pro Trp Val
                420                 425                 430
Ile Cys Ser Val Ser Glu Asp Asn Ile Met Gln Ile Trp Gln Met Ala
                435                 440                 445
Glu Asn Ile Tyr Asn Asp Glu Glu Ser Asp Val Thr Thr Ser Glu Leu
            450                 455                 460
Glu Gly Gln Gly Ser
465

<210> SEQ ID NO 16
<211> LENGTH: 482
<212> TYPE: PRT
<213> ORGANISM: Homo sapiens

<400> SEQUENCE: 16

Met Ala Gln Thr Gln Gly Thr Arg Arg Lys Val Cys Tyr Tyr Tyr Asp
1               5                   10                  15

Gly Asp Val Gly Asn Tyr Tyr Gly Gln Gly His Pro Met Lys Pro
            20                  25                  30

His Arg Ile Arg Met Thr His Asn Leu Leu Leu Asn Tyr Gly Leu Tyr
            35                  40                  45
```

-continued

```
Arg Lys Met Glu Ile Tyr Arg Pro His Lys Ala Asn Ala Glu Glu Met
    50              55              60
Thr Lys Tyr His Ser Asp Asp Tyr Ile Lys Phe Leu Arg Ser Ile Arg
65              70              75              80
Pro Asp Asn Met Ser Glu Tyr Ser Lys Gln Met Gln Arg Phe Asn Val
                85              90              95
Gly Glu Asp Cys Pro Val Phe Asp Gly Leu Phe Glu Phe Cys Gln Leu
            100             105             110
Ser Thr Gly Gly Ser Val Ala Ser Ala Val Lys Leu Asn Lys Gln Gln
            115             120             125
Thr Asp Ile Ala Val Asn Trp Ala Gly Gly Leu His His Ala Lys Lys
130             135             140
Ser Glu Ala Ser Gly Phe Cys Tyr Val Asn Asp Ile Val Leu Ala Ile
145             150             155             160
Leu Glu Leu Leu Lys Tyr His Gln Arg Val Leu Tyr Ile Asp Ile Asp
                165             170             175
Ile His His Gly Asp Gly Val Glu Glu Ala Phe Tyr Thr Thr Asp Arg
            180             185             190
Val Met Thr Val Ser Phe His Lys Tyr Gly Glu Tyr Phe Pro Gly Thr
            195             200             205
Gly Asp Leu Arg Asp Ile Gly Ala Gly Lys Gly Lys Tyr Tyr Ala Val
210             215             220
Asn Tyr Pro Leu Arg Asp Gly Ile Asp Asp Glu Ser Tyr Glu Ala Ile
225             230             235             240
Phe Lys Pro Val Met Ser Lys Val Met Glu Met Phe Gln Pro Ser Ala
                245             250             255
Val Val Leu Gln Cys Gly Ser Asp Ser Leu Ser Gly Asp Arg Leu Gly
            260             265             270
Cys Phe Asn Leu Thr Ile Lys Gly His Ala Lys Cys Val Glu Phe Val
            275             280             285
Lys Ser Phe Asn Leu Pro Met Leu Met Leu Gly Gly Gly Gly Tyr Thr
    290             295             300
Ile Arg Asn Val Ala Arg Cys Trp Thr Tyr Glu Thr Ala Val Ala Leu
305             310             315             320
Asp Thr Glu Ile Pro Asn Glu Leu Pro Tyr Asn Asp Tyr Phe Glu Tyr
                325             330             335
Phe Gly Pro Asp Phe Lys Leu His Ile Ser Pro Ser Asn Met Thr Asn
            340             345             350
Gln Asn Thr Asn Glu Tyr Leu Glu Lys Ile Lys Gln Arg Leu Phe Glu
            355             360             365
Asn Leu Arg Met Leu Pro His Ala Pro Gly Val Gln Met Gln Ala Ile
370             375             380
Pro Glu Asp Ala Ile Pro Glu Glu Ser Gly Asp Glu Asp Glu Asp Asp
385             390             395             400
Pro Asp Lys Arg Ile Ser Ile Cys Ser Ser Asp Lys Arg Ile Ala Cys
                405             410             415
Glu Glu Glu Phe Ser Asp Ser Glu Glu Gly Glu Gly Gly Arg Lys
            420             425             430
Asn Ser Ser Asn Phe Lys Lys Ala Lys Arg Val Lys Thr Glu Asp Glu
            435             440             445
Lys Glu Lys Asp Pro Glu Glu Lys Lys Glu Val Thr Glu Glu Glu Lys
450             455             460
Thr Lys Glu Glu Lys Pro Glu Ala Lys Gly Val Lys Glu Glu Val Lys
```

<210> SEQ ID NO 17
<211> LENGTH: 488
<212> TYPE: PRT
<213> ORGANISM: Homo sapiens

<400> SEQUENCE: 17

```
Met Ala Tyr Ser Gln Gly Gly Lys Lys Val Cys Tyr Tyr
1               5                   10                  15

Asp Gly Asp Ile Gly Asn Tyr Tyr Gly Gln Gly His Pro Met Lys
            20                  25                  30

Pro His Arg Ile Arg Met Thr His Asn Leu Leu Leu Asn Tyr Gly Leu
        35                  40                  45

Tyr Arg Lys Met Glu Ile Tyr Arg Pro His Lys Ala Thr Ala Glu Glu
    50                  55                  60

Met Thr Lys Tyr His Ser Asp Glu Tyr Ile Lys Phe Leu Arg Ser Ile
65                  70                  75                  80

Arg Pro Asp Asn Met Ser Glu Tyr Ser Lys Gln Met Gln Arg Phe Asn
                85                  90                  95

Val Gly Glu Asp Cys Pro Val Phe Asp Gly Leu Phe Glu Phe Cys Gln
            100                 105                 110

Leu Ser Thr Gly Gly Ser Val Ala Gly Ala Val Lys Leu Asn Arg Gln
        115                 120                 125

Gln Thr Asp Met Ala Val Asn Trp Ala Gly Gly Leu His His Ala Lys
    130                 135                 140

Lys Ser Glu Ala Ser Gly Phe Cys Tyr Val Asn Asp Ile Val Leu Ala
145                 150                 155                 160

Ile Leu Glu Leu Leu Lys Tyr His Gln Arg Val Leu Tyr Ile Asp Ile
                165                 170                 175

Asp Ile His His Gly Asp Gly Val Glu Glu Ala Phe Tyr Thr Thr Asp
            180                 185                 190

Arg Val Met Thr Val Ser Phe His Lys Tyr Gly Glu Tyr Phe Pro Gly
        195                 200                 205

Thr Gly Asp Leu Arg Asp Ile Gly Ala Gly Lys Gly Lys Tyr Tyr Ala
    210                 215                 220

Val Asn Phe Pro Met Arg Asp Gly Ile Asp Asp Glu Ser Tyr Gly Gln
225                 230                 235                 240

Ile Phe Lys Pro Ile Ile Ser Lys Val Met Glu Met Tyr Gln Pro Ser
                245                 250                 255

Ala Val Val Leu Gln Cys Gly Ala Asp Ser Leu Ser Gly Asp Arg Leu
            260                 265                 270

Gly Cys Phe Asn Leu Thr Val Lys Gly His Ala Lys Cys Val Glu Val
        275                 280                 285

Val Lys Thr Phe Asn Leu Pro Leu Leu Met Leu Gly Gly Gly Gly Tyr
    290                 295                 300

Thr Ile Arg Asn Val Ala Arg Cys Trp Thr Tyr Glu Thr Ala Val Ala
305                 310                 315                 320

Leu Asp Cys Glu Ile Pro Asn Glu Leu Pro Tyr Asn Asp Tyr Phe Glu
                325                 330                 335

Tyr Phe Gly Pro Asp Phe Lys Leu His Ile Ser Pro Ser Asn Met Thr
            340                 345                 350

Asn Gln Asn Thr Pro Glu Tyr Met Glu Lys Ile Lys Gln Arg Leu Phe
```

```
                355                 360                 365
Glu Asn Leu Arg Met Leu Pro His Ala Pro Gly Val Gln Met Gln Ala
            370                 375                 380
Ile Pro Glu Asp Ala Val His Glu Asp Ser Gly Asp Glu Asp Gly Glu
385                 390                 395                 400
Asp Pro Asp Lys Arg Ile Ser Ile Arg Ala Ser Asp Lys Arg Ile Ala
                405                 410                 415
Cys Asp Glu Glu Phe Ser Asp Ser Glu Asp Glu Gly Glu Gly Gly Arg
            420                 425                 430
Arg Asn Val Ala Asp His Lys Lys Gly Ala Lys Lys Ala Arg Ile Glu
            435                 440                 445
Glu Asp Lys Lys Glu Thr Glu Asp Lys Lys Thr Asp Val Lys Glu Glu
            450                 455                 460
Asp Lys Ser Lys Asp Asn Ser Gly Glu Lys Thr Asp Thr Lys Gly Thr
465                 470                 475                 480
Lys Ser Glu Gln Leu Ser Asn Pro
                485

<210> SEQ ID NO 18
<211> LENGTH: 430
<212> TYPE: PRT
<213> ORGANISM: Homo sapiens

<400> SEQUENCE: 18

Met Ala Ala Asn Met Tyr Arg Val Gly Asp Tyr Val Tyr Phe Glu Asn
1               5                   10                  15
Ser Ser Ser Asn Pro Tyr Leu Ile Arg Arg Ile Glu Glu Leu Asn Lys
            20                  25                  30
Thr Ala Asn Gly Asn Val Glu Ala Lys Val Val Cys Phe Tyr Arg Arg
        35                  40                  45
Arg Asp Ile Ser Ser Thr Leu Ile Ala Leu Ala Asp Lys His Ala Thr
    50                  55                  60
Leu Ser Val Cys Tyr Lys Ala Gly Pro Gly Ala Asp Asn Gly Glu Glu
65                  70                  75                  80
Gly Glu Ile Glu Glu Glu Met Glu Asn Pro Glu Met Val Asp Leu Pro
                85                  90                  95
Glu Lys Leu Lys His Gln Leu Arg His Arg Glu Leu Phe Leu Ser Arg
            100                 105                 110
Gln Leu Glu Ser Leu Pro Ala Thr His Ile Arg Gly Lys Cys Ser Val
        115                 120                 125
Thr Leu Leu Asn Glu Thr Glu Ser Leu Lys Ser Tyr Leu Glu Arg Glu
    130                 135                 140
Asp Phe Phe Tyr Ser Leu Val Tyr Asp Pro Gln Gln Lys Thr Leu Leu
145                 150                 155                 160
Leu Ala Asp Lys Gly Glu Ile Arg Val Gly Asn Arg Tyr Gln Ala Asp
                165                 170                 175
Ile Thr Asp Leu Leu Lys Glu Gly Glu Asp Gly Arg Asp Gln Ser Arg
            180                 185                 190
Arg Leu Glu Thr Gln Val Trp Glu Ala His Asn Pro Leu Thr Asp Lys
        195                 200                 205
Gln Ile Asp Gln Phe Leu Val Val Ala Arg Ser Val Gly Thr Phe Ala
    210                 215                 220
Arg Ala Leu Asp Cys Ser Ser Ser Val Arg Gln Pro Ser Leu His Met
225                 230                 235                 240
```

Ser Ala Ala Ala Ser Arg Asp Ile Thr Leu Phe His Ala Met Asp
                245                 250                 255

Thr Leu His Lys Asn Ile Tyr Asp Ile Ser Lys Ala Ile Ser Ala Leu
            260                 265                 270

Val Pro Gln Gly Gly Pro Val Leu Cys Arg Asp Glu Met Glu Glu Trp
        275                 280                 285

Ser Ala Ser Glu Ala Asn Leu Phe Glu Glu Ala Leu Glu Lys Tyr Gly
    290                 295                 300

Lys Asp Phe Thr Asp Ile Gln Gln Asp Phe Leu Pro Trp Lys Ser Leu
305                 310                 315                 320

Thr Ser Ile Ile Glu Tyr Tyr Tyr Met Trp Lys Thr Thr Asp Arg Tyr
                325                 330                 335

Val Gln Gln Lys Arg Leu Lys Ala Ala Glu Ala Glu Ser Lys Leu Lys
            340                 345                 350

Gln Val Tyr Ile Pro Asn Tyr Asn Lys Pro Asn Pro Asn Gln Ile Ser
        355                 360                 365

Val Asn Asn Val Lys Ala Gly Val Val Asn Gly Thr Gly Ala Pro Gly
    370                 375                 380

Gln Ser Pro Gly Ala Gly Arg Ala Cys Glu Ser Cys Tyr Met Ser Ser
385                 390                 395                 400

Leu Arg Ile Leu Leu Asp Ile Leu Glu Glu Ile Trp Trp Leu Glu Asn
                405                 410                 415

Ala Asn Pro Val Arg Trp Arg Glu Ala Arg Thr Lys Pro Gln
            420                 425                 430

<210> SEQ ID NO 19
<211> LENGTH: 668
<212> TYPE: PRT
<213> ORGANISM: Homo sapiens

<400> SEQUENCE: 19

Met Ala Ala Asn Met Tyr Arg Val Gly Asp Tyr Val Tyr Phe Glu Asn
1               5                   10                  15

Ser Ser Ser Asn Pro Tyr Leu Val Arg Arg Ile Glu Glu Leu Asn Lys
                20                  25                  30

Thr Ala Asn Gly Asn Val Glu Ala Lys Val Val Cys Leu Phe Arg Arg
            35                  40                  45

Arg Asp Ile Ser Ser Ser Leu Asn Ser Leu Ala Asp Ser Asn Ala Arg
        50                  55                  60

Glu Phe Glu Glu Glu Ser Lys Gln Pro Gly Val Ser Glu Gln Gln Arg
65                  70                  75                  80

His Gln Leu Lys His Arg Glu Leu Phe Leu Ser Arg Gln Phe Glu Ser
                85                  90                  95

Leu Pro Ala Thr His Ile Arg Gly Lys Cys Ser Val Thr Leu Leu Asn
            100                 105                 110

Glu Thr Asp Ile Leu Ser Gln Tyr Leu Glu Lys Glu Asp Cys Phe Phe
        115                 120                 125

Tyr Ser Leu Val Phe Asp Pro Val Gln Lys Thr Leu Leu Ala Asp Gln
    130                 135                 140

Gly Glu Ile Arg Val Gly Cys Lys Tyr Gln Ala Glu Ile Pro Asp Arg
145                 150                 155                 160

Leu Val Glu Gly Glu Ser Asp Asn Arg Asn Gln Gln Lys Met Glu Met
                165                 170                 175

Lys Val Trp Asp Pro Asp Asn Pro Leu Thr Asp Arg Gln Ile Asp Gln
            180                 185                 190

```
Phe Leu Val Val Ala Arg Ala Val Gly Thr Phe Ala Arg Ala Leu Asp
            195                 200                 205

Cys Ser Ser Ser Ile Arg Gln Pro Ser Leu His Met Ser Ala Ala Ala
210                 215                 220

Ala Ser Arg Asp Ile Thr Leu Phe His Ala Met Asp Thr Leu Gln Arg
225                 230                 235                 240

Asn Gly Tyr Asp Leu Ala Lys Ala Met Ser Thr Leu Val Pro Gln Gly
                245                 250                 255

Gly Pro Val Leu Cys Arg Asp Glu Met Glu Glu Trp Ser Ala Ser Glu
                260                 265                 270

Ala Met Leu Phe Glu Glu Ala Leu Glu Lys Tyr Gly Lys Asp Phe Asn
            275                 280                 285

Asp Ile Arg Gln Asp Phe Leu Pro Trp Lys Ser Leu Ala Ser Ile Val
290                 295                 300

Gln Phe Tyr Tyr Met Trp Lys Thr Thr Asp Arg Tyr Ile Gln Gln Lys
305                 310                 315                 320

Arg Leu Lys Ala Ala Glu Ala Asp Ser Lys Leu Lys Gln Val Tyr Ile
                325                 330                 335

Pro Thr Tyr Thr Lys Pro Asn Pro Asn Gln Ile Ile Ser Val Gly Ser
                340                 345                 350

Lys Pro Gly Met Asn Gly Ala Gly Phe Gln Lys Gly Leu Thr Cys Glu
            355                 360                 365

Ser Cys His Thr Thr Gln Ser Ala Gln Trp Tyr Ala Trp Gly Pro Pro
            370                 375                 380

Asn Met Gln Cys Arg Leu Cys Ala Ser Cys Trp Ile Tyr Trp Lys Lys
385                 390                 395                 400

Tyr Gly Gly Leu Lys Thr Pro Thr Gln Leu Glu Gly Ala Thr Arg Gly
                405                 410                 415

Thr Thr Glu Pro His Ser Arg Gly His Leu Ser Arg Pro Glu Ala Gln
                420                 425                 430

Ser Leu Ser Pro Tyr Thr Thr Ser Ala Asn Arg Ala Lys Leu Leu Ala
            435                 440                 445

Lys Asn Arg Gln Thr Phe Leu Leu Gln Thr Thr Lys Leu Thr Arg Leu
            450                 455                 460

Ala Arg Arg Met Cys Arg Asp Leu Leu Gln Pro Arg Arg Ala Ala Arg
465                 470                 475                 480

Arg Pro Tyr Ala Pro Ile Asn Ala Asn Ala Ile Lys Ala Glu Cys Ser
                485                 490                 495

Ile Arg Leu Pro Lys Ala Ala Lys Thr Pro Leu Lys Ile His Pro Leu
                500                 505                 510

Val Arg Leu Pro Leu Ala Thr Ile Val Lys Asp Leu Val Ala Gln Ala
            515                 520                 525

Pro Leu Lys Pro Lys Thr Pro Arg Gly Thr Lys Thr Pro Ile Asn Arg
530                 535                 540

Asn Gln Leu Ser Gln Asn Arg Gly Leu Gly Ile Met Val Lys Arg
545                 550                 555                 560

Ala Tyr Glu Thr Met Ala Gly Ala Gly Val Pro Phe Ser Ala Asn Gly
                565                 570                 575

Arg Pro Leu Ala Ser Gly Ile Arg Ser Ser Gln Pro Ala Ala Lys
                580                 585                 590

Arg Gln Lys Leu Asn Pro Ala Asp Ala Pro Asn Pro Val Val Phe Val
            595                 600                 605
```

```
Ala Thr Lys Asp Thr Arg Ala Leu Arg Lys Ala Leu Thr His Leu Glu
610                 615                 620

Met Arg Arg Ala Ala Arg Arg Pro Asn Leu Pro Leu Lys Val Lys Pro
625                 630                 635                 640

Thr Leu Ile Ala Val Arg Pro Pro Val Pro Leu Pro Ala Pro Ser His
                645                 650                 655

Pro Ala Ser Thr Asn Glu Pro Ile Val Leu Glu Asp
            660                 665

<210> SEQ ID NO 20
<211> LENGTH: 19296
<212> TYPE: DNA
<213> ORGANISM: Homo sapiens

<400> SEQUENCE: 20
ccttcagttc ttaaagcgct gcaattcgct gctgcagcca tatttcttac tctctcgggg    60
ctggaagctt cctgactgaa gatctctctg cacttggggt tctttctaga acattttcta   120 gtccccaac  acccttatg  gcgtatttct taaaaaaat  cacctaaatt ccataaaata   180
tttttttaaa ttctatactt tctcctagtg tcttcttgac acgtcctcca tatttttta    240 aagaaagtat ttggaatatt tgaggcaat  ttttaatatt taaggaattt ttctttggaa   300 tcattttttgg ttgacatctc tgttttttgt ggatcagttt tttactcttc cactctcttt  360
tctatatttt gcccatcggg gctgcggata cctggtttta ttatttttc  tttgcccaac   420 ggggccgtgg atacctgcct tttaattctt tttattcgc  ccatcggggc cgcggatacc   480 tgcttttat  tttttttcc  ttagcccatc ggggtatcgg atacctgctg attcccttcc   540
cctctgaacc cccaacactc tggcccatcg gggtgacgga tatctgcttt ttaaaaattt   600 tcttttttg  gcccatcggg gcttcggata cctgcttttt tttttttttat ttttccttgc  660 ccatcgggc  ctcggatacc tgctttaatt tttgttttc  tggcccatcg gggccgcgga   720 tacctgctttt gatttttttt tttcatcgcc catcggtgct tttatggat  gaaaaaatgt   780 tggttttgtg ggttgttgca ctctctggaa tatctacact ttttttttgct gctgatcatt   840 tggtggtgtg tgagtgtacc taccgctttg gcagagaatg actctgcagt taagctaagg   900
gcgtgttcag attgtggagg aaaagtggcc gccattttag acttgccgca taactcggct   960
tagggctagt cgtttgtgct aagttaaact agggaggcaa gatggatgat agcaggtcag  1020
gcagaggaag tcatgtgcat tgcatgagct aaacctatct gaatgaattg atttggggct  1080
tgttaggagc tttgcgtgat tgttgtatcg ggaggcagta agaatcatct tttatcagta  1140
caagggacta gttaaaaatg aaggttagg  aaagactaag gtgcagggct taaaatggcg  1200
attttgacat tgcggcattg ctcagcatgg cgggctgtgc tttgttaggt tgtccaaaat  1260
ggcggatcca gttctgtcgc agtgttcaag tggcgggaag gccacatcat gatgggcgag  1320
gctttgttaa gtggttagca tggtggtgga catgtgcggt cacacaggaa agatggcgg   1380 ctgaaggtct tgccgcagtg taaaacatgg cgggcctctt tgtctttgct gtgtgctttt  1440
cgtgttgggt tttgccgcag ggacaatatg gcaggcgttg tcatatgtat atcatggctt  1500
ttgtcacgtg gacatcatgg cgggcttgcc gcattgttaa agatggcggg ttttgccgcc  1560
tagtgccacg cagagcggga gaaaaggtgg gatggacagt gctggattgc tgcataaccc  1620
aaccaattag aaatgggggt ggaattgatc acagccaatt agagcagaag atggaattag  1680
actgatgaca cactgtccag ctactcagcg aagacctggg tgaattagca tggcacttcg  1740
cagctgtctt tagccagtca ggagaaagaa gtggaggggc cacgtgtatg tctcccagtg  1800
```

```
ggcggtacac caggtgtttt caaggtctttt tcaaggacat ttagcctttc cacctctgtc   1860
ccctcttatt tgtcccctcc tgtccagtgc tgcctcttgc agtgctggat atctggctgt   1920
gtggtctgaa cctccctcca ttcctctgta ttggtgcctc acctaaggct aagtatacct   1980
ccccccccac ccccaacccc cccaactcc ccaccccac ccccaccccc ccacctcccc    2040
acccccctac cccctaccc ccctaccccc ctctggtctg ccctgcactg cactgttgcc   2100
atgggcagtg ctccaggcct gcttggtgtg gacatggtgg tgagccgtgg caaggaccag   2160
aatggatcac agatgatcgt tggccaacag gtggcagaag aggaattcct gccttcctca   2220
agaggaacac ctaccccttg gctaatgctg gggtcggatt ttgatttata tttatctttt   2280
ggatgtcagt catacagtct gattttgtgg tttgctagtg tttgaattta agtcttaagt   2340
gactattata gaaatgtatt aagaggcttt atttgtagaa ttcactttaa ttacatttaa   2400
tgagttttg ttttgagttc cttaaaattc cttaaagttt ttagcttctc attacaaatt   2460
ccttaacctt tttttggcag tagatagtca aagtcaaatc atttctaatg ttttaaaaat   2520
gtgctggtca ttttctttga aattgactta actattttcc tttgaagagt ctgtagcaca   2580
gaaacagtaa aaaatttaac ttcatgacct aatgtaaaaa agagtgtttg aaggtttaca   2640
caggtccagg ccttgctttg ttcccatcct tgatgctgca ctaattgact aatcacctac   2700
ttatcagaca ggaaacttga attgctgtgg tctggtgtcc tctattcaga cttattatat   2760
tggagtattt caattttcg ttgtatcctg cctgcctagc atccagttcc tccccagccc    2820
tgctcccagc aaaccctag tctagcccca gccctactcc caccccgccc cagccctgcc   2880
ccagccccag tcccctaacc ccccagccct agccccagtc ccagtcctag ttcctcagtc   2940
ccgcccagct tctctcgaaa gtcactctaa ttttcattga ttcagtgctc aaaataagtt   3000
gtccattgct tatcctatta tactgggata ttccgtttac ccttggcatt gctgatcttc   3060
agtactgact ccttgaccat tttcagttaa tgcatacaat cccatttgtc tgtgatctca   3120
ggacaaagaa tttccttact cggtacgttg aagttaggga atgtcaattg agagctttct   3180
atcagagcat tattgcccac aatttgagtt acttatcatt ttctcgatcc cctgcccttta  3240
aaggagaaac catttctctg tcattgcttc tgtagtcaca gtcccaattt tgagtagtga   3300
tcttttcttg tgtactgtgt tggccaccta aaactctttg cattgagtaa aattctaatt   3360
gccaataatc ctacccattg gattagacag cactctgaac cccatttgca ttcagcaggg   3420
ggtcgcagac aacccgtctt ttgttggaca gttaaaatgc tcagtcccaa ttgtcatagc   3480
tttgcctatt aaacaaaggc accctactgc gcttttttgct gtgcttctgg agaatcctgc   3540
tgttcttgga caattaaaga acaaagtagt aattgctaat tgtctcaccc attaatcatg   3600
aagactacca gtcgcccttg catttgcctt gaggcagcgc tgactacctg agatttaaga   3660
gtttcttaaa ttattgagta aaatcccaat tatccatagt tctgttagtt acactatggc   3720
ctttgcaaac atctttgcat aacagcagtg ggactgactc attcttagag ccccttccct   3780
tggaatatta atggatacaa tagtaattat tcatggttct gcgtaacaga gaagacccac   3840
ttatgtgtat gcctttatca ttgctcctag atagtgtgaa ctacctacca ccttgcatta   3900
atatgtaaaa cactaattgc ccatagtccc actcattagt ctaggatgtc ctctttgcca   3960
ttgctgctga gttctgacta cccaagtttc cttctcttaa acagttgata tgcataattg   4020
catatattca tggttctgtg caataaaaat ggattctcac cccatcccac cttctgtggg   4080
atgttgctaa cgagtgcaga ttattcaata acagctcttg aacagttaat ttgcacagtt   4140
```

```
gcaattgtcc agagtcctgt ccattagaaa gggactctgt atcctatttg cacgctacaa    4200
tgtgggctga tcacccaagg actcttcttg tgcattgatg ttcataattg tatttgtcca    4260
cgatcttgtg cactaaccct tccactccct ttgtattcca gcaggggacc cttactactc    4320
aagacctctg tactaggaca gtttatgtgc acaatcctaa ttgattagaa ctgagtcttt    4380
tatatcaagg tccctgcatc atctttgctt tacatcaaga gggtgctggt tacctaatgc    4440
ccctcctcca gaaattattg atgtgcaaaa tgcaatttcc ctatctgctg ttagtctggg    4500
gtctcatccc ctcatattcc ttttgtctta cagcaggggg tacttgggac tgttaatgcg    4560
cataattgca attatggtct tttccattaa attaagatcc caactgctca caccctctta    4620
gcattacagt agagggtgct aatcacaagg acatttcttt tgtactgtta atgtgctact    4680
tgcatttgtc cctcttcctg tgcactaaag accccactca cttccctagt gttcagcagt    4740
ggatgacctc tagtcaagac cttttgcacta ggatagttaa tgtgaaccat ggcaactgat    4800
cacaacaatg tctttcagat cagatccatt ttatcctcct tgttttacag caagggatat    4860
taattaccta tgttaccttt ccctgggact atgaatgtgc aaaattccaa tgttcatggt    4920
ctctcccttt aaacctatat tctacccctt ttacattata gaaagggatg ctggaaaccc    4980
agagtccttc tcttgggact cttaatgtgt atttctaatt atccatgact cttaatgtgc    5040
atattttcaa ttgcctaatt gatttcaatt gtctaagaca tttcaaatgt ctaattgatt    5100
agaactgagt cttttatatc aagctaatat ctagctttta tatcaagcta atatcttgac    5160
ttctcagcat catagaaggg ggtactgatt tcctaaagtc tttcttgaat ttctattatg    5220
caaaattgcc ctgaggccgg gtgtggtggc tcacacctgt aatcccagca ctttgggagg    5280
ctgaggtggg aagatccctt actgccagga gtttgagacc agcctggcca acattaaaaa    5340
aaaaaaaaag taagacaatt gccctggaat cccatccccc tcacacctcc ttggcaaagc    5400
agcaggagtg ctaactagct agtgcttctt ctcttatact gcttaaatgc gcataattag    5460
cagtagttga tgtgccccta tgttagagta gaatcccgct tccttgctcc atttgcatta    5520
ctgcaggagc ttctaactag cctgaattca ctctcttgga ctgttaatgt gcatacttat    5580
atttgctgct gtacttttt accatgtaag gaccccaccc actgtattta catcccagct    5640
ggaagtacct actacttaag acccttagac tagtaaagtt agcgtgcata atcttaggtg    5700
ttatatacac attttcagtt gcatacagtt gtgcctttta tcaggactcc tgtacttatc    5760
aaagcagaga gtgctaatca atattaagcc cttctcttcg aactgtagat ggcatgtaat    5820
tgcagttgtc aatggtcctt caattagact tgggtttctg acctatcaca ccctctttgc    5880
tttattgcat ggggtactat tcacttaagg ccccctttctc aaactgttaa tgtgcctaat    5940
gacaattaca tcagtatcct tccttttgaa ggacagcatg gttggtgaca cctaaggccc    6000
catttcttgg cctcccaata tgtgtgattg tatttgtcga ggttgctatg cactagagaa    6060
ggaaagtgct cccctcatcc ccacttttcc cttccagcag gaagtgccca ccccataaga    6120
cccttttatt tggagagtct aggtgcacaa ttgtaagtga ccacaagcat gcatcttgga    6180
catttatgtg cgtaatcgca cactgctcat tccatgtgaa taaggtccta ctctccgacc    6240
ccttttgcaa tacagaaggg ttgctgataa cgcagtcccc ttttcttggc atgttgtgtg    6300
tgattataat cgtctgggat cctatgcact agaaaaggag ggtcctctcc acatacctca    6360
gtctcacctt tcccttccag cagggagtgc ccactccata agactctcac atttggacag    6420
tcaaggtgcg taattgttaa gtgaacacaa ccatgcacct tagacatgga tttgcataac    6480
tacacacagc tcaacctatc tgaataaaat cctactctca gaccccttttt gcagtacagc    6540
```

```
aggggtgctg atcaccaagg cccttttcc tggcctggta tgcgtgtgat tatgtttgtc    6600
ccggttcctg tgtattagac atggaagcct cccctgccac actccacccc caatcttcct    6660
ttcccttccg gcagggagtg ccctctccat aagacgctta cgtttggaca atcaaggtgc    6720
acagttgtaa gtgaccacag gcatacacct tggacattaa tgtgcataac cactttgccc    6780
attccatctg aataaggtcc tactctcaga cccttttgc agtacagcag gggtgctgat    6840
caccaaggcc cctttcttg gcctgttatg tgcgtgatta tatttgtctg ggttcctgtg    6900
tattagacaa ggaagccttc ccccgcccc cacccccact cccagtcttc ctttccttc    6960
cagcagggag tgcccctcc ataagatcat tacatttgga caatcaaggt gcacaattat    7020
aagtgaccac agccatgcac cttggacatt attggacatt aatgtgcgta actgcacatg    7080
gcccatccca tctgaataag gtcctactct cagatgccct tgcagtaca gcaggggtac    7140
tgaatcacca aggcccttt tcttggcctg ttatgtgtgt gattatattt atcccagttt    7200
ctgtgtaata gacatgaaag cctccctgc acacccccac ctccaatctt cctttccctt    7260
ccaccaggga gtgtccactc catataccct tacatttgga caatcaaggt gcacaattgt    7320
aagtgagcat aggcactcac cttggacatg aatgtgcata actgcacatg gcccatccca    7380
tctgaataag gtcctactct cagacccttt tgcagtaca gcagggggtgc tgatcaccaa    7440
ggccccttt cctggcctgt tatgtgtgtg attatatttg ttccagttcc tgtgtaatag    7500
acatggaagc ctcccctgcc acactccacc cccaatcttc ctttcccttc tggcaggaag    7560
tacccgctcc ataagaccct tacatttgga cagtcaaggt gcacaattgt atgtgaccac    7620
aaccatgcac cttggacata aatgtgtgta actgcacatg gcccatccca tctgaataag    7680
gtcctactct cagaccccttt tgcagtaca gtaggtgtgc tgataaccaa ggcccctctt    7740
cctggcctgt taacgtatgt gattatattt gtctgggttc cagtgtataa gacatggaag    7800
cctcccctgc cccaccccac cctcaatctt ctttccctt ctggcaggga gtgccagctc    7860
cataagaacc ttacatttgg acagtcaagg tgcacaattc taagtgaccg cagccatgca    7920
ccttggtcaa taatgtgtgt aactgcacac ggcctatctc atctgaataa ggccttactc    7980
tcagacccct tttgcagtac agcaggggtg ctgataacca aggcccattt tcctggcctg    8040
ttatgtgtgt gattatattt gtccaggttt ctgtgtacta gacaaggaag cctcctctgc    8100
cccatcccat ctacgcataa tctttctttt cctcccagca gggagtgctc actccataag    8160
acccttacat ttggacaatc aaggtgcaca attgtaagtg accacaacca tgcatcttgg    8220
aaatttatgt gcataactgc acatggctta tcctatttga ataaagtcct actctcagac    8280
ccctttgca gtatagctgg ggtgctgatc actgaggcct cttgcttgg cttgtctata    8340
ttcttgtgta ctagataagg gcaccttctc atggactccc tttgcttttc aacaaggagt    8400
acccactact tttaagatt cttatatttg tccaaagtac atggttttaa ttgaccacaa    8460
caatgtccct tggacattaa tgtatgtaat caccacatgg ttcatcctaa ttaaacaaag    8520
ttctaccttc tcaccctcca tttgcagtat accaggggttg ctgaccccct aagtcccctt    8580
ttcttggctt gttgacatgc ataattgcat ttatgttggt tcttgtgccc tagacaagga    8640
tgccccacct ctttcaata gtgggtgccc actcctttatg atctttacat ttgaacagtt    8700
aatgtgaata attgcagttg tccacaaccc tatcacttct aggaccatta tacctctttt    8760
gcattactgt ggggtatact gtttccctcc aaggcccctt ctggtggact atcaacatat    8820
aattgaaatt ttcttttgtc tttgtcagta gattaaggtc atacccccatc acctttcctt    8880
```

-continued

```
tgtagtacaa cagggtgtcc tgatcaacca aagtcctgtt gttttggact gttaatatgt      8940
gcaattacat ttgctcctga tctgtgcact agataaggat cctacctact ttcttagtgt      9000
ttttagcagg tagtgcccac tactcaagac tgtcacttgg aatgttcatg tgcacaaact      9060
caattctcta agcatgttcc tgtaccacct ttgctttaga gcaggggat gatattcact       9120
aagtgcccct tcttttggac ttaatatgca ttaatgcaat tgtccacctc ttcttttaga      9180
ctaagagttg atctccacat attcccttg catcaggggc atgttaatta tgaatgaacc       9240
cttttctttt aatattaatg tcataattgt atttgtggac ctgtgtagga gaaaaagacc      9300
ctatgttcct cccattaccc tttggattgc tgctgagaag tgttaactac tcataatctc      9360
agctcttgga caattaatag cattaataac aattatcaag ggcactgatc attagataag      9420
actcctgctt cctcgttgct tacatcgggg gtactgaccc actaaggccc cttgtactgt      9480
taatgtgaat atttgcaatt atatatgtct ccttctggta gagtgggata ttatgcccta      9540
gtatcccctt tgcattactg cagggctgc tgactactca aaacttctcc tgggactgtt       9600
aataggcaca atggcagtta tcaatggttt tctccctccc tgaccttgtt aagcaagcgc      9660
cccaccccac ccttagtttc ccatggcata ataaagtata agcattggag tattccatgc      9720
acttgtctat caaacagtgg tccatactcc caacccttt gcattgcgcc agtgtgtaaa       9780
atcacaggta gccatggtgt catgctttat atacgaagtc ttccctctct ctgccccttg      9840
tgtgcccttg gccccttttt acagactatt gctcacaatc tcaggtgtcc atatttgcag      9900
ctattaggta agattgtgct gtctccctct tcccttccct ctgccctgcc cttttgcct      9960
ctttgctggg taatgttgac cagacaaggc cctttctctt ggacttaaac aattctcagt     10020
tgcactttcc ttggtcccac ccattataca tgaacccctc tacttccttt cgcattgctt     10080
ctgagtatgc tgactaccca aagcccttc tgtgttatta ataaacacag tactgattgt      10140
cccatttttc agcccatcag tccaagatct ccctaccact ttggtgtgtt ggtgcagtgt     10200
tgactatgaa aagcaggcct gaactaggtg ataagcctt cactcatttt ctttcattta      10260
ttaatgatcc tagtttcaat tattgtcaga ttctggggac aagaaccatt cttgcccacc     10320
tgtgttactg ctttactgtg caaaatactg aaggcaagtc agacccaggg agctggattg     10380
ccatccttta ttttgtgttt ccagtgtaca ctataaaatt gtctccccag gaaggaaggt     10440
tggcactttc tctgcattct tctttccaga gcagattgcc tggttaagaa tctcttgttg     10500
tccccttttgt atattgttat tgtaaagtgc caaatgccag gatacagcca gaaaaattgc    10560
ttattattat taaaaaaatt tttttaagaa agacatctgg attgtagggt ggactcgata     10620
acctggtcat tatttttttg aagccaaaat atccatttat actatgtacc tggtgaccag    10680
tgtctctcat tttaactgag ggtggtgggt ctgtggatag aacactgact cttgctattt    10740
taatatcaaa gatattctag agtggaactc ttaagaccag tatctttgtg tgggctttac    10800
cagcattcac ttttagaaaa actacctaaa ttttataatc ctttaatttc ttcatctgga    10860
gcacctgccc ctacttattt caagaagatt gcagtaaaac gattaaatga gggaacatat    10920
gcagaggtgc ttttaaaaag catatgccac cttttttatt aattattata taaaatgaag    10980
catttaatta tagtaataat ttgaagtagt ttgaagtacc acactgaggt gaggacttaa    11040
aaatgataag acgagttccc tattttataa gaaaaataag ccaaaattaa atattctttt    11100
ggatataaat ttcaacagtg agatagctgc ctagtggaaa tgaataatat cccagccact    11160
agtgtacagg gtgttttgtg gcacaggatt atgtaatatg gaactgctca agcaaataac    11220
tagtcatcac aacagcagtt ctttgtaata actgaaaaag aatattgttt ctcggagaag    11280
```

```
gatgtcaaaa gatcggccca gctcagggag cagtttgccc tactagctcc tcggacagct    11340
gtaaagaaga gtctctggct ctttagaata ctgatcccat tgaagatacc acgctgcatg    11400
tgtccttagt agtcatgtct ccttaggctc ctcttggaca ttctgagcat gtgagacctg    11460
aggactgcaa acagctataa gaggctccaa attaatcata tctttccctt tgagaatctg    11520
gccaagctcc agctaatcta cttggatggg ttgccagcta tctggagaaa aagatcttcc    11580
tcagaagaat aggcttgttg ttttacagtg ttagtgatcc attccctttg acgatcccta    11640
ggtggagatg gggcatgagg atcctccagg ggaaaagctc actaccactg gcaacaacc     11700
ctaggtcagg aggttctgtc aagatacttt cctggtccca gataggaaga taaagtctca    11760
aaaacaacca ccacacgtca agctcttcat tgttcctatc tgccaaatca ttatacttcc    11820
tacaagcagt gcagagagct gagtcttcag caggtccaag aaatttgaac acactgaagg    11880
aagtcagcct tcccacctga agatcaacat gcctggcact ctagcacttg aggatagctg    11940
aatgaatgtg tatttctttg tctctttctt tcttgtcttt gctctttgtt ctctatctaa    12000
agtgtgtctt acccatttcc atgtttctct tgctaatttc tttcgtgtgt gcctttgcct    12060
cattttctct ttttgttcac aagagtggtc tgtgtcttgt cttagacata tctctcattt    12120
ttcattttgt tgctatttct ctttgctctc ctagatgtgg ctcttctttc acgctttatt    12180
tcatgtctcc tttttgggtc acatgctgtg tgctttttgt ccttttcttg ttctgtctac    12240
ctctcctttc tctgcctacc tctcttttct ctttgtgaac tgtgattatt tgttaccct     12300
tccccttctc gttcgtttta aatttcacct ttttctgag tctggcctcc tttctgctgt     12360
ttctacttt tatctcacat ttctcatttc tgcatttcct ttctgcctct cttgggctat     12420
tctctctctc ctccctgcg tgcctcagca tctcttgctg tttgtgattt tctatttcag     12480
tattaatctc tgttggcttg tatttgttct ctgcttcttc cctttctact cacctttgag    12540
tatttcagcc tcttcatgaa tctatctccc tctctttgat ttcatgtaat ctctccttaa    12600
atatttcttt gcatatgtgg gcaagtgtac gtgtgtgtgt gtcatgtgtg gcagaggggc    12660
ttcctaaccc ctgcctgata ggtgcagaac gtcggctatc agagcaagca ttgtggagcg    12720
gttccttatg ccaggctgcc atgtgagatg atccaagacc aaaacaaggc cctagactgc    12780
agtaaaaccc agaactcaag tagggcagaa ggtggaaggc tcatatggat agaaggccca    12840
aagtataaga cagatggttt gagacttgag acccgaggac taagatgaa agcccatgtt      12900
ccaagataga tagaagcctc aggcctgaaa ccaacaaaag cctcaagagc caagaaaaca    12960
gagggtggcc tgaattggac cgaaggcctg agttggatgg aagtctcaag gcttgagtta    13020
gaagtcttaa gacctgggac aggacacatg gaaggcctaa gaactgagac ttgtgacaca    13080
aggccaacga cctaagatta gcccagggtt gtagctggaa gacctacaac ccaaggatgg    13140
aaggcccctg tcacaaagcc tacctagatg gatagaggac ccaagcgaaa aaggtatctc    13200
aagactaacg gccggaatct ggaggcccat gacccagaac ccaggaagga tagaagcttg    13260
aagacctggg gaaatcccaa gatgagaacc ctaaacccta cctcttttct attgtttaca    13320
cttcttactc ttagatattt ccagttctcc tgtttatctt taagcctgat tcttttgaga    13380
tgtactttt gatgttgccg gttaccttta gattgacagt attatgcctg ggccagtctt      13440
gagccagctt taaatcacag cttttaccta tttgttaggc tatagtgttt tgtaaacttc    13500
tgtttctatt cacatcttct ccacttgaga gagacaccaa aatccagtca gtatctaatc    13560
tggcttttgt taacttccct caggagcaga cattcatata ggtgatactg tatttcagtc    13620
```

```
ctttcttttg accccagaag ccctagactg agaagataaa atggtcaggt tgttggggaa    13680
aaaaaagtgc caggctctct agagaaaaat gtgaagagat gctccaggcc aatgagaaga    13740
attagacaag aaatacacag atgtgccaga cttctgagaa gcacctgcca gcaacagctt    13800
ccttctttga gcttaggtga gcaggattct ggggtttggg atttctagtg atggttatgg    13860
aaagggtgac tgtgcctggg acaaagcgag gtcccaaggg gacagcctga actccctgct    13920
catagtagtg gccaaataat ttggtggact gtgccaacgc tactcctggg tttaataccc    13980
atctctaggc ttaaagatga gagaacctgg gactgttgag catgtttaat actttccttg    14040 attttttct tcctgtttat gtgggaagtt gatttaaatg actgataatg tgtatgaaag    14100
cactgtaaaa cataagagaa aaaccaatta gtgtattggc aatcatgcag ttaacatttg    14160
aaagtgcagt gtaaattgtg aagcattatg taaatcaggg gtccacagtt tttctgtaag    14220
gggtcaaatc ataaatactt tagactgtgg gccatatggt ttctgttaca tatttgtttt    14280
ttaaacaacg tttttataag gtcaaaatca ttcttagttt ttgagccaat tggatttggc    14340
ctgctgttca tagcttacca cccctgatg tattatttgt tattcagaga aaatttctga    14400
atactactag tttccttttc tgtgcctgtc cctgtgctag gcactaaaaa tgcaatgatt    14460
attgatatct aggtgacctg aaaaaaaata gtgaatgtgc tttgtaaact gtaaagcact    14520
tgtattctac tgtgataagc gttgtggata caaagaaagg agcaagcata aaaaagtgct    14580
ctttcaaaag gatatagtac tatgcagaca caaggaattg tttgataaat gaataaatta    14640
tatgtatatt tgaggccaat ttgtgtttgc tgctctggta attttgagta aaaatgcagt    14700
attccaggta tcagaaacga aaacacatgg aaactgcttt taaactttaa aatatactga    14760
aaacataagg gactaagctt gttgtggtca cctataatgt gccagatacc atgctgggtg    14820
ctagagctac caaggggga aaagtattct catagaacaa aaaatttcag aaaggtgcat    14880
attaaagtgc tttgtaaact aaagcatgat acaaatgtca atgggctaca tatttatgaa    14940
tgaatgaatg gatgaatgaa tattaagtgc ctcttacata ccagctattt tgggtactgt    15000
aaaatacaag attaattctc ctatgtaata agaggaaagt ttatcctcta tactattcag    15060
atgtaaggaa tgatatattg cttaattta aacaatcaag actttactgg tgaggttaag    15120
ttaaattatt actgatacat ttttccaggt aaccaggaaa gagctagtat gaggaaatga    15180
agtaatagat gtgagatcca gaccgaaagt cacttaattc agcttgcgaa tgtgcttct    15240 aaattataaa gcacttgtaa atgaaaaatt tgatgctttc tgtatgaata aactttctg    15300 taagctaggt attgtctcta caaaattctc attgtatagt taaccacag tgagaagggt    15360 tctataagta gttatacaaa ccaagggttt aaatacctgt taaatagatc aattttgatt    15420
gcctactatg tgaactcact gttaaaggca ctgaaaattt atcatatttc atttagccac    15480
agccaaaaat aaggcaatac ctatgttagc attttgtgaa ctctaaggca ccatataaat    15540
gtaactgttg atttttctcac ttggtgctgg gtactaggtt tataaaattg tatgatagtt    15600
attatattgt gcaaataaag taggaaaatt tgaataacaa tgattatctt ttgaatacgc    15660
atacgcaagg gattggttgt ctgaagaatg ccactatagt agttatctat tgtgtgccaa    15720
tctcattgct aggcattggg gatgcaaaga taaaccatct ttattgtgtc ttgggtagca    15780
gaagaaaata tgtgtaaaat caatttataa tttgtaaact gccacccata tataagctat    15840
atctgctgaa tgatcattga ttactcttat ccttagagat aacaactggg ggcacaaaca    15900
tttattatca ttattgaacc tacaacagag atctatgtgt agatttacaa agcctacagt    15960
tctatacaga taggaatgaa ctattggctt actgaatggt gattactttc tgtggggctc    16020
```

-continued

```
ggaactacat gccctaggat ataaaaatga tgttatcatt atagagtgct cacagaagga   16080
aatgaagtaa tataggtgtg agatccagac caaaagtcat ttaacaagtt tattcagtga   16140
tgaaaacatg ggacaaatgg actaatataa ggcagtgtac taagctgagt agagagataa   16200
agtcctgtcc agaagataca tgcttcctgg cctgattgag gagatggaaa atttttgcaa   16260
aaaacaaggt gttgtggtct tccatccagt ttcttaagtg ctgatgataa aagtgaatta   16320
gacccacctt gacctggcct acagaagtaa aggagtaaaa ataaatgcct caggcgtgct   16380
ttttgattca tttgataaac aaagcatctt ttatgtggaa tataccattc tgggtcctga   16440
ggataagaga gatgagggca ttagatcact gacagctgaa gatagaagaa catctttggt   16500
ttgattgttt aaataatatt tcaatgccta ttctctgcaa ggtactatgt ttcgtaaatt   16560
aaataggtct ggcccagaag acccactcaa ttgcctttga gattaaaaaa aaaaaaaaaa   16620
agaaagaaaa atgcaagttt cttcaaaat aaagagacat ttttcctagt ttcaggaatc    16680
ccccaaatca cttcctcatt ggcttagttt aaagccagga gactgataaa agggctcagg   16740
gtttgttctt taattcatta actaaacatt ctgcttttat tacagttaaa tggttcaaga   16800
tgtaacaact agttttaaag gtatttgctc attggtctgg cttagagaca ggaagacata   16860
tgagcaataa aaaaagatt cttttgcatt taccaattta gtaaaaattt attaaaactg     16920
aataaagtgc tgttcttaag tgcttgaaag acgtaaacca aagtgcactt tatctcattt   16980
atcttatggt ggaaacacag gaacaaattc tctaagagac tgtgtttctt tagttgagaa   17040
gaaacttcat tgagtagctg tgatatgttc gatactaagg aaaaactaaa cagatcacct   17100
ttgacatgcg ttgtagagtg ggaataagag agggcttttt attttttcgt tcatacgagt   17160
attgatgaag atgatactaa atgctaaatg aaatatatct gctccaaaag gcatttattc   17220
tgacttggag atgcaacaaa aacacaaaaa tggaatgaag tgatactctt catcaaacag   17280
aagtgactgt tatctcaacc atttttgttaa atcctaaaca gaaaacaaaa aaaatcatga   17340
cgaaaagaca cttgcttatt aattggcttg gaaagtagaa tataggagaa aggttactgt   17400 ttatttttt tcatgtattc attcattcta caaatatatt cgggtgccaa taggtacttg    17460
gtataaggtt tttggcccca gagacatggg aaaaaaatgc atgccttccc agagaatgcc   17520
taatactttc cttttggctt gttttcttgt tagggggcatg gcttagtccc taaataacat   17580
tgtgtggttt aattcctact ccgtatctct tctaccactc tggccactac gataagcagg   17640
tagctgggtt ttgtagtgag cttgctcctt aagttacagg aactctcctt ataatagaca   17700
cttcattttc ctagtccatc cctcatgaaa aatgactgac cactgctggg cagcaggagg   17760
gatgatgacc aactaattcc caaaccccag tctcattggt accagccttg gggaaccacc   17820
tacacttgag ccacaattgg ttttgaagtg catttacaag gttgtctat tttcagttct    17880 ttactttta catgctgaca catacataca ctgcctaaat agatctcttt cagaaacaat    17940
cctcagataa cgcatagcaa aatggagatg gagacatgat ttctcatgca acagcttctc   18000
taattatacc ttagaaatgt tctccttttt atcatcaaat ctgctcaaga agggcttttt   18060
atagtagaat aatatcagtg gatgaaaaca gcttaacatt ttaccatgct taagttttaa   18120
gaataaaata aaaattggaa ataattggcc aaaattgaaa ggaaaaattt ttttaaaatt   18180
tctctaaatg taggcctggc tgggctttga ccttttccgt ttttaaatca ctcacagagg   18240
gtgggacagg aggaagagtg aaggaaaagg tcaaacctgt tttaagggca acctgccttt   18300
gttctgaatt ggtcttaaga acattaccag ctccaggttt aaattgttca gtttcatgca   18360
```

```
gttccaatag ctgatcattg ttgagatgag acaaaatcc tttgtcctca ctagtttgct   18420 ttacatttttt gaaaagtatt attttttgtcc aagtgcttat caactaaacc ttgtgttagg  18480
taagaatgga atttattaag tgaatcagtg tgacccttct tgtcataaga ttatcttaaa   18540
gctgaagcca aaatatgctt caaaagaaga ggactttatt gttcattgta gttcatacat   18600
tcaaagcatc tgaactgtag tttctatagc aagccaatta catccataag tggagaagga   18660
aatagataaa tgtcaaagta tgattggtgg agggagcaag gttgaagata atctggggtt   18720
gaaattttct agttttcatt ctgtacattt ttagttagac atcagatttg aaatattaat   18780 gtttacctttt caatgtgtgg tatcagctgg actcagtaac accccttttct tcagctgggg  18840 atggggaatg gattattgga aaatggaaag aagaaagtaa ctaaaagcct tccttttcaca  18900 gtttctggca tcactaccac tactgattaa acaagaataa gagaacattt tatcatcatc   18960
tgctttattc acataaatga agttgtgatg aataaatctg cttttatgca gacacaagga   19020
attaagtggc ttcgtcattg tccttctacc tcaaagataa tttattccaa aagctaagat   19080
aaatggaaga ctcttgaact tgtgaactga tgtgaaatgc agaatctctt ttgagtcttt   19140
gctgtttgga agattgaaaa atattgttca gcatgggtga ccaccagaaa gtaatcttaa   19200
gccatctaga tgtcacaatt gaaacaaact ggggagttgg ttgctattgt aaaataaaat   19260
atactgtttt gaaaactttg aaaaaaaaaa aaaaaa                             19296
```

```
<210> SEQ ID NO 21
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 21 tgttttttttg tttattgggg ttgtg                                          25

<210> SEQ ID NO 22
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 22
taaattttaa attaattaaa ttat                                            24

<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 23
tgttttagaa agaattttaa gtgtagaga                                       29

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
agggagcagt tgccctact                                                  20
```

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
cacatgcagc gtggtatctt                                              20

<210> SEQ ID NO 26
<211> LENGTH: 8199
<212> TYPE: DNA
<213> ORGANISM: Homo sapiens

<400> SEQUENCE: 26

| | | | | | |
|---|---|---|---|---|---|
| ttgccctact | agctcctcgg | acagctgtaa | agaagagtct | ctggctcttt | agaatactgt | 60 |
| aagtactact | tcgtagctat | taagtaatct | ttttcctatt | ctattttctt | tctcttagat | 120 |
| gccacctata | gaaaagtcag | agggtccagt | aagtttcttt | ccttcttccc | acctcatctg | 180 |
| caatatatat | atatagagag | agaaatagat | acatacatac | atgcataaat | acacatatgt | 240 |
| gagttaacca | gcagaactgt | agaattaata | ttgtggaccc | agctctatgc | taggttacac | 300 |
| tgataacctg | ggtaggaatg | atatcatcct | atataatttc | attcctgaga | tgattttatc | 360 |
| gttgaggagc | taatgtgagc | acatttgaaa | taactttaga | aaataataag | tgctgttttg | 420 |
| tgtgaatcat | aagtagtagt | tttaggaagg | gaacccacaa | ggatttgaag | ttgatagaat | 480 |
| aaacttaagg | aagtgggttt | gctttttctc | tttaagccaa | gataggatta | atattgcagc | 540 |
| catctggata | gtccagttgg | tttatttaa | tttcatttgt | ttttaccctc | ttttggagcc | 600 |
| atggaaagag | atgaaaggga | tagagcatag | ccattgtgtt | tggctatttg | cgaaggttgg | 660 |
| caaattagtg | attgctaaat | ctcataagct | tgagtatttt | aaagttcaga | gattgagggc | 720 |
| ataaatctaa | tacttcggct | ccttccacaa | ttttactaca | tttctgccca | agaacagatg | 780 |
| accatggata | atgcatatcg | tagatacttt | ttaagtttgg | aaccttttg | ccaagagggt | 840 |
| agtggagaag | tgaagtcaaa | accttgacct | tccttgccta | ctttatgctg | tagtttatat | 900 |
| accttctttc | ctcccacctt | tcgtaaagct | aaaagaagct | tagcctcctt | aatgttttcc | 960 |
| agctgacaaa | atattgttta | acataacatt | cgaaactttt | tttctggtgc | acattcatgc | 1020 |
| atcacagcag | gagcaacaag | aaccatataa | gtgaactggc | ttcacttata | gcccgtttta | 1080 |
| attcatatcc | atatttcctc | agggcttgtt | tccatgcctc | ccagccccac | tccatatgct | 1140 |
| taacaacatt | gtctggctga | ctgagggtta | tatacatcat | ggtcttgaac | cttcttggaa | 1200 |
| acatggtctg | tgccattgtt | tctcaaaccc | aagtaatgct | tcatgatgaa | acaccttcta | 1260 |
| aaggaacaaa | attttctgag | atcctaaaaa | aatgtgtttt | gaggaacact | gacttaacaa | 1320 |
| agatatttga | aatgtaaata | tgttttccaa | tttcacgttg | tctttgtcaa | agatgtgttt | 1380 |
| tatataactt | atgtagaact | tggggatcca | ttagaatata | ttcacaaatc | cccagggtta | 1440 |
| tcaccccaat | ttgagaaacc | ctggtctatg | cttatgaaat | cttctattgg | taattaaatt | 1500 |
| gtcattcatt | gtcaacatac | aattataatt | attattggaa | tttgttttaa | atgaatgaat | 1560 |
| ttggaggtga | ttctgtacct | taagtcaaga | ggaaggatgg | cttgattta | ggtggattga | 1620 |
| ttatactaga | tagcatccaa | aggtgaatct | tgaagctgta | tttaaattca | ttgcttgaaa | 1680 |
| taatttccac | ccttaagaaa | aatctctagc | aattgtaaaa | agggatgctc | tggaaatgtg | 1740 |

-continued

```
ggcatcttca aaatagagat aattcttgtg ttagttcaac aaatattatt gtaccaggtg   1800
ctggaataaa tagcaaaacc aaagacagga tttatatcaa ggaatttgct ttcttatgga   1860
ggatgcagaa ggaaatcatt atggttttgg gcagaaatgc ttagacttta gtcctggctc   1920
tgagtttggt tcagatcacc atcaatctga ccatctcgag actgctagtg aaataagata   1980
ggggcttata tcaaatacct aaatccctga aaatgacatt ttgtgatttg gaaaattttc   2040
aaaagtctaa tgaaggaaac ttttttggca tttcttaaaa tgattattgt catttctttt   2100 ctgactttc cctttataaa accttaacat gtaggattgg aggaagtttt ctgaccattt   2160
tctcatatcc tctttcagct ttatctttct gtaacttcca tttctctagc cacctcccta   2220
aattacagaa gactgtgaga cccagggctg ctgtgattag gcattcataa tttcttttca   2280
gggtgtttgt gccctgatta tcaaatgtac agcttgaagg gagttcatgt cttaaagtaa   2340
tgaattaaga gttgaccttt gttgactgct aaaatattct tatatgtgaa agcatcctgg   2400
aaaaatacgt taccagctta aagagaaaga aactaatgat tatatctgaa ctgagctaat   2460
gcctcttctc ttcccccaaa ccttatcagt ttggatggca aagagtaatg atgtgtcagt   2520
taaacagagc taatgccttc ctctgccttg tcttaaagac tggattggga gaaaattgat   2580
attctcacta ccatattttg ggctgtaggc aagtagcatt ttacacaggt ttccttcaaa   2640
aatccaactc aagttggagc tcatgtattt aagacatagc tggcctgctg aatttaacaa   2700
gttaaacttc agtggccatg tacagttata tatcactata tatatgtgta ttaggctgtc   2760
gagttggtca tgttttttgtt ggtgacttag gctttacttg atagctcttc cttgaccttt   2820
ccaaattgag tactgataca tggagcttgg gcttcttctg catcttatac aaatgagttt   2880
ggtaaagaag cctctccttt actgttttga tgtttatatt agaaataact tttgattatt   2940 tttttttcatg ttaggatgag aaactgaaac aaaatgtaaa tttgaccggt gctagacttc   3000
ttaaattatg ggtagactta aagtattatt ttccttaacc aattagaatg ctagtcttct   3060
agtgttcccg gaaacatgag aggttatgca gtagacccaa gcaataccct cttattacat   3120
aatcaagtgc gtataagaat ttaaaaatag ggatatgact ggaacatcac tgtactttac   3180
caggtcccat tataaaatta tctatgttac tttacccata gctttgaaaa ctagtggcat   3240
agtatatttt atagtatgct gttagtgtga ttggcattga acagtgatgg gatataatca   3300
ctctacaatc tatatgttat taaagttttc cagcccttata gatctccctt gactgaaaat   3360
tagctactaa cttacgactt atttttttaca gcagattgac taggtctttc caggaaatct   3420
gttgatgtac aaaaacaaag tttaattgct aatgtttttt taaaaaataa ctttttgata   3480
ttacggatac ctggttattt gggccttgta tattttaaca tcaaaattac ctattataaa   3540
tccatataaa cagaaaagaa agagagtaag tctttagatc agatctgcaa acaatgatgg   3600
tacgtactgt agaaaaatct ggaacataga cttaccagtt cttaggttcc attttgcttg   3660
ctttttaaaa actgtgtctt ataagtcttc agcaactggt tgggagattt ttagaaaaaa   3720 taaccttta atgttagaac agtgtagaga tttacagaat gattctgaag atagagtttc   3780
tgtgtacttc acacccagtt tttcccagtg ttaacatttt acattagttt ggtacatttg   3840
tcacaacaaa ccaatattga tacattatta ttaactagag tccatatttt attcagattt   3900
ccttagtttt tccttaatgt tcttttttgtg ttccaggatc ccattgaaga taccacgctg   3960
catgtgtcct tagtagtcat gtctccttag gctcctcttg gtaatgacag tttctcagac   4020
tctttgtttt tgatgaactt cacagttttg aggactaatg gtccagtatt ctatagaatg   4080
tctctctatt ggaatttgtc tgatgttctt ctcatgacta gattgggttt atgagtgttt   4140
```

```
aggaggaaga ccacaaaggt agagtgccat tcttatcact tatcaagagt acatactatc   4200
aacatgactt atcactgttt atgttatcct taatcacctg tctgaggtac tatttgtcag   4260
gtttctccag cgtaaaatta gtctttattt ctccatttcc ctactatact gttcacatag   4320
gaagtcacta tgtgcagcca gcacttaagg aatgggaaat taccttccac ctcattgagg   4380
gcagagtatt tacataaatt atttggaatt cttttgcaca ggatgtcttt tctccacaat   4440
gtattgtgtt tattcagtca tttatatcag tatgatctca gggatatttt atactctggg   4500
ttataataca gtattacttt attctgttgt tcaaattgtt ccagctttgg ccattgggag   4560
gtctttcatt tggctttgat ataacceccat gaatgtgggt tttttgtttg agcactttct   4620
tattttggaa actacaacat gcttcagact catttgcata tctcctgcct ggacctaaaa   4680
tgatgtattt ctgcaaggag ccttgatact ttttattgga gagtaatatt agaaatcaag   4740
aagtgaatgc taggtgcgct cattactact ggagtgtcat tccttcaaga ccttttcagt   4800
tgacaagagc aaggagatat atatttgcat tctaacgtgt gtatatgcac atagctataa   4860
atatatataa ccatctgtat ctatattaaa ctaaatgtgt ttataccctac gtctccaact   4920 ctaatcattg ccacatggat cattatagtc tcacctcctt gcttatctgt tacctcccat   4980
ttctacagtg agaaacctgg cttggttggg aaatttttct gttaatatta cggtagtgag   5040
tgtttgacat ttgcttctat ggttaagttt agggagagtt tagctgtagg gtattcttga   5100
aactagaaat gaccccttctg ccctaaatgt ttctgccagt tttgaaacgt aaaataggtt   5160
gcagaaacaa actttatctt aagaaccaga atttacttca atccacattt tgacattgat   5220
tttcagatta aattattctg atatcgccag gtaagctgtt ccttgggtat gcatttcttc   5280
tttccgtttt tttctaagag ctaaaggacc ctgagaacac tggaggtggg aaaggaaggg   5340
aaaggcatgt tcacacgtgg gataggaaag gttcatttac tgacctccag ctagccttcc   5400
aaagtgccta tttaagaccc aaggagtaga tgtcttcctt ggcaattgta acccaaatat   5460 aattttttaac ctttcaattt tagtcaagaa agttggtgtg ctgttacaaa aagtgccctg   5520
attaacagca ttgtcatgtg cattgcatat taatcagcaa tttaaaataa catgaaatta   5580
tgttgagtat aattttaata ttttatatta gatattagtt tgagacagtg tttctcaagt   5640
ctgtataata agtttgatag tagggaggtt ttctctcaag aaaagaatta ttcagtgtgc   5700
acctacataa tcactgctta gattctacaa ttaatatttt gctatatttg attaaacgtt   5760
ttctgtaaaa gaaaatatt attatgtact atttaggttt atgggaataa ttgttaagtt   5820
aaagtgtatg aacaaacctg gaatgaaatc tgtttgccta catctataat acaactataa   5880
aacatagcag atgtacaaat tagtagttaa tagataacta aaatgcaaat atggcactac   5940
tattatagta ttatagttttc ttttgagtgg cgtgtctgta atatcacatg ctgtgttgat   6000
gcacttcacc aaaactgctgt tttcaaactg ctttaaatcc tgccattata gcacatagca   6060
atgctatttc actttcattt ggcacaaaac acatttatat attgtttgct tctcttcttt   6120
tctgtaatcc ccaggcaaca aaactagaac atttgccact aatctggcaa cgtggtccta   6180
tattatgaag tagtcatata gctgatctaa actatcctta cagtgaaatg agagtattgt   6240
gaaagttttg tagaaagctc cccatatgtc ctgagaatct atgcacagac cccacagtta   6300
aaagaccttt gaattgtggg aagacatggg tttaagtatc acttggttac cttctatttg   6360
tgtaacattg aggtagtttc atcttctggg ttcccagttt ccttagagaa tgaaaatgtt   6420
gaattatgtg atttttttttt tttttgaga cggagttttg ctctttcgcc caggctggag   6480
```

| | | | | |
|---|---|---|---|---|
| tgaagtagca | cgatctcgac | tcactgcaac | ctccttcccc | catgatcaag | caattctcct | 6540 |
| gcctcagcct | cccaagtagc | tgggattaca | ggcacccgcc | ccccacccc | cgccccagc | 6600 |
| taatgtttgt | atttttagta | cagatggagt | tttgccgtgt | tggccaggct | ggtctcgaac | 6660 |
| ttctgacctc | aggtgatcca | ctcgccttgg | cctcccaaag | tgctaggatt | acaggcatga | 6720 |
| gccactgcgc | ctggcctatg | tgattattaa | tatcacgtct | agctgtgaca | attctgtctg | 6780 |
| atgctggagt | atttgaacca | gatggctggc | tgtgccactc | agttattctc | tccataagac | 6840 |
| tttgatattt | tgttggtctg | caagatgacg | gattctcaaa | attcttgtca | gtgaatattg | 6900 |
| aaccctagtg | aaatgtatgg | ttctgtatca | gttccaaaat | gtaaccactt | tctctagcct | 6960 |
| tagattccca | gttccaaaat | gtaaccattt | tctctagcct | tagattcccg | ttaagggaaa | 7020 |
| gggaatgctc | tttgagtatg | tcatcaccat | agtaacaggc | aaaactagag | ggctttgatg | 7080 |
| ctaaagcaag | atactccata | aatatgctta | agaagacttg | gggagactgg | aatagttgtt | 7140 |
| ccctttaga | tgccagtgta | taaatgaatt | tgagctagga | tccgtttatt | taaaatttct | 7200 |
| ttaggtgtat | ttgcttgcat | atggagtgca | catttactct | cattaatgga | gttttaggaa | 7260 |
| gcagtagagt | aaatgcataa | acatgtatga | accgccatgt | ttaactggaa | gcctgcattt | 7320 |
| ggaagtcaag | tatctaatct | tagattaaat | taggatgggg | aaggatgttg | gcaagagatt | 7380 |
| ttgaagcttg | ttctgcttat | attgagaaca | tcatagaaca | gtttggcctt | tttaaagcta | 7440 |
| gagaatagtg | ttgaataagt | gatgttccat | atattcctgt | ttgacattga | cataaaggtt | 7500 |
| tcctcatgat | acagtaatcc | ctgatcaggg | atctggaagc | ctgtattcat | ttaaggtact | 7560 |
| caggtttaac | atactgggtg | cttttcacac | catactatac | agtaccatgc | aaagtgcttt | 7620 |
| caagactgca | aatttggctt | agatcccctt | tagtgagctc | ctatgctata | gtaaaggtag | 7680 |
| atagccaatt | attaaaaaca | gtcaagacaa | ttgcacctct | aagcagtagt | agcagttgcc | 7740 |
| acaccacctt | gaatcttgaa | gtattttcag | caacaggatg | accattagcc | acaaatttag | 7800 |
| tgtcagccct | taaggtcggt | attggtttga | cccatatttt | catgtagttc | ttttcttca | 7860 |
| cttgtctaat | cttcccgtgt | actgccaggg | cttgtcatta | gaggacttta | gggagaccaa | 7920 |
| gcaggctaga | aagtagagac | aggagatacc | tatgtctaat | gcttcagttt | atacttccta | 7980 |
| ggttttttc | attggggttt | ttgtaactct | tttggtatcc | taccggtgct | ttggtagcct | 8040 |
| actgaaccct | gtctttcttc | ttaaggacat | tctgagcatg | tgagacctga | ggactgcaaa | 8100 |
| cagctataag | aggctccaaa | ttaatcatat | cttttccttt | gagaatctgg | ccaagctcca | 8160 |
| gctaatctac | ttggatgggt | tgccagctat | ctggagaaa | | | 8199 |

<210> SEQ ID NO 27
<211> LENGTH: 3578
<212> TYPE: DNA
<213> ORGANISM: Homo sapiens

<400> SEQUENCE: 27

| | | | | |
|---|---|---|---|---|
| aatttcacct | tttttctgag | tctggcctcc | tttctgctgt | ttctactttt | tatctcacat | 60 |
| ttctcatttc | tgcatttcct | ttctgcctct | cttgggctat | tctctctctc | ctcccctgcg | 120 |
| tgcctcagca | tctcttgctg | tttgtgattt | tctatttcag | tattaatctc | tgttggcttg | 180 |
| tatttgttct | ctgcttcttc | cctttctact | cacctttgag | tatttcagcc | tcttcatgaa | 240 |
| tctatctccc | tctctttgat | ttcatgtaat | ctctccttaa | atatttcttt | gcatatgtgg | 300 |
| gcaagtgtac | gtgtgtgtgt | gtcatgtgtg | cagagggggc | ttcctaaccc | ctgcctgata | 360 |
| ggtgcagaac | gtcggctatc | agagcaagca | ttgtggagcg | gttccttatg | ccaggctgcc | 420 |

```
atgtgagatg atccaagacc aaaacaaggc cctagactgc agtaaaaccc agaactcaag      480
tagggcagaa ggtggaaggc tcatatggat agaaggccca agtataaga cagatggttt       540 gagacttgag acccgaggac taagatggaa agcccatgtt ccaagataga tagaagcctc      600
aggcctgaaa ccaacaaaag cctcaagagc caagaaaaca gagggtggcc tgaattggac      660
cgaaggcctg agttggatgg aagtctcaag gcttgagtta aagtcttaa gacctgggac       720 aggacacatg gaaggcctaa gaactgagac ttgtgacaca aggccaacga cctaagatta      780
gcccagggtt gtagctggaa gacctacaac ccaaggatgg aaggcccctg tcacaaagcc      840
tacctagatg gatagaggac ccaagcgaaa aaggtatctc aagactaacg ccggaatct       900 ggaggcccat gacccagaac ccaggaagga tagaagcttg aagacctggg gaaatcccaa      960
gatgagaacc ctaaacccta cctcttttct attgtttaca cttcttactc ttagatattt      1020
ccagttctcc tgtttatctt aagcctgat tcttttgaga tgtactttt gatgttgccg        1080 gttacctttta gattgacagt attatgcctg ggccagtctt gagccagctt aaatcacag      1140 cttttaccta tttgttaggc tatagtgttt tgtaaacttc tgtttctatt cacatcttct      1200
ccacttgaga gagacaccaa aatccagtca gtatctaatc tggcttttgt taacttccct      1260
caggagcaga cattcatata ggtgatactg tatttcagtc ctttcttttg accccagaag      1320
ccctagactg agaagataaa atggtcaggt tgttggggaa aaaaaagtgc caggctctct      1380
agagaaaaat gtgaagagat gctccaggcc aatgagaaga attagacaag aaatacacag      1440
atgtgccaga cttctgagaa gcacctgcca gcaacagctt ccttctttga gcttaggtga      1500
gcaggattct ggggtttggg atttctagtg atggttatgg aaagggtgac tgtgcctggg      1560
acaaagcgag gtcccaaggg gacagcctga actccctgct catagtagtg gccaaataat      1620
ttggtggact gtgccaacgc tactcctggg tttaataccc atctctaggc ttaaagatga      1680
gagaacctgg gactgttgag catgtgtaat actttccttg atttttttct tcctgtttat      1740
gtgggaagtt gatttaaatg actgataatg tgtatgaaag cactgtaaaa cataagagaa      1800
aaaccaatta gtgtattggc aatcatgcag ttaacatttg aaagtgcagt gtaaattgtg      1860
aagcattatg taaatcaggg gtccacagtt tttctgtaag gggtcaaatc ataaatactt      1920
tagactgtgg gccatatggt ttctgttaca tatttgtttt ttaaacaacg ttttttataag     1980 gtcaaaatca ttcttagttt ttgagccaat tggatttggc ctgctgttca tagcttacca      2040
ccccctgatg tattatttgt tattcagaga aaatttctga atactactag tttccttttc      2100
tgtgcctgtc cctgtgctag gcactaaaaa tgcaatgatt attgatatct aggtgacctg      2160
aaaaaaaata gtgaatgtgc tttgtaaact gtaaagcact tgtattctac tgtgataagc      2220
gttgtggata caaagaaagg agcaagcata aaaaagtgct ctttcaaaag gatatagtac      2280
tatgcagaca caaggaattg tttgataaat gaataaatta tatgtatatt tgaggccaat      2340
ttgtgtttgc tgctctggta attttgagta aaaatgcagt attccaggta tcagaaacga      2400
aaacacatgg aaactgcttt taaactttaa aatatactga aaacataagg gactaagctt      2460
gttgtggtca cctataatgt gccagatacc atgctgggtg ctagagctac caaaggggga      2520
aaagtattct catagaacaa aaaatttcag aaaggtgcat attaaagtgc tttgtaaact      2580
aaagcatgat acaaatgtca atgggctaca tatttatgaa tgaatgaatg gatgaatgaa      2640
tattaagtgc ctcttacata ccagctattt tgggtactgt aaaatacaag attaattctc      2700
ctatgtaata agaggaaagt ttatcctcta tactattcag atgtaaggaa tgatatattg      2760
```

-continued

| | |
|---|---|
| cttaattttta aacaatcaag actttactgg tgaggttaag ttaaattatt actgatacat | 2820 |
| ttttccaggt aaccaggaaa gagctagtat gaggaaatga agtaatagat gtgagatcca | 2880 |
| gaccgaaagt cacttaattc agcttgcgaa tgtgctttct aaattataaa gcacttgtaa | 2940 |
| atgaaaaatt tgatgctttc tgtatgaata aactttctg taagctaggt attgtctcta | 3000 |
| caaaattctc attgtatagt taaccacag tgagaagggt tctataagta gttatacaaa | 3060 |
| ccaagggttt aaatacctgt taaatagatc aattttgatt gcctactatg tgaactcact | 3120 |
| gttaaaggca ctgaaaattt atcatatttc atttagccac agccaaaaat aaggcaatac | 3180 |
| ctatgttagc attttgtgaa ctctaaggca ccatataaat gtaactgttg attttctcac | 3240 |
| ttggtgctgg gtactaggtt tataaaattg tatgatagtt attatattgt gcaaataaag | 3300 |
| taggaaaatt tgaataacaa tgattatctt tgaatacgc atacgcaagg gattggttgt | 3360 |
| ctgaagaatg ccactatagt agttatctat tgtgtgccaa tctcattgct aggcattggg | 3420 |
| gatgcaaaga taaccatct ttattgtgtc ttgggtagca aagaaaata tgtgtaaaat | 3480 |
| caatttataa tttgtaaact gccacccata tataagctat atctgctgaa tgatcattga | 3540 |
| ttactcttat ccttagagat aacaactggg ggcacaaa | 3578 |

<210> SEQ ID NO 28
<211> LENGTH: 390
<212> TYPE: PRT
<213> ORGANISM: Homo sapiens

<400> SEQUENCE: 28

```
Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
```

```
                225                 230                 235                 240
        Thr Gly Arg Arg Gly Asp Leu Ala Thr Ile His Gly Met Asn Arg Pro
                            245                 250                 255

Phe Leu Leu Leu Met Ala Thr Pro Leu Glu Arg Ala Gln His Leu Gln
                            260                 265                 270

Ser Ser Arg His Arg Arg Ala Leu Asp Thr Asn Tyr Cys Phe Ser Ser
                            275                 280                 285

Thr Glu Lys Asn Cys Cys Val Arg Gln Leu Tyr Ile Asp Phe Arg Lys
                    290                 295                 300

Asp Leu Gly Trp Lys Trp Ile His Glu Pro Lys Gly Tyr His Ala Asn
        305                 310                 315                 320

Phe Cys Leu Gly Pro Cys Pro Tyr Ile Trp Ser Leu Asp Thr Gln Tyr
                            325                 330                 335

Ser Lys Val Leu Ala Leu Tyr Asn Gln His Asn Pro Gly Ala Ser Ala
                            340                 345                 350

Ala Pro Cys Cys Val Pro Gln Ala Leu Glu Pro Leu Pro Ile Val Tyr
                            355                 360                 365

Tyr Val Gly Arg Lys Pro Lys Val Glu Gln Leu Ser Asn Met Ile Val
                    370                 375                 380

Arg Ser Cys Lys Cys Ser
        385                 390

<210> SEQ ID NO 29
<211> LENGTH: 288
<212> TYPE: PRT
<213> ORGANISM: Homo sapiens

<400> SEQUENCE: 29

Met Val Gly Val Gly Gly Gly Asp Val Glu Asp Val Thr Pro Arg Pro
        1               5                   10                  15

Gly Gly Cys Gln Ile Ser Gly Arg Gly Ala Arg Gly Cys Asn Gly Ile
                    20                  25                  30

Pro Gly Ala Ala Ala Trp Glu Ala Ala Leu Pro Arg Arg Arg Pro Arg
                35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
        65                  70                  75                  80

Asp Arg Gly Arg Gly Arg Ala Leu Pro Gly Gly Arg Leu Gly Gly Arg
                            85                  90                  95

Gly Arg Gly Arg Ala Pro Glu Arg Val Gly Gly Arg Gly Arg Gly Arg
                        100                 105                 110

Gly Thr Ala Ala Pro Arg Ala Ala Pro Ala Ala Arg Gly Ser Arg Pro
                    115                 120                 125

Gly Pro Ala Gly Thr Met Ala Ala Gly Ser Ile Thr Thr Leu Pro Ala
        130                 135                 140

Leu Pro Glu Asp Gly Gly Ser Gly Ala Phe Pro Pro Gly His Phe Lys
        145                 150                 155                 160

Asp Pro Lys Arg Leu Tyr Cys Lys Asn Gly Gly Phe Phe Leu Arg Ile
                            165                 170                 175

His Pro Asp Gly Arg Val Asp Gly Val Arg Glu Lys Ser Asp Pro His
                        180                 185                 190

Ile Lys Leu Gln Leu Gln Ala Glu Glu Arg Gly Val Val Ser Ile Lys
                    195                 200                 205
```

```
Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
            275                 280                 285
```

<210> SEQ ID NO 30
<211> LENGTH: 3808
<212> TYPE: DNA
<213> ORGANISM: Homo sapiens

<400> SEQUENCE: 30

```
cttcctggac tgggatcccc ggctaaatat agctgtttct gtcttacaac acaggctcca     60
gtatataaat caggcaaatt ccccatttga gcatgaacct ctgaaaactg ccggcatctg    120
aggtttcctc caaggccctc tgaagtgcag cccataatga aggtcttggc ggcagtacac    180
agcccagggg gagccgttcc ccaacaacct ggacaagcta tgtgccccca cgtgacgga     240
cttcccgccc ttccacgcca acggcacgga aaggccaag ctggtggagc tgtaccgcat     300
agtcgtgtac cttggcacct ccctgggcaa catcacccgg accagaaga tcctcaaccc     360
cagtgccctc agcctccaca gcaagctcaa cgccaccgcc gacatcctgc gaggcctcct    420
tagcaacgtg ctgtgccgcc tgtgcagcaa gtaccacgtg ggccatgtgg acgtgaccta    480
cggccctgac acctcgggta aggatgtctt ccagaagaag aagctgggct gtcaactcct    540
ggggaagtat aagcagatca tcgccgtgtt ggcccaggcc ttctagcagg aggtcttgaa    600
gtgtgctgtg aaccgaggga tctcaggagt tgggtccaga tgtggggcc tgtccaaggg    660
tggctgggc ccagggcatc gctaaaccca aatgggggct gctggcagac cccgagggtg    720
cctggccagt ccactccact ctgggctggg ctgtgatgaa gctgagcaga gtggaaactt    780
ccatagggag ggagctagaa gaaggtgccc cttcctctgg gagattgtgg actggggagc    840
gtgggctgga cttctgcctc tacttgtccc tttggcccct tgctcacttt gtgcagtgaa    900
caaactacac aagtcatcta caagagccct gaccacaggg tgagacagca gggcccaggg    960
gagtggacca gccccagca aattatcacc atctgtgcct tgctgcccc ttaggttggg    1020
acttaggtgg gccagagggg ctaggatccc aaaggactcc ttgtccccta gaagtttgat   1080
gagtggaaga tagagagggg cctctgggat ggaaggctgt cttcttttga ggatgatcag   1140
agaacttggg cataggaaca atctggcaga agtttccaga aggaggtcac ttggcattca   1200
ggctcttggg gaggcagaga agccaccttc aggcctggga aggaagacac tgggaggagg   1260
agaggcctgg aaagctttgg taggttcttc gttctcttcc ccgtgatctt ccctgcagcc   1320
tgggatggcc agggtctgat ggctggacct gcagcagggg tttgtggagg tgggtagggc   1380
agggcaggt tgctaagtca ggtgcagagg ttctgaggga cccaggctct tcctctgggt   1440
aaaggtctgt aagaaggggc tggggtagct cagagtagca gctcacatct gaggccctgg   1500
gaggccttgt gaggtcacac agaggtactt gaggggact ggaggccgtc tctggtcccc   1560
agggcaaggg aacagcagaa cttagggtca gggtctcagg gaaccctgag ctccaagcgt   1620
gctgtgcgtc tgacctggca tgatttctat ttattatgat atcctattta tattaactta   1680
```

| | |
|---|---|
| ttggtgcttt cagtggccaa gttaattccc ctttccctgg tccctactca acaaaatatg | 1740 |
| atgatggctc ccgacacaag cgccagggcc agggcttagc agggcctggt ctggaagtcg | 1800 |
| acaatgttac aagtggaata agccttacgg gtgaagctca gagaagggtc ggatctgaga | 1860 |
| gaatggggag gcctgagtgg gagtgggggg ccttgctcca ccccccccca tcccctactg | 1920 |
| tgacttgctt tagggtgtca gggtccaggc tgcaggggct gggccaattt gtggagaggc | 1980 |
| cgggtgcctt tctgtcttga ttccagggg ctggttcaca ctgttcttgg gcgccccagc | 2040 |
| attgtgttgt gaggcgcact gttcctggca gatattgtgc ccctggagc agtgggcaag | 2100 |
| acagtccttg tgcccaccc tgtccttgtt tctgtgtccc catgctgcct ctgaaatagc | 2160 |
| gccctggaac aaccctgccc ctgcacccag catgctccga cacagcaggg aagctcctcc | 2220 |
| tgtggcccgg acaccatag acggtgcggg gggcctggct gggccagacc ccaggaaggt | 2280 |
| ggggtagact gggggggatca gctgcccatt gctcccaaga ggaggagagg gaggctgcag | 2340 |
| atgcctggga ctcagaccag gaagctgtgg gccctcctgc tccaccccca tcccactccc | 2400 |
| acccatgtct gggctcccag gcaggaacc cgatctcttc ctttgtgctg ggccaggcg | 2460 |
| agtggagaaa cgccctccag tctgagagca ggggagggaa ggaggcagca gagttggggc | 2520 |
| agctgctcag agcagtgttc tggcttcttc tcaaaccctg agcgggctgc cggcctccaa | 2580 |
| gttcctccga caagatgatg gtactaatta tggtactttt cactcacttt gcacctttcc | 2640 |
| ctgtcgctct ctaagcactt tacctggatg gcgcgtgggc agtgtgcagg caggtcctga | 2700 |
| ggcctggggt tggggtggag ggtgcggccc ggagttgtcc atctgtccat cccaacagca | 2760 |
| agacgaggat gtggctgttg agatgtgggc cacactcacc cttgtccagg atgcagggac | 2820 |
| tgccttctcc ttcctgcttc atccggctta gcttgggct ggctgcattc ccccaggatg | 2880 |
| ggcttcgaga aagacaaact tgtctggaaa ccagagttgc tgattccacc cgggggggccc | 2940 |
| ggctgactcg cccatcacct catctccctg tggacttggg agctctgtgc caggcccacc | 3000 |
| ttgcggccct ggctctgagt cgctctccca cccagcctgg acttggcccc atgggaccca | 3060 |
| tcctcagtgc tccctccaga tcccgtccgg cagcttggcg tccaccctgc acagcatcac | 3120 |
| tgaatcacag agcctttgcg tgaaacagct ctgccaggcc gggagctggg tttctcttcc | 3180 |
| cttttatct gctggtgtgg accacacctg gcctggccg gaggaagaga gagtttacca | 3240 |
| agagagatgt ctccgggccc ttatttatta tttaaacatt ttttaaaaa gcactgctag | 3300 |
| tttacttgtc tctcctcccc atcgtcccca tcgtcctcct tgtccctgac tggggcact | 3360 |
| tccaccctga cccagccagt ccagctctgc cttgccggct ctccagagta gacatagtgt | 3420 |
| gtggggttgg agctctggca cccggggagg tagcatttcc ctgcagatgg tacagatgtt | 3480 |
| cctgccttag agtcatctct agttccccac ctcaatcccg gcatccagcc ttcagtcccg | 3540 |
| cccacgtgct agctccgtgg gcccaccgtg cggccttaga ggtttccctc cttcctttcc | 3600 |
| actgaaaagc acatggcctt gggtgacaaa ttcctctttg atgaatgtac cctgtgggga | 3660 |
| tgtttcatac tgacagatta ttttattta ttcaatgtca tatttaaaat atttattttt | 3720 |
| tataccaaat gaatactttt tttttaaga aaaaaagag aaatgaataa agaatctact | 3780 |
| cttggctggc aaaaaaaaaa aaaaaaa | 3808 |

<210> SEQ ID NO 31
<211> LENGTH: 2217
<212> TYPE: DNA
<213> ORGANISM: Homo sapiens

<400> SEQUENCE: 31

```
ccccgccgcc gccgcccttc gcgccctggg ccatctccct cccacctccc tccgcggagc      60
agccagacag cgagggcccc ggccgggggc aggggggacg ccccgtccgg ggcaccccc      120 cggctctgag ccgcccgcgg ggccggcctc ggcccggagc ggaggaagga gtcgccgagg     180
agcagcctga ggccccagag tctgagacga ggccgccgcc gccccgccac tgcggggagg     240 aggggggagga ggagcgggag gagggacgag ctggtcggga gaagaggaaa aaaacttttg    300
agacttttcc gttgccgctg ggagccggag gcgcgggac ctcttggcgc gacgctgccc     360
cgcgaggagg caggacttgg ggaccccaga ccgcctccct ttgccgccgg ggacgcttgc     420
tccctccctg ccccctacac ggcgtccctc aggcgcccc attccggacc agccctcggg     480
agtcgccgac ccggcctccc gcaaagactt ttccccagac ctcgggcgca ccccctgcac    540
gccgccttca tccccggcct gtctcctgag ccccgcgca tcctagaccc tttctcctcc    600
aggagacgga tctctctccg acctgccaca gatccctat tcaagaccac ccaccttctg     660
gtaccagatc gcgcccatct aggttatttc cgtgggatac tgagcacccc ccggtccaag    720
cctcccctcc accactgcgc ccttctccct gaggacctca gctttccctc gaggccctcc    780
taccttttgc cgggagaccc ccagcccctg caggggcggg gcctccccac cacaccagcc    840
ctgttcgcgc tctcggcagt gccggggggc gccgcctccc ccatgccgcc ctccgggctg   900
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagccccc gagccagggg    1080 gaggtgccgc ccggcccgct gcccgaggcc gtgctcgccc tgtacaacag cacccgcgac   1140
cgggtggccg gggagagtgc agaaccggag cccgagcctg aggccgacta ctacgccaag    1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg    1440
ctggcaccca gcgactcgcc agagtggtta tcttttgatg tcaccggagt tgtgcggcag   1500
tggttgagcc gtggagggga aattgagggc tttcgcctta gcgcccactg ctcctgtgac    1560
agcagggata acacactgca agtggacatc aacgggttca ctaccggccg ccgaggtgac   1620
ctggccacca ttcatggcat gaaccggcct ttcctgcttc tcatggccac cccgctggag   1680
agggcccagc atctgcaaag ctcccggcac cgccgagccc tggacaccaa ctattgcttc    1740
agctccacgg agaagaactg ctgcgtgcgg cagctgtaca ttgacttccg caaggacctc    1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccgggcg cctcggcggc ggcgtgctgc gtgccgcagg cgctggagcc gctgcccatc    1980
gtgtactacg tgggccgcaa gcccaaggtg gagcagctgt ccaacatgat cgtgcgctcc    2040
tgcaagtgca gctgaggtcc cgccccgccc cgccccgccc cggcaggccc ggccccaccc    2100
cgccccgccc ccgctgcctt gcccatgggg gctgtattta aggacacccg tgccccaagc    2160
ccacctgggg ccccattaaa gatggagaga ggactgcgga aaaaaaaaaa aaaaaaa       2217
```

<210> SEQ ID NO 32
<211> LENGTH: 6774
<212> TYPE: DNA

<213> ORGANISM: Homo sapiens

<400> SEQUENCE: 32

```
cggccccaga aaacccgagc gagtaggggg cggcgcgcag gagggaggag aactgggggc      60
gcgggaggct ggtgggtgtg gggggtggag atgtagaaga tgtgacgccg cggcccggcg     120
ggtgccagat tagcggacgc ggtgcccgcg gttgcaacgg gatcccgggc gctgcagctt     180
gggaggcggc tctccccagg cggcgtccgc ggagacaccc atccgtgaac cccaggtccc     240
ggccgccgg ctcgccgcgc accaggggcc ggcggacaga agagcggccg agcggctcga      300
ggctggggga ccgcgggcgc ggccgcgcgc tgccggcgg gaggctgggg ggccggggcc      360
ggggccgtgc cccggagcgg gtcggaggcc ggggccgggg ccggggacg gcggctcccc      420
gcgcggctcc agcggctcgg ggatcccggc cgggccccgc agggaccatg gcagccggga     480
gcatcaccac gctgcccgcc ttgcccgagg atggcggcag cggcgccttc ccgcccggcc     540
acttcaagga ccccaagcgg ctgtactgca aaaacggggg cttcttcctg cgcatccacc     600
ccgacggccg agttgacggg gtccgggaga agagcgaccc tcacatcaag ctacaacttc     660
aagcagaaga gagaggagtt gtgtctatca aaggagtgtg tgctaaccgt tacctggcta     720
tgaaggaaga tggaagatta ctggcttcta aatgtgttac ggatgagtgt ttctttttg     780
aacgattgga atctaataac tacaatactt accggtcaag gaaatacacc agttggtatg     840
tggcactgaa acgaactggg cagtatataaac ttggatccaa aacaggacct gggcagaaag     900
ctatactttt tcttccaatg tctgctaaga gctgatttta atggccacat ctaatctcat     960
ttcacatgaa agaagaagta tattttagaa atttgttaat gagagtaaaa gaaaataaat    1020
gtgtatagct cagtttggat aattggtcaa acaattttt atccagtagt aaaatatgta    1080
accattgtcc cagtaaagaa aaataacaaa agttgtaaaa tgtatattct ccctttata    1140
ttgcatctgc tgttacccag tgaagcttac ctagagcaat gatctttttc acgcatttgc    1200
tttattcgaa aagaggcttt taaaatgtgc atgtttagaa acaaaatttc ttcatggaaa    1260
tcatatacat tagaaaatca cagtcagatg tttaatcaat ccaaaatgtc cactatttct    1320
tatgtcattc gttagtctac atgtttctaa acatataaat gtgaatttaa tcaattcctt    1380
tcatagttt ataattctct ggcagttcct tatgatagag tttataaaac agtcctgtgt    1440
aaactgctgg aagttcttcc acagtcaggt caattttgtc aaacccttct ctgtacccat    1500
acagcagcag cctagcaact ctgctggtga tgggagttgt attttcagtc ttcgccaggt    1560
cattgagatc catccactca catcttaagc attcttcctg gcaaaaattt atggtgaatg    1620
aatatggctt taggcggcag atgatataca tatctgactt cccaaaagct ccaggatttg    1680
tgtgctgttg ccgaatactc aggacggacc tgaattctga tttttaccca gtctcttcaa    1740
aaacttctcg aaccgctgtg tctcctacgt aaaaaaagag atgtacaaat caataataat    1800
tacactttta gaaactgtat catcaaagat tttcagttaa agtagcatta tgtaaaggct    1860
caaaacatta ccctaacaaa gtaaagtttt caatacaaat tctttgcctt gtggatatca    1920
agaaatccca aaatattttc ttaccactgt aaattcaaga agcttttgaa atgctgaata    1980
tttctttggc tgctacttgg aggcttatct acctgtacat ttttggggtc agctcttttt    2040
aacttcttgc tgctcttttt cccaaaaggt aaaaatatag attgaaaagt taaacatttt    2100
tgcatggctg cagttccttt gtttcttgag ataagattcc aaagaactta gattcatttc    2160
ttcaacaccg aaatgctgga ggtgtttgat cagttttcaa gaaacttgga atataaataa    2220
ttttataatt caacaaaggt tttcacattt tataaggttg attttttcaat taaatgcaaa    2280
```

```
tttgtgtggc aggattttta ttgccattaa catattttg tggctgcttt ttctacacat    2340
ccagatggtc cctctaactg ggctttctct aattttgtga tgttctgtca ttgtctccca    2400
aagtatttag gagaagccct ttaaaaagct gccttcctct accactttgc tggaaagctt    2460
cacaattgtc acagacaaag attttttgttc caatactcgt tttgcctcta tttttcttgt    2520
ttgtcaaata gtaaatgata tttgcccttg cagtaattct actggtgaaa acatgcaaa    2580 gaagaggaag tcacagaaac atgtctcaat cccatgtgc tgtgactgta gactgtctta    2640
ccatagactg tcttacccat cccctggata tgctcttgtt ttttccctct aatagctatg    2700
gaaagatgca tagaaagagt ataatgtttt aaaacataag gcattcgtct gccatttttc    2760
aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt ttccttaata agaaagtaa tttttactct gatgtgcaat    3180
acatttgtta ttaaatttat tatttaagat ggtagcacta gtcttaaatt gtataaaata    3240
tcccctaaca tgtttaaatg tccatttta ttcattatgc tttgaaaaat aattatgggg    3300
aaatacatgt ttgttattaa atttattatt aaagatagta gcactagtct taaatttgat    3360
ataacatctc ctaacttgtt taaatgtcca ttttttattct ttatgtttga aaataaatta    3420
tggggatcct atttagctct tagtaccact aatcaaaagt tcggcatgta gctcatgatc    3480
tatgctgttt ctatgtcgtg gaagcaccgg atggggtag tgagcaaatc tgccctgctc    3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgcttta ttctgttgta ttttttatta ttttaatata    3780
ctgtaagcca aactgaaata acatttgctg tttataggt ttgaagaaca taggaaaaac    3840
taagaggttt tgttttttatt ttttgctgatg aagagatatg tttaaatatg ttgtattgtt    3900
ttgtttagtt acaggacaat aatgaaatgg agtttatatt tgttattctc attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgatttttt    4140
aagaaggcag tttgtcaatt ttaatcttgt ggataccttt atactcttag ggtattattt    4200
tatacaaaag ccttgaggat tgcattctat tttctatatg acctcttga tatttaaaaa    4260 acactatgga taacaattct tcatttacct agtattatga aagaatgaag gagttcaaac    4320
aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt tcattttcta    4560
gctgctttca gggttttatg aattttcagg caaagcttta atttatacta agcttaggaa    4620
```

| | | | | |
|---|---|---|---|---|
| gtatggctaa | tgccaacggc | agttttttc | ttcttaattc | cacatgactg | aggcatatat | 4680 |
| gatctctggg | taggtgagtt | gttgtgacaa | ccacaagcac | ttttttttt | tttaaagaaa | 4740 |
| aaaaggtagt | gaattttaa | tcatctggac | tttaagaagg | attctggagt | atacttaggc | 4800 |
| ctgaaattat | atatatttgg | cttggaaatg | tgttttcctt | caattacatc | tacaagtaag | 4860 |
| tacagctgaa | attcagagga | cccataagag | ttcacatgaa | aaaaatcaat | ttatttgaaa | 4920 |
| aggcaagatg | caggagagag | gaagccttgc | aaacctgcag | actgctttt | gcccaatata | 4980 |
| gattgggtaa | ggctgcaaaa | cataagctta | attagctcac | atgctctgct | ctcacgtggc | 5040 |
| accagtggat | agtgtgagag | aattaggctg | tagaacaaat | ggccttctct | ttcagcattc | 5100 |
| acaccactac | aaaatcatct | tttatatcaa | cagaagaata | agcataaact | aagcaaaagg | 5160 |
| tcaataagta | cctgaaacca | agattggcta | gagatatatc | ttaatgcaat | ccattttctg | 5220 |
| atggattgtt | acgagttggc | tatataatgt | atgtatggta | ttttgatttg | tgtaaaagtt | 5280 |
| ttaaaaatca | agctttaagt | acatggacat | ttttaaataa | aatatttaaa | gacaatttag | 5340 |
| aaaattgcct | taatatcatt | gttggctaaa | tagaataggg | gacatgcata | ttaaggaaaa | 5400 |
| ggtcatggag | aaataatatt | ggtatcaaac | aaatacattg | atttgtcatg | atacacattg | 5460 |
| aatttgatcc | aatagtttaa | ggaataggta | ggaaaatttg | gtttctattt | ttcgatttcc | 5520 |
| tgtaaatcag | tgacataaat | aattcttagc | ttattttata | tttccttgtc | ttaaatactg | 5580 |
| agctcagtaa | gttgtgttag | gggattattt | ctcagttgag | actttcttat | atgacatttt | 5640 |
| actatgtttt | gacttcctga | ctattaaaaa | taaatagtag | atacaatttt | cataaagtga | 5700 |
| agaattatat | aatcactgct | ttataactga | ctttattata | tttatttcaa | agttcattta | 5760 |
| aaggctacta | ttcatcctct | gtgatggaat | ggtcaggaat | ttgttttctc | atagtttaat | 5820 |
| tccaacaaca | atattagtcg | tatccaaaat | aaccttaat | gctaaacttt | actgatgtat | 5880 |
| atccaaagct | tctcattttc | agacagatta | atccagaagc | agtcataaac | agaagaatag | 5940 |
| gtggtatgtt | cctaatgata | ttatttctac | taatggaata | aactgtaata | ttagaaatta | 6000 |
| tgctgctaat | tatatcagct | ctgaggtaat | ttctgaaatg | ttcagactca | gtcggaacaa | 6060 |
| attggaaaat | ttaaatttt | attcttagct | ataaagcaag | aaagtaaaca | cattaatttc | 6120 |
| ctcaacattt | ttaagccaat | taaaaatata | aaagatacac | accaatatct | tcttcaggct | 6180 |
| ctgacaggcc | tcctggaaac | ttccacatat | ttttcaactg | cagtataaag | tcagaaaata | 6240 |
| aagttaacat | aactttcact | aacacacaca | tatgtagatt | tcacaaaatc | cacctataat | 6300 |
| tggtcaaagt | ggttgagaat | atattttta | gtaattgcat | gcaaaatttt | tctagcttcc | 6360 |
| atccttctc | cctcgtttct | tcttttttg | ggggagctgg | taactgatga | aatcttttcc | 6420 |
| caccttttct | cttcaggaaa | tataagtggt | tttgttggt | taacgtgata | cattctgtat | 6480 |
| gaatgaaaca | ttggagggaa | acatctactg | aatttctgta | atttaaaata | ttttgctgct | 6540 |
| agttaactat | gaacagatag | aagaatctta | cagatgctgc | tataaataag | tagaaaatat | 6600 |
| aaatttcatc | actaaaatat | gctatttaa | aatctatttc | ctatattgta | tttctaatca | 6660 |
| gatgtattac | tcttattatt | tctattgtat | gtgttaatga | ttttatgtaa | aaatgtaatt | 6720 |
| gcttttcatg | agtagtatga | ataaaattga | ttagtttgtg | ttttcttgtc | tccc | 6774 |

<210> SEQ ID NO 33
<211> LENGTH: 379
<212> TYPE: PRT
<213> ORGANISM: Homo sapiens

<400> SEQUENCE: 33

```
Met Ala Ala Ala Ala Gln Gly Gly Gly Gly Glu Pro Arg Arg
 1               5                  10                  15

Thr Glu Gly Val Gly Pro Gly Val Pro Gly Glu Val Glu Met Val Lys
                 20                  25                  30

Gly Gln Pro Phe Asp Val Gly Pro Arg Tyr Thr Gln Leu Gln Tyr Ile
             35                  40                  45

Gly Glu Gly Ala Tyr Gly Met Val Ser Ser Ala Tyr Asp His Val Arg
 50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
                195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
                260                 265                 270

Ile Asn Met Lys Ala Arg Asn Tyr Leu Gln Ser Leu Pro Ser Lys Thr
                275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
                340                 345                 350

Asp Asp Leu Pro Lys Glu Arg Leu Lys Glu Leu Ile Phe Gln Glu Thr
                355                 360                 365

Ala Arg Phe Gln Pro Gly Val Leu Glu Ala Pro
370                 375
```

<210> SEQ ID NO 34
<211> LENGTH: 357
<212> TYPE: PRT
<213> ORGANISM: Homo sapiens

<400> SEQUENCE: 34

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Val Gly Gln Ser Pro Ala Ala Val Gly Leu Gly Ala Gly
            340                 345                 350

Glu Gln Gly Gly Thr
        355

<210> SEQ ID NO 35
<211> LENGTH: 335
<212> TYPE: PRT
<213> ORGANISM: Homo sapiens

<400> SEQUENCE: 35
```

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
                115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
                195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Ala Leu Asp Leu Leu Asp Arg Met Leu Thr Phe Asn Pro Asn
                260                 265                 270

Lys Arg Ile Thr Val Glu Glu Ala Leu Ala His Pro Tyr Leu Glu Gln
                275                 280                 285

Tyr Tyr Asp Pro Thr Asp Glu Pro Val Ala Glu Glu Pro Phe Thr Phe
    290                 295                 300

Ala Met Glu Leu Asp Asp Leu Pro Lys Glu Arg Leu Lys Glu Leu Ile
305                 310                 315                 320

Phe Gln Glu Thr Ala Arg Phe Gln Pro Gly Val Leu Glu Ala Pro
                325                 330                 335

<210> SEQ ID NO 36
<211> LENGTH: 366
<212> TYPE: PRT
<213> ORGANISM: Homo sapiens

<400> SEQUENCE: 36

Pro Arg Arg Thr Glu Gly Val Gly Pro Gly Val Pro Gly Glu Val Glu
1               5                   10                  15

Met Val Lys Gly Gln Pro Phe Asp Val Gly Pro Arg Tyr Thr Gln Leu
                20                  25                  30

Gln Tyr Ile Gly Glu Gly Ala Tyr Gly Met Val Ser Ser Ala Tyr Asp
            35                  40                  45
```

His Val Arg Lys Thr Arg Val Ala Ile Lys Lys Ile Ser Pro Phe Glu
    50                  55                  60

His Gln Thr Tyr Cys Gln Arg Thr Leu Arg Glu Ile Gln Ile Leu Leu
65                  70                  75                  80

Arg Phe Arg His Glu Asn Val Ile Gly Ile Arg Asp Ile Leu Arg Ala
                85                  90                  95

Ser Thr Leu Glu Ala Met Arg Asp Val Tyr Ile Val Gln Asp Leu Met
            100                 105                 110

Glu Thr Asp Leu Tyr Lys Leu Leu Lys Ser Gln Gln Leu Ser Asn Asp
        115                 120                 125

His Ile Cys Tyr Phe Leu Tyr Gln Ile Leu Arg Gly Leu Lys Tyr Ile
    130                 135                 140

His Ser Ala Asn Val Leu His Arg Asp Leu Lys Pro Ser Asn Leu Leu
145                 150                 155                 160

Ile Asn Thr Thr Cys Asp Leu Lys Ile Cys Asp Phe Gly Leu Ala Arg
                165                 170                 175

Ile Ala Asp Pro Glu His Asp His Thr Gly Phe Leu Thr Glu Tyr Val
            180                 185                 190

Ala Thr Arg Trp Tyr Arg Ala Pro Glu Ile Met Leu Asn Ser Lys Gly
        195                 200                 205

Tyr Thr Lys Ser Ile Asp Ile Trp Ser Val Gly Cys Ile Leu Ala Glu
    210                 215                 220

Met Leu Ser Asn Arg Pro Ile Phe Pro Gly Lys His Tyr Leu Asp Gln
225                 230                 235                 240

Leu Asn His Ile Leu Gly Ile Leu Gly Ser Pro Ser Gln Glu Asp Leu
                245                 250                 255

Asn Cys Ile Ile Asn Met Lys Ala Arg Asn Tyr Leu Gln Ser Leu Pro
            260                 265                 270

Ser Lys Thr Lys Val Ala Trp Ala Lys Leu Phe Pro Lys Ser Asp Ser
        275                 280                 285

Lys Ala Leu Asp Leu Leu Asp Arg Met Leu Thr Phe Asn Pro Asn Lys
    290                 295                 300

Arg Ile Thr Val Glu Glu Ala Leu Ala His Pro Tyr Leu Glu Gln Tyr
305                 310                 315                 320

Tyr Asp Pro Thr Asp Glu Pro Val Ala Glu Glu Pro Phe Thr Phe Ala
                325                 330                 335

Met Glu Leu Asp Asp Leu Pro Lys Glu Arg Leu Lys Glu Leu Ile Phe
            340                 345                 350

Gln Glu Thr Ala Arg Phe Gln Pro Gly Val Leu Glu Ala Pro
        355                 360                 365

<210> SEQ ID NO 37
<211> LENGTH: 360
<212> TYPE: PRT
<213> ORGANISM: Homo sapiens

<400> SEQUENCE: 37

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr

```
            50                  55                  60
Cys Gln Arg Thr Leu Arg Glu Ile Lys Ile Leu Leu Arg Phe Arg His
 65                  70                  75                  80

Glu Asn Ile Ile Gly Ile Asn Asp Ile Ile Arg Ala Pro Thr Ile Glu
                 85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
            115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
            195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
            275                 280                 285

Leu Leu Asp Lys Met Leu Thr Phe Asn Pro His Lys Arg Ile Glu Val
            290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
            355                 360

<210> SEQ ID NO 38
<211> LENGTH: 360
<212> TYPE: PRT
<213> ORGANISM: Homo sapiens

<400> SEQUENCE: 38

Met Ala Ala Ala Ala Ala Gly Ala Gly Pro Glu Met Val Arg Gly
 1               5                  10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
 50                  55                  60
```

Cys Gln Arg Thr Leu Arg Glu Ile Lys Ile Leu Arg Phe Arg His
 65                  70                  75                  80

Glu Asn Ile Ile Gly Ile Asn Asp Ile Ile Arg Ala Pro Thr Ile Glu
             85                  90                  95

Gln Met Lys Asp Val Tyr Ile Val Gln Asp Leu Met Glu Thr Asp Leu
        100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360

<210> SEQ ID NO 39
<211> LENGTH: 360
<212> TYPE: PRT
<213> ORGANISM: Homo sapiens

<400> SEQUENCE: 39

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

```
Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asn Gln Leu Gln Gln Ile Met Arg Leu Thr Gly
225                 230                 235                 240

Thr Pro Pro Ala Tyr Leu Ile Asn Arg Met Pro Ser His Glu Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 40
<211> LENGTH: 360
<212> TYPE: PRT
<213> ORGANISM: Homo sapiens

<400> SEQUENCE: 40

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
                20                  25                  30

Gly Ala Tyr Gly Ser Val Cys Ala Ala Phe Asp Thr Lys Thr Gly Leu
            35                  40                  45

Arg Val Ala Val Lys Lys Leu Ser Arg Pro Phe Gln Ser Ile Ile His
        50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
```

```
                        85                  90                  95
Glu Glu Phe Asn Asp Val Tyr Leu Val Thr His Leu Met Gly Ala Asp
                    100                 105                 110
Leu Asn Asn Ile Val Lys Cys Gln Lys Leu Thr Asp Asp His Val Gln
                115                 120                 125
Phe Leu Ile Tyr Gln Ile Leu Arg Gly Leu Lys Tyr Ile His Ser Ala
130                 135                 140
Asp Ile Ile His Arg Asp Leu Lys Pro Ser Asn Leu Ala Val Asn Glu
145                 150                 155                 160
Asp Cys Glu Leu Lys Ile Leu Asp Phe Gly Leu Ala Arg His Thr Asp
                165                 170                 175
Asp Glu Met Thr Gly Tyr Val Ala Thr Arg Trp Tyr Arg Ala Pro Glu
                180                 185                 190
Ile Met Leu Asn Trp Met His Tyr Asn Gln Thr Val Asp Ile Trp Ser
                195                 200                 205
Val Gly Cys Ile Met Ala Glu Leu Leu Thr Gly Arg Thr Leu Phe Pro
210                 215                 220
Gly Thr Asp His Ile Asp Gln Leu Lys Leu Ile Leu Arg Leu Val Gly
225                 230                 235                 240
Thr Pro Gly Ala Glu Leu Leu Lys Lys Ile Ser Ser Glu Ser Ala Arg
                245                 250                 255
Asn Tyr Ile Gln Ser Leu Thr Gln Met Pro Lys Met Asn Phe Ala Asn
                260                 265                 270
Val Phe Ile Gly Ala Asn Pro Leu Ala Val Asp Leu Leu Glu Lys Met
                275                 280                 285
Leu Val Leu Asp Ser Asp Lys Arg Ile Thr Ala Ala Gln Ala Leu Ala
290                 295                 300
His Ala Tyr Phe Ala Gln Tyr His Asp Pro Asp Asp Glu Pro Val Ala
305                 310                 315                 320
Asp Pro Tyr Asp Gln Ser Phe Glu Ser Arg Asp Leu Leu Ile Asp Glu
                325                 330                 335
Trp Lys Ser Leu Thr Tyr Asp Glu Val Ile Ser Phe Val Pro Pro Pro
                340                 345                 350
Leu Asp Gln Glu Glu Met Glu Ser
                355                 360

<210> SEQ ID NO 41
<211> LENGTH: 297
<212> TYPE: PRT
<213> ORGANISM: Homo sapiens

<400> SEQUENCE: 41

Met Ser Gln Glu Arg Pro Thr Phe Tyr Arg Gln Glu Leu Asn Lys Thr
1               5                   10                  15
Ile Trp Glu Val Pro Glu Arg Tyr Gln Asn Leu Ser Pro Val Gly Ser
                20                  25                  30
Gly Ala Tyr Gly Ser Val Cys Ala Ala Phe Asp Thr Lys Thr Gly Leu
            35                  40                  45
Arg Val Ala Val Lys Lys Leu Ser Arg Pro Phe Gln Ser Ile Ile His
        50                  55                  60
Ala Lys Arg Thr Tyr Arg Glu Leu Arg Leu Leu Lys His Met Lys His
65                  70                  75                  80
Glu Asn Val Ile Gly Leu Leu Asp Val Phe Thr Pro Ala Arg Ser Leu
                85                  90                  95
```

```
Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Gly Lys Leu Thr Ile Tyr Pro His
        275                 280                 285

Leu Met Asp Ile Glu Leu Val Met Ile
    290                 295

<210> SEQ ID NO 42
<211> LENGTH: 307
<212> TYPE: PRT
<213> ORGANISM: Homo sapiens

<400> SEQUENCE: 42

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175
```

```
Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Leu Ser
            245                 250                 255

Thr Cys Trp Arg Arg Cys Leu Tyr Trp Thr Gln Ile Arg Glu Leu Gln
            260                 265                 270

Arg Pro Lys Pro Leu His Met Pro Thr Leu Leu Ser Thr Thr Ile Leu
            275                 280                 285

Met Met Asn Gln Trp Pro Ile Leu Met Ile Ser Pro Leu Lys Ala Gly
            290                 295                 300

Thr Ser Leu
305

<210> SEQ ID NO 43
<211> LENGTH: 364
<212> TYPE: PRT
<213> ORGANISM: Homo sapiens

<400> SEQUENCE: 43

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
            115                 120                 125

Phe Leu Val Tyr Gln Leu Leu Arg Gly Leu Lys Tyr Ile His Ser Ala
130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
            195                 200                 205

Val Gly Cys Ile Met Ala Glu Leu Leu Gln Gly Lys Ala Leu Phe Pro
        210                 215                 220

Gly Ser Asp Tyr Ile Asp Gln Leu Lys Arg Ile Met Glu Val Val Gly
```

```
                 225                 230                 235                 240
        Thr Pro Ser Pro Glu Val Leu Ala Lys Ile Ser Ser Glu His Ala Arg
                        245                 250                 255

Thr Tyr Ile Gln Ser Leu Pro Pro Met Pro Gln Lys Asp Leu Ser Ser
                        260                 265                 270

Ile Phe Arg Gly Ala Asn Pro Leu Ala Ile Asp Leu Leu Gly Arg Met
                        275                 280                 285

Leu Val Leu Asp Ser Asp Gln Arg Val Ser Ala Ala Glu Ala Leu Ala
                        290                 295                 300

His Ala Tyr Phe Ser Gln Tyr His Asp Pro Glu Asp Glu Pro Glu Ala
        305                 310                 315                 320

Glu Pro Tyr Asp Glu Ser Val Glu Ala Lys Glu Arg Thr Leu Glu Glu
                        325                 330                 335

Trp Lys Glu Leu Thr Tyr Gln Glu Val Leu Ser Phe Lys Pro Pro Glu
                        340                 345                 350

Pro Pro Lys Pro Pro Gly Ser Leu Glu Ile Glu Gln
                        355                 360

<210> SEQ ID NO 44
<211> LENGTH: 367
<212> TYPE: PRT
<213> ORGANISM: Homo sapiens

<400> SEQUENCE: 44

Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
                20                  25                  30

Val Gly Ser Gly Ala Tyr Gly Ala Val Cys Ser Ala Val Asp Gly Arg
                35                  40                  45

Thr Gly Ala Lys Val Ala Ile Lys Lys Leu Tyr Arg Pro Phe Gln Ser
        50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
                115                 120                 125

Arg Ile Gln Phe Leu Val Tyr Gln Met Leu Lys Gly Leu Arg Tyr Ile
                130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
                180                 185                 190

Ala Pro Glu Val Ile Leu Asn Trp Met Arg Tyr Thr Gln Thr Val Asp
                195                 200                 205

Ile Trp Ser Val Gly Cys Ile Met Ala Glu Met Ile Thr Gly Lys Thr
                210                 215                 220

Leu Phe Lys Gly Ser Asp His Leu Asp Gln Leu Lys Glu Ile Met Lys
225                 230                 235                 240
```

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Lys Lys Asp
            260                 265                 270

Phe Ala Ser Ile Leu Thr Asn Ala Ser Pro Leu Ala Val Asn Leu Leu
            275                 280                 285

Glu Lys Met Leu Val Leu Asp Ala Glu Gln Arg Val Thr Ala Gly Glu
        290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
            340                 345                 350

Pro Pro Arg Gln Leu Gly Ala Arg Val Ser Lys Glu Thr Pro Leu
        355                 360                 365

<210> SEQ ID NO 45
<211> LENGTH: 365
<212> TYPE: PRT
<213> ORGANISM: Homo sapiens

<400> SEQUENCE: 45

Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Val Cys Ser Ala Ile Asp Lys Arg Ser Gly
        35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

```
Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
                340                 345                 350

Ala Arg Lys Asp Ser Arg Arg Arg Ser Gly Met Lys Leu
                355                 360                 365

<210> SEQ ID NO 46
<211> LENGTH: 427
<212> TYPE: PRT
<213> ORGANISM: Homo sapiens

<400> SEQUENCE: 46

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Ile Leu
            35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
                100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Leu
            195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
```

```
                    260                 265                 270
Lys Leu Phe Pro Asp Val Leu Phe Pro Ala Asp Ser Glu His Asn Lys
                275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
                355                 360                 365

Asn Gly Val Ile Arg Gly Gln Pro Ser Pro Leu Gly Ala Ala Val Ile
            370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Ala Gly Pro Leu Gly Cys Cys Arg
            420                 425

<210> SEQ ID NO 47
<211> LENGTH: 427
<212> TYPE: PRT
<213> ORGANISM: Homo sapiens

<400> SEQUENCE: 47

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205
```

```
Trp Ser Val Gly Cys Ile Met Gly Glu Met Ile Lys Gly Gly Val Leu
        210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Lys Leu Gln Pro Thr Val
                    245                 250                 255

Arg Thr Tyr Val Glu Asn Arg Pro Lys Tyr Ala Gly Tyr Ser Phe Glu
                260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
        290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Gly Ala Ala Val Ile
370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Ala Gly Pro Leu Gly Cys Cys Arg
            420                 425

<210> SEQ ID NO 48
<211> LENGTH: 384
<212> TYPE: PRT
<213> ORGANISM: Homo sapiens

<400> SEQUENCE: 48

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Ile Leu
            35                  40                  45

Glu Arg Asn Val Ala Ile Lys Lys Leu Ser Arg Pro Phe Gln Asn Gln
        50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
                100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160
```

```
Ser Asp Cys Thr Leu Lys Ile Leu Asp Phe Gly Leu Ala Arg Thr Ala
            165                 170                 175

Gly Thr Ser Phe Met Met Thr Pro Tyr Val Val Thr Arg Tyr Tyr Arg
        180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Met Ile Lys Gly Gly Val Leu
    210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Ala Gln Val Gln Gln
    370                 375                 380

<210> SEQ ID NO 49
<211> LENGTH: 384
<212> TYPE: PRT
<213> ORGANISM: Homo sapiens

<400> SEQUENCE: 49

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
```

```
                145                 150                 155                 160
        Ser Asp Cys Thr Leu Lys Ile Leu Asp Phe Gly Leu Ala Arg Thr Ala
                        165                 170                 175

Gly Thr Ser Phe Met Met Thr Pro Tyr Val Val Thr Arg Tyr Tyr Arg
                        180                 185                 190

Ala Pro Glu Val Ile Leu Gly Met Gly Tyr Lys Glu Asn Val Asp Leu
                        195                 200                 205

Trp Ser Val Gly Cys Ile Met Gly Glu Met Val Cys His Lys Ile Leu
                        210                 215                 220

Phe Pro Gly Arg Asp Tyr Ile Asp Gln Trp Asn Lys Val Ile Glu Gln
        225                 230                 235                 240

Leu Gly Thr Pro Cys Pro Glu Phe Met Lys Lys Leu Gln Pro Thr Val
                        245                 250                 255

Arg Thr Tyr Val Glu Asn Arg Pro Lys Tyr Ala Gly Tyr Ser Phe Glu
                        260                 265                 270

Lys Leu Phe Pro Asp Val Leu Phe Pro Ala Asp Ser Glu His Asn Lys
                        275                 280                 285

Leu Lys Ala Ser Gln Ala Arg Asp Leu Leu Ser Lys Met Leu Val Ile
                        290                 295                 300

Asp Ala Ser Lys Arg Ile Ser Val Asp Glu Ala Leu Gln His Pro Tyr
        305                 310                 315                 320

Ile Asn Val Trp Tyr Asp Pro Ser Glu Ala Glu Ala Pro Pro Pro Lys
                        325                 330                 335

Ile Pro Asp Lys Gln Leu Asp Glu Arg Glu His Thr Ile Glu Glu Trp
                        340                 345                 350

Lys Glu Leu Ile Tyr Lys Glu Val Met Asp Leu Glu Glu Arg Thr Lys
                        355                 360                 365

Asn Gly Val Ile Arg Gly Gln Pro Ser Pro Leu Ala Gln Val Gln Gln
                        370                 375                 380

<210> SEQ ID NO 50
<211> LENGTH: 1354
<212> TYPE: PRT
<213> ORGANISM: Homo sapiens

<400> SEQUENCE: 50

Met Ser Thr Gly Asp Ser Phe Glu Thr Arg Phe Glu Lys Met Asp Asn
        1               5                   10                  15

Leu Leu Arg Asp Pro Lys Ser Glu Val Asn Ser Asp Cys Leu Leu Asp
                        20                  25                  30

Gly Leu Asp Ala Leu Val Tyr Asp Leu Asp Phe Pro Ala Leu Arg Lys
                        35                  40                  45

Asn Lys Asn Ile Asp Asn Phe Leu Ser Arg Tyr Lys Asp Thr Ile Asn
                        50                  55                  60

Lys Ile Arg Asp Leu Arg Met Lys Ala Glu Asp Tyr Glu Val Val Lys
        65                  70                  75                  80

Val Ile Gly Arg Gly Ala Phe Gly Glu Val Gln Leu Val Arg His Lys
                        85                  90                  95

Ser Thr Arg Lys Val Tyr Ala Met Lys Leu Leu Ser Lys Phe Glu Met
                        100                 105                 110

Ile Lys Arg Ser Asp Ser Ala Phe Phe Trp Glu Glu Arg Asp Ile Met
                        115                 120                 125

Ala Phe Ala Asn Ser Pro Trp Val Val Gln Leu Phe Tyr Ala Phe Gln
                        130                 135                 140
```

-continued

```
Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
            180                 185                 190

Gly Phe Ile His Arg Asp Val Lys Pro Asp Asn Met Leu Leu Asp Lys
        195                 200                 205

Ser Gly His Leu Lys Leu Ala Asp Phe Gly Thr Cys Met Lys Met Asn
    210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285

Lys Ile Met Asn His Lys Asn Ser Leu Thr Phe Pro Asp Asp Asn Asp
    290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Thr Val
            340                 345                 350

Ala Pro Val Val Pro Asp Leu Ser Ser Asp Ile Asp Thr Ser Asn Phe
        355                 360                 365

Asp Asp Leu Glu Glu Asp Lys Gly Glu Glu Thr Phe Pro Ile Pro
    370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
        435                 440                 445

Met Glu Gln Lys Cys Arg Thr Ser Asn Ile Lys Leu Asp Lys Ile Met
450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
                485                 490                 495

Glu Tyr Gln Arg Lys Ala Glu Gln Glu Asn Glu Lys Arg Arg Asn Val
            500                 505                 510

Glu Asn Glu Val Ser Thr Leu Lys Asp Gln Leu Glu Asp Leu Lys Lys
        515                 520                 525

Val Ser Gln Asn Ser Gln Leu Ala Asn Glu Lys Leu Ser Gln Leu Gln
    530                 535                 540

Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
```

-continued

```
                565                 570                 575
Gln Leu Glu Ser Leu Asn Arg Glu Leu Gln Glu Arg Asn Arg Ile Leu
                580                 585                 590
Glu Asn Ser Lys Ser Gln Thr Asp Lys Asp Tyr Tyr Gln Leu Gln Ala
                595                 600                 605
Ile Leu Glu Ala Glu Arg Arg Asp Arg Gly His Asp Ser Glu Met Ile
610                 615                 620
Gly Asp Leu Gln Ala Arg Ile Thr Ser Leu Gln Glu Val Lys His
625                 630                 635                 640
Leu Lys His Asn Leu Glu Lys Val Glu Gly Glu Arg Lys Glu Ala Gln
                645                 650                 655
Asp Met Leu Asn His Ser Glu Lys Glu Lys Asn Asn Leu Glu Ile Asp
                660                 665                 670
Leu Asn Tyr Lys Leu Lys Ser Leu Gln Gln Arg Leu Glu Gln Glu Val
                675                 680                 685
Asn Glu His Lys Val Thr Lys Ala Arg Leu Thr Asp Lys His Gln Ser
                690                 695                 700
Ile Glu Glu Ala Lys Ser Val Ala Met Cys Glu Met Glu Lys Lys Leu
705                 710                 715                 720
Lys Glu Glu Arg Glu Ala Arg Glu Lys Ala Glu Asn Arg Val Val Gln
                725                 730                 735
Ile Glu Lys Gln Cys Ser Met Leu Asp Val Asp Leu Lys Gln Ser Gln
                740                 745                 750
Gln Lys Leu Glu His Leu Thr Gly Asn Lys Glu Arg Met Glu Asp Glu
                755                 760                 765
Val Lys Asn Leu Thr Leu Gln Leu Glu Gln Glu Ser Asn Lys Arg Leu
770                 775                 780
Leu Leu Gln Asn Glu Leu Lys Thr Gln Ala Phe Glu Ala Asp Asn Leu
785                 790                 795                 800
Lys Gly Leu Glu Lys Gln Met Lys Gln Glu Ile Asn Thr Leu Leu Glu
                805                 810                 815
Ala Lys Arg Leu Leu Glu Phe Glu Leu Ala Gln Leu Thr Lys Gln Tyr
                820                 825                 830
Arg Gly Asn Glu Gly Gln Met Arg Glu Leu Gln Asp Gln Leu Glu Ala
                835                 840                 845
Glu Gln Tyr Phe Ser Thr Leu Tyr Lys Thr Gln Val Lys Glu Leu Lys
                850                 855                 860
Glu Glu Ile Glu Glu Lys Asn Arg Glu Asn Leu Lys Lys Ile Gln Glu
865                 870                 875                 880
Leu Gln Asn Glu Lys Glu Thr Leu Ala Thr Gln Leu Asp Leu Ala Glu
                885                 890                 895
Thr Lys Ala Glu Ser Glu Gln Leu Ala Arg Gly Leu Leu Glu Glu Gln
                900                 905                 910
Tyr Phe Glu Leu Thr Gln Glu Ser Lys Lys Ala Ala Ser Arg Asn Arg
                915                 920                 925
Gln Glu Ile Thr Asp Lys Asp His Thr Val Ser Arg Leu Glu Glu Ala
                930                 935                 940
Asn Ser Met Leu Thr Lys Asp Ile Glu Ile Leu Arg Arg Glu Asn Glu
945                 950                 955                 960
Glu Leu Thr Glu Lys Met Lys Lys Ala Glu Glu Tyr Lys Leu Glu
                965                 970                 975
Lys Glu Glu Glu Ile Ser Asn Leu Lys Ala Ala Phe Glu Lys Asn Ile
                980                 985                 990
```

```
Asn Thr Glu Arg Thr Leu Lys Thr Gln Ala Val Asn Lys Leu Ala Glu
        995                 1000                1005

Ile Met Asn Arg Lys Asp Phe Lys Ile Asp Arg Lys Lys Ala Asn
    1010                1015                1020

Thr Gln Asp Leu Arg Lys Lys Glu Lys Glu Asn Arg Lys Leu Gln
    1025                1030                1035

Leu Glu Leu Asn Gln Glu Arg Glu Lys Phe Asn Gln Met Val Val
    1040                1045                1050

Lys His Gln Lys Glu Leu Asn Asp Met Gln Ala Gln Leu Val Glu
    1055                1060                1065

Glu Cys Ala His Arg Asn Glu Leu Gln Met Gln Leu Ala Ser Lys
    1070                1075                1080

Glu Ser Asp Ile Glu Gln Leu Arg Ala Lys Leu Leu Asp Leu Ser
    1085                1090                1095

Asp Ser Thr Ser Val Ala Ser Phe Pro Ser Ala Asp Glu Thr Asp
    1100                1105                1110

Gly Asn Leu Pro Glu Ser Arg Ile Glu Gly Trp Leu Ser Val Pro
    1115                1120                1125

Asn Arg Gly Asn Ile Lys Arg Tyr Gly Trp Lys Lys Gln Tyr Val
    1130                1135                1140

Val Val Ser Ser Lys Lys Ile Leu Phe Tyr Asn Asp Glu Gln Asp
    1145                1150                1155

Lys Glu Gln Ser Asn Pro Ser Met Val Leu Asp Ile Asp Lys Leu
    1160                1165                1170

Phe His Val Arg Pro Val Thr Gln Gly Asp Val Tyr Arg Ala Glu
    1175                1180                1185

Thr Glu Glu Ile Pro Lys Ile Phe Gln Ile Leu Tyr Ala Asn Glu
    1190                1195                1200

Gly Glu Cys Arg Lys Asp Val Glu Met Glu Pro Val Gln Gln Ala
    1205                1210                1215

Glu Lys Thr Asn Phe Gln Asn His Lys Gly His Glu Phe Ile Pro
    1220                1225                1230

Thr Leu Tyr His Phe Pro Ala Asn Cys Asp Ala Cys Ala Lys Pro
    1235                1240                1245

Leu Trp His Val Phe Lys Pro Pro Pro Ala Leu Glu Cys Arg Arg
    1250                1255                1260

Cys His Val Lys Cys His Arg Asp His Leu Asp Lys Lys Glu Asp
    1265                1270                1275

Leu Ile Cys Pro Cys Lys Val Ser Tyr Asp Val Thr Ser Ala Arg
    1280                1285                1290

Asp Met Leu Leu Leu Ala Cys Ser Gln Asp Glu Gln Lys Lys Trp
    1295                1300                1305

Val Thr His Leu Val Lys Lys Ile Pro Lys Asn Pro Pro Ser Gly
    1310                1315                1320

Phe Val Arg Ala Ser Pro Arg Thr Leu Ser Thr Arg Ser Thr Ala
    1325                1330                1335

Asn Gln Ser Phe Arg Lys Val Val Lys Asn Thr Ser Gly Lys Thr
    1340                1345                1350

Ser

<210> SEQ ID NO 51
<211> LENGTH: 1388
<212> TYPE: PRT
```

<213> ORGANISM: Homo sapiens

<400> SEQUENCE: 51

Met Ser Arg Pro Pro Thr Gly Lys Met Pro Gly Ala Pro Glu Thr
1               5                   10                  15

Ala Pro Gly Asp Gly Ala Gly Ala Ser Arg Gln Arg Lys Leu Glu Ala
            20                  25                  30

Leu Ile Arg Asp Pro Arg Ser Pro Ile Asn Val Glu Ser Leu Leu Asp
                35                  40                  45

Gly Leu Asn Ser Leu Val Leu Asp Leu Asp Phe Pro Ala Leu Arg Lys
        50                  55                  60

Asn Lys Asn Ile Asp Asn Phe Leu Asn Arg Tyr Glu Lys Ile Val Lys
65                  70                  75                  80

Lys Ile Arg Gly Leu Gln Met Lys Ala Glu Asp Tyr Asp Val Val Lys
                85                  90                  95

Val Ile Gly Arg Gly Ala Phe Gly Glu Val Gln Leu Val Arg His Lys
            100                 105                 110

Ala Ser Gln Lys Val Tyr Ala Met Lys Leu Leu Ser Lys Phe Glu Met
        115                 120                 125

Ile Lys Arg Ser Asp Ser Ala Phe Phe Trp Glu Glu Arg Asp Ile Met
130                 135                 140

Ala Phe Ala Asn Ser Pro Trp Val Val Gln Leu Phe Tyr Ala Phe Gln
145                 150                 155                 160

Asp Asp Arg Tyr Leu Tyr Met Val Met Glu Tyr Met Pro Gly Gly Asp
                165                 170                 175

Leu Val Asn Leu Met Ser Asn Tyr Asp Val Pro Glu Lys Trp Ala Lys
            180                 185                 190

Phe Tyr Thr Ala Glu Val Val Leu Ala Leu Asp Ala Ile His Ser Met
        195                 200                 205

Gly Leu Ile His Arg Asp Val Lys Pro Asp Asn Met Leu Leu Asp Lys
    210                 215                 220

His Gly His Leu Lys Leu Ala Asp Phe Gly Thr Cys Met Lys Met Asp
225                 230                 235                 240

Glu Thr Gly Met Val His Cys Asp Thr Ala Val Gly Thr Pro Asp Tyr
                245                 250                 255

Ile Ser Pro Glu Val Leu Lys Ser Gln Gly Gly Asp Gly Phe Tyr Gly
            260                 265                 270

Arg Glu Cys Asp Trp Trp Ser Val Gly Val Phe Leu Tyr Glu Met Leu
        275                 280                 285

Val Gly Asp Thr Pro Phe Tyr Ala Asp Ser Leu Val Gly Thr Tyr Ser
    290                 295                 300

Lys Ile Met Asp His Lys Asn Ser Leu Cys Phe Pro Glu Asp Ala Glu
305                 310                 315                 320

Ile Ser Lys His Ala Lys Asn Leu Ile Cys Ala Phe Leu Thr Asp Arg
                325                 330                 335

Glu Val Arg Leu Gly Arg Asn Gly Val Glu Glu Ile Arg Gln His Pro
            340                 345                 350

Phe Phe Lys Asn Asp Gln Trp His Trp Asp Asn Ile Arg Glu Thr Ala
        355                 360                 365

Ala Pro Val Val Pro Glu Leu Ser Ser Asp Ile Asp Ser Ser Asn Phe
    370                 375                 380

Asp Asp Ile Glu Asp Asp Lys Gly Asp Val Glu Thr Phe Pro Ile Pro
385                 390                 395                 400

```
Lys Ala Phe Val Gly Asn Gln Leu Pro Phe Ile Gly Phe Thr Tyr Tyr
                405                 410                 415
Arg Glu Asn Leu Leu Leu Ser Asp Ser Pro Ser Cys Arg Glu Thr Asp
            420                 425                 430
Ser Ile Gln Ser Arg Lys Asn Glu Glu Ser Gln Glu Ile Gln Lys Lys
        435                 440                 445
Leu Tyr Thr Leu Glu Glu His Leu Ser Asn Glu Met Gln Ala Lys Glu
    450                 455                 460
Glu Leu Glu Gln Lys Cys Lys Ser Val Asn Thr Arg Leu Glu Lys Thr
465                 470                 475                 480
Ala Lys Glu Leu Glu Glu Ile Thr Leu Arg Lys Ser Val Glu Ser
                485                 490                 495
Ala Leu Arg Gln Leu Glu Arg Glu Lys Ala Leu Leu Gln His Lys Asn
            500                 505                 510
Ala Glu Tyr Gln Arg Lys Ala Asp His Glu Ala Asp Lys Lys Arg Asn
        515                 520                 525
Leu Glu Asn Asp Val Asn Ser Leu Lys Asp Gln Leu Glu Asp Leu Lys
    530                 535                 540
Lys Arg Asn Gln Asn Ser Gln Ile Ser Thr Glu Lys Val Asn Gln Leu
545                 550                 555                 560
Gln Arg Gln Leu Asp Glu Thr Asn Ala Leu Leu Arg Thr Glu Ser Asp
                565                 570                 575
Thr Ala Ala Arg Leu Arg Lys Thr Gln Ala Glu Ser Ser Lys Gln Ile
            580                 585                 590
Gln Gln Leu Glu Ser Asn Asn Arg Asp Leu Gln Asp Lys Asn Cys Leu
        595                 600                 605
Leu Glu Thr Ala Lys Leu Lys Leu Glu Lys Glu Phe Ile Asn Leu Gln
    610                 615                 620
Ser Ala Leu Glu Ser Glu Arg Arg Asp Arg Thr His Gly Ser Glu Ile
625                 630                 635                 640
Ile Asn Asp Leu Gln Gly Arg Ile Cys Gly Leu Glu Glu Asp Leu Lys
                645                 650                 655
Asn Gly Lys Ile Leu Leu Ala Lys Val Glu Leu Glu Lys Arg Gln Leu
            660                 665                 670
Gln Glu Arg Phe Thr Asp Leu Glu Lys Glu Lys Ser Asn Met Glu Ile
        675                 680                 685
Asp Met Thr Tyr Gln Leu Lys Val Ile Gln Gln Ser Leu Glu Gln Glu
    690                 695                 700
Glu Ala Glu His Lys Ala Thr Lys Ala Arg Leu Ala Asp Lys Asn Lys
705                 710                 715                 720
Ile Tyr Glu Ser Ile Glu Glu Ala Lys Ser Glu Ala Met Lys Glu Met
                725                 730                 735
Glu Lys Lys Leu Leu Glu Glu Arg Thr Leu Lys Gln Lys Val Glu Asn
            740                 745                 750
Leu Leu Leu Glu Ala Glu Lys Arg Cys Ser Leu Leu Asp Cys Asp Leu
        755                 760                 765
Lys Gln Ser Gln Gln Lys Ile Asn Glu Leu Leu Lys Gln Lys Asp Val
    770                 775                 780
Leu Asn Glu Asp Val Arg Asn Leu Thr Leu Lys Ile Glu Gln Glu Thr
785                 790                 795                 800
Gln Lys Arg Cys Leu Thr Gln Asn Asp Leu Lys Met Gln Thr Gln Gln
                805                 810                 815
Val Asn Thr Leu Lys Met Ser Glu Lys Gln Leu Lys Gln Glu Asn Asn
```

-continued

```
            820                 825                 830
His Leu Met Glu Met Lys Met Asn Leu Glu Lys Gln Asn Ala Glu Leu
            835                 840                 845
Arg Lys Glu Arg Gln Asp Ala Asp Gly Gln Met Lys Glu Leu Gln Asp
            850                 855                 860
Gln Leu Glu Ala Glu Gln Tyr Phe Ser Thr Leu Tyr Lys Thr Gln Val
            865                 870                 875                 880
Arg Glu Leu Lys Glu Glu Cys Glu Glu Lys Thr Lys Leu Gly Lys Glu
                                885                 890                 895
Leu Gln Gln Lys Lys Gln Glu Leu Gln Asp Glu Arg Asp Ser Leu Ala
            900                 905                 910
Ala Gln Leu Glu Ile Thr Leu Thr Lys Ala Asp Ser Glu Gln Leu Ala
            915                 920                 925
Arg Ser Ile Ala Glu Glu Gln Tyr Ser Asp Leu Glu Lys Glu Lys Ile
            930                 935                 940
Met Lys Glu Leu Glu Ile Lys Glu Met Met Ala Arg His Lys Gln Glu
945                             950                 955                 960
Leu Thr Glu Lys Asp Ala Thr Ile Ala Ser Leu Glu Glu Thr Asn Arg
                                965                 970                 975
Thr Leu Thr Ser Asp Val Ala Asn Leu Ala Asn Glu Lys Glu Glu Leu
            980                 985                 990
Asn Asn Lys Leu Lys Asp Val Gln Glu Gln Leu Ser Arg Leu Lys Asp
            995                 1000                1005
Glu Glu Ile Ser Ala Ala Ala Ile Lys Ala Gln Phe Glu Lys Gln
            1010                1015                1020
Leu Leu Thr Glu Arg Thr Leu Lys Thr Gln Ala Val Asn Lys Leu
            1025                1030                1035
Ala Glu Ile Met Asn Arg Lys Glu Pro Val Lys Arg Gly Asn Asp
            1040                1045                1050
Thr Asp Val Arg Arg Lys Glu Lys Glu Asn Arg Lys Leu His Met
            1055                1060                1065
Glu Leu Lys Ser Glu Arg Glu Lys Leu Thr Gln Gln Met Ile Lys
            1070                1075                1080
Tyr Gln Lys Glu Leu Asn Glu Met Gln Ala Gln Ile Ala Glu Glu
            1085                1090                1095
Ser Gln Ile Arg Ile Glu Leu Gln Met Thr Leu Asp Ser Lys Asp
            1100                1105                1110
Ser Asp Ile Glu Gln Leu Arg Ser Gln Leu Gln Ala Leu His Ile
            1115                1120                1125
Gly Leu Asp Ser Ser Ser Ile Gly Ser Gly Pro Gly Asp Ala Glu
            1130                1135                1140
Ala Asp Asp Gly Phe Pro Glu Ser Arg Leu Glu Gly Trp Leu Ser
            1145                1150                1155
Leu Pro Val Arg Asn Asn Thr Lys Lys Phe Gly Trp Val Lys Lys
            1160                1165                1170
Tyr Val Ile Val Ser Ser Lys Lys Ile Leu Phe Tyr Asp Ser Glu
            1175                1180                1185
Gln Asp Lys Glu Gln Ser Asn Pro Tyr Met Val Leu Asp Ile Asp
            1190                1195                1200
Lys Leu Phe His Val Arg Pro Val Thr Gln Thr Asp Val Tyr Arg
            1205                1210                1215
Ala Asp Ala Lys Glu Ile Pro Arg Ile Phe Gln Ile Leu Tyr Ala
            1220                1225                1230
```

```
Asn Glu Gly Glu Ser Lys Lys Glu Gln Glu Phe Pro Val Glu Pro
        1235                1240                1245

Val Gly Glu Lys Ser Asn Tyr Ile Cys His Lys Gly His Glu Phe
    1250                1255                1260

Ile Pro Thr Leu Tyr His Phe Pro Thr Asn Cys Glu Ala Cys Met
    1265                1270                1275

Lys Pro Leu Trp His Met Phe Lys Pro Pro Ala Leu Glu Cys
    1280                1285                1290

Arg Arg Cys His Ile Lys Cys His Lys Asp His Met Asp Lys Lys
    1295                1300                1305

Glu Glu Ile Ile Ala Pro Cys Lys Val Tyr Tyr Asp Ile Ser Thr
    1310                1315                1320

Ala Lys Asn Leu Leu Leu Leu Ala Asn Ser Thr Glu Glu Gln Gln
    1325                1330                1335

Lys Trp Val Ser Arg Leu Val Lys Lys Ile Pro Lys Lys Pro Pro
    1340                1345                1350

Ala Pro Asp Pro Phe Ala Arg Ser Ser Pro Arg Thr Ser Met Lys
    1355                1360                1365

Ile Gln Gln Asn Gln Ser Ile Arg Arg Pro Ser Arg Gln Leu Ala
    1370                1375                1380

Pro Asn Lys Pro Ser
    1385

<210> SEQ ID NO 52
<211> LENGTH: 25
<212> TYPE: RNA
<213> ORGANISM: Artificial sequence
<220> FEATURE:
<223> OTHER INFORMATION: SiRNA oligonucleotide

<400> SEQUENCE: 52
aggucaaggg caagcccgac cugaa                                        25

<210> SEQ ID NO 53
<211> LENGTH: 25
<212> TYPE: RNA
<213> ORGANISM: Artificial sequence
<220> FEATURE:
<223> OTHER INFORMATION: SiRNA oligonucleotide

<400> SEQUENCE: 53
uucaggucgg gcuugcccuu gaccu                                        25

<210> SEQ ID NO 54
<211> LENGTH: 360
<212> TYPE: PRT
<213> ORGANISM: Homo sapiens

<400> SEQUENCE: 54

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
```

```
                65                  70                  75                  80
Gly Val Gly Leu Val Pro Gln Gly Gly Leu Glu Thr Ser Gln Pro Glu
                    85                  90                  95
Gly Glu Ala Gly Val Gly Val Glu Ser Asn Ser Asp Gly Ala Ser Pro
                100                 105                 110
Glu Pro Cys Thr Val Thr Pro Gly Ala Val Lys Leu Glu Lys Glu Lys
                115                 120                 125
Leu Glu Gln Asn Pro Glu Glu Ser Gln Asp Ile Lys Ala Leu Gln Lys
            130                 135                 140
Glu Leu Glu Gln Phe Ala Lys Leu Leu Lys Gln Lys Arg Ile Thr Leu
145                 150                 155                 160
Gly Tyr Thr Gln Ala Asp Val Gly Leu Thr Leu Gly Val Leu Phe Gly
                165                 170                 175
Lys Val Phe Ser Gln Thr Thr Ile Cys Arg Phe Glu Ala Leu Gln Leu
                180                 185                 190
Ser Phe Lys Asn Met Cys Lys Leu Arg Pro Leu Leu Gln Lys Trp Val
                195                 200                 205
Glu Glu Ala Asp Asn Asn Glu Asn Leu Gln Glu Ile Cys Lys Ala Glu
            210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
                245                 250                 255
Leu Gln Gln Ile Ser His Ile Ala Gln Gln Leu Gly Leu Glu Lys Asp
                260                 265                 270
Val Val Arg Val Trp Phe Cys Asn Arg Arg Gln Lys Gly Lys Arg Ser
                275                 280                 285
Ser Ser Asp Tyr Ala Gln Arg Glu Asp Phe Glu Ala Ala Gly Ser Pro
            290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
                325                 330                 335
Val Pro Phe Pro Glu Gly Glu Ala Phe Pro Pro Val Ser Val Thr Thr
                340                 345                 350
Leu Gly Ser Pro Met His Ser Asn
                355                 360

<210> SEQ ID NO 55
<211> LENGTH: 1411
<212> TYPE: DNA
<213> ORGANISM: Homo sapiens

<400> SEQUENCE: 55
ccttcgcaag ccctcatttc accaggcccc cggcttgggg cgccttcctt ccccatggcg      60
ggacacctgg cttcggattt cgccttctcg cccctccag gtggtggagg tgatgggcca     120 gggggggccgg agccgggctg ggttgatcct cggacctggc taagcttcca aggccctcct    180
ggagggccag gaatcgggcc gggggttggg ccaggctctg aggtgtgggg gattccccca    240 tgcccccgc cgtatgagtt ctgtgggggg atggcgtact gtgggcccca ggttggagtg    300
gggctagtgc cccaaggcgg cttggagacc tctcagcctg agggcgaagc aggagtcggg    360
gtggagagca actccgatgg ggcctccccg gagccctgca ccgtcacccc tggtgccgtg    420
aagctggaga aggagaagct ggagcaaaac ccggaggagt cccaggacat caaagctctg    480
```

-continued

```
cagaaagaac tcgagcaatt tgccaagctc ctgaagcaga agaggatcac cctgggatat      540
acacaggccg atgtgggget caccctgggg gttctatttg ggaaggtatt cagccaaacg      600
accatctgcc gctttgaggc tctgcagctt agcttcaaga acatgtgtaa gctgcggccc      660
ttgctgcaga agtgggtgga ggaagctgac aacaatgaaa atcttcagga gatatgcaaa      720
gcagaaaccc tcgtgcaggc ccgaaagaga aagcgaacca gtatcgagaa ccgagtgaga      780
ggcaacctgg agaatttgtt cctgcagtgc ccgaaaccca cactgcagca gatcagccac      840
atcgcccagc agcttgggct cgagaaggat gtggtccgag tgtggttctg taaccggcgc      900
cagaagggca agcgatcaag cagcgactat gcacaacgag aggattttga ggctgctggg      960 tctccttttct cagggggacc agtgtccttt cctctggccc cagggcccca ttttggtacc     1020
ccaggctatg ggagccctca cttcactgca ctgtactcct cggtcccttt ccctgagggg     1080
gaagcctttc ccctgtctct cgtcaccact ctgggctctc ccatgcattc aaactgaggt     1140
gcctgccctt ctaggaatgg gggacagggg gaggggagga gctagggaaa gaaaacctgg      1200
agtttgtgcc agggttttg ggattaagtt cttcattcac taaggaagga attgggaaca      1260
caaagggtgg gggcagggga gtttggggca actggttgga gggaaggtga agttcaatga     1320
tgctcttgat tttaatccca catcatgtat cacttttttc ttaaataaag aagcctggga     1380
cacagtagat agacacactt aaaaaaaaaa a                                     1411
```

<210> SEQ ID NO 56
<211> LENGTH: 317
<212> TYPE: PRT
<213> ORGANISM: Homo sapiens

<400> SEQUENCE: 56

```
Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205
```

```
Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 57
<211> LENGTH: 2520
<212> TYPE: DNA
<213> ORGANISM: Homo sapiens

<400> SEQUENCE: 57
ggatggttgt ctattaactt gttcaaaaaa gtatcaggag ttgtcaaggc agagaagaga      60
gtgtttgcaa aaggggggaaa gtagtttgct gcctctttaa gactaggact gagagaaaga     120
agaggagaga gaaagaaagg gagagaagtt tgagccccag gcttaagcct ttccaaaaaa     180
taataataac aatcatcggc ggcggcagga tcggccagag gaggagggaa gcgcttttt     240 tgatcctgat tccagtttgc ctctctcttt ttttccccca aattattctt cgcctgattt     300
tcctcgcgga gccctgcgct cccgacaccc ccgcccgcct ccctcctcc tctcccccg      360 cccgcgggcc cccaaagtc ccggccgggc cgagggtcgg cggccgccgg cgggccgggc     420
ccgcgcacag cgcccgcatg tacaacatga tggagacgga gctgaagccg ccgggcccgc     480
agcaaacttc gggggggcgg ggcggcaact ccaccgcggc ggcggccggc ggcaaccaga     540 aaacagccc ggaccgcgtc aagcggccca tgaatgcctt catggtgtgg tcccgcgggc      600
agcggcgcaa gatggcccag gagaacccca agatgcacaa ctcggagatc agcaagcgcc     660
tgggcgccga gtggaaactt ttgtcggaga cggagaagcg gccgttcatc gacgaggcta     720
agcggctgcg agcgctgcac atgaaggagc acccggatta taaataccgg ccccggcgga     780
aaaccaagac gctcatgaag aaggataagt acacgctgcc cggcgggctg ctggcccccg     840
gcggcaatag catggcgagc ggggtcgggg tgggcgccgg cctgggcgcg ggcgtgaacc     900
agcgcatgga cagttacgcg cacatgaacg gctggagcaa cggcagctac agcatgatgc     960
aggaccagct gggctacccg cagcacccgg gcctcaatgc gcacggcgca gcgcagatgc    1020
agcccatgca ccgctacgac gtgagcgccc tgcagtacaa ctccatgacc agctcgcaga    1080
cctacatgaa cggctcgccc acctacagca tgtcctactc gcagcagggc acccctggca    1140
tggctcttgg ctccatgggt tcggtggtca agtccgaggc cagctccagc ccccctgtgg    1200
ttacctcttc ctcccactcc agggcgccct gccaggccgg ggacctccgg gacatgatca    1260
gcatgtatct ccccggcgcc gaggtgccgg aacccgccgc ccccagcaga cttcacatgt    1320
cccagcacta ccagagcggc ccggtgcccg gcacggccat taacggcaca ctgcccctct    1380
cacacatgtg agggccggac agcgaactgg aggggggaga aattttcaaa gaaaacgag     1440 ggaaatggga ggggtgcaaa agaggagagt aagaaacagc atggagaaaa cccggtacgc    1500
```

```
tcaaaagaa aaaggaaaaa aaaaaatccc atcacccaca gcaaatgaca gctgcaaaag   1560
agaacaccaa tcccatccac actcacgcaa aaaccgcgat gccgacaaga aaacttttat   1620
gagagagatc ctggacttct ttttggggga ctattttgt acagagaaaa cctggggagg    1680
gtggggaggg cggggaatg gaccttgtat agatctggag gaaagaaagc tacgaaaaac    1740 ttttaaaag ttctagtggt acggtaggag ctttgcagga agtttgcaaa agtctttacc    1800
aataatattt agagctagtc tccaagcgac gaaaaaatg ttttaatatt tgcaagcaac    1860
ttttgtacag tatttatcga gataaacatg gcaatcaaaa tgtccattgt ttataagctg   1920
agaatttgcc aatatttttc aaggagaggc ttcttgctga attttgattc tgcagctgaa   1980
atttaggaca gttgcaaacg tgaaagaag aaaattattc aaatttggac attttaattg    2040
tttaaaaatt gtacaaaagg aaaaaattag aataagtact ggcgaaccat ctctgtggtc    2100
ttgtttaaaa agggcaaaag ttttagactg tactaaattt tataacttac tgttaaaagc   2160
aaaaatggcc atgcaggttg acaccgttgg taatttataa tagcttttgt tcgatcccaa   2220 cttccatt tgttcagata aaaaaaacca tgaaattact gtgtttgaaa tattttctta    2280
tggtttgtaa tatttctgta aatttattgt gatattttaa ggttttcccc cctttatttt   2340
ccgtagttgt attttaaaag attcggctct gtattatttg aatcagtctg ccgagaatcc   2400
atgtatatat ttgaactaat atcatcctta taacaggtac attttcaact taagttttta   2460
ctccattatg cacagtttga gataaataaa ttttttgaaat atggacactg aaaaaaaaaa   2520
```

<210> SEQ ID NO 58
<211> LENGTH: 479
<212> TYPE: PRT
<213> ORGANISM: Homo sapiens

<400> SEQUENCE: 58

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
            35                  40                  45

Ser His Met Lys Arg Leu Pro Pro Val Leu Pro Gly Arg Pro Tyr Asp
        50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
                100                 105                 110

Leu Thr His Pro Pro Glu Ser Val Ala Ala Thr Val Ser Ser Ser Ala
            115                 120                 125

Ser Ala Ser Ser Ser Ser Ser Pro Ser Ser Gly Pro Ala Ser Ala
        130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190
```

-continued

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 59
<211> LENGTH: 2949
<212> TYPE: DNA
<213> ORGANISM: Homo sapiens

<400> SEQUENCE: 59
agtttcccga ccagagagaa cgaacgtgtc tgcgggcgcg cggggagcag aggcggtggc     60
gggcggcggc ggcaccggga gccgccgagt gaccctcccc cgcccctctg gcccccacc    120 ctcccacccg cccgtggccc gcgcccatgg ccgcgcgcgc tccacacaac tcaccggagt    180
ccgcgccttg cgccgccgac cagttcgcag ctccgcgcca cggcagccag tctcacctgg    240
cggcaccgcc cgcccaccgc ccggccaca gccctgcgc cacggcagc actcgaggcg       300 accgcgacag tggtggggga cgctgctgag tggaagagag cgcagcccgg ccaccggacc    360
tacttactcg ccttgctgat tgtctatttt tgcgtttaca acttttctaa gaacttttgt    420
atacaaagga acttttaaa aaagacgctt ccaagttata tttaatccaa agaagaagga    480
tctcggccaa tttggggttt tgggttttgg cttcgtttct tctcttcgtt gactttgggg    540

```
ttcaggtgcc ccagctgctt cgggctgccg aggaccttct gggcccccac attaatgagg    600
cagccacctg gcgagtctga catggctgtc agcgacgcgc tgctcccatc tttctccacg    660
ttcgcgtctg gcccggcggg aagggagaag acactgcgtc aagcaggtgc cccgaataac    720
cgctggcggg aggagctctc ccacatgaag cgacttcccc cagtgcttcc cggccgcccc    780
tatgacctgg cggcggcgac cgtggccaca gacctggaga gcggcggagc cggtgcggct    840
tgcggcggta gcaacctggc gcccctacct cggagagaga ccgaggagtt caacgatctc    900
ctggacctgg actttattct ctccaattcg ctgacccatc ctccggagtc agtggccgcc    960
accgtgtcct cgtcagcgtc agcctcctct tcgtcgtcgc cgtcgagcag cggccctgcc   1020
agcgcgccct ccacctgcag cttcacctat ccgatccggg ccgggaacga cccgggcgtg   1080
gcgccgggcg gcacgggcgg aggcctcctc tatggcaggg agtccgctcc ccctccgacg   1140
gctcccttca acctggcgga catcaacgac gtgagcccct cgggcggctt cgtggccgag   1200
ctcctgcggc cagaattgga cccggtgtac attccgccgc agcagccgca gccgccaggt   1260
ggcgggctga tgggcaagtt cgtgctgaag gcgtcgctga gcgcccctgg cagcgagtac   1320
ggcagcccgt cggtcatcag cgtcagcaaa ggcagccctg acggcagcca cccgtggtg    1380 gtggcgccct acaacggcgg gccgccgcgc acgtgcccca agatcaagca ggaggcggtc   1440
tcttcgtgca cccacttggg cgctggaccc cctctcagca atggccaccg gccggctgca   1500
cacgacttcc ccctggggcg gcagctcccc agcaggacta ccccgaccct gggtcttgag   1560
gaagtgctga gcagcaggga ctgtcaccct gccctgccgc ttcctcccgg cttccatccc   1620
cacccggggc ccaattaccc atccttcctg cccgatcaga tgcagccgca agtccgcccg   1680
ctccattacc aagagctcat gccacccggt tcctgcatgc cagaggagcc caagccaaag   1740
aggggaagac gatcgtggcc ccggaaaagg accgccaccc acacttgtga ttacgcgggc   1800
tgcggcaaaa cctacacaaa gagttcccat ctcaaggcac acctgcgaac ccacacaggt   1860
gagaaacctt accactgtga ctgggacggc tgtggatgga aattcgcccg ctcagatgaa   1920
ctgaccaggc actaccgtaa acacacgggg caccgcccgt tccagtgcca aaaatgcgac   1980
cgagcatttt ccaggtcgga ccacctcgcc ttacacatga agaggcattt ttaaatccca   2040
gacagtggat atgacccaca ctgccagaag agaattcagt atttttttact tttcacactg   2100 tcttcccgat gagggaagga gcccagccag aaagcactac aatcatggtc aagttcccaa   2160
ctgagtcatc ttgtgagtgg ataatcagga aaaatgagga atccaaaaga caaaaatcaa   2220
agaacagatg gggtctgtga ctggatcttc tatcattcca attctaaatc cgacttgaat   2280
attcctggac ttacaaaatg ccaaggggt gactggaagt tgtggatatc agggtataaa   2340
ttatatccgt gagttggggg agggaagacc agaattccct tgaattgtgt attgatgcaa   2400
tataagcata aagatcacc ttgtattctc tttaccttct aaaagccatt attatgatgt   2460
tagaagaaga ggaagaaatt caggtacaga aacatgttt aaatagccta aatgatggtg   2520
cttggtgagt cttggttcta aaggtaccaa acaaggaagc caaagttttc aaactgctgc   2580
atactttgac aaggaaaatc tatatttgtc ttccgatcaa catttatgac ctaagtcagg   2640
taatatacct ggtttacttc tttagcattt ttatgcagac agtctgttat gcactgtggt   2700
ttcagatgtg caataatttg tacaatggtt tattcccaag tatgccttaa gcagaacaaa   2760
tgtgtttttc tatatagttc cttgccttaa taaatatgta atataaattt aagcaaacgt   2820
ctattttgta tatttgtaaa ctacaaagta aaatgaacat tttgtggagt ttgtattttg   2880
```

-continued

```
catactcaag gtgagaatta agttttaaat aaacctataa tatttatct gaaaaaaaaa    2940 aaaaaaaaa                                                          2949
```

<210> SEQ ID NO 60
<211> LENGTH: 454
<212> TYPE: PRT
<213> ORGANISM: Homo sapiens

<400> SEQUENCE: 60

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
```

|  |  |  |  |  |  |  |  |  |  |  |  |
|--|--|--|--|--|--|--|--|--|--|--|--|
|  |  | 355 |  |  |  | 360 |  |  |  | 365 |  |
| Val | Lys | Arg | Arg | Thr | His | Asn | Val | Leu | Glu | Arg | Gln | Arg | Arg | Asn | Glu |
|  | 370 |  |  |  |  | 375 |  |  |  |  | 380 |

Val Lys Arg Arg Thr His Asn Val Leu Glu Arg Gln Arg Arg Asn Glu
   370             375               380

Leu Lys Arg Ser Phe Phe Ala Leu Arg Asp Gln Ile Pro Glu Leu Glu
385             390                 395              400

Asn Asn Glu Lys Ala Pro Lys Val Val Ile Leu Lys Lys Ala Thr Ala
            405                 410             415

Tyr Ile Leu Ser Val Gln Ala Glu Glu Gln Lys Leu Ile Ser Glu Glu
            420             425             430

Asp Leu Leu Arg Lys Arg Arg Glu Gln Leu Lys His Lys Leu Glu Gln
        435             440             445

Leu Arg Asn Ser Cys Ala
    450

<210> SEQ ID NO 61
<211> LENGTH: 2379
<212> TYPE: DNA
<213> ORGANISM: Homo sapiens

<400> SEQUENCE: 61

```
gaccccgag ctgtgctgct cgcggccgcc accgcgggc cccggccgtc cctggctccc      60
ctcctgcctc gagaagggca gggcttctca gaggcttggc gggaaaaaga acggagggag    120
ggatcgcgct gagtatataaaa gccggttttc ggggctttat ctaactcgct gtagtaattc  180
cagcgagagg cagagggagc gagcgggcgg ccggctaggg tggaagagcc gggcgagcag    240
agctgcgctg cgggcgtcct gggaagggag atccggagcg aataggggc ttcgcctctg     300
gcccagccct cccgctgatc ccccagccag cggtccgcaa ccttgccgc atccacgaaa     360
ctttgcccat agcagcgggc gggcactttg cactggaact acaacacccc gagcaaggac    420
gcgactctcc cgacgcgggg aggctattct gcccatttgg ggacacttcc ccgccgctgc    480
caggacccgc ttctctgaaa ggctctcctt cagctgctt agacgctgga ttttttcgg     540
gtagtggaaa accagcagcc tcccgcgacg atgcccctca acgttagctt caccaacagg   600
aactatgacc tcgactacga ctcggtgcag ccgtatttct actgcgacga ggaggagaac    660
ttctaccagc agcagcagca gagcgagctg cagccccgg cgcccagcga ggatatctgg     720
aagaaattcg agctgctgcc caccccgccc ctgtcccta gccgccgctc cgggctctgc    780
tcgccctcct acgttgcggt cacacccttc tcccttcggg gagacaacga cggcggtggc   840
gggagcttct ccacggccga ccagctggag atggtgaccg agctgctggg aggagacatg   900
gtgaaccaga gtttcatctg cgacccggac gacgagacct tcatcaaaaa catcatcatc    960
caggactgta tgtggagcgg cttctcggcc gccgccaagc tcgtctcaga aagctggcc   1020
tcctaccagg ctgcgcgcaa agacagcgg agcccgaacc ccgccgcgg ccacagcgtc   1080
tgctccacct ccagcttgta cctgcaggat ctgagcgccg ccgcctcaga gtgcatcgac    1140
ccctcggtgg tcttccccta ccctctcaac gacagcagct cgcccaagtc ctgcgcctcg   1200
caagactcca gcgccttctc tccgtcctcg gattctctgc tctcctcgac ggagtcctcc   1260
ccgcagggca gccccgagcc cctggtgctc catgaggaga caccgcccac caccagcagc   1320
gactctgagg aggaacaaga agatgaggaa gaaatcgatg ttgttctctg tggaaaagagg   1380
caggctcctg gcaaaggtc agagtctgga tcaccttctg ctggaggcca cagcaaacct   1440
cctcacagcc cactggtcct caagaggtgc acgtctcca cacatcagca aactacgca    1500
gcgcctccct ccactcggaa ggactatcct gctgccaaga gggtcaagtt ggacagtgtc   1560
```

```
agagtcctga gacagatcag caacaaccga aaatgcacca gccccaggtc ctcggacacc    1620
gaggagaatg tcaagaggcg aacacacaac gtcttggagc gccagaggag gaacgagcta    1680
aaacggagct ttttgccct gcgtgaccag atcccggagt tggaaaacaa tgaaaaggcc     1740
cccaaggtag ttatccttaa aaaagccaca gcatacatcc tgtccgtcca agcagaggag    1800
caaaagctca tttctgaaga ggacttgttg cggaaacgac gagaacagtt gaaacacaaa    1860
cttgaacagc tacggaactc ttgtgcgtaa ggaaaagtaa ggaaaacgat tccttctaac    1920
agaaatgtcc tgagcaatca cctatgaact tgtttcaaat gcatgatcaa atgcaacctc    1980
acaaccttgg ctgagtcttg agactgaaag atttagccat aatgtaaact gcctcaaatt    2040
ggactttggg cataaaagaa cttttttatg cttaccatct ttttttttc tttaacagat     2100 ttgtatttaa gaattgtttt taaaaaattt taagatttac acaatgtttc tctgtaaata    2160
ttgccattaa atgtaaataa ctttaataaa acgtttatag cagttacaca gaatttcaat    2220
cctagtatat agtacctagt attataggta ctataaaccc taattttttt tatttaagta    2280
cattttgctt tttaaagttg attttttct attgttttta gaaaaataa aataactggc       2340 aaatatatca ttgagccaaa tcttaaaaaa aaaaaaaa                             2379
```

<210> SEQ ID NO 62
<211> LENGTH: 5489
<212> TYPE: DNA
<213> ORGANISM: Artificial sequence
<220> FEATURE:
<223> OTHER INFORMATION: OSKM expression cassette: OCT4-F2A-KLF4-IRES-SOX2-E2A SEQUENCE

<400> SEQUENCE: 62

```
atggctggac acctggcttc agacttcgcc ttctcacccc caccaggtgg gggtgatggg      60
tcagcagggc tggagccggg ctgggtggat cctcgaacct ggctaagctt ccaagggcct    120
ccaggtgggc ctggaatcgg accaggctca gaggtattgg ggatctcccc atgtccgccc    180
gcatacgagt tctgcggagg gatggcatac tgtggacctc aggttggact gggcctagtc    240
ccccaagttg gcgtggagac tttgcagcct gagggccagg caggagcacg agtggaaagc    300
aactcagagg gaacctcctc tgagccctgt gccgaccgcc caatgccgt gaagttggag      360 aaggtggaac caactcccga ggagtcccag gacatgaaag ccctgcagaa ggagctagaa    420
cagtttgcca agctgctgaa gcagaagagg atcaccttgg ggtacaccca ggccgacgtg    480
gggctcaccc tgggcgttct ctttggaaag gtgttcagcc agaccaccat ctgtcgcttc    540
gaggccttgc agctcagcct taagaacatg tgtaagctgc ggcccctgct ggagaagtgg    600
gtggaggaag ccgacaacaa tgagaacctt caggagatat gcaaatcgga gaccctggtg    660
caggcccgga gagaaagcg aactagcatt gagaaccgtg tgaggtggag tctggagacc    720
atgtttctga gtgcccgaa gccctcccta cagcagatca ctcacatcgc caatcagctt    780
gggctagaga aggatgtggt tcgagtatgg ttctgtaacc ggcgcagaa gggcaaaaga     840 tcaagtattg agtattccca acgagaagag tatgaggcta cagggacacc tttcccaggg    900
ggggctgtat cctttcctct gccccaggt ccccactttg gcaccccagg ctatggaagc     960
ccccacttca ccacactcta ctcagtccct tttcctgagg gcgaggcctt tccctctgtt   1020
cccgtcactg ctctgggctc tcccatgcat tcaaacggaa gtggcgtgaa acagactttg   1080
aattttgacc ttctcaagtt ggcgggagac gtggagtcca acccagggcc catgctgtc    1140 agcgacgctc tgctcccgtc cttctccacg ttcgcgtccg gcccggcggg aagggagaag   1200
```

```
acactgcgtc cagcaggtgc cccgactaac cgttggcgtg aggaactctc tcacatgaag   1260
cgacttcccc cacttcccgg ccgcccctac gacctggcgg cgacggtggc cacagacctg   1320
gagagtggcg gagctggtgc agcttgcagc agtaacaacc cggccctcct agcccggagg   1380
gagaccgagg agttcaacga cctcctggac ctagacttta tcctttccaa ctcgctaacc   1440
caccaggaat cggtggccgc caccgtgacc acctcggcgt cagcttcatc ctcgtcttcc   1500
ccagcgagca gcggccctgc cagcgcgccc tccacctgca gcttcagcta tccgatccgg   1560 gccggggtg acccgggcgt ggctgccagc aacacaggtg gagggctcct ctacagccga   1620
gaatctgcgc cacctcccac ggcccccttc aacctggcgg acatcaatga cgtgagcccc   1680
tcgggcggct tcgtggctga gctcctgcgg ccggagttgg acccagtata cattccgcca   1740
cagcagcctc agccgccagg tggcgggctg atgggcaagt ttgtgctgaa ggcgtctctg   1800
accacccctg gcagcgagta cagcagccct tcggtcatca gtgttagcaa aggaagccca   1860
gacggcagcc accccgtggt agtggcgccc tacagcggtg gccgccgcg catgtgcccc   1920 aagattaagc aagaggcggt cccgtcctgc acggtcagcc ggtccctaga ggcccatttg   1980
agcgctggac cccagctcag caacggccac cggcccaaca cacacgactt ccccctgggg   2040
cggcagctcc ccaccaggac taccccctaca ctgagtcccg aggaactgct gaacagcagg   2100
gactgtcacc ctggcctgcc tcttccccca ggattccatc cccatccggg cccaactac   2160 cctcctttcc tgccagacca gatgcagtca caagtcccct ctctccatta tcaagagctc   2220
atgccaccgg gttcctgcct gccagaggag cccaagccaa agaggggaag aaggtcgtgg   2280
ccccggaaaa gaacagccac ccacacttgt gactatgcag gctgtggcaa aacctatacc   2340
aagagttctc atctcaaggc acacctgcga actcacacag gcgagaaacc ttaccactgt   2400
gactgggacg gctgtgggtg gaaattcgcc cgctccgatg aactgaccag gcactaccgc   2460
aaacacacag gcaccggcc cttcagtgc cagaagtgtg acagggcctt ttccaggtcg   2520
gaccaccttg ccttacacat gaagaggcac ttttaaagat ccctcccccc ccctaacgt   2580 tactggccga agccgcttgg aataaggccg gtgtgcgttt gtctatatgt tattttccac   2640
catattgccg tcttttggca atgtgagggc ccggaaacct ggccctgtct tcttgacgag   2700
cattcctagg ggtctttccc ctctcgccaa aggaatgcaa ggtctgttga atgtcgtgaa   2760
ggaagcagtt cctctggaag cttcttgaag acaaacaacg tctgtagcga cccttttgcag   2820 gcagcggaac cccccacctg gcgacaggtg cctctgcggc caaaagccac gtgtataaga   2880
tacacctgca aaggcggcac aaccccagtg ccacgttgtg agttggatag ttgtggaaag   2940
agtcaaatgg ctctcctcaa gcgtattcaa caagggctg aaggatgccc agaaggtacc   3000
ccattgtatg ggatctgatc tggggcctcg gtgcacatgc tttacatgtg tttagtcgag   3060
gttaaaaaaa cgtctaggcc ccccgaacca cggggacgtg gttttccttt gaaaaacacg   3120
atgataatat ggccacacat atgatgtata acatgatgga gacggagctg aagccgccgg   3180
gcccgcagca agcttcgggg ggcggcggcg gaggaggcaa cgccacggcg gcggcgaccg   3240
gcggcaacca gaagaacagc ccggaccgcg tcaagaggcc catgaacgcc ttcatggtat   3300
ggtcccgggg gcagcggcgt aagatggccc aggaaccc caagatgcac aactcggaga   3360
tcagcaagcg cctgggcgcg gagtggaaac ttttgtccga gaccgagaag cggccgttca   3420
tcgacgaggc caagcggctg cgcgctctgc acatgaagga gcaccggat tataaatacc   3480 ggccgcggcg gaaaaccaag acgctcatga agaaggataa gtacacgctt cccggaggct   3540
```

```
tgctggcccc cggcgggaac agcatggcga gcggggttgg ggtgggcgcc ggcctgggtg    3600
cgggcgtgaa ccagcgcatg gacagctacg cgcacatgaa cggctggagc aacggcagct    3660
acagcatgat gcaggagcag ctgggctacc cgcagcaccc gggcctcaac gctcacggcg    3720
cggcacagat gcaaccgatg caccgctacg acgtcagcgc cctgcagtac aactccatga    3780
ccagctcgca gacctacatg aacggctcgc ccacctacag catgtcctac tcgcagcagg    3840 gcaccccgg tatggcgctg ggctccatgg gctctgtggt caagtccgag gccagctcca    3900
gcccccccgt ggttacctct tcctcccact ccagggcgcc ctgccaggcc ggggacctcc    3960
gggacatgat cagcatgtac ctccccggcg ccgaggtgcc ggagcccgct gcgcccagta    4020
gactgcacat ggcccagcac taccagagcg gcccggtgcc cggcacggcc attaacggca    4080
cactgcccct gtcgcacatg ggtagtgggc aatgtactaa ctacgctttg ttgaaactcg    4140
ctggcgatgt tgaaagtaac cccggtccta tgcccctcaa cgtgaacttc accaacagga    4200
actatgacct cgactacgac tccgtacagc cctatttcat ctgcgacgag gaagagaatt    4260
tctatcacca gcaacagcag agcgagctgc agccgcccgc gcccagtgag gatatctgga    4320
agaaattcga gctgcttccc accccgcccc tgtccccgag ccgccgctcc gggctctgct    4380
ctccatccta tgttgcggtc gctacgtcct tctcccaag ggaagacgat gacggcggcg    4440
gtggcaactt ctccaccgcc gatcagctgg agatgatgac cgagttactt ggaggagaca    4500
tggtgaacca gagcttcatc tgcgatcctg acgacgagac cttcatcaag aacatcatca    4560
tccaggactg tatgtggagc ggtttctcag ccgctgccaa gctggtctcg gagaagctgg    4620
cctcctacca ggctgcgcgc aaagacagca ccagcctgag ccccgcccgc gggcacagcg    4680
tctgctccac ctccagcctg tacctgcagg acctcaccgc cgccgcgtcc gagtgcattg    4740 accccctcagt ggtctttccc tacccgctca acgacacgca ctcgcccaaa tcctgtacct    4800
cgtccgattc cacggccttc tctccttcct cggactcgct gctgtcctcc gagtcctccc    4860
cacgggccag ccctgagccc ctagtgctgc atgaggagac accgcccacc accagcagcg    4920
actctgaaga agagcaagaa gatgaggaag aaattgatgt ggtgtctgtg gagaagaggc    4980 aaaccctgc caagaggtcg gagtcgggct catctccatc ccgaggccac agcaaacctc    5040
cgcacagccc actggtcctc aagaggtgcc acgtctccac tcaccagcac aactacgccg    5100 caccccctc cacaaggaag gactatccag ctgccaagag ggccaagttg acagtggca    5160 gggtcctgaa gcagatcagc aacaaccgca agtgctccag ccccaggtcc tcagacacgg    5220
aggaaaacga caagaggcgg acacacaacg tcttggaacg tcagaggagg aacgagctga    5280
agcgcagctt ttttgccctg cgtgaccaga tccctgaatt ggaaaacaac gaaaaggccc    5340
ccaaggtagt gatcctcaaa aaagccaccg cctacatcct gtccattcaa gcagacgagc    5400
acaagctcac ctctgaaaag gacttattga ggaaacgacg agaacagttg aaacacaaac    5460
tcgaacagct tcgaaactct ggtgcataa                                      5489
```

<210> SEQ ID NO 63
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 63

```
ccggctaagt ggattgagtg cctttctcga gaaaggcact caatccactt agttttg         58
```

```
<210> SEQ ID NO 64
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 64
aattcaaaaa ctaagtggat tgagtgcctt tctcgagaaa ggcactcaat ccacttag      58

<210> SEQ ID NO 65
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 65
ccgggcgcta tgattcttcc aaccactcga gtggttggaa gaatcatagc gcttttg       58

<210> SEQ ID NO 66
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 66
aattcaaaaa gcgctatgat tcttccaacc actcgagtgg ttggaagaat catagcgc      58

<210> SEQ ID NO 67
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 67
acaactaacc taaccaaat tataca                                          26

<210> SEQ ID NO 68
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 68 tgttttttg tttatcgggg tcgcg                                           25

<210> SEQ ID NO 69
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 69
cgaattatac gacaaatcta aataacg                                        28

<210> SEQ ID NO 70
<211> LENGTH: 203
<212> TYPE: DNA
<213> ORGANISM: Artificial sequence
<220> FEATURE:
<223> OTHER INFORMATION: 203bp amplicon covering human XIST
      transcription start site
```

<400> SEQUENCE: 70

```
gggtaaattt tgaaccaacc aaatcacaaa gatgtccggc tttcaatctt ctaggccacg      60
cctcttatgc tctctccgcc ctcagccccc ccttcagttc ttaaagcgct gcaattcgct     120
gctgcagcca tatttcttac tctctcgggg ctggaagctt cctgactgaa gatctgttct     180
agaaagaacc ccaagtgcag aga                                             203
```

<210> SEQ ID NO 71
<211> LENGTH: 1902
<212> TYPE: DNA
<213> ORGANISM: Homo sapiens

<400> SEQUENCE: 71

```
atgaccgaag aagcatgccg aacacggagt cagaaacgag cgcttgaacg ggacccaaca      60
gaggacgatg tggagagcaa gaaaataaaa atggagagag gattgttggc ttcagattta     120
aacactgacg gagacatgag ggtgacacct gagccgggac aggtccaac ccaaggattg      180
ctgagggcaa cagaggccac ggccatggcc atgggcagag gcgaagggct ggtgggcgat     240
gggcccgtgg acatgcgcac ctcacacagt gacatgaagt ccgagaggag accccctca     300
cctgacgtga ttgtgctctc cgacaacgag cagccctcga gcccgagagt gaatgggctg     360
accacggtgg ccttgaagga gactagcacc gaggccctca tgaaaagcag tcctgaagaa     420
cgagaaagga tgatcaagca gctgaaggaa gaattgaggt tagaagaagc aaaactcgtg     480
ttgttgaaaa agttgcggca gagtcaaata caaaaggaag ccaccgccca gaagcccaca     540
ggttctgttg ggagcaccgt gaccaccct ccccccgcttg ttcggggcac tcagaacatt     600
cctgctggca agccatcact ccagacctct tcagctcgga tgcccggcag tgtcataccc     660
ccgcccctgg tccgaggtgg gcagcaggcg tcctcgaagc tggggccaca ggcgagctca     720
caggtcgtca tgcccccact cgtcagggg gctcagcaaa tccacagcat taggcaacat     780
tccagcacag ggccaccgcc cctcctcctg gccccccggg cgtcggtgcc cagtgtgcag     840
attcagggac agaggatcat ccagcagggc ctcatccgcg tcgccaatgt tcccaacacc     900
agcctgctcg tcaacatccc acagcccacc ccagcatcac tgaaggggac aacagccacc     960
tccgctcagg ccaactccac ccccactagt gtggcctctg tggtcacctc tgccgagtct    1020
ccagcaagcc gacaggcggc cgccaagctg gcgctgcgca acagctgga gaagacgcta    1080
ctcgagatcc ccccacccaa gccccagcc ccagagatga cttcctgcc cagcgccgcc    1140
aacaacgagt tcatctacct ggtcggcctg gaggaggtgg tgcagaacct actggagaca    1200
caaggcagga tgtcggccgc cactgtgctg tcccgggagc cctacatgtg tgcacagtgc    1260
aagacggact tcacgtgccg ctggcgggag gagaagagcg cgccatcat gtgtgagaac    1320
tgcatgacaa ccaaccagaa gaaggcgctc aaggtggagc acaccagccg gctgaaggcc    1380
gcctttgtga ggcgctgca gcaggaacag gagattgagc agcggctcct gcagcagggc    1440
acggcccctg cacaggccaa ggccgagccc accgctgccc cacaccccgt gctgaagcag    1500
gtcataaaac cccggcgtaa gttggcgttc cgctcaggag aggcccgcga ctggagtaac    1560
ggggctgtgc tacaggcctc cagccagctg tcccggggtt cggccacgac gccccgaggt    1620
gtcctgcaca cgttcagtcc gtcacccaaa ctgcagaact cagcctcggc cacagccctg    1680
gtcagcagga ccggcagaca ttctgagaga accgtgagcg ccggcaaggg cagcgccacc    1740
tccaactgga agaagacgcc cctcagcaca ggcgggaccc ttgcgtttgt cagcccaagc    1800
```

| | |
|---|---|
| ctggcggtgc acaagagctc ctcggccgtg gaccgccagc gagagtacct cctggacatg | 1860 |
| atcccacccc gctccatccc ccagtcagcc acgtggaaat ag | 1902 |

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72

| | |
|---|---|
| cagggctgaa gagaagatgg | 20 |

<210> SEQ ID NO 73
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 73

| | |
|---|---|
| acaggaggtg ggaatctga | 19 |

<210> SEQ ID NO 74
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 74

| | |
|---|---|
| ggtaccggat actcaggcca ggcccagaaa | 30 |

<210> SEQ ID NO 75
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 75

| | |
|---|---|
| ctcgagtcca cagacctctg gcact | 25 |

<210> SEQ ID NO 76
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 76

| | |
|---|---|
| ggtacccatt gagtccaaat cctctttact aggtg | 35 |

<210> SEQ ID NO 77
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 77

| | |
|---|---|
| ctcgagctga ggctcatgct gctgg | 25 |

<210> SEQ ID NO 78
<211> LENGTH: 20

```
<212> TYPE: DNA
<213> ORGANISM: Artificial sequence
<220> FEATURE:
<223> OTHER INFORMATION: Single strand DNA oligonucleotide

<400> SEQUENCE: 78
agggagcagt ttgccctact                                               20

<210> SEQ ID NO 79
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 79
cacatgcagc gtggtatctt                                               20

<210> SEQ ID NO 80
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 80
agtgattctc ctgcctcagc                                               20

<210> SEQ ID NO 81
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 81
cttctgcttc aggagcttgg                                               20

<210> SEQ ID NO 82
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 82
ggaatgggag gacaggattt                                               20

<210> SEQ ID NO 83
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 83
aacagccgga gcagaagata                                               20

<210> SEQ ID NO 84
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 84
```
aaggatgttg aacgggcaga                                                   20

<210> SEQ ID NO 85
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 85
tccgttggaa ctgatgga                                                     18

<210> SEQ ID NO 86
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 86
tgacactggc aaacaatgc a                                                  21

<210> SEQ ID NO 87
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 87
ggtccttttc accagcaagc t                                                 21

<210> SEQ ID NO 88
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 88
cgccaccaaa ctgagatgat                                                   20

<210> SEQ ID NO 89
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 89
cacattgtag tgggcagtgg                                                   20

<210> SEQ ID NO 90
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 90
cagtcgctac atcaccatcc                                                   20

<210> SEQ ID NO 91
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 91
tttcctctcc tttgctctgc                                                 20

<210> SEQ ID NO 92
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 92
aactcaagaa ggcggatgg                                                  19

<210> SEQ ID NO 93
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 93
cggtgcgtcc tttaatcct                                                  19

<210> SEQ ID NO 94
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 94
cgcctcggct acaacaacta                                                 20

<210> SEQ ID NO 95
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 95
cgcctcggct acaacaacta                                                 20

<210> SEQ ID NO 96
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 96
aaacgtgctg ctctacgaca                                                 20

<210> SEQ ID NO 97
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 97
tagtcgatga cgtgctggag                                                 20
```

<210> SEQ ID NO 98
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 98
ctacagcgcg tcatcgacta					20

<210> SEQ ID NO 99
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 99
tcgttggaga tgacaagttc c					21

<210> SEQ ID NO 100
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 100
gcgctccgag aatttaaaga					20

<210> SEQ ID NO 101
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 101
gtcgctgctg ttagcgaag					19

<210> SEQ ID NO 102
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 102
gatttgtggg cctgaagaaa					20

<210> SEQ ID NO 103
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 103
cagatccatg gaggaaggaa					20

<210> SEQ ID NO 104
<211> LENGTH: 19
<212> TYPE: DNA
<213> ORGANISM: Artificial sequence
<220> FEATURE:
<223> OTHER INFORMATION: Single strand DNA oligonucleotide

```
<400> SEQUENCE: 104
agctgctgga gctcgtctt                                              19

<210> SEQ ID NO 105
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 105
cgcctgttct ggaaccatac                                             20

<210> SEQ ID NO 106
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 106
taaattttaa attaattaaa ttat                                        24

<210> SEQ ID NO 107
<211> LENGTH: 29
<212> TYPE: DNA
<213> ORGANISM: Artificial Sequence
<220> FEATURE:
<223> OTHER INFORMATION: Single strand DNA oligonucleotide

<400> SEQUENCE: 107
tgttttagaa agaattttaa gtgtagaga                                   29

<210> SEQ ID NO 108
<211> LENGTH: 2457
<212> TYPE: DNA
<213> ORGANISM: Homo sapiens
<220> FEATURE:
<221> NAME/KEY: misc_feature
<222> LOCATION: (1)..(37)
<223> OTHER INFORMATION: 1st exon
<220> FEATURE:
<221> NAME/KEY: misc_feature
<222> LOCATION: (531)..(536)
<223> OTHER INFORMATION: Premature polyA signal
<220> FEATURE:
<221> NAME/KEY: misc_feature
<222> LOCATION: (1033)..(1038)
<223> OTHER INFORMATION: Premature polyA signal
<220> FEATURE:
<221> NAME/KEY: misc_feature
<222> LOCATION: (1051)..(1056)
<223> OTHER INFORMATION: Premature polyA signal
<220> FEATURE:
<221> NAME/KEY: misc_feature
<222> LOCATION: (1569)..(1574)
<223> OTHER INFORMATION: Premature polyA signal
<220> FEATURE:
<221> NAME/KEY: misc_feature
<222> LOCATION: (1669)..(2457)
<223> OTHER INFORMATION: 2nd exon
<220> FEATURE:
<221> NAME/KEY: misc_feature
<222> LOCATION: (1712)..(1714)
<223> OTHER INFORMATION: Putative translation start site

<400> SEQUENCE: 108
accgtcgggg accccaagc tccgtcctcc gcttcctgct ctctttatcc cgccccgct  60
```

```
ccttctgggc caacgccgcc agtgactatt cccagggatc cctcagagct gaggacgccg      120
cggccgcatc cccatttggg accttgcccc gactccgacc tccggatctc cagctccacc      180
aaacctcgaa gccaccatcc gcccccaaac tgccgctgcg ccaggctttc ggaggggagt      240
cgtggcaaca gccattagga tgcactaagc agggcacttc ctgagcccaa ggacaccgag      300
gggcattcac tgagtgaatg gggatgtgct gctaataact aacactaatt gaccacctgc      360
cgtgtgccca tcctcttcga acatgcaact tccttgttcc ttatcttgtt actgtctctt      420
tctctctgcc agaatccaat cctcacaagg gcagggactg gggtctgttt tgttaactgc      480
catatcacaa tgcctggcac gaaggaagat tcttgaatta tgaatggag attaaattat       540 aatttaaaag cctggcatga actgagcacc ttctgcatgc ttatcacccg ctactgacat      600
atagttcact ttttttttt tttttttttt gagacggagt tttgctctta tctcccaggc       660
tggagtgcaa gtggtgtgat ctcagctcac tgcaacctcc gcctcccggg ttcaagcgat      720
tcttctgcct cagcctcccg agtagctggg attacaggcg tccaccacca ctcctggcta      780
atttttttgt gtttttatta gagacagggt ttcgcaatgt tgggcaggct ggtctcgaac      840
tcctgacctc aggtgatcca cccgactcgg cctccaaagt gctgggatta caggcgtgag      900
ccattgtgcc ccgcccccctt tttaacctag tttgttgtct ctcaccccga ccagaatata     960
accttcatga gggctacagt tgttgtcta tttattgccc aactccatgt ccttgccaca      1020
cagtaggttc ccaataaatg tatgttgaat aattaataaa gactacattc taatgataat     1080
ggctaacaga ccacgtgatt tacatattta tttggtttat tatattatct gcctctgcct     1140
tttagaacat aaaccttctg ggggtgggaa tgttgggtcc ctactgtctg gcaggcactg     1200
tgctgggcta gggttcaatg gtgaccaaaa ccggcaaaat cctgccctcc ctctgtcatg     1260
gggaggaact gctaatgggc atggggattc ttttctgggt gaggaaaatg ttctaaaatt     1320
tacttatggt gatagttgca caacttcgtg aatatgctaa aacccgttaa attggacact     1380
agctggctga acttgatggg atgtaaatta catctcaata aagctgtttg ggaaatccag     1440
ccttcacagt tgttgattcg cgtgaggagg gaaggagaga tggggggacg tgggacaggg     1500
agaaaacaac ataaatcata tatatatagc atgcaaattg gaaggtgatc agcacacaat     1560
aggcattcaa taaatgttga ataatgaca ccccactgtc tccttgccct caaatggtct      1620
cccctaacgt atccctgtt gtcttgcttc ttctcttccc acttgcagag cctgctgccc      1680
acgtctcttc cctgagctgc ctgctggggt catggagctg ccaacaaagc ctggcacctt     1740
cgacctgggc ctggccacat ggagcccttc cttccagggg gaaacccacc gggctcaggc     1800
acgccgcagg gatgttggca ggcagctgcc tgagtacaag gctgtggtgg tgggcgccag     1860
tggcgtgggg aagagtgcgc tgaccatcca gctgaaccac cagtgcttcg tggaggacca     1920
cgaccccacc atccaggatt cctactggaa ggagttgacc ctggacagtg ggactgcat      1980 tctgaatgtg ctggacacag cagggcaggc catccatagg gccctgcgtg accagtgcct     2040
ggctgtctgt gatggtgtgc tgggcgtctt cgctctcgat gaccccctcgt ctctgatcca    2100 gctgcagcag atatgggcca cctggggccc tcaccccgcc cagccccttg tcctcgtggg    2160
caacaagtgt gaccttgtga ccactgctgg agatgctcat gccgctgctg cagccctcgc    2220
acacagctgg ggggcccact tcgtggagac ctcggccaaa acacggcaag gcgtggagga    2280
ggccttttcc ctgctggtcc atgagatcca gagggtccag gaggccatgg cgaaggagcc    2340
catggcaagg tcctgtaggg agaagacccg gcaccagaag gccacctgcc actgtggctg    2400
ctctgtggcc tgaaggtctt ggccaagaaa tgtagacctt tccccaggcc agggtga       2457
```

<210> SEQ ID NO 109
<211> LENGTH: 826
<212> TYPE: DNA
<213> ORGANISM: Homo sapiens
<220> FEATURE:
<221> NAME/KEY: misc_feature
<222> LOCATION: (81)..(83)
<223> OTHER INFORMATION: Putative translation start site

<400> SEQUENCE: 109

| | | | | | |
|---|---|---|---|---|---|
| accgtcgggg | accccccaagc | tccgtcctcc | gcttcctagc | ctgctgccca | cgtctcttcc | 60 |
| ctgagctgcc | tgctggggtc | atggagctgc | caacaaagcc | tggcaccttc | gacctgggcc | 120 |
| tggccacatg | gagcccttcc | ttccagggggg | aaacccaccg | ggctcaggca | cgccgcaggg | 180 |
| atgttggcag | gcagctgcct | gagtacaagg | ctgtggtggt | gggcgccagt | ggcgtgggca | 240 |
| agagtgcgct | gaccatccag | ctgaaccacc | agtgcttcgt | ggaggaccac | gaccccacca | 300 |
| tccaggattc | ctactggaag | gagttgaccc | tggacagtgg | ggactgcatt | ctgaatgtgc | 360 |
| tggacacagc | agggcaggcc | atccataggg | ccctgcgtga | ccagtgcctg | gctgtctgtg | 420 |
| atggtgtgct | gggcgtcttc | gctctcgatg | acccctcgtc | tctgatccag | ctgcagcaga | 480 |
| tatgggccac | ctggggccct | caccccgccc | agcccttgt | cctcgtgggc | aacaagtgtg | 540 |
| accttgtgac | cactgctgga | gatgctcatg | ccgctgctgc | agccctcgca | cacagctggg | 600 |
| gggcccactt | cgtggagacc | tcggccaaaa | cacggcaagg | cgtggaggag | gccttttccc | 660 |
| tgctggtcca | tgagatccag | agggtccagg | aggccatggc | gaaggagccc | atggcaaggt | 720 |
| cctgtaggga | gaagacccgg | caccagaagg | ccacctgcca | ctgtggctgc | tctgtggcct | 780 |
| gaaggtcttg | gccaagaaat | gtagacccttt | ccccaggcca | gggtga | | 826 |

<210> SEQ ID NO 110
<211> LENGTH: 7979
<212> TYPE: DNA
<213> ORGANISM: Artificial Sequence
<220> FEATURE:
<223> OTHER INFORMATION: reverse tetracycline transactivator (M2rtTA) - vector

<400> SEQUENCE: 110

| | | | | | |
|---|---|---|---|---|---|
| cgataatcaa | cctctggatt | acaaaatttg | tgaaagattg | actggtattc | ttaactatgt | 60 |
| tgctcctttt | acgctatgtg | gatacgctgc | tttaatgcct | ttgtatcatg | ctattgcttc | 120 |
| ccgtatggct | ttcatttctc | cctccttgta | taaatcctgg | ttgctgtctc | tttatgagga | 180 |
| gttgtggccc | gttgtcaggc | aacgtggcgt | ggtgtgcact | gtgtttgctg | acgcaacccc | 240 |
| cactggttgg | ggcattgcca | ccacctgtca | gctcctttcc | gggactttcg | ctttcccccct | 300 |
| ccctattgcc | acggcggaac | tcatcgccgc | ctgccttgcc | cgctgctgga | caggggctcg | 360 |
| gctgttgggc | actgacaatt | ccgtggtgtt | gtcggggaaa | tcatcgtcct | ttccttggct | 420 |
| gctcgcctgt | gttgccacct | ggattctgcg | cgggacgtcc | ttctgctacg | tcccttcggc | 480 |
| cctcaatcca | gcggaccttc | cttcccgcgg | cctgctgccg | gctctgcggc | ctcttccgcg | 540 |
| tcttcgcctt | cgccctcaga | cgagtcggat | ctccctttgg | gccgcctccc | cgcatcgata | 600 |
| ccgtcgacct | cgagacctag | aaaaacatgg | agcaatcaca | agtagcaata | cagcagctac | 660 |
| caatgctgat | tgtgcctggc | tagaagcaca | agaggaggag | gaggtgggtt | ttccagtcac | 720 |
| acctcaggta | cctttaagac | caatgactta | caaggcagct | gtagatctta | gccacttttt | 780 |
| aaaagaaaag | gggggactgg | aagggctaat | tcactcccaa | cgaagacaag | atatccttga | 840 |

```
tctgtggatc taccacacac aaggctactt ccctgattgg cagaactaca caccagggcc    900
agggatcaga tatccactga cctttggatg gtgctacaag ctagtaccag ttgagcaaga    960
gaaggtagaa gaagccaatg aaggagagaa cacccgcttg ttacaccctg tgagcctgca   1020
tgggatggat gacccggaga gagaagtatt agagtggagg tttgacagcc gcctagcatt   1080
tcatcacatg gcccgagagc tgcatccgga ctgtactggg tctctctggt tagaccagat   1140
ctgagcctgg gagctctctg gctaactagg gaacccactg cttaagcctc aataaagctt   1200
gccttgagtg cttcaagtag tgtgtgcccg tctgttgtgt gactctggta actagagatc   1260
cctcagaccc ttttagtcag tgtggaaaat ctctagcagg gcccgtttaa acccgctgat   1320
cagcctcgac tgtgccttct agttgccagc catctgttgt ttgcccctcc cccgtgcctt   1380
ccttgaccct ggaaggtgcc actcccactg tcctttccta ataaaatgag gaaattgcat   1440
cgcattgtct gagtaggtgt cattctattc tggggggtgg ggtggggcag gacagcaagg   1500
gggaggattg ggaagacaat agcaggcatg tgagcaaaag gccagcaaaa ggccaggaac   1560
cgtaaaaagg ccgcgttgct ggcgtttttc cataggctcc gcccccctga cgagcatcac   1620
aaaaatcgac gctcaagtca gaggtggcga acccgacag gactataaag ataccaggcg   1680
tttccccctg gaagctccct cgtgcgctct cctgttccga ccctgccgct taccggatac   1740
ctgtccgcct ttctcccttc gggaagcgtg gcgctttctc atagctcacg ctgtaggtat   1800
ctcagttcgg tgtaggtcgt tcgctccaag ctgggctgtg tgcacgaacc ccccgttcag   1860
cccgaccgct gcgccttatc cggtaactat cgtcttgagt ccaacccggt aagacacgac   1920
ttatcgccac tggcagcagc cactggtaac aggattagca gagcgaggta tgtaggcggt   1980
gctacagagt tcttgaagtg gtggcctaac tacggctaca ctagaagaac agtatttggt   2040
atctgcgctc tgctgaagcc agttaccttc ggaaaaagag ttggtagctc ttgatccggc   2100
aaacaaacca ccgctggtag cggtggtttt tttgtttgca agcagcagat tacgcgcaga   2160
aaaaaggat ctcaagaaga tcctttgatc ttttctacgg ggtctgacgc tcagtggaac   2220
gaaaactcac gttaagggat tttggtcatg agattatcaa aaaggatctt cacctagatc   2280
cttttaaatt aaaaatgaag ttttaaatca atctaaagta tatatgagta aacttggtct   2340
gacagttacc aatgcttaat cagtgaggca cctatctcag cgatctgtct atttcgttca   2400
tccatagttg cctgactccc cgtcgtgtag ataactacga tacgggaggg cttaccatct   2460
ggccccagtg ctgcaatgat accgcgagac ccacgctcac cggctccaga tttatcagca   2520
ataaccagc cagccggaag ggccgagcgc agaagtggtc ctgcaacttt atccgcctcc   2580
atccagtcta ttaattgttg ccgggaagct agagtaagta gttcgccagt taatagtttg   2640
cgcaacgttg ttgccattgc tacaggcatc gtggtgtcac gctcgtcgtt ggtatggct   2700
tcattcagct ccggttccca acgatcaagg cgagttacat gatcccccat gttgtgcaaa   2760
aaagcggtta gctccttcgg tcctccgatc gttgtcagaa gtaagttggc cgcagtgtta   2820
tcactcatgg ttatggcagc actgcataat tctcttactg tcatgccatc cgtaagatgc   2880
ttttctgtga ctggtgagta ctcaaccaag tcattctgag aatagtgtat gcggcgaccg   2940
agttgctctt gcccggcgtc aatacgggat aataccgcgc cacatagcag aactttaaaa   3000
gtgctcatca ttggaaaacg ttcttcgggg cgaaaactct caaggatctt accgctgttg   3060
agatccagtt cgatgtaacc cactcgtgca cccaactgat cttcagcatc ttttactttc   3120
accagcgttt ctgggtgagc aaaaacagga aggcaaaatg ccgcaaaaaa gggaataagg   3180
```

```
gcgacacgga aatgttgaat actcatactc ttccttttc  aatattattg aagcatttat  3240
cagggttatt gtctcatgag cggatacata tttgaatgta tttagaaaaa taaacaaata  3300
ggggttccgc gcacatttcc ccgaaaagtg ccacctgacg tcgacggatc gggagatctc  3360
ccgatcccct atggtgcact ctcagtacaa tctgctctga tgccgcatag ttaagccagt  3420
atctgctccc tgcttgtgtg ttggaggtcg ctgagtagtg cgcgagcaaa atttaagcta  3480
caacaaggca aggcttgacc gacaattgca tgaagaatct gcttagggtt aggcgttttg  3540
cgctgcttcg cgatgtacgg gccagatata cgcgttgaca ttgattattg actagttatt  3600
aatagtaatc aattacgggg tcattagttc atagcccata tatggagttc cgcgttacat  3660
aacttacggt aaatggcccg cctggctgac cgcccaacga ccccgccca  ttgacgtcaa  3720
taatgacgta tgttcccata gtaacgccaa tagggacttt ccattgacgt caatgggtgg  3780
agtatttacg gtaaactgcc cacttggcag tacatcaagt gtatcatatg ccaagtacgc  3840
cccctattga cgtcaatgac ggtaaatggc ccgcctggca ttatgcccag tacatgacct  3900
tatgggactt tcctacttgg cagtacatct acgtattagt catcgctatt accatggtga  3960
tgcggttttg gcagtacatc aatgggcgtg gatagcggtt tgactcacgg ggatttccaa  4020
gtctccaccc cattgacgtc aatgggagtt tgttttggca ccaaaatcaa cgggactttc  4080
caaaatgtcg taacaactcc gccccattga cgcaaatggg cggtaggcgt gtacggtggg  4140
aggtctatat aagcagcgcg ttttgcctgt actgggtctc tctggttaga ccagatctga  4200
gcctgggagc tctctggcta actagggaac ccactgctta agcctcaata aagcttgcct  4260
tgagtgcttc aagtagtgtg tgcccgtctg ttgtgtgact ctggtaacta gagatccctc  4320
agaccctttt agtcagtgtg gaaaatctct agcagtggcg cccgaacagg gacttgaaag  4380
cgaaagggaa accagaggag ctctctcgac gcaggactcg gcttgctgaa gcgcgcacgg  4440
caagaggcga ggggcggcga ctggtgagta cgccaaaaat tttgactagc ggaggctaga  4500
aggagagaga tgggtgcgag agcgtcagta ttaagcgggg gagaattaga tcgcgatggg  4560
aaaaaattcg gttaaggcca gggggaaaga aaaaatataa attaaaacat atagtatggg  4620
caagcaggga gctagaacga ttcgcagtta atcctggcct gttagaaaca tcagaaggct  4680
gtagacaaat actgggacag ctacaaccat cccttcagac aggatcagaa gaacttagat  4740
cattatataa tacagtagca accctctatt gtgtgcatca aaggatagag ataaaagaca  4800
ccaaggaagc tttagacaag atagaggaag agcaaaacaa aagtaagacc accgcacagc  4860
aagcggccgc tgatcttcag acctggagga ggagatatga gggacaattg gagaagtgaa  4920
ttatataaat ataaagtagt aaaaattgaa ccattaggag tagcacccac caaggcaaag  4980
agaagagtgg tgcagagaga aaaaagagca gtgggaatag gagctttgtt ccttgggttc  5040
ttgggagcag caggaagcac tatgggcgca gcgtcaatga cgctgacggt acaggccaga  5100
caattattgt ctggtatagt gcagcagcag aacaatttgc tgagggctat tgaggcgcaa  5160
cagcatctgt tgcaactcac agtctgggc  atcaagcagc tccaggcaag aatcctggct  5220
gtggaaagat acctaaagga tcaacagctc ctggggattt ggggttgctc tggaaaactc  5280
atttgcacca ctgctgtgcc ttggaatgct agttggagta taaatctct  ggaacagatt  5340
tggaatcaca cgacctggat ggagtgggac agagaaatta caattacac  aagcttaata  5400
cactccttaa ttgaagaatc gcaaaaccag caagaaaaga atgaacaaga attattggaa  5460
ttagataaat gggcaagttt gtggaattgg tttaacataa caaattggct gtggtatata  5520
aaattattca taatgatagt aggaggcttg gtaggtttaa gaatagtttt tgctgtactt  5580
```

-continued

```
tctatagtga atagagttag gcagggatat tcaccattat cgtttcagac ccacctccca    5640
accccgaggg gacccgacag gcccgaagga atagaagaag aaggtggaga gagagacaga    5700
gacagatcca ttcgattagt gaacggatcg gcactgcgtg cgccaattct gcagacaaat    5760
ggcagtattc atccacaatt ttaaaagaaa aggggggatt gggggggtaca gtgcagggga    5820
aagaatagta gacataatag caacagacat acaaactaaa gaattacaaa aacaaattac    5880
aaaaattcaa aattttcggg tttattacag ggacagcaga gatccagttt ggttaattaa    5940
cccgtgtcgg ctccagatct ggcctccgcg ccgggttttg gcgcctcccg cgggcgcccc    6000
cctcctcacg gcgagcgctg ccacgtcaga cgaaggcgc agcgagcgtc ctgatccttc     6060
cgcccggacg ctcaggacag cggcccgctg ctcataagac tcggccttag aaccccagta    6120
tcagcagaag gacattttag gacgggactt gggtgactct agggcactgg ttttcttttcc   6180
agagagcgga acaggcgagg aaaagtagtc ccttctcggc gattctgcgg agggatctcc    6240
gtggggcggt gaacgccgat gattatataa ggacgcgccg ggtgtggcac agctagttcc    6300
gtcgcagccg ggatttgggt cgcggttctt gtttgtggat cgctgtgatc gtcacttggt    6360
gagtagcggg ctgctgggct ggccggggct ttcgtggccg ccgggccgct cggtgggacg    6420
gaagcgtgtg gagagaccgc caagggctgt agtctgggtc cgcgagcaag gttgccctga    6480
actgggggtt gggggggagcg cagcaaaatg gcggctgttc ccgagtcttg aatgaaagac    6540
gcttgtgagg cgggctgtga ggtcgttgaa acaaggtggg gggcatggtg ggcggcaaga    6600
acccaaggtc ttgaggcctt cgctaatgcg ggaaagctct tattcgggtg agatgggctg    6660
gggcaccatc tggggaccct gacgtgaagt ttgtcactga ctggagaact cggtttgtcg    6720
tctgttgcgg gggcggcagt tatgcggtg ccgttgggca gtgcacccgt acctttggga    6780
gcgcgcgccc tcgtcgtgtc gtgacgtcac ccgttctgtt ggcttataat gcagggtggg    6840
gccacctgcc ggtaggtgtg cggtaggctt ttctccgtcg caggacgcag ggttcgggcc    6900
tagggtaggc tctcctgaat cgacaggcgc cggacctctg gtgaggggag ggataagtga    6960
ggcgtcagtt tctttggtcg gttttatgta cctatcttct taagtagctg aagctccggt    7020
tttgaactat gcgctcgggg ttggcgagtg tgttttgtga agttttttag gcacctttttg   7080
aaatgtaatc atttgggtca atatgtaatt ttcagtgtta gactagtaaa ttgtccgcta    7140
aattctggcc gtttttggct tttttgttag acgaagcttg ggcccgggaa ttaattcacc    7200
atgtctagac tggacaagag caaagtcata aacggcgctc tggaattact caatggagtc    7260
ggtatcgaag gcctgacgac aaggaaactc gctcaaaagc tgggagttga gcagcctacc    7320
ctgtactggc acgtgaagaa caagcgggcc ctgctcgatg ccctgccaat cgagatgctg    7380
gacaggcatc atacccactt ctgccccctg gaaggcgagt catggcaaga ctttctgcgg    7440
aacaacgcca agtcattccg ctgtgctctc ctctcacatc gcgacggggc taaagtgcat    7500
ctcggcaccc gcccaacaga gaaacagtac gaaaccctgg aaaatcagct cgcgttcctg    7560
tgtcagcaag gcttctccct ggagaacgca ctgtacgctc tgtccgccgt gggccacttt    7620
acactgggct gcgtattgga ggaacaggag catcaagtag caaaagagga aagagagaca    7680
cctaccaccg attctatgcc cccacttctg agacaagcaa ttgagctgtt cgaccggcag    7740
ggagccgaac ctgccttcct tttcggcctg gaactaatca tatgtggcct ggagaaacag    7800
ctaaagtgcg aaagcggcgg gccggccgac gcccttgacg attttgactt agacatgctc    7860
ccagccgatg cccttgacga ctttgacctt gatatgctgc ctgctgacgc tcttgacgat    7920
```
tttgaccttg acatgctccc cgggtaacta agtaaggatc aattcgatat caagcttat    7979

<210> SEQ ID NO 111
<211> LENGTH: 1201
<212> TYPE: DNA
<213> ORGANISM: Homo sapiens

<400> SEQUENCE: 111
aatattagag tctcaacccc caataaatat aggactggag atgtctgagg ctcattctgc    60
cctcgagccc accgggaacg aaagagaagc tctatctccc ctccaggagc ccagctatga   120
actccttctc cacaagcgcc ttcggtccag ttgccttctc cctggggctg ctcctggtgt   180
tgcctgctgc cttccctgcc ccagtacccc caggagaaga ttccaaagat gtagccgccc   240
cacacagaca gccactcacc tcttcagaac gaattgacaa acaaattcgg tacatcctcg   300
acggcatctc agccctgaga aggagacat gtaacaagag taacatgtgt gaaagcagca   360
aagaggcact ggcagaaaac aacctgaacc ttccaaagat ggctgaaaaa gatggatgct   420
tccaatctgg attcaatgag gagacttgcc tggtgaaaat catcactggt cttttggagt   480
ttgaggtata cctagagtac ctccagaaca gatttgagag tagtgaggaa caagccagag   540
ctgtgcagat gagtacaaaa gtcctgatcc agttcctgca gaaaaaggca aagaatctag   600
atgcaataac caccccctgac ccaaccacaa atgccagcct gctgacgaag ctgcaggcac   660
agaaccagtg gctgcaggac atgacaactc atctcattct gcgcagcttt aaggagttcc   720
tgcagtccag cctgagggct cttcggcaaa tgtagcatgg gcacctcaga ttgttgttgt   780
taatgggcat tccttcttct ggtcagaaac ctgtccactg gcacagaac ttatgttgtt    840
ctctatggag aactaaaagt atgagcgtta ggacactatt ttaattattt ttaatttatt   900
aatatttaaa tatgtgaagc tgagttaatt tatgtaagtc atatttatat ttttaagaag   960
taccacttga aacatttat gtattagttt tgaaataata atggaaagtg ctatgcagt   1020
ttgaatatcc tttgtttcag agccagatca tttcttggaa agtgtaggct tacctcaaat   1080
aaatggctaa cttatacata tttttaaaga aatatttata ttgtatttat ataatgtata   1140
aatggttttt ataccaataa atggcatttt aaaaaattca gcaaaaaaaa aaaaaaaaa   1200
a                                                                  1201

<210> SEQ ID NO 112
<211> LENGTH: 1902
<212> TYPE: DNA
<213> ORGANISM: Homo sapiens

<400> SEQUENCE: 112
atgaccgaag aagcatgccg aacacggagt cagaaacgag cgcttgaacg ggacccaaca    60
gaggacgatg tggagagcaa gaaaataaaa atggagagag gattgttggc ttcagattta   120
aacactgacg gagacatgag ggtgacacct gagccgggag caggtccaac ccaaggattg   180
ctgagggcaa cagaggccac ggccatggcc atgggcagag gcgaagggct ggtgggcgat   240
gggcccgtgg acatgcgcac ctcacacagt gacatgaagt ccgagaggag acccccctca   300
cctgacgtga ttgtgctctc cgacaacgag cagccctcga gccgagagt gaatgggctg   360
accacggtgg ccttgaagga gactagcacc gaggccctca tgaaaagcag tcctgaagaa   420
cgagaaagga tgatcaagca gctgaaggaa gaattgaggt tagaagaagc aaaactcgtg   480
ttgttgaaaa agttgcggca gagtcaaata caaaaggaag ccaccgccca gaagcccaca   540
ggttctgttg ggagcaccgt gaccacccct ccccgcttg ttcggggcac tcagaacatt   600

```
cctgctggca agccatcact ccagacctct tcagctcgga tgcccggcag tgtcataccc      660
ccgcccctgg tccgaggtgg gcagcaggcg tcctcgaagc tggggccaca ggcgagctca      720
caggtcgtca tgcccccact cgtcaggggg gctcagcaaa tccacagcat taggcaacat      780
tccagcacag ggccaccgcc cctcctcctg gccccccggg cgtcggtgcc cagtgtgcag      840
attcagggac agaggatcat ccagcagggc ctcatccgcg tcgccaatgt tcccaacacc      900
agcctgctcg tcaacatccc acagcccacc ccagcatcac tgaaggggac aacagccacc      960
tccgctcagg ccaactccac ccccactagt gtggcctctg tggtcacctc tgccgagtct     1020
ccagcaagcc gacaggcggc cgccaagctg gcgctgcgca acagctgga gaagacgcta      1080 ctcgagatcc ccccacccaa gcccccagcc ccagagatga acttcctgcc cagcgccgcc     1140
aacaacgagt tcatctacct ggtcggcctg gaggaggtgg tgcagaacct actggagaca     1200
caaggcagga tgtcggccgc cactgtgctg tcccgggagc cctacatgtg tgcacagtgc     1260
aagacggact tcacgtgccg ctggcgggag gagaagagcg cgccatcat gtgtgagaac      1320 tgcatgacaa ccaaccagaa gaaggcgctc aaggtggagc acaccagccg gctgaaggcc     1380
gcctttgtga aggcgctgca gcaggaacag gagattgagc agcggctcct gcagcagggc     1440
acggcccctg cacaggccaa ggccgagccc accgctgccc cacacccgt gctgaagcag       1500 gtcataaaac cccggcgtaa gttggcgttc cgctcaggag aggcccgcga ctggagtaac     1560
ggggctgtgc tacaggcctc cagccagctg tcccgggtt cggccacgac gccccgaggt      1620
gtcctgcaca cgttcagtcc gtcacccaaa ctgcagaact cagcctcggc cacagccctg     1680
gtcagcagga ccggcagaca ttctgagaga ccgtgagcg ccggcaaggg cagcgccacc      1740
tccaactgga agaagacgcc cctcagcaca ggcgggaccc ttgcgtttgt cagcccaagc     1800
ctggcggtgc acaagagctc ctcggccgtg gaccgccagc gagagtacct cctggacatg     1860
atcccacccc gctccatccc ccagtcagcc acgtggaaat ag                         1902

<210> SEQ ID NO 113
<211> LENGTH: 123
<212> TYPE: DNA
<213> ORGANISM: Homo sapiens
<220> FEATURE:
<221> NAME/KEY: misc_feature
<222> LOCATION: (1)..(123)
<223> OTHER INFORMATION: P66 alpha coiled-coil domain coding sequence

<400> SEQUENCE: 113
cctgaagaac gagaaaggat gatcaagcag ctgaaggaag aattgaggtt agaagaagca       60
aaactcgtgt tgttgaaaaa gttgcggcag agtcaaatac aaaaggaagc caccgcccag      120
aag                                                                   123

<210> SEQ ID NO 114
<211> LENGTH: 41
<212> TYPE: PRT
<213> ORGANISM: Homo sapiens
<220> FEATURE:
<221> NAME/KEY: MISC_FEATURE
<222> LOCATION: (1)..(41)
<223> OTHER INFORMATION: P66 alpha coiled-coil domain

<400> SEQUENCE: 114

Pro Glu Glu Arg Glu Arg Met Ile Lys Gln Leu Lys Glu Glu Leu Arg
1               5                   10                  15

Leu Glu Glu Ala Lys Leu Val Leu Leu Lys Lys Leu Arg Gln Ser Gln
```

```
              20                  25                  30

Ile Gln Lys Glu Ala Thr Ala Gln Lys
        35                  40

<210> SEQ ID NO 115
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 115
aaaaaaaccg gtcctgaaga acgagaaagg                                          30

<210> SEQ ID NO 116
<211> LENGTH: 27
<212> TYPE: DNA
<213> ORGANISM: Artificial Sequence
<220> FEATURE:
<223> OTHER INFORMATION: Single strand DNA oligonucleotide

<400> SEQUENCE: 116
aaaaaactta agcttctggg cggtggc                                             27

<210> SEQ ID NO 117
<211> LENGTH: 426
<212> TYPE: PRT
<213> ORGANISM: Homo sapiens

<400> SEQUENCE: 117

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220
```

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
            245                 250                 255

Leu Gly Lys Lys Lys Lys Glu Glu Gly Glu Gly Lys Lys Lys
        260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
            325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 118
<211> LENGTH: 232
<212> TYPE: PRT
<213> ORGANISM: Homo sapiens

<400> SEQUENCE: 118

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
    130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

```
Ser Cys Phe Ser Lys Arg Ser Cys Val Pro Glu Gly Met Val Cys
            180             185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
210             215                 220

Ile Ser Glu Cys Lys Cys Ser Cys
225             230

<210> SEQ ID NO 119
<211> LENGTH: 88
<212> TYPE: PRT
<213> ORGANISM: Homo sapiens

<400> SEQUENCE: 119

Met Lys Val Leu Ala Val His Ser Pro Gly Gly Ala Val Pro Gln
1               5                   10                  15

Gln Pro Gly Gln Ala Met Trp Pro Gln Arg Asp Gly Leu Pro Ala Leu
            20                  25                  30

Pro Arg Gln Arg His Gly Glu Gly Gln Ala Gly Gly Ala Val Pro His
        35                  40                  45

Ser Arg Val Pro Trp His Leu Pro Gly Gln His His Pro Gly Pro Glu
    50                  55                  60

Asp Pro Gln Pro Gln Cys Pro Gln Pro Pro Gln Ala Gln Arg His
65                  70                  75                  80

Arg Arg His Pro Ala Arg Pro Pro
                85

<210> SEQ ID NO 120
<211> LENGTH: 212
<212> TYPE: PRT
<213> ORGANISM: Homo sapiens

<400> SEQUENCE: 120

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175
```

-continued

```
Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
        210

<210> SEQ ID NO 121
<211> LENGTH: 433
<212> TYPE: PRT
<213> ORGANISM: Homo sapiens

<400> SEQUENCE: 121

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
```

```
                        325                 330                 335
Thr Pro Thr Ala Arg Leu Thr Pro Leu Glu Ala Cys Ala His Ser Phe
                340                 345                 350
Phe Asp Glu Leu Arg Asp Pro Asn Val Lys Leu Pro Asn Gly Arg Asp
            355                 360                 365
Thr Pro Ala Leu Phe Asn Phe Thr Thr Gln Glu Leu Ser Ser Asn Pro
        370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                405                 410                 415
Asp Arg Gly Gln Thr Asn Asn Ala Ala Ser Ala Ser Ala Ser Asn Ser
                420                 425                 430
Thr

<210> SEQ ID NO 122
<211> LENGTH: 420
<212> TYPE: PRT
<213> ORGANISM: Homo sapiens

<400> SEQUENCE: 122

Met Ser Gly Arg Pro Arg Thr Thr Ser Phe Ala Glu Ser Cys Lys Pro
1               5                   10                  15
Val Gln Gln Pro Ser Ala Phe Gly Ser Met Lys Val Ser Arg Asp Lys
                20                  25                  30
Asp Gly Ser Lys Val Thr Thr Val Val Ala Thr Pro Gly Gln Gly Pro
            35                  40                  45
Asp Arg Pro Gln Glu Val Ser Tyr Thr Asp Thr Lys Val Ile Gly Asn
        50                  55                  60
Gly Ser Phe Gly Val Val Tyr Gln Ala Lys Leu Cys Asp Ser Gly Glu
65                  70                  75                  80
Leu Val Ala Ile Lys Lys Val Leu Gln Asp Lys Arg Phe Lys Asn Arg
                85                  90                  95
Glu Leu Gln Ile Met Arg Lys Leu Asp His Cys Asn Ile Val Arg Leu
                100                 105                 110
Arg Tyr Phe Phe Tyr Ser Ser Gly Glu Lys Lys Asp Glu Val Tyr Leu
            115                 120                 125
Asn Leu Val Leu Asp Tyr Val Pro Glu Thr Val Tyr Arg Val Ala Arg
        130                 135                 140
His Tyr Ser Arg Ala Lys Gln Thr Leu Pro Val Ile Tyr Val Lys Leu
145                 150                 155                 160
Tyr Met Tyr Gln Leu Phe Arg Ser Leu Ala Tyr Ile His Ser Phe Gly
                165                 170                 175
Ile Cys His Arg Asp Ile Lys Pro Gln Asn Leu Leu Leu Asp Pro Asp
                180                 185                 190
Thr Ala Val Leu Lys Leu Cys Asp Phe Gly Ser Ala Lys Gln Leu Val
            195                 200                 205
Arg Gly Glu Pro Asn Val Ser Tyr Ile Cys Ser Arg Tyr Tyr Arg Ala
        210                 215                 220
Pro Glu Leu Ile Phe Gly Ala Thr Asp Tyr Thr Ser Ser Ile Asp Val
225                 230                 235                 240
Trp Ser Ala Gly Cys Val Leu Ala Glu Leu Leu Leu Gly Gln Pro Ile
                245                 250                 255
Phe Pro Gly Asp Ser Gly Val Asp Gln Leu Val Glu Ile Ile Lys Val
```

|     |     |     | 260 |     |     |     | 265 |     |     |     | 270 |     |
| --- | --- | --- | --- | --- | --- | --- | --- | --- | --- | --- | --- | --- |
| Leu | Gly | Thr | Pro | Thr | Arg | Glu | Gln | Ile | Arg | Glu | Met | Asn | Pro | Asn | Tyr |
|     |     |     | 275 |     |     |     | 280 |     |     |     | 285 |     |

Thr Glu Phe Lys Phe Pro Gln Ile Lys Ala His Pro Trp Thr Lys Val
            290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
            325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
            355                 360                 365

Ser Asn Pro Pro Leu Ala Thr Ile Leu Ile Pro Pro His Ala Arg Ile
            370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
            405                 410                 415

Ser Asn Ser Thr
            420

<210> SEQ ID NO 123
<211> LENGTH: 2175
<212> TYPE: DNA
<213> ORGANISM: Homo sapiens

<400> SEQUENCE: 123

| agtacagtat | aaaacttcac | agtgccaata | ccatgaagag | gagctcagac | agctcttacc | 60 |
| acatgataca | agagccggct | ggtggaagag | tggggaccag | aaagagaatt | tgctgaagag | 120 |
| gagaaggaaa | aaaaaaacac | caaaaaaaaa | aataaaaaaa | tccacacaca | caaaaaaacc | 180 |
| tgcgcgtgag | gggggaggaa | aagcagggcc | ttttaaaaag | gcaatcacaa | caacttttgc | 240 |
| tgccaggatg | cccttgcttt | ggctgagagg | atttctgttg | gcaagttgct | ggattatagt | 300 |
| gaggagttcc | cccaccccag | gatccgaggg | gcacagcgcg | gcccccgact | gtccgtcctg | 360 |
| tgcgctggcc | gccctcccaa | aggatgtacc | caactctcag | ccagagatgg | tggaggccgt | 420 |
| caagaagcac | attttaaaca | tgctgcactt | gaagaagaga | cccgatgtca | cccagccggt | 480 |
| acccaaggcg | gcgcttctga | acgcgatcag | aaagcttcat | gtgggcaaag | tcggggagaa | 540 |
| cgggtatgtg | gagatagagg | atgacattgg | aaggagggca | gaaatgaatg | aacttatgga | 600 |
| gcagacctcg | gagatcatca | cgtttgccga | gtcaggaaca | gccaggaaga | cgctgcactt | 660 |
| cgagatttcc | aaggaaggca | gtgacctgtc | agtggtggag | cgtgcagaag | tctggctctt | 720 |
| cctaaaagtc | cccaaggcca | acaggaccag | gaccaaagtc | accatccgcc | tcttccagca | 780 |
| gcagaagcac | ccgcagggca | gcttggacac | aggggaagag | gccgaggaag | tgggcttaaa | 840 |
| gggggagagg | agtgaactgt | tgctctctga | aaaagtagta | gacgctcgga | agagcacctg | 900 |
| gcatgtcttc | cctgtctcca | gcagcatcca | gcggttgctg | gaccagggca | agagctccct | 960 |
| ggacgttcgg | attgcctgtg | agcagtgcca | ggagagtggc | gccagcttgg | ttctcctggg | 1020 |
| caagaagaag | aagaaagaag | aggagggggga | agggaaaaag | aagggcggag | gtgaaggtgg | 1080 |
| ggcaggagca | gatgaggaaa | aggagcagtc | gcacagacct | ttcctcatgc | tgcaggcccg | 1140 |
| gcagtctgaa | gaccacccct | catcgccggcg | tcggcggggc | ttggagtgtg | atggcaaggt | 1200 |

```
caacatctgc tgtaagaaac agttctttgt cagtttcaag gacatcggct ggaatgactg      1260
gatcattgct ccctctggct atcatgccaa ctactgcgag ggtgagtgcc cgagccatat      1320
agcaggcacg tccgggtcct cactgtcctt ccactcaaca gtcatcaacc actaccgcat      1380
gcggggccat agcccctttg ccaacctcaa atcgtgctgt gtgcccacca agctgagacc      1440
catgtccatg ttgtactatg atgatggtca aaacatcatc aaaaaggaca ttcagaacat      1500
gatcgtggag gagtgtgggt gctcatagag ttgcccagcc caggggggaaa gggagcaaga     1560 gttgtccaga gaagacagtg gcaaaatgaa gaaattttta aggtttctga gttaaccaga      1620
aaaatagaaa ttaaaaacaa aacaaaaaaa aaaacaaaaa aaaacaaaag taaattaaaa      1680
acaaaacctg atgaaacaga tgaaggaaga tgtggaaaaa atccttagcc agggctcaga     1740
gatgaagcag tgaaagagac aggaattggg agggaaaggg agaatggtgt acccttatt      1800 tcttctgaaa tcacactgat gacatcagtt gtttaaacgg ggtattgtcc tttccccct      1860 tgaggttccc ttgtgagcct tgaatcaacc aatctagtct gcagtagtgt ggactagaac      1920
aacccaaata gcatctagaa agccatgagt ttgaaagggc ccatcacagg cactttccta     1980
cccaattacc caggtcataa ggtatgtctg tgtgacactt atctctgtgt atatcagcat      2040
acacacacac acacacacac acacacacac acacaggcat ttccacacat tacatatata      2100
cacatactgg taaaagaaca atcgtgtgca ggtggtcaca cttccttttt ctgtaccact      2160
tttgcaacaa aacaa                                                      2175
```

__ISOLATED NAIVE PLURIPOTENT STEM CELLS AND METHODS OF GENERATING SAME__

RELATED APPLICATIONS

This application claims the benefit of priority under 35 USC § 119(e) of U.S. Provisional Patent Application Nos. 61/932,935 filed on Jan. 29, 2014, 61/878,769 filed on Sep. 17, 2013 and 61/814,920 filed on Apr. 23, 2013.

This application is also related to co-filed, co-pending and co-assigned PCT Patent Application No. PCT/IB2014/060954 having international filing date of Apr. 23, 2014, entitled "ISOLATED NAIVE PLURIPOTENT STEM CELLS AND METHODS OF GENERATING SAME" by Yaqub HANNA, Noa NOVERSHTERN and Yoach RAIS.

The contents of the above applications are incorporated herein by reference in their entirety.

SEQUENCE LISTING STATEMENT

The ASCII file, entitled 58870SequenceListing.txt, created on Apr. 22, 2014, comprising 312,565 bytes, submitted concurrently with the filing of this application is incorporated herein by reference.

FIELD AND BACKGROUND OF THE INVENTION

The present invention, in some embodiments thereof, relates to isolated naive pluripotent stem cell, novel culture medium which can be used to generate same and methods of generating and culturing same and, more particularly, but not exclusively, to methods of improving dedifferentiation of somatic cells for generation of induced pluripotent stem cells.

ESC-like cells, termed induced pluripotent (iPS) cells can be generated from somatic cells by ectopic expression of different transcription factors, originally Oct4, Sox2, Klf4 and c-Myc (Takahashi and Yamanaka, 2006), that share all defining features with naive mouse ESCs (Takahashi and Yamanaka, 2006; Hanna et al., 2009a). The reprogramming process typically requires extensive cell proliferation of a period of at least one week, after which a certain fraction of the cell progeny successfully converts into ES-like state in an unpredictable pattern and with different time latencies (Hanna et al., 2009b). Great progress has been achieved in identifying additional and alternative transcriptional factors and small molecules that can substitute some of the exogenous factor or boost reprogramming efficiency when combined with Oct4, Sox2, Klf4 and c-Myc (OSKM) (Orkin and Hochedlinger, 2011). A variety of enzymes and chromatin remodelers have been identified to cooperate with the reprogramming factors in facilitating the required early and late chromatin changes leading to authentic iPSC reprogramming in a fraction of donor cell progeny (e.g., Wdr5, Utx, Tet2) (Ang et al., 2011; Mansour et al., 2012; Onder et al., 2012).

Despite of these advances, the reprogramming efficiency of somatic cells remains to be low, even in the most optimized reprogramming recipes used (up to 0.1-20%) (Hanna et al., 2010b). Further, per a starting individual somatic epigenome challenged with the overexpression of reprogramming factors, the outcome is highly stochastic, and the majority of cells assume different levels of reprogramming (Hanna et al., 2009b). The latter has allowed the isolation of a variety of intermediate populations identified by surface markers that can be further challenged and perturbed to generate iPSCs in a random manner (Polo et al., 2012). Biological systems—based approaches for modeling the nature of stochastic elements and progression of reprogramming have revealed that while somatic cell reprogramming involves thousands of molecular changes, as few as one rate limiting event may adequately recapitulate the experimentally observed kinetics by clonal cell monitoring (Hanna et al., 2009b). The identity of such stochastic rate limiting element(s) remains to be defined.

Further, the fact that only fully reprogrammed ES-like cells have been derived via cell fusion or nuclear transfer reprogramming approaches with no evidence for partially reprogrammed cells, suggests that reprogramming by nuclear transfer or cell fusion may follow a more synchronized and deterministic pattern, in comparison to OSKM induced reprogramming (Hanna et al., 2010b). The above raises the hypothesis of whether it is feasible to devise deterministic direct iPSC reprogramming approaches, and whether additional genetic manipulations together with transcription factor transduction may enable synchronized and deterministic in vitro reprogramming.

Embryonic stem cells (ESCs) were first isolated from mouse embryos by explanting the inner cell mass (ICM) of developing embryos in vitro in the presence of the leukemia inhibitory factor (LIF) cytokine and mouse embryonic feeder (MEF) cells (Hanna et al., 2010a; Takahashi and Yamanaka, 2006). Mouse ESCs recapitulate molecular signatures of the nascent ICM and are, therefore, termed as "naive pluripotent cells" (Hanna, 2010; Hanna et al., 2010a; 2009a; Takahashi and Yamanaka, 2006). This includes expression of Oct4, Nanog and Klf pluripotency genes, lack of epiblast and somatic early lineage specific markers, and maintenance of a pre X-inactivation state with both X chromosomes active in female cells. Further, the cells retain a non-restricted developmental potential as they can robustly differentiate into all cell types in vitro and, upon injection into the mouse blastocyst, they efficiently contribute to the three germ layers and to the germ-line of chimeric animals (Hanna et al., 2010a; 2009b). Finally, the high growth rate and open chromatin confirmation of mouse ES cells, has rendered these cells as one of the most valuable tools for mouse genetics by allowing efficient gene specific targeting via homologous recombination (Hanna et al., 2010a; Orkin and Hochedlinger, 2011).

Recently, a dramatically different type of pluripotent cells, termed EpiSCs, were derived by explanting the post-implantation epiblast in growth conditions supplemented with FGF2 [also known as "basic fibroblast growth factor (bF-GF)"] and Activin (Ang et al., 2011; Mansour et al., 2012; Onder et al., 2012; Tesar et al., 2007). Although EpiSCs are pluripotent, they have a restricted developmental potential in comparison to ESCs and therefore are termed as "primed pluripotent cells". EpiSCs are highly inefficient in generating animal chimeras, have already undergone X chromosome inactivation, and demonstrate heterogeneous expression of early lineage-commitment markers (Hanna et al., 2009a; 2010a). Hanna Y., et al. (2009a) have recently defined the relationships between the two distinct types of pluripotent states. Whereas naive murine pluripotent cells can differentiate into a primed EpiSC-like state in vitro by promoting Activin and FGF2 signaling, EpiSCs can epigenetically revert back to ESC-like naive pluripotency by defined signaling stimuli.

Remarkably, ESCs derived from humans nearly share several defining features with EpiSC cells, rather than with mouse ESCs. In contrast to mouse ESCs, the maintenance of human ES cells requires FGF2 and Activin (rather than LIF/Stat3 signaling), they are highly sensitive to passaging as single cells, display heterogeneous expression of epiblast and lineage commitment markers, and utilize the proximal enhancer element to drive the expression of Oct4 in the post-implantation Epiblast (rather than the distal Oct4 enhancer active in the ICM) (Hanna et al., 2009a; 2009b). Thus, the molecular and biological similarities of human ESCs with mouse epiblast EpiSCs suggest that human ESCs correspond to the primed pluripotent state rather than the naive state of mouse ESCs and that this could be the underlying reason for the biological properties of conventional human ESCs that impede their use for disease related research (Hanna et al., 2010b; Polo et al., 2012). This includes laborious culture conditions, low gene targeting efficiencies by homologous recombination and the dramatic heterogeneity in differentiation propensity among different human ESC and iPSC lines (Hanna et al., 2009b; 2010a).

The fact that conventional/primed human ESCs are derived from the ICM has mistakenly suggested that the primed state is the only or "default" state of pluripotency that can be isolated in humans (Hanna et al., 2010a). However, revisiting this concept was provoked following the work of the present inventors on defining the in vitro stability and identity of pluripotent state in relatively "non-permissive" mouse strains for naive ES derivation (yielded exclusively EpiSC-like pluripotent cells until recently) (Hanna et al., 2009a). Mouse naive ESC cells can be derived from Non-obese diabetogenic (NOD) mice blastocysts only if additional signaling molecules or transcription factors are exogenously provided together with LIF cytokine (e.g. Naive NOD ESC and iPSCs could be propagated in PD0325901/CHIR99021/LIF or Kenopaullone/CHIR99-021/LIF or constitutive expression of Klf4/Lif and c-Myc/LIF conditions) (Hanna et al., 2009a). In the absence of these additional factors (or in LIF only conditions), the naive state, even if isolated from the mouse ICM, is masked by in vitro acquisition of pluripotent state that is nearly indistinguishable from EpiSC cells in a process that probably imitates in vivo differentiation during normal early development (Hanna et al., 2009a). These findings allowed the generation of fully pluripotent naive ES and iPS cells from previously considered "non-permissive' strains. Experiments in NOD mice have raised the question whether appropriate conditions that allow derivation of naive or mouse ESC-like stem cell in humans have not been devised yet and that stabilization of a naive human pluripotent state requires additional undefined factors (similar or different from those applied to NOD mouse and rat ESCs/iPSCs) (Hanna et al., 2009a). Further support for the possibility that explanted blastocysts differentiate in vitro into a primed state was generated by close monitoring of X chromosome dynamics in human female ESC lines derived in vitro and demonstrated that the cells undergo X chromosome inactivation as a part of an in vitro adaptation process following this derivation, and this can be accelerated by high oxygen concentrations, and attenuated partially by addition of LIF or specific types of feeder cells that provide undefined signals (Lengner et al., 2010; Okamoto et al., 2011; Tomoda et al., 2012). These results indicated that XaXa (X-active, X-active, based on absence of XIST bodies) naive cells might be present in the human ICM, and that in vitro captured conventional human ESCs poorly reflect their ICM counterparts (Okamoto et al., 2011).

These observations have raised the possibility that appropriate conditions may have not been devised to allow isolation of naive stem cells from a range of species that have yielded thus far primed or EpiSC-like cells, possibly including humans (Hanna et al., 2009a). Indeed in a follow-up work evidence was provided for the possibility to derive alternative human pluripotent cell states that more extensively share defining features with murine ESCs. As previously shown (Hanna et al., 2010b), a screening approach was taken that involved introducing reprogramming factors and/or small molecules that support the naive pluripotent state led to in vitro stabilization of a novel pluripotent cell state that shares several defining features with murine ESCs (Hanna et al., 2010b). The propagation in LIF cytokine and ERK1/2 inhibitor PD0325901 and GSK3b inhibitor CHIR99021 (abbreviated as 2i supplemented conditions—two small molecule inhibitors of ERK1/2 signaling and GSK3β to promote WNT signaling, abbreviated as "PD/CH" or "2i" conditions) together with over-expression of OCT4/KLF4 or KLF2/KLF4 induced conversion of conventional human ES and iPS cells to what was then mistakenly referred as human naive pluripotent state reminiscent of that of mouse ESCs (Hanna et al., 2010b). These previously described naive human ESCs were pluripotent by several available criteria including embryonic body differentiation and in vivo teratoma formation. Importantly, they were epigenetically and molecularly distinct from conventional "primed" human ESCs/iPSCs. "Naive" hPSCs generated by Hanna et al., 2010b exhibited XIST methylation on both X alleles, high single cell cloning efficiency and showed a gene expression pattern that resembled that of naive mouse ES cells (lack of MHC class I expression, and clustered with murine naive ESCs in cross-species unbiased gene clustering for 9773 expressed orthologue genes) (Hanna et al., 2010b). Nevertheless, a major limitations and unsolved questions remain that cast doubt on the true pluripotency of previously published/established lines and their stability. Only transgene dependent naive ESC/iPSCs could be maintained for over 18 passages. Forskolin enabled replacement of exogenous factors together with 2i/LIF, but only for no more than 19 passages and the cultures retained high differentiation propensity (Hanna et al., 2010b). XIST was completely methylated in the previously referred naive human ESC/iPSCs and the cells lacked any XIST transcription (Hanna et al., 2010b), which is inconsistent with in vivo results on human blastocysts that clearly show XIST transcription (without forming XIST bodies, i.e., XIST coated X chromosomes) (Okamoto et al., 2011). Collectively, these findings suggest that the isolated cells thus far do not reflect authentic features of human ICM, and retain a compromised pluripotency and enhanced propensity for differentiation. Substantial published data generated by many different groups highlight the rationale behind the concept that genetically unmodified pluripotent naive human stem cells have not been adequately isolated so far, and that the conditions allowing expansion of such cells and their molecular properties (if they indeed are proven to exist) are not known (De Los Angeles et al., 2012; Hanna et al., 2010b).

Additional background art includes Xu Y., et al., 2013 (Journal of Biological Chemistry, 288: 9767-9778); Luo M., et al., 2013 (Stem Cells. March 26. doi: 10.1002/stem.1374. [Epub ahead of print]); International Application No. PCT/US08/04516 ("Reprogramming of Somatic Cells", Jaenisch; Rudolf; et al).

SUMMARY OF THE INVENTION

According to an aspect of some embodiments of the present invention there is provided an isolated (e.g., primate e.g., human) naive pluripotent stem cell (PSC), comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene; and/or an expression level of transcription factor E3 (TFE3) is characterized by a nucleus to cytoplasm expression ratio which is equal to or higher than 1 as determined by an immunostaining assay.

According to some embodiments of the invention, the isolated primate (e.g., human) naive PSC of some embodiments of the invention, being in a pluripotent state, wherein when the isolated naive PSC is incubated in the presence of an agent selected from the group consisting of Bone morphogenetic protein 4 (BMP4), JNK inhibitor, and P38 inhibitor, the naive PSC remains in the pluripotent state, and maintains a pluripotent phenotype.

According to some embodiments of the invention, the primate (e.g., human) naive PSC is characterized by reduced methylation of CpG islands as compared to a level of methylation of the CpG islands in a primate (e.g., human) primed PSC.

According to an aspect of some embodiments of the present invention there is provided an isolated population of naive PSCs comprising at least 10% of the isolated primate (e.g., human) naive PSC cells of some embodiments of the invention.

According to an aspect of some embodiments of the present invention there is provided a cell culture comprising the isolated naive PSC of some embodiments of the invention, or the isolated population of naive PSCs of some embodiments of the invention and a culture medium.

According to some embodiments of the invention, the culture medium is capable of maintaining the naive PSC in an undifferentiated and pluripotent state for at least 10 passages.

According to an aspect of some embodiments of the present invention there is provided a culture medium comprising an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor.

According to an aspect of some embodiments of the present invention there is provided a culture medium comprising an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor.

According to some embodiments of the invention the STAT3 activator is selected from the group consisting of leukemia inhibitory factor (LIF) and interleukin 6 (IL6).

According to some embodiments of the invention the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix1294, and stem cell factor (SCF).

According to some embodiments of the invention the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix1294, and stem cell factor (SCF).

According to some embodiments of the invention, the STAT3 activator comprises the LIF, and wherein the at least one agent comprises the PKC inhibitor.

According to some embodiments of the invention, the STAT3 activator comprises the LIF, and wherein the at least one agent comprises the TGFβ1 and the protein kinase C inhibitor.

According to some embodiments of the invention, the culture medium further comprises an FGFR inhibitor.

According to some embodiments of the invention, the culture medium further comprises TGFR inhibitor.

According to some embodiments of the invention, the STAT3 activator comprises the LIF and wherein the at least one agent comprises the TGFβ1 and the protein kinase C inhibitor.

According to some embodiments of the invention, the culture medium further comprises an FGFR inhibitor.

According to some embodiments of the invention, the STAT3 activator comprises the LIF, and wherein the at least one agent comprises the bFGF and the TGFβ1.

According to some embodiments of the invention, the culture medium further comprises a ROCK inhibitor.

According to some embodiments of the invention, the culture medium further comprises a protein kinase C inhibitor.

According to some embodiments of the invention, the STAT3 activator comprises the LIF and wherein the at least one agent comprises the bFGF, the ROCK inhibitor, a bone morphogenetic protein (BMP) inhibitor, the NOTCH inhibitor, and a transforming growth factor receptor (TGFR) inhibitor.

According to some embodiments of the invention, the culture medium further comprises a Sonic Hedgehog pathway (SHH) inhibitor.

According to some embodiments of the invention, the STAT3 activator comprises the LIF and wherein the at least one agent comprises the NOTCH inhibitor, and a fibroblast growth factor receptor (FGFR) inhibitor.

According to some embodiments of the invention, the culture medium further comprises an agent selected from the group consisting of insulin-like growth factor II (IGFII), stem cell factor (SCF) and transforming growth factor beta 1 (TGFβ1).

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the culture medium of some embodiments of the invention further comprises an FGFR inhibitor.

According to some embodiments of the invention, the culture medium of some embodiments of the invention further comprises a TGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, TGFβ1 and a protein kinase C inhibitor.

According to some embodiments of the invention, the culture medium of some embodiments of the invention further comprises a FGFR inhibitor.

According to an aspect of some embodiments of the present invention there is provided a culture medium comprising leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the culture medium of some embodiments of the invention further comprises a ROCK inhibitor.

According to some embodiments of the invention, the culture medium of some embodiments of the invention further comprises a protein kinase C inhibitor.

According to some embodiments of the invention, the culture medium of some embodiments of the invention further comprising a factor selected from the group consisting of: bone morphogenetic protein 4 (BMP4), IGF1, IGFII, Forskolin, FGFR inhibitor, TGFR inhibitor, Kenpaullone, BayK8644, Bix1294, and stem cell factor (SCF).

According to some embodiments of the invention, the culture medium of some embodiments of the invention further comprising BMP type I receptors (ALK2,3,6) inhibitor.

According to some embodiments of the invention, the culture medium of some embodiments of the invention further comprises ascorbic Acid.

According to some embodiments of the invention, the culture medium of some embodiments of the invention further comprises oleic Acid.

According to some embodiments of the invention, the culture medium of some embodiments of the invention further comprises Linoleic Acid.

According to some embodiments of the invention, the culture medium of some embodiments of the invention further comprises Pipecolic Acid.

According to some embodiments of the invention, the culture medium of some embodiments of the invention being devoid of animal serum.

According to some embodiments of the invention, the culture medium of some embodiments of the invention further comprises serum replacement.

According to an aspect of some embodiments of the present invention there is provided a cell culture comprising cells and the culture medium of some embodiments of the invention.

According to some embodiments of the invention, the culture medium is capable of maintaining naive pluripotent stem cell in an undifferentiated state for at least 2 passages.

According to an aspect of some embodiments of the present invention there is provided a method of generating a naive pluripotent stem cell (PSC), comprising incubating a non-naive PSC cell under conditions which allow generation of the naive PSC from the non-naive PSC, wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, and/or an expression level of transcription factor E3 (TFE3) in the naive PSC is characterized by a nucleus to cytoplasm expression ratio which is equal to or higher than 1 as determined by an immunostaining assay, thereby generating the naive PSC.

According to some embodiments of the invention, the PSC is a primate PSC.

According to some embodiments of the invention, the PSC is a human PSC.

According to some embodiments of the invention, the conditions comprise the culture medium of some embodiments of the invention.

According to some embodiments of the invention, the conditions comprise hypoxia.

According to some embodiments of the invention, the conditions comprise a culture medium comprising an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor, wherein the STAT3 activator is selected from the group consisting of leukemia inhibitory factor (LIF) and interleukin 6 (IL6).

According to some embodiments of the invention, the conditions comprise a culture medium comprising an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor, wherein the STAT3 activator is selected from the group consisting of leukemia inhibitory factor (LIF) and interleukin 6 (IL6).

According to some embodiments of the invention, the conditions comprise a culture medium which further comprises at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix1294, and stem cell factor (SCF).

According to some embodiments of the invention, the conditions comprise a culture medium which further comprises at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix1294, and stem cell factor (SCF).

According to some embodiments of the invention, the conditions include a culture medium which comprises leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the conditions include a culture medium which comprises leukemia inhibitor factor (LIF), an ERK1/2 inhibitor, a GSK3b inhibitor, a p38 inhibitor, and a JNK inhibitor.

According to some embodiments of the invention, the conditions include a culture medium which comprises leukemia inhibitor factor (LIF), an ERK1/2 inhibitor, a GSK3b inhibitor, a p38 inhibitor, a JNK inhibitor, and a BMP inhibitor.

According to some embodiments of the invention, the culture medium further comprises FGFR inhibitor.

According to some embodiments of the invention, the culture medium further comprises TGFR inhibitor.

According to some embodiments of the invention, the conditions include a culture medium which comprises leukemia inhibitor factor (LIF), an ERK1/2 inhibitor, a GSK3b inhibitor, a p38 inhibitor, a JNK inhibitor, TGFβ1 and a protein kinase C inhibitor.

According to some embodiments of the invention, the culture medium further comprises FGFRi.

According to some embodiments of the invention, the conditions include a culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the culture medium further comprises a ROCK inhibitor.

According to some embodiments of the invention, the culture medium further comprises a protein kinase C inhibitor.

According to some embodiments of the invention, the culture medium further comprises a factor selected from the group consisting of: bone morphogenetic protein 4 (BMP4), IGF1, IGFII, Forskolin, FGFR inhibitor, TGFR inhibitor, Kenpaullone, BayK8644, Bix1294, and stem cell factor (SCF).

According to some embodiments of the invention, the culture medium further comprises an ascorbic acid.

According to some embodiments of the invention, the culture medium further comprises an oleic Acid.

According to some embodiments of the invention, the culture medium further comprises a Linoleic Acid.

According to some embodiments of the invention, the culture medium further comprises a Pipecolic Acid.

According to some embodiments of the invention, the culture medium being devoid of animal serum.

According to some embodiments of the invention, the culture medium further comprises serum replacement.

According to some embodiments of the invention, the culture medium further comprises an MBD3 inhibitor.

According to some embodiments of the invention, the culture medium further comprises a chromodomain helicase DNA binding protein 4 (CHD4) inhibitor.

According to some embodiments of the invention, the culture medium further comprises P66 alpha coiled-coil domain.

According to some embodiments of the invention, the non-naive PSC is selected from the group consisting of a primed PSC, a blastocyst, an induced pluripotent stem cell (iPSC) and a somatic cell.

According to some embodiments of the invention, wherein when the non-naive PSC comprises a somatic cell then the method further comprising subjecting the somatic cell to de-differentiation conditions, to thereby obtain an induced pluripotent stem cell.

According to some embodiments of the invention, the de-differentiation conditions comprise expressing within the somatic cell at least two growth factors selected from the group consisting of Oct4, Sox2, Klf4 and c-Myc.

According to an aspect of some embodiments of the present invention there is provided a method of improving generation of induced pluripotent stem cells (iPSCs) from a somatic cell, comprising:

(a) expressing within the somatic cell at least two growth factors selected from the group consisting of Oct4, Sox2, Klf4 and c-Myc; and (b) inhibiting Mbd3 expression and/or activity in the somatic cell, thereby improving generation of the iPSCs from a somatic cell.

According to some embodiments of the invention, inhibiting Mbd3 activity is performed by inhibiting binding of the Mbd3 to the nucleosome remodeling and deacetylase (NuRD) complex.

According to some embodiments of the invention, inhibiting the binding of the Mbd3 to the NuRD complex is performed using a chromodomain helicase DNA binding protein 4 (CHD4) inhibitor.

According to some embodiments of the invention, inhibiting the binding of the Mbd3 to the NuRD complex is performed using a P66 alpha coiled-coil domain.

According to some embodiments of the invention, inhibiting the Mbd3 expression is performed using a protein kinase C (PKC) inhibitor.

According to some embodiments of the invention, the method further comprising exogenously expressing embryonic stem (ES) cell expressed Ras (ERAS) coding sequence or activating endogenous expression of the ERAS in the somatic cell.

According to some embodiments of the invention, expressing is effected for at least 48 hours such that the inhibiting the Mbd3 is effected to 10-30% of a level of the Mbd3 prior to the expressing.

According to some embodiments of the invention, expressing is effected for about 48 hours and the inhibiting is effected after the about 48 hours.

According to some embodiments of the invention, the iPSC is a murine iPSC.

According to some embodiments of the invention, the method of some embodiments of the invention, further comprising culturing the murine iPSC in a medium which comprises LIF, an ERK1/2 inhibitor, and a GSK3b inhibitor.

According to some embodiments of the invention, wherein when the iPSC is a primate (e.g., human) iPSC, the method further comprises: (c) culturing the primate (e.g., human) iPSC in a culture medium which comprises LIF, an ERK1/2 inhibitor, a GSK3b inhibitor, a P38 inhibitor, a JNK inhibitor, basic fibroblast growth factor (bFGF) and transforming growth factor-beta 1 (TGFβ1).

According to some embodiments of the invention, the medium further comprises a ROCK inhibitor.

According to some embodiments of the invention, wherein step (c) is performed following about 48 hours from the expressing of step (a).

According to some embodiments of the invention, expressing is performed using DNA transfection of the growth factors.

According to some embodiments of the invention, expressing is performed using RNA transfection of the growth factors.

According to some embodiments of the invention, expressing is performed using protein transfection of the growth factors.

According to some embodiments of the invention, the PSC is selected from the group consisting of embryonic stem cell (ESC), induced pluripotent stem cells (iPSCs), and embryonic germ cell (EGC).

According to some embodiments of the invention, the naive PSC expresses XIST.

According to some embodiments of the invention, the naive PSC is devoid of XIST bodies.

According to some embodiments of the invention, the naive ESC is capable of X-inactivation when induced to differentiate.

According to some embodiments of the invention, the naive PSC is capable to differentiate into the endodermal, mesodermal and ectodermal embryonic germ layers.

According to some embodiments of the invention, the naive PSC is capable of being maintained in the undifferentiated and pluripotent state for more than 20 passages in culture.

According to some embodiments of the invention, the naive PSC expresses a lower level of MHC class I as compared to a primed PSC under identical detection assay conditions, and wherein the primed PSC exhibits one methylated and one unmethylated allele of XIST, expresses XIST, exhibits XIST bodies and exhibits a H3K27me3/polycomb focus.

According to some embodiments of the invention, the naive PSC is characterized by at least 10% more RNA polymerase II pausing on chromosomes as compared to a primed PSC under identical assay conditions, and wherein the primed PSC exhibits one methylated and one unmethylated allele of XIST, expresses XIST, exhibits XIST bodies and exhibits a H3K27me3/polycomb focus.

According to some embodiments of the invention, the isolated naive PSC has an inhibited p38 pathway as compared to a primed PSC.

According to some embodiments of the invention, the isolated naive PSC has an inhibited JNK pathway as compared to a primed PSC.

According to some embodiments of the invention, the isolated naive PSC has an inhibited ROCK pathway as compared to a primed PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), Albumax I, LIF, ERK1/2 inhibitor, GSK3b inhibitor, p38 inhibitor, JNK inhibitor and a protein kinase C inhibitor, thereby generating the naive PSC.

According to some embodiments of the invention, the culture medium further comprises FGFR inhibitor.

According to some embodiments of the invention, the culture medium further comprises TGFR inhibitor.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), Albumax I (Invitrogen), LIF, TGFβ1, ERK1/2 inhibitor, GSK3b inhibitor, p38 inhibitor, JNK inhibitor and a protein kinase C inhibitor, thereby generating the naive PSC.

According to some embodiments of the invention, the culture medium further comprises FGFRi.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), Albumax I (Invitrogen), LIF, bFGF, TGFβ1, ERK1/2 inhibitor, GSK3b inhibitor, p38 inhibitor, and JNK inhibitor, thereby generating the naive PSC.

According to an aspect of some embodiments of the present invention there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), defined lipid concentrate (Gibco), LIF, bFGF, TGFβ1, ERK1/2 inhibitor, GSK3b inhibitor, p38 inhibitor, JNK inhibitor, and an MBD3 inhibitor, thereby generating the naive PSC.

According to an aspect of some embodiments of the present invention there is provided an isolated naive pluripotent stem cell obtainable by the method of some embodiments of the invention.

According to some embodiments of the invention, the naive pluripotent stem cell comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

According to an aspect of some embodiments of the invention, there is provided a method of generating differentiated cells, comprising subjecting the naive pluripotent stem cells generated according to some embodiments of the invention, or the isolated naive pluripotent stem cells of some embodiments of the invention to differentiation conditions, thereby generating differentiated cells.

According to an aspect of some embodiments of the invention, there is provided a method of generating a primordial germ cell, comprising culturing a primate (e.g., human) naive pluripotent stem cell in a culture medium selected capable of inducing the primate naive pluripotent stem cells into primordial germ cell, wherein the culture medium comprises a Rho kinase (ROCK) inhibitor and bone morphogenetic protein 4 (BMP4), thereby generating the primordial germ cell.

According to some embodiments of the invention, the primate naive pluripotent stem cell comprises:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

According to some embodiments of the invention, the primordial germ cell is characterized by CD61 (intergrin beta 3) expression pattern.

According to some embodiments of the invention, the primordial germ cell is characterized by CD61$^+$/SSEA4$^+$ expression pattern.

According to some embodiments of the invention, the culture medium used by the method of generating primordial germ cell further comprises at least one agent selected from the group consisting of: leukemia inhibitory factor (LIF), Stem Cell Factor (SCF) and Epidermal Growth Factor (EGF).

According to an aspect of some embodiments of the invention, there is provided an isolated population of primate primordial germ cells comprising primate primordial germ cells generated according to the method of some embodiments of the invention.

According to some embodiments of the invention, the isolated population of primate primordial germ cells comprising at least 50% of primordial germ cells characterized by CD61$^+$/SSEA4$^+$ expression pattern.

According to some embodiments of the invention, there is provided a method of treating a subject in need thereof, comprising administering the primordial germ cells of some embodiments of the invention to a gonad tissue of the subject, thereby treating the subject in need thereof.

According to some embodiments of the invention, the subject suffers from infertility.

According to an aspect of some embodiments of the invention, there is provided a kit comprising the primate primordial germ cells of some embodiments of the invention and a medicament for treating infertility.

According to an aspect of some embodiments of the invention, there is provided a method of generating a chimeric animal, comprising introducing the isolated naive primate (e.g., human) PSC of some embodiments of the invention, or the primordial germ cells of some embodiments of the invention into a pre-implantation embryo of a host animal, thereby generating the chimeric animal.

According to some embodiments of the invention, the method further comprising allowing said pre-implantation embryo to grow ex vivo or in vivo.

According to some embodiments of the invention, the introducing is performed in vivo.

According to some embodiments of the invention, the introducing is performed in vitro or ex vivo.

According to some embodiments of the invention, the pre-implantation embryo comprises at least 4 cells.

According to some embodiments of the invention, the pre-implantation embryo comprises no more than 128 cells.

According to some embodiments of the invention, the host animal is a mouse.

According to some embodiments of the invention, the isolated naïve PSC or the primordial germ cell is allogeneic to the host animal.

According to some embodiments of the invention, the isolated naïve PSC or the primordial germ cell is xenogeneic to the host animal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 3G:
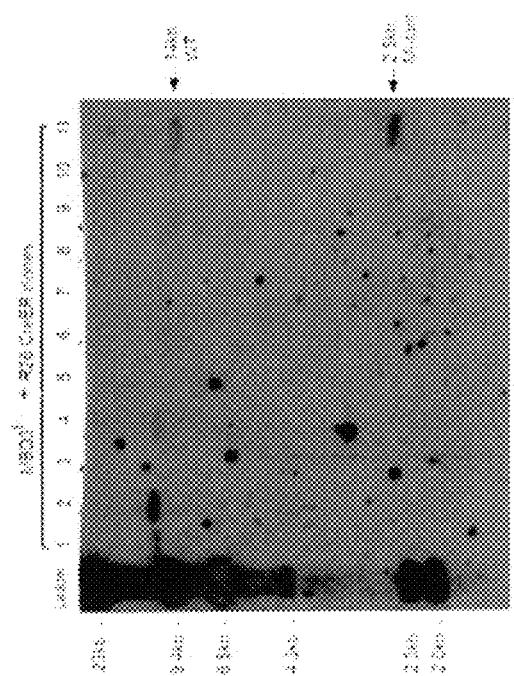

FIGS. 1A-N show that Mbd3 inhibition boosts epigenetic reversion of mouse primed pluripotent cells to naive pluripotency. FIGS. 1A-B: An siRNA screen for factors that can boost epigenetic reversion of primed EpiSCs into naive ESCs. Nanog-GFP mouse EpiSCs were used for the screening, and Nanog-GFP reactivation is used as a specific marker for naive pluripotency formation after expansion in 2i/LIF conditions. FIG. 1A: Schematic illustration depicting the siRNA screen. FIG. 1B: A histogram depicting percentage of Nanog-GFP expressing cells as a result of inhibition with the tested siRNAs. Note that Mbd3 inhibition led to a dramatic increased in EpiSC reprogramming into naive ESCs. FIGS. 1C-G: Mbd3$^{+/+}$ and Mbd3$^{flox/-}$ EpiSCs were tested for reversion into naive cells in 2i/LIF. FIG. 1C: Schematic illustration of the reversion assay from EpiSCs into Naive ES-like colonies. FIGS. 1D-G: Microscopy photographs depicting formation of naive ES-like colonies from Mbd3$^{+/+}$ EpiSCs (FIG. 1D) or Mbd3$^{flox/-}$ EpiSCs (FIG. 1E). Note the dramatically increased reprogramming efficiency in Mbd3 depleted cells. FIGS. 1F-G: Mbd3$^{flox/-}$ Rosa26-CreER$^{+/-}$ Nanog-GFP$^{+/-}$ cells are shown under phase microscopy (FIG. 1F) and fluorescence microscopy (FIG. 1G). Note the homogenous reactivation of Nanog-GFP marker (FIG. 1G). FIG. 1H: Single cell cloning efficiency and quantification for EpiSC reprogramming efficiency into naive ESCs from different mutant lines. Notably, pBRY-Mbd3 rescue constructs stably expressed in the indicated lines, reduced reprogramming efficiency back to those observed in Mbd3$^{+/+}$ WT cells. Shown is a histogram depicting average percentage of Nanog-GFP$^{+}$ cells following the reversion of the various mutant lines towards naive cells in 2i/LIF conditions. FIGS. 1I-J are Western blot analyses indicating Mbd3 expression levels in different mutant ES lines. Mbd3$^{flox/-}$ cells had over 80% reduction in Mbd3 expression levels in comparison to Mbd3$^{+/+}$ cells. Mbd3$^{-/-}$ cells has complete absence of Mbd3 protein. FIGS. 1K-L are photographs of Agouti colored chimeras obtained from reprogrammed EpiSCs following Mbd3 depletion. Shown are two examples of chimeric mice generated after microinjection of reverted cells into naive pluripotency. The agouti coat color originates from the injected cells, while black coat color originates from the host mouse. These results indicated that the reverted cells are functionally pluripotent as naive cells and can give rise to differentiated cells upon differentiation in vivo. FIG. 1M is a schematic illustration depicting generation of chimeras for the purpose of isolating day E8.5 PGCs. Mbd3$^{flox/-}$ and Mbd3$^{+/+}$ ESC lines (with or without Mbd3 overexpression pBRY-Mbd3 rescue allele, as indicated) were targeted with Oct4-GFP reporter and injected into host chimeras. FIG. 1N—a histogram depicting evaluation of generation of naive ES-like cells from PGCs. Day E8.5 primordial germ cells (PGCs) were sorted into naive conditions [N2B27 and 2i/LIF/SCF (Stem Cell Factor, 10 ng/ml)/bFGF (basic fibroblast growth factor, 8 ng/ml)] and evaluated for efficiency to generate ES-like embryonic germ cells (EG cells). Mbd3 depleted PGCs convert ex vivo into naive ES-like cells with efficiency nearing 100%.

FIGS. 1O-T are images depicting confocal immunostaining analysis for temporal Mbd3 expression in developing mouse embryos. FIG. 1O—zygote stage; FIG. 1P—2 cell stage; FIG. 1Q—8 cell stage; FIG. 1R—Morula stage; FIG. 1S—Blastocyst at embryonic day 3.25; FIG. 1T—Blastocyst at embryonic day 3.75. Arrows indicate polar body. Note the reduction in Mbd3 expression after fertilization, and how it gets re-expressed at the late blastocyst stage. Right panels represent enlargement of the highlighted dashed areas.

FIGS. 2A-O show derivation of ESCs from Mbd3 blastocysts. FIG. 2A—a schematic illustration of generation of naive mouse ESCs. Mbd3$^{+/-}$ heterozygous mice were mated, and ESCs were derived from blastocysts in naive defined 2i/LIF conditions. Mbd3$^{-/-}$ ESCs were obtained at expected Mendelian ratio. FIGS. 2B-C are images of the Mbd3$^{-/-}$ ES cells initial colony at day 9 (FIG. 2B) and of the naive Mbd3$^{-/-}$ ESCs established and imaged at passage 4 (FIG. 2C), showing ES like morphology. FIGS. 2D-E—Images of MBD3 wild type (+/+) and depleted (-/-) ESCs stained for alkaline phosphatase (AP) pluripotent stem cells marker. Note the significant AP staining in the MBD3$^{-/-}$ ESCs demonstrating they normally express stem cell markers. FIGS. 2F-G—images of immuno-staining for Oct4 of MBD3$^{+/-}$ (heterozygotes) (FIG. 2F) and MBD3$^{-/-}$ (depleted) (FIG. 2G). These results indicate that Mbd3 is dispensable for establishing pluripotency in vivo and in vitro, and that Mbd3 depleted ES cells are indistinguishable from wild type ES and iPS cells. FIGS. 2H-O are Western blot analyses for pluripotency markers of MBD3 wild type (+/+) or depleted (-/-) ESCs. FIG. 2H—Mbd3; FIG. 2I—Gapdh; FIG. 2J—Sox2; FIG. 2K—Sall4; FIG. 2L—Klf4; FIG. 2M—Mi2β; FIG. 2N—Klf5; FIG. 2O—c-Myc.

FIGS. 3A-G depict genetically engineered systems for deterministic reprogramming in mouse cells. FIG. 3A—The present inventors have established a reprogrammable mouse Mbd3$^{+/+}$ and Mbd3$^{flox/-}$ iPSC lines carrying (1) an Oct4-GFP reporter, (2) mCherry constitutively expressed marker, (3) m2RtTa and (4) a TetO inducible OKSM polycistronic cassette. These lines were injected into host blastocysts, and their differentiated derivatives were re-isolated in vitro. Subsequently, reprogramming efficiency and progression can be analyzed following DOX induction. This exact system allows 6 day 100% reprogramming as shown in FIGS. 4A-O. Further, this transgenic system allows non-restricted derivation of homogenous somatic cells, which will be harvested every 24 hours during the 7-day course of iPSC completion following DOX treatment. FIGS. 3B-D—photographs of isolated Mbd3$^{flox/-}$ ESCs at phase contrast (FIG. 3B), and fluorescence microscopy. FIG. 3C—staining for mCherry expression (red); FIG. 3D—staining for Oct4-GFP expression (green). FIGS. 3E-F—Western blot analyses using anti-Mbd3$^{-/-}$ (FIG. 3E) and anti Hsp90 (FIG. 3F) staining. Show is Mbd3 expression in Mbd3$^{-/-}$ ESCs/iPSCs, with or without addition of pBRY-Mbd3 rescue transgene (recovery clones). FIG. 3G—Southern blot analysis showing correct gene targeting of the Rosa26 locus with Cre-ER knock in construct introduced into Mbd3$^{flox/-}$ ESCs. Altogether, the results show genetically engineered systems for deterministic reprogramming in mouse cells.

FIGS. 4A-P show deterministic and synchronized reprogramming of mouse fibroblasts into iPSCs following Mbd3 depletion. FIG. 4A—Mbd3 WT and depleted (flox/- or -/-) cells were directly infected with lentiviruses expressing a polycistronic OKSM cassette, and expanded in mouse naive 2i/LIF conditions. Reprogramming efficiency was evaluated by measuring percentage of Oct4-GFP$^{+}$ cells, and it was noted that of >95% Oct4-GFP$^{+}$ levels was observed in Mbd3 depleted cells. FIG. 4B—Secondary reprogrammable fibroblasts, carrying an Oct4-GFP reporter and a mCherry constitutively expressed marker, were single cell sorted and subjected to DOX reprogramming. Reprogramming efficiency at day 10 was calculated by dividing the number of Oct4-GFP+ wells by mCherry+ wells (mCherry was used to normalize for plating efficiency). The 2i/LIF conditions were applied starting from day 2. Please note that in Mbd3 depleted samples (flox/- or -/-) all mcherry+ clones became Oct4-GFP$^{+}$ cells (indicated as green). Only Mbd3$^{+/+}$ samples had mCherry+ clonal populations that did not turn on the specific pluripotency marker Oct4-GFP (and thus indicated as red colored boxes). FIGS. 4C-E depict immunostaining analyses of the Mbd3$^{+/+}$ iPSC (FIG. 4C), the Mbd3$^{flox/-}$ iPSC (FIG. 4D) or the Mbd3$^{-/-}$ iPSC (FIG. 4E) clones for the Oct4 (left), Nanog (middle) or Alkaline Phosphatase (AP) (right) pluripotency markers. Note that iPSCs obtained following Mbd3 depletion normally express all pluripotency markers tested as in wild type Mbd3$^{+/+}$ cells. FIGS. 4F-G are photographs of Agouti coat colored chimera (FIG. 4F) and germ-line transmission from Mbd3$^{flox/-}$ iPSCs derived (FIG. 4G). This indicates that Mbd3 depleted iPSCs can give rise to adult chimeric animals following injection into host mice, and are pluripotent. FIGS. 4H-I are images depicting live imaging of reprogramming of Mbd3$^{+/+}$ (FIG. 4H) and Mdb3$^{flox/-}$ (FIG. 4I) cells, after plating 50 cells per well. Note the dramatically increased ES-like colony formation in Mbd3$^{flox/-}$ cells. FIGS. 4J-O are images depicting immunofluorescence of Mdb3$^{+/+}$ (FIGS. 4J, 4K and 4L) or Mdb3$^{flox/-}$ (FIGS. 4M, 4N and 4O) cells stained for mCherry (FIGS. 4J and 4M), Oct4-GFP (FIGS. 4K and 4N) and mCherry Oct4-GFP (FIGS. 4L and 4O). By day 6 mCherry+ and Oct4-GFP+ nearly >90% co-localize in Mbd3$^{flox/-}$ cells, and not in WT cells. FIG. 4P A graph indicating cumulative Oct4-GFP$^+$ colony formation nearing 99% in Mbd3$^{flox/-}$ cells (red graph) by day 6 based on live imaging follow-up. Note the narrow window of synchronized Oct4-GFP activation at days 4-5 (red line and blue bar).

Figures 4Q, 4R:
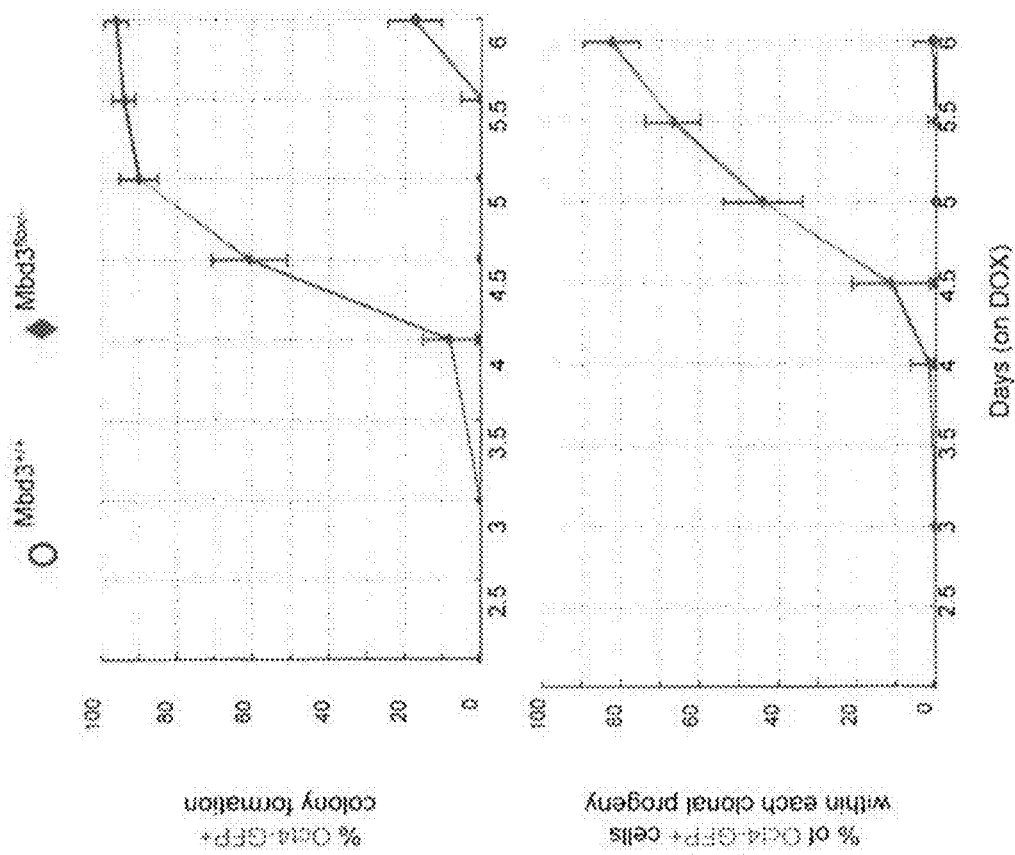

FIGS. 4Q-R depict radically efficient and synchronized iPSC reprogramming to pluripotency. FIG. 4Q—A graph indicating cumulative Oct4-GFP+ colonies for Mbd3$^{flox/-}$ (red plot) and Mbd3$^{+/+}$ (blue plot) based on live imaging follow-up. Statistics of Oct4-GFP activation were calculated from all segmented colonies. Note the narrow window of synchronized Oct4-GFP activation at days 4-5. FIG. 4R-A graph indicating the average fraction of Oct4-GFP+ cells within single colonies measured with live imaging follow-up. Approximately 85% of cells within individual Mbd3$^{flox/-}$ clonal population became Oct4-GFP$^+$ cells by day 6. Plot values indicate the mean and error bars indicate standard deviation calculated over 4 replicates (wells) in each sample and time point.

Figure 5F:
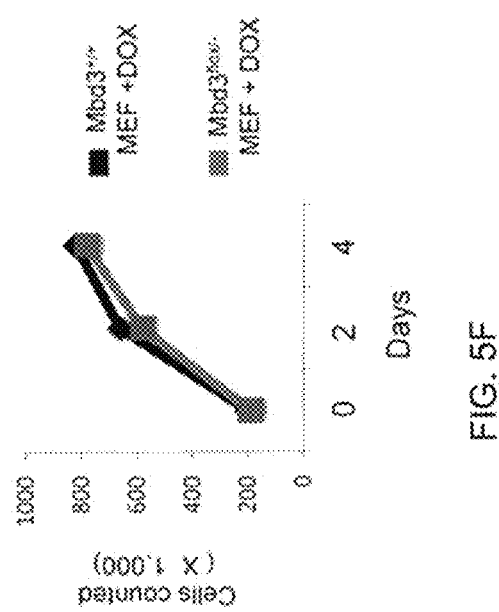

FIGS. 5A-F show comparative analysis of Mbd3 depleted somatic cell properties during reprogramming. FIG. 5A—A histogram depicting the results of RT-PCR analysis demonstrating relative transgene induction levels in different somatic cells (from BU-V19-OSKM transgenic reprogrammable systems) in the presence or absence of DOX as indicated. Results are presented with +/-s.d. (standard deviation) of 3 replicates per sample. Transgene induction level was not altered in Mbd3 depleted MEF or B cells on DOX for 8 days. FIGS. 5B-C—Western blot analysis using anti heat shock protein 90 (Hsp90) (FIG. 5B) and anti-Mbd3 (FIG. 5C) antibodies, validating Mbd3 protein reduction in NGFP1 knockdown (KD) cells. FIG. 5D—A histogram depicting the results of RT-PCR analysis demonstrating relative transgene induction levels in different somatic cells (from NGFP1 transgenic reprogrammable systems) in the presence or absence of DOX as indicated. Results are presented with +/-s.d. of 3 replicates per sample. Transgene induction level was not altered in Mbd3 depleted MEF (mouse embryonic fibroblasts) or B cells on DOX for 8 days. FIG. 5E is a histogram depicting the results of a flow cytometry based detection of apoptosis in wild type and Mbd3 depleted MEFs and B cells following DOX induction. The results indicate that apoptosis levels were similar upon transgene induction in both cell samples. Overall, the results presented in FIGS. 5A-E exclude changes or defects in transgene induction or proliferation as underlying causes for enhanced reprogramming in Mbd3 depleted somatic cells.

FIG. 5F A similar growth kinetics was observed in Mbd3$^{+/+}$ and Mbd3$^{flox/-}$ MEFs upon DOX mediated transgene induction. One representative experiment is shown out of 2 performed. Overall, the results presented in FIGS. 5A-E exclude changes in transgene induction or proliferation as predominant causes for enhanced reprogramming in Mbd3 depleted somatic cells.

Figure 6A:
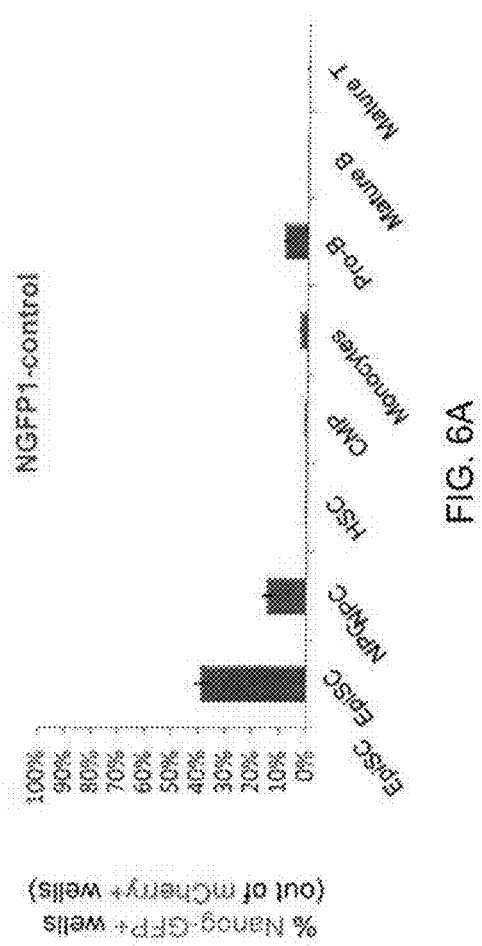
Figure 6B:
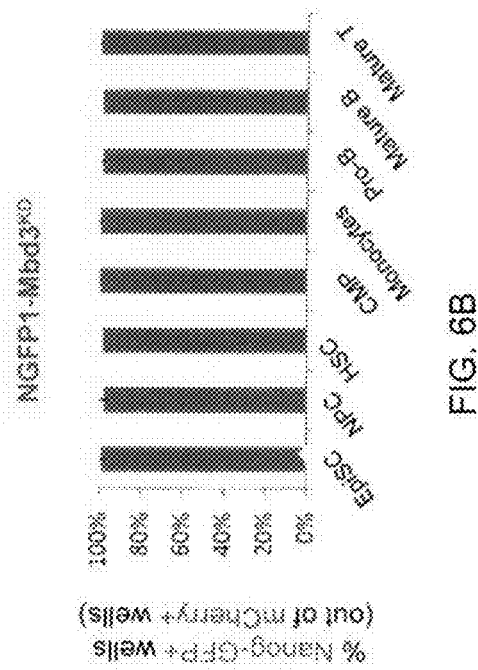

FIGS. 6A-B show that Mbd3 deletion renders deterministic and complete reprogramming of multiple adult somatic cell types. Indicated somatic cells from NGFP1-control (FIG. 6A), NGFP1-Mbd3$^{KD}$ [knockdown (KD)] (FIG. 6B) adult chimeras were isolated and subjected to single cell reprogramming and evaluation of Nanog-GFP expression after 8 days of DOX. "EpiSC" Epiblast stem cells; "NPC"— Neural precursors; "HSC"—Hematopoietic Stem Cell; "CMP"—Common Myeloid progenitor; "Monocytes"— blood cells macrophages; "Pro-B lymphocytes"; "Mature B"—mature B lymphocytes; "Mature T"—mature T cells. Near 100% efficiency was obtained from all Mbd3$^{flox/-}$ (Mbd3-depleted) somatic cell types tested. Average of 2-3 independent experiments per each cell type is shown.

Figure 7:
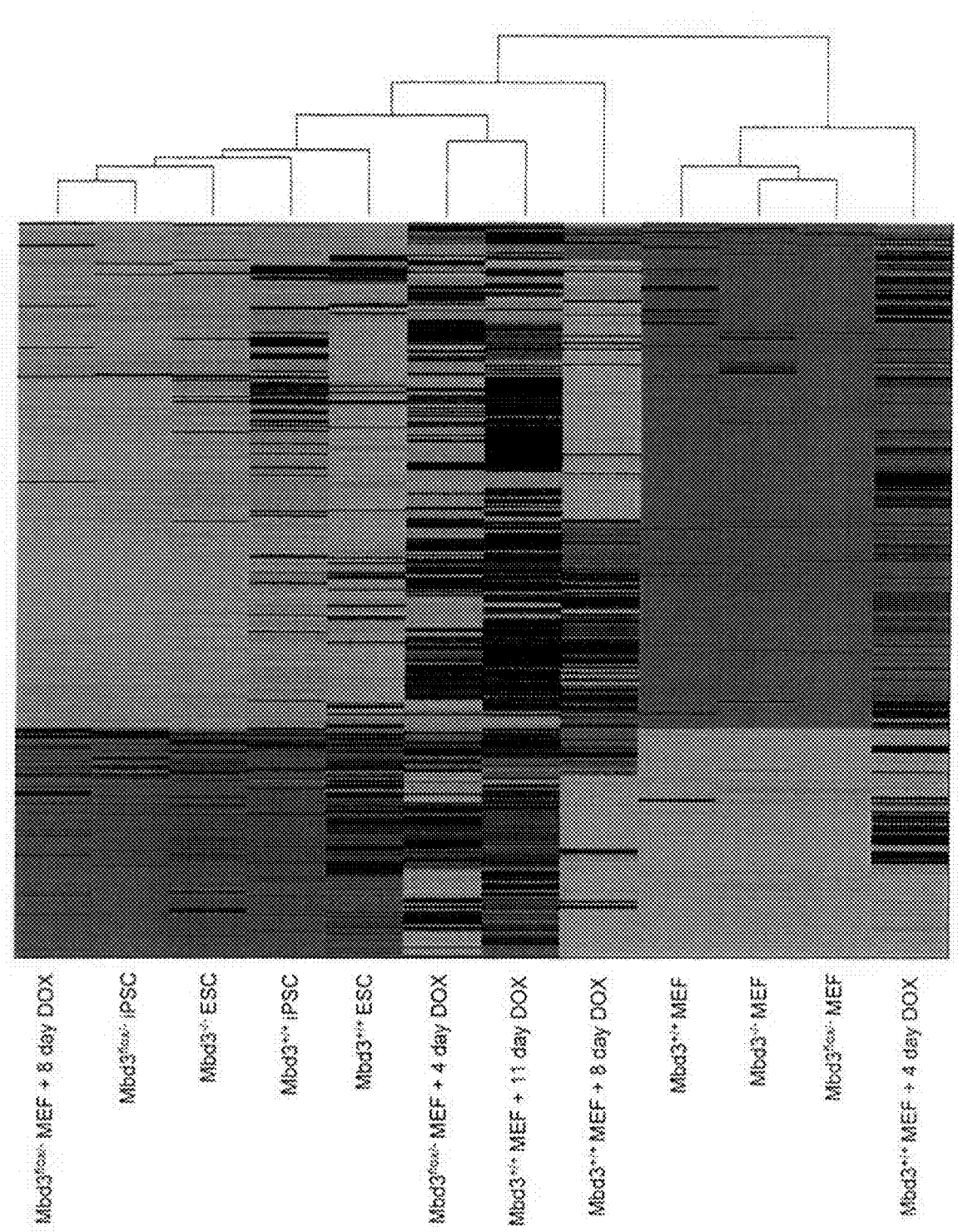

FIG. 7 shows that Mbd3 depleted cells are completely reprogrammed and transcriptionally indistinguishable from ESCs/iPSCs by 8 days of DOX induction. Gene expression analysis was conducted on the indicated genetically matched mouse samples. Mbd3$^{flox/-}$, but not Mbd3$^{+/+}$, MEFs clustered differently from donor somatic MEFs only after 4 days of OKSM (DOX) induction. By day 8, flox/- cells were transcriptionally indistinguishable from established ESCs and iPSCs line. Mbd3$^{+/+}$ population even after 11 days of longer reprogramming did not cluster with pluripotent ESCs-iPSC lines. These findings support complete reprogramming in donor somatic cells following OSKM overexpression together with Mbd3 inhibition.

Figure 8O:
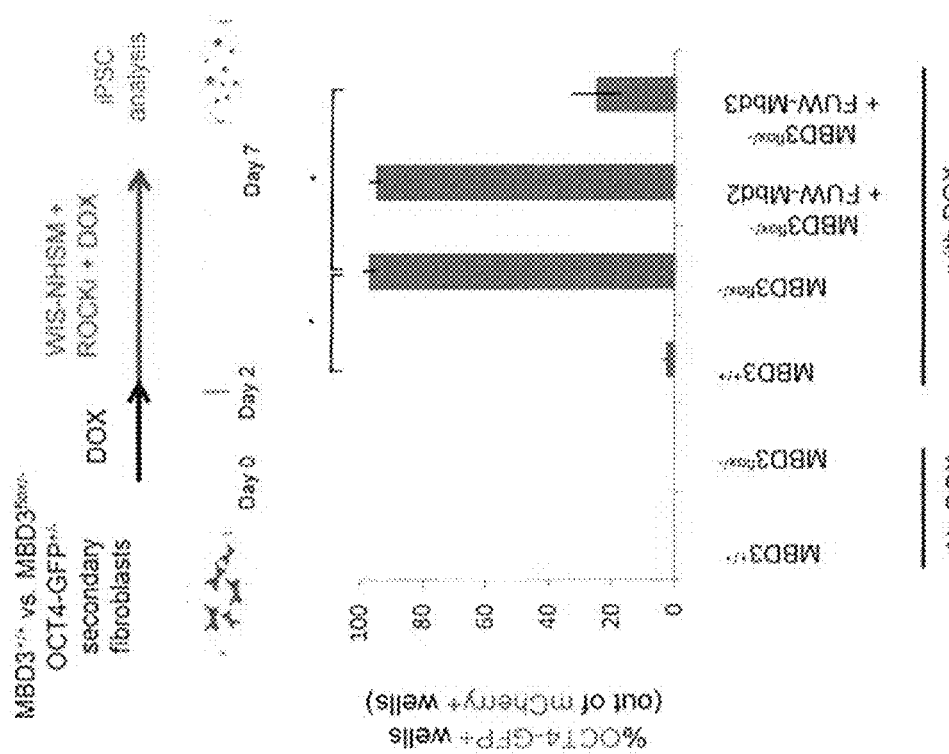

FIGS. 8A-Q show deterministic and synchronized reprogramming following Mbd3 depletion in mouse and human cells. FIGS. 8A-D Images of Mbd3$^{flox/-}$ (FIGS. 8A and 8C) and Mbd3$^{+/+}$ cells at day 8 (FIGS. 8A and 8B) or at passage 2 (FIGS. 8C and 8D). Note that colonies obtained following Mbd3$^{flox/-}$ somatic cell reprogramming have ESC-like morphology and become GFP homogenous for Nanog expression at passage 1. In WT cells, most colonies are not fully reprogrammed and do not have ES-like morphology. FIG. 8E A histogram depicting quantification of Nanog-GFP positive cells. By quantifying amount of Nanog-GFP positive cells at time of detection (day 8 for Mbd3-KD cells), it is notable that >99% of cells within each clonal population at day 8 in Mbd3 KD cells are positive. For other reprogramming combinations shown, when a clonal population becomes positive (above 0.5% threshold set), a minority of cells turns on Nanog-GFP, indicating that only a fraction of the clone successfully reprogrammed. These findings support deterministic and synchronized completion of reprogramming by inhibition of Mbd3 expression and function in naive pluripotency promoting growth conditions. FIGS. 8F-K show flow cytometry analyses of a partially reprogrammed cell clone containing OSKM transgenes, without reactivation of the Oct4-GFP reporter following treatment with: FIG. 8F—untreated; FIG. 8G—scrambled siRNA day 20; FIG. 8H—untreated day 20; FIG. 8I—5-aza+TSA Day 20; FIG. 8J—Mbd3 siRNA Day 5; FIG. 8K—Mbd3 siRNA Day 6. Mbd3 knockdown resulted in complete and rapid completion of reprogramming. 4-Aza and TSA treatment, previously reported to promote reprogramming, only activates a fraction of the cells. These results demonstrate that Mbd3 elimination potently opens the gateway of reprogramming to pluripotency. FIG. 8L—Mbd3$^{flox/-}$ human ES cells were generated by genetic engineering with TALE nuclease effectors. Targeting strategy for a floxed conditional allele is shown. FIGS. 8M-N—Western blot analyses of correctly targeted MBD3$^{flox/-}$ clone, based on southern blot verification, using anti-MBD3 antibody (FIG. 8M) or anti-HSP90 antibody (FIG. 8N). Note the over 90% reduction in MBD3 protein expression levels (comparable reduction to that seen in mouse flox/- cells FIGS. 1I-J. FIG. 8O—MBD3$^{+/+}$ and MBD3$^{flox/-}$ iPSCs carrying DOX inducible OKSM transgene were labeled with constitutively expressed mCherry and targeted with an OCT4-GFP knock-in allele. In vitro differentiated fibroblasts from the latter lines were reprogrammed as indicated in the scheme. 98-100% of human Mbd3$^{flox/-}$ fibroblasts become GFP+ IPSCs after 8 days of transgene induction. These results demonstrate a similar effect in mouse and human reprogramming for Mbd3 inhibition. Error bars indicate s.d. of 2 biological replicates. * Indicates significant P value <0.01 in comparison to MBD3$^{+/+}$ samples (n=2). FIGS. 8P-Q—Images of MBD3$^{flox/-}$ cells in WIS-NHSM medium. MBD depleted human pluripotent stem cells have a dramatic round mouse-ESC like morphology, and grow homogenously. These results indicate that Mbd3 inhibition might further improve WIS-NHSM naive growth conditions (described herein).

Figure 8S:
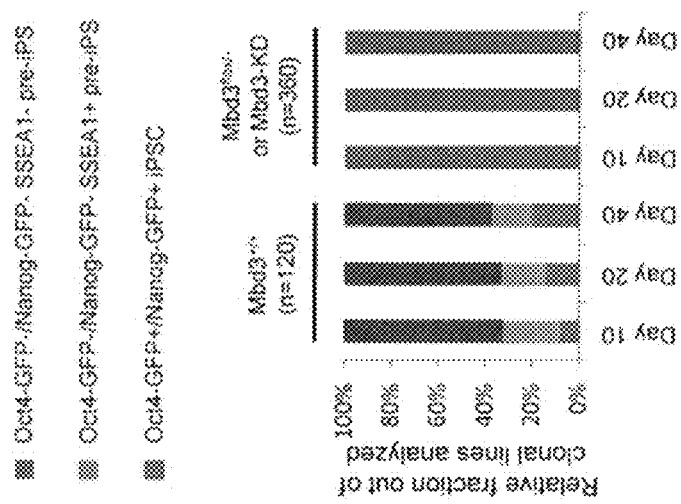
Figure 8R:
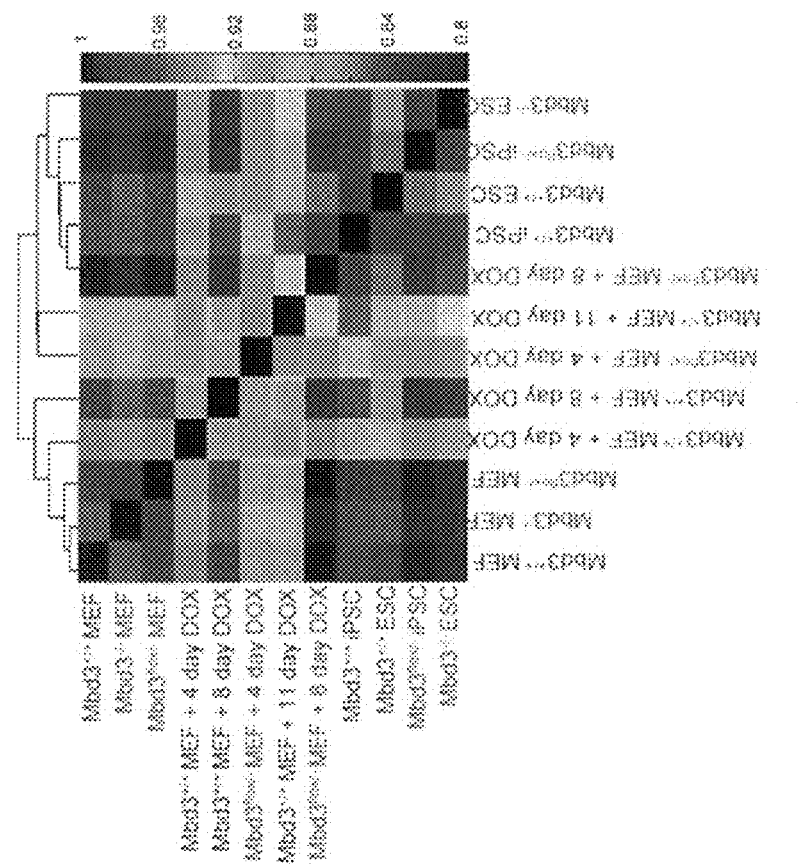

FIGS. 8R-S Alleviating Mbd3 expression facilitates transition to ground state pluripotency in mouse and human cells. FIG. 8R—Spearman correlation matrix between the indicated genetically matched mouse samples, measured over gene expression levels of all 16,620 expressed genes. The matrix is clustered with Hierarchical clustering producing the dendrogram shown. Note that after 4 days of OKSM (DOX) induction, Mbd3$^{flox/-}$ MEFs, but not Mbd3$^{+/+}$ MEFs, were more similar to established ESC and iPSC lines, than to the original somatic MEFs. By day 8, Mbd3$^{flox/-}$ cells are transcriptionally indistinguishable from ESCs and iPSCs. Mbd3$^{+/+}$ population did not cluster with ESCs and iPSCs even after 11 days of OKSM induction. FIG. 8S—Monoclonal lines established from Mbd3$^{+/+}$ and flox/- secondary cells and reprogrammed in 2i-LIF+DOX. Fraction of pre-iPS clones that did not reactivate Oct4 or Nanog GFP markers (either SSEA1 positive or negative) is shown. GFP negative clones could not be established from Mbd3 depleted cells, as they all became fully reprogrammed already by day 10.

Figure 9:
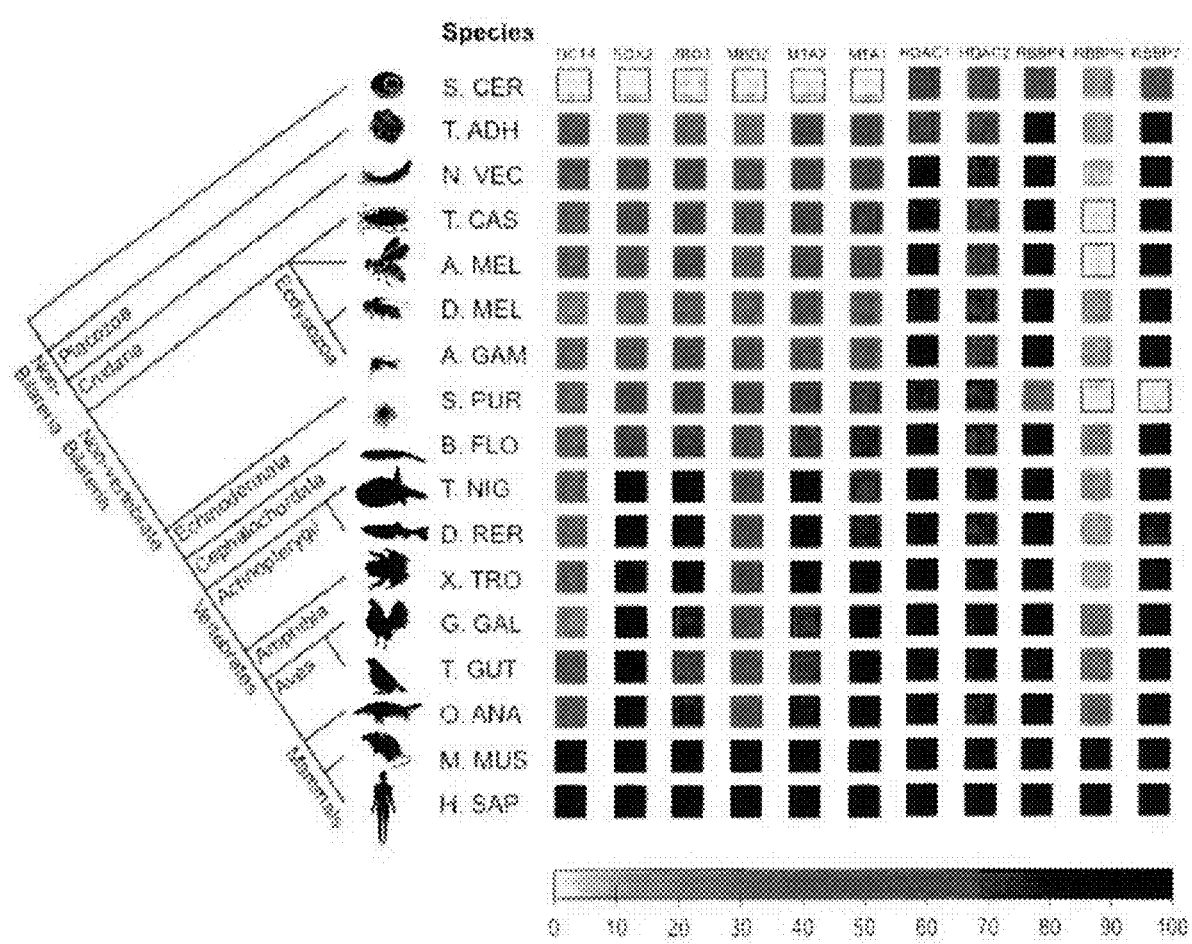

FIG. 9 is schematic presentation of evolutionary analysis of the NuRD complex and other associated proteins. The present inventors assigned orthologs for many human proteins that are either known to be part of the NuRD complex (or are related to these proteins), from 15 representative metazoan species (mouse—*M. musculus*, platypus—*O. anatinus*, zebra finch—*T. guttata*, chicken—*G. gallus*, frog—*X. tropicalis*, zebrafish—*D. rerio*, pufferfish—*T. nigroviridis*, lancelet—*B. floridae*, sea urchin—*S. purpuratus*, mosquito—*A. gambiae*, fruit fly—*D. melanogaster*, honeybee—*A. mellifera*, beetle—*T. castaneum*, sea anemone—*N. vectensis*, trichoplax—*T. adhaerens*), and the yeast *S. cerevisiae*, as an outgroup. The last metazoan in this list—*T. adhaerens*, represents a basal group of metazoan, and is used to study the origins of animal multicellularity. Proteins that have an ortholog in *T. adhaerens* were likely to be present in the basal multicellular animals, while proteins that appear in yeast precede animal multicellularity. The analysis indicates that Mbd3 and other NuRD components are conserved in all multi-cellular organisms, and thus inhibition of Mbd3 function may potentially promote direct reprogramming in many (or even all) multicellular organisms. The color scale indicates degree of homology, i.e., percentage of sequence similarity between proteins.

FIGS. 10A-P demonstrate that siRNA inhibition of MBD3 promotes human iPSC reprogramming by OSKM. FIG. 10A—A schematic illustration depicting secondary human reprogrammable fibroblasts carrying DOX inducible OSKM transgenes, being subjected to the depicted reprogramming protocol with DOX. FIGS. 10B-C—Western blot analyses using anti MBD3 antibody (FIG. 10B) or anti-Hsp90 antibody (FIG. 10C) of cells treated with MBD3 siRNA, with a control siRNA, or remained untreated. Note the reduction of MBD3 in cells treated with MBD3 siRNA, but not in cells treated with the control siRNA or in untreated cells. FIG. 10D—In WIS-NHSM growth conditions, Knockdown of Mbd3 at days 2 and 4, but not with scrambled control siRNA, dramatically increased the formation of alkaline phosphatase+ iPSC clones. FIG. 10E—Schematic illustration of a single round reprogramming. Human fibroblasts are subject to treatment with MBD3 siRNA at 7 and 2 days prior to mRNA transfection with the OSKM and Lin28 factors. FIGS. 10F-O are images of the formed iPSCs. FIG. 10F—Day 7 iPS colony, passage 0; FIG. 10G—iPSCs at passage 3; FIGS. 10I-J—IPSCs (Passage 7) stained with Dapi (blue, nuclear staining) (FIG. 10I) and with OCT4 (red) (FIG. 10J); FIGS. 10L-M—IPSCs (Passage 10) stained with Dapi (blue, nuclear staining) (FIG. 10L) and with Nanog (red) (FIG. 10M); FIGS. 10N-O—IPSCs (Passage 10) stained with Dapi (blue, nuclear staining) (FIG. 10N) and with TRA1-60 (green) (FIG. 10O); FIGS. 10H, 10K and 10P histological staining of cells differentiated from the iPSCs. In vivo Teratoma formation generated from P8 iPSCs showing differentiation into ectoderm (FIG. 10H), mesoderm (FIG. 10K) and ectoderm (FIG. 10P) embryonic germ layers. These results show that at day 7 MBD3 siRNA treatment of human fibroblasts allows generation of iPSCs in WIS-NHSM conditions, by single round of reprogramming with mRNA transfection with OSKM and Lin28 factors, and alleviates the need for many rounds of repeated mRNA transfections. These results indicate that inhibition of MBD3 expression and/or function promotes iPSC formation by transient mRNA or other transient transfection protocols (with protein or cDNAs).

FIGS. 11A-P demonstrate mechanisms of Mbd3 function and influence on reprogramming to pluripotency. FIGS. 11A-H are immunoblot analyses using anti MBD3 antibody (FIGS. 11A-D) or anti-FLAG antibody (FIGS. 11E-11). Constructs encoding Flag-tagged OCT4 (FIGS. 11A and 11E), or KLF4 (FIGS. 11C and 11G) or SOX2 (FIGS. 11B and 11F) or HDAC1 (used as a positive control; FIGS. 11D and 11H) were transfected into HEK293T cells in combination with MBD3. The cell lysates were immunoprecipitated (IP) with an anti-Flag antibody (or anti-IgG as control), followed by an immunoblot analysis (IB). The expression levels in whole-cell lysates or IP extract were determined by IB anti-Flag (FIGS. 11E-H) or anti-Mbd3 (FIGS. 11A-D). This analysis demonstrates direct interaction of Mbd3 with OSK pluripotency factors. FIGS. 11I-P—are immunoblot analyses using anti MBD3 antibody (FIGS. 11I-L) or anti-FLAG antibody (FIGS. 11M-P). Reproducing the experiment in FIGS. 11A-H, but by overexpressing of Mbd2, instead of Mbd3. Constructs encoding Flag-tagged OCT4 (FIGS. 11I and 11M), or KLF4 (FIGS. 11K and 11O) or SOX2 (FIGS. 11J and 11N) or HDAC1 (used as a positive control; FIGS. 11L and 11P) were transfected into HEK293T cells in combination with MBD2. This analysis demonstrated lack of enriched or specific interaction for MBD2 with reprogramming factors OSK. These results indicate that Mbd3 directly interacts with reprogramming pluripotency factors, and thus by recruiting the NuRD complex, it inhibits their activity and prevents the reactivation of their downstream target genes.

Figure 12D:
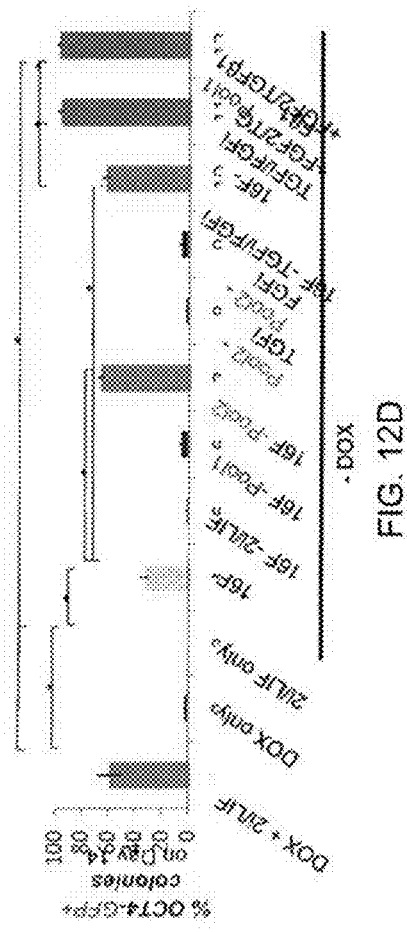
Figure 12S:
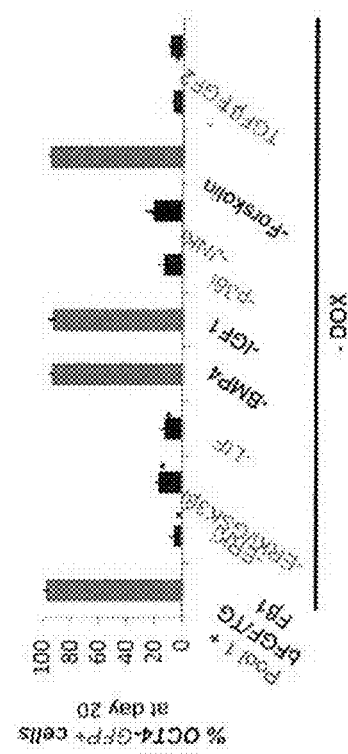
Figure 12T:
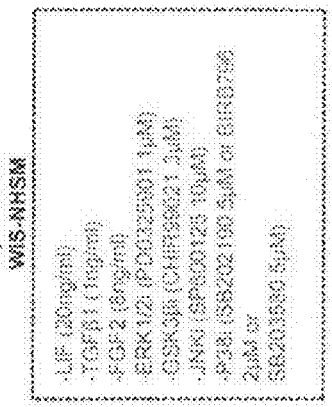
Figures 12U, 12V:
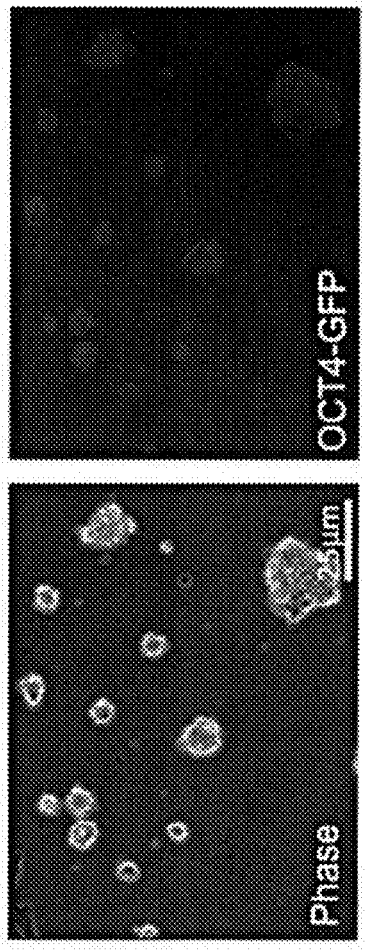

FIGS. 12A-V demonstrate in vitro stabilization of transgene independent and long-term stable naive human pluripotent cells. FIG. 12A—A schematic illustration depicting the strategy used for calibrating conditions to isolate naive transgene independent iPSCs in the presence of ERK inhibition. The present inventors used C2 human iPSC line carrying DOX-inducible lentiviruses (TetO) encoding Oct4, Sox2, Klf4 and c-Myc. This cell line was targeted with TALE effector nuclease to insert a GFP-2A-Puro allele in the endogenous OCT4 locus. GFP+ C2 cells can be grown in 2i/LIF conditions but only with the presence of DOX, and approximately 60% of correctly targeted clones specifically expressed GFP. The present inventors screened for addition of small molecule factors and cytokines that allow obtaining Oct4-GFP positive cells in the absence of DOX and presence of ERK inhibition. Two Pools of combined factors were used for the screen as indicated. Pool 1: ERKi, GSK3βI, LIF, BMP4, IGF, P38i. JNKi, Forskolin. Pool 2: FGFi, TGFi, Kenpaullone, Go6983, BayK8644, Bix1294, ROCKi and SCF. FIGS. 12B-C—microscopic images depicting phase contrast (FIG. 12B) and GFP fluorescence staining (green, FIG. 12C) of the C2 correctly targeted iPS clones used for the screen. FIG. 12D—A histogram depicting the percentage of Oct4-GFP$^+$ colonies on day 14 (s.d.m; n=3) in the presence of different combinations of factors as indicated. Cells were expanded in the DOX+2iLIF as well as in various media such as DOX only (DOX is used to induce OSKM transgenic factors), 2i/LIF only, 16F (pools 1 and 2 combined); with the 16F medium with the following omitted (marked with "−") or added (marked with "+") factors: −2i/LIF, −pool1, −pool2, −TGFi/−FGFi, −TGFi/−FGFi+ FGF2 (bFGF) and TGFβ1; with pool 2 with the following omitted factors: −TGFi, −FGFi; and pool 1 with FGF2 and TGFβ1. Note that the presence of 2i/LIF or pool1 is essential for maintaining DOX-independent OCT4-GFP+ cells. Also note, TGFi and FGFi negatively influence DOX-independent OCT4-GFP+ cells, and that addition of TGFβ1 and FGF2 positively support maintenance of DOX-independent OCT4-GFP+ cells in the context of 2i/LIF medium. FIG. 12E-A histogram depicting percentage of Oct4-GFP$^+$ colonies on day 20 relative to control cells in the presence of different combinations of factors as indicated. Cells were expanded in the 14F+ bFGF/TGFβ1 medium which includes the 14 factors [which are the 16 factors of pools 1 and 2, yet without inhibitors of FGF and TGF pathways] and with TGFβ1 and bFGF. Next, from this medium combination (14F+bFGF/TGFβ1) the present inventors have eliminated the factors shown near the "X" axis, e.g., ERKi (shown as "−ERki" in FIG. 12E), etc., in order to determine the essential factors required for maintaining Oct4-GFP$^+$ cells in the absence of DOX. This analysis indicates that ERKi, CHIR, P38i, JNKi, LIF, bFGF and TGFB were essential components. Removing any of them resulted in significant deterioration and differentiation of C2 Oct4-GFP+ cells in the absence of DOX. FIG. 12F-A histogram depicting percentage of Oct4-GFP+ colonies on day 8 relative to control cells. For further optimizing naive growth conditions and substitute of Knockout serum replacement, Knockout serum replacement can be substitute only with using N2 supplement and either 1% albumax or 1% Defined fatty acid mix concentrate (FAA) (Invitrogen). FIG. 12G—Summary of essential elements calibrated to expand human naive pluripotent cells for long term and without exogenous transgenes. This media is termed WIS-NHSM (Weizmann Institute of Science—Naive Human Stem cell Medium). FIG. 12H—A histogram depicting percentage of Oct4-GFP+ colonies on day 8 relative to control cells grown under various conditions as indicated. Note that naive human iPSCs can be grown without feeder cells either on Matrigel coated plates or 0.2% gelatin+1 ng/ml vitronectin coated plates (but not gelatin alone). FIG. 12I—Karyotype of transgene independent C1 naive pluripotent cell line in WIS-NHSM media. FIGS. 12J-K—images depicting phase contrast (FIG. 12J) or fluorescence (FIG. 12K) microscopy of C2 iPSC clones expanded in WIS-NHSM independent of DOX and shows homogenous Oct4-GFP expression. Note Oct4-GFP expression (green staining, FIG. 12K) demonstrating the cells are pluripotent. FIGS. 12L-N—images of morphological staining of teratoma formation from the C2 iPS clone line shown in FIGS. 12I-K. Note the differentiation into cells of the mesoderm (FIG. 12L), endoderm (FIG. 12M) and ectoderm (FIG. 12N) embryonic germ layers, demonstrating the pluripotency of the naive C2 iPSC cell line. FIGS. 12O-R—are images depicting iPSCs that were derived from BJ fibroblasts. Human naive iPSCs can be directly formed from human BJ fibroblasts, following direct infection with an OKSM polycistronic cassette delivered by a lentivirus. FIG. 12O—phase contrast of iPSC colonies at day 6 DOX in WIS-NHSMP3 medium; FIG. 20P—phase contrast of BJ iPSC at passage 3; FIG. 12Q—fluorescent microscopy showing Nanog expression (green staining) of BJ fibroblasts derived iPS cells at passage 8. The inset shows DAPI staining (blue); FIG. 12R—fluorescent microscopy showing SSEA4 expression (red staining) of BJ iPSC cells at passage 13. The inset shows DAPI staining (blue); Altogether, FIGS. 12O-R show that the established BJ iPSC line expressed all pluripotency marker tested. FIG. 12S—Cells were expanded in the presence of bFGF/TGFβ and Pool1 factors, and the essential factors required for maintaining OCT4-GFP+ cells in the absence of DOX were determined by screening for loss of GFP upon withdrawal of these components (green font). One out of three independent replicate experiments is shown. * t-test P value <0.01 (between indicated samples marked by connecting lines). Error bars indicate s.d.m (n=4). FIG. 12T—Summary of essential elements calibrated to expand human naive pluripotent cells for long term and without exogenous transgenes. This optimized media is termed WIS-NHSM (Weizmann Institute of Science—Naive human Stem cell Medium). FIG. 12U—Components of optimized WIS-NHSM conditions. FIG. 12V—Representative large-field view of OCT4-GFP+ hiPSC colonies grown in WIS-NHSM media.

Figure 13W:
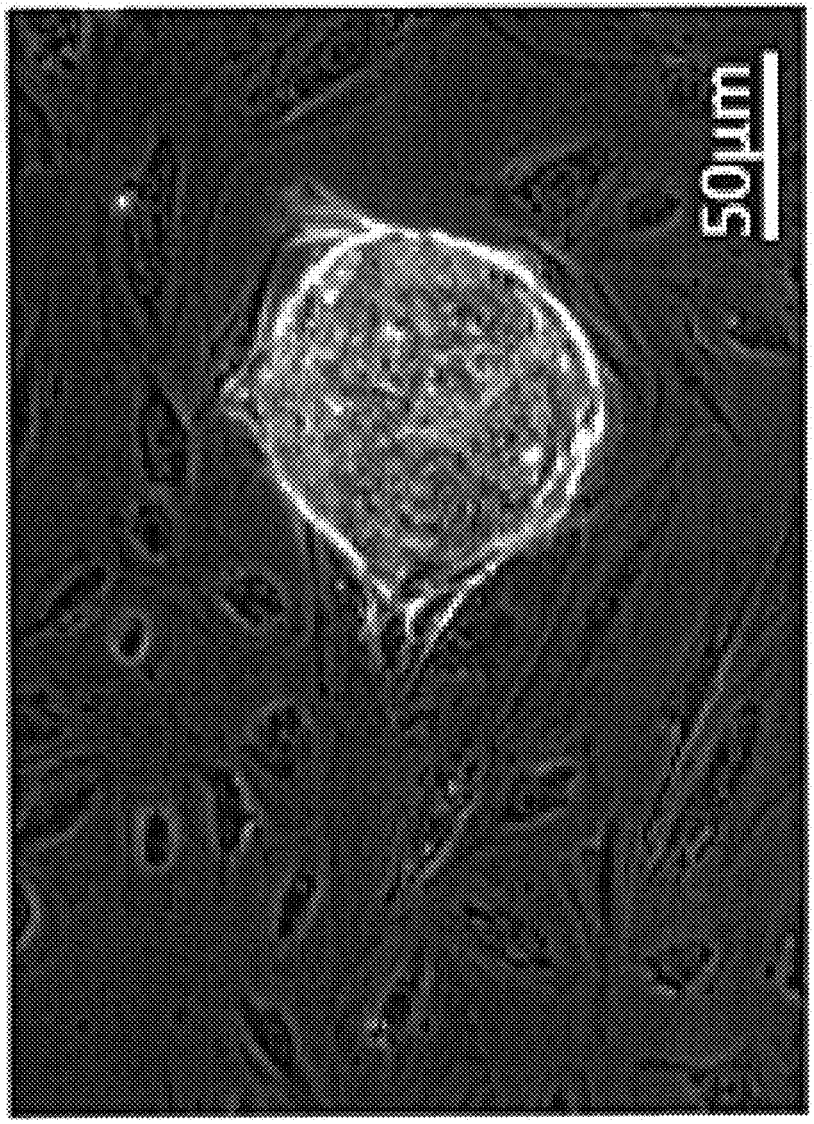

FIGS. 13A-W demonstrate the derivation of human naive iPSCs and ESCs from already established primed/conventional ESCs lines or blastocysts. FIG. 13A—A schematic illustration depicting epigenetic reversion of primed/conventional human ESCs to ground state naive state, and without genetic modifications. Primed already established cell line H1, H9, BGO1, WIBR2, WIBR3 hESCs and C1, C2 iPSCs were plated on gelatin/vitronectin-coated plates and grown in WISNHSM conditions. Within 5 days, many cells differentiate, but round dome colonies emerge. After trypsinization and passaging, homogenous naive ESC/iPSC lines can be established. FIGS. 13B-E are microscopic phase contrast images. FIG. 13B—Primed BG01 hESC; FIG. 13C—naive BGO1 cell line at passage 2; FIG. 13D—BGO1 cell line on day 5 in the WIS-NHSM medium; FIG. 13E—BGO1 cell line at passage 31. FIGS. 13F-J are microscopic images demonstrating expression of pluripotent markers by naive BGO1, as a representative example. FIG. 13F—naive BG01 hESC stained with Hoechst (left panel, blue nuclear staining) Nanog (middle panel, green staining) and a merged image of Hoechst and Nanog (right panel). FIG. 13G—naive BG01 hESC at passage 41 (46 XY) stained with Hoechst (left panel, blue nuclear staining), SSEA3 (middle panel, red staining) and a merged image of Hoechst and SSEA3 (right panel). FIG. 13H—naive BG01 hESC at passage 41 (46 XY) stained with Hoechst (left panel, blue nuclear staining), SSEA4 (middle panel, red staining) and a merged image of Hoechst and SSEA4 (right panel). FIG. 24I—naive BG01 hESC at passage 41 (46 XY) stained with Hoechst (left panel, blue nuclear staining), TRA1-60 (second from left panel, red staining), a merged image of Hoechst and TRA1-60 (third from left panel) and alkaline phosphatase (AP) staining (pink-purple staining, right panel). FIG. 13J—naive BG01 hESC at passage 41 (46 XY) stained with Hoechst (left panel, blue nuclear staining), Oct4 (second from left panel, red staining), TRA1-81 (third from left panel) and a merged image of TRA-81 and Oct4 staining (right panel). The results presented in FIGS. 13F-J demonstrate that the naive pluripotent stem cells (PSCs) express all known human pluripotent markers, and retain a normal 46XY male karyotype after many passages in the absence of exogenous transgenes. All naive lines described here in show no signs of deterioration, crisis or decay with expansion (for over 70 passages thus far). FIGS. 13K-M are images depicting morphological staining of teratomas formed from the naive PSCs. Shown are cells of the mesoderm (FIG. 13K), ectoderm (FIG. 13L) and endoderm (FIG. 13M) embryonic germ layers, demonstrating that the naive PSCs are pluripotent as shown by their ability to generate differentiated teratomas in vivo. FIG. 13N a schematic illustration depicting generation of a human naive PSC from a blastocyst. A Human ICM-blastocyst was plated on feeder cells in WIS-NHSM conditions. At day 6-8, the original outgrowth was trypsinized, and naive pluripotent cell lines were established in WIS-NHSM conditions on gelatin/vitronectin coated plates independent of feeders (representative images at P3 of established lines is shown). FIG. 13O—Images depicting phase contrast microscopy of a naive PSC at passages 0 (day 6) and 3, formed from a human blastocyst that was cultured in WIS-NHSM medium. FIG. 13P—images of a fluorescence microscopy showing a naive WIS1 hESC stained with Hoechst (upper panel, blue staining), nanog (second from top panel, green staining), SSEA4 (third from top panel, red staining), and a merged image of the Hoechst, Nanog and SSEA4 (bottom panel). FIG. 13Q—images of a fluorescence microscopy showing a naive WIS1 hESC stained with Hoechst (upper panel, blue staining), OCT4 (green staining, middle panel), and a merged image of Hoechst and OCT4 (bottom panel). FIG. 13R—images of a fluorescence microscopy showing a naive WIS1 hESC stained with Hoechst (upper panel, blue staining), SSEA3 (green staining, middle panel), and a merged image of Hoechst and SSEA3 (bottom panel). FIGS. 13S-U—images depicting morphological staining of teratomas formed from the naive WIS1 hESC line. Shown are cells of the endoderm (FIG. 13S), mesoderm (FIG. 13T), and ectoderm (FIG. 13U) embryonic germ layers. The results shown in FIGS. 13P-U demonstrate that the naive WIS1 hESC line is pluripotent based on pluripotency marker expression (FIGS. 13P-R) and teratoma differentiation in vivo (FIGS. 13S-U). FIG. 13V—Naive hiPSCs can be directly formed from human BJ fibroblasts, following reprogramming with mRNA transfection in WIS-NHSM conditions. Note distinct domed colony emerging 10 days after factor transduction. FIG. 13W—Naïve hiPSCs can be directly formed from human BJ fibroblasts in WIS-NHSM conditions.

Figures 14C, 14D:
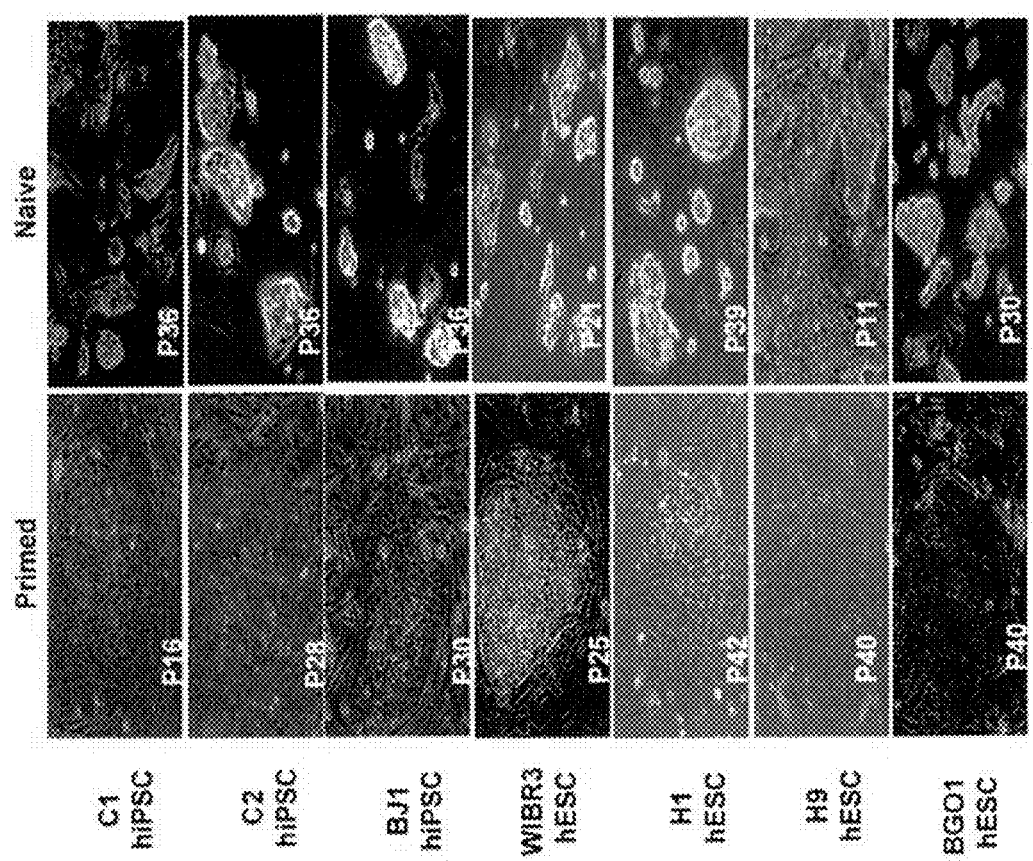
Figures 14A, 14B:
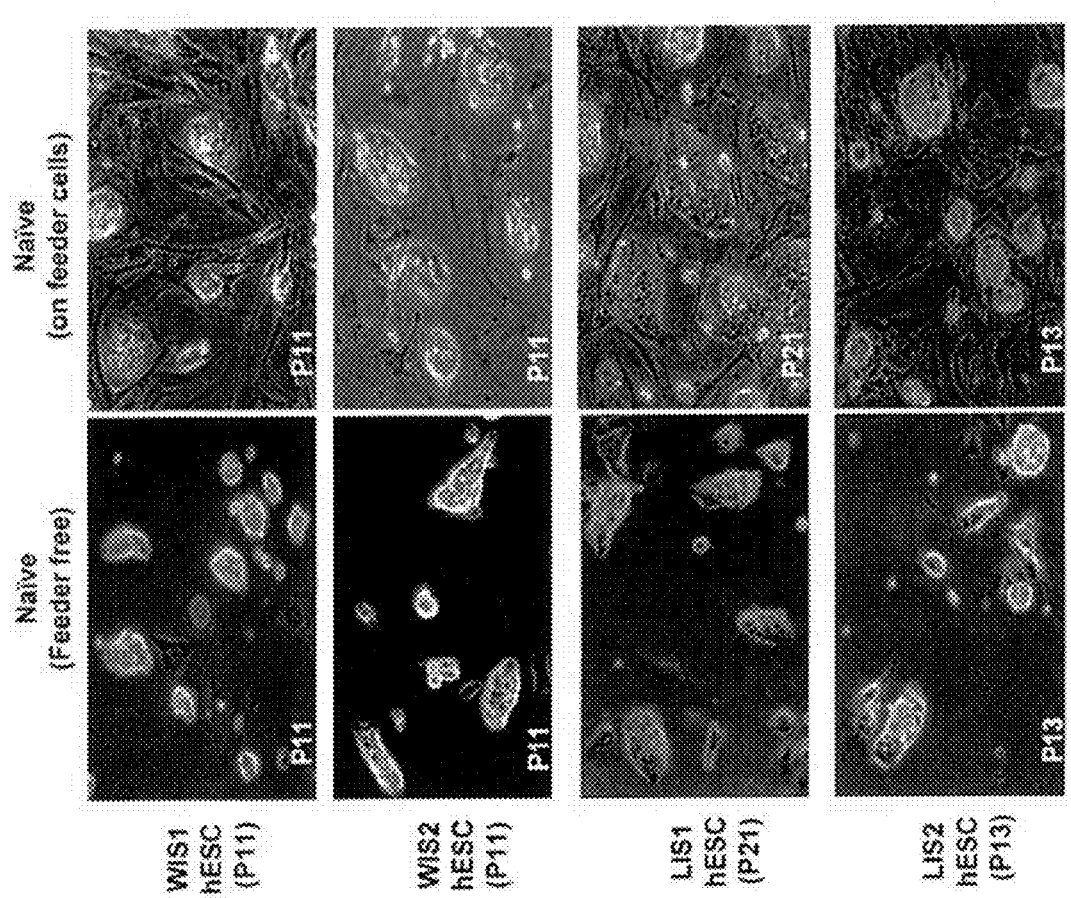

FIGS. 14A-D are images (phase contrast microscopy) depicting the morphology of genetically matched naive and primed human pluripotent cell lines. FIGS. 14A-B—Representative images showing distinct morphology for embryo-derived naive hESCs in WIS-NHSM conditions (Marked as "WIS1 hESC", "WIS2 hESC", "LIS1 hESC" and "LIS2 hESC" grown on feeder cells (FIG. 14B) or without feeder cells (FIG. 14A). FIGS. 14C-D—Representative images showing distinct morphology for conventional/primed pluripotent cells lines (FIG. 14C), versus genetically matched naive hESCs and hiPSCs grown in WIS-NHSM conditions (FIG. 14D). Naive cells display a more domed morphology and with a less distinct cell-cell boundary. P indicates the passage number. For naive cells, P indicates number of passages already achieved in naive WIS-NHSM conditions. For primed cells, P includes number of passages already achieved in naive WIS-NHSM conditions (6 passages) and in primed conditions.

FIGS. 15A-M demonstrate signaling state and karyotype of human naive iPSCs and ESCs. Western blot analyses of primed or naive human pluripotent cells (Passage 25) (WIBR3 hESC) using antibodies directed against total and phosphorylated forms of distinct signaling adaptors. FIG. 15A—pERK1/2 42,44; FIG. 15B—Total ERK1/2; FIG. 15C—HSP90; FIG. 15D—Total p38; FIG. 15E—pP38 180, 182; FIG. 15F—HSP90. FIG. 15G—pSTAT3 705; FIG. 15H—Total STAT3; FIG. 15I—pβCatenin 33,37; FIG. 15J—βCatenin; FIG. 15K—pJNK1,2; FIG. 15L—JNK; FIG. 15M—HSP90. Note that human WIBR3 naive hESCs that are grown in WIS-NHSM conditions show specific blocked and reduced activity for ERK1, P38 and JNK in naive pluripotency. Consistent with the essence of LIF in WIS-NHSM phosphorylated STAT3 levels accumulate in naive hESCs. Samples were loaded in triplicates for demonstrating consistency. Similar results were obtained when analyzing naive and primed C1 hiPSCs, WIS2 hESCs (not shown). FIGS. 15H-I are karyotypes of different naive human ESCs and iPSCs.

FIGS. 15N-S demonstrate karyotype and clonal stability of human naive pluripotent cells. Shown are representative karyotype analysis results indicating normal karyotypes of different naive hESC and hiPSCs. FIG. 15N—C1 naive hiPSC; FIG. 15O—WIS1 naive hESC; FIG. 15P—WIBR3 naive hESC; FIG. 15Q—BG01 naive hESC; FIG. 15R—LIS1 naive hESC; FIG. 15S—LIS2 naive hESC. The passage number (p) at which cells were harvested for karyotyping is indicated. These data indicate that naive hESCs and hiPSCs can be established from both sexes, and maintain a normal karyotype without a dramatic tendency to acquire chromosomal abnormalities.

Figure 15U:
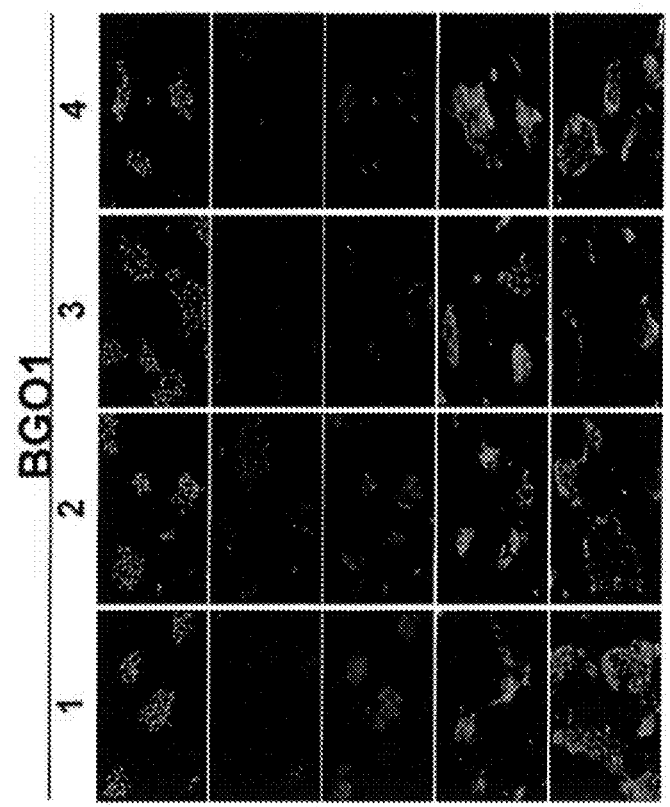
Figure 15T:
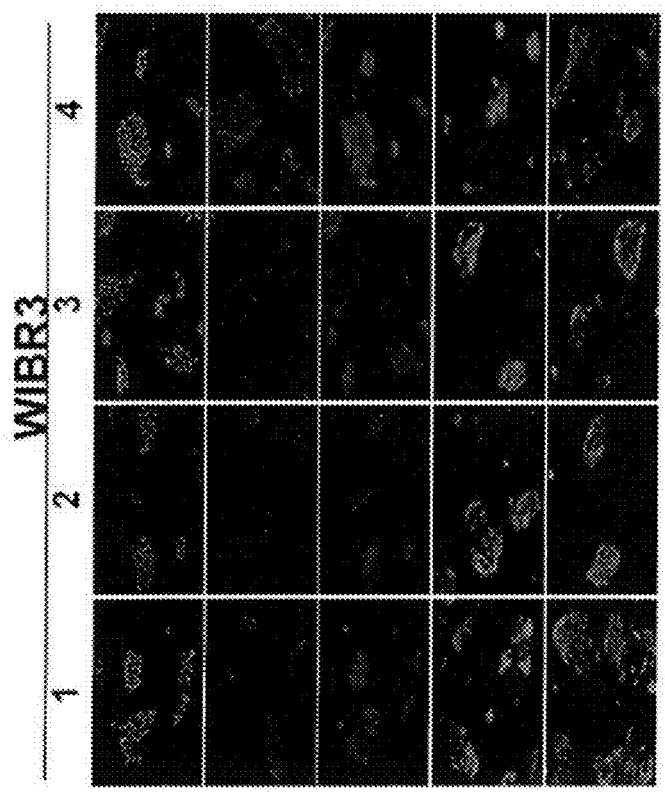

FIGS. 15T-U—Immunostaining for pluripotency markers on individually subcloned lines (labeled 1-4) from naive hESC lines WIBR3 (FIG. 15T) and BGO1 (FIG. 15UO). Note that both naive hESC lines express OCT4, nanog, Tra-1-60, Tra-1-81 and SSEA4.

FIGS. 16A-H are images depicting immunostaining analyses for pluripotency markers on naive WIBER3 hESCs. FIG. 16A—Hoechst (blue staining, left panel), TRA1-80 (green staining, middle panel), and a merged image (right panel); FIG. 16B—Hoechst (blue staining, left panel), TRA1-80 (green staining, middle panel), and a merged image (right panel); FIG. 16C—Hoechst (blue staining, left panel), KLF4 (red staining, middle panel), and a merged image (right panel); FIG. 16D—Hoechst (blue staining, left panel), KLF4 (red staining, middle panel), and a merged image (right panel); FIG. 16E—Hoechst (blue staining, left panel), SSEA1 (middle panel), and a merged image (right panel); FIG. 16F—Hoechst (blue staining, upper panel), TRA1-60 (green staining, second panel), Nanog (red staining, third panel), and a merged image (bottom panel); FIG. 16G—Hoechst (blue staining, upper panel), E-cadherin (green staining, second panel), Oct4 (red staining, third panel), and a merged image (bottom panel); FIG. 16H—Hoechst (blue staining, upper panel), SSEA4 (green staining, second panel), OCT4 (red staining, third panel), and a merged image (bottom panel); The immunostaining results show that the naive hESC line exhibits positive staining for all known human pluripotency markers tested. Notably, SSEA1, which is specific for mouse and not human pluripotent cells, is not expressed in human naive ESCs and iPSCs (FIG. 16E, middle panel).

FIGS. 17A-H are images depicting immunostaining analyses for pluripotency markers on naive C1 hiPSC. FIG. 17A—Hoechst (blue staining, left panel), TRA1-80 (green staining, middle panel), and a merged image (right panel); FIG. 17B—Hoechst (blue staining, left panel), TRA1-80 (green staining, middle panel), and a merged image (right panel); FIG. 17C—Hoechst (blue staining, left panel), KLF4 (red staining, middle panel), and a merged image (right panel); FIG. 17D—Hoechst (blue staining, left panel), Nanog (red staining, middle panel), and a merged image (right panel); FIG. 17E—Hoechst (blue staining, left panel), SSEA1 (middle panel), and a merged image (right panel); FIG. 17F—Hoechst (blue staining, upper panel), TRA1-60 (green staining, second panel), Nanog (red staining, third panel), and a merged image (bottom panel); FIG. 17G—Hoechst (blue staining, upper panel), E-cadherin (green staining, second panel), Oct4 (red staining, third panel), and a merged image (bottom panel); FIG. 17H—Hoechst (blue staining, upper panel), SSEA4 (green staining, second panel), OCT4 (red staining, third panel), and a merged image (bottom panel); The immunostaining results show that the naive C1 hiPSC line exhibits positive staining for all known human pluripotency markers tested. Notably, SSEA1, which is specific for mouse and not human pluripotent cells, is not expressed in human naive iPSCs and ESCs (FIG. 17E, middle panel).

FIGS. 18A-F are images depicting immunostaining analyses for pluripotency markers on naive C2 hiPSC (FIGS. 18A-F). FIG. 18A—Hoechst (blue staining, upper panel), KLF4 (red staining, second panel), and a merged image (bottom panel); FIG. 18B—Hoechst (blue staining, upper panel), TRA1-81 (yellow staining, second panel), and a merged image (bottom panel); FIG. 18C—Alkaline phosphatase (AP; upper panel), Hoechst (blue staining, second panel), SSEA1 (third panel), and a merged image (bottom panel); FIG. 18D—Hoechst (blue staining, upper panel), TRA1-60 (yellow staining, second panel), Nanog (red staining, third panel), and a merged image (bottom panel); FIG. 18E—Hoechst (blue staining, upper panel), E-cadherin (green staining, second panel), Oct4 (red staining, third panel), and a merged image (bottom panel); FIG. 18F—Hoechst (blue staining, upper panel), SSEA4 (green staining, second panel), Oct4 (red staining, third panel), and a merged image (bottom panel); The immunostaining results show that the naive C2 hiPSC line exhibits positive staining for all known human pluripotency markers tested. Notably, SSEA1, which is specific for mouse and not human pluripotent cells, is not expressed in human naive iPSCs and ESCs (FIG. 18C, third panel from the top).

FIGS. 19A-I are images demonstrating the in vitro differentiation potential of human naive ESCs and iPSCs. Shown are images for day 6 EB structures from the indicated cell lines (defined by name and passage number). Images indicate differentiated embryonic body structures. FIG. 19A—Naive WIBR3EBs (Passage 21); FIG. 19B—Naive H1 EBs (Passage 51); FIG. 19C—Naive BG01 EBs (Passage 41); FIG. 19D—Naive C1 EBs (Passage 21); FIG. 19E—Naive C2 EBs (Passage 27); FIG. 19F—Naive WIS1 EBs (passage 13); FIG. 19G—Naive WIS2 EBs (passage 21); FIG. 19H—Naive LIS1 EBs (passage 17); FIG. 19I—Naive LIS2 EBs (passage 11). These results demonstrate that human naive iPSCs and ESCs can differentiate into Embryoid Bodies (EBs) in vitro.

FIGS. 19J-O—qRT-PCR analysis for expression of lineage differentiation markers (FIG. 19J—BRACHYURY; FIG. 19K—SOX17; FIG. 19L—PAX6; FIG. 19M—AFP; FIG. 19N—SOX1) and a pluripotency marker (FIG. 19O—OCT4). EBs were generated from the following cell lines: WIBR3 ESC, H1 ESC, BG01 ESC, C1 iPSC, C2 iPSC, WIS1 ESC, WIS2 ESC, LIS1 ESC and LIS2 ESC. All cell lines tested showed marked upregulation of lineage commitment genes and down regulation of OCT4 pluripotency marker, consistent with lineage differentiation. Relative qRT-PCR expression levels were normalized to levels expressed in naive pluripotent cells prior to differentiation.

FIGS. 20A-L are images demonstrating the in vivo differentiation potential of human naive ESCs and iPSCs. Human naive iPSCs and ESCs expanded in WIS-NHSM conditions for the indicated number of passages. The cells were harvested and injected in immune-deficient mice subcutaneously, and examined for teratoma formation. FIG. 20A—Naive WIBR3 hESC (Passage 9); FIG. 20B—Naive WIBR3 hESC (passage 22); FIG. 20C—Naive WIBR3 hESC (passage 40); FIG. 20D—Naive H1 hESC (Passage 22); FIG. 20E—Naive BG01 hESC (passage 38); FIG. 20F—Naive H9 hESC (passage 20); FIG. 20G—Naive WIBR1 hESC (passage 21); FIG. 20H—Naive C2 hiPSC (passage 41); FIG. 20I—Naive C1 hiPSC (passage 51); FIG. 20J—Naive BJ1 hiPSC (passage 25); FIG. 20K—Naive LIS1 hESC (Passage 9); FIG. 20L—Naive LIS2 hESC (passage 9). All tested lines gave rise to well differentiated mature teratomas with cells from the three germ lineages: endoderm, mesoderm and ectoderm. "P" indicates passage number in WIS-NHSM conditions at which cells were harvested and injected.

FIGS. 20M-T—Individual subcloned naive lines from WIBR3 (FIGS. 20M-P) and BGO1 (FIGS. 20Q-T) hESC lines (sub clones numbered 1-4) were also found pluripotent with competency to form mature teratomas.

FIGS. 21A-L demonstrate distinct signaling dependence and response for human naive ESCs/iPSCs that resembles murine ESCs/iPSCs. Shown are histograms depicting colony formation of pluripotent cell lines in various media. Cell populations were equally divided and plated on gelatin/vitronectin coated plates in the indicated growth medium in which these cell lines are normally maintained (mouse naive cells in a medium containing 2i/LIF, naive hESCs/iPSCs in a WIS-NHSM medium, mouse EpiSCs and human primed ESCS/iPSCs in a KSR/bFGF/TGFβ medium). 36 hours later the wells were supplemented with the indicated inhibitors or growth factors. After 14 days (2 passages), wells were analyzed for Oct4-GFP pluripotency marker expression by FACS, to determine the relative percentage of pluripotent colonies. Pluripotent cell frequency was normalized to an internal control, as indicated by "Growth medium" only on the far left column (For naive cells growth medium was WIS-NHSM, and for primed cells was conventional KSR/bFGF/TGFβ containing medium as specified in methods). When components already included in WIS-NHSM were supplemented, this yielded a 2-fold increase in their relative concentration. Normalized percentages lower than 50% are defined as "sensitive" to the presence of the supplemented inhibitor. FIG. 21A—Naive 129 mESC; FIG. 21B—Primed 129 mEpiSC; FIG. 21C—Naive WIBR3 hESC; FIG. 21D—Primed/conventional WIBR3 hESC; FIG. 21E—Naive C1 hiPSC; FIG. 21F—Primed/conventional C1 hiPSC; FIG. 21G—naive C1 hESC; FIG. 21H—primed C1 hESC; FIG. 21I—Naive WIS1 hESC; FIG. 21J—Primed WIS1 hESC; FIG. 21K—LIS1 hESC; FIG. 21L—primed LIS1 hESC. Note that human naive ESCs remain pluripotent in the presence of different ERK, GSK3β and RAF inhibitors. Human naive pluripotent cells do not differentiate in response to BMP4 (up to 5-10 ng/ml BMP4) or forskolin supplementation. Primed human ESCs/iPSCs differentiated upon ERK, GSK3b, RAF inhibition, or stimulation with BMP4 or forskolin. Importantly, naive human ESCs/iPSCs are unique from any previously reported naive pluripotent lines, in that they rely on LIF and bFGF/TGFβ signaling (together with presence of multiple ERK, p38 and JNK inhibitors).

FIGS. 22A-K demonstrate unique signaling requirement and response for naive hESCs/iPSCs. Naive hESCs/iPSCs grown in WIS-NHSM conditions supplemented with 5 ng/ml BMP4 remain pluripotent, and can differentiate into teratomas in vivo. Shown are images of morphological staining the teratomas formed by the naive PSCs. FIGS. 22A-C—Naive H1 hESC [Passage 32 with BMP4 (5 ng/ml]; FIGS. 22D-F—Naive C1 hiPSC [Passage 25 with BMP4 (5 ng/ml)]; FIG. 22G—Naive H1 constitutively active Stat3 (expanded under "naive conditions" WIS-NHSM conditions without LIF). FIG. 22H—Naive WIS1-Stat3-CA (expanded in naive WIS-NHSM conditions without LIF). Note differentiation into endoderm (FIGS. 22A, 22D, 22G (left panel) and 22H (left panel)), mesoderm (FIGS. 22B, 22E, 22G (middle panel), and 22H (middle panel)) and ectoderm (FIGS. 22C, 22F, 22G (right panel) and 22H (right panel)) embryonic germ layers. FIGS. 22I-K are immunofluorescence images depicting expression of pluripotent markers in naive hESCs/iPSCs carrying a constitutively activate Stat3 mutant. FIG. 22I—Hoechst (blue staining, upper panel), Nanog (green staining, second panel), SSEA4 (red staining, third panel), and a merged image (bottom panel); FIG. 22J—Hoechst (blue staining, upper panel), Oct4 (green staining, second panel), and a merged image (bottom panel); FIG. 22K—Hoechst (blue staining, upper panel), SSEA3 (green staining, second panel), and a merged image (bottom panel). The results show that the naive hESCs/iPSCs carrying a constitutively activate Stat3 mutant remain pluripotent in the absence of exogenous LIF from WIS-NHSM media, based on teratoma formation and immunostaining for pluripotency markers. These results show that naive hESCs/iPSCs described herein share defining features with rodent naive PSCs in their dependence on LIF/Stat3 signaling to remain pluripotent in WIS-NHSM conditions, and tolerance for exogenous BMP4 cytokine, at least at low levels of BMP4 up to 5 ng/ml 10 ng/ml as tested herein.

Figure 23A:
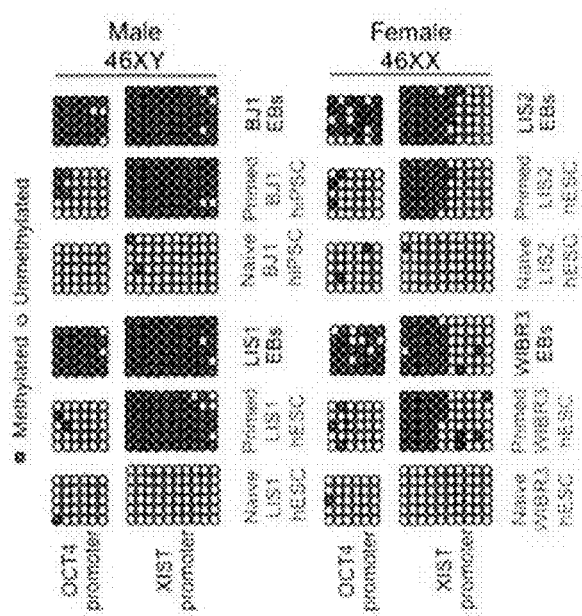
Figure 23C:
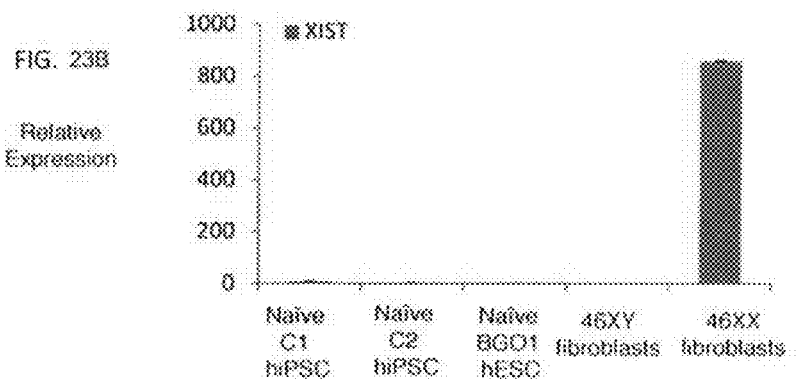
Figure 23D:
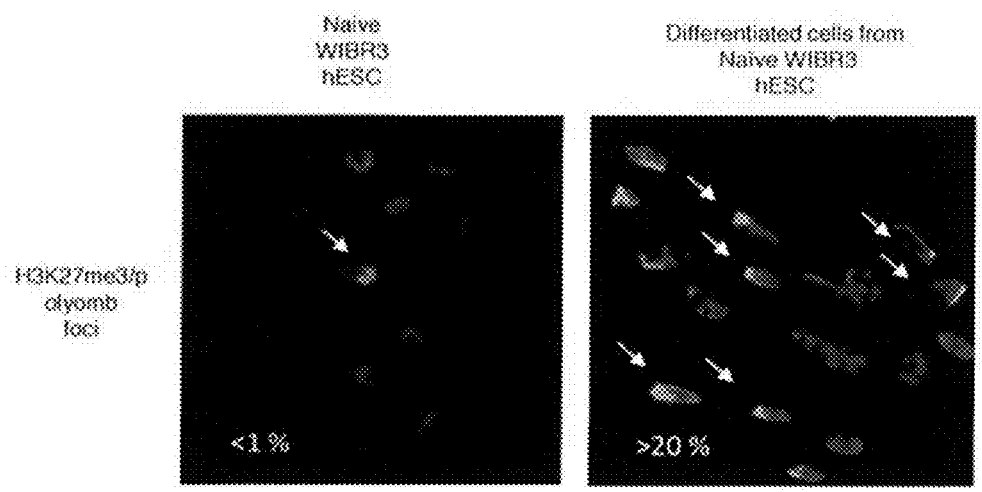

FIGS. 23A-D demonstrate that female Naive hESCs/iPSCs retain a unique pre-X inactivation state in WIS-NHSM conditions. FIG. 23A—Shown are bisulfite sequencing analyses of six CpG sites in single clones of an XIST promoter amplicon (lower panels). Note that in naive cells both alleles are demethylated, while in primed cells one of the alleles becomes silenced. Methylation of Oct4 locus CpG are shown as controls (upper panels). FIG. 23B A histogram depicting quantification of an RT-PCR analysis of the XIST transcript in various naive and somatic cells. Note the low expression levels of XIST in naive hESCs/iPSCs, in comparison to female differentiated fibroblast cells that upregulate XIST expression. FIGS. 23C-D Immuno-fluorescence analysis showing presence of H3K27me3/polycomb bodies. FIG. 23C—Naive WIBR3 hESC; FIG. 23D—Differentiated cells from naive WIBR3 hESC. Note the trace numbers of cells that were found to have H3K27me3/polycomb bodies in nuclei of naive cells (FIG. 23C) as compared to the significant presence of H3K27me3/polycomb bodies in the differentiated cells therefrom. Thus, upon differentiation the numbers of H3K27me3/polycomb bodies dramatically increase, indicating that female human naive cells are capable to initiate X chromosome inactivation following differentiation. The results indicate that the X chromosome in female naive iPSCs/hESCs grown in WIS-NHSM conditions is in a pre-activated state resembling that described in human ICM.

FIGS. 24A-C demonstrate that the naive human ESCs/iPSCs exhibit a distinct transcriptional program. FIG. 24A—Hierarchical clustering of differentially expressed genes on different conventional/primed and naive hESC/hiPSC lines as indicated. Note how all naive hESCs/iPSCs clustered independently from all primed samples. Note how naive WIBR3 hESCs, when transferred again (re-primed) into conventional primed growth conditions, cluster with all other primed samples indicating that these states are inter-convertable by growth conditions. FIGS. 24B-C—Histograms of surface expression of MHC class I using FACS analysis on the indicated naive and primed cell lines. FIG. 24B—WIBR3 hESC; FIG. 24C—C1 hiPSC. 293HEK cells were used as a control for differentiated cells (that typically express high MHC class I levels). Median Fluorescence Intensity (MFI) values are indicated. This shows that naive cells express no/low levels of MHC class I, while primed cells express medium and higher levels of MHC class I. No stain curves for each cell line are also included to have accurate controls for the MHC class I stained samples.

Figure 25A:
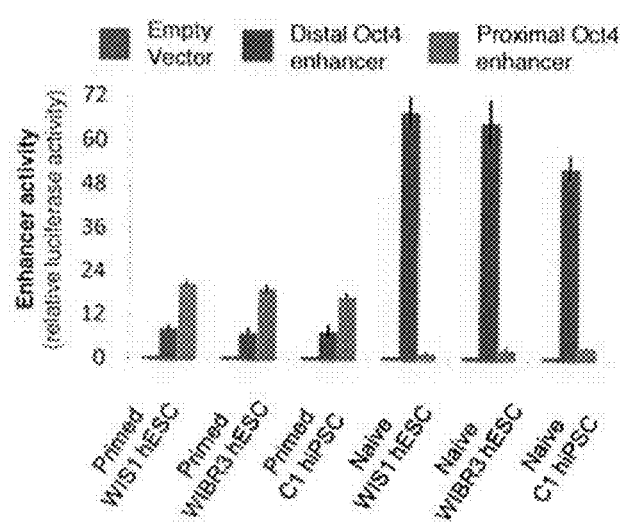

FIGS. 25A-M demonstrate presence of a unique Oct4 enhancer utilization in naive hESCs/hiPSCs. FIG. 25A—A histogram depicting evaluation of human Oct4 distal enhancer and proximal enhancer reporter gene activity in the indicated pluripotent cell lines. Baseline activity was analyzed by transfecting with an empty vector. Predominant utilization of distal enhancer is clearly evident in hESCs/iPSCs grown in naive WIS-NHSM conditions. FIGS. 25B-M—flow cytometry analyses of WIBR3 hESCs that were stably transfected with either: 1) Oct4-GFP-2A reporter that marks all types of pluripotent cells [naive and primed; (FIGS. 25C, 25E, 25G)]; 2) deltaDE-Oct4-GFP-2A-Puro that is typically more active in primed pluripotent cells [based on data in mice (FIGS. 25I, 25K and 25M)]; 3) DeltaPE-OCT4GFP-2A-Puro that is typically more active in naive pluripotent cells [FIGS. 25H, 25J and 25L) or non-transfected WIBR3 hESCs [FIGS. 25B, 25D and 25F]. FIGS. 25B—C and 25H-I—cells grown under naive WIS-NHSM growth conditions. FIGS. 25D-E and 25J-K—cells grown in a conventional/primed bFGF/TGFβ medium. FIGS. 25F-G and 25L-M—cells grown in a differentiation medium; cells were subjected to flow cytometry analyses after 21 days in a differentiation medium, when the cells were differentiated into fibroblasts. These analyses show that detaPE-Oct4-GFP reporter is more active in naive WIS-NHSM conditions (FIG. 25H), relative to primed/conventional conditions (FIG. 25J), or to cells differentiated into fibroblasts (FIG. 25L). On the other hand, delatDE-OCT4-GFP reporter is active in primed/conventional conditions (FIG. 25K) rather than in naive conditions (FIG. 25I) or in cells differentiated into fibroblasts (FIG. 25M). These results indicate that the naive hESCs/iPSCs according to some embodiments of the invention retain a unique epigenetic stability and configuration. MFI=Median fluorescence intensity.

Figure 26A:
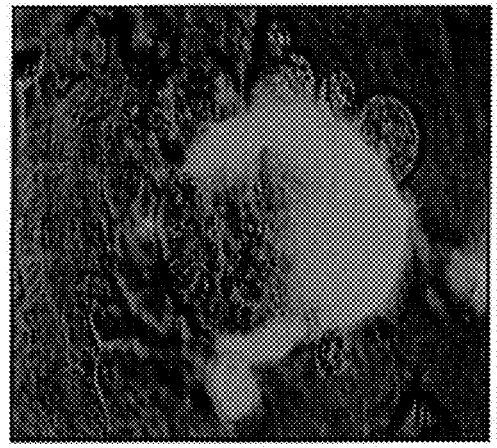
Figure 26B:
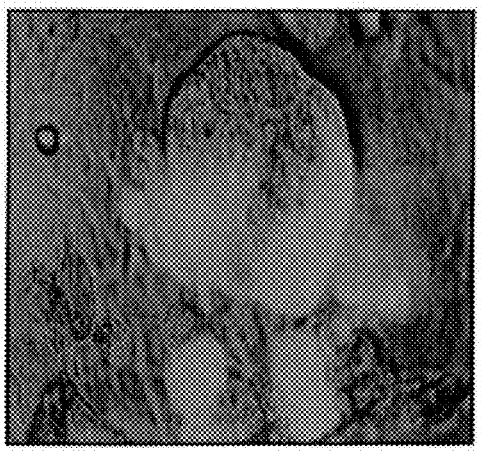
Figure 26C:
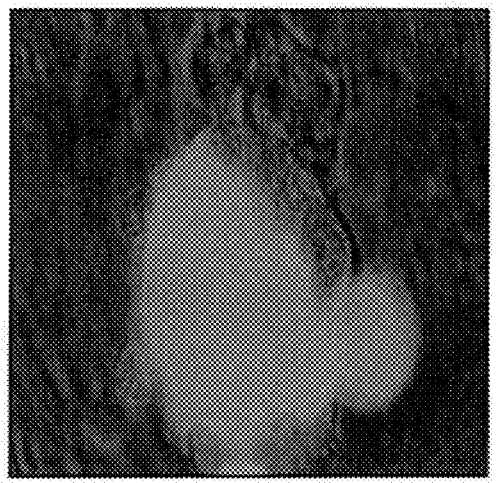
Figure 26D:
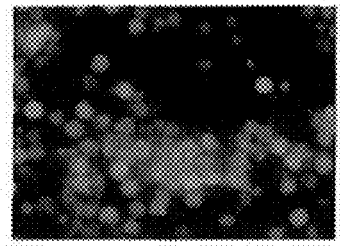
Figure 26E:
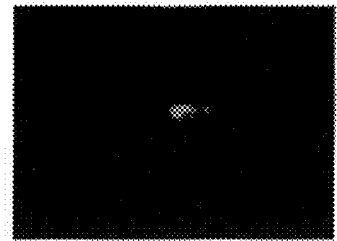
Figure 26F:
Figure 26G:
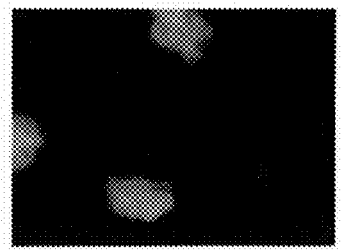
Figure 26H:
Figure 26I:
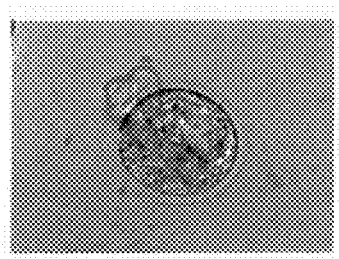
Figure 26J:
Figure 26K:
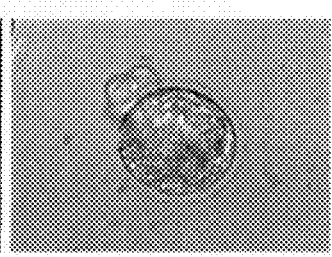

FIGS. 26A-K depict cross species mouse-human chimeric embryos. FIGS. 26A-C—shown are images demonstrating that naive human iPSCs can contribute to mouse development in vivo. Human naive C2 iPSCs were constitutively labeled with GFP and BCL-2 overexpression vector. Cells were aggregated with developing mouse embryo morulas, and 24 hours GFP cells were viable in developing early mouse embryos. These results indicate that human naive cells grown in WIS-NHSM conditions can contribute to cross-species chimeric organisms. FIGS. 26D-K show how GFP labeled human naive iPSCs can be injected into E2.5 mouse morulas, and remain integrated in blastocysts at E3.5. FIG. 26D loading of human naive GFP+ (positive) iPSCs; FIG. 26E injection of the cells shown in FIG. 26D into mouse morula; FIGS. 26F-H show the injected cells into the mouse morula at the day of injection (Inj.) under bright field (FIG. 26F), EGFP (Enhanced Green Fluorescent Protein) (FIG. 26G) and a merged image (FIG. 26H). FIGS. 26I-K show the injected cells into the mouse morula at one day after injection. FIG. 26I—bright field; FIG. 26J—EGFP; FIG. 26K—Merged image.

FIG. 27 depicts the nucleic acid sequence of the XIST amplicon (SEQ ID NO:70) formed using bisulfite sequencing according to some embodiments of the invention, with the CpG islands highlighted in yellow. Note that in the shown amplicon there are six CpG islands.

Figure 28C:
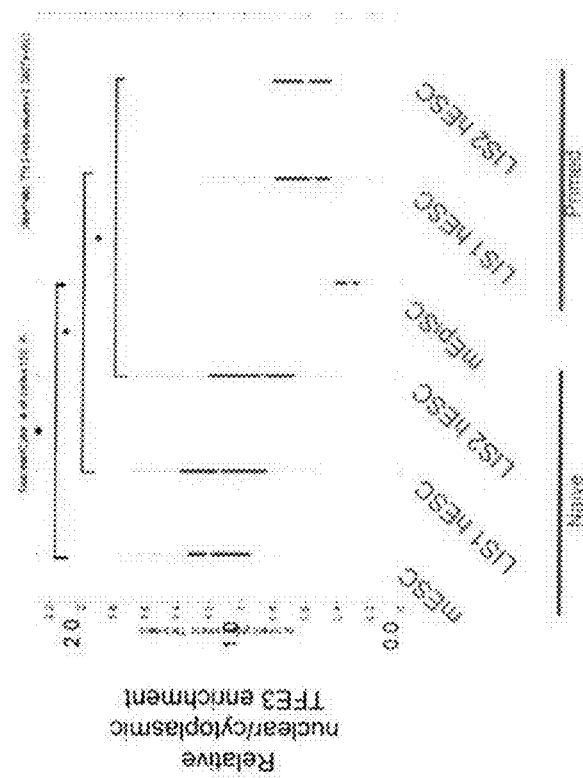
Figures 28A, 28B:
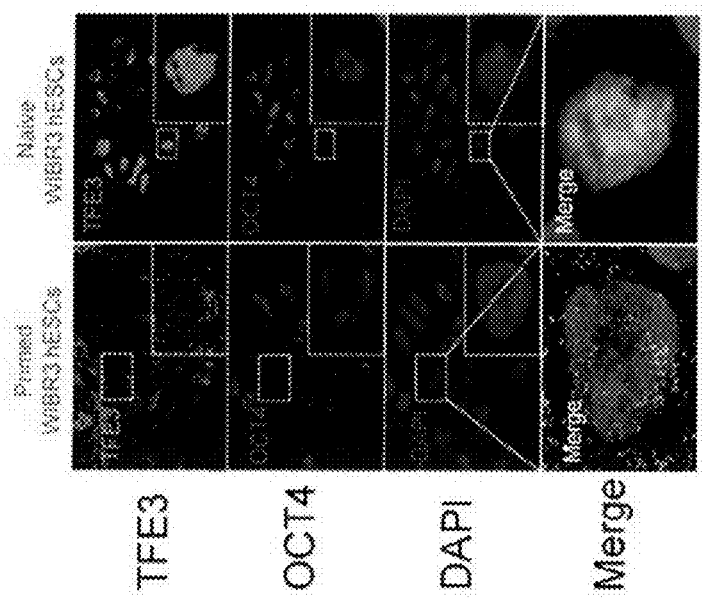

FIGS. 28A-C depict nuclear/cytoplasm ratio in the expression level of transcripts in naive human ESCs. FIGS. 28A-B—Naive and primed hESCs were double immunostained for TFE3 and OCT4. Cells were counter-stained for DAPI (nuclear staining). Representative confocal images are shown for primed LIS2 hESC line and naive LIS2 hESC line. Insets are enlargements of the dashed boxes. Predominant nuclear localization was observed in naive hESCs but not in cells grown under primed conditions. FIG. 28C—Quantitative unbiased imaging analysis for preferential nuclear localization was conducted on randomly selected 200 cells from independent image frames per sample. Box and whisker plots of nuclear/cytoplasmic TFE3 ratios in naive and primed mouse and human ESCs are shown. Naive hESCs showed distributions similar to those in naive mESCs, and the nuclear enrichment was lost in primed human and mouse ESCs*t-test P values $<1\times10^{-100}$.

FIGS. 29A-D depict epigenetic configuration of human naive pluripotency. FIGS. 29A-B are immunostaining analyses for OCT4 and DNMT3B [DNA (cytosine-5)-methyltransferase 3 beta] in human naive (FIG. 29B) and primed (FIG. 29A) cells. Human naive cells down-regulate DNMT3B protein expression, but not OCT4 protein expression. FIGS. 29C-D are histograms of the change in methylation between primed and naive samples in human and mouse. The histograms depict the distribution of the per-CpG difference in methylation, calculated for all CpGs residing in CpG rich regions (>4% CpG content) and having a coverage of ≥10× in both samples. For clarity, only CpGs with a non-zero change in methylation are included in the histogram. The distribution is left-skewed, indicating a general reduction in methylation in the naive samples.

Figures 30F, 30G:
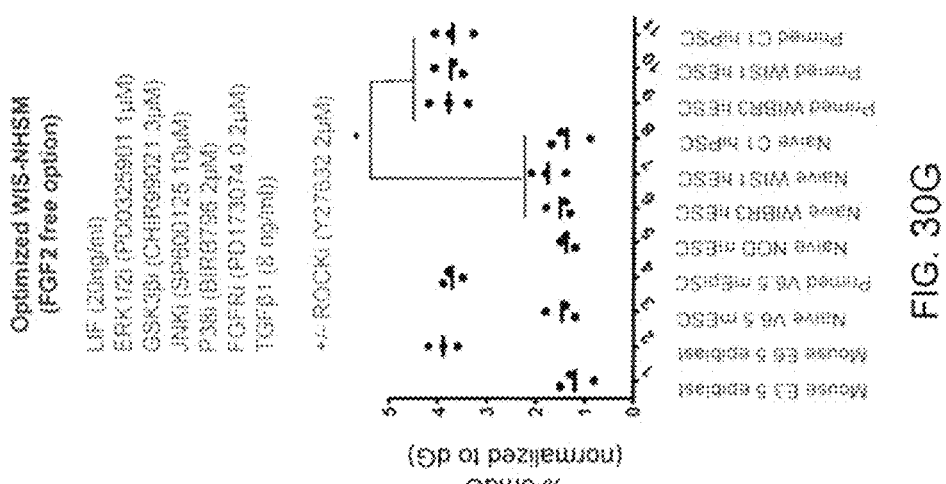
Figures 30H, 30I:
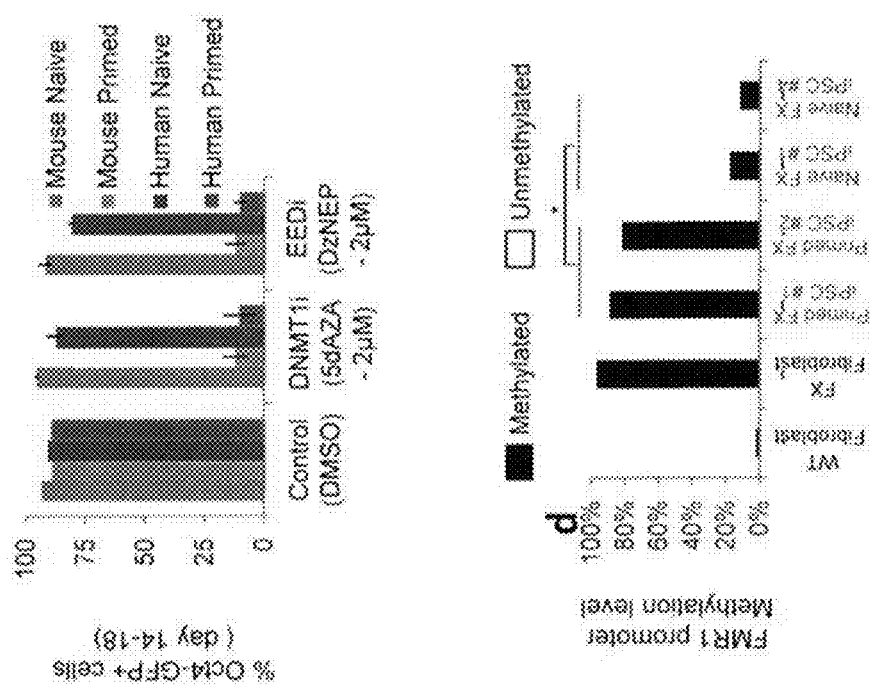

FIGS. 30A-I depict DNA methylation changes in human naive pluripotency. FIGS. 30A-C are Western blot analyses for DNMT3A (FIG. 30A), DNMT3B (FIG. 30B) and HSP90 (FIG. 30C) levels in human primed and naive ESCs/iPSCs. Note the significant downregulation of the expression levels of DNMT3A (FIG. 30A), DNMT3B (FIG. 30B) in the naive human PSCs as compared to primed PSCs. FIG. 30D—Histogram of the change in methylation between primed WIBR3 cells and naive LIS2 cells. The histogram depicts the distribution of the per-CpG difference in methylation, calculated for all CpGs residing in CpG rich regions (>4% CpG content) and having a coverage of ≥10× in both samples. For clarity, only CpGs with a non-zero change in methylation are included in the histogram. The bar-plot on the right counts the number of CpGs in which this difference exceeds two standard-deviations, and the naive sample has lower methylation (blue) or the primed sample has lower methylation (green). The dotted line indicates the expected number of CpGs with a difference that exceeds two standard deviation assuming a normal distribution. FIG. 30E—The same analysis as in FIG. 30D above was applied to the two samples, this time considering all CpGs having a coverage of ≥10× in both samples, regardless of the region's CpG content. FIG. 30F—Composition of naive WIS-NHSM medium that is devoid of FGF2 and TGFB cytokines, and instead retains PKCi, FGFRi and TGFRi. The medium includes: LIF (20 ng/ml), ERK1/2i (PD0325901 1 µM), GSK3βi (CHIR99021 3 µM), JNKi (SP600125 10 µM), P38i (BIRB796 2 µM), FGFRi (PD173074 0.2 µM), TGFβ1 (8 ng/ml)+/−ROCKi (Y27632 2 µM). FIG. 30G—Human naive iPSCs and ESCs expanded for 8 days under these conditions (with the medium having the composition as described in FIG. 30F above) show dramatic reduction in total methylated cytosine levels (mdC), as determined by LC-MS quantitative analysis and normalized to dG abundance levels. FIG. 30H—Human and mouse naive and primed cells were expanded in the presence or absence of inhibitors for DNA methylation (5d-AZA) or EED polycomb component (DzNEP). Only naive cells retain their pluripotency after passaging in the presence of these inhibitors. Pluripotency measurement was conducted by following Oct4-GFP specific reporter levels. FIG. 30I—Relative methylation of FMR1 promoter region in naive and primed human iPSCs derived from Fragile X male patient fibroblasts. Naive human Fragile X iPSCs show predominant loss of methylation at FMR1 promoter in Fragile X patients. * t-test P value <0.05.

FIGS. 31A-E depict numerical description of direct iPSC reprogramming following Mbd3 depletion. FIG. 31A—Secondary NGFP1-control (Mbd3$^{+/+}$), Nanog over expression (NGFP1-Nanog$^{OE}$) and Mbd3 depleted (NGFP1-Mbd3$^{KD}$) Pre-B cells were subjected to DOX reprogramming and measured weekly using FACS (for monoclonal wells), and also with daily polyclonal Nanog-GFP follow-up in the first 8 days of reprogramming. FIGS. 31B-C—Cumulative percentage of Nanog-GFP+ wells versus time on DOX, measured for various clonal B-cell-derived populations. NGFP1-control, NGFP1-Nanog$^{OE}$ and NGFP1-Mbd3$^{KD}$ latencies show distinctly different cumulative distributions. One representative experiment is shown out of 2 performed. FIG. 31B—days on DOX; FIG. 31C—Cell divisions on DOX. FIGS. 31D-E—Fitting of NGFP1-control (FIG. 31D) and NGFP1-Mbd3$^{KD}$ (FIG. 31E) reprogramming latencies (measured in days) to a deterministic step function model, using adjusted R$^2$ (see details in methods) statistics for goodness of fit. NGFP1-Mbd3$^{KD}$ is tightly fitted to a deterministic step function model (R²>0.9) in comparison to NGFP1-control (R²=0.55).

Figure 32F:
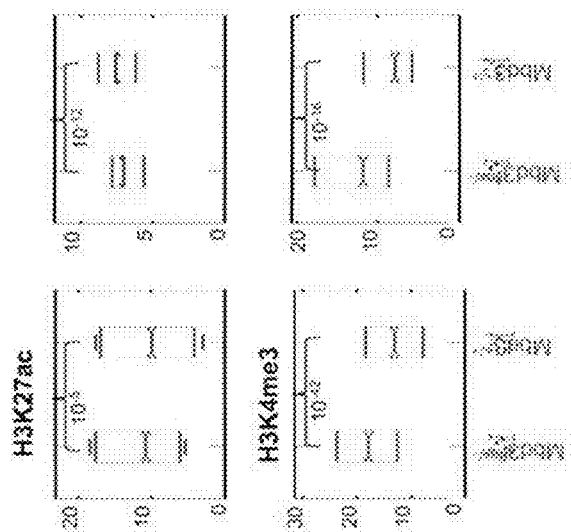
Figure 32E:
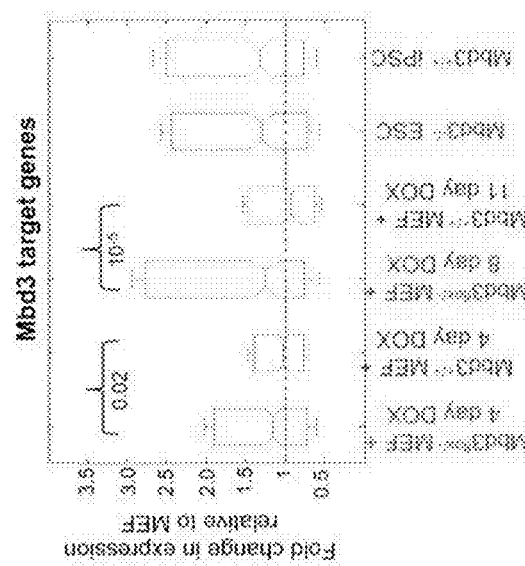
Figure 32H:
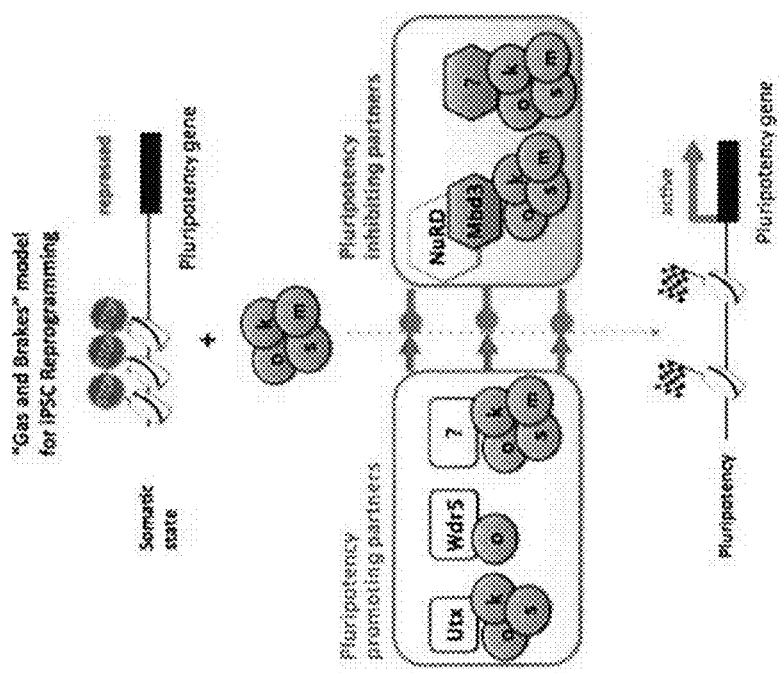
Figure 32G:
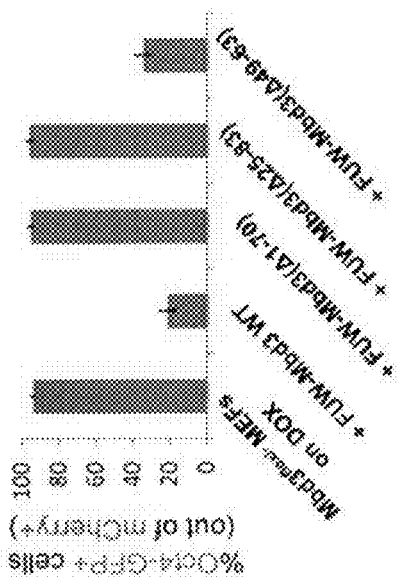

FIGS. 32A-H depict mechanisms for Mbd3 inhibitory effect on OSKM during reprogramming to pluripotency. FIGS. 32A-B—Constructs encoding Flag-tagged OCT4, c-MYC, KLF4, SOX2, NANOG or HDAC1 (used as a positive control) were transfected into HEK293T cells in combination with Mbd3. The cell lysates were immunoprecipitated (IP) with an anti-Flag antibody (or anti-IgG as control), followed by an immunoblot analysis (IB). The expression levels in whole-cell lysates or IP extract were determined by IB with anti-Flag (FIG. 32B) or anti-Mbd3 (FIG. 32A). This analysis demonstrates direct interaction of Mbd3 with OSKM pluripotency factors, but not with Nanog. Hdac 1 was used as appositive control. FIG. 32C-Functional enrichment of Mbd3 direct targets as was measured in somatic MEFs before and after OSKM induction. FIG. 32D—Functional enrichment of Mi2β (Chd4) direct targets as was measured in somatic MEFs before and after OSKM induction. Color levels indicate enrichment P-values (calculated using Fisher exact test) that pass FDR threshold of 0.0001%. White indicates enrichments falling below that threshold. FIG. 32E—Distribution of gene expression fold-change relative to MEF of Mbd3$^{+/+}$ samples (blue) and Mbd3$^{flox/-}$ samples (red) throughout reprogramming (0, 4 days, 8 days, 11 days and iPSC/ESC). Box plot centers indicate the median value, and box edges indicate the 25$^{th}$ and 75$^{th}$ percentiles. P-values of distribution differences indicated in the graph were estimated with paired sample t-test. This analysis was calculated with all identified binding targets of Mbd3 (1400 genes) from Mbd3$^{+/+}$ cells following OSKM induction. Results show general activation of Mbd3 targets throughout the reprogramming process and specifically accelerated activation of Mbd3 targets in the Mbd3$^{flox/-}$ samples. FIG. 32F-Distribution of histone marks and Oct4 binding levels in z-score values at day 4 after OSKM (DOX) induction. This analysis was done over all identified binding targets of Mbd3 (1400 genes) from Mbd3$^{+/+}$ samples. Box plot centers indicate the median value, and box edges indicate the 25$^{th}$ and 75$^{th}$ percentiles. P-values of distribution differences indicated in the graph were estimated with paired sample t-test. Results show a significant induction of H3K27ac and H3K4me3 while reduction of H3K27me3 in Mbd3$^{flox/-}$ sample, compared to Mbd3$^{+/+}$, as well as induction of Oct4 binding in Mbd3$^{flox/-}$ samples. FIG. 32G—Reprogramming efficiency of Mbd3$^{flox/-}$ MEFs after infection with lentiviruses encoding wild-type and different mutant Mbd3 inserts as indicated in the panel. Error bars indicate s.d. of biological triplicates. * Indicates significant P value <0.001 in comparison to uninfected control sample. FIG. 32H—Scheme depicting mechanistic model for inducing pluripotency in somatic cells.

FIGS. 33A-G—depict Knockdown screen for epigenetic repressors in EpiSCs. FIG. 33A—Knockdown efficiency of the indicated siRNA pools in EpiSCs measured by qRT-PCR. Expression values for each gene were normalized to those measured in control siRNA. Error bars indicated s.d. * indicates student t test p Value <0.05. FIGS. 33B-C—Phase images of Mbd3$^{+/+}$ (FIG. 33B) and Mbd3$^{flox/-}$ (FIG. 33C) EpiSC lines in this study. The cell lines had typical flat morphology when expanded on gelatin/vitronectin or Matrigel coated plates (feeder free conditions). FIGS. 33D-E—Oct4 Immunostaining on EpiSC lines. Mbd3$^{+/+}$ EpiSC (FIG. 33D), Mbd3$^{flox/-}$ EpiSC (FIG. 33E); FIGS. 33F-G—EpiSC lines were pluripotent as evident by their ability to form mature differentiated teratomas upon microinjection subcutaneously in immune-deficient mice. Mbd3$^{+/+}$ EpiSC (FIG. 33F), Mbd3$^{flox/-}$ EpiSC (FIG. 33G).

FIGS. 34A-C depict derivation of ESCs from Mbd3$^{-/-}$ blastocysts. FIG. 34A-B Histograms depicting RT-PCR analyses for Oct4 and trophoblast marker expression of Mbd3$^{+/+}$ (FIG. 34A) and Mbd3$^{-/-}$ (FIG. 34B) ESCs expanded either in FBS/LIF or 2i/LIF conditions. Only Mbd3$^{-/-}$ ESCs and only in serum conditions upregulate trophoblast differentiation markers. Stringent serum free 2i/LIF conditions maintain Mbd3$^{-/-}$ ESCs indistinguishably from Mbd3$^{+/+}$ ESCs. Error bars indicate s.d. of biological triplicate samples. FIG. 34C—Agouti chimera derived following blastocyst microinjection with Mbd3$^{-/-}$ ESC line carrying rescue expression transgene for Mbd3.

Figures 35A, 35B:
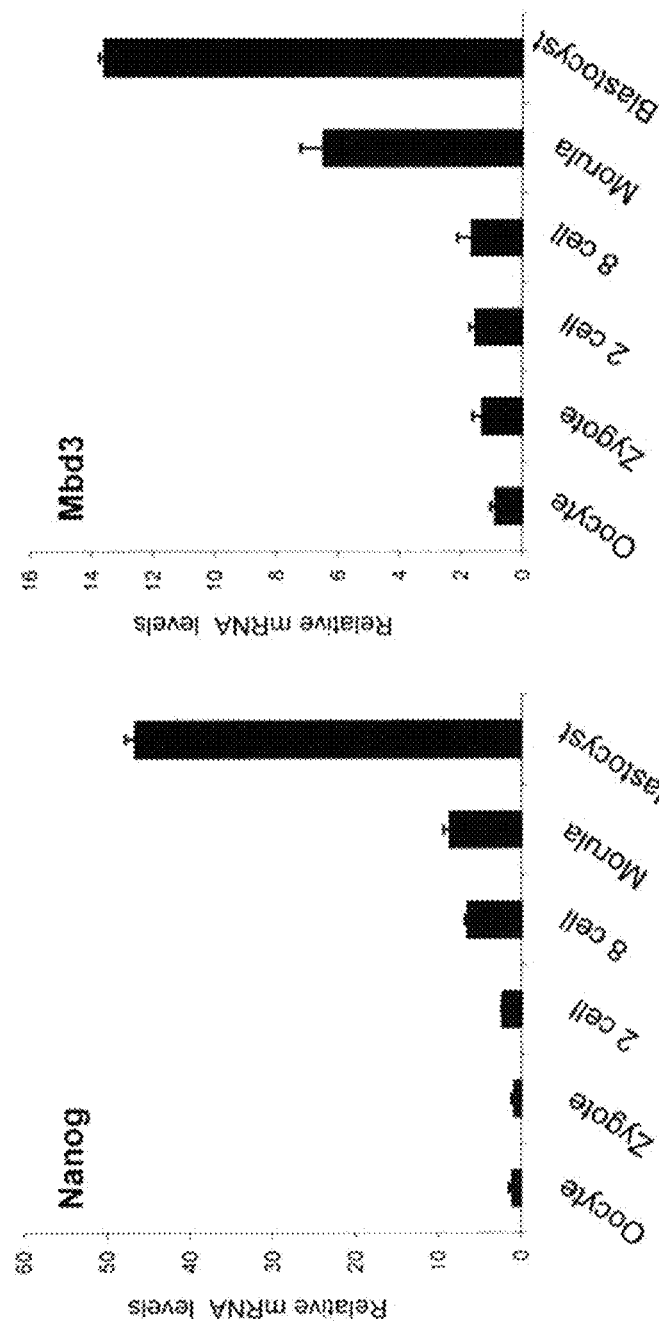
Figure 35C:
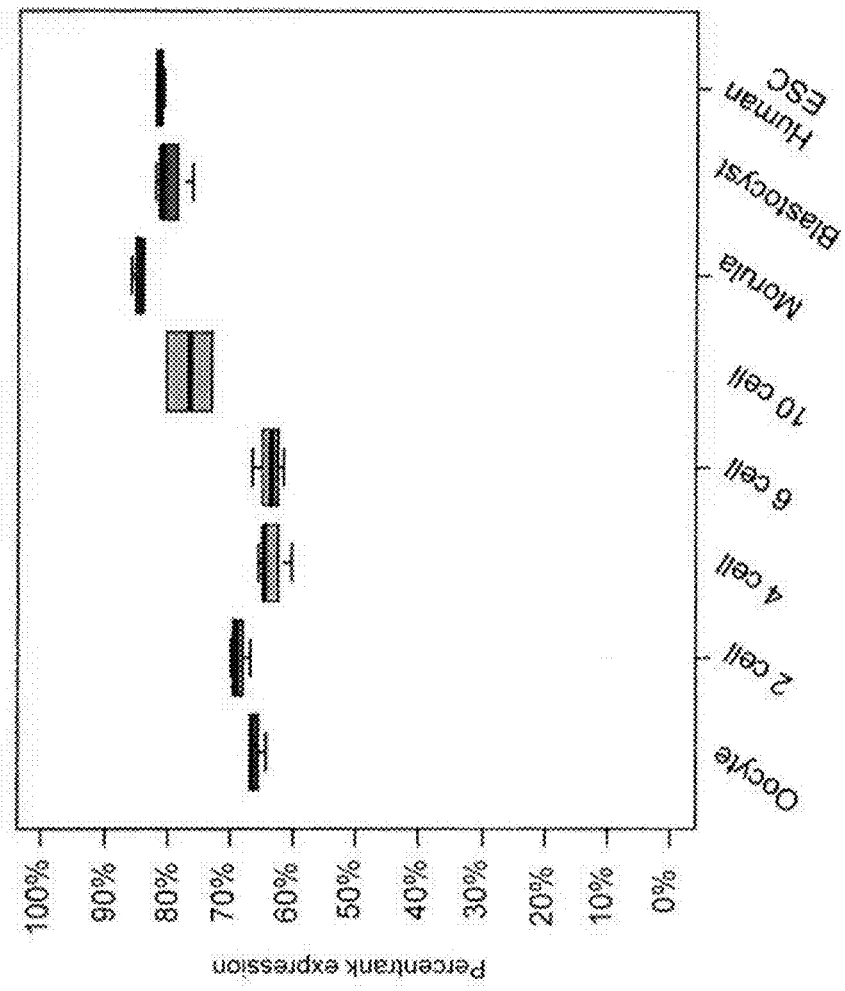

FIGS. 35A-C depict transcriptional expression of Mbd3 during pre-implantation development. FIGS. 35A-B—RT-PCR analyses demonstrating the expression of Mbd3 (FIG. 35B) and Nanog (FIG. 35A) during early mouse development, presented as a relative quantification column scheme. Error bars indicate s.d. of biological triplicates. Mbd3 transcript is detected at low levels in oocytes while Mbd3 protein is readily detected by immunostaining in oocytes and zygotes (FIGS. 36A-D and FIGS. 1O-T), consistent with maternal inheritance. Mbd3 transcription becomes increased towards the end of pre-implantation development at the morula and blastocyst stages, consistent with re-expression of Mbd3 protein in late blastocyst stage (FIGS. 1O-T). FIG. 35C—Relative transcriptional levels of MBD3 in human pre-implantation embryos based on available repository transcriptional measurements in early human developing embryos [intranet (dot) cmrb (dot) eu/Human_embryos/home.html], and showing a similar trend to that measured in mouse embryos. These data show that Mbd3 transcription is increased at late stages of pre-implantation development, consistent with protein immunostaining data showing prominent expression at late blastocyst stage (FIGS. 1O-T).

Figures 36I, 36J:
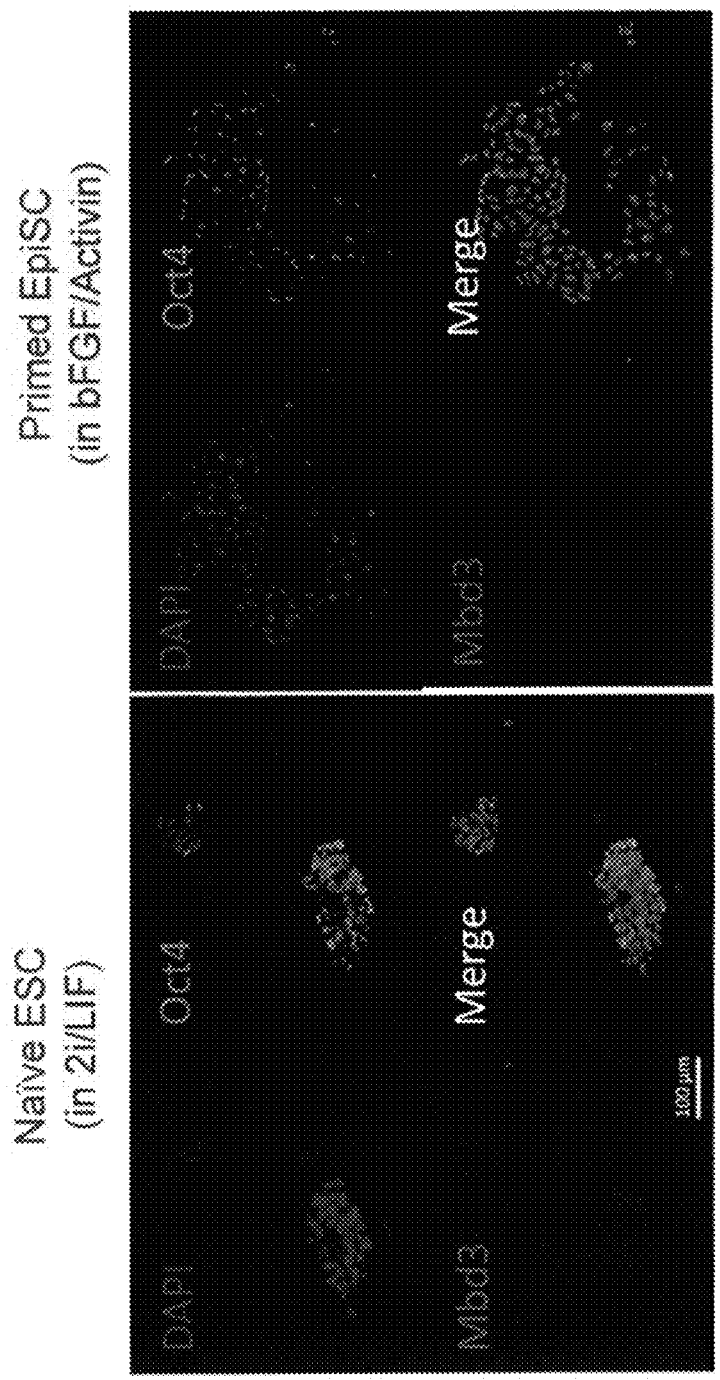

FIGS. 36A-J depict immunostaining analysis for Mbd3. FIGS. 36A-D—Immunostaining for Mbd3 in mouse oocytes, indicating maternal inheritance of Mbd3. FIGS. 36E-H—Immunostaining for Mbd3 and lineage markers in E5.5 post-implantation epiblast, indicating prominent expression as seen in late-blastocyst stage (FIGS. 1O-T). FIGS. 36I-J—Immunostaining analysis for Mbd3, showing prominent nuclear expression in pluripotent cells expanded in defined naive and primed growth conditions. These results exclude perturbation for nuclear localization of Mbd3 protein in naive 2i/LIF conditions.

Figures 37A, 37B, 37C:
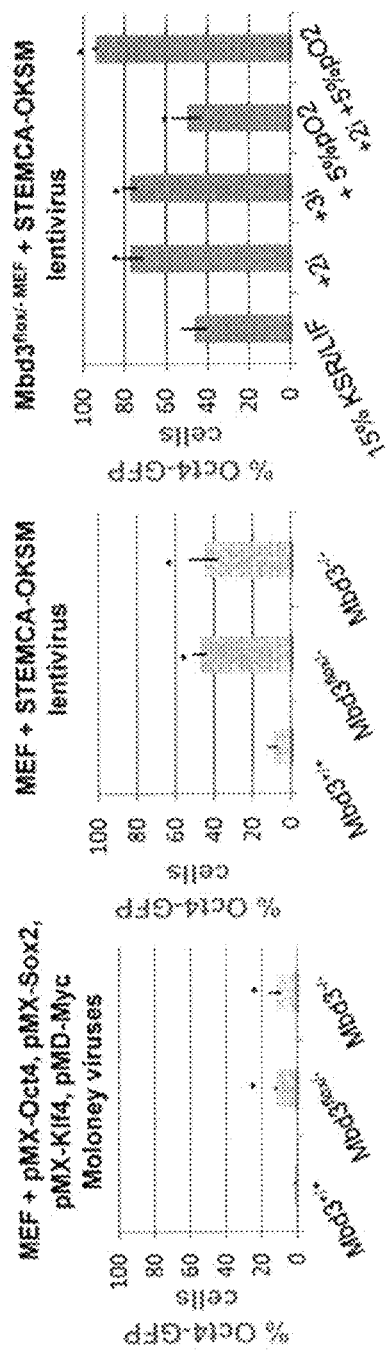

FIGS. 37A-C depict comparative analysis of Mbd3 depleted somatic cell properties during reprogramming. FIG. 37A—Reprogramming efficiency following infection with indicated MEF lines with moloney retroviruses encoding individual factors. FIG. 37B—Reprogramming efficiency following infection with indicated MEF lines with polycistronic OKSM encoding lentivirus. FIG. 37C—Mbd3$^{flox/-}$ MEFs were infected with polycistronic OKSM vector in LIF containing ES medium with or without the indicated exogenous supplements. * Indicates student t-test p value <0.01 relative to Mbd3$^{+/+}$ control. Reprogramming efficiency was evaluated by Oct4-GFP levels on day 9 following transduction without cell splitting during the process.

Figures 38A, 38B:
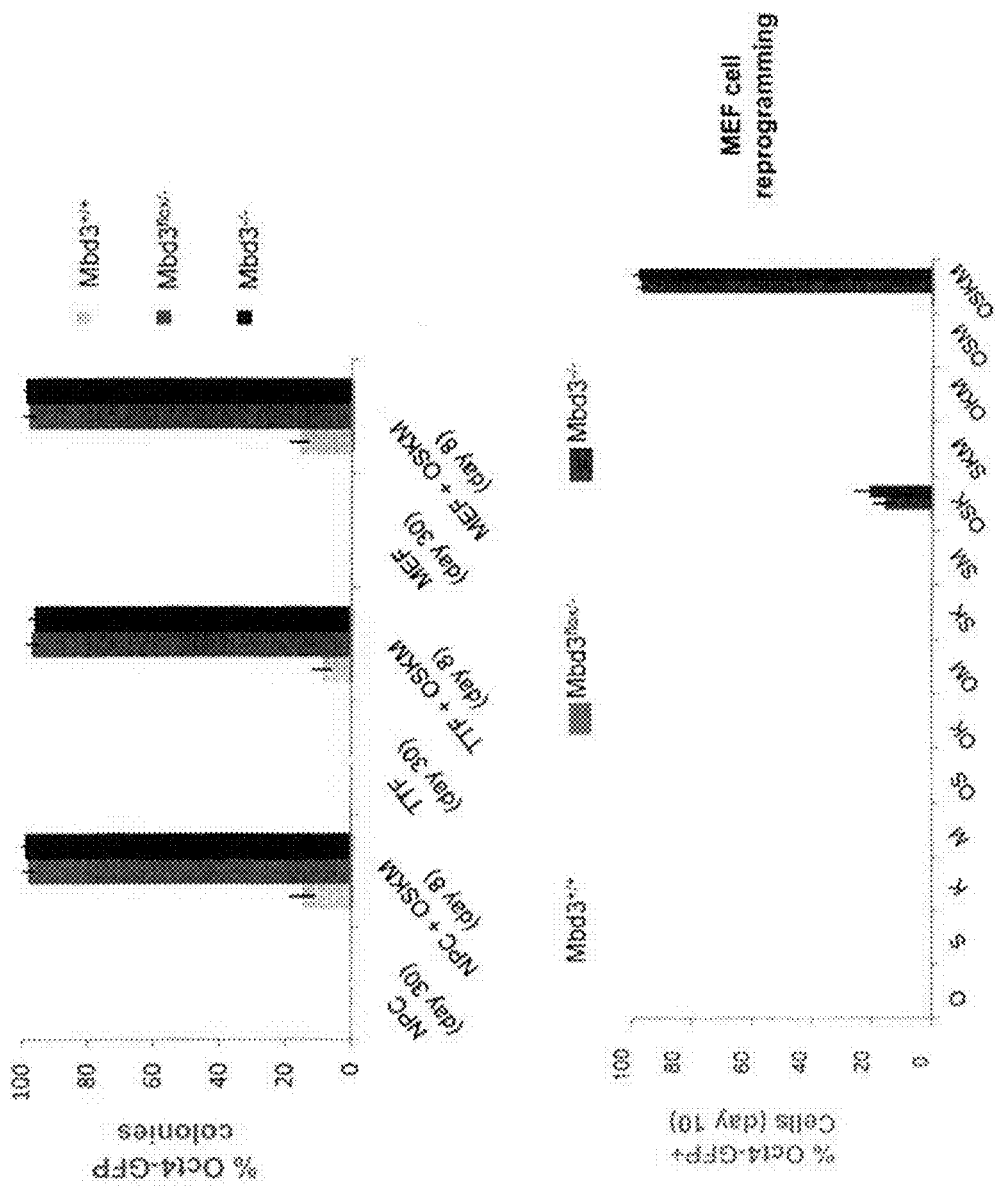
Figures 40D, 40E:
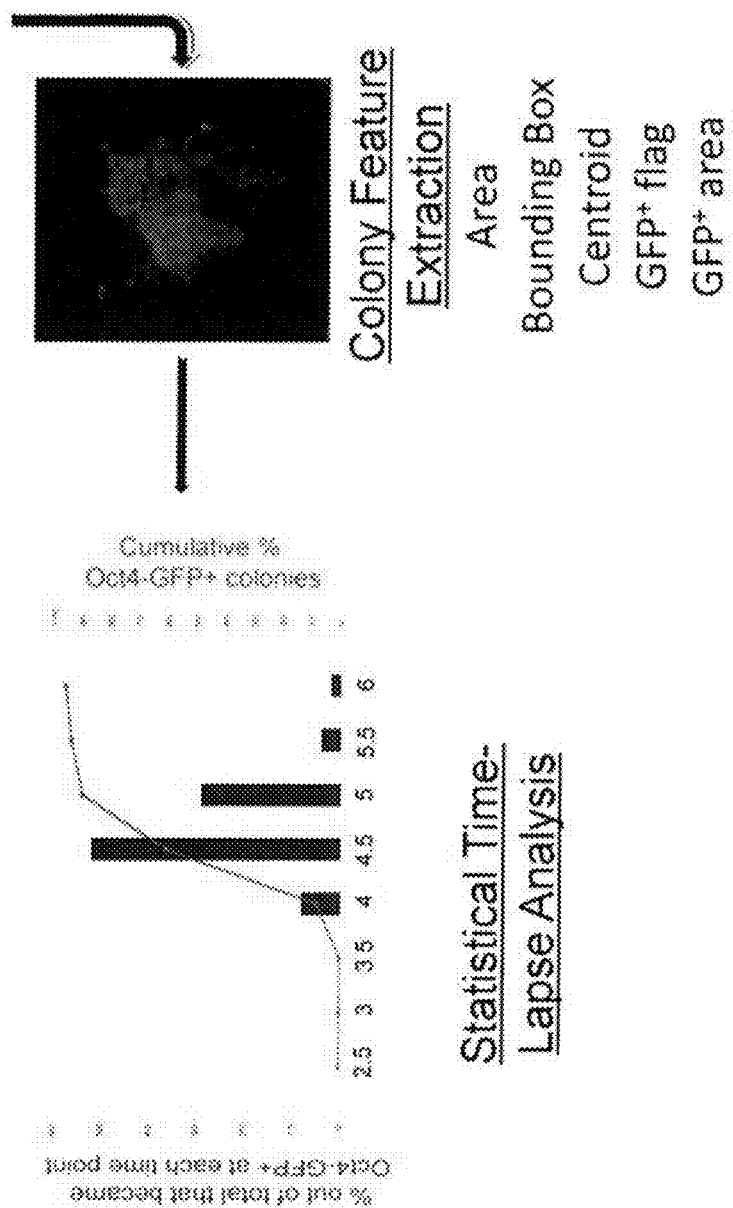

FIGS. 38A-B show that Mbd3 depletion renders deterministic and radically efficient reprogramming of multiple adult somatic cell types. FIG. 38A—Mbd3$^{+/+}$, Mbd3$^{-/-}$ and Mbd3$^{flox/-}$ MEFs, adult tail tip derived fibroblast (TTF) and neural precursor cells (NPC) were tested for iPSC formation in 2i/LIF with or without OKSM lentiviral transduction.

This analysis indicates that OKSM is essential for iPS formation, and that Mbd3 depletion alone is not sufficient to reprogram any of these cells types to pluripotency (even after 30 days of follow up). FIG. 38B-Reprogramming efficiency of MEFs following transduction with the indicated combinations of reprogramming factors at day 10. Polycistronic lentiviral vectors were used for OSK and OSKM combinations. Error bars indicate s.d. of replicate samples.

FIGS. 39A-D depict teratoma formation by Mbd3$^{-/-}$ iPSCs. FIGS. 39A-C—Randomly selected Mbd3$^{-/-}$ iPSC clones (clones 1, 2, and 3) were expanded and injected subcutaneously in immunodeficient mice. All lines generated teratomas containing differentiated cells from the three germ lineages (mesoderm, endoderm and ectoderm). These results are consistent with results obtained from Mbd3$^{-/-}$ ESCs (Kaji et al. development 2007). The latter cells (without reconstitution of Mbd3 expression) have restricted developmental potential when it comes to formation of high-contribution chimeras, but can for differentiated teratomas (Kaji et al. development 2007). Further, note that Mbd3$^{flox/-}$ somatic cells also reprogram with 100% efficiency, and adult chimeras can be obtained with germ-line transmission without exogenous overexpression of Mbd3. From the technical perspectives, Mbd3 small molecule inhibitors will hopefully be discovered in the future, as they will allow easier regulation of Mbd3 expression and activity without genetic manipulations during reprogramming and differentiation. FIG. 39D—Mbd3$^{-/-}$ iPSCs can retain normal karyotype (40) after expansion in 2i/LIF defined conditions. P indicates passage number.

FIGS. 40A-E depict time-lapse live microscopic imaging and tracking of cell reprogramming. Schematic representation of the main steps of automated segmentation protocol. This protocol was used to automatically analyze time-lapse full well mosaic data, measured for two fluorescent wavelengths. The main protocol steps include: filtering plate margins, applying adaptive detection for each channel and time point, isolating dense colonies using specific morphological filter, clustering using low-pass-filter (LPF) and connected components clustering, extracting colony information and Oct4-GFP activation information per colony and conducting statistical analysis over all time-points information (see methods).

FIGS. 41A-D depict time evolution of mCherry and Oct4-GFP reactivation in full well mosaic (FIG. 41A) and 3 representative single Mbd3$^{flox/-}$ colonies (FIGS. 41B-D) out of approximately 100 colonies tracked.

Figure 42D:
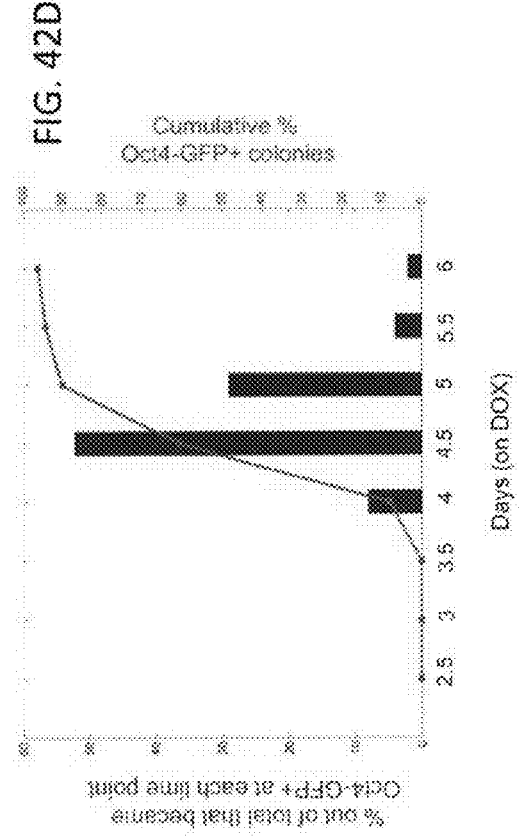
Figure 42E:
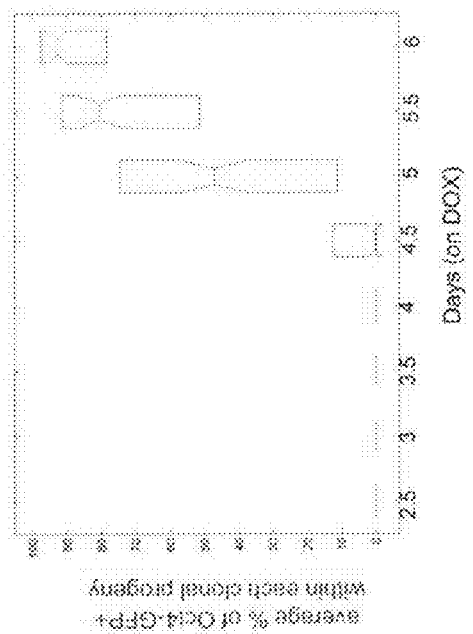
Figure 42A:
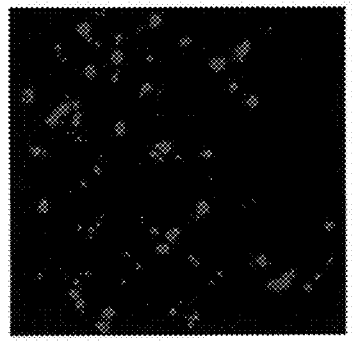
Figure 42B:
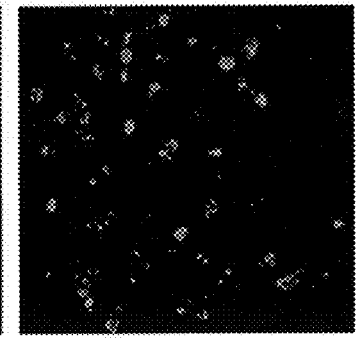
Figure 42C:
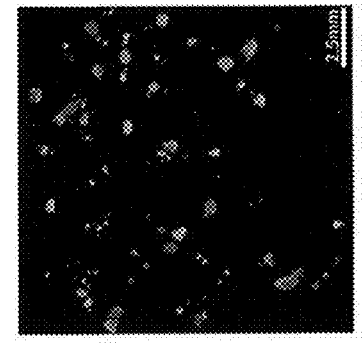

FIGS. 42A-E—Time-lapse live imaging of deterministic iPSC reprogramming. FIGS. 42A-C—Full well mosaic images of mCherry (FIG. 42A), Oct4-GFP (FIG. 42B) and combined channels (FIG. 42C) at day 6 following DOX in 2i/LIF 5% pO$_2$ conditions. ES-like mCherry+ colonies are abundant and co-localize with Oct4-GFP signal in Mbd3$^{flox/-}$ cells. FIG. 42D—Cumulative distribution of Oct4-GFP+ colonies (red graph) and density function of Oct4-GFP+ activation (blue bar plot) for Mbd3$^{flox/-}$, statistics were analyzed from all detected colonies (approximately 100 segmented colonies per well). Results show a very narrow window of synchronized Oct4-GFP activation around day 4.5, more than 50% of the colonies reactivated Oct4-GFP at 0.5 day interval. One representative experiment is shown out of 4 performed. FIG. 42E—Box-plot graph showing the distribution of intra-colony progeny Oct4-GFP activation (which is the ratios of Oct4-GFP+ & mCherry+ pixels out of all mCherry+ pixels within each segmented colony), as a function of time after induction, Box plot centers indicate the median values, and box edges indicate the 25$^{th}$ and 75$^{th}$ percentiles. Statistics were calculated from 100 segmented colonies (all detected colonies). At day 6, 95% of Mbd3$^{flox/-}$ colonies have more than 85% Oct4-GFP positive progeny cells.

FIGS. 43A-B depict radically enhanced Oct4-GFP reactivation and iPSC formation. Flow cytometry measurements of Oct4-GFP reactivation dynamics in 2i/LIF following DOX (OSKM) induction in Mbd3$^{flox/-}$ (FIG. 43B) or Mbd3$^{+/+}$ (FIG. 43A) cells. Mbd3$^{flox/-}$ secondary cells synchronously and rapidly reactivate Oct4-GFP by day 7 in the entire donor cell population. Importantly, wells at the indicated time points were harvested for analysis without prior passaging and splitting during the reprogramming course. 1 out of 3 independent experiments is shown. (FSC forward scatter). Note the dramatic reactivation of Oct4-GFP occurring in the narrow time window at days 4-5, as also seen in microscopic time-lapse live imaging measurements.

FIGS. 44A-B depict characterization of the effect for Mbd3 expression reconstitution during deterministic reprogramming of somatic cells to pluripotency. FIG. 44A—Scheme demonstrates experimental strategy for defining the temporal ability of Mbd3 during reprogramming to inhibit iPS formation. FIG. 44B-Secondary OSKM reprogrammable Mbd3$^{flox/-}$ MEFs were tested for their amenability to reprogramming following over-expression of Mbd3, Mbd2 or empty FUW lentiviruses at different time points during reprogramming. Mbd2 or mock-vector transfection, did not result in a decrease in iPSC reprogramming efficiency. Introducing Mbd3 drastically reduced iPSC formation when delivered before day 5 in reprogramming. 1 out of 2 representative experiments is shown. Average of duplicates is shown per condition. Error bars indicate s.d.

Figure 45A:
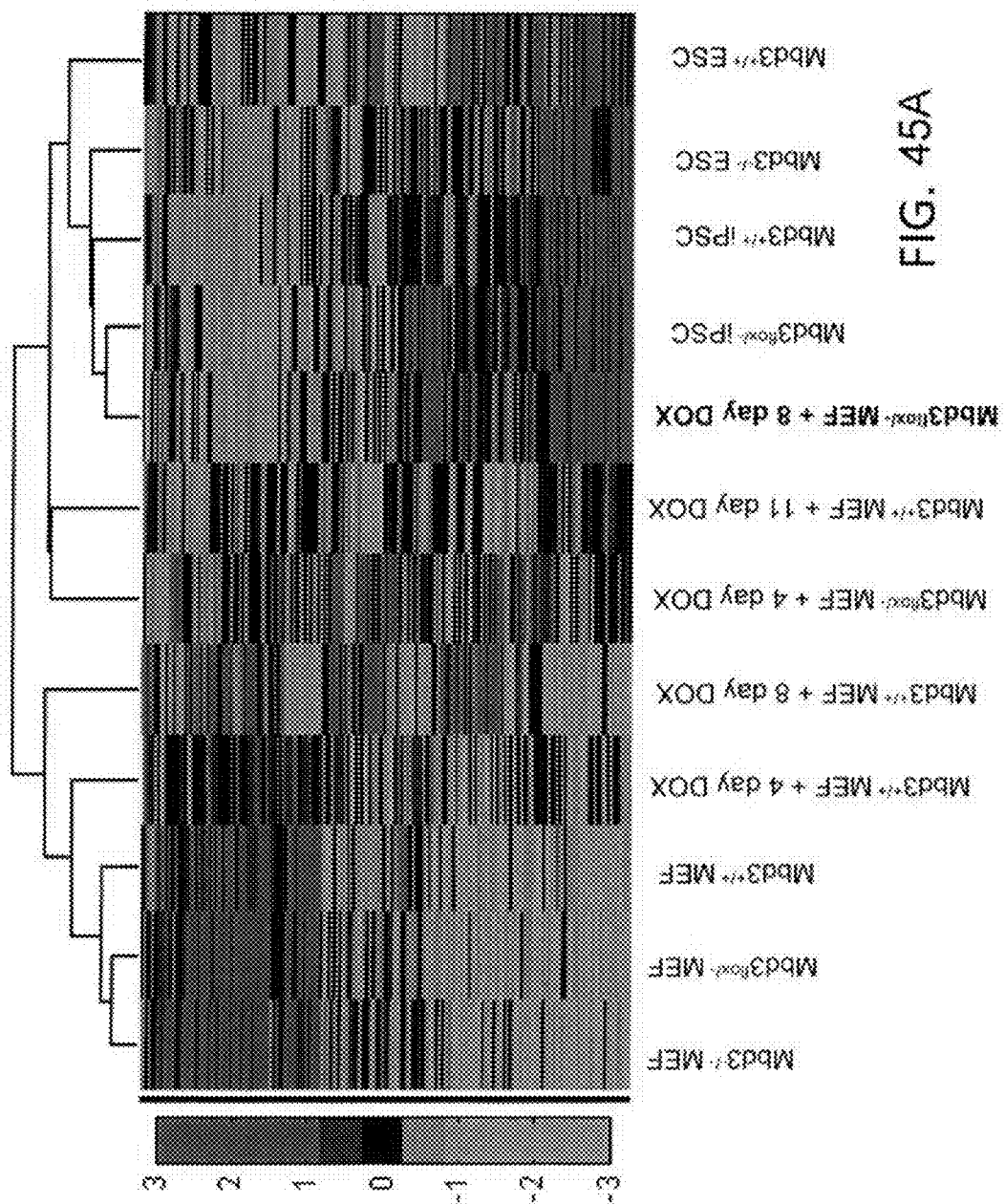
Figure 45B:
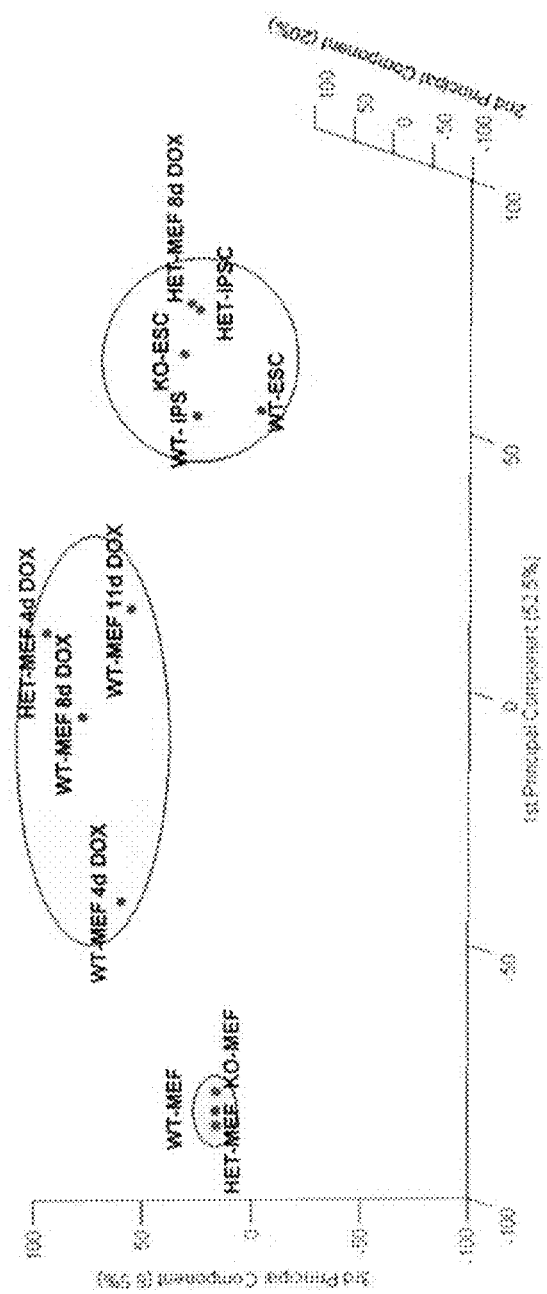

FIGS. 45A-B depict gene expression analysis during iPSC reprogramming following Mbd3 depletion. FIG. 45A—Gene expression was measured in donor fibroblasts before and after DOX induction and compared to established pluripotent iPSCs and ESC lines. Clustering of full gene signature (16,620 genes) by hierarchical clustering using Spearman correlation as a distance metric and average linkage. Results show that Mbd3$^{flox/-}$, but not Mbd3$^{+/+}$, MEFs clustered differently from donor somatic MEFs only after 4 days of OKSM (DOX) induction. By day 8, Mbd3$^{flox/-}$ cells were transcriptionally indistinguishable from established ESCs and iPSCs line. Mbd3$^{+/+}$ population cluster with Mbd3$^{flox/-}$ 4 day cells even after 11 days of longer reprogramming, and did not cluster with pluripotent ESCs-iPSC lines. FIG. 45B-Clustering of the full gene expression signature (16,620 genes) by principle component analysis (PCA) that detects the principle components with the largest variation in the data. Plotted principle components explain more than 80% of data variation. Samples in each colored ellipse show similar dynamics, where Mbd3$^{flox/-}$ 8 day cells are transcriptionally indistinguishable from established ESC and iPSC lines. (KO=Mbd3$^{-/-}$, HET=Mbd3$^{flox/-}$, WT=Mbd3$^{+/+}$).

FIGS. 46A-E depict gene expression pattern changes during iPSC reprogramming. Single gene expression progression describes the extent to which each gene reaches its expression value in iPSC. These values were quantified using the following transformation $$\hat{X}_j(t) = \max\left(\frac{X_j(t) - X_j(\text{MEF\_Mbd3}^{+/+})}{\overline{X}_j(IPS) - \overline{X}_j(MEF)}, 0\right)$$

Figure 46C:
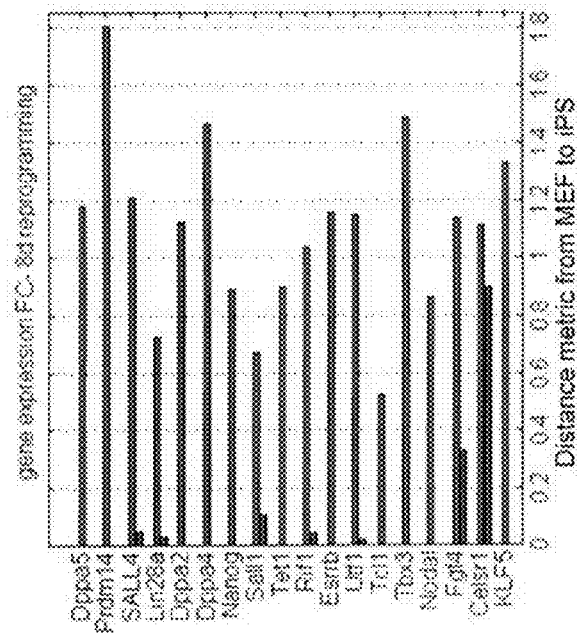
Figure 46A:
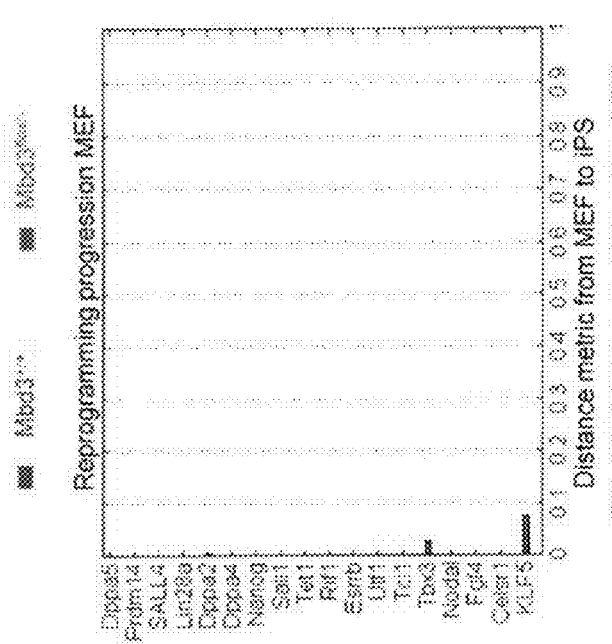
Figure 46B:
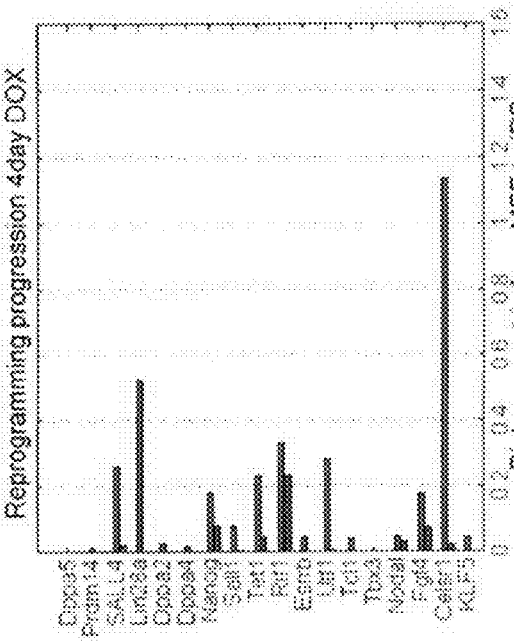
Figure 46E:
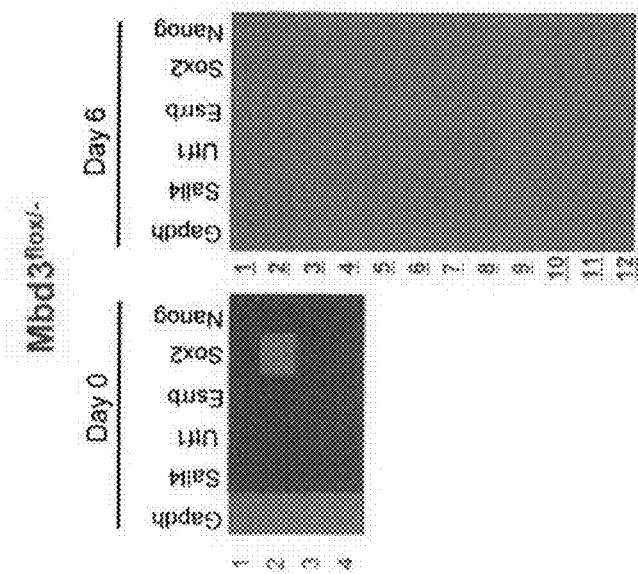
Figure 46D:
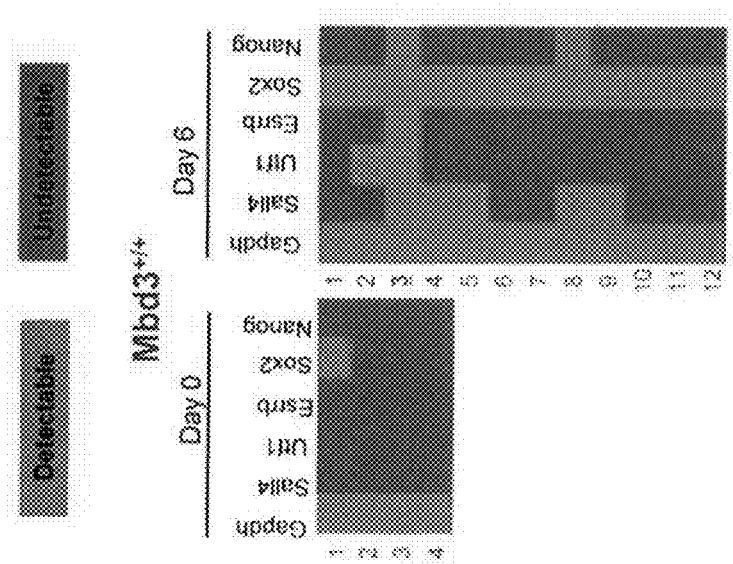

This transformation represents a distance from MEF expression values (set to 0) towards iPS values (set to 1). Selected group of pluripotency related genes or selected targets of Mbd3, are plotted in different time points after DOX induction. Red bars represent progression of gene expression in Mbd3$^{flox/-}$ and blue bars represent progression of gene expression in Mbd3$^{+/+}$. FIG. 46A—Absence of initial transcription of bona fide pluripotency genes can be seen in MEF samples (both Mbd3$^{flox/-}$ and Mbd3$^{+/+}$). FIG. 46B—Fast induction of multiple pluripotency related genes including Sall4, Lin28a, Utf1 and Nanog can be seen 4 days after OSKM induction in Mbd3$^{flox/-}$, but not Mbd3$^{+/+}$. FIG. 46C—These genes reach their levels observed in iPS/ES cells (around 1) by day 8, in Mbd3$^{flox/-}$ but in most cases not in Mbd3$^{+/+}$. FIGS. 46D-E—Single cell qRT-PCR analysis for detection of pluripotency gene markers. Analysis was conducted on Mbd3$^{+/+}$ (FIG. 46D) and Mbd3$^{flox/-}$ (FIG. 46E) MEFs before (day 0) and 6 days after DOX induction. Genes that were expressed above detection level are marked in green (and undetected are marked in red). Only in Mbd3$^{flox/-}$ samples and only after DOX, 12/12 analyzed cells showed reactivation of all pluripotency markers tested. It is noted that endogenous Sox2 reactivation by RT-PCR is robust in 2i/LIF+DOX in WT cells, indicating that it does not stringently reflect authentic pluripotency reactivation.

Figure 47A:
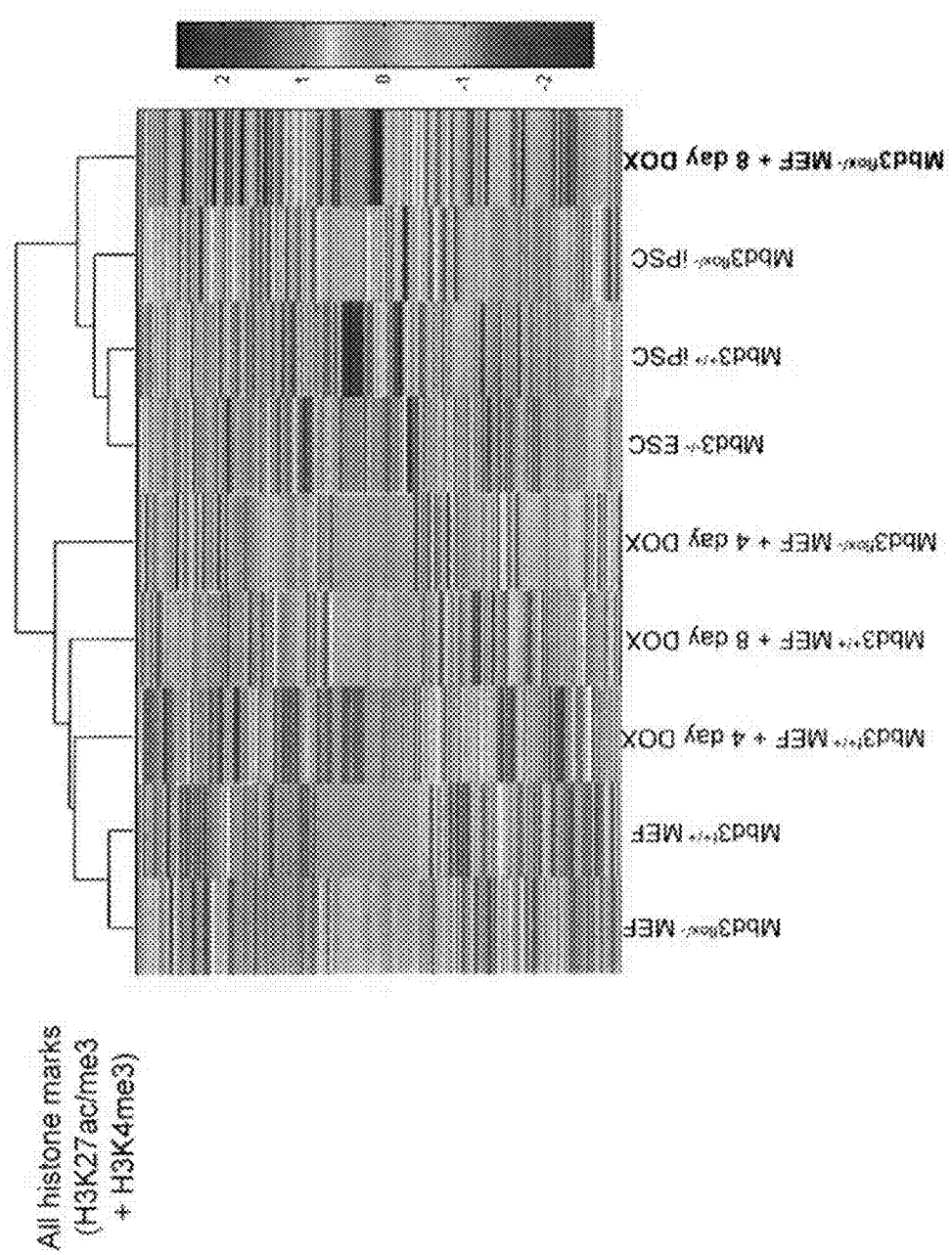
Figure 47B:
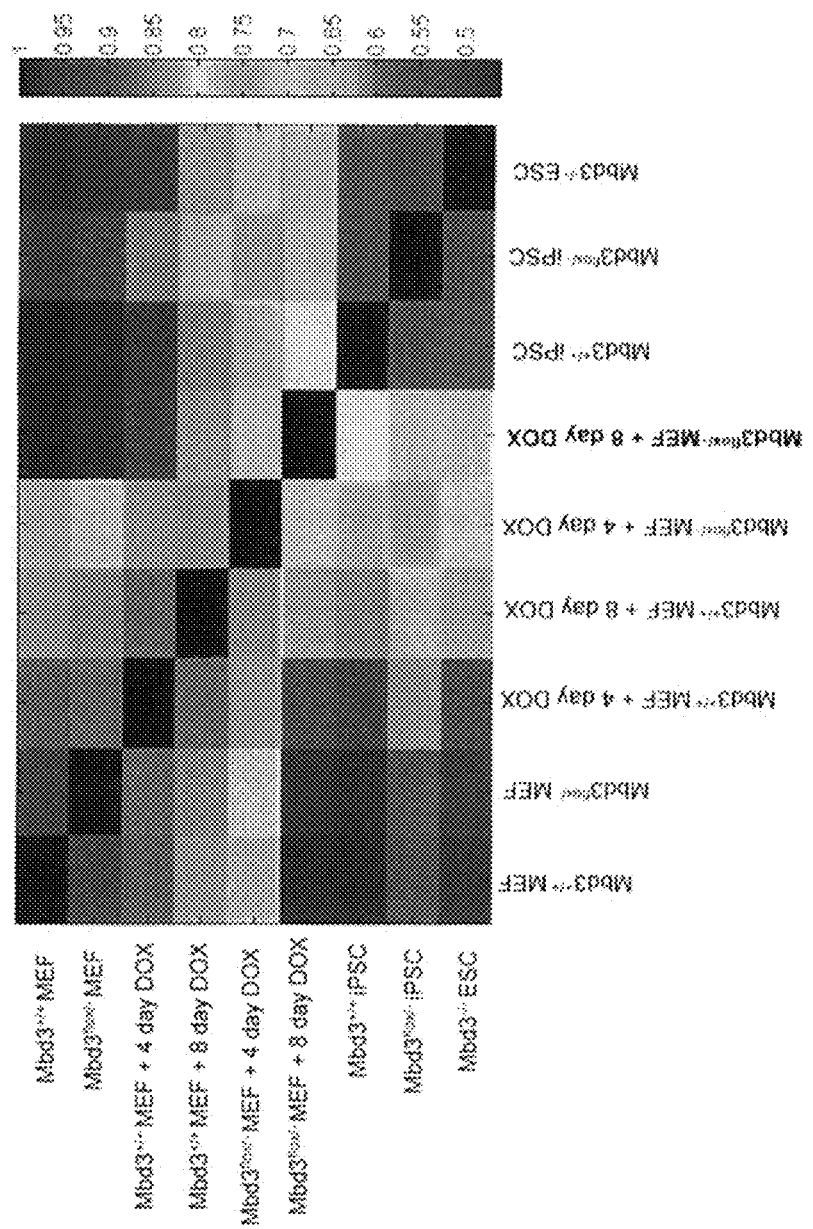

FIGS. 47A-B depict clustering of all histone marks values, as measured over differentially expressed genes. Chromatin IP-Seq (IP=Immunoprecipitation) was performed in donor fibroblasts before and after DOX induction and compared to chromatin ChIP-Seq from established pluripotent iPSCs and ESC lines. Gene profiles of H3K4me3, H3K27me3 and H3K27ac were extracted and normalized to z-score. For the current analysis the value of each gene and each histone mark was chosen as the max value of the appropriate z-score profile. Clustering was carried out on concatenate vectors including all histone marks (H3K4me3, H3K27me3 and H3K27ac) for each gene. FIG. 47A—Hierarchical clustering of H3K4me3, H3K27me3 and H3K27ac focusing on the top 1323 genes whose gene expression differentiated between wild type MEF and ESC samples (see methods). Hierarchical clustering was calculated using Spearman correlation as a distance metric and average linkage. Results show that by day 8 Mbd3$^{flox/-}$, but not Mbd3$^{+/+}$, were epigenetically similar to established ESCs and iPSCs line. FIG. 47B—Spearman correlation between the vectors described above (1323 genes with all histone marks). Here too, Mbd3$^{flox/-}$, but not Mbd3$^{+/+}$, MEFs clustered differently from donor somatic MEFs only after 4 days of OKSM (DOX) induction. By day 8, Mbd3$^{flox/-}$ cells show epigenetic signature that strongly correlates with established ESCs and iPSCs line. Mbd3$^{+/+}$ population does not show strong correlation with pluripotent ESCs-iPSC lines even after 8 days of reprogramming.

Figure 48A:
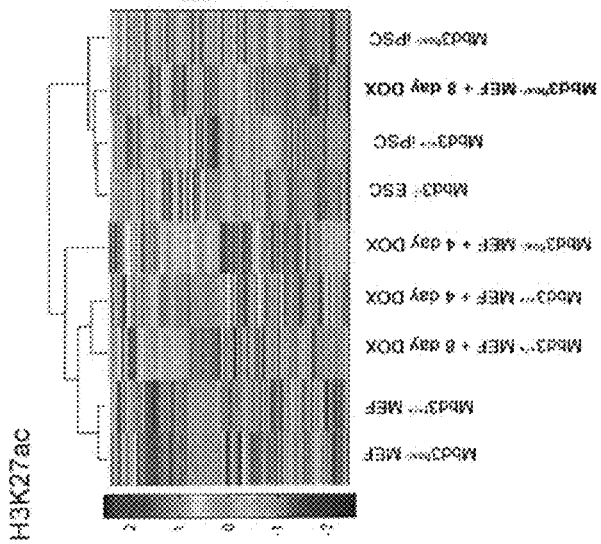
Figure 48B:
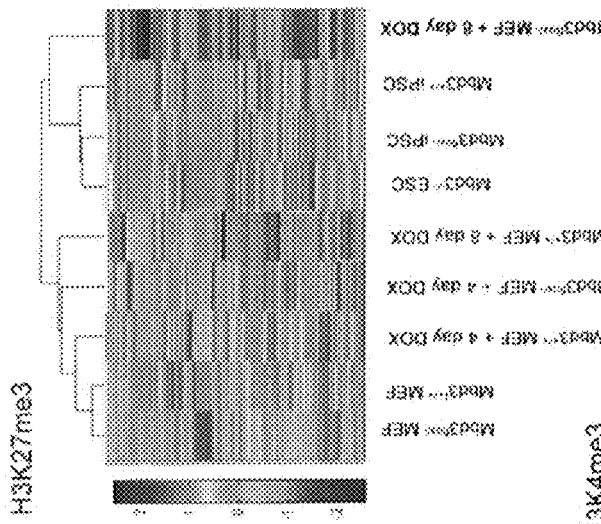
Figure 48C:
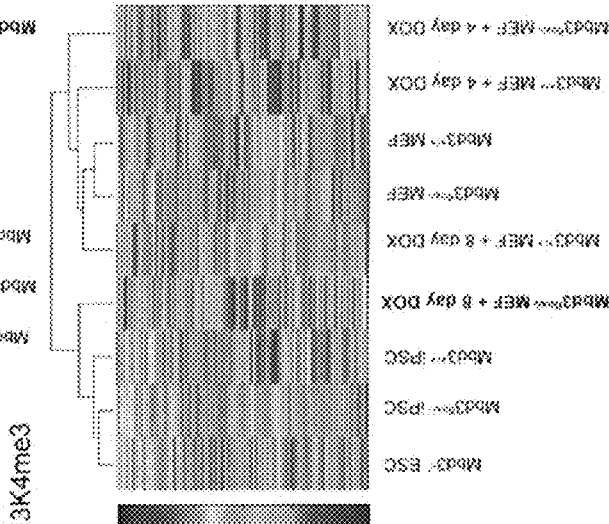

FIGS. 48A-C depict clustering of each histone mark separately. Hierarchical clustering of H3K27me3 (FIG. 48A), H3K27ac (FIG. 48B) and H3K4me3 (FIG. 48C) z-score values focusing on the top 1323 genes whose gene expression differentiated between wild type MEF and ES samples (see methods). Hierarchical clustering was calculated using Spearman correlation as a distance metric and average linkage. Results show that even when considering each histone mark separately, by day 8 Mbd3$^{flox/-}$, but not Mbd3$^{+/+}$, were epigenetically similar to established ESC and iPSC lines.

Figure 49A:
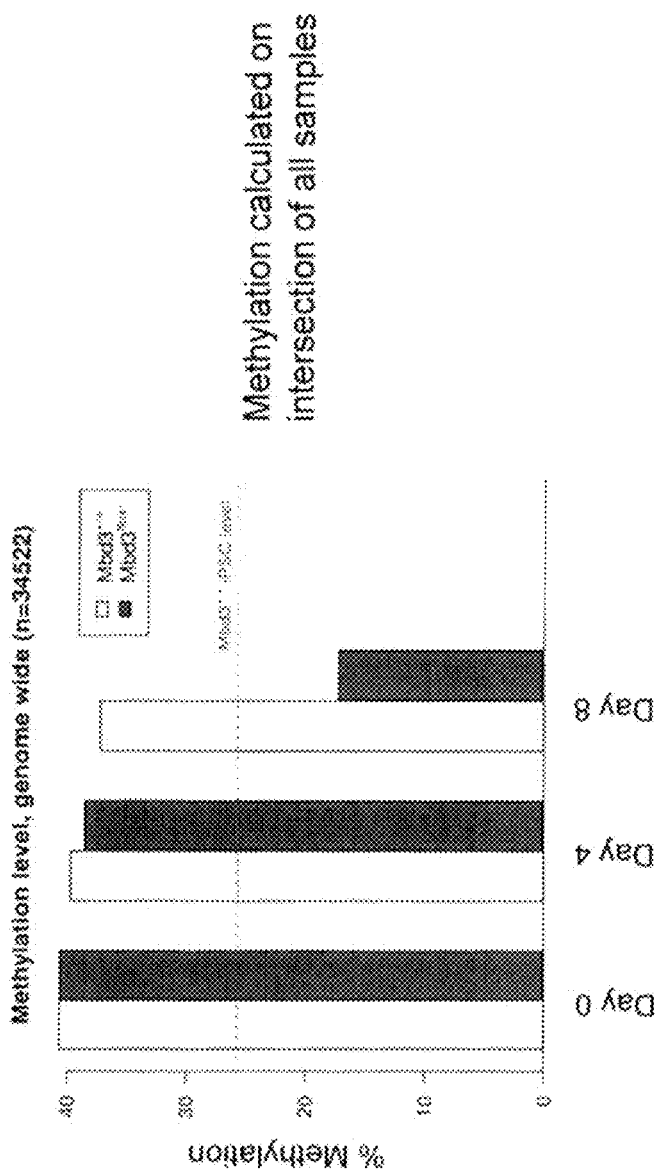
Figure 49B:
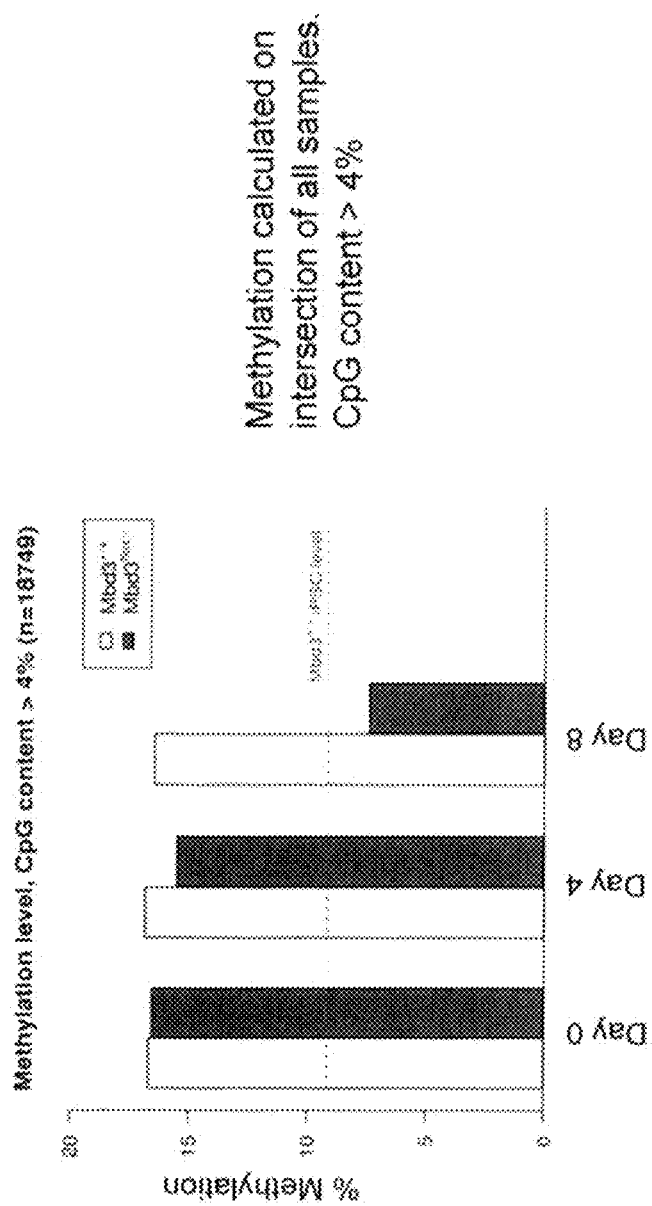

FIGS. 49A-B depict changes in DNA methylation level during deterministic reprogramming. FIG. 49A—Average level of DNA methylation drops after 8 days of OSKM (DOX) induction in Mbd3$^{flox/-}$ cells, but not in Mbd3$^{+/+}$ ones. Genome-wide methylation levels were assayed using reduced representation bisulfite sequencing (RRBS, see methods). Methylation level was calculated separately for each CpG dinucleotide and then averaged across all CpGs that were covered by 5 or more distinct sequencing reads (34,522 CpG sites in total). The average methylation level of low-passage Mbd3$^{+/+}$ iPSCs (calculated across the same set of CpGs) is provided as a dashed line for reference. FIG. 49B—The same analysis of average methylation was repeated as in (a). However only the 18,749 CpGs (out of 34,522) that reside in CpG rich areas (i.e. CpG abundance >4%) were used.

FIGS. 50A-C depict deterministic and synchronized iPSC reprogramming following Mbd3 depletion in 2i/LIF conditions. FIG. 50A—Representative examples of partially reprogrammed (Pre-iPSC lines) generated from secondary Mbd3$^{+/+}$ MEFs and expanded in 2i/LIF+DOX conditions. Note the lack of Oct4-GFP expression in mCherry+ pre-iPSC lines. Subcloned Oct4-GFP+/mCherry+ iPSC line is shown as a positive control (bottom panel row). FIG. 50B—Previously described (Mikkelsen, T. S. et al. Nature 454, 49-55, 2008) partially reprogrammed (intermediate pre-iPS) cell lines BIV1, MCV6 and MCV8 were subjected to 2 rounds of transfection with either control (scrambled) or Mbd3 siRNA and expanded in 2i/LIF conditions. Mbd3 depletion resulted in dramatic conversion of the majority of cells into pluripotent iPSCs. Error bars indicate s.d. of biological replicates. FIG. 50C—Adult chimera generated from rescued BIV1 iPSCs as evident by agouti coat color contribution.

Figure 51:
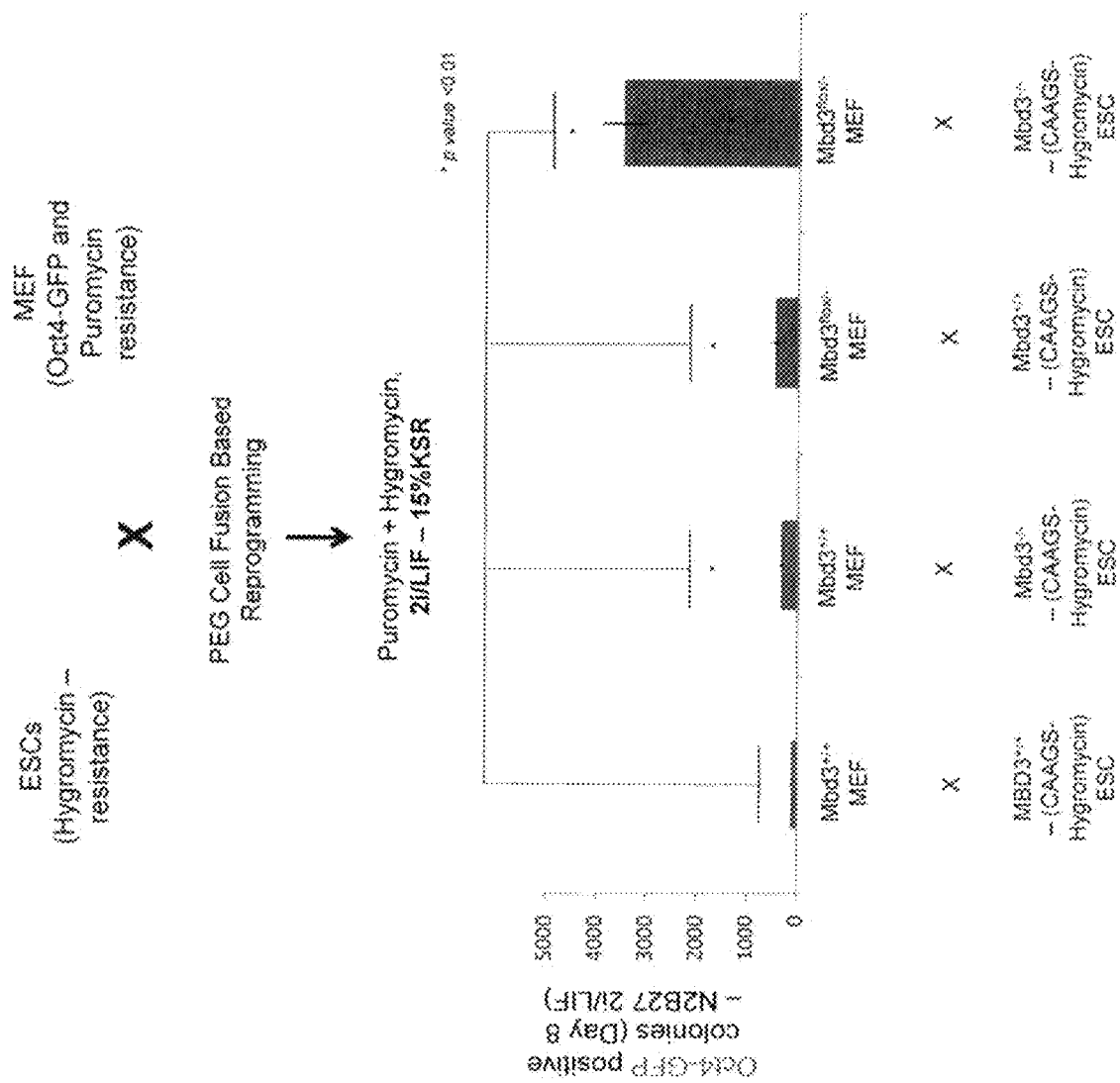

FIG. 51 depicts enhancing cell fusion based reprogramming by Mbd3 depletion in 2i/LIF conditions. Inhibiting Mbd3 expression promotes robust reprogramming to pluripotency via cell fusion reprogramming assay between somatic MEFs and ESCs. Mbd3$^{+/+}$ and Mbd3$^{-/-}$ ESCs (that do not carry Oct4-GFP reporter) were made transgenic with a construct encoding constitutive CAAGS promoter driven Hygromycin resistance cassette. Their ability to reprogram wild type of Mbd3 depleted (Mbd3$^{flox/-}$) MEFs (carrying Oc4-GFP reporter and constitutive Puromycin resistance cassette) via PEG mediated cell fusion was evaluated. PEG cells fusion was conducted and cells were incubated in Puromycin+Hygromycin to select for double resistant colonies. Reactivation of Oct4-GFP transgenes in reprogrammed MEFs in 2i/LIF condition was used to quantify cell fusion reprogramming efficiency. The results clearly indicate that depleting Mbd3 and donor and recipient cells results in radical acceleration of reprogramming somatic cells to Nanog+ pluripotency in 2i/Lif. For each of the panels, one out of 2 independently performed experiments is shown. * indicates student t-test P value <0.01. Error bars indicate s.d.

Figure 52A:
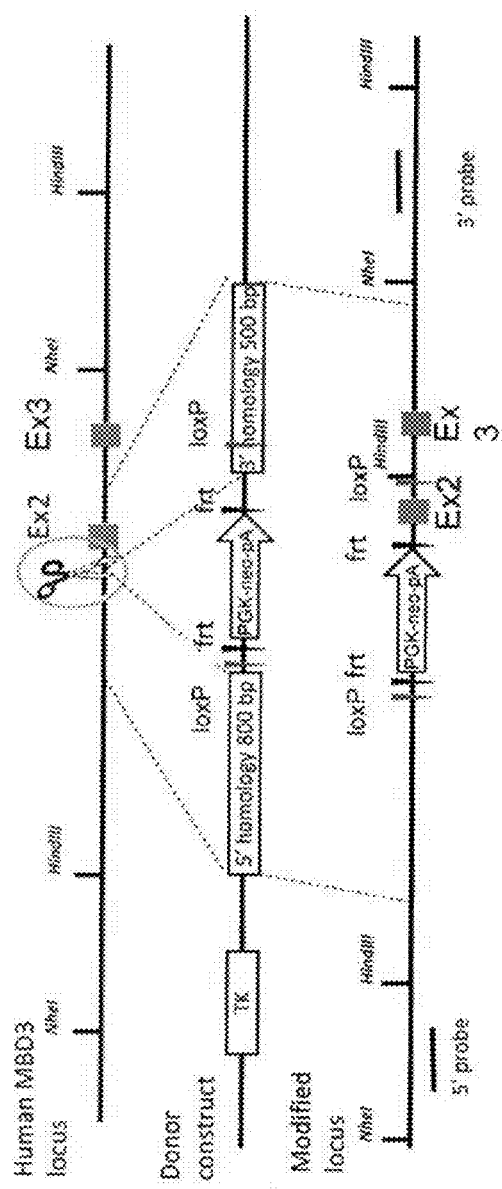
Figure 52B:
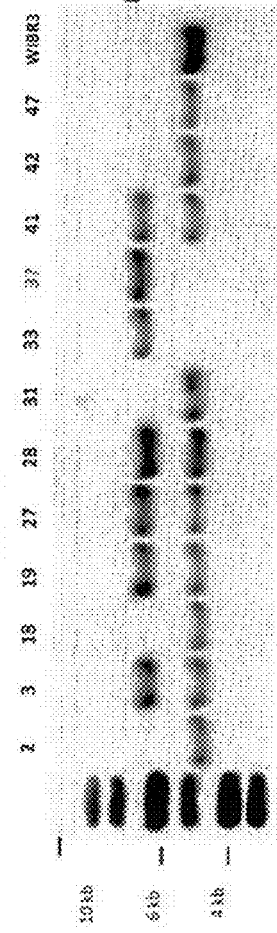
Figure 52C:
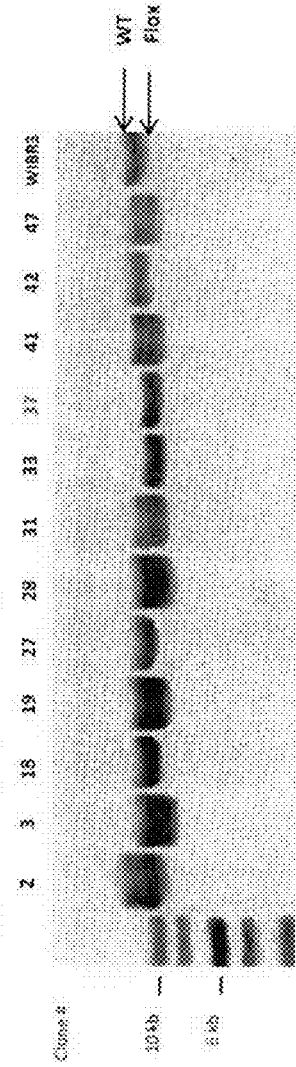

FIGS. 52A-C demonstrate TALE nuclease based targeting of MBD3 locus in human pluripotent cells. FIG. 52A—Schematic overview depicting the targeting strategy for generating of conditional knockout allele of MBD3 that allows excision of Exon 2 following Cre recombinase transfection. Southern blot probes are shown as black lines, exons as blue boxes. Digestion sites for NheI and HindIII are indicated. FIGS. 52B-C—Southern blot analyses following targeting of human WIBR3 hESC lines with the 5' probe (FIG. 52B) and with the 3' probe (FIG. 52C). Targeting efficiency was high and allowed isolation of clones where both alleles were correctly modified following a single round of targeting. Southern blot analysis indicates correct 5' and 3' targeting of both Mbd3 alleles in WIBR3 hESC clones #33 and #37. Clone #37 showing hypomorphic expression of MBD3 protein (FIGS. 8M-N) was selected for further experimental follow up and analysis.

Figures 53A, 53B:
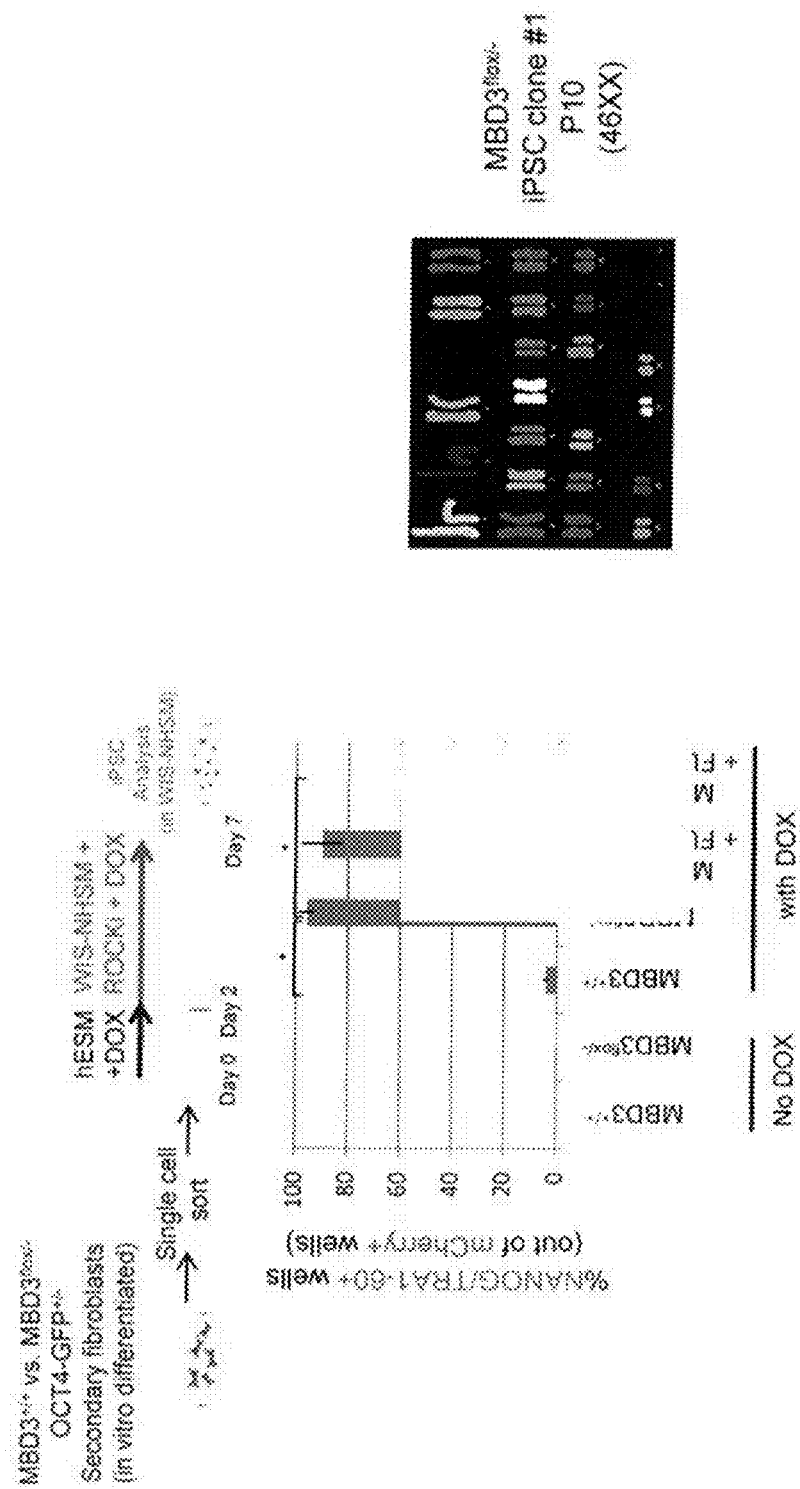

FIGS. 53A-E demonstrate that depleting Mbd3 expression facilitates human iPSC formation from in vitro differentiated fibroblasts. FIG. 53A—MBD3$^{+/+}$ and MBD3$^{flox/-}$ iPSCs carrying DOX inducible OKSM transgene were labeled with constitutively expressed mCherry and targeted with an OCT4-GFP knock-in allele[54] (Hockemeyer, D. et al. *Nat Biotechnol* 29, 731-734, 2011). In vitro differentiated fibroblasts from the latter lines were reprogrammed as indicated in the scheme. >95% of human Mbd3$^{flox/-}$ fibroblasts became NANOG/TRA1-60+ IPSCs after 8 days of transgene induction. Error bars indicate s.d. of biological replicates. * Indicates significant P value <0.001 in comparison to MBD3$^{+/+}$ samples. FIG. 53B—Normal karyotype of Mbd3$^{flox/-}$ iPSC clone maintained in WIS-NHSM growth conditions. FIG. 53C-E—Pluripotency of randomly selected iPSC clones (1, 2, and 3) as evident by teratoma formation and generation of differentiated cells form three germ lineages (mesoderm, endoderm and ectoderm).

FIGS. 54A-G demonstrate that siRNA inhibition of MBD3 promotes human iPSC reprogramming by OSKM. FIGS. 54A-B—MBD3 siRNA treatment of human primary fibroblasts allows generation of iPSCs by only two rounds of reprogramming with mRNA transfection with OSKM and LIN28 factors, (STEMGENT) and alleviates the need for many rounds of repeated mRNA transfections with pluripotency factors. Note the number of nanog+/SSEA4+ colonies at day 8 in cells treated with MBD3 siRNA, but not in cells treated with the control siRNA (FIG. 54B). FIG. 54C—Representative human iPSC clones (1 and 2) are shown at different time points and passages (P indicates passage number; day 7 and passage 11). FIGS. 54D-F—Pluripotency of randomly selected clones (1 and 2) is shown by specific staining for OCT4 and SSEA4 pluripotency markers (FIG. 54D) and teratoma formation (FIGS. 54E and 54F). FIG. 54G—Human naive cells were injected subcutaneously into SCID immune-deficient mice and formed after 4-8 weeks well differentiated teratoma tumors with differentiation into the three lineages [(endoderm (left), ectoderm (middle) and mesoderm (right)]. This indicates the cells are functionally pluripotent. These results indicate that inhibition of MBD3 expression and/or function promotes iPSC formation by transient mRNA or other transient transfection protocols for iPSC reprogramming.

Figures 55A, 55B:
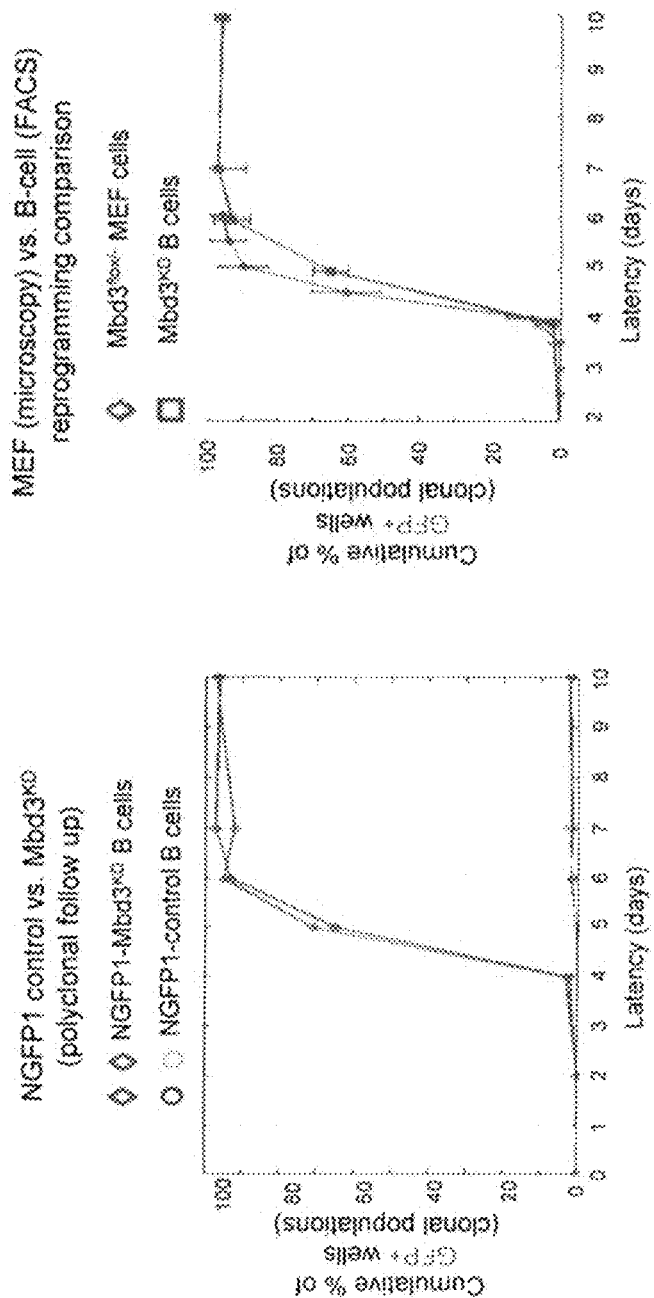
Figures 55C, 55D:
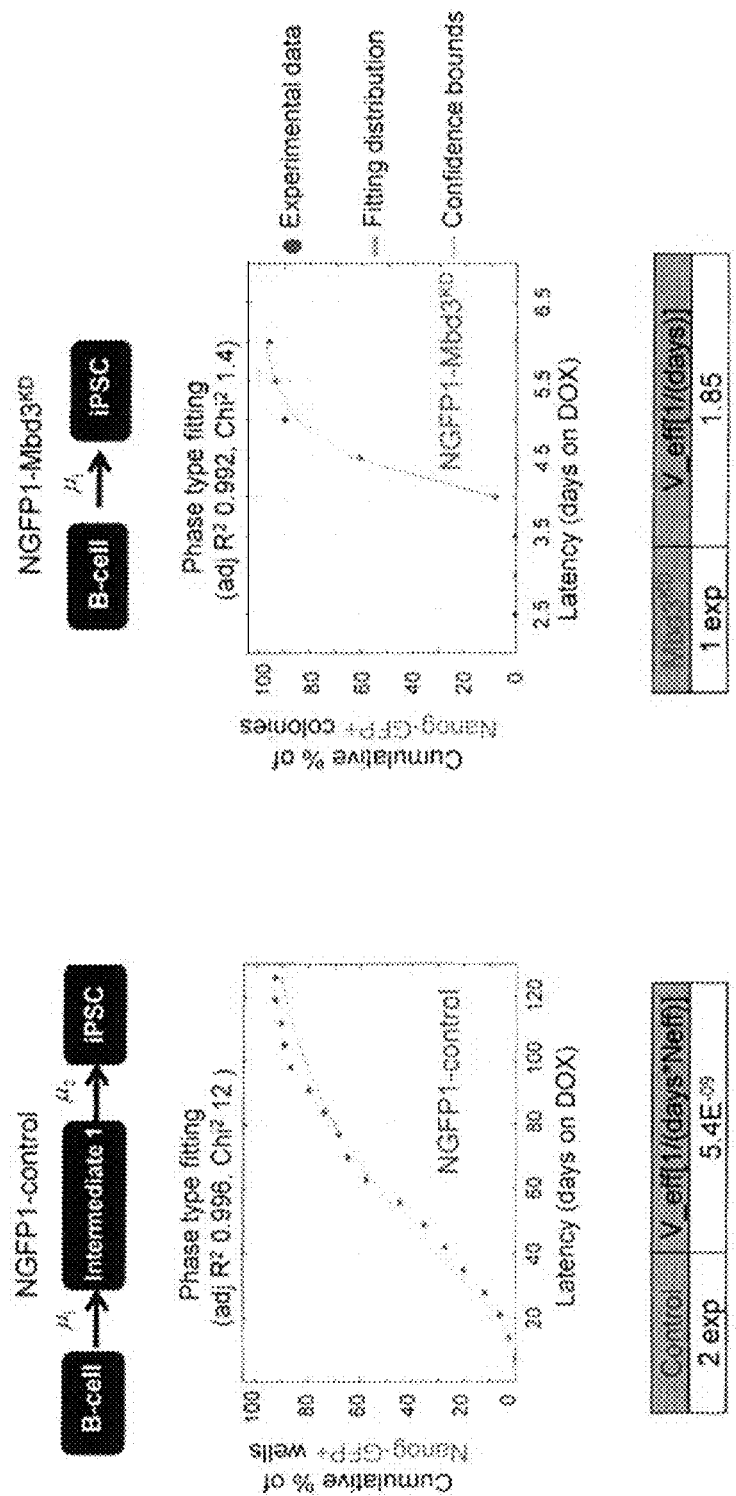

FIGS. 55A-D depict reprogramming kinetics following Mbd3 depletion. FIG. 55A—Cumulative percentage of GFP+ wells versus time (in days), measured by FACS. Two replicates of NGFP1-control and NGFP1-Mbd3$^{KD}$ measured daily over 10 days. Results show fast Nanog-GFP activation of >95% of NGFP1-Mbd3$^{KD}$ cells between day 4 and 6. FIG. 55B—NGFP1-Mbd3$^{KD}$ pre-B cells reprogramming measured by FACS and Mbd3$^{flox/-}$ MEFs reprogramming measured by microscopy live imaging show similar kinetics. Graph values indicate the mean and error bars indicate standard deviation calculated over 4 MEF replicates and 2 B-cell replicates. FIGS. 55C-D—NGFP1-control (FIG. 55C) and NGFP1-Mbd3$^{KD}$ (FIG. 55D) reprogramming latencies (measured in days), fitted to multiple tandem rate limiting step models. FIG. 55C (middle) Fitting plot of NGFP1-Mbd3$^{+/+}$ to multi-phase process with two exponential transitions and single intermediate state. FIG. 55D (middle)—Fitting plot of NGFP1-Mbd3$^{KD}$ to single exponential transition with no intermediate states. Fitting was done using both nonlinear regression with adjusted $R^2$ statistic and weighted nonlinear fit by chi$^2$ minimization (see details in methods). Note that NGFP1-Mbd3$^{+/+}$ fits poorly to a single transition process and best fits to a process with 1-2 intermediates phases (FIGS. 56A-F, 57A-D). NGFP1-Mbd3$^{KD}$ on the other hand, fits optimally to single exponential transition with no intermediate states (adj $R^2$=0.992). The reprogramming rate as calculated from the transition rate of the model fit is indicated at the bottom of the panels. Note that the rates are scaled differently due to differences in measurements of polyclonal and monoclonal assays (see methods).

Figures 56A, 56B:
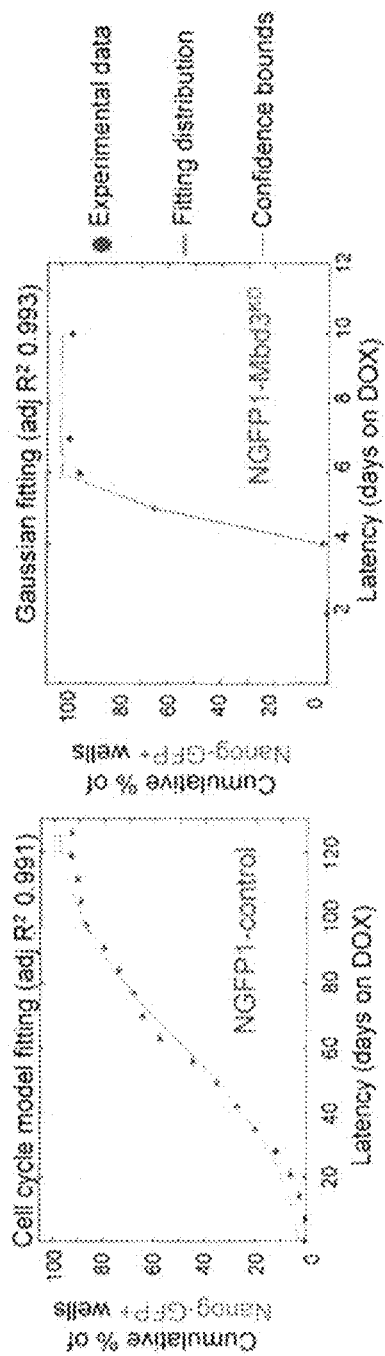

FIGS. 56A-F depict statistical analysis using Gaussian distribution. NGFP1-control and NGFP1-Mbd3$^{KD}$ reprogramming latencies were fit to Gaussian distribution. FIGS. 56A-B—Goodness of fit plots for fitting of NGFP1-Mbd3$^{+/+}$ (FIG. 56A) and NGFP1-Mbd3$^{KD}$ (FIG. 56B) to Gaussian distribution. FIG. 56C-D—Graphs showing 12-fold reduction in average reprogramming time (FIG. 56C), and 80-fold reduction in Mbd3$^{KD}$ standard deviation (FIG. 56D). FIGS. 56E-F—Graphs showing synchronized transformation from somatic state to iPS after 6 cell cycles (FIG. 56E) with variability (standard deviation) less than half cell cycle (FIG. 56F). Error bars represent 95% confidence intervals for the parameters, as estimated by maximum likelihood.

Figures 57A, 57B:
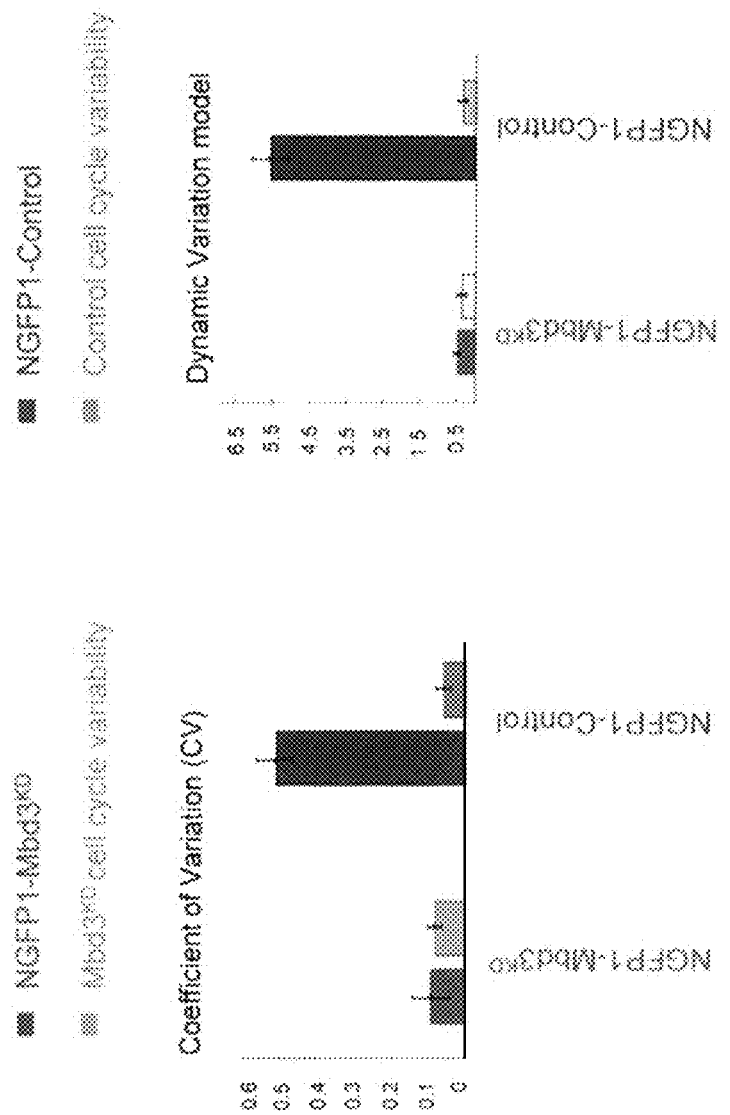

FIGS. 57A-E depict quantification of iPSC reprogramming after integrating cell cycle variability. The variability observed in the reprogramming latency measurements was quantified and further compared to the inherent cell cycle variability. FIG. 57A—The coefficient of variation (CV=std/mean) of each sample (Mbd3$^{KD}$ and Mbd3$^{+/+}$, dark red and blue colors) was compared with the coefficient of variation of the cell cycle measured for that sample (light red and blue colors). The graph shows that while the coefficient of variation in the Mbd3$^{+/+}$ sample is 0.5, the Mbd3$^{KD}$ coefficient of variation is reduced to 0.09, tightly proximal to the cell cycle estimated coefficient of variation (0.08). Error bars represent 95% confidence intervals for the coefficient of variation, as estimated by maximum likelihood and calculated by propagation of error (see methods). FIG. 57B—Using a Brownian motion (BM) model, the present inventors have estimated the dynamic variability for each sample (see methods). This variability is the ratio of the Brownian motion standard deviation ($\sigma$) divided by the Brownian motion drift parameter ($v$), where $\sigma/v>1$ corresponds with a high variability dynamics. The present inventors show that while the dynamic variability in the Mbd3$^{+/+}$ sample is $\sigma/v>5$, the Mbd3$^{KD}$ and cell cycle measurements show both a dynamic variation of $\sigma/v\approx0.5$. Error bars represent 95% confidence intervals for the coefficient of variation, as estimated by maximum likelihood and calculated by propagation of error (see methods). FIG. 57C—Illustration of the first passage time model. In this Brownian motion (BM) model, the present inventors assume that reprogramming time depends on the first time in which some master regulator (i.e. Nanog or Oct4) transient from their low inactive state to high expression state by passing a fixed expression threshold. FIGS. 57D-E—The present inventors have then fitted the cell cycle time distribution (see methods) to the observed reprogramming latency. By this method the present inventors show a perfect fit ($R^2$=0.999) between the Mbd3$^{KD}$ dynamic and cell cycle model (FIG. 57E), but not in the control Mbd3$^{+/+}$ dynamics ($R^2$=0.73) (FIG. 57D).

FIGS. 58A-D depict modeling of a multiple rate-limiting process in the context of iPSC reprogramming. NGFP1-Mbd3$^{+/+}$ and NGFP1-Mbd3$^{KD}$ reprogramming latencies were fit to multiple tandem rate limiting step models. Each experimental dataset was tested against models with 1 to 5 exponential transitions. Fitting was done with nonlinear regression and adjusted $R^2$ statistic (see methods). FIG.

58A—Fitting of NGFP1-Mbd3$^{+/+}$ to single exponential transition with no intermediate states. Note that NGFP1-Mbd3$^{+/+}$ fit poorly (adj $R^2$=0.94) to a single transition process. FIG. 58B—Fitting of NGFP1-Mbd3$^{+/+}$ to multi-phase process with two exponential transitions and single intermediate state. Note that NGFP1-Mbd3$^{+/+}$ fit reasonably (adj $R^2$=0.996) to two exponential transitions process. FIG. 58C—Fitting of NGFP1-Mbd3$^{+/+}$ to multi-phase process with three exponential transitions and two intermediate states. Note that NGFP1-Mbd3$^{+/+}$ fit optimally (adj $R^2$=0.998) to three exponential transitions process. FIG. 58D—adjusted $R^2$ values obtained with the different models for NGFP1-Mbd3$^{+/+}$ (blue) and NGFP1-Mbd3 (red), indicating that the best fit model for NGFP1-Mbd3$^{KD}$ is a single exponential transition with no intermediate states, and the best fit model for NGFP1-Mbd3$^{+/+}$ is a multi-phase process with three exponential transitions and two intermediate states.

Figure 59A:
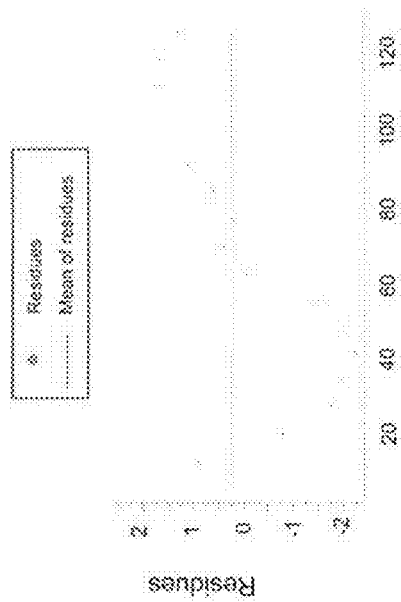
Figure 59B:
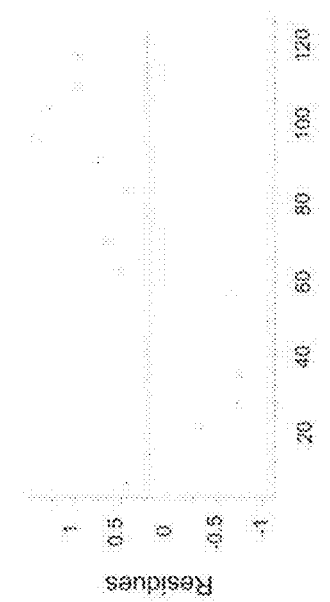
Figure 59C:
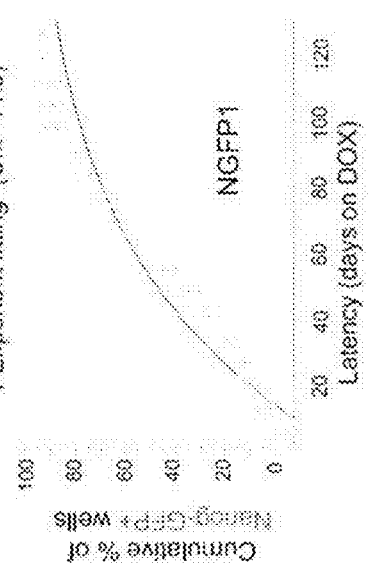
Figure 59D:
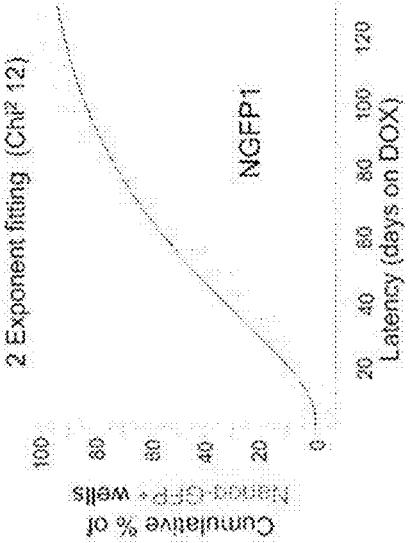
Figure 59E:
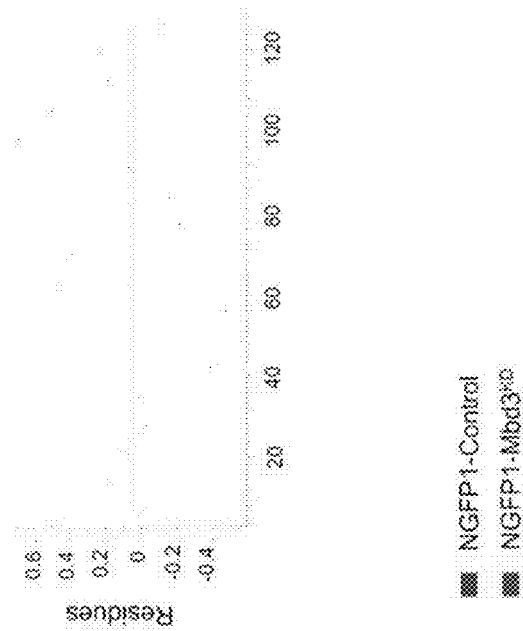
Figure 59F:
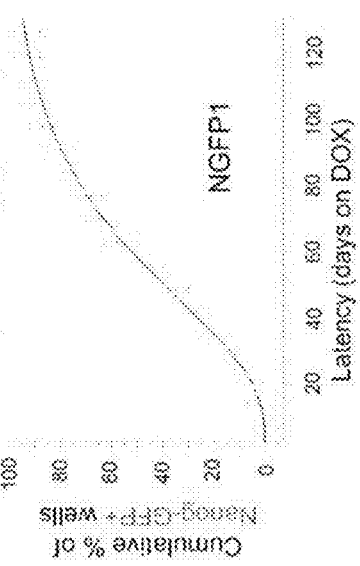
Figure 59G:
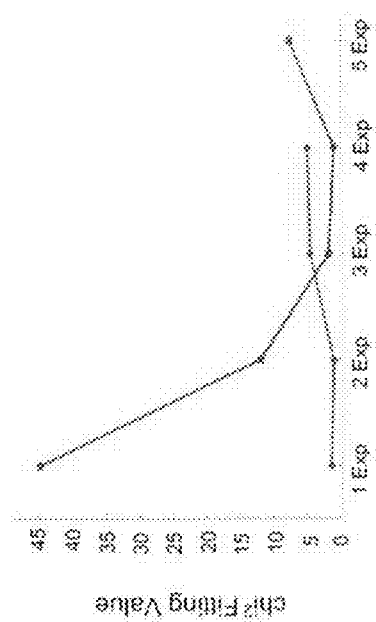

FIGS. 59A-G depict modeling of a multiple rate-limiting process in the context of iPSC reprogramming. The fitting results were validated using a second fitting procedure based on weighted nonlinear fit by chi$^2$ minimization (see methods). For each model the graphical goodness of fit is given in the left panels (FIGS. 59A, C, E), and the observational errors (residuals) are given in the right panels (FIGS. 59B, D, F). FIGS. 59A-B—Fitting of NGFP1-Mbd3$^{+/+}$ to single exponential transition with no intermediate states. FIGS. 59C-D—Fitting of NGFP1-Mbd3$^{+/+}$ to multi-phase process with two exponential transitions and single intermediate state. FIGS. 59E-F Fitting of NGFP1-Mbd3$^{+/+}$ to multi-phase process with three exponential transitions and two intermediate states. FIG. 59G—Chi$^2$ values obtained with the different models for NGFP1-Mbd3$^{+/+}$ (blue) and NGFP1-Mbd3 (red), indicating that the best fit model for NGFP1-Mbd3$^{KD}$ is a single exponential transition with no intermediate states, and the best fit model for NGFP1-Mbd3$^{+/+}$ is multi-phase process with three exponential transitions and two intermediate states.

Figures 60A, 60B:
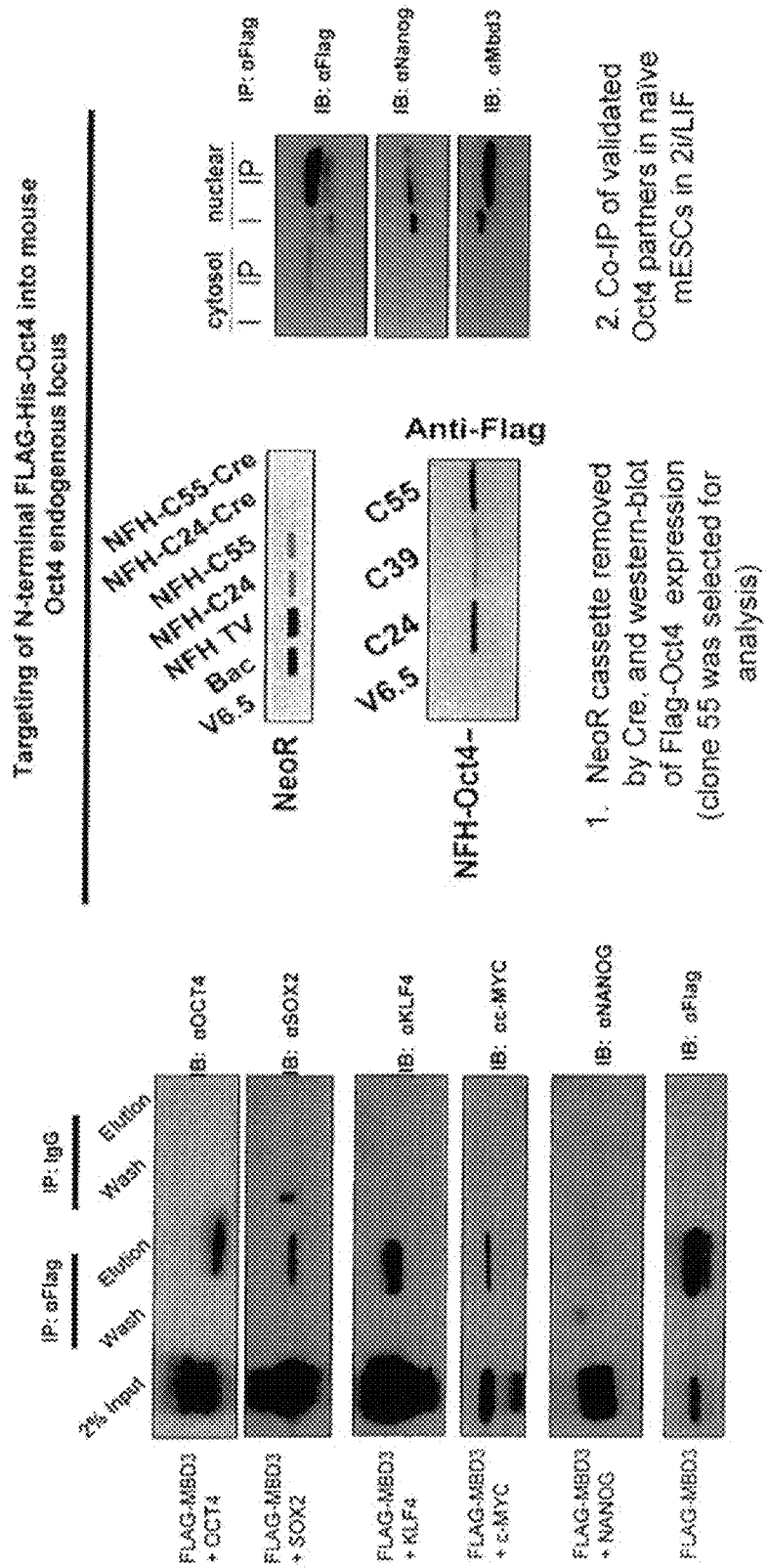
Figure 60C:
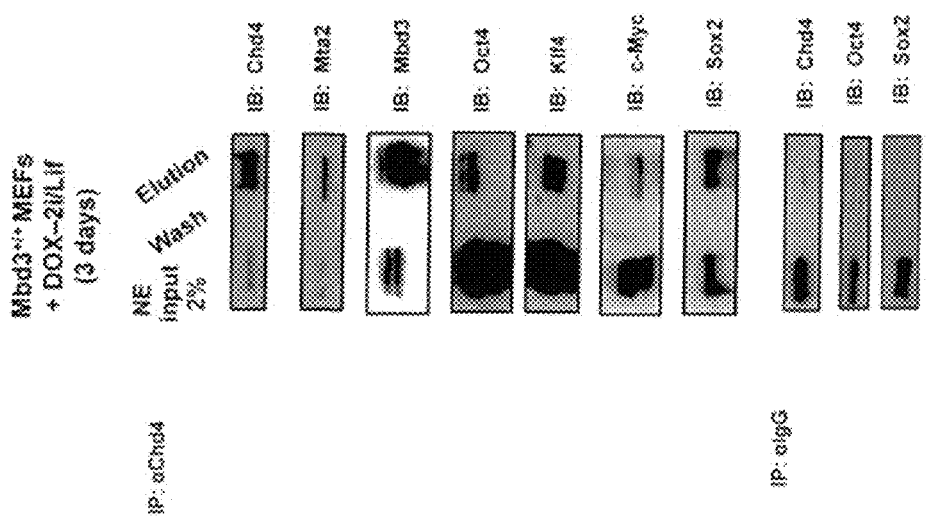

FIGS. 60A-C depict direct interaction of Mbd3/NuRD with OSKM pluripotency factors during reprogramming. FIG. 60A—Over-expression of Flag-tagged Mbd3 simultaneously with Oct4, Sox2, Klf4, c-Myc or Nanog in HEK293 cells was followed by Co-immunoprecipitation (co-IP) assay. Immunoblot analysis (IB) using antibodies against Oct4, Sox2, Klf4, c-Myc and Nanog showed specific binding between Mbd3 and the pluripotent factors except Nanog. FIG. 60B—A knock in targeting strategy in murine V6.5 ESCs with a targeting construct generating endogenously labeled Flag-tagged Oct4 allele. This line shows specific co-IP for Mbd3 with Oct4 in 2i/LIF conditions. Co-IP with Nanog is shown as a positive control. FIG. 60C—Co-IP assay of Chd4 (Mi2b), the core subunit of the NuRD complex, in secondary Mbd3$^{+/+}$ fibroblasts 3 days after Dox induction and applying 2i/LIF conditions. Co-IP for NuRD component, Chd4, followed by IB analysis indicated specific pull-down of other Mbd3/NuRD components (Mbd3 and Mta2) and OSKM reprogramming factors.

FIGS. 61A-C demonstrate that Mbd3 binds pluripotent proteins in ESC but not Mbd2. FIG. 61A—The present inventors established an ESC line carrying recovery of Flag-tagged Mbd3 transgene inserted in Mbd3$^{-/-}$ ESC line. Co-immunoprecipitation using flag beads followed by western blot shows that Mbd3 strongly binds the Mi2b and Mta2 members of the NuRD complex, but not Mbd2. Moreover, Mbd3 interacts with Sal14 pluripotency reprogramming factor in ESCs. FIGS. 61B-C—A control ESC line shows that Mta2, a member of the NuRD complex, binds either Mbd3 or Mbd2 (FIG. 61B). But, pull down of Mbd2 does not show any interaction with Mbd3 (FIG. 61C). These assays recapitulate observation in many other cell lines where Mbd2 and Mbd3 form mutually exclusive complexes (Le Guezennec, X. et al. Mol. Cell. Biol. 26, 843-851, 2006; Aguilera, C. et al. Nature 469, 231-235, 2011).

FIGS. 62A-C demonstrate that MBD domain of Mbd3 is critical for direct interaction with OSKM reprogramming factors. Deletion mutations in the MBD site of Mbd3 was designed in order to find the binding region of Mbd3. Flag-tagged mutation constructs were co-transfected with Oct4, Sox2, Klf4 and c-Myc in HEK 293T cells for 48 hours followed by Co-immunoprecipitation with anti-flag beads and immunoblot against Oct4, Klf4, Sox2 and c-Myc. This analysis showed loss of binding and interaction between Mbd3 and OSKM when deletion covering 25-49 amino acid region of Mbd3 were used (as schematically shown in FIG. 62C).

Figure 63:
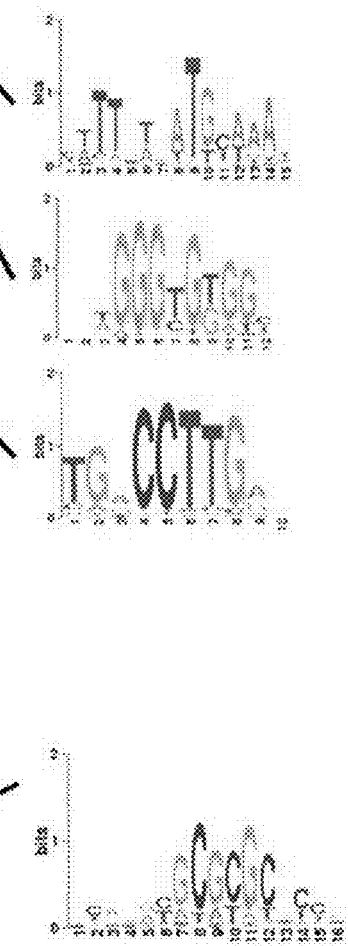

FIG. 63 depicts motif enrichment analysis for Mbd3 binding following reprogramming. Top motifs abundant among Mbd3 binding regions following OSKM induction. Shown are the sequence logos of selected motifs, along with associated factors, the Z score and the P values. The motifs were inferred using SeqPos software in Cistrome package (see methods).

FIGS. 64A-H depict the effect of Mbd3 depletion on targets common to OSKM and Mi2b. FIGS. 64A-D—Profiles of Mi2b (Chd4) binding read densities at day 4 for Mbd3$^{+/+}$ (blue) and Mbd3$^{flox/-}$ (red) samples. The profiles describe read density normalized to z-score between 1 Kb upstream and downstream to TSS. Each plot includes genes that have been characterized previously (Sridharan, R., et al., Cell 36: 364-77, 2009) to be binding targets of one of the OSKM factors (Oct4, Sox2, Klf4 and c-Myc), the z-score profile is averaged over all genes included in the factor binding target set. Figures show a reduction in Mi2b binding to OSKM targets upon Mbd3 depletion. FIGS. 64E-F—Western blot indicating protein depletion efficiency upon siRNA transfection of either Mbd3 or Chd4 targeting siRNA pools. FIGS. 64G-H—Reprogramming efficiency of Mbd3$^{+/+}$ secondary MEFS, following knockdown of Mbd3 or Chd4 (as depicted in scheme). Error bars indicate s.d. * Indicates student t-test p value <0.01.

Figures 65A, 65B:
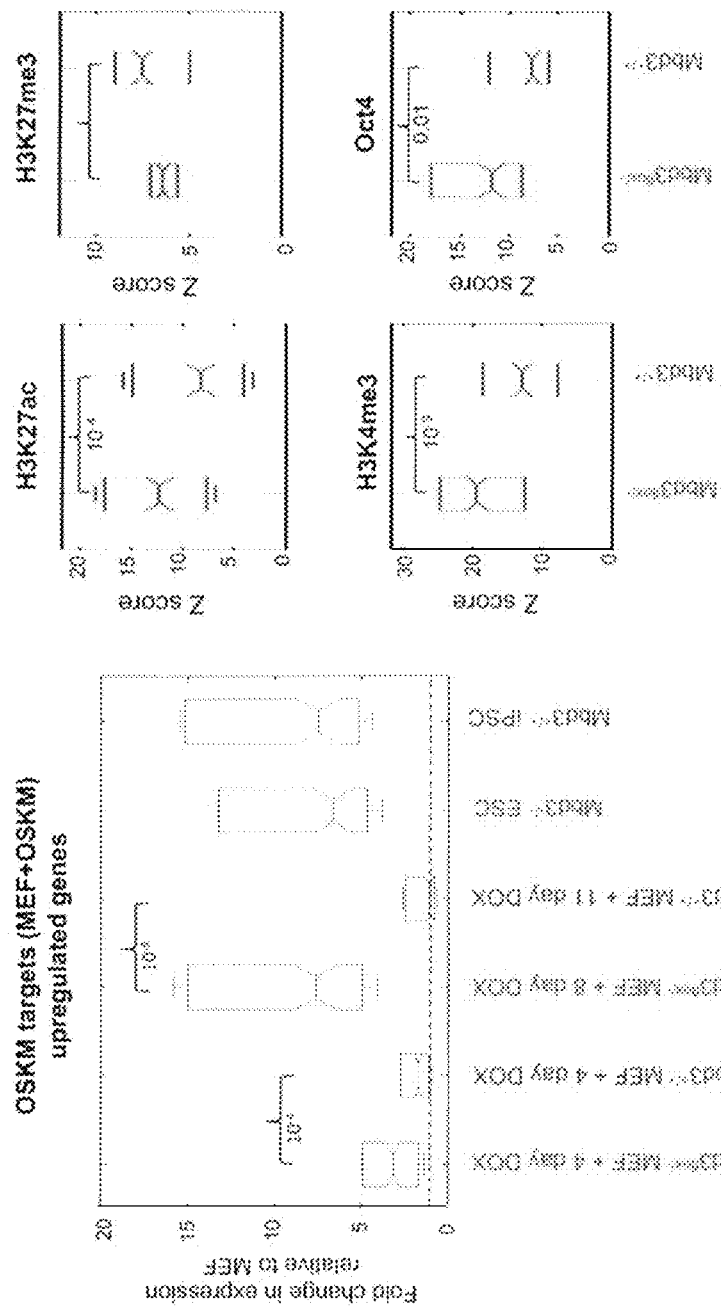
Figures 65C, 65D, 65E:
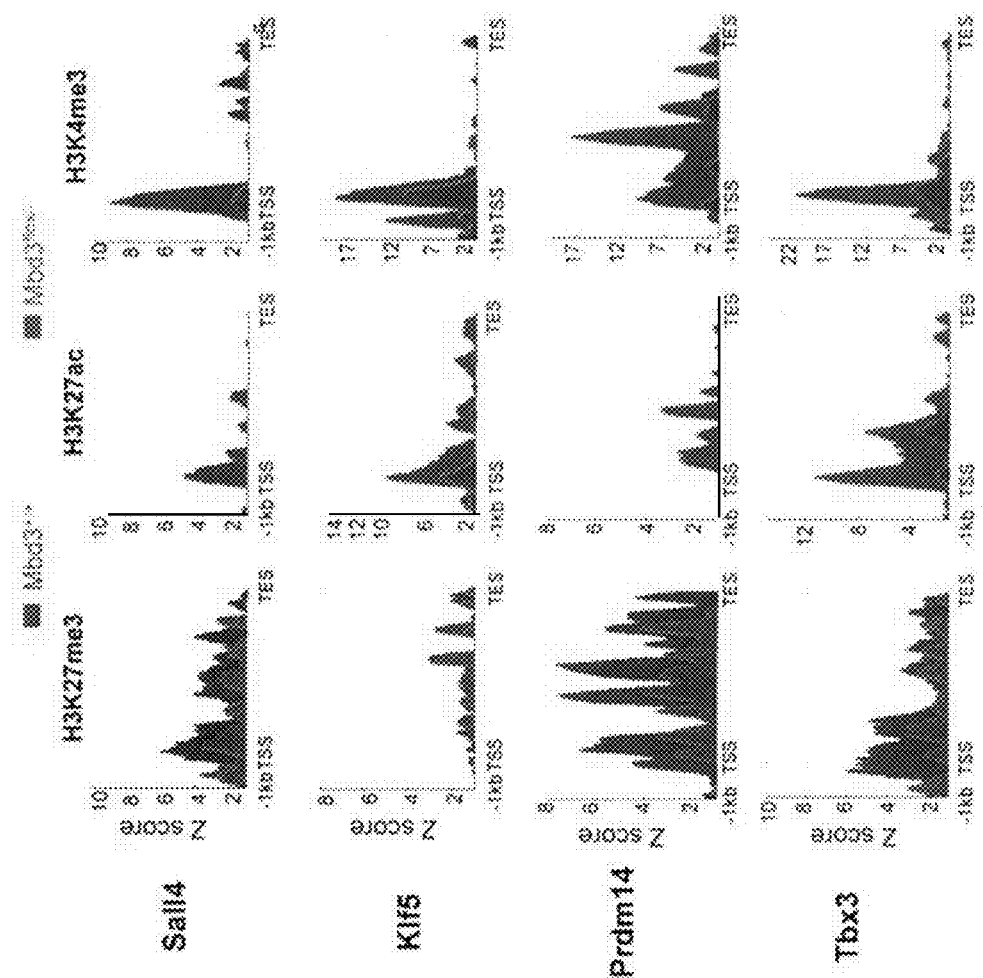

FIGS. 65A-E depict the effect of Mbd3 depletion on OSKM target genes. FIGS. 65A-B—Box plot centers indicate the median value, and box edges indicate the 25$^{th}$ and 75$^{th}$ percentiles. P-values of distribution differences indicated in the graph (in each panel) were estimated with paired sample t-test. FIG. 65A—Distribution of gene expression fold-change relative to MEF of Mbd3$^{+/+}$ samples (blue) and Mbd3$^{flox/-}$ samples (red) throughout reprogramming (0, 4 days, 8 days and iPS/ES) as described in FIG. 32F, but here calculated over 2928 genes that were previously found to be bound by at least one of the following factors in OSKM induced MEFs or ESCs: Oct4, Sox2, Klf4, c-Myc and Nanog (Sridharan, R., et al. Cell, 36:364-77, 2009) and are upregulated during reprogramming of wild type cells. FIG. 65B—Distribution of histone marks and Oct4 binding levels in z-score values at day 4 after OSKM (DOX) induction, calculated from the same set of 2928 genes described above. Results show enhanced transcription activation of OSKM targets in the Mbd3$^{flox/-}$ samples, and a significant induction of H3K27ac and H3K4me3 while reduction of H3K27me3 in Mbd3$^{flox/-}$ sample, compared to Mbd3$^{+/+}$, as well as mild induction of Oct4 binding in Mbd3$^{flox/-}$ samples. FIGS. 65C-E—Profiles of H3K27me3 (FIG. 65C), H3K27ac (FIG. 65D) and H3K4me3 (FIG. 65E) read densities at day 4, are plotted for four representative OSKM target genes (Sal14, Klf5, Prdm14 and Tbx3). The profiles describe read density normalized to z-score between 1 Kb upstream to TSS and TES. Mbd3$^{flox/-}$ profiles of H3K27ac and H3K4me3 (red area) are significantly increased (>3 Std), and H3K27me3 significantly reduced, in comparison to Mbd3$^{+/+}$ sample (blue area).

Figures 66A, 66B:
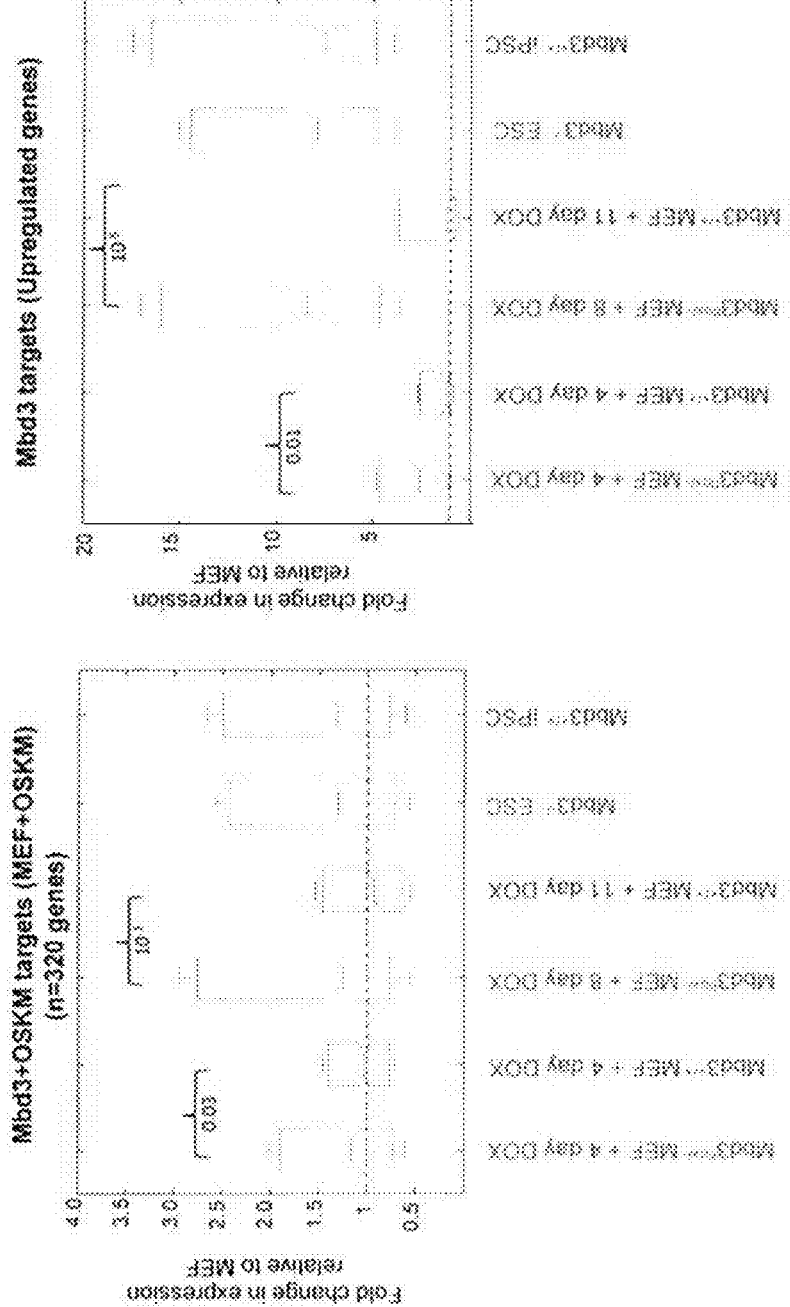

FIGS. 66A-F depict the effect of Mbd3 depletion on OSKM and Mbd3. Box plot centers indicate the median value, and box edges indicate the $25^{th}$ and $75^{th}$ percentiles. P-values of distribution differences indicated in the graph were estimated with paired sample t-test. FIG. 66A—Same as in FIG. 65A, but calculated over genes that are bound by both OSKM and Mbd3 targets (n=320 genes) FIG. 66B-Same as in 65B but calculated over genes that are bound by Mbd3 and are upregulated during reprogramming (differentially expressed gene signature described in methods). Results here show similar trends to what was described in FIGS. 65A-B. FIGS. 66C-F—Distribution of histone marks and Oct4 binding levels in z-score values in Mbd3 depleted (Mbd3$^{flox/-}$) or wild type (Mbd3$^{+/+}$) cells. The results presented in FIGS. 66C-F demonstrate that in the Mbd3 depleted samples, during reprogramming Mbd3 targets and/ or OSKM targets acquire more open chromatin and get easily and fully reactivated.

Figure 67A:
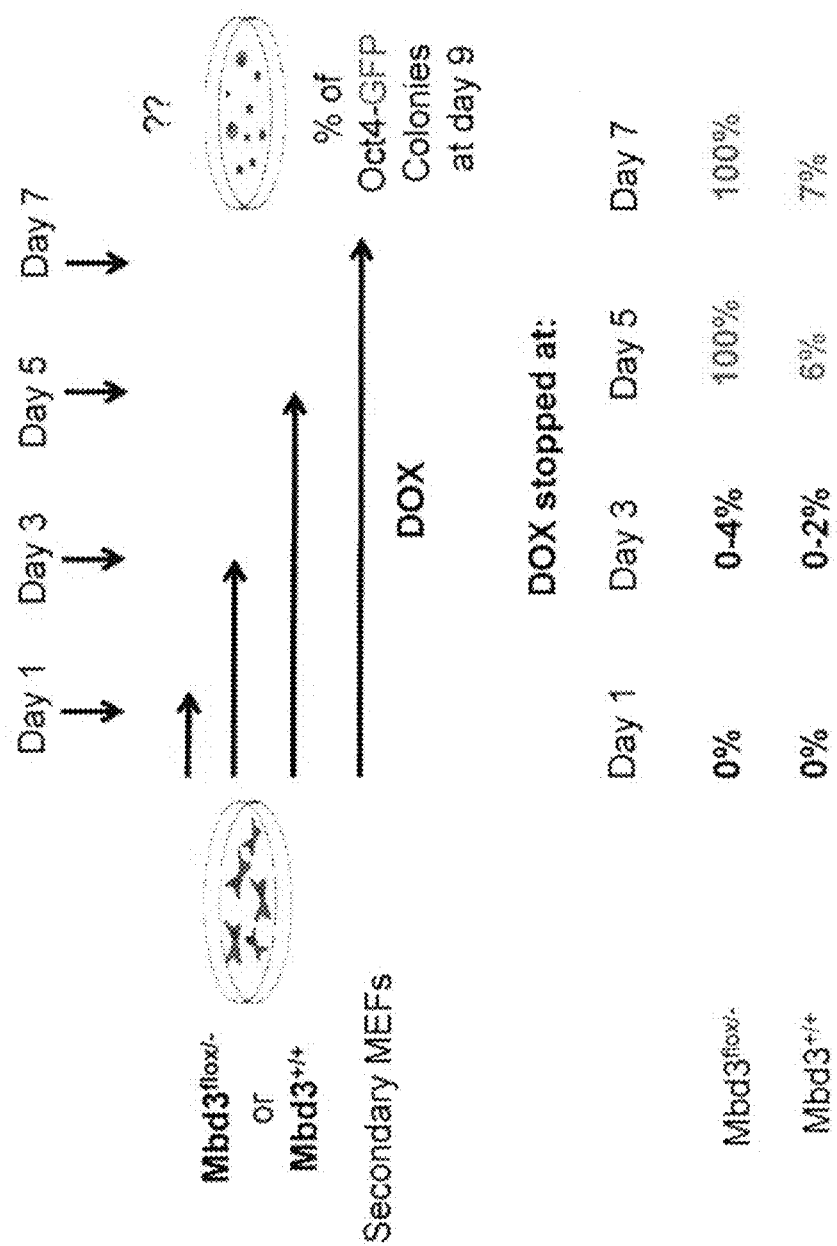
Figures 67B, 67C, 67D:
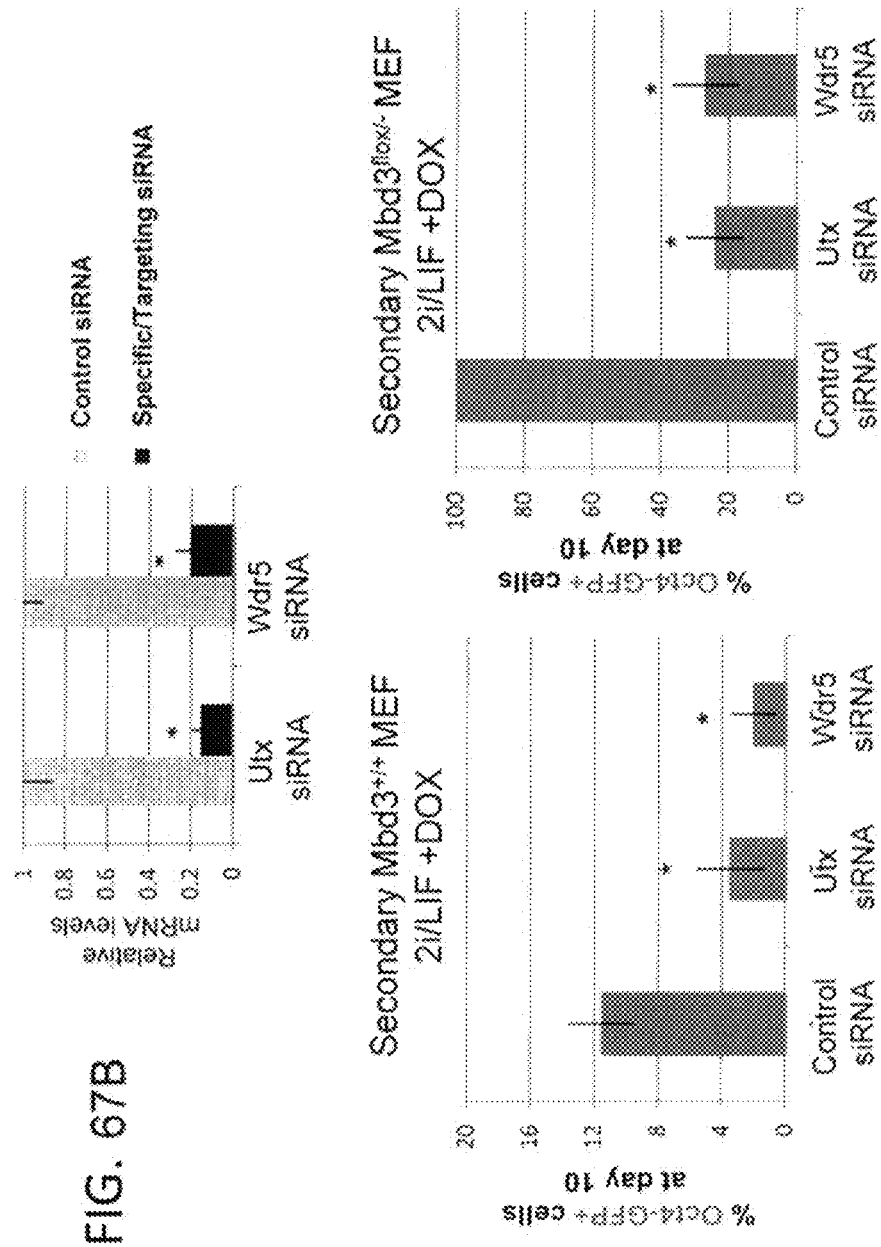

FIGS. 67A-D demonstrate that pluripotency promoting epigenetic activators are essential for both deterministic and stochastic iPSC formation. FIG. 67A—Requirement for DOX mediated transgene induction during iPSC reprogramming form Mbd3$^{+/+}$ and Mbd3$^{flox/-}$ secondary MEFS. Percentage of Oct4-GFP colonies was quantified at final set time point on day 9. Similar time frame for minimal DOX induction was required for iPSC formation in both cell samples. FIGS. 67B-D—Specific knockdown of Utx [lysine (K)-specific demethylase 6A; KDM6A, Gene ID: 7403] and Wdr5 [WD repeat domain 5; Gene ID: 11091] epigenetic regulators that are required for iPSC formation (Mansour et al. 2012, Nature 488, 409-413; Ang Y.—S. et al 2011, Cell 145, 183-197) significantly inhibited iPSC formation in both Mbd3$^{+/+}$ and Mbd3$^{flox/-}$ cells. * indicates p value <0.01 in comparison to control siRNA sample. One out of 2 independent experiments is shown. s.d. was based on measurements in duplicate identical samples.

Figures 68I, 68J, 68K:
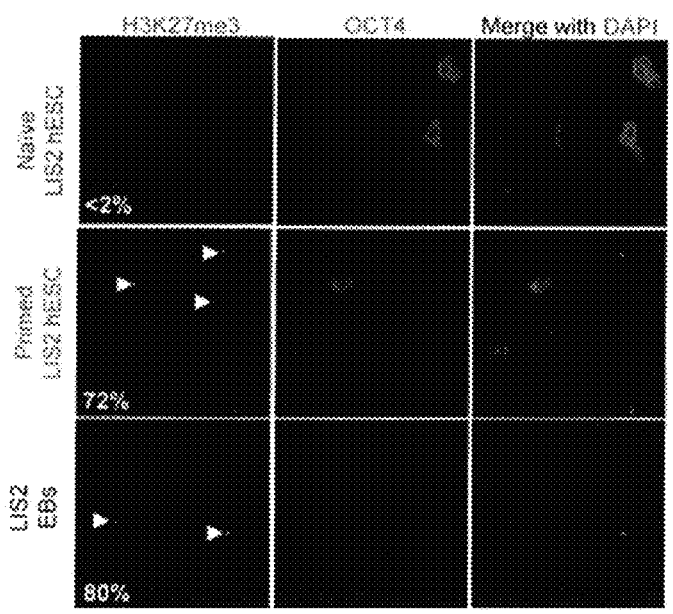

FIGS. 68A-K demonstrate that naive human stem cells share defining epigenetic features with mouse ESCs. FIG. 68A-B—As representative examples, characterization for WIS1 (FIG. 68A) and WIS2 (FIG. 68B) naive hESCs is shown. The cells were taken at the indicated passage number (Passage 31 for WIS1, and Passage 27 for WIS2) and express all human pluripotent markers tested (i.e., NANOG, TRA-1-60, OCT4, TRA-1-81, SSEA3, SOX2 and SSEA4), and do not express SSEA1. All naive lines described herein show no signs of deterioration, crisis or decay with expansion (for over 30-70 passages thus far tested). FIGS. 68C-H—The pluripotent capacity of the naive human cells WIS1 at passage 33 (FIGS. 68C, E and G) and WIS2 at passage 19 (FIGS. 68D, F, H) was evaluated by the ability to form teratomas with cells of all three embryonic germ layers. Representative hematoxylin and eosin staining of teratoma sections are shown. FIGS. 68C-D—differentiation into endoderm; FIGS. 68E-F—differentiation into mesoderm; FIGS. 68G-H—differentiation into ectoderm. FIGS. 68I-K—Representative confocal images obtained after double immunostaining for OCT4 and H3K27me3 on naive (FIG. 68I), primed (FIG. 68J) and differentiated samples (Embryoid bodies, obtained from naive cells; FIG. 68K). Naive female pluripotent cells nearly lack the formation of H3K27 m3 foci that mark the inactive X allele (FIG. 68I, less than 2% of the cells exhibit the H3K27 m3 foci). Primed cells, while they retain OCT4 pluripotency marker expression, H3K27me3 foci (one per nucleus) became clearly detectable in the majority of cells (FIG. 68J, left panel, arrowhead). Upon differentiation into somatic cells, the naive pluripotent cells lose OCT4 expression and acquire H3K27 m3 nuclear foci (FIG. 68K). Average percentages of positive counted nuclei from 150-200 cells per sample are indicated.

Figure 69A:
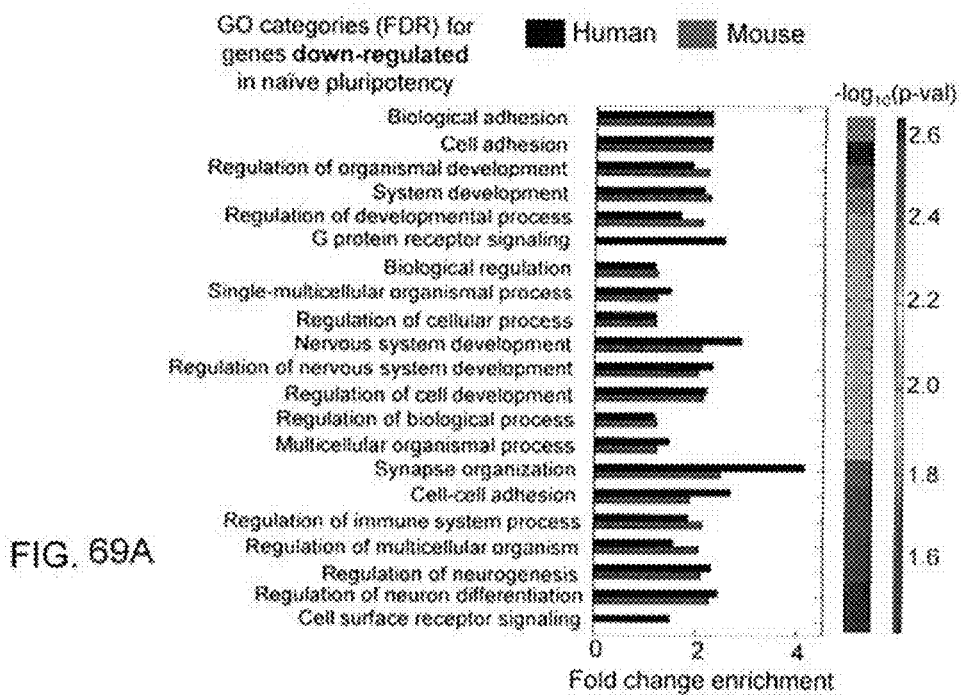
Figure 69B:
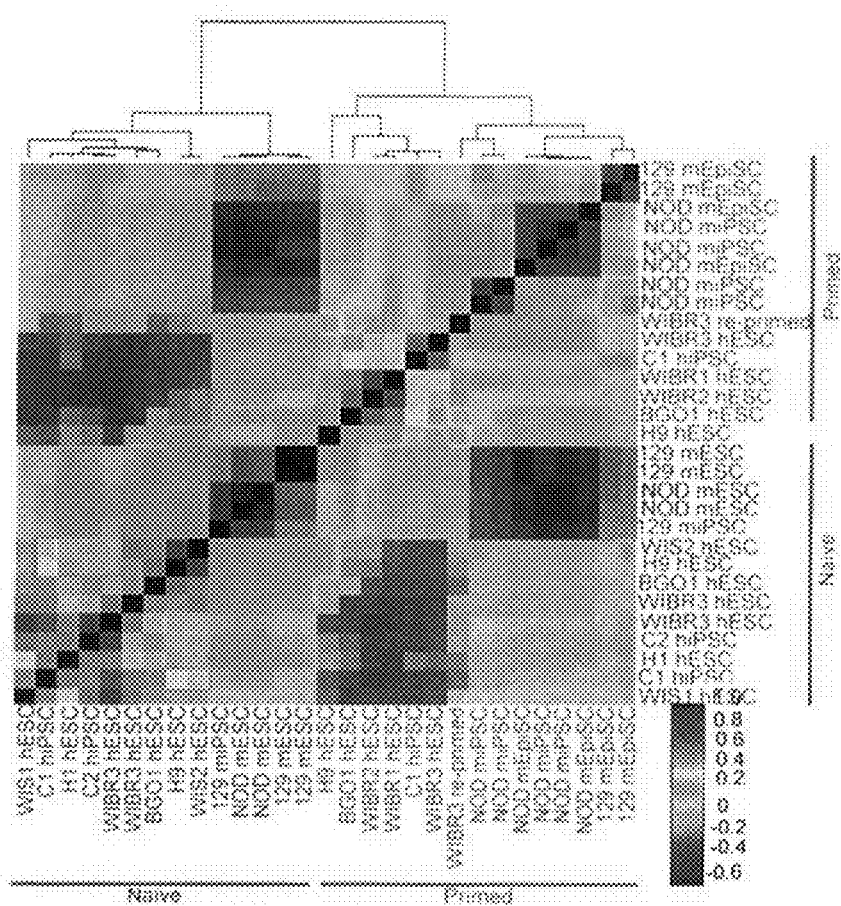
Figure 69H:
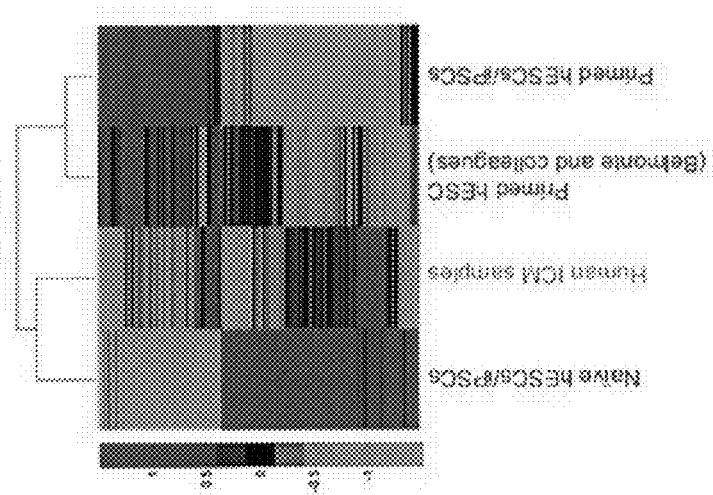
Figure 69I:
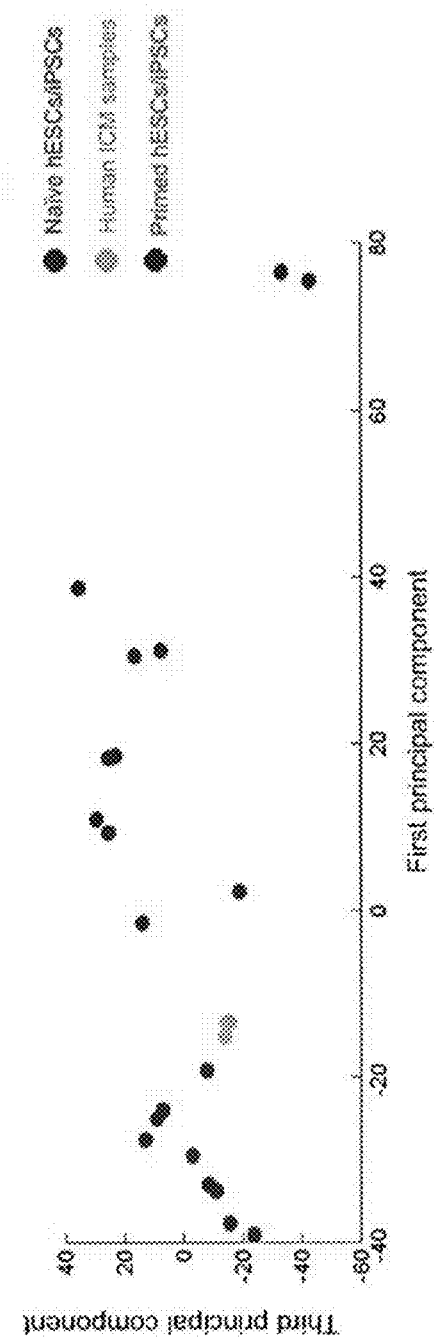

FIGS. 69A-I depict global transcriptional profile of human naive pluripotency. FIG. 69A—Go categories significantly enriched for genes up-regulated in primed compared to naive human cell lines, with their (−log 10) FDR-corrected P-value. The respective mouse fold-enrichment values for the categories that are also significant in mouse are indicated. FIG. 69B—Cross-species hierarchical clustering of naive and primed pluripotent cells from mice and humans. Gene expression in naive mESCs and naive hESCs/ hiPSCs formed a distinct group apart from mEpiSCs and primed/conventional hESCs and hiPSCs. Mouse cells include "129" and "NOD"; all the rest are human cells. Correlation matrix of gene expression was clustered using Spearman correlation and average linkage. Color bar indicates correlation strength. FIGS. 69C-D—Gene expression across different naive samples is less noisy and more homogenous than across different primed samples. A box plot showing the median and quartiles of the distributions of the coefficients of variance ($\sigma/\mu$) calculated for each of the homologous genes. The naive distributions are significantly smaller (single-tail t-test, p=0) than the primed ones. FIG. 69C human naive versus human primed pluripotent stem cells; FIG. 69D—mouse naive versus mouse primed pluripotent stem cells. FIGS. 69E-F—Naive human (FIG. 69F) and primed human (FIG. 69E) hESCs were double immunostained for TFE3 and OCT4. Representative confocal images are shown for LIS2 hESC line. Insets are enlargements of the dashed boxes. Oct4 staining is localized to the nucleus in both states of cells (primed and naive). On the other hand, a predominant nuclear localization is shown for TFE3 in naive hESCs but not in primed conditions, demonstrating that TFE3 shuttles and changes between the states of the cells. FIG. 69G—Quantitative unbiased imaging analysis for preferential nuclear localization was conducted on randomly selected 200 cells from independent image frames per sample. Box and whisker plots of nuclear/ cytoplasmic TFE3 ratios in naive and primed mouse and human ESCs are shown. Naive hESCs showed distributions similar to those in naive mESCs, and the nuclear enrichment was lost in primed human and mouse ESCs * t-test P values $<1\times10^{-100}$. FIG. 69H—Transcriptional comparison of in vitro and in vivo isolated human pluripotent cells. Hierarchical clustering of the mean expression profile of differentially expressed genes between Naive and Primed samples (FDR<0.05), in the different groups [Naive (this study), Primed (this study), Belmonte's primed ESCs, and human ICMs (Belmonte and colleagues (Vassena, R. et al. Waves of early transcriptional activation and pluripotency program initiation during human preimplantation development. *Development* 138, 3699-3709, 2011)], using Spearman correlation. Note that while primed ESC samples previously derived by Belmonte and colleagues cluster with the primed samples derived herein, human ICM samples cluster with the naïve samples expanded in WIS-NHSM conditions. FIG. 69I—Principal Component Analysis showing that human ICM samples are closer to Naïve than to Primed samples (along the 1st principal component axis). Primed samples are also more dispersed, showing higher variability and heterogeneity, and not as closely grouped as human Naïve and ICM samples are.

FIGS. 70A-J depict epigenetic configuration of human naive pluripotency. FIGS. 70A-B—Profiles of H3K27me3 chromatin mark of developmental genes in human (FIG. 70A) and mouse (FIG. 70B), naive (blue) and primed (red), represented as normalized read-density. Human profiles indicate average and s.d. (error-bars) calculated over 5 different cell lines (C1, LIS2, WIBR3, WIBR3-MBD3mut and BGO1). Average difference between plots is indicated alongside variance and P-values (calculated with paired-sample t-test). FIGS. 70C-D—Chromatin landscape of 5 pluripotent example genes. H3K27me3 and H3K4me3 marks are shown for naive (blue) and primed (red) cell lines, in both human (FIG. 70C) and mouse (FIG. 70D), showing high consistency between the organisms. FIGS. 70E-F—Same as in FIGS. 70C-D for 5 developmental genes. FIG. 70E—human; FIG. 70F—mouse; FIG. 70G—Representative relative transcript levels in human naive and primed WIBR3 cells. * t-test P value <0.01. Error bars indicate s.d. (n=3). FIG. 70H—Immunostaining for OCT4 (left panels) and DNMT3B (right panels) in human naive cells (lower panels) and primed cells (upper panels). Human naive cells down-regulate MBD3, but not OCT4, protein expression. FIGS. 70I-J—Histograms of the change in methylation between primed and naive samples in human (FIG. 70I) and mouse (FIG. 70J). The histograms depict the distribution of the per-CpG difference in methylation, calculated for all CpGs residing in CpG rich regions (>4% CpG content) and having a coverage of ≥10× in both samples. For clarity, only CpGs with a non-zero change in methylation are included in the histogram. The distribution is left-skewed, indicating a general reduction in methylation in the naive samples.

Figure 71D:
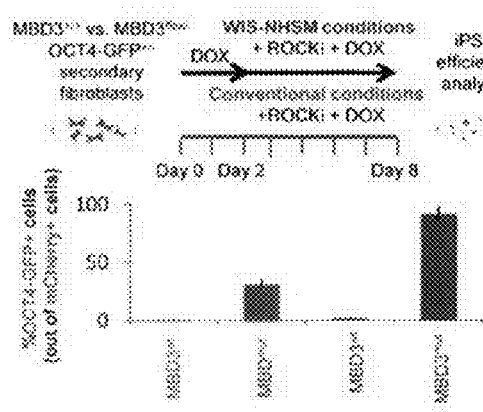
Figure 71E:
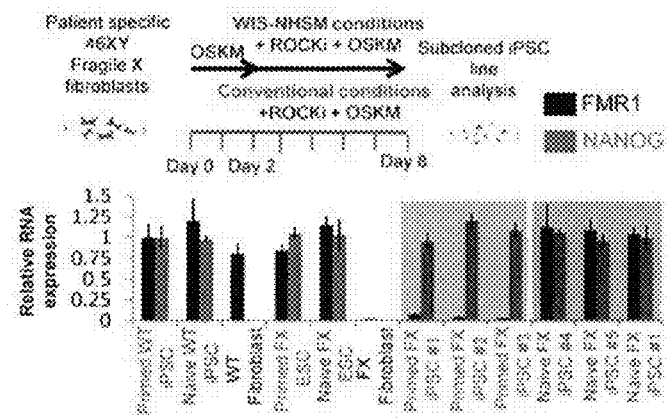
Figure 71G:
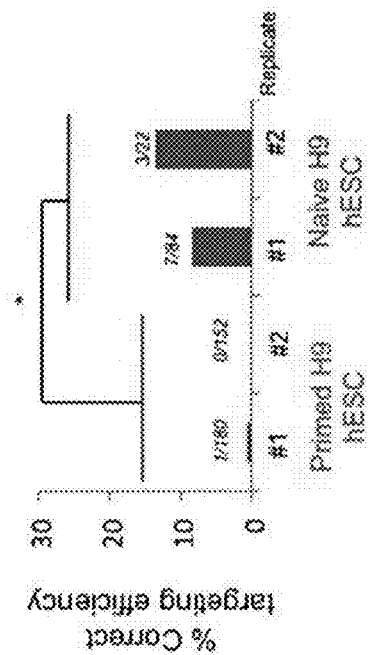
Figure 71F:
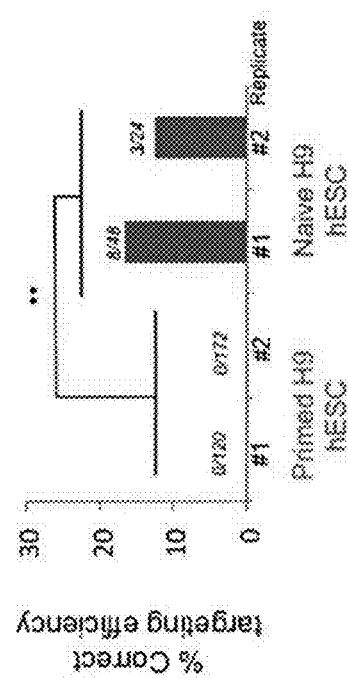

FIGS. 71A-G depict signaling and functional characteristics of human naive pluripotency. FIG. 71A—LIF/Stat3 is required for stabilization of the in vitro stability of naive hESC/hiPSCs in WIS-NHSM. Naive V6.5 NOD mESCs, naive WIS1 and H1 hESCs, and BJ naive hiPSCs were electroporated with mock a pBRY-CAGGS-flox-DsRedT4-IRES-Puro control plasmid, a plasmid encoding a dominant negative Stat3 Y705F mutant (Stat3-DN), or a plasmid Stat3-C constitutively active mutant (pBRY-Stat3-CA). Cells were passaged three times in the presence of puromycin selection. After 20 days, colonies positive for OCT4 pluripotency markers were counted and normalized to colonies from cells electroporated with empty vector. (n=3 for each condition and error bars indicate s.d.). * Student's t test P value <0.01. FIGS. 71B-C—Upper panels indicate schemes for gene targeting of OCT4 (FIG. 71C) and COL1A (FIG. 71B) loci. Tables indicate number and percentage of correctly targeted ES clones, as determined by both 5' and 3' southern blot validation strategies. FIG. 71D—Secondary iPSC reprogramming efficiency of wild-type and MBD3 depleted (MBD3$^{mut}$) cells when reprogramming in naive (blue scheme) or primed/conventional (red scheme) conditions. Error bars indicate s.d.m (n=3). * Indicates t-test P value <0.01. FIG. 71E—Relative transcript expression of FMR1 and NANOG genes in cells isolated from healthy or Fragile X patients. Error bars indicate s.d.m (n=3). FIGS. 71F-G—Targeting strategy by homologous recombination of COL1A locus in H9 ESCs. Correct targeting efficiency in different H9 naïve and primed pluripotent cell experimental replicates is shown. Correct targeting was scored after confirmation with both 5' and 3' southern blot analysis on extracted DNA from analyzed clones. ** Indicates significant P value <0.02. b, as in a, but for OCT4 locus. * Indicates significant P value <0.05.

Figure 72A:
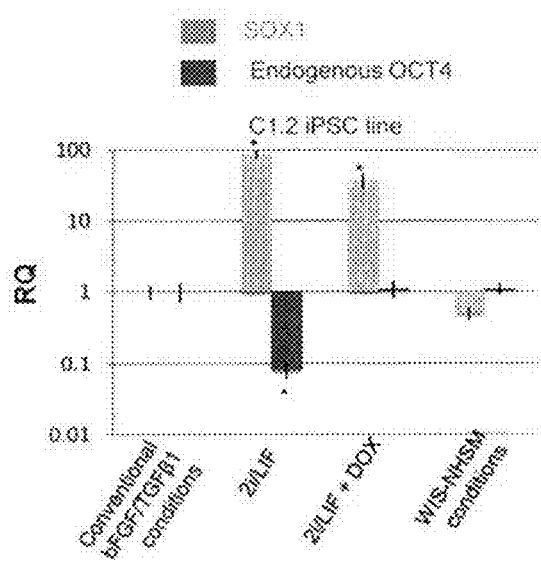
Figure 72C:
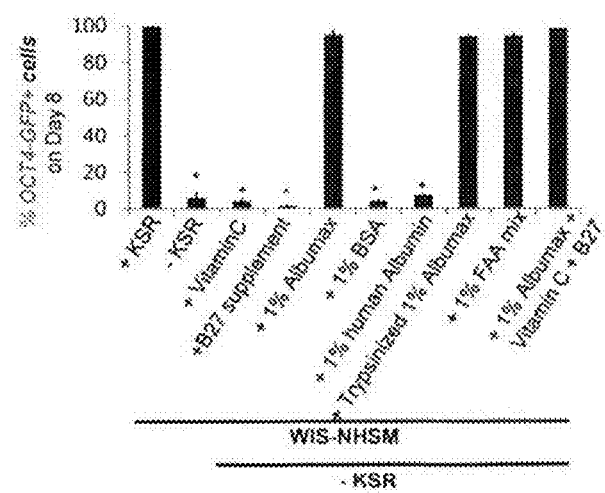
Figure 72B:
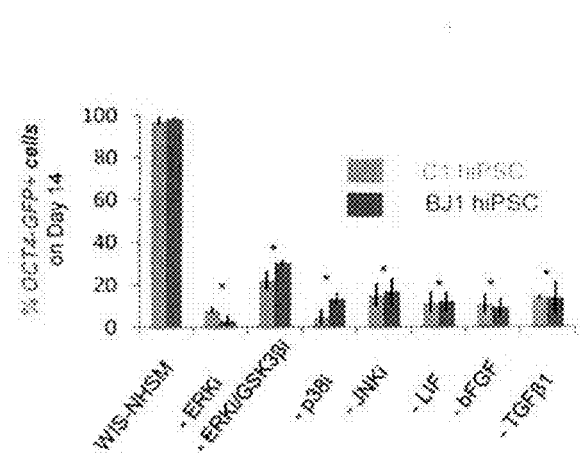
Figure 72D:
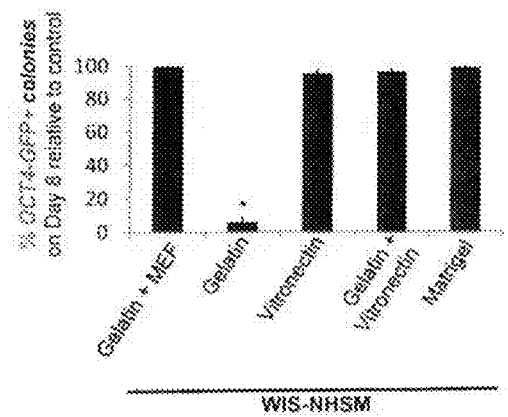

FIGS. 72A-D demonstrate defining and optimizing conditions for capturing transgene independent human naive pluripotent iPSCs. FIG. 72A—qRT-PCT analysis for relative expression of endogenous OCT4 pluripotency marker and SOX1 neural markers. Relative values to those measured in primed/conventional 1.2 iPSC lines are shown. In the presence of DOX, the cells express the endogenous pluripotency OCT4 (consistent with previously described results and teratoma formation ability of these cells (Hanna, J. et al. Proc. Natl. Acad. Sci. U.S.A. 107, 9222-9227, 2010), however SOX1 is significantly upregulated, consistent with unstable pluripotency maintenance in these conditions (Hanna, J. et al. Proc. Natl. Acad. Sci. U.S.A. 107, 9222-9227, 2010). WIS-NHSM conditions that were optimized in this study maintain OCT4 expression and do not acquire aberrant SOX1 upregulation. Error bars indicate s.d. one representative experiment is shown out of two performed. FIG. 72B—Genetically unmodified BJ1 naive hiPSC line generated by mRNA reprogramming approach, showed similar dependence to that observed to C1.2 naive hiPSC line (expanded without DOX), in WIS-NHSM conditions (FIG. 12S). These results exclude leakiness in C1 line as an independent parameter contributing to naive pluripotency in WIS-NHSM. This data is consistent with the ability to robustly generate naive genetically unmodified hESCs throughout the study in WIS-NHSM conditions. * student's t test P value <0.01 relative to control WIS-NHSM conditions. FIG. 72C—For further optimizing naive growth conditions, 1% Albumax can be substituted by using either 15% KSR (knockout serum replacement) or 1% chemically defined lipid concentrate (Invitrogen). 1% albumax was used in WIS-NHSM defined throughout the study and used for molecular analysis of naive cells. FIG. 72D—OCT4-GFP+ levels for naive pluripotent cells expanded in WIS-NHSM media on tissue culture plates coated with the indicated components. Naive hiPSCs can be grown without feeder cells either on matrigel coated plates, vitronectin coated plates or 0.2% gelatin+1 ng/ml vitronectin coated plates (but not gelatin alone). * student's t test P value <0.01 relative to control Gelatin+feeder cells (MEF) condition. One representative experiment is shown out of 3 performed.

FIGS. 73A-F depict immunostaining for pluripotency markers on newly embryo derived naive hESCs. FIGS. 73A-B—The LIS1 (FIG. 73B), LIS2 (FIG. 73A), WIS1, and WIS2 ESC lines established from human ICM in WIS-NHSM conditions were analyzed, and showed a strong uniform staining for all indicated human pluripotency markers (OCT4, NANOG, SSEA3, SSEA4, TRA1-60, TRA1-81 and Sox2). Notably, SSEA1, which is specific for mouse (both naive and primed stem cells) and not human pluripotent cells, is not expressed on naive hESCs. FIGS. 73C-F—Expression of KLF2 and ESRRB pluripotency factors in naive hESCs. FIG. 73C naive LIS2 hESC; FIG. 73D naive WIBR3 hESC; FIG. 73E naive V6.5 mESC; FIG. 73F primed mEpiSCs. Representative confocal double immunostaining images demonstrating expression of KLF2 and ESRRB pluripotency factors in naive human and mouse ESCs.

FIGS. 74A-D depict enhanced growth rate and single cell cloning efficiency of human naive pluripotent stem cells. FIG. 74A—Population doubling time of various mouse and human pluripotent stem cell lines. After plating each cell lines in replicates, cells were harvested at days 2, 4 and 6 and there growth was normalized by counting cell number at each stage and calculating growth rate relative to the number of cells harvested and counted at day 2 (rather than number of plated cells to account for variability in survival after plating). Error bars represent s.d., and P values represent t-test of average from primed hESC/hiPSC lines to average of naive hESC/hiPSC lines. FIG. 74B—Single-cell cloning efficiency of different pluripotent stem cell lines as determined by the number of wells containing NANOG+ colonies 6 days after plating (with or without ROCK inhibitor as indicated in the figure). * indicates student's t-test P value <0.01 between the average of the compared groups. Error bars indicate s.d. These results highlight an enhanced single cell survival and cloning efficiency of naive pluripotent cells, in comparison to conventional hESCs/hiPSCs. FIG. 74C—Cross species differences in ERAS protein expression influence remaining growth properties differences between genetically unmodified human and mouse naive PSCs. Single-cell cloning efficiency of different pluripotent stem cell lines as determined by the number of wells containing Nanog+ colonies 6 days after plating (without using ROCK inhibitor as indicated in the figure). * indicates student's t-test P value <0.01 between the average of the compared groups. Error bars indicate s.d. These results highlight a relatively compromised single cell survival and cloning efficiency of Eras knockout naive mESCs, in comparison to conventional ESCs/iPSCs. Reconstitution of ERAS in naive hESCs rescues their relative deficiency in single cell colony formation assay. FIG. 74D—Mouse ESC derivation efficiency in 2i/LIF/MEF feeder conditions, from WT or Eras KO ICMs. Error bars indicate s.d.m. Student t-test P value is indicated.

FIGS. 75A-I depict predominant utilization of distal enhancer element in mouse and human naive pluripotency. FIG. 75A—Schematic illustration demonstrating the relative localization of the evolutionary conserved distal and proximal enhancer elements in the human OCT4 locus. Distal enhancer (DE) and proximal enhancer (PE) are highlighted in the human OCT4 locus, and were accordingly deleted in ΔPE and ΔDE reporter constructs used in this study. Insertion site of GFP-2A-Puromuycin resistance cassette by BAC recombineering is indicated. FIGS. 75B-E— WIS1 (FIGS. 75B and 75C) and LIS2 (also referred to as "LIS39" herein) (FIGS. 75D-E) naive hESCs were stably transfected with ΔPE-OCT4-GFP-2A reporter construct that marks naive pluripotency configuration. GFP expression was specifically detected by flow cytometry in naive pluripotent cells (FIGS. 75B and 75D), while their genetically matched primed cells generated after 10 days in primed/conventional hESC conditions did not show GFP expression (FIGS. 75C and 75E). FIGS. 75F-G—Similar results were obtained when the ΔPE reporter was inserted in naive murine V6.5 ESCs, that showed specific down regulation of GFP activity after transferring the cells to mEpiSC primed media (FIG. 75G). Therefore, the human ΔPE-Oct4-GFP-2A-PURO reporter showed similar specific activity in mESCs expanded in 2i/LIF, but not primed mEpiSCs (FIGS. 75F and G), further supporting the specificity of the reporter used and the similarity between mouse and human naive pluripotent configurations. FIGS. 75H-I—naive C1.2 hiPSC propagated in WIS-NHSM media showed specific expression of GFP marker (FIG. 75H), while C1 cells grown in previously described 2i/LIF+DOX conditions (to induced OSK transgenes) down regulate GFP activity and had a heterogeneous expression pattern (FIG. 75I). The latter is consistent with data in FIGS. 12A-C and 72A-D, indicating the previously described (Hanna, J. et al. Proc. Natl. Acad. Sci. U.S.A. 107, 9222-9227, 2010) transgene dependent naive pluripotent cells are unstable relatively to the genetically unmodified and transgene independent cells described in this study.

Figure 76A:
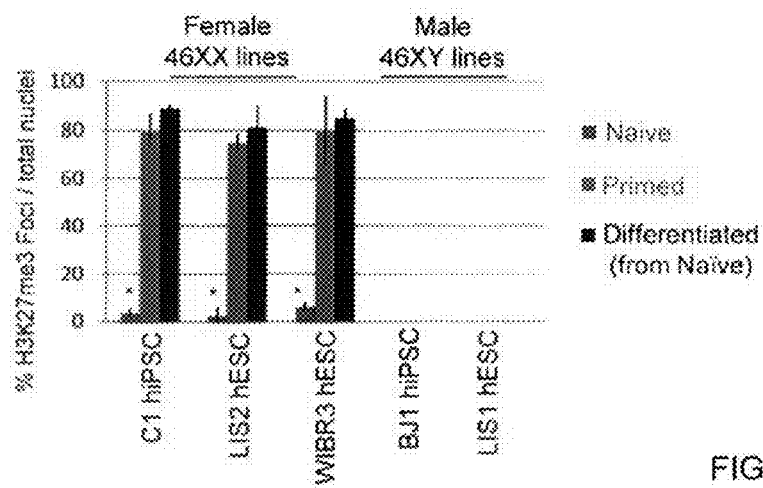
Figure 76C:
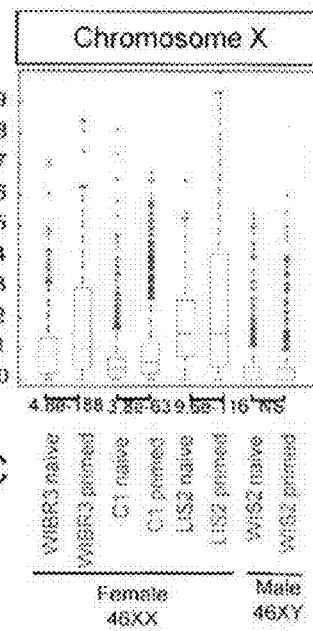
Figure 76B:
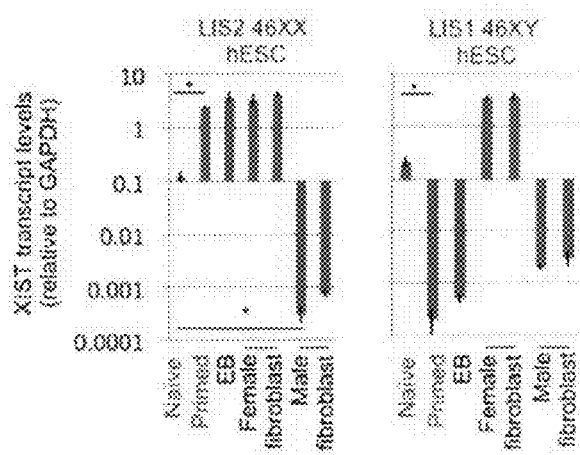

FIGS. 76A-C demonstrate that female naive hESCs/hiPSCs retain a unique pre-X inactivation state in WIS-NHSM conditions. FIG. 76A—Confocal images obtained after double immunostaining for OCT4 and H3K27me3 on naive, primed and differentiated samples were analyzed and quantified for the fraction of cells with nuclear H3K27me3 foci that mark the inactive X allele. Average percentages of 150-200 individual cells counted per sample from at least ten independent frames are shown. Error bars indicate s.d. * indicates student's t-test P value <0.01 when comparing samples to naive pluripotent cells. Naive female pluripotent cells have very low H3K27 m3 foci. In primed and differentiated cells, H3K27me3 foci (one per nucleus) became clearly detectable in the majority of cells. Male lines do not exhibit H3K27me3 foci/clouds in any of the states as expected. FIG. 76B—qRT-PCR analysis indicates no/low expression levels of XIST in naive hESCs/iPSCs, in comparison to female differentiated fibroblast cells that upregulate XIST expression. Error bars indicate s.d.m (n=3)* indicate student's t-test P value <0.01. FIG. 76C—H3K9m3 level [RPKM (read-per-kilo base-per-million reads)] distributions of all the genes in chromosome X. Distributions of H3K9me3 RPKM levels in chromosome X genes, measured in the different cell lines. Boxes $25^{th}$ and $75^{th}$ percentiles, horizontal lines median, crosses outliers. RPKM were measured for each gene between 1 Kb upstream to TSS (Transcription Start Site) and TES (Transcription Ending Site). Shown are 4 human cell lines (WIBR3, C1, LIS2, WIS2). Blue naive cell lines, Red primed cell lines. Lines WIBR3, C1 and LIS2 are females and BGO1 is a male cell line. Distributions of H3K9me3 in female primed cells are significantly higher compared to their naive counterparts, while in male cells they are the same. P-values were calculated with 1-tail paired-sample t-test.

Figure 77A:
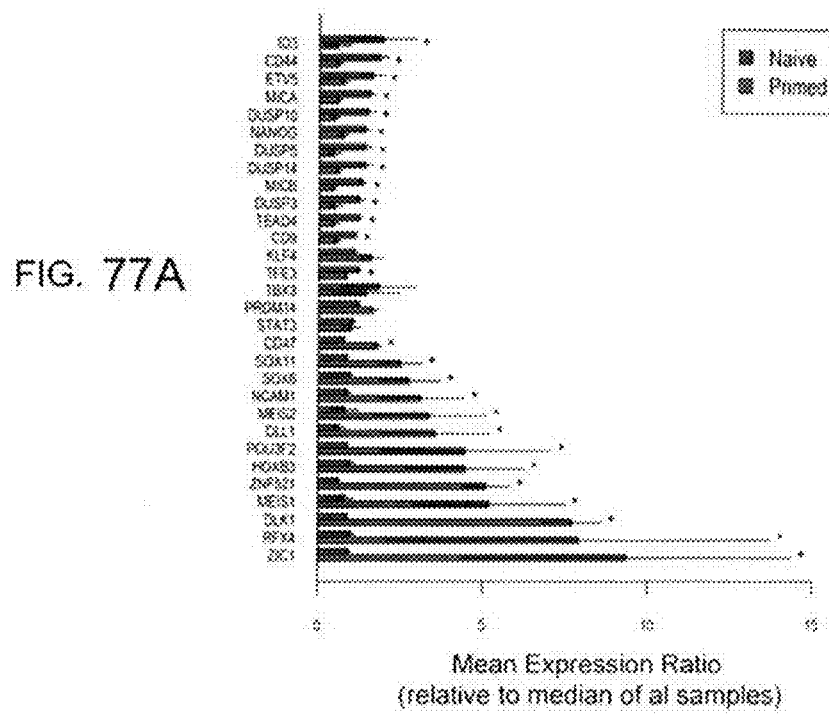
Figure 77B:
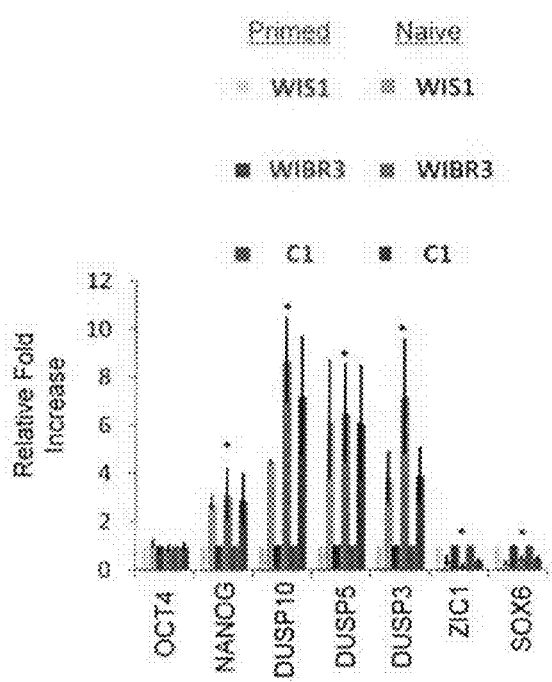

FIGS. 77A-B depict distinct transcriptome for human naive ESCs/iPSCs. FIG. 77A—Microarray transcriptional profile of selected pluripotency and lineage-specific marker genes, their mean expression ratio in primed hESCs and naive hESCs relative to the median of all samples. Values are shown in natural scale. Error bars represent SEM of each gene. Asterisks denote statistically significant differentially expressed genes in which the false discovery rate was <0.05 between the naive and primed groups of samples. Panel was generated by R software. FIG. 77B—qRT-PCR validation analysis for gene upregulated or down regulated in naive vs. primed human pluripotent cells. * Indicates student t-test P value <0.01 for comparisons between naive and primed samples. Error bars indicate s.d.m (n=3).

Figure 78:
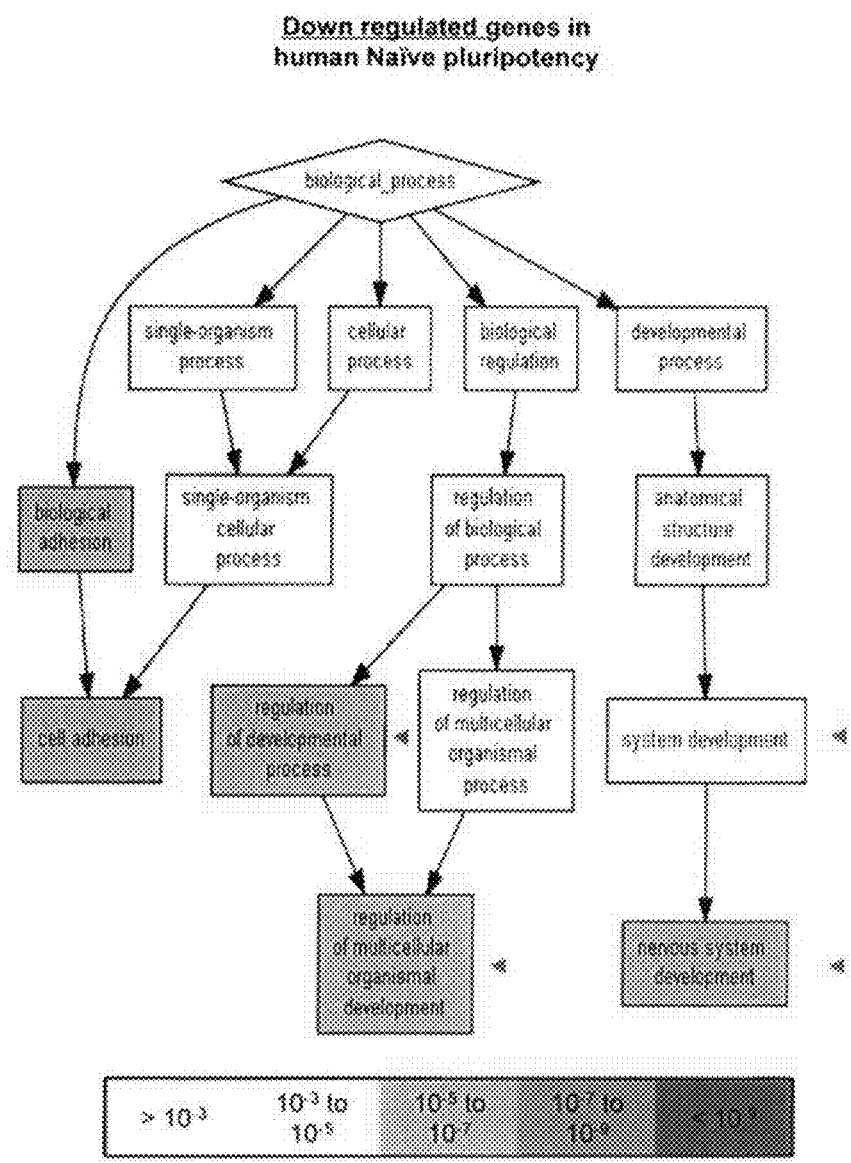

FIG. 78 depicts GO ontology analysis for genes down regulated in human naive pluripotency. GO ontology categories enriched for and down-regulated genes in naive pluripotency, checked and visualized using the online tool GOrilla. Color bar shows p-values, the figure shows only trees containing GO terms with p-values <10-5, resulting in FDR corrected p-values <0.05.

Figure 79A:
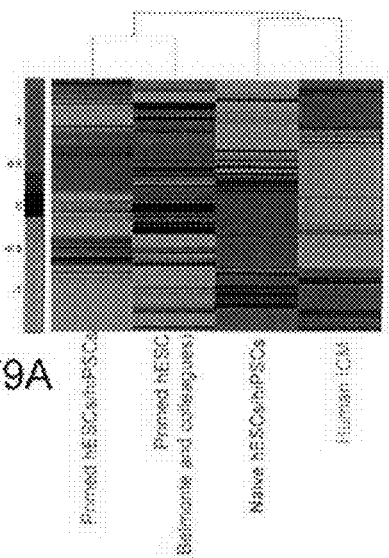
Figure 79B:
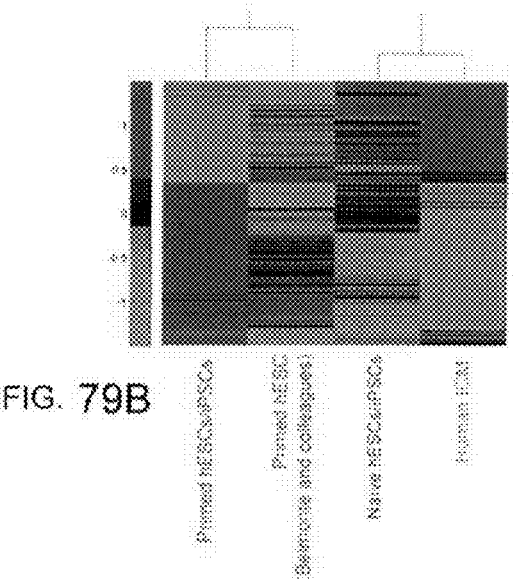

FIGS. 79A-D depict transcriptional comparison of in vitro and in vivo isolated human pluripotent cells. FIG. 79A—Hierarchical clustering of gene expression of genes differentially expressed between Naive and Primed samples, in human cell lines and in the human inner-cell-mass (ICM), using Spearman correlation. Note that while the ESC samples previously derived by Belmonte and colleagues cluster with the Primed samples derived herein, the human ICM samples cluster with the Naive samples. FIG. 79B—

Figure 79C:
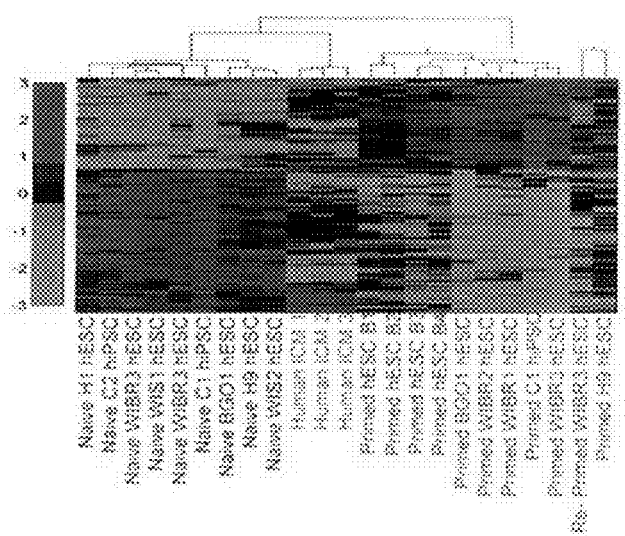
Figure 79D:
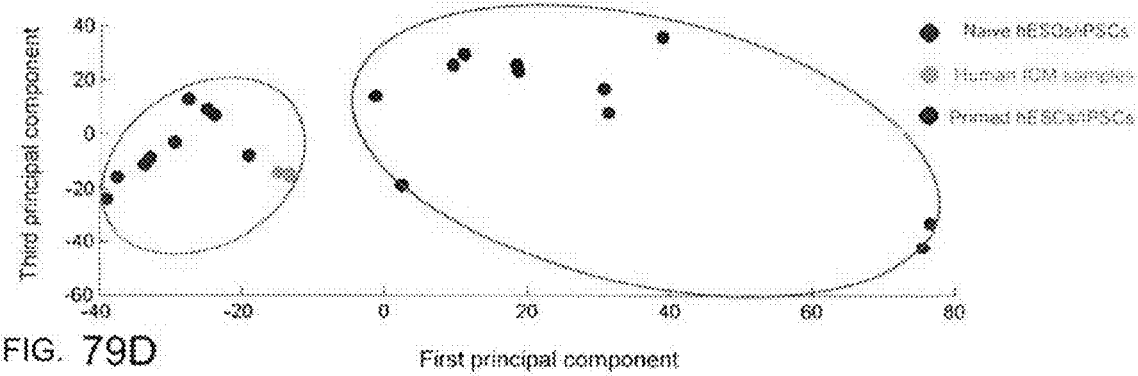

Hierarchical clustering of the mean expression profile of all the genes in the different groups (Naive, Primed, Belmonte's ESCs, and ICM), using Spearman correlation. FIG. 79C—Hierarchical clustering of the mean expression profile of differentially expressed genes in all individual samples. FIG. 79D-Principal Component Analysis showing that human ICM samples are closer to Naive than to Primed samples (along the 1st principal component axis). Primed samples are also more dispersed, showing higher variability and heterogeneity, and not as closely grouped as Naive and ICM samples are.

FIGS. 80A-D depict distinct MHC class I and TFE3 protein cellular localization pattern in naive human pluripotent cells. Shown are representative confocal images of double immunostaining for OCT4 and TFE3 followed by fluorescence intensity profiling of the yellow-dashed box area. FIG. 80A—Naive mESC; FIG. 80B—Naive WIBR3 hESC; FIG. 80C—Primed mEpiSC; FIG. 80D—Primed WIBR3 hESC. This analysis demonstrated overlap between OCT4 nuclear expression with TFE3 in mouse and human pluripotent cells (naive and primed). These representative images reveal strict nuclear localization of TFE3 in naive pluripotency, while primed pluripotency is associated with increased cytoplasmic localization of TFE3 both in mice and human primed cell lines. Y-axis represents fluorescence intensity, profiling measured with Zen blue 2011 software. See FIG. 3e and Methods for systematic unbiased quantifications.

FIGS. 81A-D depict enhanced surface E-CADHERIN expression in human naive pluripotent cells. Representative confocal immunostaining images for the expression of E-CADHERIN and OCT4 on genetically matched naive (FIGS. 81A and 81C) and primed (FIGS. 81B and 81D) hESCs. The samples were processed simultaneously and analyzed under identical conditions. Insets represent enlargements of boxed areas. While E-CADHERIN is expressed in primed hESCs, its expression becomes homogenously distributed and more enhanced in humane naive hESCs expanded in WIS-NHSM conditions.

FIGS. 82A-B depict cross-species clustering of naive and primed pluripotency. FIG. 82A—Cross-species gene expression hierarchical clustering of all 9,803 orthologous genes represented on both mouse and human gene arrays used in this study, clustered using Pearson correlation. Naive mouse and human pluripotent cells formed a distinct group apart from primed mEpiSCs and conventional/primed hESCs and hiPSCs. Heat map showing row-normalized expression levels (log-ratio) with red and green colors representing up and down regulated genes, respectively. Naive cells are labeled in blue, primed cells are labeled in red. Mouse samples were obtained from either 129 or NOD strains. This analysis strikingly confirms that pluripotent cells lines preferentially cluster based on naive and primed configuration, rather by the species of origin. FIG. 82B—Boxplot of gene-specific gene expression levels in Primed samples showing higher noise and heterogeneity than in Naive samples. This pattern is consistent with the genome-wide data in FIGS. 69A-G. Five out of nine genes are significantly more variable, tested by F-test of equality of variances).

Figures 83A, 83B, 83C, 83D:
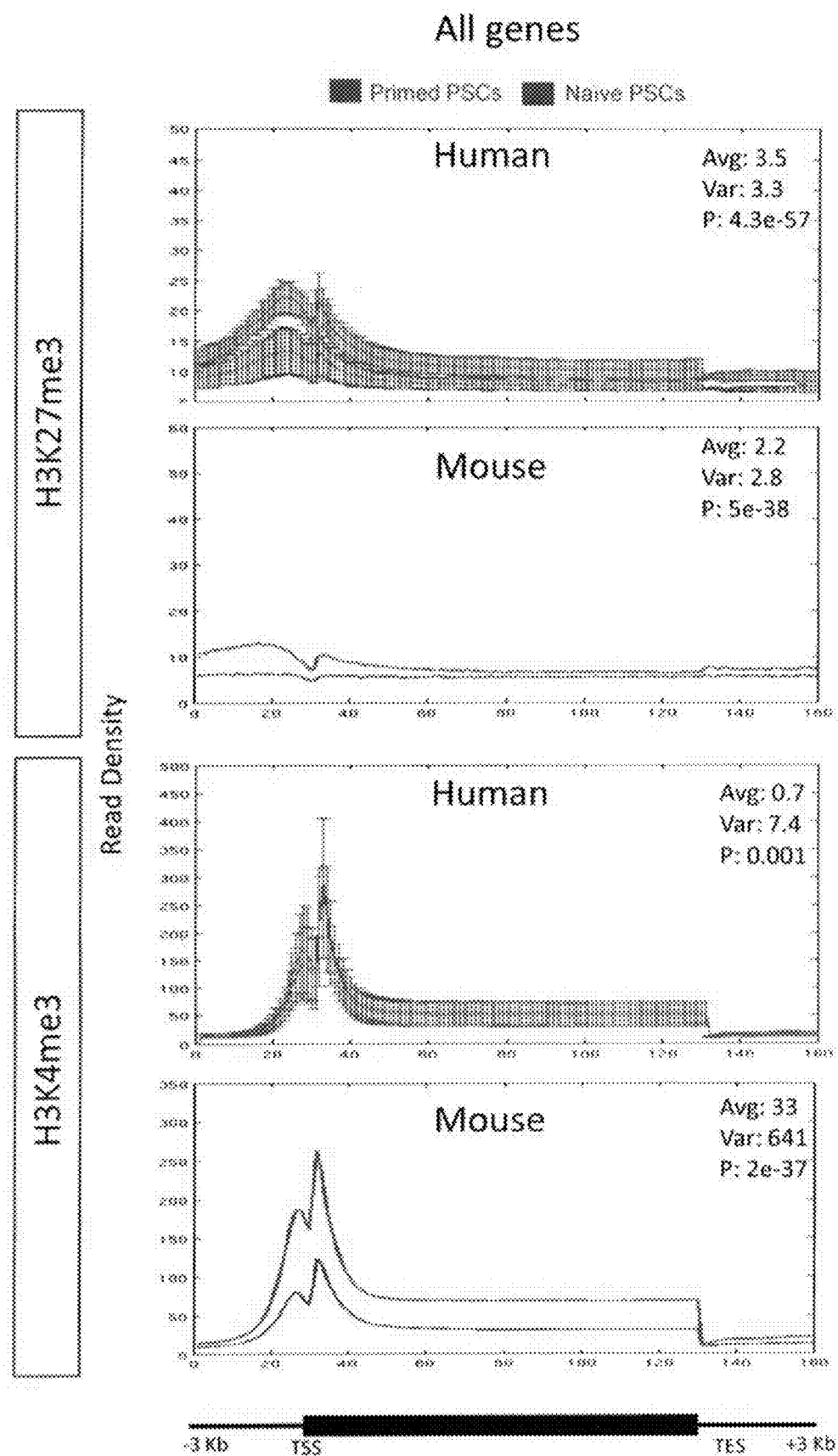

FIGS. 83A-D depict global H3K27me3 and H3K4me3 deposition in naive and primed pluripotent cells. Profiles of H3K27me3 (FIGS. 83A-B) and H3K4me3 (FIGS. 83C-D) chromatin modifications of all RefSeq genes in human (n=43,463; FIGS. 83A and 83C) and mouse (n=30,480; FIGS. 83B and 83D), naive (blue) and primed (red), represented as normalized read-density. Human profiles indicate average and s.d. (error-bars) calculated over 5 different cell lines (C1, LIS2, WIBR3, WIBR3-MBD3$^{mut}$ and BGO1). Average difference between plots is indicated alongside variance and P-values (calculated with paired-sample t-test).

FIGS. 84A-G depict gnome wide redistribution of H3K27me3 in human naive pluripotency. FIGS. 84A-B—Distribution of H3K27me3 peaks in different genomic components (promoter, gene-body and intergenic region), as a function of the peak density (represented as RPKM, read-per-kilobase-per-million-reads), in human cell lines (WIBR3, C1 and BGO1). In addition to a reduction in total number of peaks in naive conditions, the peaks distribute differently from primed, with lower number of peaks in promoters and gene bodies, compared to primed conditions. FIG. 84C—Western blot analysis for quantifying total H3K27me3 levels in naive and primed LIS2 hESC samples. Total levels of H3K27me3 were not significantly altered between naive and primed samples (similar to what was observed in mice). Similar results were seen in WIBR3 and C1 cell lines (data not shown). FIGS. 84D-E—Number of enhancers of class I (active transcription) and class II (poised) in naive (blue) vs. primed (red) human (FIG. 84D) and mouse (FIG. 84E). In human, numbers correspond to common enhancers in lines WIBR3 and C1. The number of reads was normalized by down-sampling such that the number of reads in all human samples is identical, and so is the number of reads in all mouse samples. A dramatic decrease in class II enhancers can be seen in the naive cells in both human and mouse. FIGS. 84 F-G—Expression level distribution of genes associated with class I and class II enhancers, present in either naive cells only (blue) or in primed cells only (red) in human (FIG. 84F) or mouse (FIG. 84G) cells. Expression level distribution of all genes is presented as control. Boxes represent 25th and $75^{th}$ quantiles, and whiskers represent min and max values that are not outliers. Analysis shows that Primed state specific class II enhancers continue to retain very low expression levels in both naive and primed states (despite the loss of H3K27me3 mark in naive pluripotency over their enhancer). P-values (t-test) indicate significant differences between distributions in naive and primed cells.

Figure 85B:
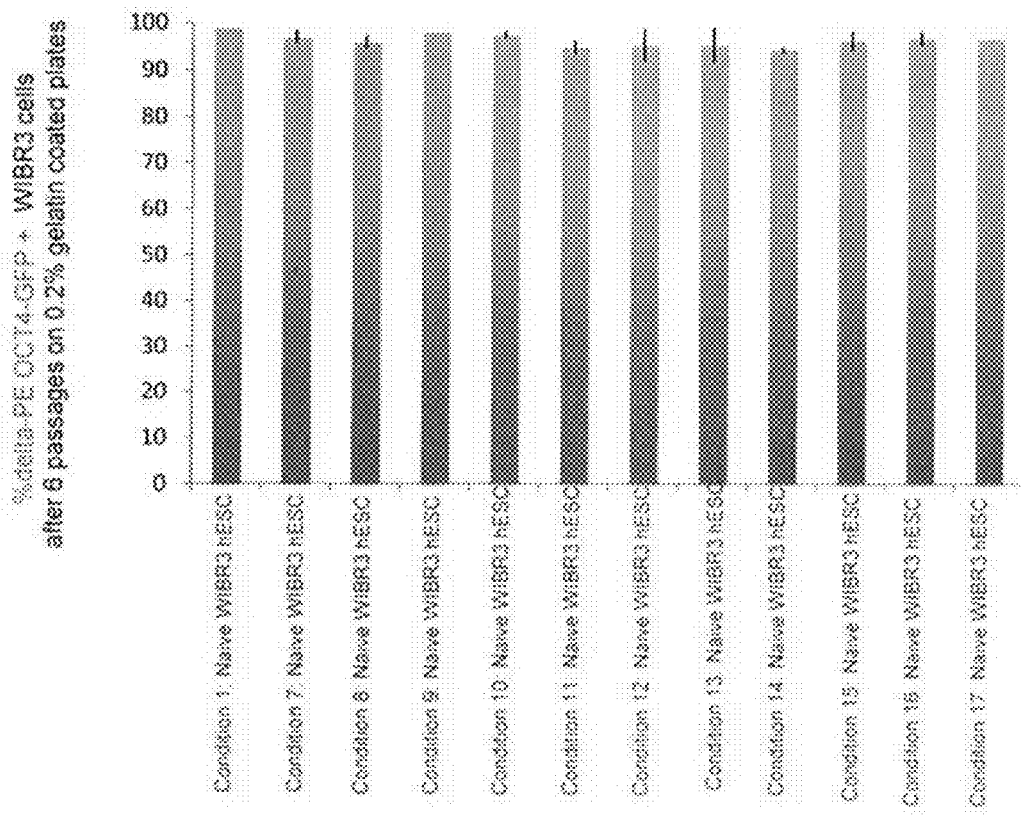
Figure 85C:
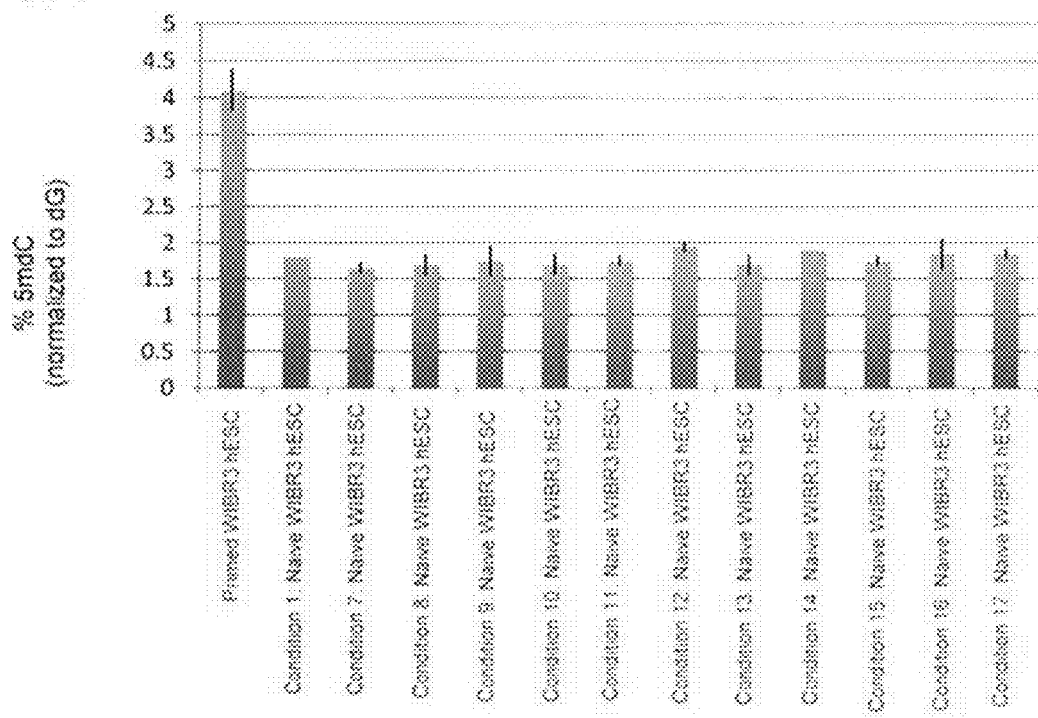

FIGS. 85A-C—Primed/conventional WIBR3 human ESCs were passaged in 12 different WIS-NHSM based conditions. FIG. 85A depicts the compositions of the different variations of the WIS-NHSM conditions used in this experiment, in addition to the basic medium of KO-DMEM, supplemented with 1% ALBUMAX, 50 microgram/ml (μg/ml) L-ascorbic acid, N2 supplement (Invitrogen) and additional 6.25 mg human insulin. Small molecules and cytokines were included as indicated in combinations of conditions 1-12. Cells were expanded on 0.2% Gelatin coated plates for 25 days (6 passages). FIG. 85B—A histogram depicting OCT4-GFP+ levels as evaluated by FACS analysis to measure the pluripotency maintenance in these conditions. Error bars indicate s.d. n=2. FIG. 85C A histogram depicting the percentage of methylated cytosine. Genomic DNA was harvested and was subjected to quantification of methylated cytosine frequency by mass spectrometry. Error bars indicate s.d. n=2 replicates. Primed cells were used as a reference control sample.

Figure 86A:
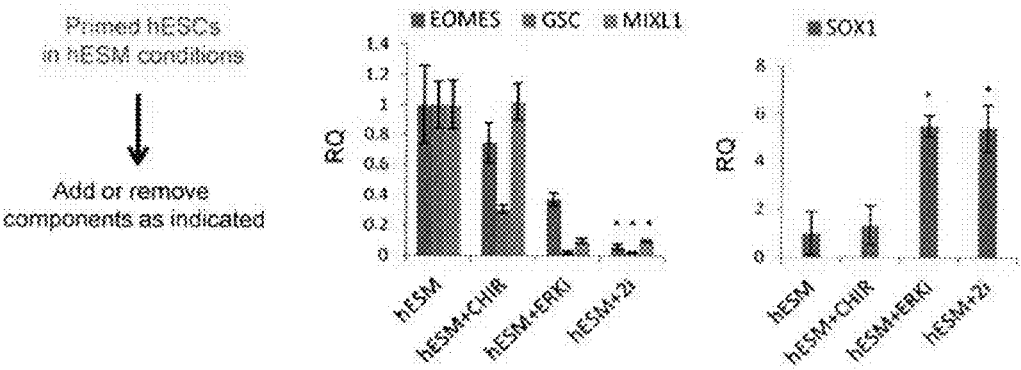
Figure 86B:
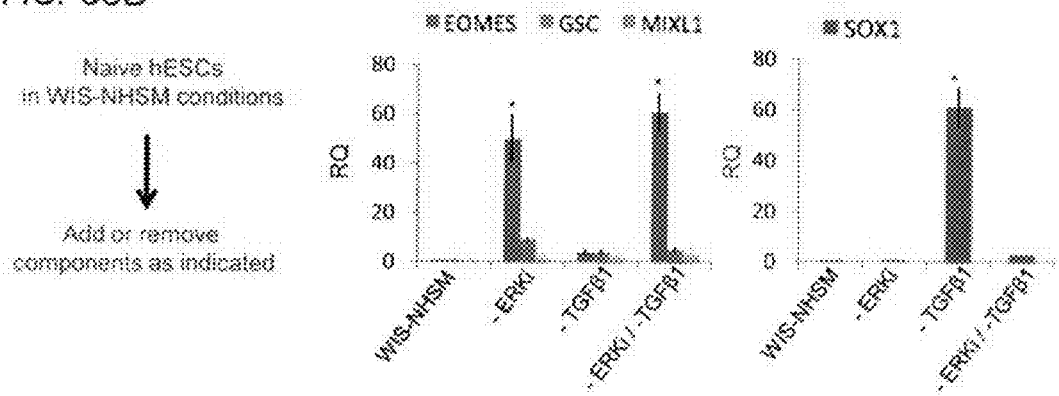
Figure 86C:
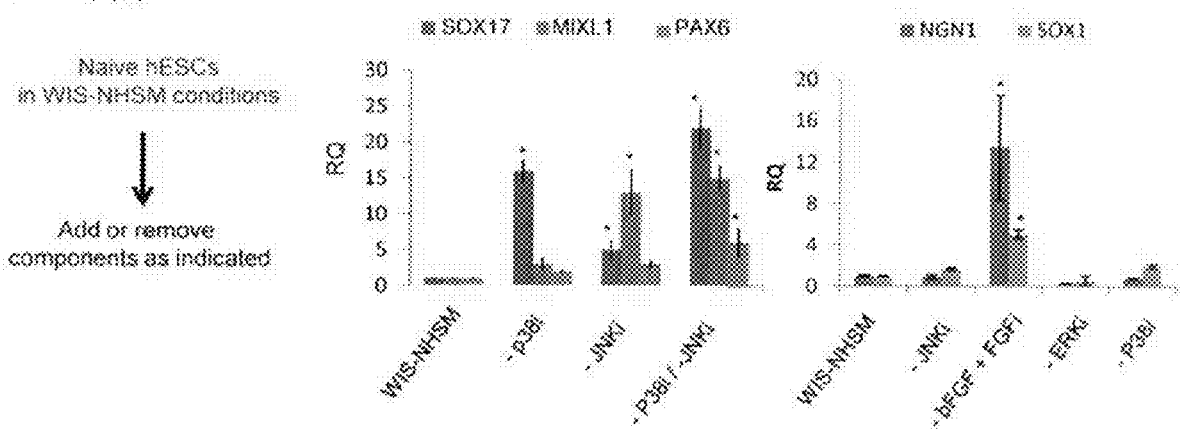

FIGS. 86A-C depict the influence of MAPK signaling perturbation on human naive and primed pluripotent cells. FIG. 86A—qRT-PCR for expression of the indicated lineage commitment genes in different conditions. Supplementing primed hESCs with ERKi, GSK3βi (CHIR99021) or both (21) results in upregulation of SOX1 neural marker, consistent with their tendency to differentiation upon ERK inhibition. FIG. 86B—naive WIS1 hESCs expanded in WIS- NHSM conditions, were expanded after omitting the indicated factors from WIS-NHSM conditions for 72 hours. qRT-PCR of lineage commitment genes is shown. The results indicate that TGFβ blocks the SOX1 inductive effect induced by the presence of ERKi in the medium. FIG. 86C—qRT-PCR analysis for lineage commitment gene upregulation 72 hours after withdrawal of p38i and/or JNKi from WIS-NHSM conditions. These results indicate that the components in WIS-NHSM conditions cooperatively promote pluripotency stability and counter-balance and neutralize pro-differentiation effects induced by some of the ingredients. Error bars indicate s.d.m (n=3). Representative results of one out of three biological replicates experiments is shown. * indicates student's t-test P value <0.01.

Figure 87A:
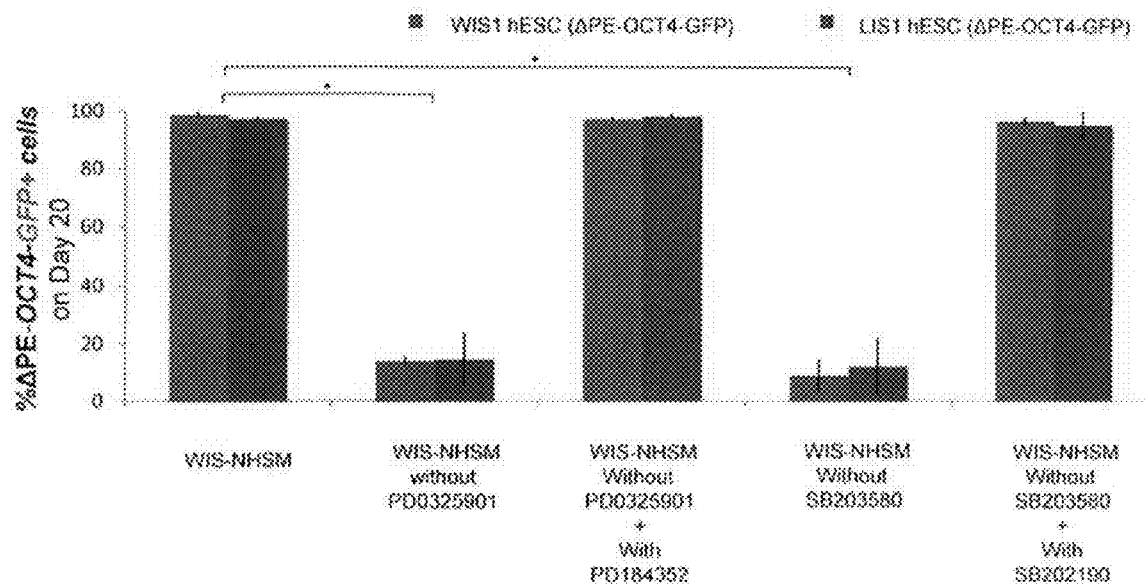
Figure 87B:
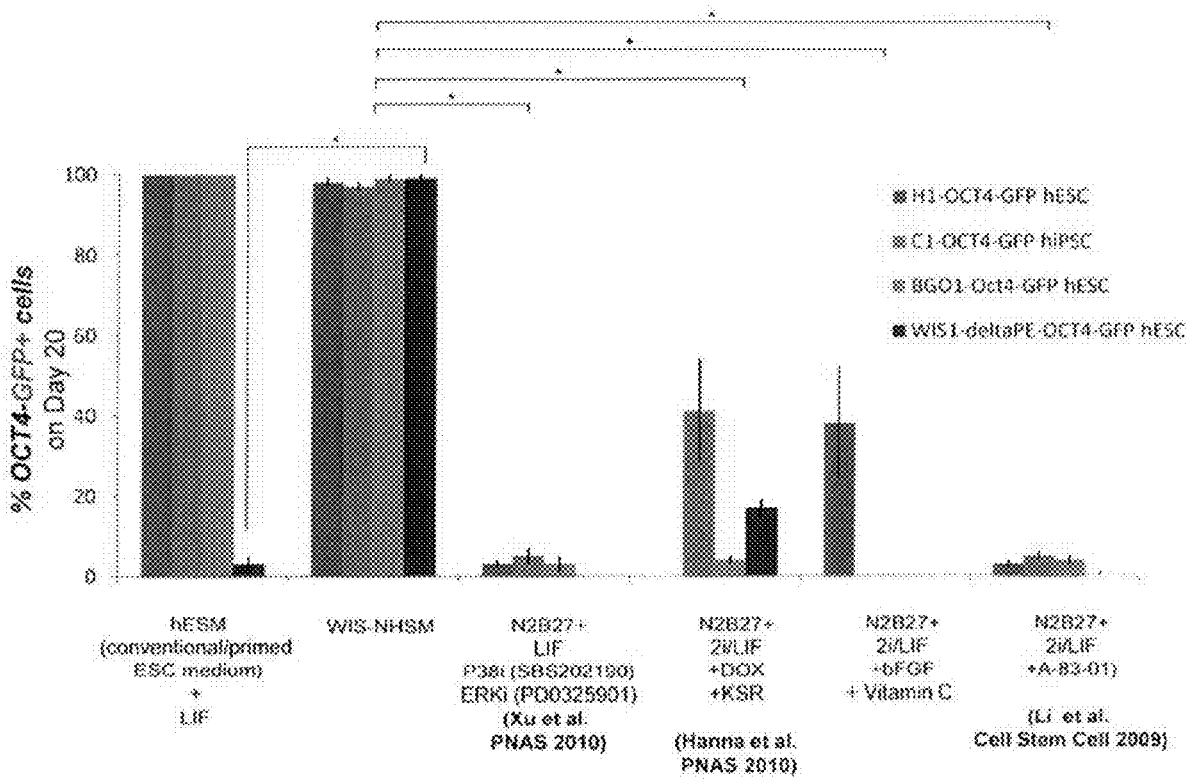

FIGS. 87A-B depict signaling requirements for maintaining naive hESCs and hiPSCs. FIG. 87A—WIS1 and LIS1 naive hESCs were targeted with the ΔPE-OCT4-GFP reporter and analyzed for the ability to retain naive pluripotency in different conditions as indicated. OCT4-GFP+ levels detected by FACS from two experimental replicates were averaged. Error bars indicate s.d. The results indicate ERK inhibition is essential for maintaining hESCs in WIS-NHSM, and this effect can be achieved by using two different ERK inhibitor (PD 0325901 or PD184352). b, p38 inhibition is essential for maintaining hESCs in WIS-NHSM, and this effect can be achieved by using two different p38 kinase inhibitors (SB203580 or SB202190). FIG. 87B—Different hESCs and hiPSC line carrying OCT4-GFP or ΔPE-OCT4 GFP reporter were used to evaluate different conditions for their ability to maintain pluripotency and specifically naive pluripotency (by ΔPE-Construct). Only WIS-NHSM conditions enabled maintenance of all cell lines tested while activating both OCT4-GFP and ΔPE-OCT4-GFP reporter. * Indicates student t-test P values <0.01 between indicated compared samples/groups. Error bars indicate s.d.m between well replicates (n=3).

FIGS. 88A-J demonstrate different defined growth conditions which enable maintenance of mouse naive pluripotency. FIGS. 88A-G—V6.5 mESCs carrying the naive pluripotency specific ΔPE-Oct4-GFP reporter were maintained in distinct chemically defined growth conditions as indicated in the panel labels: FIG. 88A—N2B27 LIF; FIG. 88B—N2B27 ERKi/GSK3βi (2i)/LIF; FIG. 88C—N2B27 p38i/GSK3βi/LIF; FIG. 88D—N2B27 JNKi/GSK3βi/LIF; FIG. 88E—WIS-NHSM; FIG. 88F—WIS-NHSM without FGF2/TGFβ; FIG. 88G—mEpiSCs medium (with FGF2/TGFβ). The analysis indicates that naive GFP+ mESCs can be maintained in LIF, GSK3βi together with either ERK1/2i, p38i or JNKi. FIGS. 88H-J—Representative images of high-contribution chimeras generated after blastocyst microinjection of the indicated lines. FIG. 88H—N2B27 p38i/GSK3βi/LIF; FIG. 88I—N2B27 JNKi/GSK3βi/LIF; FIG. 88J-WIS-NHSM. Agouti coat color indicates high-level chimera contribution.

Figure 89D:
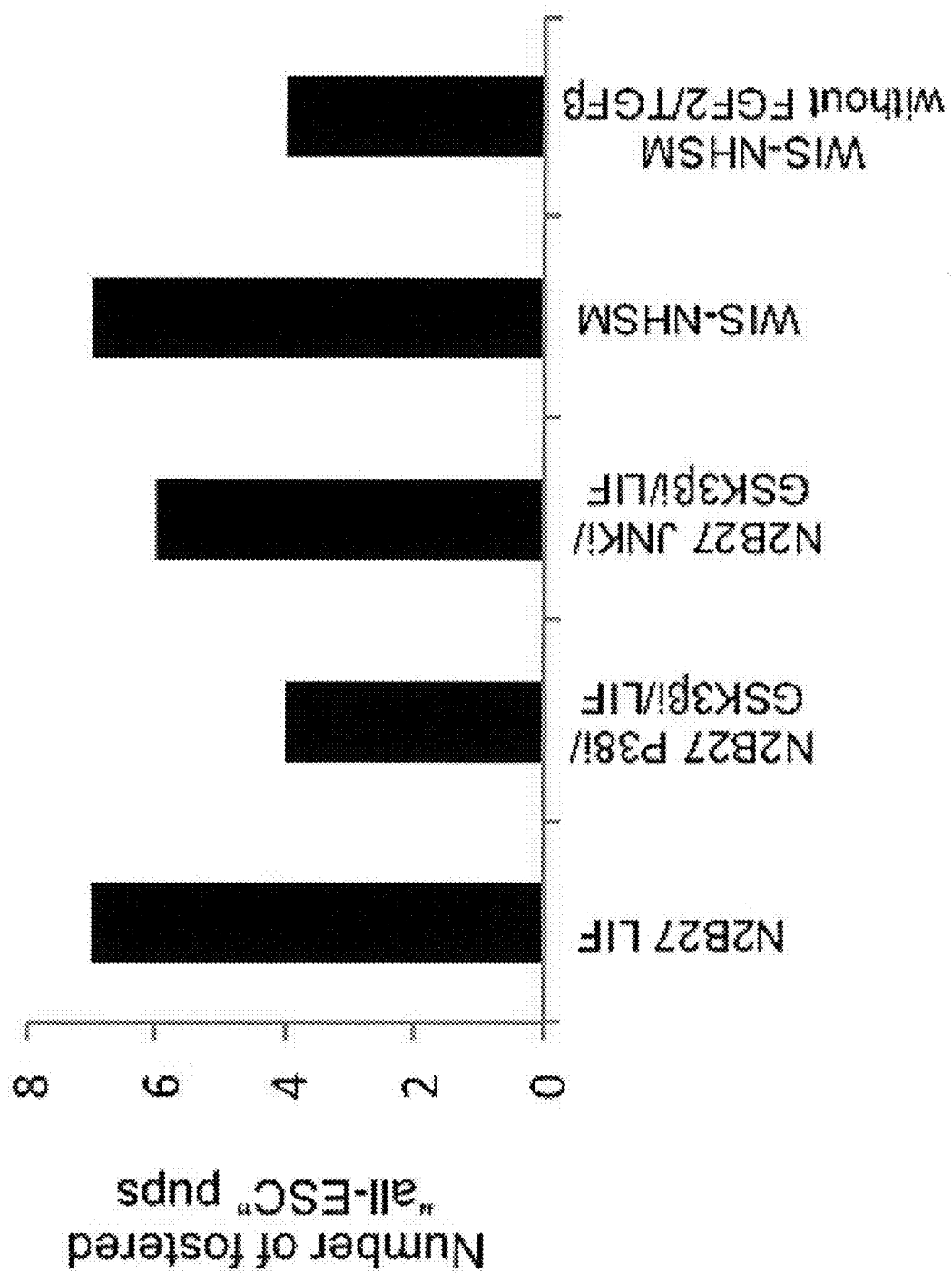

FIGS. 89A-D depict competence of different mouse naive growth conditions in tetraploid embryo complementation assay. FIG. 89A—V6.5 naive mESCs were expanded in the indicated conditions for 12 passages, after which they were tested for tetraploid complementation assay to form all-ESC animals. The analysis indicates unrestricted developmental potential is equivalently obtained at the functional level when naive mESCs are expanded with either p38i, JNKi or ERK1/2i (together with supplementation of LIF and GSK3βi in all conditions). FIGS. 89B-C—Representative images of "all-ESC" agouti coat colored animals obtained. FIG. 89D—Competence of different mouse naïve growth conditions in tetraploid embryo complementation assay. V6.5 naïve mESCs were expanded in the indicated conditions for 12 passages, after which they were tested for tetraploid complementation assay to form all-ESC animals. The analysis indicates unrestricted developmental potential is equivalently obtained at the functional level when naïve mESCs are expanded with p38i, Jnki or Erk1/2i (together with supplementation of LIF and GSK3βi in all conditions).

Figure 90:
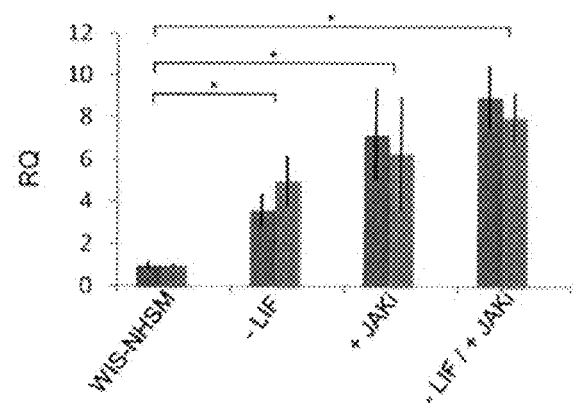

FIG. 90 depicts LIF/STAT3 signaling dependence by naive hESCs/iPSCs. qRT-PCR levels of the indicated lineage commitment genes after subjecting naive WIS1 hESCs to LIF withdrawal and/or supplementation with JAK small molecule inhibitor (JAKi 0.6 µM) for 72 hours. Averages of biological triplicates are indicated, as normalized levels to un-stimulated control. Error bars indicate s.d.m (n=3). Interfering with LIF/STAT3 signaling results in specific upregulation of lineage commitments genes in naive hESCs. * Indicates student t test P values <0.01 compared to control WIS-NHSM conditions. Error bars indicate s.d.

Figure 91A:
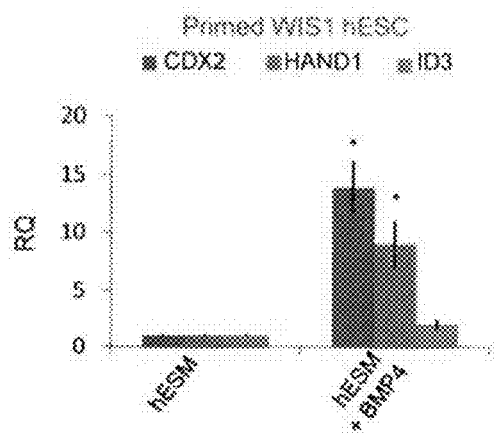
Figure 91B:
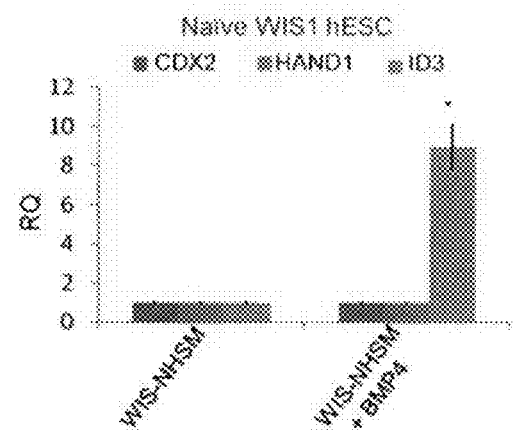
Figure 91C:
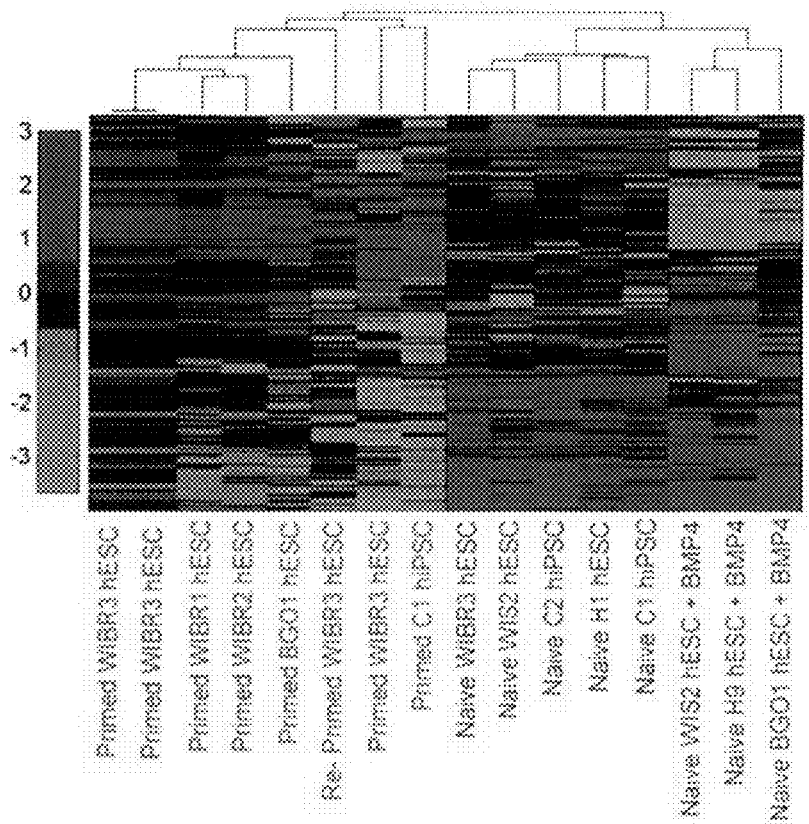

FIGS. 91A-C depict unique signaling requirement and response to BMP4 for naive hESCs/iPSCs. FIGS. 91A-B—qRT-PCR levels of the indicated commitment genes after subjecting naive (FIG. 91B) and primed (FIG. 91A) WIS1 hESCs to BMP4 for 72 hours. Averages of biological triplicates are indicated, as normalized levels to un-stimulated control. Error bars indicate s.d.m (n=3). Naive WIBR3 hESCs upregulated ID3 (inhibitor of DNA binding 3, dominant negative helix-loop-helix protein; Gene ID: 3399) in response to BMP4 (5-10 ng/ml bone morphogenetic protein 4), but not trophoblast early markers CDX2 (caudal type homeobox 2; Gene ID: 1045) and HAND1 (heart and neural crest derivatives expressed 1; Gene ID: 9421). This is reminiscent of naive mESCs to BMP4 where it was shown to support and maintain their pluripotency by up regulating Id3 [Ying, Q.-L., et al. *Cell* 115, 281-292 (2003). BMP Induction of Id Proteins Suppresses Differentiation and Sustains Embryonic Stem Cell Self-Renewal in Collaboration with STAT3]. Primed WIBR3 hESCs upregulate trophoblast differentiation markers CDX2 and HAND1 in response to BMP4 and do not upregulate ID3. FIG. 91C—Global gene expression analysis indicates that naive WIS2, H9 and BGO1 expanded with the addition of BMP4 for 12 passages, retain a transcriptional program that clusters with naive hESCs and hiPSCs, rather than primed cells. Hierarchical clustering of genome-wide gene expression of human cell lines, using Euclidean distance. Naive hESC and hiPSCs either with or without BMP4 clustered separately from conventional/primed hESCs/hiPSCs, as shown by the dendrogram. Heat map showing row-normalized expression levels with red and green colors representing up and down regulated genes, respectively. Note the two left-most genetically identical samples that were used for Batch effect correction, allowing two different datasets to be united for further analysis (see online Methods). Collectively these findings indicate a unique tolerance for naive human pluripotent cells for BMP4 that does not compromise the maintenance of the naive pluripotent state.

FIGS. 92A-D depict reprogramming efficiency of Mbd3$^{+/+}$ Secondary MEF after knockdown of Mbd3 (Mbd3 siRNA) or Chd4 (Chd4 siRNA). FIG. 92A-MEFs were subjected to reprogramming with STEMCCA-OKSM with DOX induction, and on day 3 the 2i/LIF medium was added. The indicated siRNAs were added on days 2, 4 and 6. FIGS. 92B-C—Western blot analyses indicating protein depletion efficiency on siRNA transfection of either Mbd3 (FIG. 92C) or Chd4 (FIG. 92B) targeting siRNA pools. FIG. 92D A histogram depicting reprogramming efficiency. Reprogramming efficiency was measured by quantitation of the OCT4-

GFP positive cells (assayed by FACS). Shown are Error bars indicate s.d. from average (n=3). Asterisks indicate Student's t-test P value <0.01.

FIG. 93 shows that P66a-CC interrupts Mbd3 binding to Chd4. 293T cells were transfected with both with Flag-Mbd3 (WT) and P66a-CC (SEQ ID NO:71; GenBank Accession NO. NM_017660.3) or a control vector (mCherry), Mbd3 interacting proteins were pulled down by immunoprecipitation (IP) using Flag-magnetic beads. The results indicate specific loss of Chd4 interaction with Mbd3 following the p66a-CC transfection.

Figure 94A:
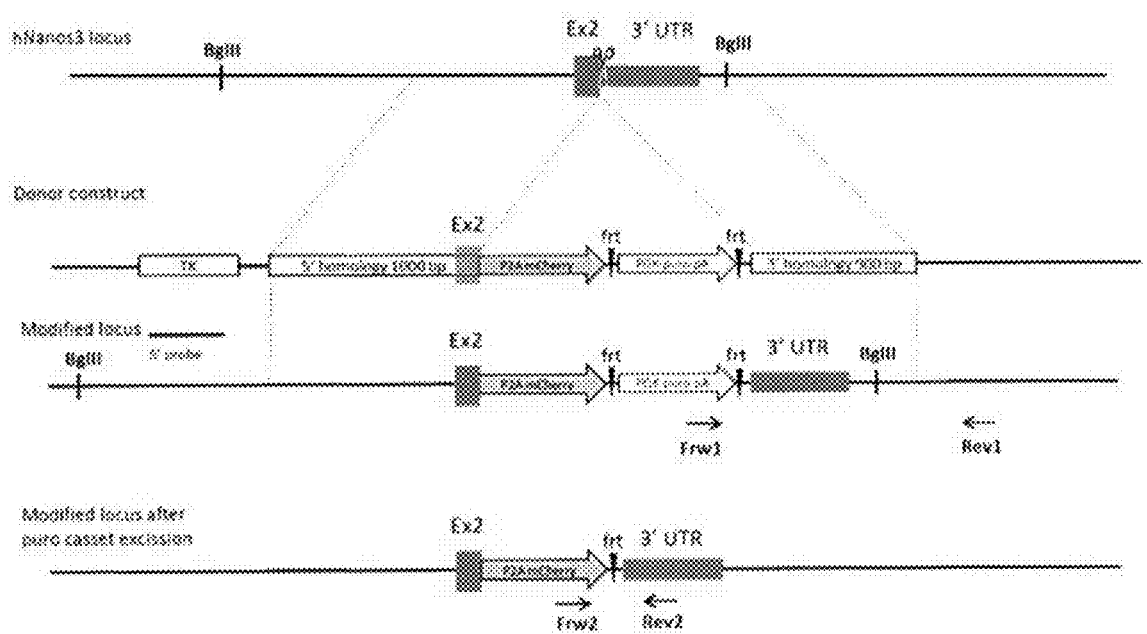
Figure 94B:
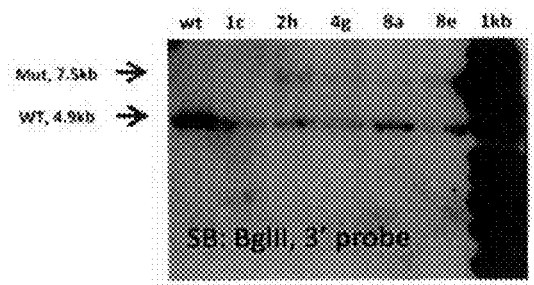

FIGS. 94A-B depict the generation of a mCherry knock in reporter allele in Nanos3 locus of a naive human ESC (WIS1). FIG. 94A A schematic illustration depicting genetic engineering via TALENs in WIS1 naive human ESCs to generate mCherry knock in reporter allele in Nanos3 locus. Scheme indicates targeting strategy. FIG. 94B—Southern blot analysis depicting correctly targeted allele (mut) in a number of WIS clones (2h, 4g, 8a, and 8e).

FIG. 95 illustrates the differentiation strategy of naive EIS1 NANOS3-cherry reporter human ESCs into primordial germ cell (PGC)-like cells (abbreviated as PGCLC). Shown are images of the cells/colonies during the differentiation process.

FIGS. 96A-I depict the process of differentiating human ESCs into primordial germ cell like cells. FIG. 96A—schematic illustration of the differentiation process. FIGS. 96B-I—FACS analyses for detecting PGCLC marker expression NANOS3-Cherry. FIG. 96B—naive ESCs; FIG. 96C—primed EpiLC; FIGS. 96D-F—cells were cultured in a PGC medium which included BMP4; FIGS. 96G-I—cells were cultured in a PGC medium which did not include BMP4. Shown are FACS results after 2 (FIGS. 96D and 96G), 4 (FIGS. 96E and 96H), and 6 (FIGS. 96F and 96I) days in the PGC medium. The Figures show specific induction of mCherry reporter at Day 2+4 and only when BMP4 is included in the differentiation medium (FIG. 96E). Note Naive ESCs do not express mCherry (FIG. 96B), neither EpiLC cells (FIG. 96C). One representative experiment is shown out of five performed. +/− indicates s.d. (n=5).

FIGS. 97A-H depict expression of PGC markers in human PGCLC cells. Shown are real-time PCR analyses for expression of different PGC markers during the induction protocol. FIG. 97A—TFAP2c (also known as AP2gamma); FIG. 97B BLIMP1 (also known as PRDM1—PR domain containing 1, with ZNF domain: Gene ID:639); FIG. 97C—PRDM14 (PR domain containing 14); FIG. 97D—STELLA (developmental pluripotency associated 3); FIG. 97E—DND1 (DND microRNA-mediated repression inhibitor 1); FIG. 97F—NANOS3 (nanos homolog 3); FIG. 97G—INTEGRIN B3 [integrin, beta 3 (platelet glycoprotein Ma, antigen CD61)]; FIG. 97H—VASA; Results clearly show that PGCLC markers are induced in protocol applied on human naive ESCs, including STELLA (FIG. 97D), INTEGRINB3 (FIG. 97G), BLIMP1 (FIG. 97B) and VASA (FIG. 97H).

Figure 98A:
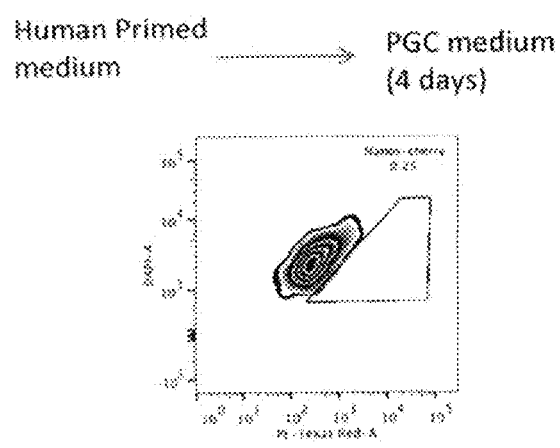
Figure 98B:
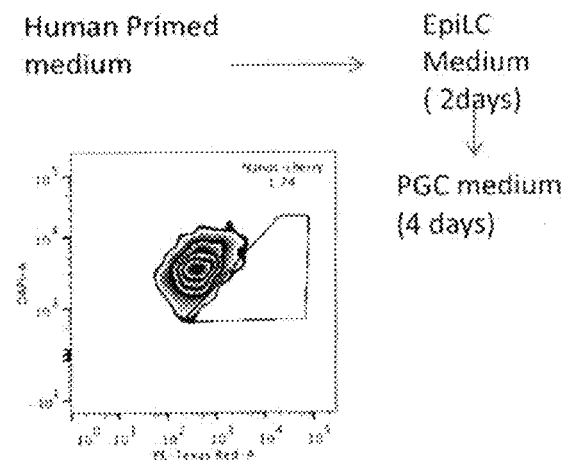

FIGS. 98A-B depict FACS analyses of conventional/primed human ESCs that were subjected to the same induction protocol as described in Example 11 of the Examples section which follows, and in FIGS. 95-97 above. FIG. 98A—FACS analysis after 4 days in PGC medium. FIG. 98B FACS analysis after subjecting the primed ESCs to epiblast medium (EpiLC medium) for 2 days, following by further 4 days in the PGC medium. Note the low nano-cherry percentage of cells in FIG. 98A (0.25%) and the slight increase of nanos-cherry positive cells in FIG. 98B (1.74%). These results show that conventional/primed human ESCs subjected to BMP4 including PGCLC induction protocol do not successfully turn on NANOS3 mCherry reporter. Results indicate the importance of using human naive pluripotent cells as a starting material for human PGCLC induction.

FIGS. 99A-G depict reprogramming of MBD3 knocked down human fibroblasts. FIG. 99A—Human BJ fibroblasts were infected with TRIPZ MBD3 shRNA lentiviruses (3.1, 3.2, 3.3 indicate three different hairpin constructs targeting MBD3). Shown is a histogram with quantification of real time PCR expression for MBD3 which was conducted after 72 hours with or without DOX induction. The results validate down-regulation of MBD3 in human fibroblasts in a DOX dependent manner. FIGS. 99B-G—Human adult dermal fibroblasts were infected with FUW-RtTA, TetO-OKSM, TetO-ERAS and Tripz-MBD3 shRNA lentiviral mix. The following DOX inducible MBD3 knockdown lentiviral clones were used: TRIPZ Human MBD3 shRNA Clone ID: V3THS_392206 (#1); V3THS_392209 (#2); V3_THS 392210 (#3). First 3 days of reprogramming were in the presence of DMEM medium supplemented with 15% FBS (fetal bovine serum)+50 microgram/ml Vitamin C+DOX (2 microgram/ml). After 3 days, NHSM conditions were applied (using the NHSM medium) with continued DOX induction. FIGS. 99B-C—Reprogramming of MBD3 knocked down human fibroblasts. Shown are the reprogrammed cells which express shMBD3-red fluorescent protein (RFP) in red fluorescence (FIG. 99B) or in bright filed (BF; FIG. 99C). FIGS. 99D-G—Reprogramming of MBD3 KD primary human fibroblasts with overexpression of OKSM and ERAS in NHSM conditions. Shown are the clonal populations with ES-like morphology appeared at days 5 (FIGS. 99D-E) and 11 (FIGS. 99F-G). Phase contrast images are shown in FIGS. 99D and 99F. Red fluorescence images are shown in FIGS. 99E and 99G. MBD3 knocked-down clones that over express ERAS develop in 5 days, and were subjected for iPSC follow up analysis.

Figures 100A, 100B, 100C, 100D:
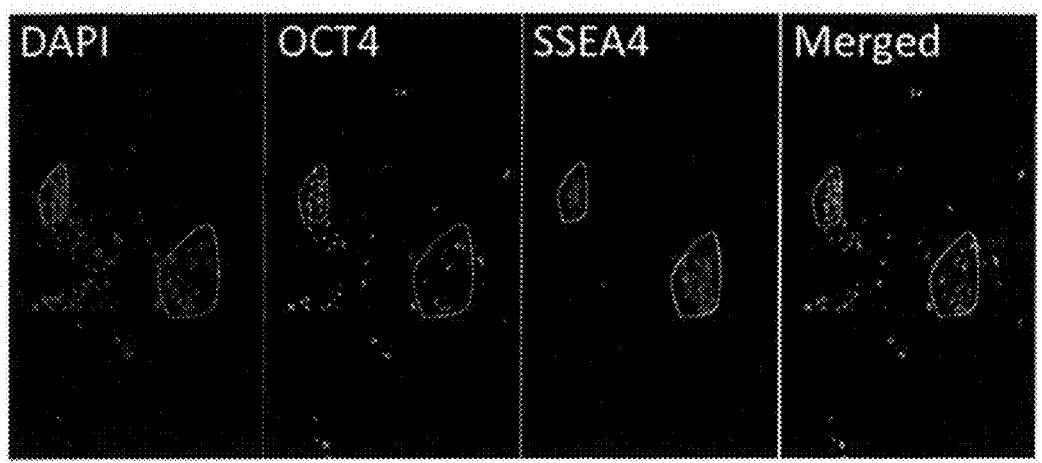
Figures 100E, 100F, 100G, 100H:
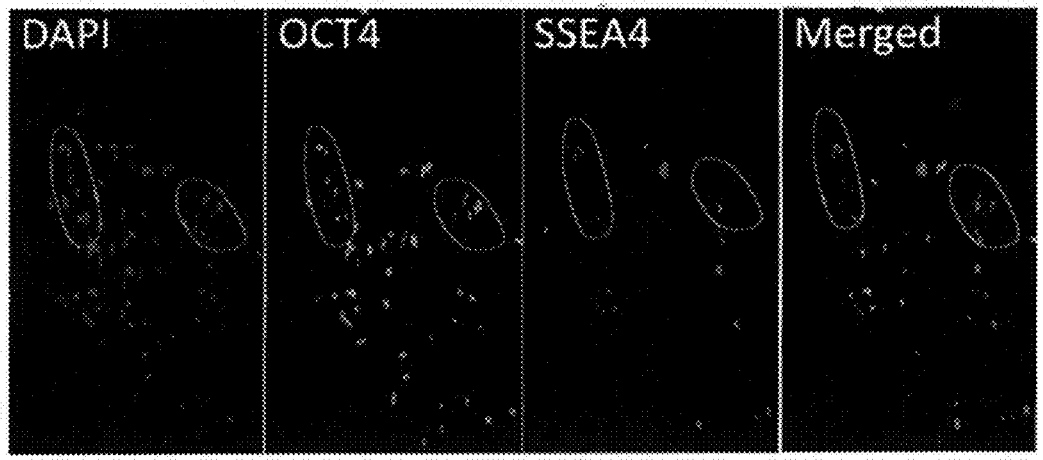
Figure 100I:
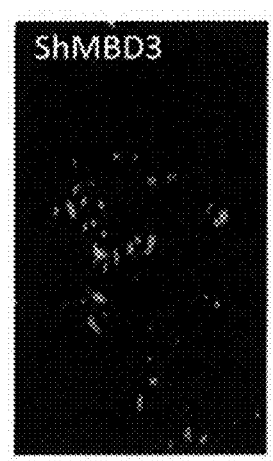
Figures 100J, 100K, 100L, 100M:
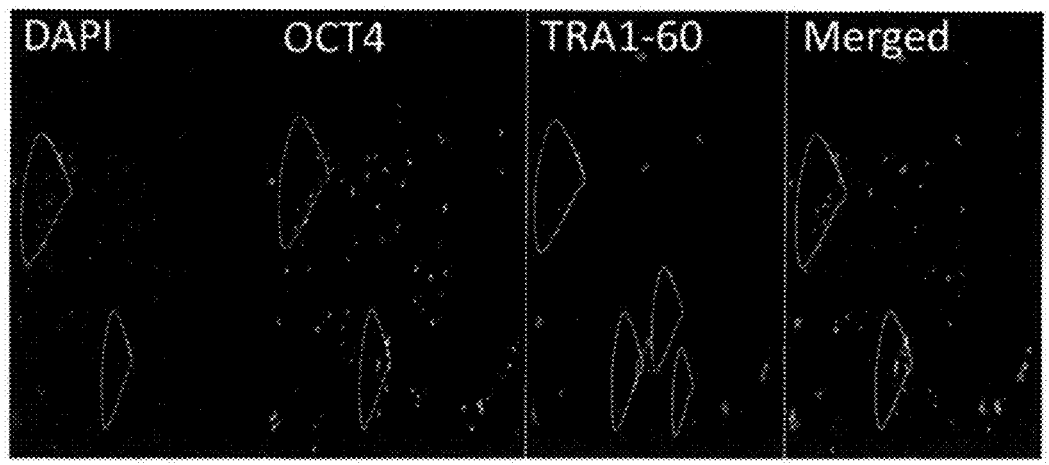
Figure 100N:
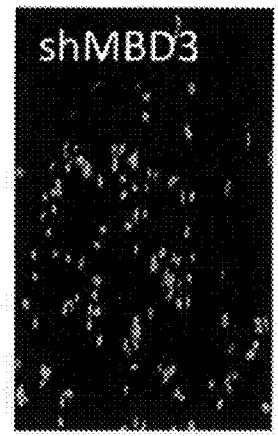
Figures 100O, 100P, 100Q, 100R:
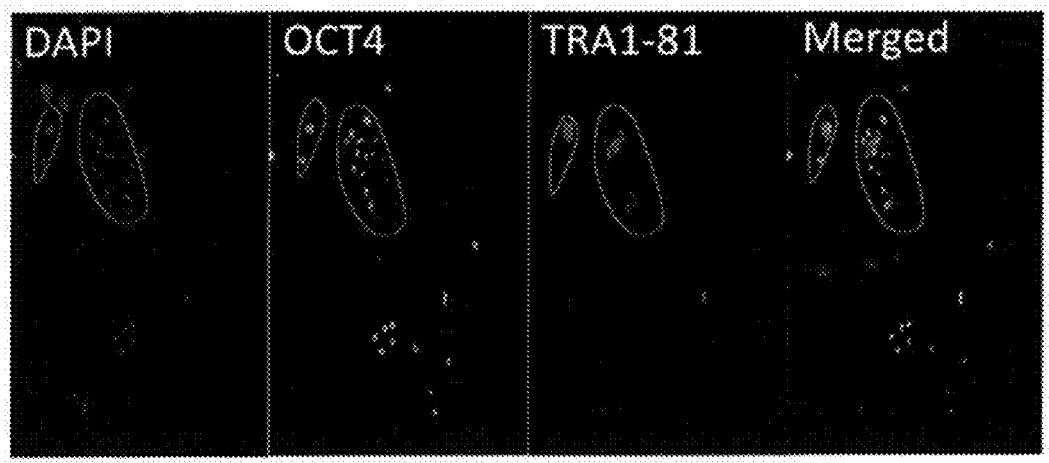
Figure 100S:
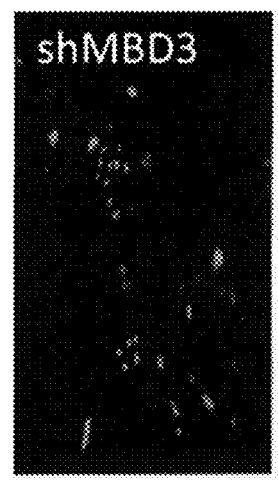
Figure 100T:
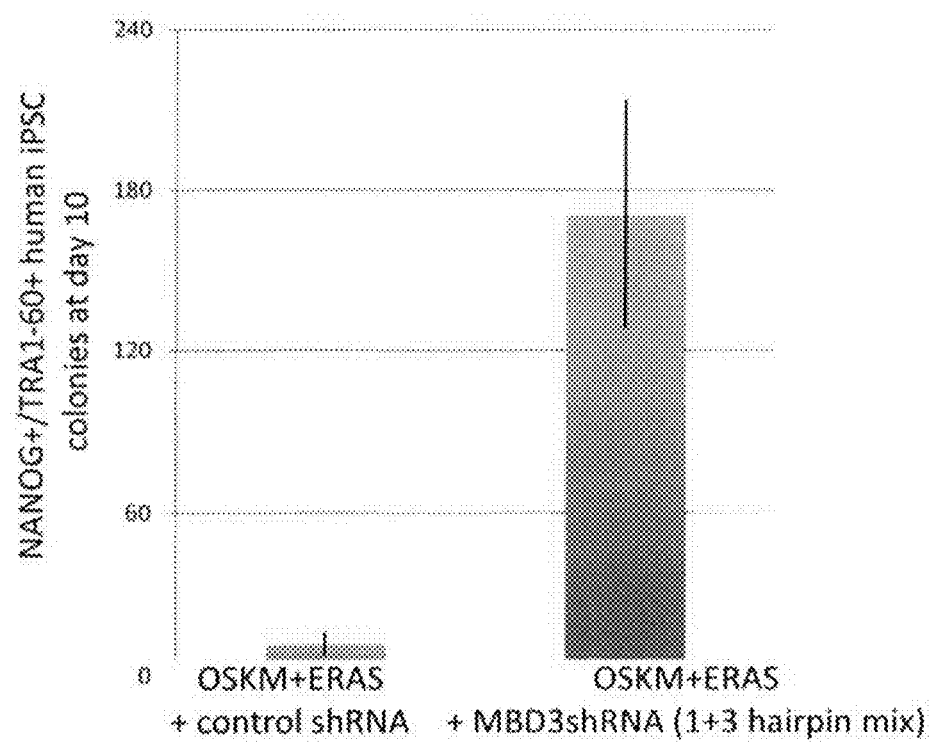

FIGS. 100A-T show staining for OCT4, SSEA4, TRA1-60 and TRA1-81 pluripotency markers on cells reprogramming in NHSM conditions following 10 days of OKSM, RtTa, ERAS and MBD3 shRNA DOX induction. FIGS. 100A-D—Cells were stained for DAPI (FIG. 100A), OCT4 (FIG. 100B), and SSEA4 (FIG. 100C). FIG. 100D—merged image. Note the co-expression of OCT4 and SSEA4. FIGS. 100E-I—Cells were stained for DAPI (FIG. 100E), OCT4 (FIG. 100F), SSEA4 (FIG. 100G). FIG. 100H—merged image showing co-expression of OCT4 and SSEA4. FIG. 100I—Staining for the MBD3-shRNA induction reporter. Note the co-localization of shMBD3 with cells expressing the OCT4 and SSEA4 pluripotency markers. FIGS. 100J-N—Cells were stained for DAPI (FIG. 100J), OCT4 (FIG. 100K), TRA1-60 (FIG. 100L). FIG. 100M—merged image showing co-expression of OCT4 and TRA1-60. FIG. 100N—Staining for the MBD3-shRNA induction reporter. Note the co-localization of shMBD3 with cells expressing the OCT4 and TRA1-60 pluripotency markers. FIGS. 100O-S—Cells were stained for DAPI (FIG. 100O), OCT4 (FIG. 100P), TRA1-81 (FIG. 100Q). FIG. 100R—merged image showing co-expression of OCT4 and TRA1-81. FIG. 100S—Staining for the MBD3-shRNA induction reporter. Note the co-localization of shMBD3 with cells expressing the OCT4 and TRA1-81 pluripotency markers. FIG. 100T—A histogram depicting quantification of the Nanog+/TRA1-60+ human iPSC colonies at day 10. Primary females adult dermal fibroblast cells (line #13) were transduced with RtTa, OSKM and ERAS vectors in WIS-NHSM conditions, with or without MBD3 knockdown via TRIPZ-MBD3 shRNAs 1+3 that were added to the reprogramming. iPSC colony numbers were counted at day 10 by staining for NANOG and TRA1-60 markers (FIG. 100T). Note the dramatic increase in iPSC formation from primary human somatic cells when MBD3 inhibition is introduced.

Figure 101A:
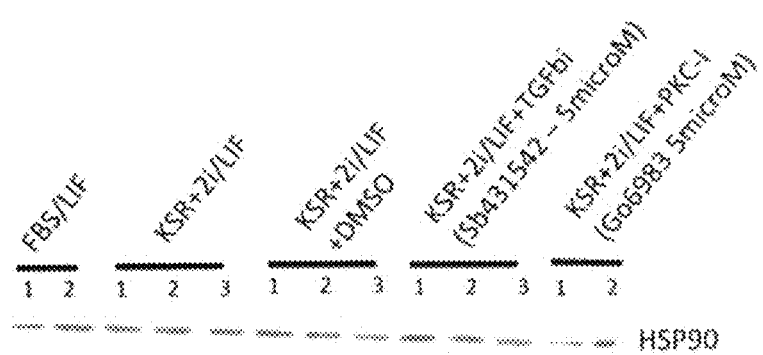
Figure 101B:

FIGS. 101A-B are Western blot analyses showing expression of MBD3 (FIG. 101B) and of HSP90 (FIG. 101A) in v6.5 mouse ES cells after different treatments. V6.5 mouse ES cells were expanded for 4 days in the indicated conditions and subjected to Western blot analysis for MBD3 protein expression. The conditions are indicated in the Figure above the lanes. Following are the abbreviations and concentrations of the indicated factors and agents. PBS=phosphate buffered saline; "LIF"=leukemia inhibitory factor, provided at a concentration of 20 nanograms/milliliter (ng/ml); KSR=knockout serum replacement; "2i/LIF"=small-molecule inhibitors CHIR99021 (CH, 3 μM—Axon Medchem) and PD0325901 (PD, 1 μM—TOCRIS), with 20 ng/ml LIF; "DMSO"=Dimethyl sulfoxide at a concentration of 0.1%; TGFRi (inhibitor of transforming growth factor receptor; SB431542 at 5 micromolar); PKC-i (inhibitor of protein kinase C; Go6983 at 5 micromolar). Note that significant depletion of MBD3 protein levels in cells treated with the PKC inhibitor (Go6983 5 microM) (PKCi). The results show that inhibition of PKC leads to down regulation in MBD3 expression in mouse embryonic stem cells.

Figure 102:
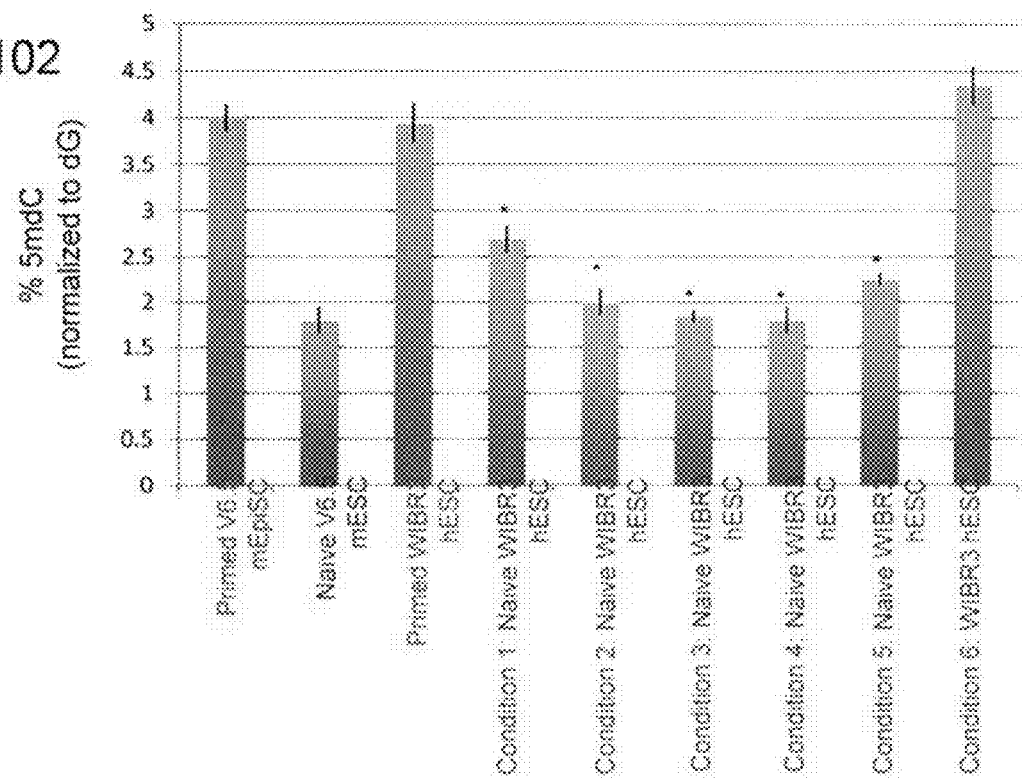

FIG. 102—A histogram depicting the effect of the various WIS-NHSM media that are specified in Table 3 (Example 13 of the Examples section which follows) on methylation of DNA (% of total methylated cytosine levels (5 mdC) normalized to dG.

Figure 103:
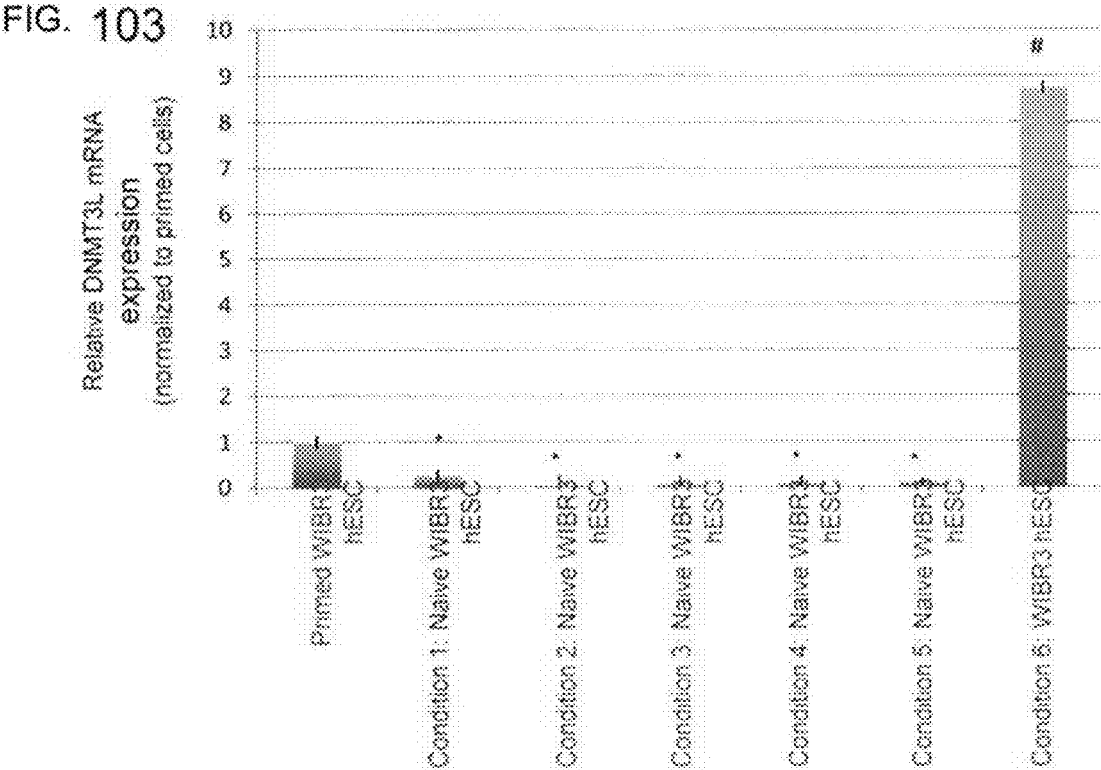

FIG. 103—A histogram depicting the effect of the various WIS-NHSM media that are specified in Table 3 (Example 13 of the Examples section which follows) on relative DNMT3L mRNA expression (normalized to primed cells).

Figure 104:
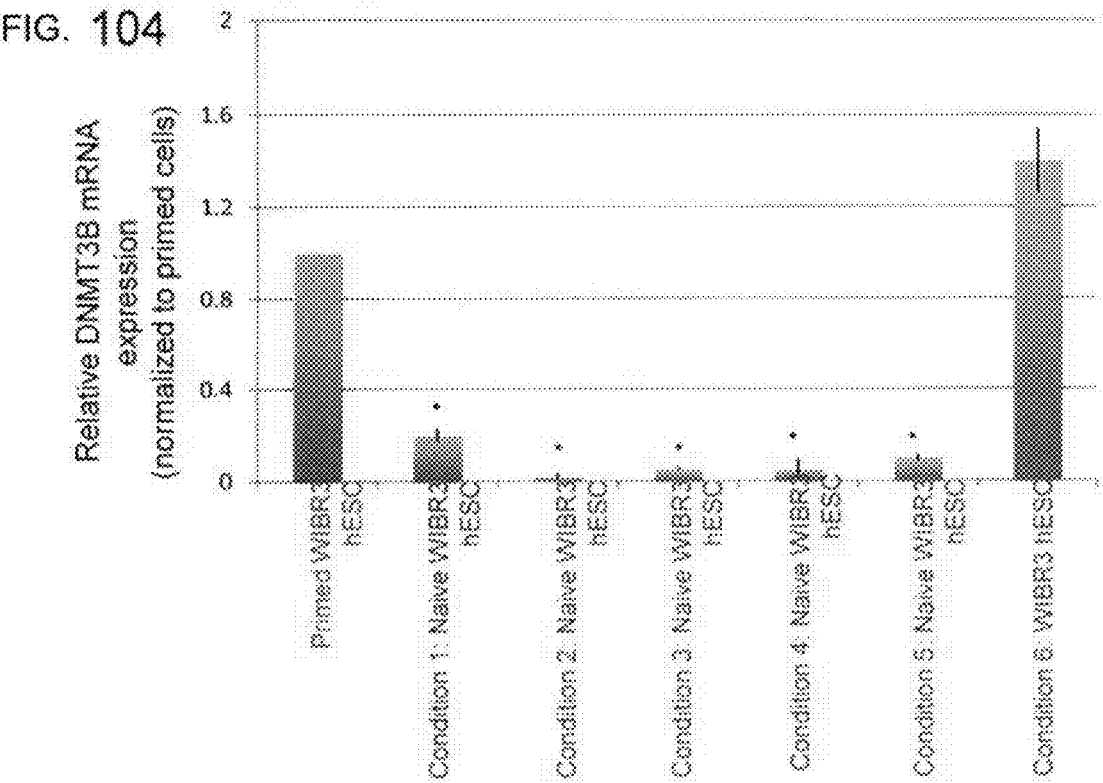

FIG. 104—A histogram depicting the effect of the various WIS-NHSM media that are specified in Table 3 (Example 13 of the Examples section which follows) on relative DNMT3B mRNA expression (normalized to primed cells).

Figure 105:
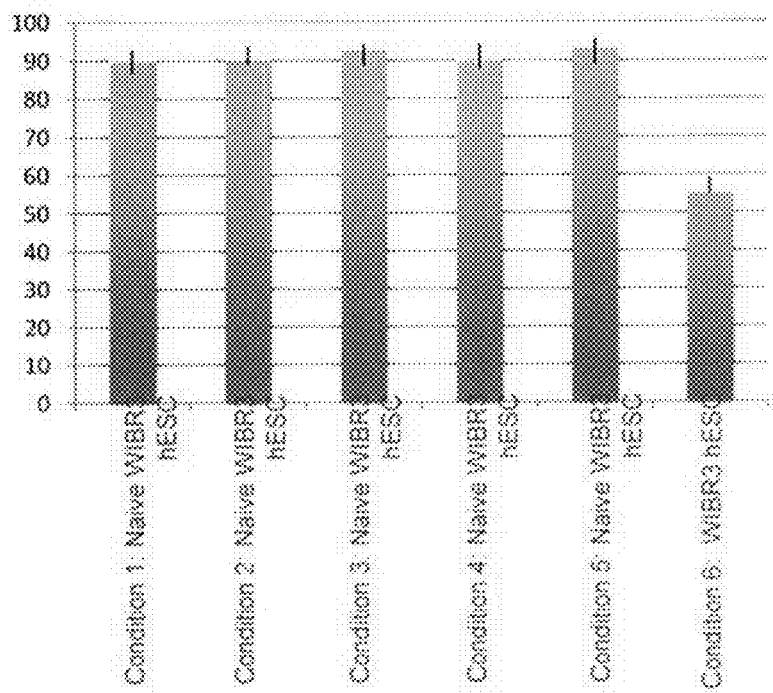

FIG. 105—A histogram depicting the effect of the various WIS-NHSM media that are specified in Table 3 (Example 13 of the Examples section which follows) on % OCT4+ WIBR3 cells after 9 passages on 0.2% gelatin plates.

FIGS. 106A-D—FACS analyses for anti human CD61 (integrin B3) expression in human naive ESCs (FIGS. 106A-B) and PGCLCs (day 4 after induction; FIGS. 106C-D) carrying the NANOs3 mCherry knock-in reporter. FIGS. 106A and 106C—control cells (not stained with the antibody); FIGS. 106B and 106D—Cells stained with anti-human CD61 (Alexa-647) antibody.

Figures 107A, 107B:
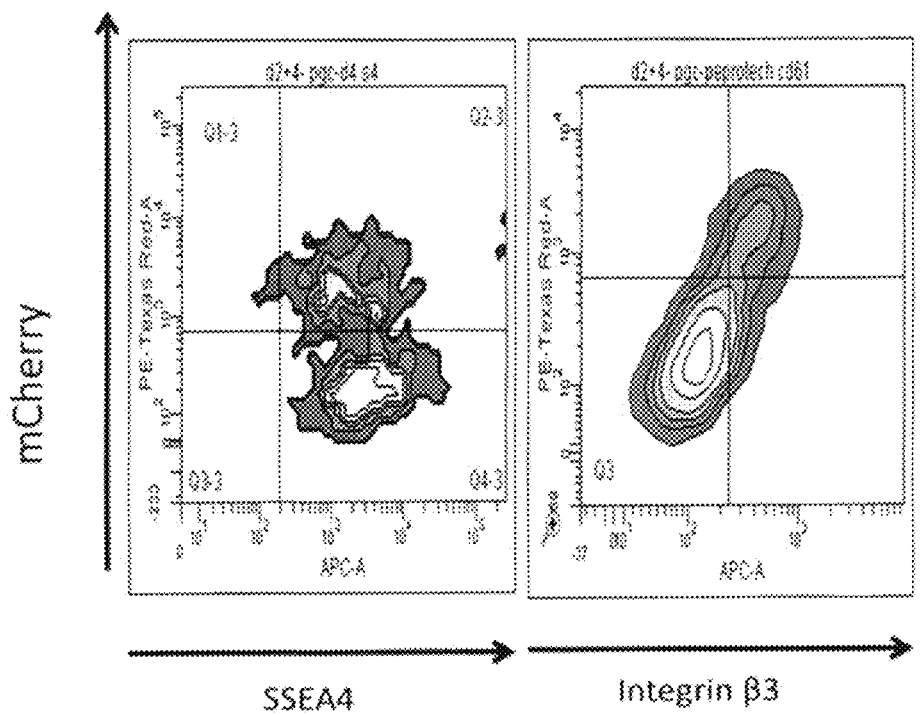
Figure 108A:
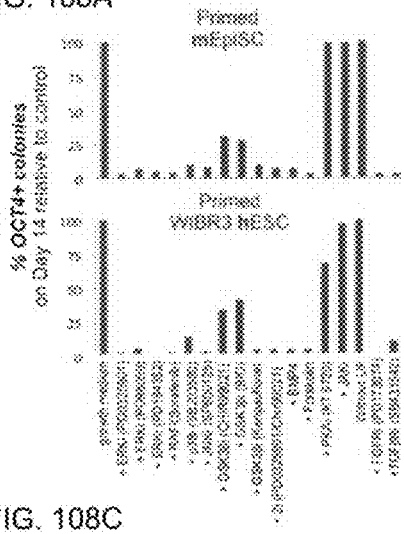
Figure 108B:
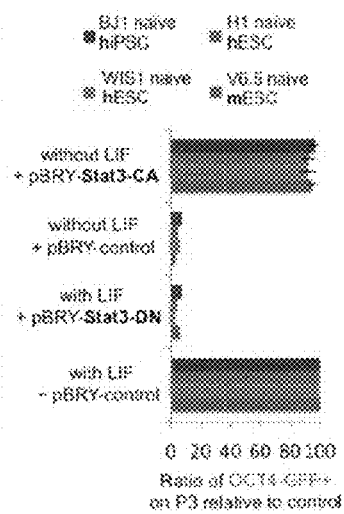
Figure 108C:
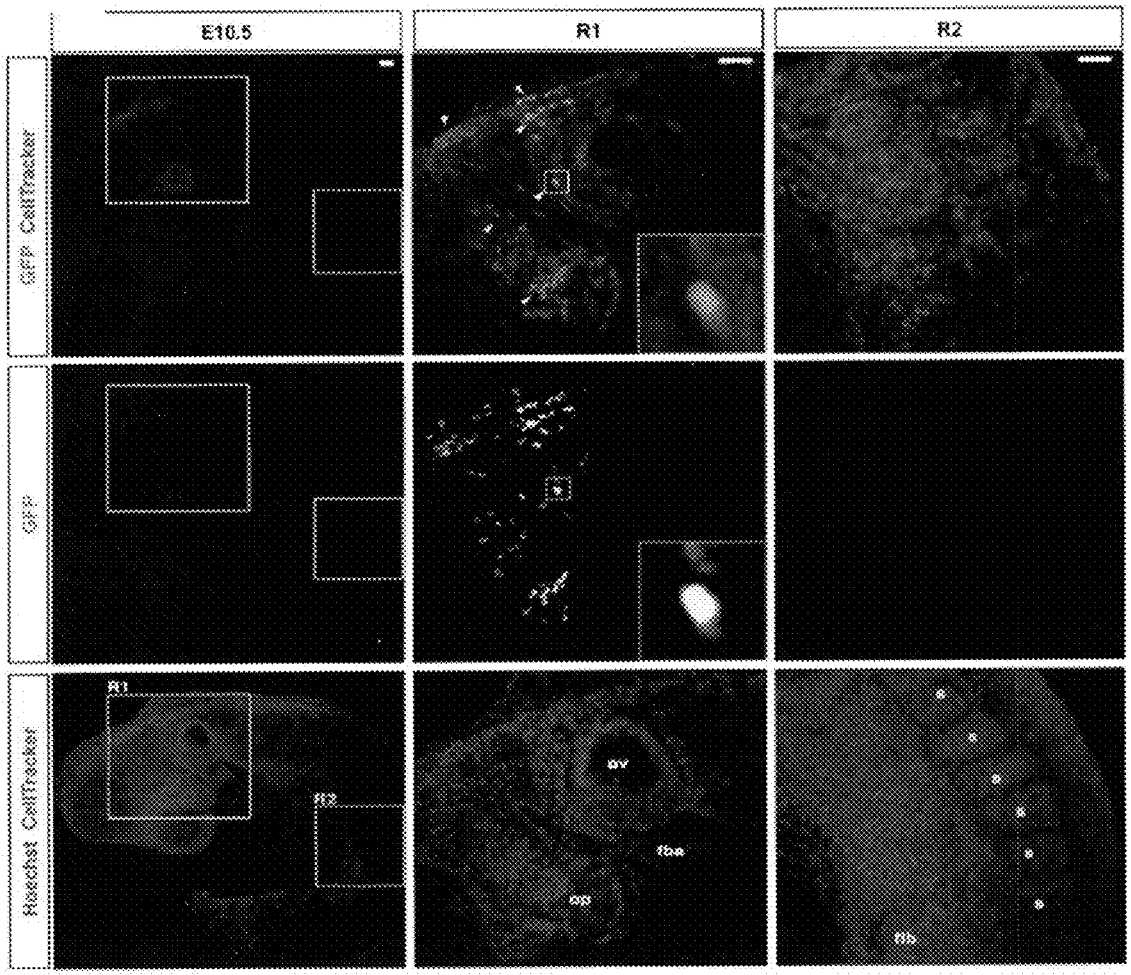

FIGS. 107A-B—FACS analyses for anti human SSEA4 (FIG. 107A) or CD61 (integrin β3; FIG. 107B) expression in human PGCLCs (day 2+4 after induction from human naive cells) carrying the NANOS3 mCherry knock-in reporter. FIGS. 108A-C—Signaling and functional characteristics of human naïve pluripotency. FIG. 108A—Pluripotency maintenance by different pluripotent cell lines cultivated in various media conditions. For defining Signaling characteristics of human and mouse pluripotent cells the present inventors tested pluripotency maintenance by different pluripotent cell lines cultivated in various media conditions. Cell populations were equally divided and plated on gelatin/vitronectin coated plates in the indicated growth medium in which these cell lines are normally maintained (mouse naïve cells—N2B27-2i/LIF, naïve hESCs/hiPSCs—WIS-NHSM, mEpiSCs and primed hESCs/hiPSCs—in KSR/bFGF/TGFβ conditions). 36 hours later the wells were supplemented with the indicated inhibitors or growth factors. After 14 days (2 passages), wells were analyzed by OCT4 immunostaining of direct detection of OCT4-GFP pluripotency reporter expression, to determine the relative percentage of undifferentiated pluripotent cells. Colony formation is normalized to an internal control, as indicated by "Growth medium" only on the far left column. When components already included in WIS-NHSM were supplemented, this yielded a 2-fold increase in their relative concentration. Normalized percentages lower than 50% are defined as "sensitive" to the presence of the supplemented inhibitor. FIG. 108B-LIF/Stat3 is required for stabilization of the in vitro stability of naïve hESC/hiPSCs in WIS-NHSM. Naïve V6.5 mESCs, naïve WIS1 and H1 hESCs, and BJ naïve hiPSCs were electroporated with mock a pBRY-CAGGS-flox-DsRedT4-IRES-Puro control plasmid, a plasmid encoding a dominant negative Stat3 Y705F mutant (Stat3-DN), or a plasmid encoding Stat3-CA constitutively active mutant (pBRY-Stat3-CA). Cells were passaged three times in the presence of puromycin selection. After 20 days, colonies positive for OCT4 pluripotency markers were counted and normalized to colonies from cells electroporated with empty vector. (n=3 for each condition and error bars indicate s.d.). FIG. 108C—Representative images showing human naive GFP labeled iPSC derived cell integration into different locations in the anterior part of an E10.5 mouse embryo. 1st column shows the whole embryo (z-stack interval is 30 um, 18 focal-planes total). The 2nd column shows a zoom in images focusing on the head region (white square R1) where the hiPSC-derived cells (GFP positive cells) are pointed out (arrowheads, z-stack interval is 20 μm, 11 stacks total). 3rd column shows the posterior part of the embryo (yellow square R2) where no GFP positive cells were detected (z-stack interval is 20 μm, 9 focal-planes total). Light-blue square in the first two images in the 2nd column represent the area shown in the insert at the corner of each image. (ov—optic vesicle, op—optic pit, fba—first branchial arch, flb—forelimb bud, s—somite). Scale bar in all images is 50 μm.

FIGS. 109A-E—Chimerism with human naïve iPSCs derived cells following mouse morula microinjection. FIG. 109A—C1 human naïve iPSCs were targeted with constitutively CAGGS promoter driven EGFP into the human AAVS1 locus via ZFN utilization. Subsequently cells were microinjected into E2.5 mouse early morulas, and micromanipulated embryos were allowed to recover and develop into blastocysts in vitro for additional 24 hours. Images show specific GFP+ human cell survival and integration in mouse pre-implantation embryos. FIG. 109B—A histogram depicting naive and primed GFP+ human iPSC survival in vitro, 24-36 hours after microinjection into mouse morulas. * Student t-test P value <0.01. Error bars indicate s.d. (n=3). Note that while the naive iPSCs survive in mouse blastocysts 24-36 hours post injection (almost 80% of the cells), only a minor fraction (less than 5%) of the primed PSC survive in the blastocyst. FIG. 109C—Representative confocal analysis following immunostaining for GFP (green) OCT4 (red) and CDX2 (magenta) was done 24 hours following mouse morula microinjections with GFP labeled naive hiPSCs. Note surviving GFP+ cells (white arrow) that specifically integrate and stain positive for OCT4, but not CDX2 (No co-localization between GFP and Cdx2 was not observed). Scale bar 10 μm. FIG. 109D-Subsequently, mouse blastocysts were implanted in vivo in mice and allowed to develop for additional 7 days in vivo (as indicated), before dissection and confocal analysis. Representative images showing robust integration of hiPSC derived cell integration into the neural folds of an E8.5 mouse embryo (upper panels). Notably, GFP was not detected in the control non-injected mouse embryos (n=3, lower panels). z-stack interval is 20 µm; 17 focal-planes total (nf—neural folds). Scale bar 50 µm. FIG. 109E—Naive hiPSC derived cells are integrated into different locations at the craniofacial region of an E10.5 mouse embryo. A sequence of different focal planes from 108C, showing multiple hiPSC derived cells integrated into different locations on the craniofacial region (arrowheads). First image in each row shows the maximum intensity projection of all z-stacks. The distance between the different focal planes appears on the upper right corner of each one. (ov—optic vesicle, op—optic pit, fba—first branchial arch). Scale bar 50 µm.

DESCRIPTION OF SPECIFIC EMBODIMENTS OF THE INVENTION

The present invention, in some embodiments thereof, relates to an isolated primate (e.g., human) naive pluripotent stem cell, novel culture medium which can be used to generate same and methods of generating and culturing same and, more particularly, but not exclusively, to methods of improving dedifferentiation of somatic cells for generation of induced pluripotent stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered the conditions, which are required for isolating and generating a primate (e.g., human) naive pluripotent stem cell, and maintaining same in the naive state.

Thus, according to an aspect of some embodiments of the invention there is provided an isolated primate (e.g., human) naive pluripotent stem cell (PSC) comprising:
an unmethylated X-inactive specific transcript (XIST) gene, wherein:
(i) when the naive PSC is a female PSC, then the naive female PSC has two unmethylated alleles of the XIST gene; and
(ii) when the naive PSC is a male PSC, then the naive male PSC has an unmethylated allele of the XIST gene, and/or
an expression level of transcription factor E3 (TFE3) characterized by a nucleus to cytoplasm expression ratio which is equal to or higher than 1 as determined by an immunostaining assay.

As used herein the phrase "pluripotent stem cell (PSC)" refers to an undifferentiated cell (e.g., a primate cell, a mammalian cell) capable of differentiating into all three embryonic germ cell layers, i.e., to the mesoderm, ectoderm and endoderm embryonic germ layers.

According to some embodiments of the invention, the pluripotent stem cell is selected from the group consisting of embryonic stem cell (ESC), induced pluripotent stem cells (iPSCs), and embryonic germ cell (EGC).

According to some embodiments of the invention, the primate naive pluripotent stem cell is of *Homo sapiens* (human), monkey, chimpanzee, Gorillas, Rhesus and/or Baboon.

The phrase "naive pluripotent stem cell (PSC)" refers to a cell capable of forming a PSC, and that exhibits a pre-X-inactivation state, and therefore is considered to be the origin of the PSC.

The pre-X-inactivation state according to some embodiments of the invention is characterized by presence of two unmethylated alleles of an X-inactive specific transcript (XIST) gene in the female cell, and presence an unmethylated allele of the XIST gene in a male cell.

The XIST gene is located on human Xq13.2 chromosome and has the sequence depicted in clone NC_000023.10 (73040486 . . . 73072588, complement, based on GenBank version GRCh37.p10. The XIST gene has a non-coding RNA which is provided in GenBank Accession NO. NR_001564.2 (SEQ ID NO:20).

According to some embodiments of the invention, presence of two unmethylated alleles of XIST gene in a female cell refers to having below about 20% of CpG methylated reads sequenced in the XIST promoter, e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% (e.g., complete absence) of CpG methylated reads sequenced in the XIST promoter.

According to some embodiments of the invention, presence of one unmethylated allele of XIST gene in a male cell refers to having below about 20% of CpG methylated reads sequenced in the XIST promoter, e.g., below about 19%, below about 18%, below about 17%, below about 16%, below about 15%, below about 14%, below about 13%, below about 12%, below about 11%, below about 10%, below about 9%, below about 8%, below about 7%, below about 6%, below about 5%, below about 4%, below about 3%, below about 2%, below about 1%, e.g., 0% of CpG methylated reads sequenced in the XIST promoter.

A non-limited example of the XIST promoter which includes CpG islands which can be either methylated or unmethylated is provided in the XIST promoter amplicon set forth by SEQ ID NO:70.

According to some embodiments of the invention, the human naive PSC is characterized by a reduced methylation of CpG islands as compared to a level of methylation of the CpG islands in a human primed PSC.

Thus, as shown in FIG. 30G, human naive iPSCs and human naive ESCs are characterized by significantly low levels of total methylated cytosine out of the total guanine nucleotides in each cell (e.g., 1-2%, FIG. 30G) as determined by Liquid Chromatography-Mass Spectrometry (LC-MS) quantitative analysis.

According to some embodiments of the invention, the human naive PSC is characterized by 0-3% of total methylated cytosine out of the total Guanine nucleotides in the naive PSC cell. For comparison, the primed PSC or a somatic cell has between 3.5%-5% of total methylated cytosine out of the total Guanine nucleotides in the primed PSC cell.

Thus, the naive pluripotent stem cell of some embodiments of the invention is in a naive state.

As used herein the phrase "naive state" refers to being in an undifferentiated state wherein both alleles of the X-inactive specific transcript (XIST) gene of the female cell are unmethylated, or wherein the XIST allele of the male cell is unmethylated.

It should be noted that the naive PSCs of some embodiments of the invention (which are in a pre-X inactivation and a naive state) can upon differentiation inactivate one of the X chromosome alleles and methylate one of the XIST genes.

According to some embodiments of the invention, the naive PSC maintains the naive state (as defined hereinabove) while being maintained (e.g., cultured) in the presence of ERK1/2 inhibitors (e.g., as exemplified here in below).

According to some embodiments of the invention, the naive PSC maintains the naive state (as defined hereinabove) while being maintained (e.g., cultured) in the absence of TGFβ signaling inhibition (e.g., in the absence of TGFβi).

According to some embodiments of the invention, the naive PSC maintains the naive state (as defined hereinabove) while being maintained (e.g., cultured) in the presence of TGFβ stimulation, e.g., in the presence of TGFβ1 and/or FGF2 stimulation.

According to some embodiments of the invention, the naive PSC maintains the naive state (as defined hereinabove) while being maintained (e.g., cultured) in the presence of ERK1/2 inhibitors and in the presence of TGFβ1 stimulation (e.g., by addition of TGFβ1) and/or FGF2 stimulation.

The phrase "primed PSC" or "conventional PSC" which are interchangeably used herein refers to a PSC which are known to date, e.g., human embryonic stem cells (hESC), human induced pluripotent stem cells (hiPSC), and human embryonic germ cells (hEGC), which are characterized by one methylated allele of XIST and one unmethylated allele of XIST in the female cell, and by one methylated allele in the male cell.

As used herein the term "isolated" refers to at least partially separated from the natural environment e.g., from the primate (e.g., mammalian) embryo or the primate (e.g., mammalian) body.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which reprogram the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

It will be appreciated that commercially available stem cells can also be used according to some embodiments of the invention. Human ES cells can be purchased from the NIH human embryonic stem cells registry [Hypertext Transfer Protocol://grants (dot) nih (dot) gov/stem_cells/registry/current (dot) htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES1, HUES 2, HUES 3, HUES 4, HUES 5, HUES 6, HUES 7, HUES 8, HUES 9, HUES10, HUES11, HUES12, HUES13, HUES14, HUES15, HUES16, HUES17, HUES18, HUES19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

Chromosome X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIC comprises several non-coding and protein-coding genes, and XIST gene was the first non-coding gene identified within the XIC.

When XIST bodies are present, then XIST is exclusively expressed from the XIC of the inactive X chromosome, and is essential for the spread of X-inactivation.

The methylation status of the XIST gene can be determined by various methods such as bisulfite sequencing [Lengner Cell 141, 872-883 (2010); Hanna et al., Cell 143, 508-525 (2010), each of which is fully incorporated herein by reference in its entirety] of the promoter region of the XIST gene. The XIST promoter region can be amplified by the following PCR primers: Forward primer (used on bisulfite treated DNA): 5'-taa att tta aat taa tta aat tat (SEQ ID NO:22), and Reverse primer (used on bisulfite treated DNA): 5'-tgt ttt aga aag aat ttt aag tgt aga ga (SEQ ID NO:23). The amplicon region amplified by the above primers (203 bp covering human XIST transcription start site) is provided in SEQ ID NO:70. A representative result of such XIST bisulfite sequencing is shown in FIG. 23A. The CpG islands in the XIST promoter amplicon are highlighted in yellow in FIG. 27.

Following is a non-limiting description of a methylation specific PCR assay for the XIST gene. Bisulfite treatment of genomic DNA is performed with the EpiTect Bisulfite kit (Qiagen, Germany). Methylation-specific PCR (MS-PCR) utilizes this sodium bisulfite treatment to distinguish methylated from unmethylated DNA. Purified, non-methylated and methylated human DNA standards (for negative and positive controls in methylation detection application) include the Human Methylated & Non-methylated DNA set (Zymo Research, USA). Each sample is analyzed in two independent MS-PCR reactions. PCR reactions included 25 µl PCR reaction mix which contained 2xPCR HotStart Premix buffer (Takara, Tokyo, Japan), 0.5 µM primer-M forward and 0.5 µM primer-M reverse in the PCR reaction amplifying the methylated imprint specifically or 0.5 µM primer-U forward and 0.5 µM primer-U reverse in the unmethylated PCR, and 2 µl of bisulfite-modified DNA. Primer pairs for methylation and unmethylation specific PCR for XIST gene include: Unmethylation forward 5'-TGTTTTTTTGTTTATTGGGGTTGTG (SEQ ID NO:21; M97168, 691-715), and Unmethylation reverse 5'-ACAACTAACCTAAACCAAATTATACA (SEQ ID NO:67; M97168, 944-970); Methylation forward 5'-TGTTTTTTTGTTTATCGGGGTCGCG (SEQ ID NO:68; M97168, 691-715) and Methylation reverse 5'-CGAATTATACGACAAATCTAAAATAACG (SEQ ID NO:69; M97168, 927-954) can be used as described elsewhere (Kawakami T, et al., Lancet. 2004 Jan. 3; 363(9402): 40-2. XIST unmethylated DNA fragments in male-derived plasma as a tumour marker for testicular cancer; which is fully incorporated herein by reference in its entirety), and with the following PCR conditions: The polymerase is activated at 95° C. for 5 minutes. DNA is amplified in 35 cycles at 94° C., 60° C., 72° C. for 45 seconds each, followed by a final extension at 72° C. for 5 minutes. The resulting PCR fragments are 264 bp (base pairs) for the methylated allele (M) and 280 bp for the unmethylated allele (U). PCR products are separated on a 2% agarose gel, stained with ethidium bromide and visualized under UV illumination.

Additionally or alternatively, the methylation status of the XIST gene can be determined using Southern blot analyses using methylation-sensitive restriction enzymes and probes specific to the XIST gene (or CpG islands), essentially as described in Lengner Cell 141, 872-883 (2010); and Hanna et al., Cell 143, 508-525 (2010), each of which is fully incorporated herein by reference in its entirety. Following is a non-limiting description of a methylation assay which can be used to determine the methylation status of the XIST gene in a cell (TAKASHI SADO et al., DEVELOPMENTAL DYNAMICS 205: 421-434 (1996). Mosaic Methylation of Xist Gene Before Chromosome Inactivation in Undifferentiated Female Mouse Embryonic Stem and Embryonic Germ Cells; which is fully incorporated herein by reference in its entirety). Genomic DNA is prepared from the cells using known methods (e.g., Sambrook et al., Molecular Cloning: A Laboratory Manual, Cold Springs Harbor Laboratory, New York (1989, 1992)). Briefly, 10 µg of DNA is digested with one of methylation sensitive enzymes (HpaII, CfoI, MZuI, SacII, and AuaI) in combination with EcoRI or EcoRI+PuuII according to the manufacturers' recommendation. Digestion is carried out overnight with 10-fold excess of each enzyme in reaction volume of 300 µl. Restricted DNA is purified by phenol extraction, precipitated with ethanol, electrophoresed on 1% or 2% agarose gel, blotted onto Hybond N+(Amersham, Buckinghamshire, UK), and probed by a cDNA fragment of Xist 5' portion (probe 1) or a genomic HpaI-MluI fragment of the 5' upstream region (probe 2) labeled by random priming. Subsequent washes are carried out in accordance with the membrane manufacturer's recommendation.

Thus, the skilled in the art is capable of distinguishing between an unmethylated allele of XIST and a methylated allele of XIST, and thus can easily distinguish between a female cell having two unmethylated alleles of the XIST gene or a female cell having one methylated and one unmethylated allele of XIST. Similarly, the skilled in the art can easily distinguish between a male cell having a methylated XIST allele or a male cell having an unmethylated XIST allele.

As mentioned, the isolated primate (e.g., human) naive PSC is in an undifferentiated and pluripotent state (capable of differentiating into all three embryonic germ layers).

Primed human PSCs such as hiPSCs or hESCs are induced to differentiation upon incubation with bone morphogenetic protein 4 (BMP4), JNK inhibitor, and P38 inhibitor [Hanna et al., Cell 143, 508-525 (2010); De Los Angeles, et al., *Curr. Opin. Genet. Dev.* 22, 272-282 (2012)].

Contrary to the known primed PSC, the naive PSC of some embodiments of the invention is "resistant" to induction of differentiation by BMP4, JNK inhibitor, and/or P38 inhibitor. Thus, as shown in FIGS. 21(A-L)-22(A-H), incubation of the naive PSC with BMP4 or forskolin did not alter the undifferentiated and pluripotent state of the Naive PSCs.

According to some embodiments of the invention, when the isolated naive PSC is incubated in the presence of an agent selected from the group consisting of Bone morphogenetic protein 4 (BMP4), JNK inhibitor, and P38 inhibitor, the naive PSC remains in the pluripotent state.

According to some embodiments of the invention, the naive PSC has an inhibited p38 pathway as compared to a primed PSC. For example, p38 activity is inhibited in the naive PSC.

According to some embodiments of the invention, the level of p38 RNA and/or phosphorylated p38 protein in the naive PSC is less than about 30%, e.g., less than about 20%, e.g., less than about 5%, e.g., less than about 0.5%, e.g., less than about 0.1% as compared to the level of p38 RNA and/or phosphorylated p38 protein, respectively, in a non-naive PSC incubated and/or cultured under the same conditions, yet without being subject to p38 inhibition.

According to some embodiments of the invention, the naive PSC has an inhibited JNK pathway as compared to a primed PSC. For example, JNK activity is inhibited in the naive PSC.

According to some embodiments of the invention, the level of JNK RNA and/or phosphorylated JNK protein in the naive PSC is less than about 30%, e.g., less than about 20%, e.g., less than about 5%, e.g., less than about 0.5%, e.g., less than about 0.1% as compared to the level of JNK RNA and/or phosphorylated JNK protein, respectively, in a non-naive PSC incubated and/or cultured under the same conditions, yet without being subject to JNK inhibition.

According to some embodiments of the invention, the naive PSC has an inhibited ROCK pathway as compared to a primed PSC. For example, ROCK activity is inhibited in the naive PSC.

According to some embodiments of the invention, the level of ROCK RNA and/or phosphorylated ROCK protein in the naive PSC is less than about 30%, e.g., less than about 20%, e.g., less than about 5%, e.g., less than about 0.5%, e.g., less than about 0.1% as compared to the level of ROCK RNA and/or phosphorylated ROCK protein, respectively, in a non-naive PSC incubated and/or cultured under the same conditions, yet without being subject to ROCK inhibition.

Monitoring the differentiation state of pluripotent stem cells—During the culturing step the pluripotent stem cells are further monitored for their differentiation state. Cell differentiation can be determined upon examination of cell or tissue-specific markers which are known to be indicative of differentiation. For example, primate PSCs may express the stage-specific embryonic antigen (SSEA) 4, the tumour-rejecting antigen (TRA)-1-60 and TRA-1-81. Undifferentiated pluripotent stem cells highly express SSEA4, TRA-1-60 and TRA-1-81 markers and down regulate their expression upon differentiation.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

Determination of PSC differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, Calif., USA).

According to an aspect of some embodiments of the invention, there is provided an isolated population of naive PSCs comprising at least about 10%, at least about 12%, at least about 14%, at least about 16%, at least about 18%, at least about 20%, at least about 22%, at least about 24%, at least about 26%, at least about 28%, at least about 30%, at least about 32%, at least about 34%, at least about 36%, at least about 38%, at least about 40%, at least about 42%, at least about 44%, at least about 46%, at least about 48%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, e.g., 100% of the isolated human naive PSC cells of some embodiments of the invention.

According to a specific embodiment of the invention the isolated population of cells is positive for one or more markers. Positive is also abbreviated by (+). Positive for a marker means that at least about 70%, 80%, 85%, 90%, 95%, or 100% of the cells in the population present detectable levels of the marker (e.g., OCT4, NANOG, TRA1-81, TRA1-60, SSEA3, SSEA4) assayed by a method known to those of skill in the art [e.g., fluorescent activated cell sorter (FACS) analysis, immunofluorescence, immunohistochemistry, Western blot analysis]. Thus, for example, the cells stain positively with anti SSEA3 antibody as determined using FACS or stained positive by immunofluorescence or immunohistochemistry using the OCT4 antibody. The OCT4, NANOG, TRA1-81, TRA1-60, SSEA3, SSEA4-positive cells according to this embodiment, stain negatively to one or more markers, e.g., SSEA1. Negative is also abbreviated by (−). Negative for a marker means that no more than about 30%, no more than about 25%, no more than about 20%, no more than about 15%, no more than about 10%, no more than about 5%, no more than about 4%, no more than about 3%, no more than about 2%, no more than about 1%, of the cells in the population present detectable levels of the marker (e.g., SSEA1) assayed by a method known to those of skill in the art such as immunofluorescence or FACS. Such a marker presentation either of a single cell or an isolated population of cells is also referred to as a signature.

As shown in FIGS. 12F and 25B-M, the present inventors have shown a population of stem cells having about 99% of naive PSC.

According to some embodiments of the invention, the naive PSC expresses XIST.

Methods of detecting XIST expression are known in the art and include for example reverse transcriptase-polymerase chain reaction (RT-PCR) analysis using XIST specific PCR primers, e.g., the forward primer: 5'-AGG-GAGCAGTTTGCCCTACT (SEQ ID NO:24), and the reverse primer: 5'-CACATGCAGCGTGGTATCTT (SEQ ID NO: 25), as shown in FIG. 23B.

According to some embodiments of the invention, the naive PSC is devoid of XIST bodies.

As used herein the phrase "XIST bodies" refers to a XIST-coated inactive X chromosome.

Methods of detecting XIST bodies are known in the art and include for example RNA fluorescent in situ hybridization. RNA fluorescence in situ hybridization (FISH) is carried out as previously described [Hanna J., et al., Cell 143, 508-525]. Briefly, human pluripotent stem cells are harvested, MEF-depleted, and cytospun onto glass slides before fixation. cDNA probes are generated to XIST exon 1 (GenBank Accession No. U80460: 61251-69449, SEQ ID NO:26) and exon 6 (GenBank Accession No. U80460: 75081-78658, SEQ ID NO:27) and labeled by nick translation (Roche) with Cy3-dUTP (Amersham), and Cot-1 DNA is labeled with fluorescein-12-dUTP using the Prime-It Fluor Labeling Kit (Stratagene).

According to some embodiments of the invention, the naive PSC is devoid of an H3K27me3/polycomb focus.

As used herein the phrase "H3K27me3/polycomb focus" refers to nuclear focus obtained following immuno-staining that corresponds to condensed inactive X chromosome.

Methods of detecting H3K27me3/polycomb focus are known in the art and include for example, the use of immuno-fluorescence analysis using anti H3K27me3 antibodies (e.g., Rabbit anti H3K27me3, Millipore, Calif., USA Catalogue number 07-449), as shown for example in FIGS. 23C-D.

According to some embodiments of the invention, the naive PSC has a low XIST expression level while being in the naive state, without inactivation of any of the X chromosomes and without presence of XIST bodies.

According to some embodiments of the invention, the naive PSC is capable of X-inactivation when induced to differentiate.

According to some embodiments of the invention, the naive PSC is capable of differentiation into the endodermal, mesodermal and ectodermal embryonic germ layers. Methods of determining ability of stem cells to differentiate into the endodermal, mesodermal and ectodermal embryonic germ layers include for example generation of embryoid bodies (in vitro) or teratomas (in vivo) as shown in the Examples section which follows and in Figures such as 12L-N, 13K-M, 13S-U, 19A-I, and 20A-T.

As used herein the phrase "embryoid bodies" (EBs) refers to three dimensional multicellular aggregates of differentiated and undifferentiated cells derivatives of three embryonic germ layers.

Embryoid bodies are formed upon the removal of the naive PSCs from feeder layers or feeder cells-free culture systems. Naive PSCs removal can be performed using type IV Collagenase treatment or Trypsin for a limited time. Following dissociation from the culturing surface, the cells are transferred to tissue culture plates containing a culture medium supplemented with serum and amino acids.

During the culturing period, EBs are further monitored for their differentiation state. Cell differentiation can be determined upon examination of cell or tissue-specific markers which are known to be indicative of differentiation. For example, EB-derived-differentiated cells may express the neurofilament 68 KD which is a characteristic marker of the ectoderm cell lineage.

The differentiation level of the EB cells can be monitored by following the loss of expression of Oct-4, and the increased expression level of other markers such as α-feto-protein, NF-68 kDa, α-cardiac and albumin. Methods useful for monitoring the expression level of specific genes are well known in the art and include RT-PCR, semi-quantitative RT-PCR, Northern blot, RNA in situ hybridization, Western blot analysis and immunohistochemistry.

Teratomas:

The pluripotent capacity of the naive PSCs of some embodiments of the invention can also be confirmed by injecting cells into SCID mice [Evans M J and Kaufman M (1983). Pluripotential cells grown directly from normal mouse embryos. Cancer Surv. 2: 185-208], which upon injection form teratomas. Teratomas are fixed using 4% paraformaldehyde and histologically examined for the three germ layers (i.e., endoderm, mesoderm and ectoderm).

In addition to monitoring a differentiation state, the naive PSCs are often also being monitored for karyotype, in order to verify cytological euploidity, wherein all chromosomes are present and not detectably altered during culturing. Cultured naive PSCs can be karyotyped using a standard Giemsa staining and compared to published karyotypes of the corresponding species.

According to some embodiments of the invention, the naive PSC is capable of being maintained in the undifferentiated and pluripotent state, while maintaining the naive state (as defined above) for more than about 20 passages in culture, e.g., for at least about 25, about 30, about 35, about 40, about 45, about 50, about 55, about 60, about 65, about 70, about 75 and about 80 passages while in culture.

According to some embodiments of the invention, the naive PSC which is maintained in the undifferentiated, pluripotent and naive state (as defined above), expresses significantly lower levels SOX1 as compared to the level of expression present in primed PSC (e.g., primed ESC) under identical SOX1 assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

According to some embodiments of the invention, the naive PSC expresses a lower level of MHC class I as compared to a primed PSC under identical detection assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

The level of MHC class I can be determined by various methods known in the art such as FACS analysis using specific antibodies to detect the surface expression of the MHC class 1 molecules (e.g., see FIGS. 24B and 24C), and using fluorescently labeled anti HLA-A,B,C antibody (BD Biosciences).

According to some embodiments of the invention, the naive PSC is characterized by at least about 10%, at least about 20%, at least about 30%, at least about 40%, at least about 50%, at least about 60%, at least about 70%, at least about 80%, at least about 90% more RNA polymerase II pausing on chromosomes as compared to a primed PSC under identical assay conditions, and wherein the primed PSC exhibits one methylated and one unmethylated allele of XIST (in a female cell) or one methylated allele of XIST (in a male cell); expresses XIST; exhibits XIST bodies; and exhibits a H3K27me3/polycomb focus.

According to some embodiments of the invention, the naive PSC exhibiting a pre-X inactivation status similar to the pre-X inactivation status of a human Inner cell mass (ICM).

According to an aspect of some embodiments of the invention, there is provided a cell culture comprising the isolated naive PSC of some embodiments of the invention, or the isolated population of naive PSCs of some embodiments of the invention and a culture medium.

According to some embodiments of the invention, the culture medium is capable of maintaining the naive PSC in an undifferentiated and pluripotent state for at least 10 passages.

The cell culture can be maintained in vitro, under culturing conditions, in which the cells are being passaged for extended periods of time (e.g., for at least 20 passages, e.g., at least about 30, 40, 50, 60, 70, 80, 90, 100 passages or more), while maintaining the cells in their naive pluripotent and undifferentiated state.

As used herein the phrase "culture medium" refers to a solid or a liquid substance used to support the growth of stem cells and maintain them in an undifferentiated state. Preferably, the phrase "culture medium" as used herein refers to a liquid substance capable of maintaining the stem cells in an undifferentiated state. The culture medium used by the present invention can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the stem cells in an undifferentiated state. For example, a culture medium can be a synthetic tissue culture medium such as Ko-DMEM (Gibco-Invitrogen Corporation products, Grand Island, N.Y., USA), DMEM/F12 (Gibco-Invitrogen Corporation products, Grand Island, N.Y., USA), or DMEM/F12 (Biological Industries, Biet Haemek, Israel), supplemented with the necessary additives as is further described hereinunder. Preferably, all ingredients included in the culture medium of the present invention are substantially pure, with a tissue culture grade.

The present inventors have identified a novel culture medium which can be used to generate naive PSC and maintain them in a pluripotent and undifferentiated state. Thus, as shown in FIGS. 12A-G, 85A-C, 102, 103, 104, and 105, and Tables 3, 4, and 5 in the Examples section which follows, following laborious experimentations the present inventors have uncovered the factors needed for maintaining naive PSCs in the "naive state", as was evidenced by the expression of OCT4-GFP+ (positive) cells and percentage of total methylated cytosine (% 5mdC).

According an aspect of some embodiments of the invention, there is provided a culture medium comprising an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor.

According an aspect of some embodiments of the invention, there is provided a culture medium comprising an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor.

As used herein the term "STAT3" refers to the signal transducer and activator of transcription 3 gene product (acute-phase response factor) (Gene ID 6774). In response to cytokines and growth factors, STAT family members are phosphorylated by the receptor associated kinases, and then form homo- or heterodimers that translocate to the cell nucleus where they act as transcription activators. Known STAT3 activators include, but are not limited to, interferon (IFN), epidermal growth factor (EGF), interleukin 5 (IL5), interleukin 6 (IL6), hepatocyte growth factor (HGF), leukemia inhibitory factor (LIF) and bone morphogenetic protein 2 (BMP2).

According to some embodiments of the invention, the STAT3 activator, which is used by the medium, cells and/or methods of some embodiments of the invention is selected from the group consisting of LIF, IL6 and EGF.

According to some embodiments of the invention, the STAT3 activator, which is used by the medium, cells and/or methods of some embodiments of the invention is selected from the group consisting of LIF, and IL6.

According to some embodiments of the invention, the STAT3 activator, which is used by the medium, cells and/or methods of some embodiments of the invention is LIF.

According to some embodiments of the invention, the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix1294, and stem cell factor (SCF).

According to some embodiments of the invention, the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix1294, and stem cell factor (SCF).

According to some embodiments of the invention, the STAT3 activator comprises the LIF, and wherein the at least one agent comprises the PKC inhibitor.

According to some embodiments of the invention, the culture medium further comprising FGFR inhibitor.

According to some embodiments of the invention, the culture medium further comprising TGFR inhibitor.

According to some embodiments of the invention, the STAT3 activator comprises the LIF and wherein the at least one agent comprises the TGFβ1 and the protein kinase C inhibitor.

According to some embodiments of the invention, the culture medium further comprising an FGFR inhibitor.

According to some embodiments of the invention, the STAT3 activator comprises the LIF, and wherein the at least one agent comprises the bFGF and the TGFβ1.

According to some embodiments of the invention, the culture medium further comprising a ROCK inhibitor.

According to some embodiments of the invention, the culture medium further comprising a protein kinase C inhibitor.

According to some embodiments of the invention, the STAT3 activator comprises the LIF and wherein the at least one agent comprises the bFGF, the ROCK inhibitor, a bone morphogenetic protein (BMP) inhibitor, the NOTCH inhibitor, and a transforming growth factor receptor (TGFR) inhibitor.

According to some embodiments of the invention, the culture medium further comprising a Sonic Hedgehog pathway (SHH) inhibitor.

According to some embodiments of the invention, the STAT3 activator comprises the LIF and wherein the at least one agent comprises the NOTCH inhibitor, and a fibroblast growth factor receptor (FGFR) inhibitor.

According to some embodiments of the invention, the culture medium further comprises an agent selected from the group consisting of insulin-like growth factor II (IGFII), stem cell factor (SCF) and transforming growth factor beta 1 (TGFβ1).

According to some embodiments of the invention, the culture medium comprising leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the culture medium further comprising a fibroblast growth factor receptor (FGFR) inhibitor (FGFRi).

According to some embodiments of the invention, the culture medium further comprising a transforming growth factor receptor inhibitor (TGFRi).

According to some embodiments of the invention, the culture medium which comprises leukemia inhibitor factor (LIF), an ERK1/2 inhibitor, a GSK3b inhibitor, a p38 inhibitor, a JNK inhibitor, and a protein kinase C inhibitor, further comprises a fibroblast growth factor receptor (FGFR) inhibitor (FGFRi).

According to some embodiments of the invention, the culture medium which comprises leukemia inhibitor factor (LIF), an ERK1/2 inhibitor, a GSK3b inhibitor, a p38 inhibitor, a JNK inhibitor, and a protein kinase C inhibitor, further comprises a transforming growth factor receptor inhibitor (TGFRi).

According to some embodiments of the invention, the culture medium which comprises leukemia inhibitor factor (LIF), an ERK1/2 inhibitor, a GSK3b inhibitor, a p38 inhibitor, a JNK inhibitor, and a protein kinase C inhibitor, further comprises a fibroblast growth factor receptor (FGFR) inhibitor (FGFRi) and a transforming growth factor receptor inhibitor (TGFRi).

According to some embodiments of the invention, the culture medium comprising leukemia inhibitor factor (LIF), an ERK1/2 inhibitor, a GSK3b inhibitor, a p38 inhibitor, a JNK inhibitor, TGFβ1 and a protein kinase C inhibitor.

According to some embodiments of the invention, medium which comprises leukemia inhibitor factor (LIF), an ERK1/2 inhibitor, a GSK3b inhibitor, a p38 inhibitor, a JNK inhibitor, TGFβ1 and a protein kinase C inhibitor further comprising FGFR inhibitor (FGFRi).

According to some embodiments of the invention, the culture medium comprising leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

As used herein the term "leukemia inhibitor factor (LIF)" refers to a polypeptide which comprises the amino acid sequence as set forth by GenBank Accession No. NP_001244064.1 (SEQ ID NO:119), encoded by the nucleotide sequence set forth in GenBank Accession No. NM_001257135 (SEQ ID NO:30). Preferably, the LIF used by the method according to some embodiments of the invention is capable of supporting, along with other factors which are described herein, the undifferentiated growth of naive primate (e.g., human) PSCs, while maintaining their pluripotent capacity. LIF can be obtained from various manufacturers such as Millipore, Peprotech, and R&D systems.

According to some embodiments of the invention, LIF is provided at a concentration range from about 0.5 nanogram per milliliter (ng/ml) to about 1000 ng/ml, e.g., about 1-1000 ng/ml, e.g., about 1-900 ng/ml, e.g., about 1-800 ng/ml, e.g., about 1-700 ng/ml, e.g., about 1-600 ng/ml, e.g., about 1-500 ng/ml, e.g., about 1-400 ng/ml, e.g., about 1-300 ng/ml, e.g., about 1-200 ng/ml, e.g., about 1-100 ng/ml, e.g., about 1-50 ng/ml, e.g., about 2-50 ng/ml, e.g., about 4-50 ng/ml, e.g., about 5-50 ng/ml, e.g., about 10-50 ng/ml, e.g., about 10-40 ng/ml, e.g., about 10-30 ng/ml, e.g., about 20 ng/ml.

As used herein the term "interleukin 6 (IL6)" refers to a polypeptide which comprises the amino acid sequence set forth by GenBank Accession No. NP_000591.1 (SEQ ID NO: 120), which is encoded by the nucleic acid set forth by GenBank Accession No. NM_000600.3 (SEQ ID NO: 111). Preferably, the IL6 used by the method according to some embodiments of the invention is capable of supporting, along with other factors which are described herein, the undifferentiated growth of naive primate (e.g., human) PSCs, while maintaining their pluripotent capacity. IL6 can be obtained from various manufacturers such as Speed BioSystems, Millipore, Peprotech, and R&D systems.

According to some embodiments of the invention, IL6 is provided at a concentration range from about 0.1 ng/ml to about 100 ng/ml, e.g., about 0.1-90 ng/ml, e.g., about 0.1-80 ng/ml, e.g., about 0.1-70 ng/ml, e.g., about 0.1-50 ng/ml, e.g., about 0.1-40 ng/ml, e.g., about 0.1-30 ng/ml, e.g., about 0.1-20 ng/ml, e.g., about 0.1-10 ng/ml, e.g., about 0.1-8 ng/ml, e.g., about 0.1-7 ng/ml, e.g., about 0.1-6 ng/ml, e.g., about 0.1-5 ng/ml, e.g., about 0.1-4 ng/ml, e.g., about 0.1-3 ng/ml, e.g., about 0.1-4 ng/ml, e.g., about 0.5-4 ng/ml, e.g., about 0.5-4 ng/ml, e.g., about 3 ng/ml.

As used herein the phrase "TGFβ1" refers to an isoform beta-1 (β1) of the transforming growth factor beta (e.g., *Homo sapiens* TGFβ$_1$, GenBank Accession No. NP_000651; SEQ ID NO:28, which is encoded by the sequence depicted in GenBank Accession No. NM_000660.5; SEQ ID NO:31). TGFβ acts in inducing transformation and also acts as a negative autocrine growth factor. TGFβ1 isoform can be obtained from various commercial sources such as R&D Systems Minneapolis Minn., USA.

According to some embodiments of the invention, TGFβ1 is provided at a concentration range from about 0.1 nanogram per milliliter (ng/ml) to about 500 ng/ml, e.g., about 0.1-400 ng/ml, e.g., about 0.1-300 ng/ml, e.g., about 0.1-200 ng/ml, e.g., about 0.1-100 ng/ml, e.g., about 0.1-50 ng/ml, e.g., about 0.1-30 ng/ml, e.g., about 0.1-20 ng/ml, e.g., about 0.1-10 ng/ml, e.g., about 0.1-8 ng/ml, e.g., about 0.1-7 ng/ml, e.g., about 0.1-6 ng/ml, e.g., about 0.1-5 ng/ml, e.g., about 0.1-4 ng/ml, e.g., about 0.1-3 ng/ml, e.g., about 0.1-2 ng/ml, e.g., about 0.5-2 ng/ml, e.g., about 0.5-1.5 ng/ml, e.g., about 1 ng/ml.

According to some embodiments of the invention, activators of TGF/ACTIVIN pathway including ACTIVIN A (also known as Inhibin beta A, INHBA, Gene ID: 3624; GenBank Accession No. NM_002192.2 (SEQ ID NO:123), which encodes GenBank Accession No. NP_002183.1; SEQ ID NO:117) can be used to replace TGFβ1.

According to some embodiments of the invention, the TGFβ1 cytokine can be replaced with recombinant Nodal and/or Activin.

The phrases "basic fibroblast growth factor (bFGF)" or "FGF2" which are interchangeably used herein refer to a polypeptide of the fibroblast growth factor (FGF) family, which bind heparin and possess broad mitogenic and angiogenic activities. The mRNA for the BFGF gene contains multiple polyadenylation sites, and is alternatively translated from non-AUG (CUG) and AUG initiation codons, resulting in five different isoforms with distinct properties. The CUG-initiated isoforms are localized in the nucleus and are responsible for the intracrine effect, whereas, the AUG-initiated form is mostly cytosolic and is responsible for the paracrine and autocrine effects of this FGF. According to some embodiments of the invention, the bFGF used by the medium of some embodiments of the invention is provided in GenBank Accession No. NP_001997 (SEQ ID NO:29). BFGF can be obtained from various manufacturers such as Peprotech, RnD systems, Millipore. According to some embodiments of the invention, the bFGF used by the medium of some embodiments of the invention is provided from R&D Systems (Catalog Number: 233-FB).

According to some embodiments of the invention, bFGF is provided at a concentration range from about 0.5 nanogram per milliliter (ng/ml) to about 500 ng/ml, e.g., about 1-500 ng/ml, e.g., about 1-400 ng/ml, e.g., about 1-300 ng/ml, e.g., about 1-200 ng/ml, e.g., about 1-100 ng/ml, e.g., about 1-80 ng/ml, e.g., about 1-70 ng/ml, e.g., about 1-70 ng/ml, e.g., about 1-60 ng/ml, e.g., about 1-50 ng/ml, e.g., about 1-40 ng/ml, e.g., about 1-30 ng/ml, e.g., about 1-20 ng/ml, e.g., about 2-20 ng/ml, e.g., about 2-10 ng/ml, e.g., about 3-10 ng/ml, e.g., about 4-10 ng/ml, e.g., about 8 ng/ml.

It will be appreciated that any of the proteinaceous factors used in the culture medium of some embodiments of the invention (e.g., the LIF, IL6, TGFβ1, or bFGF) can be recombinantly expressed or biochemically synthesized. In addition, naturally occurring proteinaceous factors such as bFGF and TGFβ can be purified from biological samples (e.g., from human serum, cell cultures) using methods well known in the art.

Biochemical synthesis of the proteinaceous factors of the present invention (e.g., the LIF, IL6, TGFβ1, or bFGF) can be performed using standard solid phase techniques. These methods include exclusive solid phase synthesis, partial solid phase synthesis methods, fragment condensation and classical solution synthesis.

Recombinant expression of the proteinaceous factors of the present invention (e.g., the LIF, IL6, TGFβ1, or bFGF) can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

For example, to generate the LIF, IL6, TGFβ1, or bFGF, a polynucleotide sequence encoding the LIF, IL6, TGFβ1, or bFGF [e.g., the polynucleotide set forth by SEQ ID NO: 30 (LIF, GenBank Accession No. NM_001257135), SEQ ID NO: 31 (TGFβ1, GenBank Accession NO. NM_000660), SEQ ID NO: 32 (BFGF, GenBank Accession NO. NM_002006), SEQ ID NO:111 (IL6, GenBank Accession No. NM_000600.3)] is preferably ligated into a nucleic acid construct suitable for expression in a host cell [i.e., a cell in which the polynucleotide encoding the polypeptide-of-choice (e.g., the LIF, IL6, TGFβ1, or bFGF) is expressed]. Preferably, to generate an LIF, IL6, TGFβ1, or bFGF with the amount and pattern of glycosylation as of the naturally occurring LIF, IL6, TGFβ1, or bFGF, the host cell employed is a eukaryotic host cell, more preferably a mammalian host cell such as human cell or CHO cell). Additional description of nucleic acid constructs (or expression vectors) which can be used to produce a polypeptide-of-interest (e.g., the proteinaceous factors described above) is provided hereinunder.

As used herein the term "ERK1" refers to the mitogen-activated protein kinase 3 (MAPK3) isoform 1 set forth by GenBank Accession No. NP_002737.2 (SEQ ID NO:33), the MAPK3 isoform 2 set forth by GenBank Accession No. NP_001035145.1 (SEQ ID NO:34), the MAPK3 isoform 3 set forth by GenBank Accession No. NP_001103361.1 (SEQ ID NO:35) and/or ERK1 set forth in GenBank Accession ID NO: M84490 (SEQ ID NO:36) having the MAPK signaling activity.

As used herein the term "ERK2" refers to the mitogen-activated protein kinase 1 (MAPK1) set forth by GenBank Accession No. NP_002736.3 (SEQ ID NO:37) and/or GenBank Accession No. NP_620407.1 (SEQ ID NO:38) having the MAPK signaling activity.

As used herein the term "ERK1/2 inhibitor" refers to any molecule capable of inhibiting the activity of ERK1/2 as determined by Western blot protein detection of phosphorylated ERK1/2 proteins.

Non-limiting examples of ERK1/2 inhibitors include PD0325901 (AXONMEDCHEM—AXON 1408), PD98059 (AXONMEDCHEM—Axon 1223), and PD184352 (AXONMEDCHEM—AXON 1368); or even inhibitors of RAF (which is upstream of ERK) such as Sorafenib or SB (AXONMEDCHEM—AXON 1397).

According to some embodiments of the invention, PD0325901 is provided at a concentration range from about 0.01 microM (μM) to about 50 μM, e.g., between about 0.05-45 μM, e.g., between about 0.1-50 μM, e.g., between about 0.1-45 μM, e.g., between about 0.1-40 μM, e.g., between about 0.1-35 μM, e.g., between about 0.1-30 μM, e.g., between about 0.1-25 μM, e.g., between about 0.1-20 μM, e.g., between about 0.1-15 μM, e.g., between about 0.1-10 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 0.9-8 μM, e.g., between 0.9-7 μM, e.g., between 0.9-6 μM, e.g., between 0.8-5 μM, e.g., between 0.8-4 μM, e.g., between 0.8-3 μM, e.g., between 0.8-2 μM, e.g., between 0.8-1.5 μM, e.g., between 0.9-1.2 μM, e.g., about 1 μM.

According to some embodiments of the invention, PD98059 is provided at a concentration range from about 0.1 microM (μM) to about 70 μM, e.g., between about 0.1-65 μM, e.g., between about 0.1-55 μM, e.g., between about 0.1-50 μM, e.g., between about 0.1-45 μM, e.g., between about 0.1-40 μM, e.g., between about 0.1-35 μM, e.g., between about 0.1-30 μM, e.g., between about 0.1-25 μM, e.g., between about 0.1-20 μM, e.g., between about 0.1-15 μM, e.g., between about 2-20 μM, e.g., between about 5-15 μM, e.g., about 10 μM, e.g., between about 0.1-10 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between about 0.8-10 μM, e.g., between about 0.9-10 μM, e.g., between about 0.9-9 μM, e.g., between about 0.9-8 μM, e.g., between about 0.9-7 μM, e.g., between about 0.9-6 μM, e.g., between 0.8-5 μM, e.g., between 0.8-4 μM, e.g., between 0.8-3 μM, e.g., between 0.8-2 μM, e.g., between 0.8-1.5 μM, e.g., between 0.9-1.2 μM.

According to some embodiments of the invention, PD184352 is provided at a concentration range from about 0.1 microM (μM) to about 70 μM, e.g., between about 0.1-60 μM, e.g., between about 0.1-50 μM, e.g., between about 0.5-50 μM, e.g., between about 0.5-45 μM, e.g., between about 0.5-40 μM, e.g., between about 0.1-35 μM, e.g., between about 0.5-30 µM, e.g., between about 0.5-25 µM, e.g., between about 0.5-20 µM, e.g., between about 0.5-15 µM, e.g., between about 0.5-10 µM, e.g., between 0.5-9 µM, e.g., between 0.5-8 µM, e.g., between 0.5-7 µM, e.g., between 0.9-6 µM, e.g., between 0.8-5 µM, e.g., between 0.8-4 µM, e.g., between 0.8-3 µM, e.g., about 3 µM. e.g., between 0.8-2 µM, e.g., between 0.8-1.5 µM, e.g., between 0.9-1.2 µM.

According to some embodiments of the invention, Sorafenib is provided at a concentration range from about 0.1 microM (µM) to about 70 µM, e.g., between about 0.1-60 µM, e.g., between about 0.1-50 µM, e.g., between about 0.5-50 µM, e.g., between about 0.5-45 µM, e.g., between about 0.5-40 µM, e.g., between about 0.1-35 µM, e.g., between about 0.5-30 µM, e.g., between about 0.5-25 µM, e.g., between about 0.5-20 µM, e.g., between about 0.5-15 µM, e.g., between about 0.5-10 µM, e.g., between 0.5-9 µM, e.g., between 0.5-8 µM, e.g., between 0.5-7 µM, e.g., between 0.9-6 µM, e.g., between 0.8-5 µM, e.g., about 5 µM, e.g., between 0.8-4 µM, e.g., between 0.8-3 µM, e.g., between 0.8-2 µM, e.g., between 0.8-1.5 µM, e.g., between 0.9-1.2 µM.

As used herein the term "GSK3b" refers to the glycogen synthase kinase 3 beta protein set forth by GenBank Accession Nos. NP_002084.2 (SEQ ID NO: 121) and/or NP_001139628.1 (SEQ ID NO: 122) having the WNT signaling regulatory activity via its kinase activity.

As used herein the term "GSK3b inhibitor" refers to any molecule capable of inhibiting the activity of GSK3b as determined by specifically inhibiting levels of phosphorylated GSK3b (out of total GSK3b present in a cell).

Non-limiting examples of GSK3b inhibitors include CHIR99021 (AXONMEDCHEM—AXON 1386), BIO (AXONMEDCHEM—Axon 1693), and Kenpaullone (TOCRIS—cat no. 1398).

According to some embodiments of the invention, CHIR99021 is provided at a concentration range of between about 0.1-50 µM, e.g., from about 0.2 µM to about 50 µM, e.g., between about 0.2-45 µM, e.g., between about 0.2-50 µM, e.g., between about 0.2-45 µM, e.g., between about 0.2-40 µM, e.g., between about 0.2-35 µM, e.g., between about 0.2-30 µM, e.g., between about 0.2-25 µM, e.g., between about 0.2-20 µM, e.g., between about 0.2-15 µM, e.g., between about 0.2-10 µM, e.g., between about 0.2-10 µM, e.g., between about 0.3-10 µM, e.g., between about 0.4-10 µM, e.g., between about 0.5-10 µM, e.g., between about 0.6-10 µM, e.g., between about 0.7-10 µM, e.g., between 0.8-10 µM, e.g., between 0.9-10 µM, e.g., between 0.9-9 µM, e.g., between 1-8 µM, e.g., between 1-7 µM, e.g., between 1-6 µM, e.g., between 1-5 µM, e.g., between 2-4 µM, e.g., about 3 µM.

According to some embodiments of the invention, BIO is provided at a concentration range of between about 0.1-70 µM, e.g., from about 0.2 µM to about 70 µM, e.g., between about 0.2-60 µM, e.g., between about 0.2-55 µM, e.g., between about 0.2-50 µM, e.g., between about 0.2-45 µM, e.g., between about 0.2-40 µM, e.g., between about 0.2-35 µM, e.g., between about 0.2-30 µM, e.g., between about 0.2-25 µM, e.g., between about 0.2-20 µM, e.g., between about 0.2-15 µM, e.g., between about 0.2-10 µM, e.g., between about 0.3-10 µM, e.g., between about 0.4-10 µM, e.g., between about 0.5-10 µM, e.g., between about 0.6-10 µM, e.g., between about 0.7-10 µM, e.g., between 0.8-10 µM, e.g., between 0.9-10 µM, e.g., between 0.9-9 µM, e.g., between 1-8 µM, e.g., between 1-7 µM, e.g., between 1-6 µM, e.g., between 1-5 µM, e.g., about 5 µM, e.g., between 2-4 µM.

According to some embodiments of the invention, Kenpaullone is provided at a concentration range of between about 0.1-70 µM, e.g., from about 0.2 µM to about 70 µM, e.g., between about 0.2-60 µM, e.g., between about 0.2-55 µM, e.g., between about 0.2-50 µM, e.g., between about 0.2-45 µM, e.g., between about 0.2-40 µM, e.g., between about 0.2-35 µM, e.g., between about 0.2-30 µM, e.g., between about 0.2-25 µM, e.g., between about 0.2-20 µM, e.g., between about 0.2-15 µM, e.g., between about 0.2-10 µM, e.g., between about 0.3-10 µM, e.g., between about 0.4-10 µM, e.g., between about 0.5-10 µM, e.g., between about 0.6-10 µM, e.g., between about 0.7-10 µM, e.g., between 0.8-10 µM, e.g., between 0.9-10 µM, e.g., between 0.9-9 µM, e.g., between 1-8 µM, e.g., between 1-7 µM, e.g., between 1-6 µM, e.g., between 1-5 µM, e.g., between 2-4 µM, e.g., about 5 µM.

As used herein the term "p38" refers to the "p38α (alpha)" mitogen-activated protein kinase 14 (MAPK14), which includes MAPK14 isoform 1 set forth by GenBank Accession No. NP_001306.1 (SEQ ID NO:39), MAPK14 isoform 2 set forth by GenBank Accession No. NP_620581.1 (SEQ ID NO:40), MAPK14 isoform 3 set forth by GenBank Accession No. NP_620582.1 (SEQ ID NO:41) and MAPK14 isoform 4 set forth by GenBank Accession No. NP_620583.1 (SEQ ID NO:42); "p3813 (beta)" (MAPK11), which is set forth by GenBank Accession No. NP_002742.3 (SEQ ID NO:43); "p38γ (gamma)" (MAPK12) which is set forth by GenBank Accession No. NP_002960.2 (SEQ ID NO:44); and/or "p386 (delta)" (MAPK13) which is set forth in GenBank Accession No. NP_002745.1 (SEQ ID NO:45), all of them having kinase activity and involved in signal transduction.

As used herein the term "p38 inhibitor" refers to any molecule (e.g., small molecules or proteins) capable of inhibiting the activity of p38 family members as determined by Western blot quantification of phosphorylated p38 levels.

Non-limiting examples of p38 inhibitors include SB203580 (AXONMEDCHEM—Axon 1363), and SB 202190 (AXONMEDCHEM—Axon 1364), LY 2228820 (AXONMEDCHEM—Axon 1895), BIRB796 (Axon Medchem 1358) and PD169316 (AXONMEDCHEM—Axon 1365).

As BMP signaling is an activator for p38 signaling, examples of p38 inhibitors also include BMP inhibitors like Dorsomorphin (AXONMEDCHEM—Axon 2150) and LDN193189 (AXON MEDCHEM AXON 1509) or other inhibitors of the BMP pathway such as recombinant NOGGIN protein [GenBank Accession No. NP_005441.1 (SEQ ID NO: 118)] can be used to replace small molecule inhibitors of BMP signaling.

According to some embodiments of the invention, PDSB203580 is provided at a concentration range of between about 0.5-70 µM, e.g., from about 1 µM to about 70 µM, e.g., between about 1-60 µM, e.g., between about 1-55 µM, e.g., between about 1-50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM, e.g., about 10 µM.

According to some embodiments of the invention, SB 202190 is provided at a concentration range of between about 0.1 µM to about 50 µM, e.g., from about 0.5 µM to about 50 µM, e.g., from about 1 µM to about 50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 1-9 µM, e.g., between about 1-8 µM, e.g., between about 1-7 µM, e.g., between about 2-7 µM, e.g., between about 3-7 µM, e.g., between about 4-7 µM, e.g., between about 4-6 µM, e.g., about 5 µM.

According to some embodiments of the invention, BIRB796 is provided at a concentration range of between about 0.05 to about 30 µM, e.g., from about 0.1 to about 30 µM, e.g., between about 0.2-30 µM, e.g., between about 0.2-25 µM, e.g., between about 0.2-20 µM, e.g., between about 0.2-15 µM, e.g., between about 0.2-10 µM, e.g., between about 0.2-8 µM, e.g., between about 0.2-6 µM, e.g., between about 0.5-6 µM, e.g., between about 0.5-5 µM, e.g., between about 0.5-4 µM, e.g., between about 0.5-3 µM, e.g., between about 0.5-2 µM, e.g., between about 1-3 µM, e.g., between about 1-2.5 µM, e.g., about 2 µM.

As used herein the term "JNK" refers to the mitogen-activated protein kinase 8 (MAPK8) protein set forth by GenBank Accession Nos. NP_620637.1 (isoform alpha2) (SEQ ID NO:46), NP_620635.1 (isoform beta2) (SEQ ID NO:47), NP_620634.1 (isoform beta1) (SEQ ID NO:48), NP_002741.1 (isoform alpha1) (SEQ ID NO:49) which are involved in a wide variety of cellular processes such as proliferation, differentiation, transcription regulation and development.

As used herein the term "JNK inhibitor" refers to any molecule capable of inhibiting the activity of JNK as determined by phosphorylation of JNK family member protein by western blot analysis.

Non-limiting examples of JNK inhibitors include SP600125 (TOCRIS—Cat no. 1496), AEG3482 (AXON-MEDCHEM—AXON 1291), and BIRB796 (AXONMED-CHEM—Axon 1358).

According to some embodiments of the invention, SP600125 is provided at a concentration range of between about 0.5-100 µM, e.g., from about 1 µM to about 100 µM, e.g., between about 1-90 µM, e.g., between about 1-80 µM, e.g., between about 1-70 µM, e.g., between about 1-60 µM, e.g., between about 1-55 µM, e.g., between about 1-50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM.

As used herein the term "protein kinase C (PKC)" refers to PKCα (alpha), PKCβ (beta), PKCγ (gamma), PKCδ (delta), PKCζ (zeta) and PKCµ (mu) protein isoforms.

As used herein the term "protein kinase C inhibitor" refers to any molecule capable of inhibiting the activity of protein kinase C as determined by reducing the levels of phosphorylated versus non phosphorylated PKC isoforms.

A non-limiting example of a protein kinase C inhibitor is Go6983 (CAS 133053-19-7), a potent, cell-permeable, reversible, and ATP-competitive inhibitor of protein kinase C (PKC) with a broad spectrum protein kinase C (PKC) inhibitor (IC50 values are 7, 7, 6, 10, 60 and 20000 nM for PKCα, PKCβ, PKCγ, PKCδ, PKCζ and PKCµ respectively). Go6983 is available from various suppliers such as Calbiochem (Catalogue number 365251-500UG), and TOCRIS (Catalogue number 2285).

According to some embodiments of the invention, Go6983 is provided at a concentration range of between about 0.5-100 µM, e.g., from about 1 µM to about 100 µM, e.g., between about 1-90 µM, e.g., between about 1-80 µM, e.g., between about 1-70 µM, e.g., between about 1-60 µM, e.g., between about 1-55 µM, e.g., between about 1-50 µM, e.g., between about 1-45 µM, e.g., between about 1-40 µM, e.g., between about 1-35 µM, e.g., between about 1-30 µM, e.g., between about 1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM.

As used herein the term "fibroblast growth factor receptor (FGFR)" refers to FGFR1, FGFR2 and FGFR3.

As used herein the term "FGFR inhibitor (or FGFR1)" refers to a molecule capable of inhibiting FGFR expression and/or activity level as determined by levels of phosphorylated FGFR1, 2, and 3.

Non-limiting examples of FGFR inhibitors include PD173074 and SU5401.

According to some embodiments of the invention, the FGFR inhibitor (FGFRi) is PD173074 and is provided in a concentration range between about 0.01-40 µM, e.g., between about 0.02-40 µM, e.g., between about 0.05-40 µM, e.g., between, about 0.1-40 µM, about 0.5-40 µM, about 1-40 µM, e.g., about 2-40 µM, about 5-40 µM, about 10-40 µM, e.g., between about 0.05-5 µM, e.g., about 0.1-5 µM.

According to some embodiments of the invention, the FGFR inhibitor (FGFRi) is SU5401 and is provided at a concentration range of about 0.1-40 µM, e.g., about 0.5-40 µM, about 1-40 µM, e.g., about 2-40 µM, about 5-40 µM, about 10-40 µM.

As used herein the term "transforming growth factor receptor (TGFR)" refers to TGF-β type I receptor ALK5, type I activin/nodal receptor ALK4 and type I nodal receptor ALK7.

As used herein the term "TGFR inhibitor (or TGFRi)" refers to a molecule capable of inhibiting TGFR expression and/or activity level as determined by phosphorylated ALK4, 5 and 7.

Non-limiting examples of TGFR inhibitors include SB431542 and A 83-01 small molecule compound.

According to some embodiments of the invention, the TGFR inhibitor is provided at a concentration range of about 0.1-30 µM, e.g., about 1-30 µM, e.g., 5-25 µM, e.g., 5-10 µM, e.g., 0.1-5 µM, e.g., 0.2-4 µM, e.g., 0.5-3 µM.

According to some embodiments of the invention, the culture medium further comprises a ROCK inhibitor.

As used herein the term "ROCK" refers to the protein set forth by GenBank Accession No. NP_005397.1 (P160ROCK; SEQ ID NO: 50); and NP_004841.2 (ROCK2; SEQ ID NO:51) having the serine/threonine kinase activity, and regulates cytokinesis, smooth muscle contraction, the formation of actin stress fibers and focal adhesions, and the activation of the c-fos serum response element.

As used herein the term "ROCK inhibitor" refers to any molecule capable of inhibiting the activity of ROCK as determined by inhibition of ROCK phosphorylation levels (detected by western blot analysis).

Non-limiting examples of ROCK inhibitors include Y27632 (TOCRIS, Catalogue number 1254).

According to some embodiments of the invention, Y27632 is provided at a concentration range of between about 0.1-100 µM, e.g., from about 0.1 µM to about 90 µM, e.g., between about 0.1-85 µM, e.g., between about 0.1-80 µM, e.g., between about 0.1-70 µM, e.g., between about 0.1-60 µM, e.g., between about 0.1-55 µM, e.g., between about 0.1-50 µM, e.g., between about 0.1-45 µM, e.g., between about 0.1-40 µM, e.g., between about 0.1-35 µM, e.g., between about 0.1-30 µM, e.g., between about 0.1-25 µM, e.g., between about 1-20 µM, e.g., between about 1-15 µM, e.g., between about 1-10 µM, e.g., between about 2-10 µM, e.g., between about 3-10 µM, e.g., between about 4-10 µM, e.g., between about 4-6 µM, e.g., about 5 µM.

According to some embodiments of the invention, the culture medium which comprises leukemia inhibitor factor (LIF), an ERK1/2 inhibitor, a GSK3b inhibitor, a p38 inhibitor, a JNK inhibitor, and a protein kinase C inhibitor, further comprises a ROCK inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor, and a fibroblast growth factor receptor (FGFR) inhibitor (FGFRi) further comprises a ROCK inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor, and a transforming growth factor receptor inhibitor (TGFRi) further comprises a ROCK inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor, a fibroblast growth factor receptor (FGFR) inhibitor (FGFRi) and a transforming growth factor receptor inhibitor (TGFRi) further comprises a ROCK inhibitor.

According some embodiments of the invention, the culture medium which comprises leukemia inhibitor factor (LIF), an ERK1/2 inhibitor, a GSK3b inhibitor, a p38 inhibitor, a JNK inhibitor, TGFβ1 and a protein kinase C inhibitor further comprises a ROCK inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, TGFβ1, a protein kinase C inhibitor and a fibroblast growth factor receptor (FGFR) inhibitor further comprises a ROCK inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1) further comprises a ROCK inhibitor.

According to some embodiments of the invention, the culture medium further comprises a protein kinase C inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1) further comprises a protein kinase C inhibitor.

According to some embodiments of the invention, the culture medium which comprises leukemia inhibitor factor (LIF), an ERK1/2 inhibitor, a GSK3b inhibitor, a p38 inhibitor, a JNK inhibitor, basic fibroblast growth factor (bFGF), transforming growth factor-beta 1 (TGFβ1) and a ROCK inhibitor further comprises a protein kinase C inhibitor.

According to some embodiments of the invention, the culture medium further comprises a factor selected from the group consisting of: bone morphogenetic protein 4 (BMP4), insulin-like growth factor 1 (IGF1), Forskolin, fibroblast growth factor receptor (FGFR) inhibitor (FGFRi), transforming growth factor receptor inhibitor (TGFRi), Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, and a protein kinase C inhibitor further comprises at least one factor selected from the group consisting of bone morphogenetic protein 4 (BMP4), insulin-like growth factor 1 (IGF1), Forskolin, fibroblast growth factor receptor (FGFR) inhibitor (FGFRi), transforming growth factor receptor inhibitor (TGFRi), Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor and a fibroblast growth factor receptor (FGFR) inhibitor (FGFRi) further comprises at least one factor selected from the group consisting of bone morphogenetic protein 4 (BMP4), insulin-like growth factor 1 (IGF1), Forskolin, transforming growth factor receptor inhibitor (TGFRi), Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor and a transforming growth factor receptor inhibitor (TGFRi) further comprises at least one factor selected from the group consisting of bone morphogenetic protein 4 (BMP4), insulin-like growth factor 1 (IGF1), Forskolin, fibroblast growth factor receptor (FGFR) inhibitor (FGFRi), Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, a protein kinase C inhibitor, a fibroblast growth factor receptor (FGFR) inhibitor (FGFRi) and a transforming growth factor receptor inhibitor (TGFRi) further comprises at least one factor selected from the group consisting of bone morphogenetic protein 4 (BMP4), insulin-like growth factor 1 (IGF1), Forskolin, Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, TGFβ1 and a protein kinase C inhibitor further comprises at least one factor selected from the group consisting of bone morphogenetic protein 4 (BMP4), insulin-like growth factor 1 (IGF1), Forskolin, fibroblast growth factor receptor (FGFR) inhibitor (FGFRi), transforming growth factor receptor inhibitor (TGFRi), Kenpaullone, BayK8644, Bix1294, and stem cell factor (SCF).

According to some embodiments of the invention, the culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1) further comprises at least one factor selected from the group consisting of bone morphogenetic protein 4 (BMP4), insulin-like growth factor 1 (IGF1), Forskolin, fibroblast growth factor receptor (FGFR) inhibitor (FGFRi), transforming growth factor receptor inhibitor (TGFRi), Kenpaullone, BayK8644, Bix1294, and stem cell factor (SCF).

According to some embodiments of the invention, the culture medium further comprises ascorbic acid.

As used herein the phrase "ascorbic acid" or "Vitamin C" which is interchangeably used herein, refers to L-ascorbic acid 2-phosphate. Ascorbic acid can be obtained from e.g., Sigma (Catalogue number A8960).

The concentration of ascorbic acid to be used with the medium of some embodiments of the invention can be about 1-300 µg/ml, e.g., about 50 µg/ml.

According to some embodiments of the invention, the culture medium further comprises oleic Acid. It should be noted that oleic Acid can be used instead of ALBUMAX® (Life Technologies) or together with ALBUMAX®.

According to some embodiments of the invention, the culture medium further comprises Linoleic Acid. It should be noted that Linoleic Acid can be used instead of ALBUMAX® (Life Technologies) or together with ALBUMAX®.

According to some embodiments of the invention, the culture medium further comprises Pipecolic Acid. It should be noted that pipecolic acid can be used instead of ALBUMAX® (Life Technologies) or together with ALBUMAX®.

According to some embodiments of the invention, the Oleic Acid (O1257, Sigma Aldrich) can be used at a concentration of about 1-200 µg/ml, e.g., about 10 µg/ml in the culture medium.

According to some embodiments of the invention, the Oleic Acid [O1008 Sigma Aldrich, dissolved in DMSO), can be used at a concentration of 1-200 µg/ml e.g., about 10 µg/ml in the culture medium.

According to some embodiments of the invention, the Pipecolic Acid [P2519 Sigma Aldrich, dissolved in DMSO), can be used at a concentration of 1-200 µg/ml e.g., about 10 µg/ml in the culture medium.

According to some embodiments of the invention, the oleic Acid-Albumin (O3008 Sigma Aldrich) can be used at a concentration of about 1-200 µg/ml, e.g., about 10 µg/ml in the culture medium.

According to some embodiments of the invention, the medium comprises Linoleic/Oleic/Albumin supplement (L9655 Sigma Aldrich) at a concentration of about 1-200 µg/ml, e.g., about 10 µg/ml in the culture medium.

A non-limiting example of a culture medium which can be used to maintain (and induce to naive state) pluripotent stem cells in a naive state include: leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1), and one or more of the following components:

a) IGFII (range 0.1-100 ng/ml final concentration);

b) IGF1 [insulin-like growth factor 1 (somatomedin C)] (range 0.1-100 ng/ml final concentration);

c) SCF (range 0.1-100 ng/ml final concentration);

d) BMP signaling inhibitor [examples include, but are not limited to: LDN193189 (AXON 1509—0.01-20 microM final concentration), K02288 (Axon 2189; 0.1-20 microM final concentration), Dorsomorphin hydrochloride (AXON 2150 0.1-20 microM final concentration);

e) NOTCH signaling inhibitors [examples include, but are not limited to the following gamma secretase inhibitors: DAPT (Axon Medchem 1484—0.05-50 microM final concentration), LY2886721 hydrochloride (Axon Medchem 1964—0.05-50 microM final concentration)], DBZ (Axon Medchem—Axon 1488—0.05-50 microM final concentration);

f) Sonic Hedgehog pathway (SHH) inhibitors [examples include, but are not limited to the following: GANT61 (SigmaAldrich—0.05-50 microM final concentration), RU-SKI 43 (Axon Medchem—Axon 2035—0.05-50 microM final concentration)];

g) ERK5 inhibitors (BIX02189 Axon 1809; range 0.1-100 microM final concentration);

h) ROCK inhibitor [Y27632 (AXON 1683)—0.05-100 microM final];

i) FGF signaling inhibitor: Non-limiting examples of FGFR inhibitors include PD173074 and SU5401; and j) TGF pathway inhibitor: Non-limiting examples of TGFR inhibitors include SB431542 and A 83-01 small molecule compound (As used herein the term "TGFR inhibitor (or TGFRi)" refers to a molecule capable of inhibiting TGFR expression and/or activity level as determined by phosphorylated ALK4, 5 and 7).

According to some embodiments of the invention, the culture medium of the invention is defined by any one of conditions 1-5, and 7-17 as described in Tables 3-5 in the Examples section which follows.

According to some embodiments of the invention, the culture medium further comprises an MBD3 inhibitor.

As used herein the term "MBD3" refers to the Methyl-CpG-binding domain 3 protein set forth by GenBank Accession No. NP_003917.1 (SEQ ID NO:7) having the co-repressor and chromatin remodeling functional activity.

As used herein the term "MBD3 inhibitor" refers to any agent (e.g., a molecule) capable of downregulating the expression level and/or activity of MBD3, and/or capable of interfering between the interaction of MBD3 with OCT4, and/or MBD3 with SOX2, and/or MBD3 and KLF4 and/or MBD3 and C-Myc, and/or inhibiting the binding of MBD3 to the nucleosome remodeling and deacetylase (NuRD). Downregulation of MBD3 can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., an antibody (e.g., a neutralizing antibody), an antagonist, e.g., small molecules which inhibit MBD3 activity or ability to directly interact with any of the reprogramming factors (Oct4, Sox2, Klf4 or c-Myc), enzymes that cleave the polypeptide and the like.

Non-limiting examples of MBD3 inhibitors include siRNA directed against MBD3 mRNA, such as those provided from Invitrogen, mBD3HSS147581(3_RNAI) (Invitrogen): AGGUCAAGGGCAAGCCCGACCUGAA (SEQ ID NO:52); and MBD3HSS147581(3_RNAI) (Invitrogen): UUCAGGUCGGGCUUGCCCUUGACCU (SEQ ID NO:53). Another suitable siRNA directed against MBD3 mRNA which can be used is the commercially available MBD3 Stealth siRNAs that include HSS147580 and HSS147581 components (Life Technologies™, catalogue number 1299001) that were found efficient for MBD3 knockdown in human cells.

According to some embodiments of the invention, inhibiting the binding of Mbd3 to the NuRD complex is performed using a chromodomain helicase DNA binding protein 4 (CHD4) inhibitor.

Non-limiting examples of CHD4 inhibitors include the human CHD4 siRNA, such as the CHD4 stealth siRNA HSS101850 available from Life Technologies™, which was found to efficiently knockdown CHD4 in human cells.

According to some embodiments of the invention, inhibiting the binding of Mbd3 to the NuRD complex is performed using a P66 alpha coiled-coil (P66α-CC) domain.

The peptide of the P66α-CC (SEQ ID NO: 114) can be added to the medium as is, or can be recombinantly expressed from a vector encoding the P66α-CC sequence (e.g., a vector which comprises the nucleotide sequence set forth in SEQ ID NO: 113).

According to some embodiments of the invention, inhibiting Mbd3 expression is performed using a protein kinase C (PKC) inhibitor (e.g., using the agents and molecules as described above).

According to some embodiments of the invention, the medium further comprises an agent which increases expression of endogenous ERAS and/or a recombinant ERAS.

According to some embodiments of the invention, the MBD3 inhibitor is provided in an amount sufficient to downregulate the expression level of the MBD3 RNA and/or protein in the cell by at least about 30%, e.g., at least about 35%, e.g., at least about 40%, e.g., at least about 45%, e.g., at least about 50%, e.g., at least about 55%, e.g., at least about 60%, e.g., at least about 65%, e.g., at least about 70%, e.g., at least about 75%, e.g., at least about 80% as compared to the expression level of the MBD3 RNA and/or protein, respectively, in the same cell when incubated and/or cultured under the same (e.g., identical) conditions yet without the MBD3 inhibitor.

According to some embodiments of the invention, the MBD3 inhibitor is provided in an amount sufficient to downregulate the expression level of the MBD3 RNA and/or protein in the cell by about 30-90%, e.g., about 30-85%, e.g., about 40-85%, e.g., about 50-85%, e.g., about 60-85%, e.g., about 70-85%, e.g., about 80-85%, e.g., about 85% as compared to the expression level of the MBD3 RNA and/or protein, respectively, in the same cell when incubated and/or cultured under the same (e.g., identical) conditions yet without the MBD3 inhibitor.

The expression level of the MBD3 in the cell can be determined by various methods such as real time reverse transcription PCR, Western blot and the like. A non-limiting example for such an assay is provided in the Examples section which follows and in FIGS. 1I-J, demonstrating about 85% inhibition of MBD3 protein level in cells transformed with the MBD3$^{flox/-}$ construct.

According to some embodiments of the invention, the culture medium is devoid of serum, e.g., devoid of any animal serum.

According to some embodiments of the invention, the culture medium is devoid of any animal contaminants, i.e., animal cells, fluid or pathogens (e.g., viruses infecting animal cells), e.g., being xeno-free.

According to some embodiments of the invention, the culture medium is devoid of human derived serum.

According to some embodiments of the invention, the culture medium further comprises a serum replacement (i.e., a substitute of serum) such as KNOCKOUT™ Serum Replacement (Gibco-Invitrogen Corporation, Grand Island, N.Y. USA), ALBUMAX®II (Gibco®; Life Technologies Invitrogen, Catalogue No. 11021-029; Lipid-rich bovine serum albumin for cell culture) or a chemically defined lipid concentrate (Gibco®; Invitrogen, Life Technologies Invitrogen, Catalogue No. 11905-031).

According to some embodiments of the invention, the culture medium further comprises N2 supplement (Gibco®; Life Technologies Invitrogen, Catalogue No. 17502-048) a chemically defined, serum-free supplement. For a 500 ml of culture medium 5 ml of the N2 mix (Invitrogen) can be added.

Alternatively, the following materials (substitute the N2 supplement) can be added to a 500 ml culture medium: Recombinant Insulin (Sigma I-1882) at a 12.5 microg/ml (μg/ml) final concentration; Apo-Transferrin (Sigma T-1147) at a 500 μg/ml final concentration; Progesterone (Sigma-P8783) at a 0.02 μg/ml final concentration; Putrescine (Sigma-P5780) at a 16 μg/ml final concentration; and 5 microL (μl) of 3 mM stock of Sodium Selenite (Sigma S5261) are added per 500 ml culture medium (e.g., the WIS-NHSM).

According to some embodiments of the invention, the KNOCKOUT™ Serum Replacement is provided at a concentration of at least 0.5%, e.g., in the range of about 0.5%-25%, e.g., about 5%, about 10%, about 15%, about 20% or about 25%.

According to some embodiments of the invention, the ALBUMAX™ is provided at a concentration of at least 0.01%, e.g., in the range of about 0.01%-10%, e.g., about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9% or about 10%, e.g., 1%.

According to some embodiments of the invention, the defined lipid concentrate is provided at a concentration of at least about 0.1%, e.g., in the range of 0.1-5%, e.g., about 0.2%, about 0.3%, about 0.4%, about 0.5%, about 0.6%, about 0.7%, about 0.8%, about 0.9%, about 1%, about 2%, about 3%, about 4%, about 5%, e.g., 1%.

According to some embodiments of the invention, the culture medium comprises the N2 supplement (e.g., 5 ml N2 per 500 ml of culture medium) and the defined lipid concentrate (5 ml defined lipid concentrate per 500 ml medium).

According to some embodiments of the invention, the culture medium comprises the N2 supplement (e.g., 5 ml N2 per 500 ml of culture medium) and ALBUMAX®II (e.g., 1% Albumax®II; Gibco®; Life Technologies Invitrogen).

According to some embodiments of the invention, the culture medium can further include antibiotics (e.g., PEN-STREP), L-glutamine, NEAA (non-essential amino acids).

According to some embodiments of the invention, the culture medium comprises KO-DMEM with N2 supplement (e.g., about 5 ml N2 per 500 ml of culture medium) with about 5 ml defined lipid concentrate per 500 ml medium, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), and JNKi (SP600125, about 5-10 μM).

According to some embodiments of the invention, the culture medium comprises KO-DMEM with N2 supplement (e.g., about 5 ml N2 per 500 ml of culture medium) with about 1-2% Albumax®II, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), and JNKi (SP600125, 5-about 10 μM).

According to some embodiments of the invention, the culture medium comprises KO-DMEM with N2 supplement (e.g., about 5 ml N2 per 500 ml of culture medium) with about 15% Kockout SR (Gibco), LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-μM).

According to an aspect of some embodiments of the invention, there is provided a cell culture comprising cells and the culture medium of some embodiments of the invention.

According to some embodiments of the invention, the cells can be any cells, e.g., prokaryotic or eukaryotic cells, e.g., primate cells, e.g., mammalian cells, e.g., human cells.

According to some embodiments of the invention, the cells can be somatic cells, stem cells, primed pluripotent stem cells, and/or naive pluripotent stem cells.

According to some embodiments of the invention, the culture medium is capable of maintaining naive pluripotent stem cell in an undifferentiated state for at least 2 passages, e.g., for at least 5, 10, 20, 30, 40, 50, 60, 70, 80, 90 or 100 passages.

According to an aspect of some embodiments of the invention, there is provided a method of generating a naive pluripotent stem cell (PSC), comprising incubating a non-naive PSC cell under conditions which allow generation of the naive PSC from the non-naive PSC, wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the PSC is a primate (e.g., mammalian, e.g., human) PSC.

According to some embodiments of the invention, the conditions comprise the culture medium of some embodiments of the invention.

According to some embodiments of the invention, the conditions comprise growing the cells in the presence of 1-20% oxygen ($O_2$) and 5% $CO_2$.

According to some embodiments of the invention, the conditions comprise hypoxia. Hypoxic conditions (hypoxia) can be induced in the presence of less than 10% $O_2$ (oxygen) in the growth environment.

The growth environment (e.g., tissue culture incubator) can include about 37° C., 5% $CO_2$, and hypoxia (less than 10% $O_2$ in the air).

According to some embodiments of the invention, the conditions comprise a culture medium which comprises an ERK1/2 inhibitor, a GSK3β inhibitor, a p38 inhibitor, a JNK inhibitor, a STAT3 activator and at least one agent selected from the group consisting of: basic fibroblast growth factor (bFGF), transforming growth factor beta 1 (TGFβ1), a protein kinase C (PKC) inhibitor, a ROCK inhibitor and a NOTCH inhibitor.

According to some embodiments of the invention, the conditions comprise a culture medium which comprises an ERK1/2 inhibitor, a GSK3β inhibitor, a p38 inhibitor, a JNK inhibitor, a STAT3 activator and at least one agent selected from the group consisting of: a transforming growth factor receptor (TGFR) inhibitor, a fibroblast growth factor receptor (FGFR) inhibitor, a protein kinase C (PKC) inhibitor, a ROCK inhibitor and a NOTCH inhibitor.

According to some embodiments of the invention, the STAT3 activator is selected from the group consisting of LIF, IL6 and EGF.

According to some embodiments of the invention, the STAT3 activator is selected from the group consisting of LIF, and IL6.

According to some embodiments of the invention, the STAT3 activator is LIF.

According to some embodiments of the invention, the culture medium further comprising at least one additional agent selected from the group consisting of: insulin-like growth factor 1 (IGF1), insulin-like growth factor II (IGFII), a bone morphogenetic protein (BMP) signaling inhibitor, a Sonic Hedgehog pathway (SHH) inhibitor, an ERK5 inhibitor, Forskolin, Kenpaullone, BayK8644, Bix1294, and stem cell factor (SCF).

According to some embodiments of the invention, the culture medium further comprising at least one additional agent selected from the group consisting of: insulin-like growth factor 1 (IGF1), insulin-like growth factor II (IGFII), bone morphogenetic protein 4 (BMP4), a Sonic Hedgehog pathway (SHH) inhibitor, an ERK5 inhibitor, Forskolin, Kenpaullone, BayK8644, Bix1294, and stem cell factor (SCF).

According to some embodiments of the invention, the STAT3 activator comprises the LIF, and wherein the at least one agent comprises the PKC inhibitor.

According to some embodiments of the invention, the culture medium further comprising FGFR inhibitor.

According to some embodiments of the invention, the culture medium further comprising TGFR inhibitor.

According to some embodiments of the invention, the STAT3 activator comprises the LIF and wherein the at least one agent comprises the TGFβ1 and the protein kinase C inhibitor.

According to some embodiments of the invention, the culture medium further comprising an FGFR inhibitor.

According to some embodiments of the invention, the STAT3 activator comprises the LIF, and wherein the at least one agent comprises the bFGF and the TGFβ1.

According to some embodiments of the invention, the culture medium further comprising a ROCK inhibitor.

According to some embodiments of the invention, the culture medium further comprising a protein kinase C inhibitor.

According to some embodiments of the invention, the STAT3 activator comprises the LIF and wherein the at least one agent comprises the bFGF, the ROCK inhibitor, a bone morphogenetic protein (BMP) inhibitor, the NOTCH inhibitor, and a transforming growth factor receptor (TGFR) inhibitor.

According to some embodiments of the invention, the culture medium further comprising a Sonic Hedgehog pathway (SHH) inhibitor.

According to some embodiments of the invention, the STAT3 activator comprises the LIF and wherein the at least one agent comprises the NOTCH inhibitor, and a fibroblast growth factor receptor (FGFR) inhibitor.

According to some embodiments of the invention, the culture medium further comprises an agent selected from the group consisting of insulin-like growth factor II (IGFII), stem cell factor (SCF) and transforming growth factor beta 1 (TGFβ1).

According to some embodiments of the invention, the conditions comprise a culture medium which comprises LIF, an ERK1/2 inhibitor, a GSK3b inhibitor, a p38 inhibitor, a JNK inhibitor, and a protein kinase C inhibitor.

According to some embodiments of the invention, the culture medium further comprising a FGFR inhibitor (FGFRi).

According to some embodiments of the invention, the culture medium further comprising a TGFR inhibitor (TGFRi).

According to some embodiments of the invention, the conditions comprise a culture medium which comprises LIF, an ERK1/2 inhibitor, a GSK3b inhibitor, a p38 inhibitor, a JNK inhibitor, and a protein kinase C inhibitor, further comprises a FGFR inhibitor (FGFRi).

According to some embodiments of the invention, the conditions comprise a culture medium which comprises LIF, an ERK1/2 inhibitor, a GSK3b inhibitor, a p38 inhibitor, a JNK inhibitor, and a protein kinase C inhibitor, further comprises a TGFRi.

According to some embodiments of the invention, the conditions comprise a culture medium which comprises LIF, an ERK1/2 inhibitor, a GSK3b inhibitor, a p38 inhibitor, a JNK inhibitor, and a protein kinase C inhibitor, further comprises a FGFR inhibitor and a TGFRi.

According to some embodiments of the invention, the conditions comprise a culture medium which comprises LIF, an ERK1/2 inhibitor, a GSK3b inhibitor, a p38 inhibitor, a JNK inhibitor, TGFβ1 and a protein kinase C inhibitor.

According to some embodiments of the invention, the conditions comprise a culture medium which comprises LIF, an ERK1/2 inhibitor, a GSK3b inhibitor, a p38 inhibitor, a JNK inhibitor, TGFβ1 and a protein kinase C inhibitor further comprising FGFR inhibitor (FGFRi).

According to some embodiments of the invention, the conditions comprise a culture medium which comprises LIF, an ERK1/2 inhibitor, a GSK3b inhibitor, a p38 inhibitor, a JNK inhibitor, bFGF and TGFβ1.

According to some embodiments of the invention, the conditions comprise a culture medium which comprises leukemia inhibitor factor (LIF), an ERK1/2 inhibitor, a GSK3b inhibitor, a p38 inhibitor, a JNK inhibitor, and a protein kinase C inhibitor.

According to some embodiments of the invention, the medium further comprises an FGFR inhibitor.

According to some embodiments of the invention, the medium further comprises a TGFR inhibitor.

According to some embodiments of the invention, the conditions comprise a culture medium which comprises leukemia inhibitor factor (LIF), an ERK1/2 inhibitor, a GSK3b inhibitor, a p38 inhibitor, a JNK inhibitor, TGFβ1 and a protein kinase C inhibitor.

According to some embodiments of the invention, the medium further comprises FGFR inhibitor.

According to some embodiments of the invention, the conditions comprise a culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the medium further comprises a ROCK inhibitor.

According to some embodiments of the invention, the medium further comprises a protein kinase C inhibitor.

According to some embodiments of the invention, the medium further comprises a factor selected from the group consisting of: bone morphogenetic protein 4 (BMP4), IGF1, Forskolin, FGFR inhibitor, TGFR inhibitor Kenpaullone, BayK8644, Bix1294, and stem cell factor (SCF).

According to some embodiments of the invention, the medium further comprises an ascorbic acid.

According to some embodiments of the invention, the medium further comprises an oleic Acid.

According to some embodiments of the invention, the medium further comprises a Linoleic Acid.

According to some embodiments of the invention, the culture medium being devoid of animal serum (e.g., devoid of bovine serum, mouse serum, being xeno-free, devoid of animal contaminants).

According to some embodiments of the invention, the culture medium further comprises serum replacement.

According to some embodiments of the invention, the culture medium further comprises an MBD3 inhibitor.

According to some embodiments of the invention, the conditions comprise a culture medium which comprises leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1).

According to some embodiments of the invention, the culture medium further comprises a ROCK inhibitor.

According to some embodiments of the invention, the culture medium further comprises an MBD3 inhibitor.

According to some embodiments of the invention, the non-naive PSC is selected from the group consisting of a primed PSC, a blastocyst, an induced pluripotent stem cell (a primed iPSC) and a somatic cell.

It should be noted that when the non-naive PSC is a primed PSC (e.g., a blastocyst, an embryonic stem cell, an embryonic germ cell, or an induced pluripotent stem cell) there is no need for exogenous expression of the Oct4, Sox2, Klf4 and c-Myc, nor for the addition of isolated Oct4, Sox2, Klf4 and/or c-Myc factors to the medium.

According to some embodiments of the invention, when the non-naive PSC is a primed PSC, a blastocyst, or an induced pluripotent stem cell (a primed iPSC) the medium does not include the Oct4, Sox2, Klf4 and/or c-Myc factors.

According to some embodiments of the invention, when the non-naive PSC is a primed PSC, a blastocyst, or an induced pluripotent stem cell (a primed iPSC) the cells are not genetically modified to express the Oct4, Sox2, Klf4 and/or c-Myc factors.

According to some embodiments of the invention, wherein when the non-naive PSC comprises a somatic cell then the method further comprising subjecting the somatic cell to de-differentiation conditions, to thereby obtain an induced pluripotent stem cell.

According to some embodiments of the invention, de-differentiation conditions comprise exogenously expressing within the somatic cell at least two growth factors selected from the group consisting of OCT4 [GenBank Accession Nos. NP_002692.2 (SEQ ID NO:54) and NM_002701.4 (SEQ ID NO:55)], SOX2 [GenBank Accession Nos. NP_003097.1 (SEQ ID NO:56) and NM_003106.3 (SEQ ID NO:57)], KLF4 [GenBank Accession Nos. NP_004226.3 (SEQ ID NO:58) and NM_004235.4 (SEQ ID NO:59)] and c-Myc [GenBank Accession Nos. NP_002458.2 (SEQ ID NO:60) and NM_002467.4 (SEQ ID NO:61)].

As used herein the phrase "exogenously expressing" refers to expressing a heterologous nucleic acid sequence which may not be naturally expressed within the cell or which overexpression in the cell is desired. The exogenous polynucleotide may be introduced into the cell in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the cell.

The term "endogenous" as used herein refers to any polynucleotide or polypeptide which is present and/or naturally expressed within the cell.

According to some embodiments of the invention, de-differentiation conditions comprise expressing within the somatic cell Klf4 and Oct4.

According to some embodiments of the invention, de-differentiation conditions comprise expressing within the somatic cell Oct4, Sox2 and Klf4.

According to some embodiments of the invention, de-differentiation conditions comprise expressing within the somatic cell Oct4, Klf4 and cMyc.

According to some embodiments of the invention, expressing the growth factors is performed using DNA transfection of the growth factors.

Methods of DNA transfections into mammalian cells are known in the art and include those described for example in FIG. 1a and in Reference (Mansour et al. 2012), which is fully incorporated herein by reference in its entirety. Further description of preparation of expression vectors and modes of administering them into cells are provided hereinunder.

According to some embodiments of the invention, expressing the growth factors is performed using RNA transfection of the growth factors.

Methods of RNA transfections into mammalian cells are known in the art and include those described for example in (Warren et al. 2010) which is fully incorporated herein by reference in its entirety.

Once obtained, the cells are cultured in a medium and being serially passaged.

It should be noted that culturing the naive PSC involves replacing the culture medium with a "fresh" medium (of identical composition) every 24-48 hours, and passaging each culture dish (e.g., a plate) to 2 or 3 culture dishes (e.g., plates) every 3-5 days. Thus, when cells in the culture reach about 60-90% confluence the supernatant is discarded, the culture dishes are washed [e.g., with phosphate buffered saline (PBS)] and the cells are subjected to enzymatic dissociation from the culture dish, e.g., using trypsinization (0.25% or 0.05% Try sin+EDTA), e.g., until single cells or cell clumps are separated from each other.

It should be noted that the culture conditions uncovered by the present inventors enables maintenance of human PSCs such as human iPSCs in the naive PSC state without the need of further exogenous expression of the Oct4, Sox2, Klf4 and/or c-Myc factors. This is in sharp contrast to all prior attempts to generate naive human PSCs which required exogenous expression of the Oct4, Sox2, Klf4 and/or c-Myc factors, and which upon withdrawal of these factors the naive PSCs spontaneously differentiated, and could not be maintained in the undifferentiated and pluripotent stem cells (See e.g., Hanna J, 2010b).

According to some embodiments of the invention, exogenous expression of the growth factors is effected for a limited time, such as for no more than 10 days in culture, e.g., for no more than 1 passage.

According to some embodiments of the invention, once the naive iPSCs are generated from the somatic cells, they are further being cultured in the culture medium of some embodiments of the invention (e.g., the WIS-NHSM medium) without exogenous expression of the Oct4, Sox2, Klf4 and/or c-Myc factors by the naive iPSCs, and without addition of the isolated Oct4, Sox2, Klf4 and/or c-Myc factors to the culture medium.

As used herein the phrase "isolated . . . factors" refers to factors which are recombinantly expressed from an expression vector in a host cell (e.g., a bacteria), being biochemically synthesized, or being isolated from a biological sample (e.g., serum or cells).

The method of some embodiments of the invention can be used to improve generation of iPSCs from somatic cells as compared to generation of iPSC from somatic cells using expression of the Oct4, Sox2, Klf4 and c-Myc factors in somatic cells without further inhibition of the Mbd3 expression.

For example, when human somatic cells are used, the method is effected using a medium which comprises leukemia inhibitor factor (LIF), an ERK1/2 inhibitor, a GSK3b inhibitor, a p38 inhibitor, a JNK inhibitor, basic fibroblast growth factor (bFGF), transforming growth factor-beta 1 (TGFβ1), and an MBD3 inhibitor, and optionally also a ROCK inhibitor. When the somatic cells are subject to de-differentiation using DNA transfection of the growth factors (e.g., at least two of the Oct4, Sox2, Klf4 and c-Myc), then the method results in at least about 30%, e.g., at least about 40%, at least about 50%, e.g., at least about 60%, at least about 70%, e.g., at least about 80%, at least about 90%, e.g., at least about 95%, at least about 99%, e.g., 100% more iPSCs as compared to the yield of the iPSCs obtained when the Oct4, Sox2, Klf4 and c-Myc are expressed using DNA transfection in the somatic cell without further inhibition of the Mbd3 expression.

For example, when human somatic cells are used, the method is effected using a medium which comprises leukemia inhibitor factor (LIF), an ERK1/2 inhibitor, a GSK3b inhibitor, a p38 inhibitor, a JNK inhibitor, basic fibroblast growth factor (bFGF), transforming growth factor-beta 1 (TGFβ1), and an MBD3 inhibitor, and optionally also a ROCK inhibitor. When the somatic cells are subject to de-differentiation using RNA transfection of the growth factors (e.g., at least two of the Oct4, Sox2, Klf4 and c-Myc), then the method results in at least about 5%, e.g., at least about 10%, at least about 20%, e.g., at least about 30%, at least about 40%, e.g., at least about 50%, at least about 60%, e.g., at least about 75%, at least about 99%, e.g., 100% more iPSCs as compared to the yield of the iPSCs obtained when the Oct4, Sox2, Klf4 and c-Myc are expressed using RNA transfection in the somatic cell without further inhibition of the Mbd3 expression. Moreover, while the prior art methods (without MBD3 inhibition and without the medium of some embodiments of the present invention) employ 10-20 rounds of RNA transfection in order to achieve de-differentiation of human somatic cells, the method of some embodiments of the invention employs 1-4 rounds of RNA transfection in order to achieve de-differentiation of human somatic cells, and thus is far more efficient and time consuming.

According to an aspect of some embodiments of the invention, there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), defined lipid concentrate (Gibco) or Albumax I (Invitrogen), LIF, bFGF, TGFβ1, ERK1/2 inhibitor, GSK3b inhibitor, p38 inhibitor, and JNK inhibitor and a protein kinase C inhibitor, thereby generating the naive PSC.

According to some embodiments of the invention, the culture medium further comprises FGFR inhibitor.

According to some embodiments of the invention, the culture medium further comprises TGFR inhibitor.

According to an aspect of some embodiments of the invention, there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), defined lipid concentrate (Gibco) or Albumax I (Invitrogen), LIF, bFGF, TGFβ1, ERK1/2 inhibitor, GSK3b inhibitor, p38 inhibitor, and JNK inhibitor and a protein kinase C inhibitor, thereby generating the naive PSC.

According to some embodiments of the invention, the culture medium further comprises FGFR inhibitor.

According to an aspect of some embodiments of the invention, there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), defined lipid concentrate (Gibco) or Albumax I (Invitrogen), LIF, bFGF, TGFβ1, ERK1/2 inhibitor, GSK3b inhibitor, p38 inhibitor, and JNK inhibitor, thereby generating the naive PSC.

According to an aspect of some embodiments of the invention, there is provided a method of generating a naive pluripotent stem cell (PSC), comprising incubating a non-naive PSC cell under conditions which allow generation of the naive PSC from the non-naive PSC, the naive PSC comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

wherein the conditions which comprise a culture medium which comprises KO-DMEM, N2 supplement (Gibco), defined lipid concentrate (Gibco), LIF, bFGF, TGFβ1, ERK1/2 inhibitor, GSK3b inhibitor, p38 inhibitor, JNK inhibitor, and an MBD3 inhibitor, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., about 5 ml N2 per 500 ml of culture medium) with about 5 ml defined lipid concentrate per 500 ml medium, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), and JNKi (SP600125, about 5-10 μM), wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., about 5 ml N2 per 500 ml of culture medium) with about 1-2% Albumax®II, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), and JNKi (SP600125, about 5-10 μM), wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., 5 ml N2 per 500 ml of culture medium) with about 15% Kockout SR (Gibco), LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-10 μM), wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., about 5 ml N2 per 500 ml of culture medium) with about 5 ml defined lipid concentrate per 500 ml medium, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-10 μM) and an MBD3 inhibitor, wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., about 5 ml N2 per 500 ml of culture medium) with about 1-2% Albumax®II, LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-10 μM), and an MBD3 inhibitor, wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to some embodiments of the invention, the method of generating a naive pluripotent stem cell (PSC) comprises incubating a non-naive PSC cell under conditions which comprise a culture medium which comprises KO-DMEM with N2 supplement (e.g., about 5 ml N2 per 500 ml of culture medium) with about 15% Kockout SR (Gibco), LIF (about 20 ng/ml), bFGF (about 8 ng/ml), TGFβ1 (about 1 ng/ml), ERK1/2i (about 1 μM of PD0325901), GSK3bi (CHIR99021, about 3 μM), p38i (SB203580, about 5 μM), JNKi (SP600125, about 5-10 μM), and an MBD3 inhibitor, wherein:

(i) when the naive PSC is a female PSC, then the naive female PSC has two unmethylated alleles of an X-inactive specific transcript (XIST) gene; and (ii) when the naive PSC is a male PSC, then the naive male PSC has an unmethylated allele of the XIST gene, thereby generating the naive PSC.

According to an aspect of some embodiments of the invention, there is provided a method of improving generation of induced pluripotent stem cells (iPSCs) from a somatic cell, comprising:

(a) expressing within the somatic cell at least two growth factors selected from the group consisting of Oct4, Sox2, Klf4 and c-Myc and (b) inhibiting Mbd3 expression in the somatic cell, and/or inhibiting binding of the Mbd3 to the nucleosome remodeling and deacetylase (NuRD) complex in the somatic cell, thereby improving generation of the iPSCs from a somatic cell.

According to some embodiments of the invention, inhibiting the binding of the Mbd3 to the NuRD complex is performed using a chromodomain helicase DNA binding protein 4 (CHD4) inhibitor.

According to some embodiments of the invention, inhibiting the binding of the Mbd3 to the NuRD complex is performed using a P66 alpha coiled-coil domain.

According to some embodiments of the invention, inhibiting the Mbd3 expression is performed using a protein kinase C (PKC) inhibitor.

As described in Example 15 of the Examples section which follows, the present inventors have uncovered that overexpression of ERAS or activation of endogenous human ERAS in pluripotent stem cells can be used to induce a naive state in pluripotent stem cells.

According to some embodiments of the invention, the method further comprising exogenously expressing ES cell expressed Ras (ERAS) coding sequence (e.g., SEQ ID NO: 109) or activating endogenous expression of the ERAS in the somatic cell.

According to some embodiments of the invention, activating endogenous expression of ERAS is performed by removing the premature poly adenylation sites of the endogenous ERAS gene (SEQ ID NO: 108), e.g., in A-1, A2 or A-3 boxed sequences in FIG. 3 by Kameda et al. Stem Cells 2005; 23:1535-1540; which is fully incorporated herein by reference in its entirety.

According to some embodiments of the invention, expressing is effected for at least 48 hours such that the inhibiting the Mbd3 is effected to 10-30% of a level of the Mbd3 prior to the expressing.

According to some embodiments of the invention, expressing is effected for about 48 hours and the inhibiting is effected after the about 48 hours.

It should be noted that when inhibition of Mbd3 is performed after 48 hours, the inhibition can be of 100% of the expression level of activity of MBD3.

According to some embodiments of the invention, the iPSC is a murine iPSC.

According to some embodiments of the invention, the method further comprising culturing the murine iPSC in a medium which comprises LIF, an ERK1/2 inhibitor, and a GSK3b inhibitor.

According to some embodiments of the invention, wherein when the iPSC is a human iPSC, the method further comprising:

(c) culturing the human iPSC in a culture medium which comprises LIF, an ERK1/2 inhibitor, a GSK3b inhibitor, a P38 inhibitor, a JNK inhibitor, basic fibroblast growth factor (bFGF) and transforming growth factor-beta 1 (TGFβ1).

According to some embodiments of the invention, step (c) is performed following about 48 hours from the beginning of expression as recited in step (a).

According to some embodiments of the invention, the medium further comprises a ROCK inhibitor.

According to some embodiments of the invention, expressing is performed using DNA transfection of the growth factors.

According to some embodiments of the invention, expressing is performed using RNA transfection of the growth factors.

According to some embodiments of the invention, expressing is performed using protein transfection of the growth factors.

It should be noted that protein transfection into cells and cell nuclei can be performed as described by Hongyan Zhou, Shili Wu, et al. "Generation of Induced Pluripotent Stem Cells Using Recombinant Proteins". Cell Stem Cell—5 Jun. 2009, Vol. 4, Issue 6, pp. 581; which is incorporated herein by reference in its entirety, essentially by conjugating signal peptides which direct the recombinant factors into the cell or cell nucleus.

According to an aspect of some embodiments of the invention, there is provided an isolated naive pluripotent stem cell obtainable by the method of some embodiments of the invention.

According to some embodiments of the invention, the naive pluripotent stem cell comprising:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene, and/or an expression level of transcription factor E3 (TFE3) characterized by a nucleus to cytoplasm expression ratio which is equal to or higher than 1 as determined by an immunostaining assay.

According to an aspect of some embodiments of the invention there is provided a method of generating differentiated cells, comprising subjecting the naive pluripotent stem cells generated according to the method of some embodiments of the invention to differentiating conditions, thereby generating the differentiated cells.

According to some embodiments of the invention, the naive PSCs of some embodiments of the invention can be used to isolate lineage specific cells.

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, yachts, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

Lineage specific cells can be obtained by directly inducing the expanded, undifferentiated naive PSCs to culturing conditions suitable for the differentiation of specific cell lineage.

Following is a non-limiting description of a number of procedures and approaches for inducing differentiation of EBs to lineage specific cells.

Neural Precursor Cells

To differentiate the EBs of some embodiments of the invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (Its medium, Okabe, S. et al., 1996, Mech. Dev. 59: 89-102). The resultant neural precursors can be further transplanted to generate neural cells in vivo (Bristle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

Oligodendrocytes and Myelinate Cells

EBs of some embodiments of the invention can differentiate to oligodendrocytes and myelinate cells by culturing the cells in modified SATO medium, i.e., DMEM with bovine serum albumin (BSA), pyruvate, progesterone, putrescine, thyroxine, triiodothyronine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

Mast Cells

For mast cell differentiation, two-week-old EBs of some embodiments of the invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

Hemato-Lymphoid Cells

To generate hemato-lymphoid cells from the EBs of some embodiments of the invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F. Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that since EBs are complex structures, differentiation of EBs into specific differentiated cells, tissue or organ may require isolation of lineage specific cells from the EBs.

Such isolation may be effected by sorting of cells of the EBs via fluorescence activated cell sorter (FACS) or mechanical separation of cells, tissues and/or tissue-like structures contained within the EBs.

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884x) available from PharMingen (PharMingen, Becton Dickinson Bio Sciences, San Jose, Calif., USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, Calif.), and glycophorin A-PE (IgG1), available from Immunotech (Miami, Fla.). Live cells (i.e., without fixation) are analyzed on a FACScan (Becton Dickinson Bio Sciences) by using propidium iodide to exclude dead cells with either the PC-LYSIS or the CELLQUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

An example for mechanical isolation of beating cardiomyocytes from EBs is disclosed in U.S. Pat. Appl. No. 20030022367 to Xu et al. Briefly, four-day-old EBs of some embodiments of the invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages [reviewed in Fijnvandraat A C, et al., Cardiovasc Res. 2003; 58: 303-12; Sachinidis A, et al., Cardiovasc Res. 2003; 58: 278-91; Stpyridis M P and Smith A G, 2003; Biochem Soc Trans. 31(Pt 1): 45-9].

In addition to the lineage-specific primary cultures, EBs of the invention can be used to generate lineage-specific cell lines which are capable of unlimited expansion in culture.

Cell lines of some embodiments of the invention can be produced by immortalizing the EB-derived cells by methods known in the art, including, for example, expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12).

Following are non-limiting examples of culturing conditions which are suitable for differentiating and/or expanding lineage specific cells from the naive PSCs of some embodiments of the invention. It should be noted that for inducing differentiation of the naive PSCs into differentiated cells, the medium which was used to maintain the cells in the naive undifferentiated and pluripotent state should be replaced with the appropriate differentiation medium.

Mesenchymal stromal cells which are CD73-positive and SSEA-4-negative can be generated from naive PSCs by mechanically increasing the fraction of fibroblast-like differentiated cells formed in cultures of naive hPSCs, essentially as described in Trivedi P and Hematti P. Exp Hematol. 2008, 36(3):350-9. Briefly, to induce differentiation of hESC the intervals between medium changes are increased to 3-5 days, and the cells at the periphery of the naive PSCs colonies become spindle-shaped fibroblast-looking cells. After 9-10 days under these conditions when about 40-50% of the cells in the culture acquire the fibroblast-looking appearance, the undifferentiated portions of naive PSCs colonies are physically removed and the remaining differentiated cells are passaged to new culture plates under the same conditions.

To induce differentiation of naive hPSCs into dopaminergic (DA) neurons, the cells can be co-cultured with the mouse stromal cell lines PA6 or MS5, or can be cultured with a combination of stromal cell-derived factor 1 (SDF-1/CXCL12), pleiotrophin (PTN), insulin-like growth factor 2 (IGF2) and ephrin B1 (EFNB1) essentially as described in Vazin T, et al., PLoS One. 2009 Aug. 12; 4(8):e6606; and in Elkabetz Y., et al., Genes Dev. 2008 Jan. 15; 22: 152-165.

To generate mesencephalic dopamine (mesDA) neurons, naive hPSCs can be genetically modified to express the transcription factor Lmx1a (e.g., using a lentiviral vector with the PGK promoter and Lmx1a) essentially as described in Friling S., et al., Proc Natl Acad Sci USA. 2009, 106: 7613-7618.

To generate lung epithelium (type II pneumocytes) from naive hPSCs, the naive PSCs can be cultured in the presence of a commercially available cell culture medium (Small Airway Growth Medium; Cambrex, College Park, Md.), or alternatively, in the presence of a conditioned medium collected from a pneumocyte cell line (e.g., the A549 human lung adenocarcinoma cell line) as described in Rippon H J., et al., Proc Am Thorac Soc. 2008; 5: 717-722.

To induce differentiation of naive hPSCs cells into neural cells, the pluripotent stem cells can be cultured for about 5 days in the presence of a serum replacement medium supplemented with TGF-b inhibitor (SB431542, Tocris; e.g., 10 nM) and Noggin (R&D; e.g., 500 ng/ml), following which the cells are cultured with increasing amounts (e.g., 25%, 50%, 75%, changed every two days) of N2 medium (Li X J., et al., Nat. Biotechnol. 2005, 23:215-21) in the presence of 500 ng/mL Noggin, essentially as described in Chambers S M., et al., Nat. Biotechnol. 2009, 27: 275-280.

The invention, according to some embodiments thereof, contemplates the use of cells, tissues and organs generated from the naive pluripotent stem cells of the invention using any differentiation protocol known in the art.

It will be appreciated that since the lineage-specific cells or cell lines obtained according to the teachings of some embodiments of the invention are developed by differentiation processes similar to those naturally occurring in the human embryo they can be further used for human cell-based therapy and tissue regeneration.

Thus, the invention according to some embodiments thereof envisages the use of the expanded and/or differentiated lineage-specific cells or cell lines of some embodiments of the invention for treating a disorder requiring cell replacement therapy.

For example, diseases presently expected to be treatable by therapeutic transplantation of PSC or PSC-derived cells include Parkinson's disease, cardiac infarcts, juvenile-onset diabetes mellitus, and leukemia (Gearhart J. Science 1998, 282:1061; Rossant and Nagy, Nature Biotech. 1999, 17:23).

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], PSC-derived cells are preferably manipulated to over-express the mutated gene prior to their administration to the individual. It will be appreciated that for other disorders, the PSC-derived cells should be manipulated to exclude certain genes.

Over-expression or exclusion of genes can be effected using knock-in and/or knock-out constructs [see for example, Fukushige, S, and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

In addition to cell replacement therapy, the lineage specific cells of some embodiments of the invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of some embodiments of the invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

According to an aspect of some embodiments of the invention, there is provided a method of generating a primordial germ cell, comprising culturing primate naive pluripotent stem cells in a culture medium selected capable of inducing the primate naive pluripotent stem cells into primordial germ cell, wherein the culture medium comprises a Rho kinase (ROCK) inhibitor and bone morphogenetic protein 4 (BMP4), thereby generating the primordial germ cell.

According to some embodiments of the invention, the primate naive pluripotent stem cell comprises:

an unmethylated X-inactive specific transcript (XIST) gene, wherein:

(i) when the naive PSC is a female PSC, then the naive female PSC has two unmethylated alleles of the XIST gene; and (ii) when the naive PSC is a male PSC, then the naive male PSC has an unmethylated allele of the XIST gene,
and/or an expression level of transcription factor E3 (TFE3) characterized by a nucleus to cytoplasm expression ratio which is equal to or higher than 1 as determined by an immunostaining assay.

According to some embodiments of the invention, the primordial germ cell is characterized by CD61 (intergrin beta 3) positive expression pattern.

According to some embodiments of the invention, the primordial germ cell is characterized by $CD61^+/SSEA4^+$ expression pattern (expression signature).

According to some embodiments of the invention, the culture medium selected capable of inducing the primate naive pluripotent stem cells into primordial germ cell further comprises at least one agent selected from the group consisting of: leukemia inhibitory factor (LIF), Stem Cell Factor (SCF) and Epidermal Growth Factor (EGF).

According to an aspect of some embodiments of the invention, there is provided an isolated population of primate primordial germ cells comprising primate primordial germ cells generated according to the method of some embodiments of the invention.

According to some embodiments of the invention, the isolated population of primate primordial germ cells comprising at least about 50%, e.g., at least about 60%, e.g., at least about 70%, e.g., at least about 80%, e.g., at least about 90%, e.g., at least about 95%, e.g., at least about 99%, e.g., 100% of primordial germ cells characterized by $CD61^+/SSEA4^+$ expression pattern.

It should be noted that the isolated primordial germ cells (PGCs) of some embodiments of the invention can be injected into adult human testis or ovary to complete their maturation and generate sperm or eggs.

According to an aspect of some embodiments of the invention, there is provided a method of treating a subject in need thereof, comprising administering the primordial germ cells of some embodiments of the invention to a gonad tissue of the subject, thereby treating the subject in need thereof.

The term "subject" refers to a mammal, e.g., a primate, preferably a human being at any age which suffer from the pathology.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to some embodiments of the invention, the subject suffers from infertility.

According to an aspect of some embodiments of the invention, there is provided a kit comprising the primate primordial germ cells of some embodiments of the invention and a medicament for treating infertility.

The kit may also include appropriate buffers and preservatives for improving the shelf-life of the kit.

The kit may include appropriate instructions for use and labels indicating FDA approval for use in treating a subject, such as treating infertility in the subject.

As shown in FIGS. 26A-C, 108A-C and 109A-E and described in Examples 8 of the Examples section which follows, the present inventors were capable of using the isolated naïve PSC of some embodiments of the invention for generation of a chimeric human-mouse organism, and to contribute to development of mouse embryo in vivo (Gafni et al. Nature 2013; December 12; 504(7479):282-6. doi: 10.1038/nature12745. Epub 2013 Oct. 30). Thus, 24 hours and later after administration of the human PSC, the injected cells were viable in the developing early mouse embryos. These results indicate that human naive cells grown in the medium of some embodiments of the invention (e.g., WIS-NHSM conditions) can contribute to cross-species chimeric organisms.

Thus, according to an aspect of some embodiments of the invention, there is provided a method of generating a chimeric animal. The method comprising introducing the isolated primate (e.g., human) naive PSC of some embodiments of the invention, or the primordial germ cells of some embodiments of the invention into a pre-implantation embryo of a host animal, thereby generating the chimeric animal.

According to some embodiments of the invention, the method further comprising allowing the chimeric animal to grow in vivo or ex vivo.

It should be noted that since the isolated naïve pluripotent stem cells or the primordial germ cells are introduced into the pre-implantation embryo they are likely to form a normal embryo.

As used herein, the phrase "chimeric animal" refers to an animal comprising cells of at least two genetically distinct individuals.

As used herein, the term "pre-implantation embryo" refers to an embryo at an 8-cell stage, 16-cell stage embryo, early morula, late morula, early blastocyst, and/or a late blastocyst.

It is noted that the chimeric animal can be composed of cells of two different individuals belonging to two different species, or to the same species.

According to some embodiments of the invention, the isolated naive PSC or the primordial germ cell is allogeneic to the host animal.

As used herein, the term "alloegeneic" refers to at least two genetically different individuals of the same species.

According to some embodiments of the invention, the isolated naive PSC or the primordial germ cell is xenogeneic to the host animal.

As used herein, the term "xenogeneic" refers to at least two individuals of different species.

According to some embodiments of the invention, the host animal is not human.

According to some embodiments of the invention, introducing the cells is performed in vivo.

Methods of in vivo administration of cells into a morula of an animal are well known in the art, such as in Gafni O, Weinberger L, Mansour A A, Manor Y S, Chomsky E, Ben-Yosef D, Kalma Y, Viukov S, Maza I, Zviran A, Rais Y, Shipony Z, Mukamel Z, Krupalnik V, Zerbib M, Geula S, Caspi I, Schneir D, Shwartz T, Gilad S, Amann-Zalcenstein D, Benjamin S, Amit I, Tanay A, Massarwa R, Novershtern N, Hanna J H. Nature. 2013 Dec. 12; 504(7479):282-6. doi: 10.1038/nature12745. Epub 2013 Oct. 30; and *Manipulating the Mouse Embryo*: A Laboratory Manual, Fourth Edition. By Richard Behringer; Marina Gertsenstein; Kristina Vintersten Nagy; Andras Nagy, each of which is fully incorporated herein by reference.

According to some embodiments of the invention, introducing the cells is performed in vitro or ex vivo via direct injection or aggregation with the developing host embryo.

According to some embodiments of the invention, the morula comprises at least 4 cells.

According to some embodiments of the invention, the morula comprises no more than 128 cells.

According to some embodiments of the invention, the host animal is a primate, e.g., a mammal.

According to some embodiments of the invention, the host animal is mouse.

According to some embodiments of the invention, the host animal is pig.

According to some embodiments of the invention, the host animal is monkey.

According to some embodiments of the invention, the host animal is chimpanzee.

It should be noted that once the chimeric animal is formed, and allowed to grow, the cells of the chimeric animal can be used for cell therapy. For example, the mature differentiated cells (e.g., hematopoietic stem cells, liver hepatocytes, insulin producing Beta cells) generated in the chimeric animal based on some embodiments of the invention can be used for transplantation in adult humans or for biomedical applications.

Thus, according to an aspect of some embodiments of the invention, there is provided a method of isolating differentiated cells, cell lineages, tissues or organs from the chimeric animal of some embodiments of the invention.

Methods of isolating such differentiated cells, tissues or organs are well known in the art and are also described hereinabove.

Thus, in case the naive PSCs that were used to form the chimeric animal are human cells, these cells can be further isolated from the formed chimeric animal and used for treating a human subject.

According to some embodiments of the invention, the method further comprises isolating human-derived (human-originated) cells or tissues from the chimeric animal.

Non-limiting examples of using such human-originated cells, tissues or organs include cell based therapy, tissue replacement, organ or tissue implantation.

Following is a non-limiting description of expression vectors and modes of administering thereof into cells which can be used to express a polypeptide-of-interest (e.g., any of the proteins described hereinabove, e.g., OCT4, c-MYC, SOX2, KLF4, LIF, bFGF, TGFβ1) in a cell.

To express an exogenous protein in mammalian cells, a polynucleotide sequence encoding the polypeptide-of-interest is preferably ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a the protein-of-interest can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMT010/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

Recombinant viral vectors are useful for in vivo expression of the protein-of-interest since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the polypeptide-of-interest of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the protein-of-interest and the heterologous protein, the protein-of-interest can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

Transformed cells are cultured under effective conditions, which allow for the expression of high amounts of the recombinant polypeptide-of-interest (e.g., the LIF, TGFβ1, bFGF, OCT4, c-myc, SOX2, KLF-4). Following a predetermined time in culture, recovery of the recombinant polypeptide is effected. The phrase "recovery of the recombinant polypeptide" used herein refers to collecting the whole fermentation medium containing the polypeptide and need not imply additional steps of separation or purification.

Thus, polypeptide-of-interest can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The polypeptide-of-interest is preferably retrieved in "substantially pure" form. As used herein, the phrase "substantially pure" refers to a purity that allows for the effective use of the polypeptide-of-interest (e.g., the LIF, TGFβ1, bFGF) in maintaining the human embryonic stem cells in an undifferentiated state while in culture.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND EXPERIMENTAL METHODS

Mouse stem cell lines and cell culture—Reprogramming and maintenance of murine naive pluripotent cells were conducted in serum-free chemically defined N2B27-based media: 240 ml DMEM/F12 (Biological Industries—custom made), 240 ml Neurobasal (Invitrogen; 21103), 5 ml N2 supplement (Invitrogen; 17502048), 5 ml B27 supplement (Invitrogen; 17504044), 15% knockout serum replacement (Invitrogen—10828), 1 mM glutamine (Invitrogen), 1% nonessential amino acids (Invitrogen), 0.1 mM β-mercaptoethanol (Sigma), penicillin-streptomycin (Invitrogen), 5 mg/ml BSA (Sigma). Naive conditions for murine PSCs included 10 ng/ml recombinant human LIF (Millipore; LIF1005) (5 µg per 500 ml). Where indicated "2i" inhibitors the following agents were added: small-molecule inhibitors CHIR99021 (CH, 3 µM-Axon Medchem) and PD0325901 (PD, 1 µM—TOCRIS). The "2i" was added 48 hours after OSKM induction.

"Primed N2B27 media" for murine cells (EpiSCs) contained 8 ng/ml recombinant human bFGF (Peprotech Asia) and 20 ng/ml recombinant human Activin (Peprotech Asia).

Stem cell lines and mice deficient for Mbd3 and their derived ES lines were obtained as previously described (Kaji et al., 2007) (Mbd3$^{flox/flox}$, Mbd3$^{flox/-}$ and Mbd3$^{+/-}$) (Kaji et al., 2006). For additional gene targeting of mouse pluripotent stem cell lines (Nanog-GFP reporter, pBRY-Mbd3 rescue constructs, Rosa26-CreER) 50 μg DNA of the targeting construct was linearized and electroporated into the indicated pluripotent cell lines, that were then subjected to selection with G418 (300 microg/ml) or Puromycin (1 microg/ml). After 10 days of antibiotic selection, drug resistant clones were analyzed for correct targeting by PCR or Southern blot analysis.

Mbd3Utx$^{+/-}$ males and females for ESC derivation in defined mouse 2i/LIF conditions were mated and E3.5 blastocysts were harvested and explanted for ESC derivation in defined mouse 2i/LIF conditions on MEF coated plates.

NGFP1-Mbd3$^{KD}$ was established by infection and sub cloning of secondary NGFP1 iPSC line with a ShRNA pLKO-Tet-On vector (addgene) as previously described (Hanna, J. et al. Nature 462, 595-601, 2009). V6.5 mouse ESCs harboring a Flag-tagged endogenous Oct4 allele (FIG. 60C) were generated by direct gene targeting as previously described (Tsai, H. H., Bourque, G. & Lufkin, T. In silico tandem affinity purification refines an Oct4 interaction list. Stem cell research Ther. 2: 26, 2011). Mycoplasma detection test are weekly conducted, to ensure exclusion of any contaminated cells. Genotyping and functional validation of Mbd3 depletion are presented throughout the study (Examples in FIGS. 1I-J and FIGS. 8M-N).

Epigenetic reversion of mouse primed epiblast cells—Male naive V6.5 (Mbd3$^{+/+}$) Nanog-GFP ESCs (Mansour et al., 2012) cells maintained in 2i/LIF conditions, were injected into BDF2 blastocysts and Epiblast. Chimeric embryos were dissected at day E6.5 and explanted on gelatin/vitronectin-coated plates in N2B27 bFGF/Activin conditions supplemented with 1 μg/ml puromycin, allowing the isolation of Nanog-GFP EpiSCs. For epigenetic reversion of murine EpiSCs to naive pluripotency, cells were passaged into N2B27 2i/LIF conditions on vitronectin (1 μg/ml) and gelatin (0.2%) coated plates (without overexpression of exogenous reprogramming factors). When epigenetic reversion assay involved single cell plating, EpiSC growth medium was supplemented with ROCK inhibitor for 24 hours before trypsinization. siRNAs (ON-TARGETplus SMARTpools) and the control siRNA (ON-TARGETplus Non-targeting pool D-001810-10-05) were purchased from Dharmacon. 10 nM siRNA or control was used for each transfection with Lipofectamine RNAiMAX (Invitrogen).

For EG (mouse embryonic germ cells) derivation experiments, Oct4-GFP+ PGC (Primordial Germ Cells) cells were sorted from E8.5 dissected chimeric embryos and single plated in N2B27 15% KSR, LIF (20 ng/ml)/SCF (10 ng/ml)/ bFGF (8 ng/ml) medium and 2i (supplemented 48 hours later). Nuclear mCherry labeling of EpiSCs and their derived PGCs was used to allow calculating plating efficiency and calculate reprogramming efficiency (reprogramming efficiency %=Oct4 or Nanog-GFP clones/mCherry+ clones).

OKSM factors: Oct4 (SEQ ID NO:54 protein), Sox2 (SEQ ID NO:56 protein), c-Myc (SEQ ID NO:60 protein) and Klf4 (SEQ ID NO:58 protein).

Reprogramming of mouse somatic cells and cell infection—Virus-containing supernatants of the different reprogramming viruses (STEMCA-OKSM polycistronic vector (SEQ ID NO:62) (Dox inducible and constitutive expression) (Mansour et al., 2012), STEMCCA-OKS polycistronic vector (DOX inducible and constitutive expression), FUW-tetO-lox-hKLF4, FUW-tetO-lox-hOCT4 and FUW-tetO-lox-hSOX2, FUW-tetO-mKlf4, FUW-tetO-mOct4, FUW-tetO-mSox2, FUW-tetO-c-Myc, FUW-Oct4-2A-Sox2, FUW-Oct4-2A-Klf4, FUW-tetO-lox-SOX2, pMXs-OCT4, pMXs-SOX2, pMXs-KLF4, pMXs-cMYC) was supplemented with the FUW-lox-M2rtTA virus (when necessary) and an equal volume of fresh culture medium for infection. Mouse fibroblast and other somatic cells types were isolated and single cell sorted from secondary transgenic reprogrammable chimeras (Hanna et al., 2009a; Mansour et al., 2012). Secondary transgenic mouse somatic cells carrying DOX inducible OSKM encoding transgene (Hanna et al. Cell 2008, Mansour et al. Nature 2012) were reprogrammed by applying mouse naive ESCs medium+ Doxycycline (DOX) (without 2i in the first 48 hours and then adding also 2i until completion of process). Human iPSC reprogramming was applied by lentiviral infection of human differentiated cells with OSKM encoding lentivirus and applying WIS-NHSM conditions starting from 48 hours after infection.

iPSCs reprogramming by using mouse naive ESCs medium 2i/LIF+DOX (1 μg/ml) (without 2i in the first 48 hours) under physiological 5% O$_2$ conditions. Mbd3$^{-/-}$ MEF (but not pluripotent cells) experience accelerated senescence and proliferation capacity loss, and thus Mbd3$^{-/-}$ cells were reprogrammed by applying tamoxifen on Mbd3$^{flox/-}$ cells after 48 hours of OSKM induction. Similarly, for acute knockdown of Mbd3 in somatic cells with Mbd3 siRNAs in an attempt to boost reprogramming, transfection were conducted at least after 48 hours of OSKM induction. Alternatively, somatic cells with hypomorphic expression (rather than complete ablation) of Mbd3 do not demonstrate proliferation defects or accelerated senescence due to the residual Mbd3 expression levels, yet they retain sufficiently reduced Mbd3 levels that allow deterministic synchronized reprogramming by OSKM (FIG. 4B). Thus the following systems were preferably and predominantly used throughout this study: Mbd3$^{flox/-}$, NGFP1-Mbd3 or WIBR3-MB-D3$^{flox/flox}$ genetic backgrounds. Notably, in the reprogramming conditions used herein, single cell plating of MEFs yielded approximately 70% survival efficiency (with or without DOX). Thus for live imaging, upon plating 150 MEFs per well the present inventors observed formation of 100-120 colonies that were tracked in Mbd3$^{flox/-}$ samples. Importantly, constitutive mCherry allowed controlling for survival after plating to obtain accurate and unbiased reprogramming efficiencies (reprogramming efficiency %=Oct4 or Nanog-GFP clones (cells)/mCherry+ clones (cells)). Equivalent reprogramming efficiencies were obtained on mouse irradiated feeder cells or gelatin, matrigel or gelatin/vitronectin coated plates. Reprogramming on irradiated DR4 MEF cells was preferably used for live imaging and single cell reprogramming experiments in order to enhance cell survival and adherence. Mbd3 Stealth siRNAs mix that includes MSS-237238, MSS-275658 and MSS-275659 components (Invitrogen), and Chd4 Stealth siRNAs mix that includes MSS-200894, MSS-200895 and MSS-200896 (Invitrogen) were used for efficient knockdown in mouse cells. Transfections were conducted with RNAiMAX (Invitrogen) according to manufacturer instructions.

DNA plasmids and TALEN gene editing—The following lentiviral and mammalian constitutive over-expression vectors were used in somatic and pluripotent cells: pBRY-Mbd3-Ires-Zeocin. Constitutively expressed lenti-viruses FUW-Mbd2 and FUW-Mbd3 were generated by insert cloning into EcoRI sites of FUW vector to generate constitutive expression following viral transduction and stable integration in somatic or PSC lines.

Flag-Mbd3 mutations and deletions were done by PCR with Q5 DNA polymerase (NEB). TALEN expressing plasmids were designed with a help of TALEN targeter 2.0 [talent (dot) cac (dot) cornell (dot) edu/] and cloned using GoldenGate TALEN kit 2.0 purchased from Addgene (Bedell, V M, et al. Nature 491: 114-8, 2012) according to the published protocol. For targeting G the present inventors have used N,N-type repeat. Donor construct was made with DNA fragments amplified from WIBR3 HUMAN ESC genomic DNA. $10^7$ ESCS were electroporated with 30 µg of donor plasmid and 10 µg of each of the TALEN expressing plasmids and grown in the presence of G418 (75 µg/ml) and 0iclovir (1 µM). Resistant clones were isolated and genomic DNA was extracted for Southern Blot and PCR analysis. For generating OCT4-GFP reporter subcloned cell lines, $10^7$ MBD3$^{+/+}$ and MBD3$^{flox/-}$ iPSCs were electroporated with 30 µg of previously described OCT4-GFP-2A-PURO knock-in donor plasmid (Hockemeyer, D. et al. Nat Biotechnol 29, 731-734, 2011; kindly provided by Prof. Jaenisch through Addgene) and 10 µg of each of the TALEN expressing plasmids and grown in the presence of Puromycin (0.4 µg/ml). Resistant clones were isolated and genomic DNA was extracted for Southern Blot and PCR analysis. In vitro differentiated fibroblasts from human ESCs/iPSCs were generated as previously described (Hockemeyer, D. et al. Cell Stem Cell 3, 346-353, 2008).

Reprogramming of human somatic cells and cell infection—Reprogramming was conducted at 5% $pO_2$ in DOX (1-2 µg/ml) supplemented conditions: 1) First 48 hours cells were incubated in conventional human ES medium (hESM—see below). 2) After 48 hours, cells were transferred until day 7-8 to naive defined growth conditions termed WIS-NHSM (see below) and supplemented with ROCKi (5 mM final concentration). 3) After 8 days DOX was withdrawn and cells were expanded in WIS-NHSM conditions. MBD3 Stealth siRNAs that includes HSS147580, HSS147581 components (Cat. #1299003) were used for efficient MBD3 knockdown in human cells. Transfections were conducted with RNAiMAX (Invitrogen) according to manufacturer instructions.

Conventional human ES conditions (hESM) include: 475 ml Knockout DMEM (Invitrogen 10829), 15% KSR (Invitrogen), 8 ng/ml recombinant bFGF (Peprotech) and 1 ng/ml recombinant TGFβ1 (Peprotech), 1 mM glutamine (Invitrogen), 1% nonessential amino acids (Invitrogen), 0.1 mM β-mercaptoethanol (Sigma), Penicillin-Streptomycin (Invitrogen).

The following serum free defined conditions, termed "WIS-NHSM" (Weizmann Institute of Science Naive human Stem cell Medium) were used to isolate, generate, derive and stabilize naive human pluripotent stem cells (PSCs and ESCs). WIS-NHSM media was generated by including: 475 ml Knockout DMEM (Invitrogen 10829), 15% KSR (Invitrogen) or 5 gr AlbuMAX (Invitrogen 11020-021), 5 ml N2 supplement (Invitrogen 17502048), 10 µg of recombinant human LIF (Peprotech), 8 ng/ml recombinant bFGF (Peprotech), 1 ng/ml recombinant TGFβ1 (Peprotech), 1 mM glutamine (Invitrogen), 1% nonessential amino acids (Invitrogen), 0.1 mM β-mercaptoethanol (Sigma), Penicillin-Streptomycin (Invitrogen) and small molecule inhibitors: PD0325901 (1 µM, ERK1/2i, AXON MEDCHEM); CHIR99021 (3 µM, GSK3βi, AXON MEDCHEM); SB203580 (5 µM, p38i, TOCRIS); SP600125 (10 µM, JNKi, TOCRIS). Throughout the study Naive hESCs/ hiPSCs were grown on 0.2% gelatin+1 ng/ml vitronectin coated plates for at least 1 hour in 37° C. Cells were passage by single cell trypsinization (0.25% or 0.05% Trysin+EDTA) every 3-4 days. Although not essential, enhanced single cell cloning efficiency can be obtained with WIS-NHSM supplementation with ROCK pathway inhibitor Y-27632 (5 µM, ROCKi Axon Medchem) for 24 hours before and after cell passaging.

Immunofluorescence staining of pre- and post-implantation embryos—For pre-implantation, oocytes and one-cell embryos were collected from the oviducts of hormone-primed B6D2F1 mice, and cultured in KSOM (Millipore) until desired stage. Immunostaining was performed as described previously with modifications (Silva, J. et al. Cell 138, 722-737, 2009). Briefly, The zona pellucida was removed using acid Tyrode's solution (Sigma). Embryos were transferred to watch-glass dish (Genenet), fixed for 15 minutes in 4% PFA in phosphate buffer (PB), rinsed three times in PBS containing 3 mg/ml PVP, permeabilized in PBS/PVP with 1% triton X-100 for 30 minutes, and blocked in blocking solution (2% normal donkey serum, 0.05% BSA, 0.01% Tween in PBS) for 1 hour. Embryos were then incubated overnight at 4° C. in primary antibodies diluted in blocking solution, washed three times in blocking solution for 15 minutes each, incubated with secondary antibodies for 1 hour at room temperature, counterstained with DAPI for 15 minutes, washed twice in PBS, and mounted in 96 well glass bottom plates for confocal imaging. Post-implantation embryos were fixed and embedded in paraffin as described previously (Acampora, D., et al. Development. 1997; 124:3639-50) with modification. Embryos in the maternal decidua, were fixed in 4% PFA/PB overnight at 4° C., washed 3 times in PBS for 30 minutes each, dehydrated and embedded in paraffin using standard procedure. Embryonic Paraffin sections (5-7 µm) were rehydrated, treated with antigen retrieval, rinsed in PBS, permeabilized in 0.1% Triton/PBS for 10 minutes, rinsed in PBT (0.02% Tween/PBS), and blocked in blocking solution (5% normal donkey serum, 0.05% BSA, in PBT) for 1 hour. Slides were then incubated in the appropriate primary and secondary antibodies diluted in blocking solution as described above, and processed as described previously (Mansour, A A, et al. Nature 488, 409-413, 2012). The following antibodies were used: mouse anti-Oct4 (1:100, C-10; Santa Cruz S.C.—5279), goat anti-Mbd3 (1:50, C-18; Santa Cruz S.C.—9402).

Immunoprecipitation and immunoblotting analyses—HEK293T cells were transfected with each cDNA clones in an expression vector using jetPEI (Polyplus transfection) and were lysed 48 hours later in lysis buffer (50 mM Tris-HCl pH 7.4, 150 mM NaCl, 1% Triton, 0.1% NP40 and 1.5 mM EDTA). The following plasmids were used for transfections in different combinations: pCaggs-Mbd3, FUW-Oct4, FUW-Klf4, FUW-Sox2, FUW-c-Myc, FUW-Nanog, pCaggs-Flag-Mbd3, pMSCV-Flag-OCT4, pMSCV-Flag-SOX2, pMSCV-Flag-KLF4, pCaggs-Flag-c-Myc, pCaggs-Flag-Nanog, pcDNA3.1-Flag-HDAC1 (obtained through addgene). 30 µl of anti-FlagM2 Magnetic beads (Sigma) were incubated for 6 hours in cell lysate fractions, for IgG control 6 µg of IgG and 50 µl of protein-G Dynabeads (Invitrogen) were added to the cell lysate for 6 hours. Both fractions (the anti-flag and anti-IgG) were loaded on Invitrogen magnetic separator and the beads were washed six times with lysis buffer. The binding proteins were eluted with 0.5 µg/ml of X3Flag peptide (sigma) buffer for the anti-flagM2 beads or by boiling with sample buffer and analyzed by SDS-polyacrylamide gel electrophoresis and immunoblotting. The immunoblot analyses were performed using the following primary antibodies: anti-Flag (clone M2, F3165, Sigma), anti-Mbd3 (A300-258A, Bethyl), anti-Nanog (A300-397A, Bethyl), anti-OCT4 (sc-9081, H134, Santa Cruz), anti-KLF4 (sc20691,H180, Santa Cruz), anti-SOX2 (#2748s, Cell signaling), anti-c-Myc (#9402s, Cell signaling)

Primordial germ cell (PGC) isolation differentiation—For EG derivation experiments, Oct4-GFP+ cells were sorted from E8.5 dissected chimeric embryos and single plated in N2B27 2i/LIF/SCF (10 ng/ml)/bFGF (8 ng/ml) medium.

RT-PCR analysis—Total RNA was isolated using the RNeasy Kit (Qiagen). Three µg of total RNA was treated with DNase I to remove potential contamination of genomic DNA using a DNA Free RNA kit (Zymo Research). 1 µg of DNase-1-treated RNA was reverse transcribed using a First Strand Synthesis kit (Invitrogen) and ultimately re-suspended in 100 µl of water. Quantitative PCR analysis was performed in triplicate using 1/50 of the reverse transcription reaction in an Viia7 platform (Applied Biosystems). Error bars indicate standard deviation of triplicate measurements for each measurement.

For single cell RT-PCR analysis, single cells from different samples were single cell sorted, and Ambion® Single Cell-to-CT™ Kit was used for sample processing according to Manufacturer Instructions. TaqMan probe based chemistry and TaqMan Real-Time PCR master mix were used on Viia7 platform for gene expression detection. The following TaqMan (Invitrogen) probes were used: Sal14 Mm00453037_s1, Esrrb Mm00442411_m1, Utf1 Mm00447703_g1; Sox2 (endogenous mouse allele specific) Mm03053810_s1; Nanog Mm02384862_g1; Gapdh Mm99999915_g1. $C_T$ cutoff of 39 cycles was used as threshold for defining transcript detection.

Knock down of human mbd3 by siRNA—The present inventors used for human cells siRNA the "Stealth" from Invitrogen, with the following catalogue numbers: Cat. No/Lot—10620318/168750 F02 "MBD3HSS147581" (3_RNAI) for -AGGUCAAGGGCAAGCCCGACCUGAA (SEQ ID NO:52), and Cat. No/Lot—10620319/168750 F03 "MBD3HSS147581" (3_RNAI) for -UUCAGGUCGGGC-UUGCCCUUGACCU (SEQ ID NO:53).

Knock down of mouse mbd3 by shRNA—For mouse cells the present inventors used the pLKO.1 lentiviral or the pLKO-Tet-On systems with the following sequences: "TRCN0000039069 F"—CCG GCT AAG TGG ATT GAG TGC CTT TCT CGA GAA AGG CAC TCA ATC CAC TTA GTT TTT G (SEQ ID NO:63) and the "TRCN0000039069 R"—AAT TCA AAA ACT AAG TGG ATT GAG TGC CTT TCT CGA GAA AGG CAC TCA ATC CAC TTA G (SEQ ID NO:64); or the "TRCN0000039071 F|—CCG GGC GCT ATG ATT CTT CCA ACC ACT CGA GTG GTT GGA AGA ATC ATA GCG CTT TTT G (SEQ ID NO:65) and the "TRCN0000039071 R"—AAT TCA AAA AGC GCT ATG ATT CTT CCA ACC ACT CGA GTG GTT GGA AGA ATC ATA GCG C (SEQ ID NO:66).

Microscopy image acquisition and analysis—Secondary OKSM inducible Mbd3$^{+/+}$ and Mbd3$^{flox/-}$ MEFs carrying Oct4-GFP pluripotency reporter and constitutively expressed nuclear mCherry marker, were plated in 12-well plates at low densities (150 cells per well) and imaged using AxioObserver Z1 (Zeiss) in %5 $O_2$, %5 $CO_2$, 37° C. controlled conditions. Plates were taken out at day 3-4 for media replacement (but without passaging/splitting) and put back for the automated live imaging stage. Full well mosaic images were taken every 12 hours for 6 days at 5× magnification, including phase contrast and two fluorescent wavelength images. In house automated segmentation protocol was developed and implemented in Matlab to analyze time-lapse measurements of full well mosaics with fluorescent mCherry and Oct4-GFP markers.

The challenge in this protocol was to implement fast segmentation of unknown number of colonies in $10^8$ pixels mosaic image. Main protocol steps (as shown in FIGS. 40A-E) include:

Adaptive Detection: Erasing the plate margins with circular filter. Defining detection threshold using median with offset (10% of the dynamic_range), and creating a binary image of detected pixels. These steps were carried out separately for each time-point and each fluorescent wavelength.

Complexity Reduction: For this task the present inventors applied a morphological filter to isolate mCherry colonies using median sliding filter (60 [µm]*60 [µm]) (Arce, G. R. Nonlinear Signal Processing: A Statistical Approach—Gonzalo R. Arce—Google Books, 2005). This filter retains only dense colonies, erasing noise and single isolated cells (a single nucleus is approximately 6 [µm]*6 [µm]), this step is crucial for reducing the dimension of the clustering task.

Colony Segmentation: The segmentation was done using Moving average filter (Low-pass filter) (60 [um]*60 [um]) (Arce, G. R. Nonlinear Signal Processing: A Statistical Approach—Gonzalo R. Arce—Google Books, 2005) to merge adjacent colony fragments into large connected colonies and then apply connected components clustering, labeling connected objects using 8-connected neighborhood.

Colony Feature Extraction: Extracting the features of each mCherry colony including area, bounding box and centroid. By overlay mCherry colony segmentation on the GFP binary image (detected pixels) the present inventors extract for each colony the GFP$^+$ indicator (0/1) and the fraction of GFP$^+$ and mCherry$^+$ pixels out of all mCherry$^+$ pixels.

This segmentation protocol was run over time-lapse mosaics collecting information on colony formation dynamics, colony GFP dynamics and ratios of offspring Oct4-GFP$^+$ cells. Colony and reprogramming dynamics features were then statistically analyzed using Matlab program, including estimation of the cumulative distribution, density function and box-plot graphical interpretation (FIGS. 42A-E). The box-plot analysis characterizes the distribution of intra-colony Oct4-GFP reactivation for all single colonies segmented, representing the distribution of offspring iPS cells within segmented colonies. In addition, movies characterizing the process dynamics were produced using customized Matlab program. The above program was validated by artificial input matrix and by collected ES mosaic image collection. In addition, robustness of detection threshold and filter sizes were measured with varying parameters (data not shown).

Chromatin Immuno-precipitation and Sequencing Library Preparation (for Examples 1-4 hereinbelow)—Chromatin Immuno-precipitation followed by deep sequencing (ChIP-Seq) was measured for the following proteins—H3K4me3, H3K27me3, H3K27ac and Mbd3—in 4 different time points throughout reprogramming: 0 (MEF), 4 days, 8 days, iPS. The binding of each protein was measured in both Mbd3$^{+/+}$ and Mbd3$^{flox/-}$ conditions, as well as in Mbd3$^{-/-}$ ES cells. Oct4 was measured in all the above conditions, excluding 8 day. Approximately 40*10$^6$ cells were cross-linked in formaldehyde (1% final concentration, 10 minutes at room temperature (RT)), and then quenched with glycine (5 minutes at RT). Fixed cells were lysed in 50 mM HEPES KOH pH 7.5, 140 mM NaCl, 1 mM EDTA, 10% Glycerol, 0.5% NP-40 alternative, 0.25% Triton supplemented with protease inhibitor at 4° C. (Roche, 04693159001), centrifuged at 950×g for 10 minutes and re-suspended in 0.2% SDS, 10 mM EDTA, 140 mM NaCl and 10 mM Tris-HCL. Cells were then fragmented with a Branson Sonifier (model S-450D) at −4° C. to size ranges between 200 and 800 bp, and precipitated by centrifugation. 10 μg of each antibody was pre-bound by incubating with Protein-G Dynabeads (Invitrogen100-07D) in blocking buffer (PBS supplemented with 0.5% TWEEN and 0.5% BSA) for 2 hours at room temperature. Washed beads were added to the chromatin lysate, and then incubated overnight. Samples were washed 5 times with RIPA buffer, twice with RIPA buffer supplemented with 500 mM NaCl, twice with LiCl buffer (10 mM TE, 250 mM LiCl, 0.5% NP-40, 0.5% DOC), once with TE (10 mM Tris-HCl pH 8.0, 1 mM EDTA), and then eluted in 0.5% SDS, 300 mM NaCl, 5 mM EDTA, 10 mM Tris Hcl pH 8.0 at 65° C. Eluate was incubated in 65° C. for 8 hours, and then treated sequentially with RNaseA (Roche, 11119915001) for 30 minutes and Proteinase K (NEB, P8102S) for two hours. DNA was purified with The Agencourt AMPure XP system (Beckman Coulter Genomics, A63881). Libraries of cross reversed ChIP DNA samples were prepared according to a modified version of the Illumina Genomic DNA protocol, as described previously[75] (Blecher-Gonen, R., et al. Nat. Protoc. 2013, 8: 539-54). Briefly, ChIP DNA was ligated to Illumina adaptors and subjected to 14 cycles of PCR amplification. Amplified products between 200 and 800 bp were purified on a 2% agarose gel. Roughly 5 picomoles of DNA library was then applied to each lane of the flow cell and sequenced on Illumina Hiseq2000 sequencer according to standard Illumina protocols. The following antibodies were used for chromatin-IP experiments: Control IgG (ChIP grade, ab46540, Abcam), Anti-Histone H3 trimethyl K4 (ChIP grade, ab8580, Abcam), Anti-Histone H3 acetyl K27 (ChIP grade, ab4729, Abcam), anti-Histone H3 trimethyl K27 (ChIP grade, 07-449, Millipore), anti-Oct4 (sc5729 (C-10), Santa Cruz), anti-Chd4 (ChIP Grade, ab70469, Abcam). For Mbd3 chip 1:1 antibody mix was used: anti-Mbd3 (Bethyl laboratories A302-528\9A) and anti-Mbd3 (ab16057, Abcam).

Alignment and Peak Detection—The present inventors used bowtie software (Langmead, B., Trapnell, C., Pop, M. & Salzberg, S. L. Ultrafast and memory-efficient alignment of short DNA sequences to the human genome. Genome Biol. (2009)) version 0.12.5 to align reads to mouse mm9 reference genome (UCSC, July 2007). The present inventors only considered reads that were uniquely aligned to the genome with up to a single mismatch, taking the single best match of each read. The present inventors identified enriched intervals of H3K4me3, H3K27me3, H3K27ac, Mbd3 and Oct4 using MACS version 1.4.1 (Zhang, Y., et al. Genome Biol. 2008, 9(9):R137). The present inventors used sequencing of whole cell extract as control in order to define a background model. Duplicate reads aligned to the exact same location are excluded by MACS default configuration. Enriched intervals were mapped to genes if they overlapped a single Kb symmetric interval around their Transcription Start Sites (Taken from RefSeq known gene table in UCSC genome browser). ChIP-seq data on wild-type samples were highly reproducible in comparison to previous publications (Sridharan, R., et al. Cell 36(2):364-77, 2009; Mikkelsen, T. S. et al. Nature 454, 49-55, 2008) (data not shown).

Motif detection (FIG. 63)—Motifs that are enriched in Mbd3 binding regions were detected using SeqPos tool in Cistrome package [cistrome (dot) org/ap/]. Mbd3 peaks in MEF, MEF+DOX and iPSC were run against Cistrome curated motif database with p-value cutoff 0.001.

Histone mark profiles (Figures C-E)—were calculated using in-house script. Shortly, this script generates a matrix of read densities in given genomic intervals. In this case, the profiles of all 29,952 Entrez genes (mm9, taken from UCSC known gene tables) were calculated between 1 kb upstream to TSS and TES. These read densities were then converted to z-score by normalizing each position by the mean and standard deviation of the sample noise $$\left(\hat{X}_j = \frac{X_j - \mu_{Noise}}{\sigma_{Noise}}\right).$$

Noise parameters were estimated for each sample from $6*10^7$ random by across the genome. Finally, to present aligned profiles, the z-score profile of each gene was binned to 20 bins upstream to TSS and another 100 quantiles between TSS to TES. The value of each bin or quantile was selected to be the max value within that interval.

In the histone mark distribution analysis (FIGS. 65A-E and 66A-J) and in the correlation and clustering of histone marks (FIGS. 47A-B and FIGS. 48A-C) each gene and each histone mark is represented with the maximal z-score measured in the profile of that gene, where the profiles were calculated as described above. Clustering of histone marks was carried out on concatenated vectors that include all marks for every gene in tandem.

Annotation Enrichment Analysis—Mbd3 target genes were tested for enrichment of functional gene sets taken from Gene Ontology [GO, geneontology (dot) org]. Protein-DNA binding annotations were taken from various publications (Boyer, L. A., et al. Cell. 2005, 122(6):947-56; Mikkelsen, T. S. et al. Nature 448, 553-560, 2007; Kim, J., et al., Cell 132(6):1049-61, 2008; Loh, Y H. et al. Nat Genet. 38, 431-440, 2006). Enrichment P values were calculated using Fisher exact test (Fisher, S., Genetiker, S., Fisher, R. A. & Genetician, S. Statistical methods for research workers, 1970) and corrected for multiple hypotheses using false discovery rate (FDR) threshold of 0.0001%.

Gene expression data acquisition, processing and analysis—Total RNA was isolated from indicated cell lines. The concentration of RNA was quantified and subjected to quality control on Agilent Bioanalyzer. 250 ng of RNA was simultaneously processed from each sample. cDNA was fragmented, labeled, and hybridized to Affymetrix Mouse Gene 1.0 ST GeneChip (Affymetrix, Santa Clara, Calif.), which contain 35,557 probes. Affymetrix arrays were used for analysis of human cell samples. Transcripts levels were processed from image files [from Affymetrix CEL files and CDF file (version V1.r3, which maps probes into 33,252 probe sets)] using RMA method (Irizarry, R. A. et al. Biostatistics, 2003, 4:249-64), which corrects for non-biological sample variation using quantile normalization, implemented by the Affymetrix "Expression Console" software. Data was further filtered to include probes that have at least one call higher than 64 ($=2^6$), resulting in 21,811 probes that are mapped to 15,815 RefSeq transcripts [ncbi (dot) nlm (dot) nih (dot) gov/RefSeq/]. Unique Entrez IDs using current annotations from Affymetrix (NetAffx Annotation Files version 33.1) and NCBI sites. Probes targeting the same gene were collapsed by median resulting in 13,894 genes. Microarray data are available at the National Center for Biotechnology Information Gene Expression Omnibus database under the series accession nos. GSE37822, GSE45352, and GSE46872. Additional human ESC samples data from previously described Affymetrix GeneChip Human Genome U133 Plus 2.0 Arrays which contain 54,675 probe sets (GSE21222; (Hanna, J. et al. *Proc. Natl. Acad. Sci. U.S.A.* 107, 9222-9227, 2010) were passed through the same processing as previously described, resulting in 15,571 genes. The two gene lists were then intersected into one list containing 12,071 genes. The batch effect resulting from two different platforms was corrected by normalizing each data set to a sample of the same genotype (WIBR3, reference samples excluded from further analyses), allowing the two datasets to be united for further analysis. The samples were hierarchically clustered using average linkage and either Spearman or Pearson correlation as a distance matrix as noted, with similar results. In order to compare the samples to Inner-Cell-Mass (ICM)-stage cells, Human pre-implantation data from Vassena et al. (Vassena, R. et al. Development 138, 3699-3709, 2011) were included. This data, from Affymetrix HuGene 1.0 st microarrays described before, was passed through the same processing as previously described, resulting in 16,953 genes before and 12,062 genes after intersection with the previous gene list. Batch effect was corrected by normalization of the new data to the mean values of its ESC samples. Differentially Expressed Genes between Naive and Primed samples were found using two-sample two-sided t-test, whose p-values were corrected for multiple hypotheses using the Benjamini-Hochberg false discovery rate (FDR) threshold of 0.05, combined with a two-fold change expression threshold. Differentially expressed genes were checked for functional enrichment using the online tool GOrilla [cbl-gorilla (dot) cs (dot) technion (dot) ac (dot) il/(Eden, E., et al. *BMC Bioinformatics* 10, 48, 2009)], with the entire gene list used as background. An FDR-corrected p-value threshold of 0.05 was used. For gene expression statistical analysis, the present inventors used "Cluster" software [rana (dot) lbl (dot) gov/EisenSoftware (dot) htm] to run hierarchical clustering on the samples, using complete linkage centered correlation as a distance metric. The present inventors used Matlab version R2011a and Version R2012b and their Bioinformatics toolbox to run Principle Component Analysis that detects the principle components with the largest variation in the data.

Gene expression analysis—Probes were mapped to Entrez Gene IDs and further filtered to include IDs that have at least one call higher than 32 ($=2^5$), resulting in 16,620 gene IDs. For gene expression analysis, the present inventors used Matlab version R2011b. Gene signatures differentially expressed between MEF samples (Mbd3$^{+/+}$, Mbd3$^{f/-}$, Mbd3$^{-/-}$ MEF samples) and ES samples (ES V6.5, Mbd3$^{-/-}$ ES, Mbd3$^{f/-}$ IPS and Mbd3$^{+/+}$ iPS) were characterize using two-sample t-test and corrected for multiple hypotheses using false discovery rate (FDR) [Benjamin, Y. and Hochberg, Y. Journal of the Royal Statistical Society Series B (Methodological), 57: 289-300, 1995]. Differentially expressed gene signatures include genes that are under FDR threshold of 5%, as well as above 4-fold change, resulting in 1,323 genes. Sample clustering with all 16,620 genes (FIG. 8R and FIGS. 45A-B) and with 1,323 differentially expressed genes (FIG. 7), was done in two ways: (1) Hierarchical clustering (Sibson, R. SLINK: An optimally efficient algorithm for the single-link cluster method. The Computer Journal 16, 30-34, 1973) using Spearman correlation as a distance metric and average linkage. (2) Principle component analysis (PCA) that detects the principle components with the largest variation in the data. Single gene progression in reprogramming (FIGS. 46A-E) were quantified using the following transformation $$\hat{X}_j(t) = \max\left(\frac{X_j(t) - X_j(\text{MEF\_Mbd3}^{+/+})}{\overline{X}_j(\text{IPS}) - \overline{X}_j(\text{MEF})}, 0\right)$$

Where, Xj(t) denotes gene j expression value at time t (e.g. Xj(4d) or Xj(MEF)) and $\overline{X}_j$(IPS), $\overline{X}_j$(MEF) denotes the averaged expression value for IPS and MEF samples, respectively. The above transformation represents a distance from MEF expression values (set to 0) towards iPS values (set to 1), where genes whose expression changes towards (up/down-regulating) their iPS value show $\hat{X}_j(t)>0$. Distribution of gene expression fold-change, relative to MEF, is presented by box plots (FIGS. 36A-J, and FIGS. 65A-E, 66A-J). Distribution difference significance was calculated with paired samples t-test.

Preparation and analysis of reduced representation bisulfite sequencing libraries—RRBS libraries were generated as described previously with slight modifications (Smith, Z. D. et al. Nature 484, 339-344, 2012). Briefly, DNA was isolated from snap-frozen cell pellets using the Quick-gDNA mini prep kit (Zymo). Isolated DNA was then subjected to MspI digestion (NEB), followed by end repair using T4 PNK/T4 DNA polymerase mix (NEB), A-tailing using Klenow fragment (3'→5' exo-) (NEB), size selection for fragments shorter than 500-bp using SPRI beads (Beckman Coulter) and ligation into a plasmid using quick T4 DNA ligase (NEB). Plasmids were treated with sodium bisulfite using the EZ DNA Methylation-Gold kit (Zymo) and the product was PCR amplified using GoTaq Hot Start DNA polymerase (Promega). The PCR products were A-taild using Klenow fragment, ligated to indexed Illumina adapters using quick T4 DNA ligase and PCR amplified using GoTaq DNA polymerase. The libraries were then size-selected to 200-500-bp by extended gel electrophoresis using NuSieve 3:1 agarose (Lonza) and gel extraction (Qiagen). Libraries were pooled and sequenced on an Illumina HiSeq 2500 system. The sequencing reads were aligned to the Mouse Genome Build 37 (mm9) using Bismark. Methylation levels were calculated and averaged only for CpGs that were covered by 5 or more distinct sequencing reads across all libraries. The CpG content "experienced" by each CpG site was defined as the number of CpG dinucleotides found within a 500-bp window surrounding the site divided by the window size.

Numerical Modeling Analysis

Data acquisition for modeling—The present inventors measured reprogramming latencies for multiple systems in order to establish empirical cumulative distributions for reprogramming dynamics. Monoclonal secondary NGFP1 (Mbd3$^{+/+}$) B-cell reprogramming dynamics with or without additional genetic perturbations (scrambled shRNA, Nanog over expression (Nanog$^{OE}$)) were measured weekly using FACS, as described before (Hanna, J. et al. Nature 462, 595-601, 2009). NGFP1-Mbd3' iPSC line was established, and Pre-B cells were harvested from chimeric animals and subjected to DOX reprogramming. Monoclonal follow-up measurements were conducted by single cell plating followed by Nanog-GFP detection at day 7 (1 week). Since monoclonal follow-up yielded 100% efficiency in NGFp1-Mbd3 KD pre-B cells, the present inventors also conducted polyclonal reprogramming experiments on NGFP1 and NGFP1-Mbd3$^{KD}$ derived pre-B cells and measured Nanog- GFP daily by FACS during the first 8-10 days of OSKM induction (FIGS. 31A-E). Finally, the monoclonal weekly measurements of NGFP1 and the polyclonal daily measurements of NGFP1-Mbd3' established latency distributions for the reprogramming dynamics. These latency distributions were fitted to multiple modeling schemes as indicated below.

Implementation of model fit—The fitting for the models (detailed below) were implemented by Matlab program performing nonlinear regression fitting with adjusted $R^2$ statistic. Definition of the adjusted $R^2$ is $$\text{Adjusted } R^2 = 1 - \frac{\sum_{i=1}^{n}(y_i - \hat{y}_i)^2}{n-m} \cdot \frac{n-1}{\sum_{i=1}^{n}(y_i - \bar{y})^2} = 1 - \frac{MSE}{\text{Var}(y)}$$

Here, $y_i$ is the measured latency distribution data point, $\hat{y}_i$ is the estimated data point according to the predicted model and $\bar{y}$ is the mean value of the measured latency distribution. In addition, n denotes the number of samples taken and m denotes the number of model parameters used for the model fitting. Some of the models were also fitted using maximum likelihood estimator as will be detailed below.

Fitting to a step function model—In the deterministic case all cells become pluripotent at the same time following to DOX induction. This behavior is well approximated by step function like dynamics. The present inventors fitted the observed reprogramming latency to a step function, where the deterministic transition time was estimated by optimizing adjusted $R^2$ statistic. The fitting was done on Matlab using nonlinear regression (FIGS. 35A-C).

Fitting to Gaussian model—In order to estimate the variability observed in the reprogramming latency measurements, we used fitting to Gaussian distribution and calculated the mean, variance and coefficient of variation (CV=std/mean) for each sample (Mbd3$^{+/+}$ and Mbd3$^{KD}$) (FIGS. 56A-F, FIGS. 57A-D). The fitting was done in Matlab using both nonlinear regression and maximum likelihood estimations.

Fitting to Brownian motion model—Biological changes (e.g. gene expression) may be described by the chemical Langevin equation (CLE) [Wilkinson, D. J. Stochastic modelling for quantitative description of heterogeneous biological systems. *Nat Rev Genet.* 10, 122-133 (2009).

$$dX_t = (\beta - \alpha \cdot X_t)dt + \sqrt{\beta + \alpha \cdot X_t} \cdot dW_t$$

Where, $X_t$ is the gene/protein expression as a function of time, $\beta$ denotes the production rate, $\alpha$ denotes the degradation rate and $W_t$ is a Wiener process (or standard Brownian motion). However, the measured reprogramming duration is one or two orders of magnitude (10d for Mbd3' and >100d for WT) higher than the production/degradation time scale. Moreover, the time between samples in the measured reprogramming latency is longer than the half-life ($T_{1/2}$) time of the production/degradation process. Therefore, due to the separation of time scales the present inventors assume that the production/degradation process is at quasi-steady state, where the steady state expression ($\beta/\alpha$) value changes slowly due to regulatory changes that effect the production rate $\beta$, possibly due to epigenetic modifications. For these slow accumulating changes, we assume a simpler linear diffusion model $$dX_t = v \cdot dt + \sigma \cdot dW_t$$

Now, $X_t$ is the quasi-steady state expression as function of time, $v \cdot t$ represents the deterministic dynamics where $v$ is called the process drift, and $\sigma \cdot W_t$ represents the gene expression noise where $\sigma$ is the standard deviation and $W_t$ is a Wiener process.

The present inventors assume that the observed reprogramming dynamics is dominated by the transition of some master regulators (possibly Nanog or Oct4) from their low inactive state to high expression state. For this transition the reprogramming latency corresponds with the first passage time distribution (see illustration in FIG. 57C), where reprogramming time depends on the first passage time of some fixed expression threshold. Therefore for a fixed (unknown) expression threshold $\alpha > X_0$, we get[87]:

$$T = \inf\{t > 0 \mid X_t = \alpha\} \sim IG(\alpha/v, \alpha^2/\sigma^2)$$

$$f_T(x) = \frac{\alpha}{\sigma\sqrt{2\pi \cdot x^3}} \exp\left\{-\frac{(\alpha - v \cdot x)^2}{2\sigma^2 x}\right\}$$

Where T is a random variable representing reprogramming time (or first passage time), $IG(:,:)$ denotes the Inverse Gaussian distribution (or Wald distribution), with the parameters $$\mu = \frac{\alpha}{v}$$

(mean) and $$\lambda = \frac{\alpha^2}{\sigma^2}$$

(shape parameter), and $f_T$ is the density function. The present inventors assume, without loss of generality, that $X_0$ is zero, elsewhere the present inventors can shift everything including $\alpha' = \alpha - X_0 > 0$.

Thus, the present inventors fit the observed reprogramming latency to Inverse Gaussian distribution using maximum likelihood estimator, finding the best fit parameters ($\mu$, $\lambda$) for each sample. Still $\alpha$ is an unknown model parameter, but the present inventors can calculate $\mu/\sqrt{\lambda} = \sigma/v$ from the fitting results, this defines the dynamic variability for each sample. This variability is the ratio of the Brownian motion standard deviation ($\sigma$) divided by the Brownian motion drift parameter ($v$), where $\sigma/v > 1$ corresponds to a high variability dynamics. The present inventors show that while the dynamics variability in the Mbd3$^{+/+}$ sample is $\sigma/v > 5$, the Mbd3$^{KD}$ and cell cycle measurements show both a dynamic variation of $\sigma/v$ 0.5 (FIG. 57B).

Propagation of error—Fitting Gaussian and inverse Gaussian distributions returns 95% confidence intervals for the parameters. Calculating the ratio for the coefficient of variation and dynamics variability, the present inventors assumed that $\sigma$ and $\mu$ are uncorrelated and used the following equation for the error:

$$\sum_{CV} = \sqrt{\sum_{\sigma}^{2} \cdot \frac{1}{\mu^2} + \sum_{\mu}^{2} \cdot \frac{\sigma^2}{\mu^4}}$$

Where $\Sigma_{CV}$, $\rho_\mu$ and $\Sigma_\sigma$ denotes the errors in the coefficient of variation, mean and standard deviation, respectively.

Modeling cell cycle duration—Doubling time parameters (mean and standard deviation) were measured as previously described in Hanna, J. et al. 2009 [Nature 462, 595-601] for the current Mbd3$^{+/+}$ and Mbd3$^{KD}$ cell lines. The present inventors sought to estimate the number of generations according to the reprogramming duration, and fit the cell cycle time distribution to the observed reprogramming latency. Note that Hanna, J. et al. 2009 (Nature 462, 595-601) showed a dependency between cell cycle duration and reprogramming latency distribution. Without being bound by any theory, the present inventors argue that the reduction in rate-limiting barriers may reduce reprogramming variability to variability explained by cell-cycles alone. Doubling time distribution was previously characterized (Duffy, K. R. et al. Science 335, 338-344, 2012) for B lymphocytes, the present inventors assume for simplicity that the cell cycle duration obeys a Gaussian distribution, this is supported by (Duffy K. R, 2012, Science 335: 338-344, FIG. 3A) and validated by applying Shapiro-Wilk normality test [Shapiro, S. S, and Wilk, M. B. An analysis of variance test for normality (complete samples). Biometrika (1965), 52: 591] on the measured doubling times (P value>0.7). In addition, a model for multiple generation cell cycle distribution should be defined, and the present inventors considered in the analysis two opposing models Dependent model: Cell cycle duration is inherited between siblings and generations. Therefore each monoclonal population (each well) represents a single sample of the cell cycle distribution ($\tau_i \sim N(\mu, \sigma)$). Hence, the time for well i to achieve K divisions is distributed by $T_i^K = K \cdot \tau_i \sim N(K \cdot \mu, K \cdot \sigma)$, where $N(:,:)$ denotes normal distribution.

Independent model: Cell cycle duration is independent between siblings and generations. Therefore for each monoclonal population (each well) i the time to achieve K divisions is a random walk process. Hence, $T_i^K = \tau_i^1 + \tau_i^2 + \ldots + \tau_i^K \sim N(K \cdot \mu, \sqrt{K} \cdot \sigma)$, where $\tau_i^j \sim N(\mu, \sigma)$ are iid (independent identically distributed) random variables.

The real biological process probably lies between those two opposing models. Correlation between siblings has been characterized (Duffy K. R, 2012, Science 335: 338-344, FIG. 2F) which supports the dependency model, however correlation deteriorates with time, thus supporting the independent behavior of multiple generation processes. Hence, the present inventors decided to check the fitting for both models (dependent and independent) in order to calculate boundaries that allow confidence in the results.

Fitting procedure consists of: 1) Estimating the mean ($\mu$) and standard deviation ($\sigma$) of doubling time in each sample (Mbd3$^{+/+}$ and Mbd3$^{KD}$), as previously described in (Hanna, Nature 2009). 2) Fitting the observed reprogramming latency to both models: $N(K \cdot \mu, K \cdot \sigma)$ for the dependent and $N(K \cdot \mu, \sqrt{K} \cdot \sigma)$ for the independent model. The mean ($\mu$) and standard deviation ($\sigma$) are empirically estimated from each sample. The fitting was done on Matlab using nonlinear regression. 3) Estimating the number of generations (K) required to account for the measured reprogramming duration, by optimizing adjusted R$^2$ statistic (see above for details on adjusted R$^2$).

Fitting of the dependent model is given in (FIGS. 57D-E), where the results of the independent model are very similar to the dependent model, as seen in the following Table 1.

TABLE 1

| | Dependent model | Independent model |
|---|---|---|
| Mbd3$^{KD}$ | Adj R$^2$ = 0.9986 | Adj R$^2$ = 0.9982 |
| Mbd3$^{+/+}$ | Adj R$^2$ = 0.73 | Adj R$^2$ = 0.69 |

Therefore the fitting results in the dependent and independent models are equivalent and should be valid to realistic cell cycle model (with partial generation dependent correlation).

Inferring structural model (Phase-Type model)—Several papers have suggested that the reprogramming process can be modeled by tandem rate limiting steps [Buganim, Y. et al. Cell 150, 1209-1222 (2012); Polo, J. M. et al. Cell 151, 1617-1632 (2012); Hanna, J. et al. Nature 462, 595-601 (2009); Smith, Z. D., et al. Nat. Biotechnol 28, 521-526 (2010)]. To study how this multiple step process changes following Mbd3 depletion in reprogramming, the present inventors applied a Phase-Type (PH) modeling (Bolch, G., Greiner, S., de Meer, H. & Trivedi, K. S. Queueing networks and Markov chains: modeling and performance evaluation with computer science applications. WILEY, Second Edition, 2006) that is a novel approach used to characterize the dynamics of finite-space continuous-time Markov chain models with a single absorbing phase (in our case iPSC phase). Mbd3$^{KD}$ and Mbd3$^{+/+}$ observed reprogramming latencies were fit to multiple tandem step model, where convergence of estimation efficiency was used in order to select the best fit model (FIGS. 55C-D, 58D, 59G). Note that for this model the present inventors used the Mbd3$^{KD}$ measurements collected by live microscopy, to allow high temporal resolution on the reprogramming transition period (sample every 12 hours). Those measurements show equivalent dynamics to Mbd3$^{KD}$ measurements acquired by FACS (FIG. 55B).

Without being bound by any theory, the present inventors describe the reprogramming process as a sequential Markov chain model with M phases, where the probability of being in phase i (i∈{1,M}) at time t is denoted by Pi(t). In this model the probability of an induced cell to be a B-cell is $P_1(t)$, the probability of being an iPSC is $P_M(t)$, and there are M−2 intermediate phases within the path from the B-cell to iPSC phases. It is assumed that transition occurs between the i$^{th}$ and (i+1)$^{th}$ phases with transition rate $\mu_i$, meaning that the current model neglects feedbacks between phases. In addition, in order to allow for a deterministic delay in the model, the present inventors incorporated to the fitting an additional parameter $t_0$ denoting a deterministic 'shift' in the model dynamics. Therefore an M phases model can be characterize by the following equations for all t>$t_0$ $$\begin{cases} \dfrac{dP_1(t-t_0)}{dt} = -\mu_1 \cdot P_1(t-t_0) \text{ for } i = 1; \\ \dfrac{dP_i(t-t_0)}{dt} = \mu_{i-1} \cdot P_{i-1}(t-t_0) - \mu_i \cdot P_i(t-t_0) \text{ for } i \in \{2, \ldots, M-1\}; \\ \dfrac{dP_M(t-t_0)}{dt} = \mu_{M-1} \cdot P_{M-1}(t-t_0) \cdot \text{ for } i = M. \end{cases}$$

This model can be solved with the following initial conditions: $P_1(t)=1$, $P_i(t)=0$ for all i>1 and for all t≤$t_0$. The solution for the M phases model defines $P_i(t)$ for all t>0 as a function of the transition rates ($\mu_i$, i∈{1, ..., M−1}) and $t_0$, in a physical context $P_i(t)$ describes the time evolution of the ratio of population of cells in phase i.

The present inventors constructed a nested fitting procedure for the fitting of Mbd3$^{KD}$ and control Mbd3$^{+/+}$ dynamics to multiple models with M varies from 2 to 6. Since the present inventors measured only the distribution of complete reprogramming latency the fit was done between the measured latency distribution of each system and the $P_M(t)$ function calculated for each model, seeking the best fit model for each measured latency distribution. The present inventors applied nonlinear regression fitting for each model with adjusted $R^2$ statistic for the rejection of over fitted models. Note that over fitting is rejected by the adjusted $R^2$ since that increased number of model parameters m decreases the adjusted $R^2$ statistic as long as the sum of squares of residuals converge (estimation efficiency convergence).

The best-fit model defines the number of phases that recapitulate the dynamics of each reprogramming system (Mbd3 and Mbd3$^{+/+}$), the fitting procedure calculates the optimized transition rates $\mu_i$ and the deterministic delay $t_0$. Consistent with previous reports [Buganim, Y. et al. Single-cell expression analyses during cellular reprogramming reveal an early stochastic and a late hierarchic phase. Cell 150, 1209-1222 (2012); Polo, J. M. et al. A Molecular Roadmap of Reprogramming Somatic Cells into iPS Cells. Cell 151, 1617-1632 (2012); Hanna, J. et al. Direct cell reprogramming is a stochastic process amenable to acceleration. Nature 462, 595-601 (2009); Smith, Z. D., Nachman, I., Regev, A. & Meissner, A. Dynamic single-cell imaging of direct reprogramming reveals an early specifying event. Nat Biotechnol 28, 521-526 (2010)], Mbd3$^{+/+}$ dynamics fit a multi-step process consisting 1 or 2 but not 0 intermediate phases (FIGS. 55C-D, 58A-D). Remarkably, Mbd3$^{KD}$ measured dynamics optimally fit a single step process with no intermediate phases (FIGS. 55C-D and 58D). In addition, the average rate of the reprogramming process was then estimated using $$v_{eff} = 1 \bigg/ \sum_{i=1}^{M-1} \frac{1}{\mu_i},$$

for each sample. Fitting results and estimated model parameters were documented (data not shown). Note that the models fit was validated using a second fitting procedure based on weighted nonlinear fit by chi$^2$ minimization. The results show (FIGS. 58A-D and FIGS. 59A-G) that the two fitting procedures gave equivalent results.

The result obtained for the Mbd3$^{KD}$ may infer a reduction in intermediate states and therefore reduction in rate-limiting barriers. It does not directly argue for stochasticity, but there is clearly a connection between the barriers and the process variability. The obtained results also have many experimental observations supporting them, such as previous established intermediate phases in reprogramming that were characterized extensively in previous works (Mikkelsen, T. S. et al. Nature 454, 49-55, 2008). The model prediction that Mbd3$^{KD}$ protocol achieves barrier free reprogramming dynamics is supported by the fact that intermediates (SSEA1 positive with negative Oct4 and Nanog) were detected in the WT (wild type) sample, but none were observed in the Mbd3 sample (FIG. 8S, and FIGS. 8F-K). Also, previously described (Mikkelsen, T. S. et al. Nature 454, 49-55, 2008) partially reprogrammed (intermediate pre-iPS) cell lines were robustly converted to iPSC upon Mbd3 depletion (FIG. 50B). Altogether those results validate experimentally the model predictions for elimination of the rate limiting barriers in the Mbd3$^{KD}$ reprogramming protocol.

Additional technical notes: First, note that the rates for Mbd3$^{KD}$ and Mbd3$^{+/+}$ are scaled differently due to differences in measurements of polyclonal and monoclonal assays (FIGS. 55C-D). For the Mbd3$^{+/+}$ monoclonal system, positive detection of iPS cells in clonal populations is defined by FACS threshold of >0.5% GFP+ cells per well, for this system the transition and overall rates should be scaled to population-averaged rate by $$\mu_i' = \frac{\mu_i}{N_{eff}},$$

according to the model previously described (Hanna, J. et al. Nature 462, 595-601, 2009), the reason behind this scaling is that each activation event (well) represent a competition between many iid (identical and independently distributed) exponential variables. On the other hand for the Mbd3 polyclonal assay, the global fraction of Nanog-GFP+ cells out of the entire population was measured daily, for this single cell measurement the transition rates need not to be scaled to population-average.

Second, note that non-linear effects such as in Hill functions may result a similar dynamics to the observed reprogramming latency, but due to the multi-well mono-clonal (homogeneous population) measurement scheme the present inventors can rule out such effects. Clearly each activation event (each well) is independent and physically isolated from all other wells so cannot be influenced by proximal well activations. In addition the reprogrammed cell lines were secondary systems with homogeneous DOX induction stable constructs. So the S function dynamic must correspond to the reprogramming latency distribution and not to other nonlinear effect.

Finally, the present inventors note that the parameter $t_0$ used in the model fitting is not the onset of the process. By examining the gene expression and chromatin results one can see that major changes in gene expression and chromatin are already evident in 4d after induction (for Mbd3$^{KD}$) and 8d (for WT) (see FIGS. 45A-B, 47A-B). The parameter $t_0$ is technical for allowing the distributions to move and fit each other, it may represent the minimum deterministic duration needed for the changes required in reprogramming. Note that for the monoclonal Mbd3$^{+/+}$ system, detection delay is due to a threshold obtained in the FACS which can be formulated by t=T$_d$♦ Log$_2$(N$_{FACS}$♦ Thr$_{FACS}$)≈4d, where T$_d$ is the doubling time (~20 hours), N$_{FACS}$ equal 5000 cells and Thr equal 0.05%. DOX induction delay is approximated by 0.5d. While that Mbd3$^{KD}$ detection delay is negligible (polyclonal assay). Reduction of those mechanistic delays from the estimated $t_0$ the present inventors get that both Mbd3$^{+/+}$ and Mbd3$^{KD}$ has approximately 3 [days] 'minimum duration' requires for the reprogramming changes to complete.

Non-linear regression assumptions—Most of the above model estimations utilized nonlinear regression as their fitting procedure. For this we assume that: 1) The observational errors, i.e. the residuals defined as a difference between observed and model-predicted values, are normally distributed. 2) The errors in observations at successive times are independent. 3) The variance of observation errors ($\sigma^2$) is the same for all the state variables and observation times. The present inventors checked the distribution of the residuals for all previous estimation problems using Kolmogorov-Smirnov and Shapiro-Wilk normality tests [Shapiro, S. S. & Wilk, M. B. An analysis of variance test for normality (complete samples). Biometrika (1965), 52: 591; Smirnov, N. JSTOR: The Annals of Mathematical Statistics, Vol. 19, No. 2 (June, 1948), pp. 279-281]. The residuals passed the normality tests with the P values reported in Supplementary table 1 in Rais Y, et al. ["Deterministic direct reprogramming of somatic cells to pluripotency". Nature. 2013 Oct. 3; 502(7469): 65-70. Epub 2013 Sep. 18], which is fully incorporated herein by reference in its entirety.

Evolutionary analysis of the NuRD complex and other associated proteins—The present inventors assigned orthologs for 15 human proteins that are either known to be part of the NuRD complex or are related to these proteins (MBD1; Gene ID: 4152; SEQ ID NO: 5), MBD2 (Gene ID: 8932; SEQ ID NO: 6), MBD3 (Gene ID: 53615; SEQ ID NO: 7), MBD4 (Gene ID: 8930; SEQ ID NO: 8), OCT4 (Gene ID: 5460; SEQ ID NO: 9), SOX2 (Gene ID: 6657; SEQ ID NO: 10), CHD4 (Gene ID: 1108; SEQ ID NO: 11), Nanog (Gene ID: 79923; SEQ ID NO: 12), RBBP4 (Gene ID: 5928; SEQ ID NO: 13), RBBP6 (Gene ID: 5930; SEQ ID NO: 14), RBBP7 (Gene ID: 5931; SEQ ID NO: 15), HDAC1 (Gene ID: 3065; SEQ ID NO: 16), HDAC2 (Gene ID: 3066; SEQ ID NO: 17), MTA1 (Gene ID: 9112; SEQ ID NO: 18), MTA2 (Gene ID: 9219; SEQ ID NO: 19), for 15 representative metazoan species (mouse—*M. musculus*, platypus—*O. anatinus*, zebra finch—*T. guttata*, chicken—*G. gallus*, frog—*X. tropicalis*, zebrafish—*D. rerio*, pufferfish—*T. nigroviridis*, lancelet—*B. floridae*, sea urchin—*S. purpuratus*, mosquito—*A. gambiae*, fruit fly—*D. melanogaster*, honeybee—*A. mellifera*, beetle—*T. castaneum*, sea anemone—*N. vectensis*, trichoplax—*T. adhaerens*), and the yeast *S. cerevisiae*, as an outgroup. The last metazoan in this list *T. adhaerens*, represents a basal group of metazoan, and is used to study the origins of animal multicellularity [Rokas, A. Annual review of genetics, 42: 235-251, 2008; Knoll, A. H. Annu. Rev. Earth Planet. Sci. 39, 217-239, 2011]. Proteins that have an ortholog in *T. adhaerens* were likely to be present in the basal multicellular animals, while proteins that appear in yeast precede animal multicellularity. The orthologs were retrieved using the COG component (version 9.0) of the STRING database (version 9.0) (Szklarczyk, D. et al. The STRING database in 2011: functional interaction networks of proteins, globally integrated and scored. Nucleic Acids Res. 39, D561-D568, 2010). The present inventors limited the analysis to orthologs that are found in the same cluster of orthologs (COG) as the human proteins (and ignored any other similar proteins, if they are assigned to a different COG). In cases where more than one ortholog (Altschul, S. F., et al. Nucleic Acids Res. 1997, 25:3389-402) for a species were found, the present inventors blasted the various orthologs of that species against the human ortholog to quantify their relative degrees of similarity. The present inventors discarded proteins that are shorter than 50 residues, or that had e-values higher than 0.001. As the closest homolog for the human protein, the present inventors chose the ortholog in the compared species with the lowest e-value from the remaining proteins. The present inventors calculated a normalized similarity score between the two orthologs, by dividing the similarity score in the length of the longer protein of the two orthologs (the human ortholog and the compared species' ortholog).

Capturing naive human pluripotent cells—The following serum free defined conditions, termed WIS-NHSM (Weizmann Institute of Science Naive human Stem cell Medium) were used to isolate, generate, derive and stabilize naive human pluripotent stem cells (iPSCs and ESCs) with the unique biological properties described in this study. WIS-NHSM-(i) medium was generated by including: 475 ml Knockout DMEM (Invitrogen 10829), 5 grams AlbuMAX (Invitrogen 11020-021), 5 ml N2 supplement (Invitrogen 17502048), 10 µg (micrograms) of recombinant human LIF (leukemia inhibitory factor) (Peprotech), 8 ng/ml recombinant bFGF (Peprotech) and 1 ng/ml recombinant TGFβ1 (Peprotech), 1 mM glutamine (Invitrogen), 1% nonessential amino acids (Invitrogen), 0.1 mM β-mercaptoethanol (Sigma), Penicillin-Streptomycin (Invitrogen) and small molecule inhibitors: PD0325901 (1 µM, ERK1/2i, Axon Medchem); CHIR99021 (3 µM, GSK3βi, Axon Medchem); SP600125 (10 µM, JNKi, TOCRIS), SB203580 (5-10 µM, p38i, TOCRIS). After further optimization the present inventors alternatively used SB202190 (5 µM, p38i, Axon Medchem) or BIRB796 (2 µM, P38i Axon Medchem) for enhanced P38 inhibition instead of using SB203580.

Throughout the study Naive hESCs/hiPSCs were grown on 0.2% gelatin+1 ng/ml vitronectin coated plates for at least 1 hour in 37° C. Notably, 1 ng/ml recombinant vitronectin or laminin (Sigma Aldrich L2020, 1 ng/ml for at least 1 hour at 37° C.) can also be used to maintain human naive cells in WIS-NHSM conditions.

Cells were passaged by single cell trypsinization (0.25% or 0.05% Trysin+EDTA) every 3-4 days. Although not essential, enhanced single cell cloning efficiency can be obtained with WIS-NHSM supplementation with ROCK pathway inhibitor Y-27632 (5 µM, ROCKi Axon Medchem) for 24 hours before and after cell passaging. Passage numbers of naive-hiPSC/hESCs indicates number of passages counted after induction or stabilization of the naive state (and do not include previous passages when the cells were established and maintained in conventional/primed ESC conditions). For transfection of mouse and human naive iPSCs/ESCs, cells were harvested with 0.05% trypsin-EDTA solution (Invitrogen), and cells resuspended in PBS were transfected with 75 µg DNA constructs (Gene Pulser Xcell System; Bio-Rad; 500 V, 25 µf, 0.4-cm cuvettes).

While the cells described and analyzed in this study were maintained as described above, the present inventors note that naive hESCs/iPSCs can be expanded on gelatin coated plates together with mitomycin C-inactivated, or gamma irradiated mouse embryonic fibroblast (MEF) feeder cells.

Further, alternative composition of WIS-NHSM is possible by replacing Albumax component with 15-20% knockout serum replacement (KSR; Invitrogen 10828-028) or chemically Defined Lipid Concentrate (GIBCO0 Invitrogen 11905-031) or Oleic Acid-Albumin (03008 Sigma Aldrich, 10 µ/ml final) or Oleic Acid (O1257, Sigma Aldrich, 10 µg/ml final concentration) or Linoleic/Oleic/Albumin supplement (L9655 Sigma Aldrich, 10 µg/ml final concentration) or Oleic Acid [O1008 Sigma Aldrich (dissolved in DMSO), 10 µg/ml final concentration].

Instead of adding 5 ml of ready N2 mix, individual components can be added to 500 ml media bottle at the indicated final concentration: 1) Recombinant Human Insulin (Sigma I-1882)—12.5 µg/ml Final concentration; 2) Apo-Transferrin (Sigma T-1147)—500 µg/ml Final concentration; 3) Progesterone (Sigma-P8783)—0.02 µg/ml Final concentration; 4) Putrescine (Sigma-P5780)—16 µg/ml Final concentration; 5) Sodium Selenite (Sigma-S5261)—add 5 µL of 3 mM stock solution per 500 ml WIS-NHSM media.

Instead of SB203580 (p38i), the WIS-NHSM medium can include SB202190 (5 µM, p38i, TOCRIS) or BIRB796 (2

μM, P38i Axon Medchem) without any change in OCT4-GFP expression in WIS-NHSM conditions.

Supplementation of Vitamin C (L-ascorbic acid 2-phosphate, Sigma, A8960, 50 microg/ml final concentration) and/or Hypoxia growth conditions (5% PO$_2$), were tested and found accommodating for expanding Oct4-GFP+ naive human ESCs and iPSCs.

Instead of KO-DMEM the following media can also be alternatively used: DMEM-F12 (Biological Industries or Invitrogen), KO-DMEM/F12 (Invitrogen12660-012), GMEM (Invitrogen 11710) or 1:1 DMEM/F12:Neurobasal mix (Invitrogen 21103-049).

Following is a non-limiting example of an alternative WIS-NHSM medium (termed "WIS-NHSM-ii") which was used to culture the naive cells of some embodiments of the invention: 425 ml Knockout DMEM (Invitrogen 10829), 74 ml of knockout serum replacement (Invitrogen 10828-028), 5 ml N2 supplement (Invitrogen 17502048), 10 μg of recombinant human LIF (Millipore, LIF1005), 8 ng/ml recombinant bFGF and 1 ng/ml recombinant TGFβ1 (Peprotech), 1 mM glutamine (Invitrogen), 1% nonessential amino acids (Invitrogen), 0.1 mM β-mercaptoethanol (Sigma), Penicillin-Streptomycin (Invitrogen) and small molecule inhibitors: PD0325901 (1 μM, ERK1/2i, AXONMEDCHEM); CHIR99021 (3 μM, GSK3bi, AXON MEDCHEM); SB203580 (5 μM, p38i, TOCRIS); SP600125 (5 μM, JNKi, TOCRIS) with or without Y-27632 (5 μM, ROCKi Axon Medchem).

Alternative composition of WIS-NHSM medium involved replacing 15% KSR with 1% albumax: 500 ml Knockout DMEM (Invitrogen 10829), 5 gr of AlbuMAX (Invitrogen 11020-021), 5 ml N2 supplement (Invitrogen 17502048), 10 μg of recombinant human LIF (Millipore, LIF1005), 8 ng/ml recombinant bFGF and 1 ng/ml recombinant TGFβ1 (Peprotech), 1 mM glutamine (Invitrogen), 1% nonessential amino acids (Invitrogen), 0.1 mM β-mercaptoethanol (Sigma), Penicillin-Streptomycin (Invitrogen) and small molecule inhibitors: PD0325901 (1 μM, ERK1/2i, AXONMEDCHEM); CHIR99021 (3 μM, GSK3bi, AXON MEDCHEM); SB203580 (5 μM, p38i, TOCRIS); SP600125 (5 μM, JNKi, TOCRIS) with or without Y-27632 (5 μM, ROCKi Axon Medchem).

Derivation of iPSCs—For derivation of iPSCs directly from fibroblasts (and not from already established iPSC lines), BJ fibroblasts or C1/2 derived secondary fibroblast cells (Hanna, J., et al. 2010. Proc. Natl. Acad. Sci. U.S.A. 107, 9222-9227) harboring doxycycline (DOX) lentiviral vectors encoding Oct4, Sox2, and Klf4 reprogramming factors (Hanna, J., et al. 2010. Proc. Natl. Acad. Sci. U.S.A. 107, 9222-9227) and a constitutively active lentivirus encoding the reverse tetracycline transactivator were grown in the presence of DOX in WIS-NHSM conditions (as described above) on vitronectin/gelatin-coated plates until initial PSC colonies were observed and subcloned.

ESC derivation form human blastocysts—The use of human preimplantation embryos for ESC derivation was performed in compliance with protocols approved by a Weizmann Institute ESCRO committee, L is hospital Institutional review committee and Israeli National Ethics Committee (7/04-043) and following the acceptance of a written informed consent. The couples' participation in the study was voluntary after signing informed consent forms and there was no monetary compensation for their embryo donation. Inner cell masses (ICMs) were isolated mechanically by laser-assisted micromanipulation from spare IVF embryos, at day 6-7 following fertilization [Ben-Yosef, D. et al. Female Sex Bias in Human Embryonic Stem Cell Lines. *Stem Cells and Development* 21, 363-372 (2012)]. The intact ICM clumps were placed on a feeder cell layer of irradiation treated DR4 mouse embryonic fibroblasts and cultured in WIS-NHSM media. Initial outgrowths of proliferating ESCs were evident by day 6, and were trypsinized into single cells, 6-10 days following ICM plating. The newly established cell lines were further propagated by trypsin and then either frozen or used for further analysis.

Small molecule compounds and cytokines—Small molecules and cytokines were purchased from Tocris, Calbiochem, Stemgent, Peprotech or Sigma, and were supplemented as indicated at the following final concentration: JAK inhibitor (420099 JAKi, 0.6 μM CAL BIOCHEM), Kenopaullone (KP, 5 μM, Sigma Aldrich), PD0325901 (PD, 1 μM, Axon Medchem); CHIR99021 (CH, 3 μM, AXON MEDCHEM), Forskolin (FK, 10 μM, TOCRIS), FGF4-Receptor inhibitors PD173074 (0.1 μM, TOCRIS) and SU5401 (2 μM, TOCRIS); TGFβ/ALK inhibitors A83-01 (1 μM, STEMGENT), PKC inhibitor Go6983 (1 μM, TOCRIS), ALK inhibitor (ALKi: SB431542, 2 μM, TOCRIS); AICAR (0.5 mM); Bix01294 (1 μM); BayK8644 (1 μM, Stemgent); SB203580 (5-10 μM, p38i, TOCRIS); SBS202190 (5 μM, p38i, TOCRIS), BIRB796 (2 μM Axon Medchem), SP600125 (10 μM, JNKi, TOCRIS); recombinant human BMP4 (5-10 ng/ml; Peprotech), recombinant human SCF (10 ng/ml, Peprotech), recombinant human IGF1 (10 ng/ml, Peprotech), Media with inhibitors was replaced every 24-48 hours.

Culture of conventional/primed human ESCs and iPSCs—The following already established conventional human ESCs and iPSC lines were used (indicated passage number of the cell line taken for conversion into naive pluripotency is indicated in parentheses): Human induced pluripotent stem cells C1 (P21) and C2 (P9) hiPSC lines (Hanna, J. et al. *Proc. Natl. Acad. Sci. U.S.A.* 107, 9222-9227, 2010) and the human embryonic stem cell (hESC) lines BGO1 (P35) (National Institutes of Health ID code BG01; BresaGen], H1 (P40), H9 (P37), WIBR1 (P13), WIBR2, WIBR3 (P11) hESCs (Lengner, C. J. et al. *Cell* 141, 872-883, 2010) were maintained in 20% pO$_2$ conditions (unless indicated otherwise) on irradiated mouse embryonic fibroblast (MEF) feeder layers or Gelatin/vitronectin coated plates, in hESC medium: 425 ml Knockout-DMEM—Invitrogen 10829) supplemented with 15% Knockout Serum Replacement (Invitrogen 10828-028), 1 mM glutamine (Invitrogen), 1% nonessential amino acids (Invitrogen), 0.1 mM β-mercaptoethanol (Sigma), 8 ng/mL bFGF (Peprotech) and 1-8 ng/ml (e.g., 1-2 ng/ml) recombinant human TGFβ1 (Peprotech). Cultures were passaged every 5-7 days either manually or, or by trypsinization (24 hour pre and 24 hour after addition of ROCK inhibitor at 5-10 nM concentration). For transfection of hiPSC and hESC lines, cells were cultured in Rho kinase (ROCK) inhibitor (Calbiochem; Y-27632) 24 hours before electroporation. Primed/conventional human ESC and iPSC cells were harvested with 0.05% trypsin-EDTA solution (Invitrogen), and cells resuspended in PBS were transfected with 75 μg DNA constructs (Gene Pulser Xcell System; Bio-Rad; 250 V, 500 μF, 0.4-cm cuvettes). Cells were subsequently plated on MEF feeder layers (DR4 MEFs for puromycin selection) in hESC medium supplemented with ROCK inhibitor for the first 24 hours, and then antibiotic selection was applied.

Mouse naive and primed stem cell lines and cultivation—Murine naive V6.5 ESCs (C57B6/129sJae) pluripotent cells were maintained and expanded in serum-free chemically defined N2B27-based media: 500 ml KO-DMEM (Invitrogen), 5 ml N2 supplement (Invitrogen; 17502048), 5 ml B27 supplement (Invitrogen; 17504044), 1 mM glutamine (Invitrogen), 1% nonessential amino acids (Invitrogen), 0.1 mM β-mercaptoethanol (Sigma), penicillin-streptomycin (Invitrogen), 5 mg/ml BSA (bovine serum albumin; Sigma). Naive 2i/LIF conditions for murine PSCs included 5 μg recombinant human LIF (Peprotech). Where indicated "2i" the following was added: small-molecule inhibitors CHIR99021 (CH, 3 μM-Axon Medchem) and PD0325901 (PD, 1 μM—TOCRIS). Murine Naive ESCs and iPSCs were expanded on gelatin-coated plates, unless indicated otherwise. Previously described Eras$^{-/Y}$ ESCs were kindly provided by Dr. Shinya Yamanaka [Takahashi, K., Mitsui, K. & Yamanaka, S, Nature 423, 541-545 (2003)]. Primed 129Jae EpiSC line (derived from E6.5 embryos) or C57BL6/129sJae EpiSC line (derived following in vitro priming of V6.5 mouse ESCs) were expanded in N2B27 with 8 ng/ml recombinant human bFGF (Peprotech Asia) and 20 ng/ml recombinant human Activin (Peprotech Asia) and 1% KSR (knockout serum replacement). Murine EpiSC were expanded on feeder free Gelatin/Vitronectin or Matrigel coated plates. Cell lines were routinely checked for Mycoplasma contaminations every month (LONZA—MYCOALERT KIT), and all samples analyzed in this study were not contaminated.

Reprogramming of somatic cells and cell infection—Virus-containing supernatants of the different reprogramming viruses: STEMCA-OKSM polycistronic vector (DOX inducible and constitutive expression) [Mansour, A. A. et al. Nature 488, 409-413 (2012)] was supplemented with the FUW-lox-M2rtTA virus (when necessary) and an equal volume of fresh culture medium for infection. For derivation of iPSCs directly from fibroblasts (and not from already established iPSC lines), BJ fibroblasts or C1.2 derived secondary fibroblast cells [Hockemeyer, D. et al. Cell Stem Cell 3, 346-353 (2008)] harboring doxycycline (DOX) lentiviral vectors encoding Oct4, Sox2, and Klf4 reprogramming factors and a constitutively active lentivirus encoding the reverse tetracycline transactivator [Hockemeyer, D. et al. Cell Stem Cell 3, 346-353 (2008)], were grown in the presence of DOX in WIS-NHSM conditions on vitronectin/gelatin-coated plates until initial iPSC colonies were observed and subcloned. Generation of BE hiPSCs form human BJ foreskin fibroblasts was conducted by OSKM and LIN28 mRNA transfection kit (Stemgent) according to manufacturers' instructions, but in WIS-NHSM conditions applied starting from day 2 of the reprogramming process. Fragile X male patient specific fibroblasts were obtained through Coriell repository (GM05131 and GM07071). iPSCs were reprogrammed either in conventional or naive (WIS-NHSM) conditions as indicated in FIGS. 21A-D and 71A-E. Previously described PCR primers were used for FMR1 gene detection [Urbach, A., et al. Stem Cell 6, 407-411 (2010)]: Forward primer: 5'-CAGGGCTGAAGAGAAGATGG-3' (SEQ ID NO:72), Reverse primer: 5'-ACAGGAGGTGGGAATCTGA-3' (SEQ ID NO:73). Pyro sequencing analysis for methylation at FMR1 locus was performed as previously described [Urbach, A., et al. Stem Cell 6, 407-411 (2010)].

Differentiation Assays of human iPSCs and ESCs—For embryoid body (EB) induced differentiation, naive hESCs/hiPSCs were trypsinized and cultured for 6-8 days in non-adherent suspension culture dishes (Corning) in DMEM supplemented with 15% fetal bovine serum. For teratoma formation and analysis, naive hESCs and iPSCs were harvested by trypsinization before injection. Cells were injected sub-cutaneously (s.c.) into 6-8 week old male NSG mice (Jackson laboratories). Tumors generally developed within 4-6 weeks and animals were sacrificed before tumor size exceeded 1.5 cm in diameter. Naive C1 hiPSCs were infected with a lentivirus harboring a VASA-EGFP reporter construct, selected with neomycin, subcloned, and subsequently used for primordial germ cell (PGC) differentiation protocol (Hanna et al., 2010b). All animal studies were conducted according to the guideline and following approval by the Weizmann Institute IACUC (approval #00960212-3).

Mouse embryo micromanipulation—Pluripotent mouse ESCs or naive human iPSCs (pre-treated with 10 μM ROCKi for 12 hours) were trypsinized and subsequently injected into BDF2 diploid mouse morulas or blastocysts, harvested from hormone primed BDF1 6 week old females. Microinjection into E2.5 morulas or E3.5 blastocysts placed in M16 medium under mineral oil was done by a flat-tip microinjection pipette. Embryos injected with human iPSCs were allowed to recover in KSOM medium (Invitrogen) supplemented with ROCKi (5 μM) for 3-9 hours before they were transplanted into surrogate pseudo-pregnant mice. A controlled number of 10-12 cells were injected into the blastocyst cavity. After injection, blastocysts were returned to KSOM media (Invitrogen) and placed at 37° C. until transferred to recipient females. Ten to fifteen injected blastocysts were transferred to each uterine horn of 2.5 days post coitum pseudo-pregnant females. 4n tetraploid complementation assay was performed by fusing BDF2 embryos at 2 cell stage [Stadtfeld, M. et al. Nature 465, 175-181 (2010)], and subsequently allowing the embryos to develop until the blastocyst stage at day 3.5, and were then utilized for PSC micro-injection. Embryos were allowed to develop into full term. Determining germ-line transmission was performed by mating chimeric animals with C57B/6 females, and continuous checking for agouti colored pups. For teratoma formation and analysis, naive hESCs and hiPSCs were harvested by trypsinization before injection. Cells were injected sub cutaneously into NSG mice (Jackson laboratories). Tumors generally developed within 4-6 weeks and animals were killed before tumor size exceeded 1.5 cm in diameter. All animal studies were conducted according to the guideline and following approval by the Weizmann Institute IACUC (approval #00960212-3). The present inventors have not excluded animals from the analysis, and did not apply randomization by blinding.

BAC recombineering and TALEN gene editing—TALEN expressing plasmids were designed with a help of TALEN targeter 2.0 and cloned using GoldenGate TALEN kit 2.0 purchased from Addgene [Bedell, V M, et al., Nature 491:114-8. (2012)] according to the published protocol. For targeting G the present inventors have used N,N-type repeat. $10^7$ ESCs/iPSCs were electroporated with 30 μg of previously described OCT4-GFP-2A-PURO knock-in donor plasmid [Hockemeyer, D. et al., Nat Biotechnol 29, 731-734 (2011)] (kindly provided by R. Jaenisch through Addgene) and 10 μg of each of the TALEN expressing plasmids and grown in the presence of antibiotic selection. Resistant clones were isolated and genomic DNA was extracted for Southern Blot and PCR analysis. OCT4-GFP-2A-PURO, ΔPE-OCT4-GFP-2A-PURO, ΔDE-OCT4-GFP-2APURO constructs were made from BAC clone containing human OCT4 gene locus by using Red/ET recombination (Gene Bridges). Briefly, GFP-2A-puro cassette was inserted into translation start site of OCT4, and then genomic region from 8 kb upstream to 10 kb downstream of TSS was subcloned into pBS vector. Proximal (PE) and distal (DE) elements were determined by homology with respective elements of mouse Oct4 described in [Bao, S. et al. Nature 461, 1292-1295 (2009)], and based on results obtained with luciferase test assay (FIG. 25A). ΔPE and ΔDE deletions were made in wild type construct by exchanging these regions with kanamycin selection cassette that was subsequently removed by restriction. Targeting vectors were linearized with SspI and electroporated into different primed and naive pluripotent cells lines as indicated. For making mouse ΔPE-Oct4-GFP reporter the present inventors have modified the previously described mGOF18ΔPE construct [Yeom, Y. I. et al. Germline regulatory element of Oct-4 specific for the totipotent cycle of embryonal cells. Development, 1996, 122(3):881-94], by pRed/ET recombination. The pgk-gb2-Neo cassette (GeneBridges) was inserted into the 3' end of cloned Oct4 genomic fragment (9.7 kb downstream of Oct4 TSS). The inserted neo cassette has the same orientation as Oct4 gene. The construct was linearized with SspI and electroporated into mouse V6.5 ESCs and used for experiments in FIGS. 86A-C and FIGS. 87A-B. For gene targeting of human OCT4 and COL1A loci, targeting vectors design and strategy were implemented as detailed in FIGS. 71B-C. Homology arms were amplified by PCR from H9 hESC derived genomic DNA. Gene targeting was introduced by using the isogenic vectors after linearization and transduction in naive and primed H9 hESCs. Correctly targeted clones were validated by southern blot screening for correct targeting by both 5' and 3' external probes (FIGS. 21A-D).

DNA constructs and plasmid cloning—The pCAG-IresPuro or pCAG-flox-DsRed-IRES-Puro vectors [Ficz G, et al. Cell Stem Cell. 2013 Sep. 5; 13(3):351-9. doi: 10.1016/j.stem.2013.06.004. Epub 2013 Jul. 11] encoded the following inserts (which were cloned by either cohesive or blunt-end ligations in XhoI-NotI sites): Stat3-CA mutant (Addgene 13373) (A662C and N664C mutations—by substituting cysteine residues for A662 and N664 of the Stat3 molecule, disulfide bonds may form between Stat3 monomers and render the molecule capable of dimerizing without a phosphate on Y705); Stat3-Y705F (dominant-negative allele Addgene 8709). Human OCT4 enhancer sequences [the Oct4DE- and Oct4PE-SV40-luciferase (Luc) constructs] were cloned into the pGL3-Promoter Vector (Promega) with the following primers: 5' hOcCT4PE KpnI: 5'-GGTACCGGATACTCAGGCCAGGCCCAGAAA-3' (SEQ ID NO:74; 3' hOCT4PE XhoI: 5'-CTCGAGTC-CACAGACCTCTGGCACT-3' (SEQ ID NO:75); 5' hOCT4DE KpnI: 5'-GGTACCCATTGAGTC-CAAATCCTCTTTACTAGGTG-3' (SEQ ID NO:76); 3' hOCT4DE XhoI: 5'-CTCGAGCTGAGGCT-CATGCTGCTGG-3' (SEQ ID NO:77). Reporter constructs were used to determine the regulation pattern of Oct4 expression and were electroporated into 0.5-3×10$^6$ cells along with the pRL-TK (Renilla) vector for normalization. Assays were performed 48 hours later using the Dual-Glo Luciferase Assay System (Promega). The basal activity of the empty luciferase vector was set as 1.0. Recombinant vitronectin was produced and purified as previously described [Chen, G. et al. Chemically defined conditions for human iPSC derivation and culture. Nat. Methods 8, 424-429 (2011)] after obtaining express ion construct through Addgene (vector 30225).

RT-PCR Analysis (Description for Examples 5-9)

Total RNA was isolated using Trizol (Invitrogen). 1 µg of DNase-1-treated RNA was reverse transcribed using a First Strand Synthesis kit (Invitrogen) and ultimately re-suspended in 100 µl of water. Quantitative PCR analysis was performed in triplicate using 1/50 of the reverse transcription reaction in an Viia7 platform (Applied Biosystems). Error bars indicate standard deviation of triplicate measurements for each measurement. RT-PCR primers used herein are: XIST-Forward: 5'-AGGGAGCAGTTTGCC CTACT-3' (SEQ ID NO:78); XIST-Reverse: 5'-CA-CATGCAGCGTGGTATCTT-3' (SEQ ID NO:79); OCT4-Forward: 5'-AGTGATTCTCCTGCCTCAGC-3' (SEQ ID NO:80); OCT4-Reverse: 5'-CTTCTGCTTCAG-GAGCTTGG-3' (SEQ ID NO:81); SOX1-Forward: 5'-GGAATGGGAGGACAGGATTT-3' (SEQ ID NO:82); SOX1-Reverse: 5'-AACAGCCGGAGCAGAAGATA-3' (SEQ ID NO:83); PAX6-Forward: 5'-AAGGATGTT-GAACGGGCAGA-3' (SEQ ID NO:84); PAX6-Reverse: 5'-TCCGTTGGAACTGATGGA GT-3' (SEQ ID NO:85); HPRT-Forward: 5'-TGACACTGGCAAAACAATGCA-3' (SEQ ID NO:86); HPRT-Reverse: 5'-GGTCCTTTT-CACCAGCAAGCT-3' (SEQ ID NO:87); EOMES-Forward: 5'-CGCCACCAAACTGAGATGAT-3' (SEQ ID NO:88); EOMES-Reverse: 5'-CACATTGTAGTGGGCAGTGG-3' (SEQ ID NO:89); CDX2-Forward: 5'-CAGTCGCTACAT-CACCATCC-3' (SEQ ID NO:90); CDX2-Reverse: 5'-TTTCCTCTCCTTTGCTCTGC-3' (SEQ ID NO:91); HAND1-Forward: 5'-AACTCAAGAAGGCGGATGG-3' (SEQ ID NO:92); HAND1-Reverse: 5'-CGGTGCGTCCTT-TAATCCT-3' (SEQ ID NO:93); GSC-Forward: 5'-CGCCTCGGCTACAACAACTA-3' (SEQ ID NO:94); GSC-Reverse: 5'-CGCCTCGGC TACAACAACTA-3' (SEQ ID NO:95); ID1-Forward: AAACGTGCTGCTC-TACGACA-3' (SEQ ID NO:96); ID1-Reverse: 5'-TAGTC-GATGACGTGCTGGAG-3' (SEQ ID NO:97); ID3-Forward: 5'-CTACAGCGCGTCATCGACTA-3' (SEQ ID NO:98); ID3-Reverse: 5'-TCGTTG-GAGATGACAAGTTCC-3' (SEQ ID NO:99); ZIC1-Forward: 5'-GCGCTCCGAGAATTTAAAGA-3' (SEQ ID NO:100); ZIC1-Reverse: 5'-GTCGCTGCTGT-TAGCGAAG-3' (SEQ ID NO:101); NANOG-Forward: 5'-GATTTGTGGGCCTGAAGAAA-3' (SEQ ID NO:102); NANOG-Reverse: 5'-CAGATCCATGGAGGAAGGAA-3' (SEQ ID NO:103); MIXL1-Forward: 5'-AGCTGCTG-GAGCTCGTCTT-3' (SEQ ID NO:104); MIXL1-Reverse: 5'-CGCCTGTTCTGGAACCATAC-3' (SEQ ID NO:105).

Immunofluorescence staining—Cells were grown for two days on glass cover slips (13 mm 1.5H; Marienfeld, 0117530) fixed with 4% paraformaldehyde/phosphate buffer for 15 minutes at room temperature, washed three times with phosphate buffered saline (PBS), and permeabilized in PBS/0.1% Triton for 10 minutes. Cells were blocked with blocking solution (2% normal donkey serum, 0.1% BSA in PBS/0.05% Tween) and incubated with primary antibody diluted in blocking solution overnight at 4° C. (Antibodies in this study have all been validated in the literature and by ourselves). Cells were then washed three times with PBS/0.05% Tween, incubated with secondary antibodies for 1 hour at room temperature, washed in PBS/0.05% Tween, counterstained with DAPI (1 µg/ml) mounted with Shandon Immu-Mount (Thermo Scientific, 9990412), and imaged. For staining of H3K27me3 and nuclear proteins, cells were permeabilized in PBS/0.5% Triton for 30 or 10 minutes, respectively, and 0.1% Triton was included in the blocking solution. All comparative experiments were done simultaneously. For MHC class I staining of human cells, anti MHC class I antibody (BE pharmingen) was used and cells were analyzed on FACS ARIA III analyzer and sorter system. The following antibodies were used at the indicated dilutions:

TABLE 2

Table 2.

| Antibody | Manufacturer (or supplier) with Catalogue number | Dilution |
|---|---|---|
| Mouse anti-TRA-1-60 | Abcam (ab16288) | 1:500 |
| Mouse anti-TRA-1-81 | Abcam (ab16289) | 1:500 |
| Mouse anti-SSEA1 (MC480) | Abcam (ab16285) | 1:100 |
| Mouse anti-SSEA4 (MC813) | Abcam (ab16287) | 1:50 |
| Rat anti-SSEA3 (MC631) | Abcam (ab16286) | 1:50 |
| Rabbit anti-Klf2 | Millipore (09-820) | 1:500 |
| Rabbit anti-Nanog | Bethyl (A300-397A) | 1:400 |
| Rabbit anti-Nanog | Abcam (ab80892) | 1:200 |
| Rabbit anti- Oct3/4 (H134 clone) | Santa Cruz (SC9081) | 1:400 |
| Mouse anti-Oct4 (C-10 clone) | Santa Cruz (SC5279) | 1:200 |
| Rabbit anti-Klf4 (H-180 clone) | Santa Cruz (SC20691) | 1:200 |
| Mouse anti-E-cadherin | Abcam (ab1416-500) | 1:100 |
| Rabbit anti-N-cadherin | Abcam (ab12221) | 1:800 |
| Rabbit anti-Sox2 | Millipore AB5603 | 1:500 |
| Mouse anti-NR3B2 (ESRRB) | R&D Systems (PP-H6705-00) | 1:1000 |
| Rabbit anti-TFE3 | Sigma (HPA023881) | 1:200; 1:500 |
| Rabbit anti-H3K27me3 | Millipore (07-449) | 1:4000 |
| Donkey anti-Mouse IgG Alexa 488 | Jackson Immuno (715-545-150) | 1:200 |
| Donkey anti-Mouse IgG RRX | Jackson Immuno (715-295-150) | 1:200 |
| Donkey anti-Mouse IgG Alexa 647 | Jackson Immuno (715-605-150) | 1:200 |
| Donkey anti-Rabbit IgG Alexa 488 | Jackson Immuno (711-545-152) | 1:200 |
| Donkey anti-Rabbit IgG RRX | Jackson Immuno (711-295-152) | 1:200 |
| Donkey anti-Rabbit IgG Alexa 647 | Jackson Immuno (711-605-152) | 1:200 |
| Donkey anti-Mouse IgM RRX | Jackson Immuno (715-295-020) | 1:200 |
| Goat anti-Rat IgM RRX | Jackson Immuno (112-295-075) | 1:200 |

Imaging, quantifications, and statistical analysis—Images were acquired with D1 inverted microscope (Carl Zeiss, Germany) equipped with DP73 camera (Olympus, Japan) or with Zeiss LSM 700 inverted confocal microscope (Carl Zeiss, Germany) equipped with 405 nm, 488 nm, 555 nm and 635 solid state lasers, using a 20× Plan-Apochromat objective (NA 0.8). All images were acquired in sequential mode. For comparative analysis, all parameters during image acquisition were kept constant throughout each experiment. Images were processed with Zen blue 2011 software (Carl Zeiss, Germany), and Adobe Photoshop CS4. X chromosome inactivation was assayed by presence of a condensed H3K27me3 staining focus per individual nucleus and quantified manually using ImageJ software (NIH) using.

Automated and quantitative image analysis for TFE3 localization—Single cell fluorescence intensity was analyzed by profile function in Zen Blue 2011 software. An in house developed automated segmentation protocol segments the cell's nucleus contained in each image. Nucleus was defined by intersection by both DAPI and OCT4 fluorescent illumination. This protocol is described in Rais et al (Rais Y., et al. Nature. 2013 Oct. 3; 502(7469):65-70. doi: 10.1038/nature12587. Epub 2013 Sep. 18) and deposited on the lab website [weizmann (dot) ac (dot) il/molgen/Hanna/Home (dot) html]. The segmented cells are then processed individually in order to estimate the ratio between intra-nucleus TFE3 intensity and cytoplasmic TFE3 intensity. Major steps in the processing: 1) Defining a bounding box containing the segmented nucleus and 10 pixels margin around the nucleus. 2) Estimating the average TFE3 intensity within nucleus mask. 3) Estimating the average TFE3 intensity within the bounding box but outside of the nucleus mask. Data were measured per sample from 200 cells obtained from at least four independent image fields. Distribution of intensity ratios for all cells is presented using box-plot. Box plot centers indicate the median value, and box edges indicate the 25th and 75th percentiles. P-values of distribution differences indicated in the graph were estimated with paired sample t-test.

Protein Western blotting analysis—Whole-cell protein extracts were isolated from human ES cells. Blots were incubated with the following antibodies in 3% BSA/TBST or PBST: pSTAT3 (9318; 1:1,000; Cell Signaling), STAT3 (C-20; 1:1,000; Santa Cruz), pβ-Catenin (9561; 1:750; Cell Signaling), β-Catenin (610153; 1:2,000; BD Biosciences), HSP90α (CA1016; 1:5,000; Calbiochem), pJNK (9251; 1:500; Cell Signaling), JNK (SC-571; 1:100; Santa Cruz), pp 38 (9215; 1:100; Cell Signaling), p38 (9212; 1:1,000; Cell Signaling), pERK (E4; 1:100; Santa Cruz), ERK1,2 (C-14; 1:100; Santa Cruz), KLF4 (AF3158; 1:200; R&D), OCT4 (H-134; 1:1,000; Santa Cruz), Nanog (397A; 1:1,000; Bethyl). Secondary antibodies were HRP-linked goat anti-mouse, goat anti-rabbit and rabbit anti-goat (1:10,000; Jackson). Blots were developed using ECL (Thermo).

Cross-species gene expression analysis—was conducted on human arrays described above and previously described mouse ESC and EpiSC gene expression datasets on an Agilent 4×44 k array platform (GSE15603; described in [Hanna, J. et al. *Cell Stem Cell* 4, 513-524 (2009)] containing 45,018 probes. Mouse data was processed as described above, resulting in 17,885 unique genes. Human-mouse orthology was downloaded from MGI [informatics (dot) jax (dot) org] containing 17,772 pairs of orthologous genes. Of these, 9,803 were mapped to the expression data of the present inventors. The expression values from mouse and human were transformed separately into relative abundance values [Liao, B. Y. *Molecular Biology and Evolution* 23, 530-540 (2005)]: For each gene, the relative abundance value is the expression value divided by the mean of expression values within the same gene across samples in the same species. The resulting expression matrix was subjected to hierarchical clustering (Spearman correlation, average linkage), as was the spearman correlation matrix of the samples. Coefficient of variance, a measure for noise defined as the standard deviation divided by the mean, was calculated separately for each of the two species and for the Naive and Primed states. The statistical significance between the distributions of coefficient of variance for the two states was calculated using single-tail t-test. Outliers were not shown in the plot, but were included in the statistical tests.

Chromatin Immuno-precipitation and Sequencing Library Preparation (for Examples 5-9 below)—Chromatin Immuno-precipitation followed by deep sequencing (ChIP-Seq) was measured for the following proteins—H3K4me3, H3K27me3, H3K4me1, H3K27Ac and H3K9me3—in mouse and human pluripotent cells (ESCs, EpiSCs and/or iPSCs) expanded in fetal bovine free and feeder free naive or primed/conventional growth conditions (FBS and feeder free expansion, on gelatin/vitronectin coated plates). Approximately 40*10$^6$ cells were cross-linked in formaldehyde (1% final concentration, 10 minutes at room temperature (RT)), and then quenched with glycine (5 minutes at RT). Fixed cells were lysed in 50 mM HEPES KOH pH 7.5, 140 mM NaCl, 1 mM EDTA, 10% Glycerol, 0.5% NP-40 alternative, 0.25% Triton supplemented with protease inhibitor at 4° C. (Roche, 04693159001), centrifuged at 950×g for 10 minutes and re-suspended in 0.2% SDS, 10 mM EDTA, 140 mM NaCl and 10 mM Tris-HCL. Cells were then fragmented with a Branson Sonifier (model S-450D) at −4° C. to size ranges between 200 and 800 bp, and precipitated by centrifugation. 10 µg of each antibody was pre-bound by incubating with Protein-G Dynabeads (Invitrogen100-07D) in blocking buffer (PBS supplemented with 0.5% TWEEN and 0.5% BSA) for 2 hours at room temperature. Washed beads were added to the chromatin lysate, and then incubated overnight. Samples were washed 5 times with RIPA buffer, twice with RIPA buffer supplemented with 500 mM NaCl, twice with LiCl buffer (10 mM TE, 250 mM LiCl, 0.5% NP-40, 0.5% DOC), once with TE (10 mM Tris-HCl pH 8.0, 1 mM EDTA), and then eluted in 0.5% SDS, 300 mM NaCl, 5 mM EDTA, 10 mM Tris Hcl pH 8.0 at 65° C. Eluate was incubated in 65° C. for 8 hours, and then treated sequentially with RNaseA (Roche, 11119915001) for 30 min and Proteinase K (NEB, P8102S) for two hours. DNA was purified with The Agencourt AMPure XP system (Beckman Coulter Genomics, A63881). Libraries of cross reversed ChIP DNA samples were prepared according to a modified version of the Illumina Genomic DNA protocol, as described previously [Blecher-Gonen, R., et al. Nat. Protoc. 2013 March; 8(3):539-54. doi: 10.1038/nprot.2013.023. Epub 2013 Feb. 21]. Briefly, ChIP DNA was ligated to Illumina adaptors and subjected to 14 cycles of PCR amplification. Amplified products between 200 and 800 bp were purified on a 2% agarose gel. Roughly 5 picomoles of DNA library was then applied to each lane of the flow cell and sequenced on Illumina Hiseq2000 sequencer according to standard Illumina protocols. The following antibodies were used for chromatin-IP experiments: Control IgG (ChIP grade, ab46540, Abcam), Anti-H3K4me3 (ab8580, Abcam), H3K27me3 (07-449, Millipore).

Chromatin IP Sequencing data analysis—The chromatin markers H3K27me3, H3K4me3, H3K4me1, H3K27Ac and H3K9me3 were measured in 4 different human pluripotent cell lines: C1, WIBR3, LIS2 (naive and primed), BGO1 and WIBR3-MBD3$^{mut}$ (naive). In addition, H3K27me3, H3K4me3, H3K4me1 and H3K27Ac were measured in mouse V6.5 naive and primed EpiSCs. H3K27me3 and H3K4me3 measurements in naive mouse ES were previously published by our group [Mansour, A. A. et al. Nature 488, 409-413 (2012)]. Each sample was accompanied by control sequencing experiment of whole cell extract input. We used bowtie software [Langmead, B., et al. Genome Biol. 2009; 10(3):R25] version 1.0.0 to align human reads to human reference genome hg19 (UCSC, February 2009) and mouse reads to mouse mm9 reference genome (UCSC, July 2007). The present inventors only considered reads that were uniquely aligned to the genome with up to a single mismatch, taking the single best match of each read. To rule out sequencing depth bias, the aligned sequences were down-sampled such that all samples had the same number of aligned reads. Human samples of the marks H3K4me3, H3K27me3, H3K4me1 and H3K27Ac, as well as whole-cell extract, were down-sampled to include 3,750,000 aligned reads. H3K9me3 samples were down-sampled to 5,900,000 aligned reads. Mouse samples of the marks H3K4me3, H3K27me3, H3K4me1 and H3K27Ac, were down-sampled to 3,420,000 aligned reads.

Chromatin profiles (FIGS. 70A-F and FIGS. 83A-D) were calculated over all RefSeq genes (n=43,463), and over developmental genes in the following way: (i) Read densities were calculated between 3 Kb upstream to TSS, and 3 Kb downstream to TES. (ii) Each gene was divided to bins of size 100, and the sum of reads in each bin was calculated. (iii) Average profile was calculated over all genes, where the gene body, which is of changing size, was represented by 100 quantiles. Genes of size less than 1 Kb were filtered out. (iv) Profiles of human samples represent mean and s.d. (error-bars) of 3 primed samples and 5 naive samples. Lastly, developmental genes were selected if they have a GO annotation that is related to development or differentiation. Using this criterion, the present inventors had 5922 RefSeq human developmental genes, and 420 RefSeq mouse developmental genes. Concrete examples of genes (FIGS. 71B-D) were processed and visualized using IGV software version 2.0 [Robinson, J. T. et al. Nat Biotechnol 29, 24-26 (2011)].

Accumulation of H3K9me3 marker on chromosome X (FIG. 76C) was also processed and visualized using IGV[69]. Here, each chromosome is represented by 100 random genes. To measure the distribution of H3K9me3 accumulation in chromosome X genes, RPKM (reads per kilobase per 5.9 million reads) was calculated for each gene (between 1 Kb upstream to TSS and TES). P-values between distributions were calculated with one-tail paired-sample t-test.

Enhancers were detected following the guidelines set by Rada-Iglesias et al. [Rada-Iglesias, A. et al. Nature 470, 279-283 (2011)]. Shortly, enhancers of type one are genomic intervals that contain H3K4me1 and H3K27Ac marks, do not contain H3K4me3 or H3K27me3 marks and are at least 500 bp away from any TSS. Enhancers of type two are genomic intervals that contain H3K4me1 and H3K27me3 marks, do not contain H3K27Ac mark, and are at least 500 bp away from any TSS. To find those enhancers the present inventors first identified enriched intervals of the marks above using MACS version 1.4.1 [Zhang, Y., Genome Biol. 2008; 9(9):R137]. The present inventors used sequencing of whole cell extract as control in order to define a background model. Duplicate reads aligned to the exact same location are excluded by MACS default configuration. Enriched intervals ("peaks") that overlap by at least 1 bp were considered as overlapping, and their union was defined as the enhancer interval, unless at least 10% of it overlapped with any of the excluded marks (e.g. H3K27me3 in the case of type one enhancers) or with TSS. To calculate the number of enhancers in human samples (FIGS. 84D-E) the present inventors only considered enhancers that are common to 2 primed cell lines C1 and WIBR3, or common to 4 naive cells lines: C1, WIBR3, WIBR3-MBD3$^{mut}$ and BGO1. The expression level of genes associated with enhancers (FIGS. 84G-F) was calculated by mapping each enhancer to the nearest gene (as long as it is at most 100 Kb away), converting it to Entrez Gene and taking its expression value from the raw gene expression dataset described above.

To detect bivalent genes the present inventors identified enriched intervals of H3K4me3 and H3K27me3 using MACS. Enriched intervals were mapped to genes if they overlapped a 3 kb interval before their Transcription Start Sites and after their Transcription End Site. Genes marked as bivalent if they had both H3K27me3 and H3K4me3. In human samples the present inventors required that the genes are bivalent in at least 2 cell lines. Distribution of H3K27me3 mark in genomic components was calculated by counting the number of H3K27me3 peaks in each component: promoter (6 Kb symmetric interval around TSS), Gene body (between 3 Kb downstream to TSS and TES), and intergenic (outside promoter and gene body). The peaks were divided to bins according to their height, calculated as RPKM.

DNA constructs inserted into human pluripotent cells. The pCAG-IresPuro or pCAG-flox-DsRed-IRES-Puro vectors (7) encoded the following inserts (which were cloned by either cohesive or blunt-end ligations in XhoI-NotI sites): Stat3-C (A662C and N664C mutations) (8), Stat3-Y705F (dominant-negative allele). Human Oct4 enhancer sequences [the Oct4DE- and Oct4PE-SV40-luciferase (Luc) constructs] were cloned into the pGL3-Promoter Vector (Promega) with the following primers: 5' hOcCT4PE KpnI: 5'-GGTACCG GATACTCAGGCCAGGCCCAGAAA-3' (SEQ ID NO:1); 3' hOCT4PE XhoI: 5'-CTCGAGTCCACA-GACCTCTGGCACT-3' (SEQ ID NO:2); 5' hOCT4DE KpnI: 5'-GGTACCCATTGAGTCCAAATCCTCTT-TACTAGGTG-3' (SEQ ID NO:3); 3' hOCT4DE XhoI: 5'-CTCGAGCTGAGGCTCATGCTGCTGG-3' (SEQ ID NO:4). Reporter constructs were used to determine the regulation pattern of Oct4 expression and were electroporated into $0.5\text{-}3\times10^{-6}$ cells along with the pRL-TK vector for normalization. Assays were performed 48 hours later using the Dual-Glo Luciferase Assay System (Promega). The basal activity of the empty luciferase vector was set as 1.0.

Generation of the NGFP1-Mbd3 KD cell line: NGFP1-Mbd3$^{KD}$ was established by infection and sub cloning of secondary NGFP1 iPSC line with a ShRNA pLKO-Tet-On vector (addgene) as previously described (Hanna et al. Nature 2009).

Immunocytochemistry and FACS Analysis—Cells were fixed in 4% paraformaldehyde in PBS and immunostained according to standard protocols using the following primary antibodies: SSEA1, SSEA4 and SSEA3 (Developmental Studies Hybridoma Bank); Tra-1-60 and Tra-1-81 (Millipore); SOX2 (R&D Systems); OCT3/4 (Santa Cruz Biotechnology); human NANOG (goat polyclonal; R&D Systems), mouse Nanog (polyclonal rabbit; Bethyl). Appropriate Alexa Fluor dye-conjugated secondary antibodies (Molecular Probes, Invitrogen) were used. For MHC class I staining of human cells, the present inventors used anti MHC class I antibody (BE pharmingen). For mouse cells, the present inventors used anti-mouse MHC class I H-2 Kb and H-2 Kd (eBioscience). Human Cells were stained with specific cell surface markers; SSEA4 conjugated APC or TRA-1-60(R) conjugated PE (R&D). Data were collected on BD FACS ARIA III and analyzed with Flowjow software.

DNA Methylation Analysis—DNA was proteinase K-treated and extracted, and 1 µg of DNA was subjected to conversion using the Qiagen EpiTect Bisulfite Kit. Promoter regions of OCT4 and XIST were amplified using previously described primers (Hanna et al., 2010b; Lengner C J, et al. (2010) Derivation of pre-x inactivation human embryonic stem cell line in physiological oxygen conditions. Cell. 2010 May 28; 141(5):872-83; Hockemeyer D, et al. (2008) A drug-inducible system for direct reprogramming of human somatic cells to pluripotency. Cell Stem Cell 3:346-353; and Soldner F, et al. (2009) Parkinson's disease patient-derived induced pluripotent stem cells free of viral reprogramming factors. Cell 136:964-977; each of which is fully incorporated herein by reference in its entirety). XIST forward primer (used on bisulfite treated DNA): 5'-taa att tta aat taa tta aat tat-3' (SEQ ID NO:106); XIST reverse primer (used on bisulfite treated DNA): 5'-tgt ttt aga aag aat ttt aag tgt aga ga-3' (SEQ ID NO:107). PCR products were cloned using the pCR2.1-TOPO vector and sequenced using the M13 forward primer. Method for LC-MS quantification of relative cytosine methylation: Mass spectrometry measurement of 5-methylcytosine (5mC) content was conducted (on human primed iPSCs/ESCs, and human naive iPSCs/ESCs expanded in a modified WIS-NHSM conditions which included PKCi and which did not include FGF2 and TGFB cytokines, as previously described [Leitch, H. G. et al. Naive pluripotency is associated with global DNA hypomethylation. Nat. Struct. Mol. Biol. 20, 311-316 (2013)] with a slight modification. Briefly, 250 ng genomic DNA from naive or primed pluripotent cells expanded without MEF feeder cells, was denatured by heating at 100° C. for 3 minutes. Samples were incubated with ¹⁄₁₀ volume of 0.1 M ammonium acetate, pH 5.3, and 2 Units (U) of nuclease P1 for 2 hours at 45° C. A ¹⁄₁₀ volume of 1 M ammonium bicarbonate and 0.002 units of phosphodiesterase I were added, followed by incubation for 2 hours at 37° C. Finally, samples were incubated for 1 hour at 37° C. with 0.5 U alkaline phosphatase. Samples were subsequently diluted in 2 mM ammonium formate, pH 5.5. The nucleosides were separated on an Agilent RRHD Eclipse Plus C18 2.1×100 mm 1.8 u column by using the HPLC system 1200 (Agilent) and were analyzed by using an Agilent 6490 triple quadrupole mass spectrometer. To calculate the concentrations of individual nucleosides within the samples analyzed, standard curves with known amounts of synthetic nucleosides were generated and used to convert the peak-area values to corresponding concentrations.

Reduced representation bisulfite sequencing (RRBS) libraries for genome wide sequencing profile of DNA methylation—RRBS libraries were generated as described previously with slight modifications [Smith, Z. D. et al. Nature 484, 339-344 (2012)]. Briefly, DNA was isolated from snap-frozen cell pellets using the Quick-gDNA mini prep kit (Zymo). Isolated DNA was then subjected to MspI digestion (NEB), followed by end repair using T4 PNK/T4 DNA polymerase mix (NEB), A-tailing using Klenow fragment (3'→5' exo-) (NEB), size selection for fragments shorter than 500-bp using SPRI beads (Beckman Coulter) and ligation into a plasmid using quick T4 DNA ligase (NEB). Plasmids were treated with sodium bisulfite using the EZ DNA Methylation-Gold kit (Zymo) and the product was PCR amplified using GoTaq Hot Start DNA polymerase (Promega). The PCR products were A-taild using Klenow fragment, ligated to indexed Illumina adapters using quick T4 DNA ligase and PCR amplified using GoTaq DNA polymerase. The libraries were then size-selected to 200-500-bp by extended gel electrophoresis using NuSieve 3:1 agarose (Lonza) and gel extraction (Qiagen). Libraries were pooled and sequenced on an Illumina HiSeq 2500 system. The sequencing reads were aligned to the Mouse Genome Build 37 (mm9) using Bismark. Methylation levels were calculated and averaged only for CpGs that were covered by 5 or more distinct sequencing reads across all libraries. The CpG content "experienced" by each CpG site was defined as the number of CpG dinucleotides found within a 500-bp window surrounding the site divided by the window size.

Protocol for Injecting Human and Primate Naive Pluripotent Stem Cells:

1. Dissect oviducts of hormone primed and mated B6D2F1 females X B6D2F1 males, and extract zygotes (as routinely done with mouse micro-manipulation).
2. Culture zygotes for 2 days in KSOM medium droplets (Zenith Biotech KSOMaa Evolve cat #ZEKS-050) covered with mineral oil at 37° C., 5% $O_2$ incubator, until they develop to morula stage.
3. Grow human naive cells to 70-90% confluence in NHSM medium on gelatin/DR4 irradiated MEF coated plates.
4. The day before cell harvesting add 10 µM ROCKi to the cells (in case not continuously used in the NHSM medium).
5. Trypsinize the cells for ~5 minutes with 0.05% trypsin, shake and pipette thoroughly to yield one cell suspension. Stop the reaction with DMEM+15% FBS and centrifuge at 1000 RPM for 3 Minutes. Aspirate and discard medium.

6. Resuspend cells in 900 μl NHSM medium, add 100 μl filtered FBS (to reduce stickiness of cells) and 10 μM ROCKi. Keep on ice until and during injections (very important). It is preferable to inject the cells as soon as they are harvested.
7. Inject 15-20 human naive cells to a mouse morula by using of Piezo (as routinely done with mouse ES injections).
8. After injection, incubate for 3-4 hours in KSOM droplets supplemented with 10 μM ROCKi covered with mineral oil.
9. After 3-4 hours transfer the morulas to KSOM droplets (without ROCKi) covered with mineral oil, incubate over night.
10. The next day, most morulas should develop to blastocysts. Transfer 15-20 blastocysts to uterus of pseudopregnant B6D2F1 female mice.

Example 1

Boosting Primed Stem Cells Reversion to Naive Pluripotency

The present inventors set out to test whether additional genetic manipulations may enable radically efficient and homogenous reprogramming towards ground state pluripotency. Recent studies have pointed out the importance of chromatin derepression in converting somatic cells into iPSCs (Mansour et al., 2012; Soufi et al., 2012). In addition, the ground state of pluripotency pertains an open chromatin configuration with reduced levels of repressive chromatin marks (Marks et al., 2012). Therefore, the present inventors aimed to conduct a loss of function screen for epigenetic repressor factors in an attempt to dramatically boost the efficiency of reprogramming to ground state pluripotency. The present inventors initially focused on reverting primed epiblast stem cells (EpiSCs) (Mansour et al., 2012), that in the absence of exogenous transcription factor over-expression, can convert within 7 days into naive pluripotent state in naive 2i/LIF (2i=PD0325901 ERK1/2 inhibitor and GSK3β inhibitor CHIR99021) growth conditions. The present inventors utilized an EpiSC line carrying a Nanog-GFP knock-in reporter that is active only in the naive ground state (Mansour et al., 2012), and applied siRNA screening in order to identify boosters of EpiSC reversion into Nanog-GFP+ naive pluripotent cells (FIGS. 1A-B, and 33A-G). While inhibition of DNA methylation and H3K27me3 by knockdown of Dnmt1 and EED/Suz12 respectively (Mikkelsen et al., 2008), increased epigenetic reversion efficiency, still only a minority of the donor cells turned on the Nanog-GFP reporter (FIG. 1A-B). Remarkably, the present inventors noted that Mbd3 inhibition using the Mbd3siRNA [mBD3HSS147581(3_RNAI) Invitrogen: AGGUCAAG-GGCAAGCCCGACCUGAA (SEQ ID NO:52); MBD3-HSS147581 (3_RNAI) Invitrogen-UUCAGGUCGGGC-UUGCCCUUGACCU; (SEQ ID NO:53)] dramatically increased the EpiSC reversion efficiency, where up to 80% of the transfected cells turned on Nanog-GFP in 2i/LIF conditions (FIGS. 1A-B) compared to <20% in control EpiSCs (FIGS. 1A-B). Such a dramatic effect was not observed with any of the other factors tested, including all other Mbd family members tested (FIGS. 1A-B).

Methyl-CpG-binding domain 3 (Mbd3; SEQ ID NO:7) is a structural component protein in the Nucleosome remodeling and Deacetylation (NuRD) complex, and together with Mbd 1, 2 and 4, was originally characterized as a protein containing a region with high homology to the methyl-CpG-binding domain (MBD) of MeCP2 (Kaji et al., 2007). Mbd2 and Mbd3 assemble into mutually exclusive distinct NuRD complexes (Le Guezennec, X. et al. Mol. Cell. Biol. 26, 843-851, 2006), which can mediate gene repression through histone deacetylation via histone deacetylase 1 (HDAC1) and 2, and chromatin remodeling ATPase activities through its chromodomain helicase DNA binding protein 3 (CHD3) (Mi2a) and CHD4 (Mi2b) subunits (Zhu et al., 2009).

Mbd3/NuRD preferentially binds and represses actively transcribed genes, and some of its components (e.g. Chd4) have also been implicated in serving as transcriptional activators at certain loci [Reynolds, N., et al., Cell Stem Cell, 2012, 10: 583-594; Günther, K. et al. Nucleic Acids Res. 2013, 41: 3010-3021].

To validate the siRNA screening results, the present inventors used Mbd3$^{+/+}$ and Mbd3$^{flox/-}$ ESCs (Kaji et al., 2007) and introduced Rosa26-CreER and a Nanog-GFP knock-in alleles by gene targeting (FIGS. 1C and 1H). EpiSCs were established from the latter engineered lines following microinjection into E3.5 blastocysts and rederivation at E6.5 from post-implantation epiblast (FIGS. 33B-G). In comparison to Mbd3$^{+/+}$ EpiSCs, Mbd3$^{flox/-}$ primed cells reverted with increased efficiency in 2i/LIF+tamoxifen conditions (FIGS. 1C and 1H), and showed homogenous Nanog-GFP reactivation, consistent with reversion to ground state pluripotency[36] (FIGS. 1D-L). Single cell clonal analysis for epigenetic reversion of EpiSCs (constitutively labeled with mCherry to control for plating efficiency) demonstrated 95% Nanog-GFP+ single cell reversion efficiency in Mbd3 depleted cells (FIGS. 1C and 1H). Importantly, Mbd3$^{flox/-}$ EpiSCs, that retain hypomorphic (~20%) Mbd3 protein expression (FIGS. 1I-J) (Kaji, K. et al. Nat Cell Biol 8, 285-292, 2006), also yielded reverted ESCs with >93% efficiencies (FIGS. 1C and 1H). Both reverted Mbd3$^{-/-}$ (after transgenic insertion of Mbd3 to rescue their differentiation deficiency (Kaji, K., et al. Development 134, 1123-1132, 2007; Kaji, K. et al. Nat Cell Biol 8, 285-292, 2006) and Mbd3$^{flox/-}$ cells can contribute to adult chimera formation (FIGS. 1I, J, K, L). Reconstitution of Mbd3 expression in Mbd3$^{-/-}$ and Mbd3$^{flox/-}$ EpiSCs inhibited reversion efficiencies in 2i/LIF down to <20% as typically observed in wild type cells (FIGS. 1C and 1H). These results directly demonstrate that reduction of Mbd3 protein levels renders nearly complete reversion of murine EpiSCs to ground state pluripotency.

The fact that lack of Mbd3 promotes reversion to pluripotency is seemingly contradictory to previous in vivo studies that had suggested that Mbd3 is essential for establishing the ground state of pluripotency after fertilization (Kaji et al., 2006; 2007). This conclusion was based on the fact that while Oct4+ cells could be observed in the inner cell mass of Mbd3$^{-/-}$ E3.5 embryos, Mbd3$^{-/-}$ ESCs could not be derived in vitro after explantation in serum/LIF derivation conditions (Kaji et al., 2006; 2007). However, already established ES cells, that can tolerate loss of Mbd3 following gene targeting, show a propensity for trophoblast differentiation in serum containing conditions (FIGS. 34A-B) (Zhu et al., 2009), which may have also underlied the previous technical inability to derive Mbd3$^{-/-}$ ESC in serum containing conditions. Thus, the present inventors revisited ESC derivation from Mbd3$^{-/-}$ E3.5 embryos in serum free 2i/LIF conditions [Ying, Q.-L. et al. The ground state of embryonic stem cell self-renewal. *Nature* 453, 519-523 (2008)], and indeed were able to isolate Mbd3$^{-/-}$ ESCs that expressed all pluripotency markers tested (FIGS. 34A-C, 2A-O). This indicates that Mbd3 is dispensable for establishing the ground state of pluripotency and mouse ESC derivation. Consistently, nuclear expression of Mbd3 protein is reduced after fertilization throughout pre-implantation development, and becomes readily detected only at the late blastocyst stage and post-implantation epiblast (FIGS. 1O-T, and FIGS. 35A-C, 36A-J). Nuclear Mbd3 protein expression is preserved after in vitro derivation in both naive and primed mouse pluripotent cells (FIGS. 36E-H). These results indicate that pre-implantation in vivo reprogramming and development are accompanied by depletion of Mbd3 expression, which gets re-expressed once pluripotency is established, consistent with a critical role for Mbd3 in allowing differentiation and exit from naive pluripotency [Reynolds, N., Stroumboulis, J., Behrens, A., Bertone, P. & Hendrich, B. NuRD suppresses pluripotency gene expression to promote transcriptional heterogeneity and lineage commitment. *Cell Stem Cell*, 2012, 10: 583-594]. Finally, the present inventors aimed to test the influence of reducing Mbd3 expression in reprogramming Oct4+ primordial germ cells into ES-like pluripotent embryonic germ (EG) cells. Typically, these cells are derived from E8.5 PGCs following explantation in ES growth conditions [Durcova-Hills, G., Tang, F., Doody, G., Tooze, R. & Surani, M. A. Reprogramming primordial germ cells into pluripotent stem cells. *PLoS ONE* 3, e3531 (2008); Leitch, H. G. et al. Embryonic germ cells from mice and rats exhibit properties consistent with a generic pluripotent ground state. *Development* 137, 2279-2287 (2010)]. Single cell sorted Mbd3$^{flox/-}$ Oct4-GFP+ E8.5 PGCs from chimeric animals, were proficient in forming EG cell colonies and lines (>95% efficiency), while PGCs isolated from chimeras generate from Mbd3$^{+/+}$ or Mbd3$^{flox/-}$ cells carrying an exogenous Mbd3 expressing transgene reprogrammed at less than 10% efficiency (FIGS. 1N-M). Collectively, these findings show that neutralizing Mbd3 expression facilitates access to ground state pluripotency from early embryonic Oct4 expressing cells.

Example 2

Alleviating Mbd3 Inhibition Facilitates Somatic Cell Reprogramming

The present inventors tested whether Mbd3 inhibition in somatic cells, that lack expression of endogenous pluripotency markers like Oct4 and are more developmentally restricted in comparison to EpiSCs and PGCs, facilitates their direct conversion to ground state pluripotency at efficiencies nearing 100%. Mbd3$^{+/+}$, Mbd3$^{flox/-}$ and Mbd3$^{-/-}$ fibroblasts carrying Oct4-GFP reporter were directly infected with O, K, S, M encoding moloney viruses, and Oct4-GFP reactivation was evaluated by flow cytometry. While Mbd3 depleted cells reprogrammed more efficiently in comparison to wild type cells, only 15% Oct4-GFP cells were obtained from Mbd3$^{flox/-}$ and Mbd3$^{-/-}$ depleted samples (FIG. 37A). This is consistent with a recent study reporting a modest up to 1.5% iPSC formation efficiency following Mbd3 knockdown [Luo, M. et al. NuRD Blocks ReprogAramming of Mouse Somatic Cells into Pluripotent Stem Cells. *Stem Cells* (2013)]. Infection with OKSM polycistronic vector [Sommer, C. A. et al. Induced pluripotent stem cell generation using a single lentiviral stem cell cassette. *Stem Cells* 27, 543-549 (2009)] dramatically increased Mbd3$^{flox/-}$ iPSC reprogramming towards 45%, likely due to enhanced transgene delivery per individual somatic cell (FIG. 37B). Given that Mbd3 depleted ESCs require serum free 2i/LIF growth conditions to optimally maintain their pluripotency (FIGS. 34A-B), the present inventors next tested whether the supplementation of a variety of exogenous factors that promote naive stem cell growth can attain maximal efficiency (FIG. 37C). Remarkably, by supplementing ES medium with 2i starting at 48 hours after transgene induction, and applying physiologic oxygen conditions, a dramatic reprogramming enhancement was obtained. Under these conditions, 95% of Mbd3$^{flox/-}$ and Mbd3$^{-/-}$ cells were Oct4-GFP positive at day 10, while only levels up to 18% were observed in control Mbd3$^{+/+}$ fibroblasts reprogrammed under identical growth and reprogramming conditions (FIG. 4A). To accurately evaluate reprogramming kinetics and efficiencies, the present inventors established "secondary reprogrammable" (Hanna et al., 2009b; Wernig et al., 2008) Mbd3$^{+/+}$ and Mbd3$^{flox/-}$ transgenic cell lines harboring a DOX inducible OKSM polycistronic cassette [Sommer, C. A. et al. Induced pluripotent stem cell generation using a single lentiviral stem cell cassette. *Stem Cells* 27, 543-549 (2009)], a constitutive nuclear mCherry marker (to allow their tracking as individual cells and control for plating efficiency), and an Oct4-GFP specific reporter (Boiani, M., Kehler, J. & Schöler, H. R. in METHODS IN MOLECULAR BIOLOGY, 2004, 254: 001-034) (FIGS. 3A-D and 3G). The latter cells were injected into host blastocyst and secondary reprogrammable MEFs were derived and utilized for reprogramming quantifications (Hanna et al., 2009b). Single cell sorting of mCherry+ Mbd3$^{flox/-}$ MEFs and subsequent reprogramming in 2i-LIF+DOX and 5% O$_2$ conditions reproducibly yielded 100% iPSC derivation efficiency by day 8. In wild type cells reprogrammed under identical conditions, no more than 20% of clones reactivated Oct4-GFP, while the majority of mCherry secondary fibroblasts cells had neither reactivated Oct4-GFP marker nor acquired ES-like morphology (FIG. 4B). Mbd3 depleted somatic cells had similar growth rates on DOX, and background viability levels compared to control wild type cells upon OSKM induction, thus excluding cell proliferation and apoptosis as potential factors underlying the observed differences in iPSC derivation efficiencies (FIGS. 5A-F). Radically high single cell reprogramming efficiency rates were obtained with multiple Mbd3$^{flox/-}$ secondary lines established harboring different OKSM integrations (FIG. 4B) and from a variety of adult progenitor and terminally differentiated cells obtained from NGFP1 iPSC line (Hanna, J. et al. *Nature* 462, 595-601, 2009) containing a DOX inducible Mbd3 specific shRNA (Mbd3-KD) allele and a Nanog-GFP knock in reporter (FIGS. 31A-E and 38A-B). All randomly tested clones stained positive for alkaline phosphatase (AP), Oct4 and Nanog pluripotency markers (FIGS. 4C-G). Mature teratomas and high contribution chimeras, some of which were germ-line transmission competent, were obtained from multiple iPSC clones (FIGS. 4C-G, and 39A-D), consistent with adequate reprogramming to ground state pluripotency.

The present inventors analyzed the reprogramming dynamics of "secondary" Mbd3$^{flox/-}$ and control Mbd3$^{+/+}$ fibroblasts by applying microscopic live imaging (Smith et al., 2010) (FIGS. 40A-E). Time-lapse measurements showed a dramatic increase in ES-like colony formation in Mbd3$^{flox/-}$ fibroblasts (FIGS. 4H-I). An in house developed algorithm that allows segmentation of single mCherry colonies and tracking of Oct4-GFP reactivation dynamics during reprogramming on clonal populations was applied (FIGS. 40A-E, 4H-I, 41A-D, 42A-E). By day 6 following DOX induction, >98% of Mbd3$^{flox/-}$ clonal populations reactivated the Oct4-GFP pluripotency marker, while only up to 15% efficiency was detected in control samples reprogrammed in identical growth conditions (including 2i/LIF and 5% pO2) (FIGS. 4J-O, 4Q, 4R). By day 6, approximately 85% of cells within each individual Mbd3$^{flox/-}$ clonal population became Oct4-GFP$^+$ cells, while <2% of cells within successfully reprogrammed Mbd3$^{+/+}$ clones turned on the Oct4-GFP marker (FIG. 4R). The latter unbiased quantitative analysis demonstrated a dramatically intra- and interclonal synchronized reactivation of Oct4-GFP occurring during a narrow window in Mbd3$^{flox/-}$ clonal populations at days 4.5-5.5 (FIGS. 4Q-R, and FIGS. 42A-E), and highlights a dramatic increase in reprogramming synchrony and efficiency following Mbd3 depletion in OSKM transduced somatic cells. Detection of Oct4-GFP by flow cytometry on polyclonal populations demonstrated similar kinetics for iPSC reprogramming (FIGS. 43A-B). Re-infection with lentiviruses encoding Mbd3, but not Mbd2, before day 5 of reprogramming had a profound inhibitory effect on iPSC generation from Mbd3$^{flox/-}$ MEFs, while reinfection after day 5 had a diminished effect (FIGS. 44A-B). The above kinetic analysis suggests that Mbd3 can inhibit reprogramming when introduced before final stages of reprogramming coinciding with endogenous Oct4/Nanog reactivation (Silva, J. et al. Cell 138, 722-737, 2009). However, once pluripotency is reestablished, Mbd3 presence is tolerated and does not compromise the maintenance of ground state pluripotency.

To evaluate the molecular extent of reprogramming in OSKM transduced Mbd3$^{flox/-}$ and Mbd3$^{+/+}$ somatic cells, the present inventors conducted global gene expression analysis on donor MEFs and at days 0, 4 and 8 following DOX induction without cell passaging, and compared them to iPSC and ESC lines. Only Mbd3$^{flox/-}$ somatic cells clustered separately from donor fibroblasts already at day 4 following DOX. Amazingly, by Day 8 they were transcriptionally indistinguishable from multiple ESC and subcloned established iPSC lines (FIG. 8R, FIGS. 45A-B, FIG. 7, and FIGS. 46A-E). Single cell RT-PCR analysis confirmed that only in Mbd3$^{flox/-}$ reprogrammed samples 100% (12/12) of single cells tested expressed all pluripotency markers recently shown to indicate successfully reprogrammed cells (Buganim, Y. et al. Cell 150, 1209-1222, 2012) (Sal14, Utf1, Esrrb, Sox2 and Nanog) (FIGS. 46D-E). Genome wide chromatin mapping for H3K27me3 (K27me3), H3K4me3 (K4me3) and H3K27acetyl (K27ac) by Chromatin Immunoprecipitation followed by sequencing analysis (Chip-Seq), also confirmed that by day 8, only Mbd3$^{flox/-}$ transduced MEFs had assumed ES-like chromatin profile (FIGS. 47A-B, 48A-C). Genome wide DNA methylation mapping by Reduced Representation Bisulfite Sequencing (RRBS) confirmed that iPSC-like methylation pattern can be seen in Mbd3$^{flox/-}$ polyclonal population sample only after 8 days of DOX treatment, but not in Mbd3$^{+/+}$ cells, consistent with results indicating CpG methylation loss predominantly occurring in later stages of successful reprogramming (Polo, J. M. et al. Cell 151, 1617-1632, 2012) (FIGS. 49A-B). Collectively, the above results indicate that Mbd3 depletion following OSKM induction in 2i/LIF conditions yields authentic molecular reestablishment of the ground state of pluripotency in the entire population of donor somatic cells and their progeny.

Following the depletion of Mbd3 expression, the present inventors were not able to isolate stable partially reprogrammed cells that did not reactivate Oct4/Nanog-GFP and could be stably expanded in vitro as typically can be obtained from OSKM transduced wild-type somatic cells (FIG. 8S, 8A-D, 8E) [Sridharan, R., et al., Cell 36(2):364-77 (2009); Mikkelsen, T. S. et al. Nature 454, 49-55 (2008); Costa Y., et al. NANOG-dependent function of TET1 and TET2 in establishment of pluripotency. Nature 495, 370-374 (21 Mar. 2013]. The residual 1-15% Oct4-GFP negative cells seen at day 6 in Mbd3$^{flox/-}$ cells (FIGS. 4Q and 4R), rapidly become GFP+ within 1-2 days of continued reprogramming (FIGS. 43A-B). The present inventors took 3 independent Mbd3$^{+/+}$ OSKM transduced partially reprogrammed lines derived by different reprogramming methods from either fibroblasts or B cells, and attempted to complete their reprogramming by Mbd3 inhibition. Remarkably, by introducing Mbd3 siRNA [mBD3HSS147581(3_RNAI) Invitrogen: 5'-AGGUCAAG-GGCAAGCCCGACCUGAA (SEQ ID NO:52); MBD3-HSS147581(3_RNAI) Invitrogen-5'-UCAGGUCGGGC-UUGCCCUUGACCU; (SEQ ID NO:53)], all 3 clones dramatically turned on Oct4-GFP or Nanog-GFP pluripotency markers following continued OSKM expression in 2i/LIF (FIGS. 8F-K and 50A-B). Finally, the expression of Mbd3 either in somatic epigenome or in pluripotent cells specifically prohibited the reprogramming of murine somatic cells to pluripotency via cell fusion (FIG. 5I) (Tada, M., et al. Current Biology, 11: 1553-1558, 2001). These results indicate that depleting Mbd3 expression opens a "gateway" to the ground state of pluripotency.

Phylogenetic analysis of Mbd3 and other NuRD complex proteins across 16 metazoan which span the entire Glade (from mammals to the simplest multicellular animal *T. adhaerens*) showed that Mbd3 and other NuRD complex proteins were found to have an ortholog in *T. adhaerens*, but not in yeast, which might imply on their appearance in the first multicellular animals alongside with Oct4 and developmental pluripotency (FIG. 9).

To functionally validate a conserved inhibitory role for MBD3 in human iPSC reprogramming (FIG. 9), the present inventors generated MBD3$^{flox/-}$ hESCs by gene editing with TALE nuclease effectors (FIG. 8L, and FIGS. 52A-C) (Hockemeyer, D. et al. *Nat Biotechnol* 29, 731-734, 2011), and validated hypomorphic MBD3 protein expression in a correctly engineered clone (FIGS. 8M-N). Fibroblasts were in vitro differentiated from MBD3$^{+/+}$ and MBD3$^{flox/-}$ hESCs and reprogrammed by OSKM transduction in recently described human naive pluripotency promoting conditions (WIS-NHSM conditions—that contain 2i/LIF+bFGF), and dramatically yielded >90% iPSC efficiency only from MBD3 depleted samples, as determined by SSEA4 and TRA1-60 staining at day 8 (FIG. 8O). Single cell reprogramming efficiency was tested following introducing OCT4-GFP knock-in reporter and a constitutive mCherry in MBD3$^{+/+}$ and MBD3$^{flox/-}$ hiPSC harboring DOX inducible OSKM factors. In vitro differentiated secondary fibroblasts from Mbd3$^{flox/-}$ cells reprogrammed at near 100% efficiency, while secondary fibroblasts differentiated and reprogrammed by same methods did not exhibit reprogramming efficiencies higher than 2% in WIS-NHSM conditions (FIG. 8O, FIGS. 53A-E). MBD3$^{flox/-}$ iPSCs were evident only after DOX induction, and this effect was inhibited by Mbd3 overexpression, thus ruling out contamination with residual primary iPSCs as a source for the high reprogramming efficiencies observed (FIG. 8O). Furthermore, dramatically increased human iPSC formation was obtained by applying MBD3 siRNA [mBD3HSS147581(3_RNAI) Invitrogen: AGGUCAAGGGCAAGCCCGACCUGAA (SEQ ID NO:52); MBD3HSS147581 (3_RNAI) Invitrogen-UUCAGGUCGGGCUUGCCCUUGACCU; (SEQ ID NO:53)] at days 2 and 4 following DOX induction in MBD3$^{+/+}$ OSKM transgenic secondary fibroblasts (FIGS. 10A-D). MBD3 siRNA treatment allowed reproducible generation of human iPSCs from adult human patient specific fibroblasts only after 2-3 rounds of OSKM+ LIN28 mRNA transfection [Warren, L. et al. Highly Efficient Reprogramming to Pluripotency and Directed Differentiation of Human Cells with Synthetic Modified mRNA. *Cell Stem Cell* (2010)] and subsequent colony detection and isolation at day 8 (FIGS. 54A-G). Taken together, these results demonstrate that inhibiting MBD3 alleviates predominant roadblocks for direct human somatic cell reprogramming to pluripotency by OSKM, and thus inhibition of MBD3 can be used in a new technology platform for boosting iPSC formation. Importantly, MBD depleted human pluripotent stem cells have a dramatic round mouse-ESC like morphology and grow homogenously (FIGS. 8P-Q). These results indicate that Mbd3 inhibition might further improve WIS-NHSM naive growth conditions (described herein).

Example 3

Numerical Description of OSKM Reprogramming Following MBD3 Depletion

The present inventors next sought to quantitatively characterize the reprogramming latency distribution for both $Mbd3^{+/+}$ and Mbd3 samples, and compare it to known deterministic behavior. To do so, the present inventors applied a previously described approach for monoclonal murine Pre-B cell weekly follow-up for reactivation of Nanog-GFP (FIG. 31A) (Hanna, J. et al. Nature 462, 595-601, 2009). A secondary OSKM transgenic NGFP1-iPSC line was rendered transgenic for a DOX inducible Mbd3 knockdown (NGFP1-Mbd3$^{KD}$) (FIGS. 5B, 5C and 5D). Indeed, only NGFP1-Mbd3$^{KD}$ derived monoclonal B cell populations converted into Nanog-GFP+ iPSCs at day 7 at 100% efficiency (FIGS. 31B-C). Subsequently, during the first 10 days of reprogramming the present inventors conducted daily Nanog-GFP detection on polyclonal NGFP1-control and NGFP1-Mbd3$^{KD}$ B cell populations. The latter cells showed a dramatic increase in reprogramming and followed similar kinetics to those measured in Mbd3$^{flox/-}$ MEFs, as measured by microscopic live imaging (FIGS. 55A-B). The present inventors next tested whether Mbd3$^{KD}$ cell reprogramming behaves like a deterministic function. In this case, the present inventors expect all cells to become pluripotent at the same time following DOX induction. Such deterministic behavior is well approximated by a step function with 0% reprogramming before a fixed deterministic time and 100% iPS formation afterwards. Fitting the clonal cells reprogramming dynamics to such deterministic step-function revealed a tight fit ($R^2>0.9$, Chi$^2=52$) of Mbd3$^{KD}$ cells, but not of control Mbd3$^{+/+}$ cells ($R^2=0.55$, Chi$^2=405$) (FIGS. 31D-E). Despite the observed similarity to a deterministic behavior, variability was still evident in the Mbd3 sample under the optimized condition devised herein. Thus, the present inventors sought to quantify and compare the variability detected in the reprogramming latency measurements in both Mbd3$^{+/+}$ and Mbd3$^{KD}$ samples, and further compare it to the inherent measured cell cycle variability (Hanna, J. et al. Nature 462, 595-601, 2009). For this purpose the present inventors used two modeling schemes. First, the present inventors fitted the observed reprogramming latency to Gaussian distribution: The present inventors estimated the coefficient of variation (CV=std/mean) of each sample, and found that while the coefficient of variation in the Mbd3$^{+/+}$ sample is 0.5, the Mbd3 coefficient of variation was reduced to 0.09, tightly proximal to the cell cycle estimated coefficient of variation (0.08) (FIGS. 56A-F and 57A). Second, the present inventors sought to use a dynamic stochastic model to estimate reprogramming variability. The present inventors used a Brownian motion (BM) model (FIG. 57C) and found that indeed Mbd3$^{KD}$ and cell cycle measurements showed the same dynamic variation, while Mbd3$^{+/+}$ samples showed higher variability (FIG. 57B and general materials and experimental methods above). To further support reduction in rate-limiting barrier(s) upon Mbd3 depletion, the present inventors modeled the dynamics of the OSKM reprogramming process using multi-step Markov chain model (Phase-Type (PH) modeling (Bolch, G., Greiner, S., de Meer, H. & Trivedi, K. S. Queueing networks and Markov chains: modeling and performance evaluation with computer science applications. WILEY, Second Edition, 2006) (FIGS. 55C-D, 58A-D, 59A-G). Finally, without being bound by any theory, the present inventors hypothesized that the reduction in ratelimiting barriers in Mbd3$^{KD}$ samples may reduce reprogramming variability to variability explained by cell cycle alone. For this purpose the present inventors fitted the observed reprogramming latency to a cell cycle model that captures the required reprogramming duration (General materials and experimental methods above and data not shown) (Hanna, J. et al. Nature 462, 595-601, 2009; Duffy, K. R. et al. Activation-Induced B Cell Fates Are Selected by Intracellular Stochastic Competition. *Science* 335, 338-344, 2012). Specifically, the present inventors estimated the number of generations according to the reprogramming duration, and fit the cell cycle time distribution to the observed reprogramming latency. By applying this method, the present inventors obtained a profound fit ($R^2=0.999$) between the Mbd3$^{KD}$ dynamic and cell cycle model, but not in the control Mbd3$^{+/+}$ dynamics ($R^2=0.73$) (FIGS. 57D-E). Altogether these results consistently show a reduction in reprogramming variability and proximity to deterministic dynamic behavior upon Mbd3 depletion, where the remaining variability can be accounted for by the inherent cell cycle variability. Importantly, these findings do not exclude the existence of alternative pathways that can further accelerate or improve the deterministic reprogramming dynamics observed in Mbd3 depleted cells following OSKM induction and/or enable deterministic induction of pluripotency without manipulating Mbd3 expression or activity (Maekawa, M. et al. Nature 474, 225-229, 2011). Further, these results show a deterministic trajectory for successfully obtaining iPSCs based on measuring reactivation of endogenous pluripotency genes as a final outcome.

Example 4

Mechanisms for Mbd3 Inhibition of IPSC Reprogramming by OSKM

Recent work has shown that the pluripotency factor Zfp281 directly recruits Mbd3/NuRD to Nanog promoter and repress its expression (Fidalgo et al., 2012), and that inhibition of Zfp5281 led to a modest 2-fold increase in iPSC formation efficiency (Fidalgo et al., 2012). Given that Mbd3 inhibition conducted here led to a much more pronounced effect, in comparison to Zfp281 depletion, this has raised the hypothesis that Mbd3 may be acting more globally in pluripotency regulation by directly interacting with many other pluripotency promoting factors. The present inventors show that Flag-Tagged Oct4, Klf4, and Sox2 specifically co-immunoprecipitated with Mbd3 following overexpression in 293HEK cells (FIGS. 11A-D, and FIGS. 11I-L). Importantly, Mbd2 did not directly interact with all other pluripotency factors tested (FIGS. 11E-H, and FIGS. 11M-P). The above could explain the distinct influence of Mbd2 and Mbd3 on reprogramming to ground state pluripotency (FIGS. 1A-B). Collectively, these results support a critical role for pluripotency factor and Mbd3 direct interaction in inhibiting iPSC formation by OSKM.

Mbd3 inhibition was a key and dominant contributor to the radically efficient progression towards pluripotency reported herein. Thus the present inventors aimed to define the mechanisms of Mbd3 inhibition of iPSC reprogramming. Inhibiting Mbd3 expression was not sufficient to induce iPSC formation in the absence of exogenous OSKM overexpression in somatic cells (even in NPCs that can be reprogrammed with Oct4 expression alone) (Kim, J. B. et al. Nature 461, 649-653, 2009) (FIG. 38A). Mbd3 did not replace exogenous OSK expression to give rise to iPSCs (FIG. 38B). The presence of exogenous c-Myc was essential to obtain iPSCs at 100% efficiency following factor transduction (FIG. 38B). Mbd3 depletion without OSKM expression does not independently lead to endogenous reactivation of bona fide pluripotency genes (FIG. 38A). Further, Mbd3 inhibitory effect on pluripotency could not be predominantly attributed to its ability to repress endogenous Nanog directly or indirectly [Luo, M. et al. NuRD Blocks ReprogAramming of Mouse Somatic Cells into Pluripotent Stem Cells. *Stem Cells* (2013); Fidalgo, M. et al. Zfp281 mediates Nanog autorepression through recruitment of the NuRD complex and inhibits somatic cell reprogramming. *Proc. Natl. Acad. Sci. U.S.A.* 109, 16202-16207 (2012)], since ectopic Nanog overexpression together with OSKM resulted in modest enhancement in iPSC formation and the process remained to follow a stochastic course (Hanna, J. et al. *Nature* 462, 595-601, 2009) (FIG. 31A and FIG. 8E). Recent work has shown that the pluripotency factor Zfp281 directly recruits Mbd3/NuRD to repress Nanog promoter activity, and that inhibition of Zfp281 led to a modest 2 fold increase in iPSC formation efficiency (Fidalgo, M. et al. Proc. Natl. Acad. Sci. U.S.A. 109, 16202-16207, 2012). Given that, in comparison to Zfp281 depletion or Nanog over-expression (Fidalgo, M. et al. Proc. Natl. Acad. Sci. U.S.A. 109, 16202-16207, 2012), Mbd3 inhibition led to a radically more pronounced effect, raised the hypothesis that Mbd3 may be acting more globally in reprogramming regulation by directly interacting with other critical pluripotency promoting factors. The present inventors established that Flag-Tagged Oct4, Klf4, Sox2 and c-Myc specifically co-immunoprecipitated with Mbd3 following exogenous overexpression in HEK293 cells (FIGS. 32A-B). Reciprocal experiments showed that Flag-tagged Mbd3 specifically co-immunoprecipitated with Oct4, Sox2, Klf4 and c-Myc, but not Nanog (FIGS. 60A-B). OSKM specifically co-immunoprecipitated with Mbd3/NuRD components in MEF cells undergoing reprogramming following 3 days of OSKM induction (FIG. 60C). Mbd3$^{-/-}$ ESCs expressing Flag-tagged Mbd3 transgene validated direct interaction of Mbd3 with Sal14 reprogramming factor, that is known to get reactivated later in the reprogramming process and cooperate with OSKM in finalizing the reprogramming process (FIG. 61A) (Buganim, Y. et al. Cell 150, 1209-1222, 2012; Mansour, A. A. et al. *Nature* 488, 409-413, 2012). These interactions were mediated via MBD domain of Mbd3, and defined deletions introduced in MBD domain abrogated co-immunoprecipitation of Mbd3 with OSKM reprogramming factors (FIGS. 62A-C). As previously seen in a variety of somatic and cancer cell lines (Le Guezennec, X. et al. Mol. Cell. Biol. 26, 843-851, 2006), Mbd2 and Mbd3 do not co-localize to the same NuRD complexes as validated by co-immunoprecipitation experiments (FIGS. 61A-C). The above explains, at least in part, the lack of dramatic influence for perturbing Mbd2 expression on reprogramming to ground state pluripotency (FIGS. 1A-B, 1A and 44A-B).

Consistent with the direct protein interactions for Mbd3/NuRD complex with OSKM reported above, genome wide ChIP-seq analysis of Mbd3 binding in DOX induced wild type MEFs, identified a global increase in Mbd3 recruitment and binding following OSKM induction (1177 binding regions in MEF compared to 8657 following OSKM induction). Only after DOX induction, Mbd3 bound genes are enriched for targets of Klf4, Oct4, Sox2 and Esrrb ($p<10^{-22}$) as well for genes with H3K4me3 active chromatin mark in ES cells ($p<10^{-38}$) (FIGS. 32C-D). Motif search analysis in Mbd3 binding locations identified 30 motifs (p<0.001), where the motifs of Klf4, Sox2, and Oct4 are among the top six ($p<10^{-30}$) (FIG. 63). Importantly, in somatic MEFs prior to OSKM induction, Mbd3 is not localized to pluripotency factor target genes (FIGS. 32C-D). NuRD component Chd4 was similarly recruited to downstream targets only after DOX induction, indicating NuRD recruitment with Mbd3 after DOX induction (FIGS. 32C-D). Chd4 localization to downstream targets of OKSM was diminished in Mbd3 depleted cells and its knockdown in Mbd3$^{+/+}$ MEFs undergoing reprogramming significantly enhanced iPSC formation (up to 50% Oct4-GFP+ cell on day 8 (FIG. 63), thus supporting the notion that Mbd3 exerts its inhibitory function on reprogramming predominantly through NuRD complex dependent functions. Notably, inhibition of Chd4 had a relatively milder effect on boosting iPSC reprogramming, in comparison to Mbd3 depletion, possibly because Chd4 (also known as Mi2b) is also found in other protein complexes whose influence on pluripotency remains to be defined (e.g. Ep300 activator complex (Reynolds, N., Development 140, 505-512, 2013). However, without being bound by any theory, the present inventors cannot exclude additional NuRD independent inhibition for Mbd3 on reprogramming.

Transcription level of Mbd3 target genes following 4 days of DOX was significantly upregulated following DOX in Mbd3 depleted samples (FIG. 32E), consistent with predominant function of Mbd3/NuRD complex as a repressor of pluripotency gene network during reprogramming. Chromatin of Mbd3 direct targets was significantly more active and open in Mbd3 depleted samples during reprogramming, including statistically significant higher levels of H3K4me3 and H3K27ac, and reduced H3K27me3 repressive chromatin mark (FIG. 32F). Further, Mbd3 depletion allowed enhanced exogenous Oct4 binding to targets of Mbd3 at day 4 following DOX ($p<10^{-16}$, FIG. 32F). Known OSKM target genes that get reactivated during iPSC formation were found to be significantly upregulated at 4 days in Mbd3 depleted cells, and retained an open chromatin confirmation in comparison to control Mbd3$^{+/+}$ cells (FIGS. 65A-E). Similar gene expression and chromatin pattern were observed with the shared targets of Mbd3 and the reprogramming factors (OSKM) (FIGS. 66A-J). Mbd3 mutants with compromised ability to directly interact with OSKM reprogramming factors were deficient in reducing reprogramming efficiency of Mbd3$^{flox/-}$ somatic cells, supporting the notion that direct OSKM-Mbd3 interactions are important for inhibiting iPSC formation (FIG. 32G). Importantly, the present inventors noted that a minimum 5-day exogenous transgene (DOX) induction was similarly required to obtain iPSCs from Mbd3$^{+/+}$ and Mbd3$^{flox/-}$ cells (FIGS. 67A-D), and that the expression of OSK interacting partners that positively propel reprogramming to pluripotency (like Utx and Wdr5) is also essential for iPSC formation in Mbd3 depleted cells (FIGS. 67B-D). Collectively, these results establish a paradigm where exogenous OSKM interact with multiple epigenetic complexes that de-repress pluripotency promoting gene networks (e.g. Wdr5 or Utx containing complexes) (Ang, Y.-S. et al. Cell 145, 183-197, 2011; Mansour, A. A. et al. Nature 488, 409-413, 2012), they also directly assemble with the Mbd3/NuRD repressor complex. As a result, Mbd3/NuRD is directly recruited to downstream OSKM target genes that are essential for propelling the reprogramming process, and potently counteracts their robust reactivation (Han, J. et al. Nature 463, 1096-1100, 2010; Doege, C. A. et al. Nature 488, 652-655, 2012; Chia, N.-Y. et al. Nature 468, 316-320, 2010). In the absence of Mbd3 inhibitory effect, OSKM interactions with pluripotency promoting epigenetic regulators predominates functionally, and drive uninterrupted progression of direct reprogramming to pluripotency.

Analysis and Discussion

Mbd3 and Deterministic Reprogramming to Ground State Naive Pluripotency

Here the present inventors identify the specific of Mbd3/NuRD repressor complex as major barrier preventing epigenetic reversion of EpiSCs, PGCs and somatic cells to ground state pluripotency by defined signaling and transcriptional input. This complex is evolutionary conserved since the emergence of multicellularity and counteracts the reprogramming potential of a variety of pluripotency factors that cooperatively establish the ground state of pluripotency. Mbd3 repression is tolerated once pluripotency is established, however when trying to enter this state the inhibitory function become dramatically rate limiting and preventing majority of cells assume the pluripotent state. Collectively, these findings show that direct reprogramming to pluripotency need not be stochastic, and that OSKM and other reprogramming methods applied thus far are reductionist. It would be interesting to investigate whether there are alternative pathways that can enable deterministic induction of pluripotency and/or further accelerate the deterministic reprogramming dynamics observed in Mbd3 depleted cells following OSKM induction. It will also be of great interest to determine whether and how is Mbd3 neutralized in vivo during pre-implantation and germ-line reprogramming.

The ability to directly reprogram somatic cells into iPSCs has boosted the scientific interest to comprehend the dynamics of epigenetic reprogramming at high resolution, and to accurately define the temporal regulation between transcription factors and chromatin remodelers throughout the entire process of iPSC formation. Despite of the great progress achieved in the field, the present inventors are still highly limited in comprehending the molecular mechanisms, dynamics and interdependence between different layers of chromatin regulation, and how they lead to the establishment of distinct pluripotent states. The latter directly results from the inefficiency and stochasticity of currently devised reprogramming methods together with the difficulty to prospectively isolate the rare cells that correctly and rapidly reprogram into iPSCs. While the study of intermediate populations has provided important insights into mechanisms of pluripotency reprogramming, such cells overly great molecular heterogeneity and retain randomness in progressive towards pluripotency. The near deterministic reprogramming strategies reported herein can allow dissection of authentic molecular events accompanying a more synchronized and non-saltatory progression pattern towards iPSCs, which is critical for molecular deciphering of the black box of reprogramming.

The present inventors show that the stochastic and a-synchronized trajectory of direct reprogramming by OSKM (Hanna, J. H., et al., Cell, 143, 508-525, 2010) can be coaxed to become radically efficient and deterministic with modified reprogramming approaches. The present inventors highlight Mbd3/NuRD repressor complex, which is naturally depleted during normal pre-implantation development (FIGS. 1O-T), as a predominant barrier preventing epigenetic reversion of EpiSCs, PGCs and somatic cells to ground state pluripotency by defined signaling and transcriptional input. A variety of critical reprogramming factors directly interact and recruit Mbd3/NuRD complex, and thus form a highly potent negative regulatory complex that restrains pluripotency gene reactivation throughout the process. Alleviating this inhibitory pathway facilitates direct and synchronized conversion into iPSCs by defined transcriptional and signaling input (FIG. 32H). It will be of great interest to explore whether direct reprogramming in the absence of Mbd3 repression improves the quality of reprogrammed cells and reduces the frequency of obtaining aberrantly reprogrammed iPSCs (Zwaka, T. P. Stem cells: Troublesome memories. Nature. 2010, 467: 280-1). Finally, the inefficiency and stochasticity of currently devised reprogramming methods together with the difficulty to prospectively isolate the rare cells that correctly and rapidly reprogram into iPSCs, have restricted the ability to characterize the temporal regulation between transcription factors and chromatin remodelers throughout the entire process of iPSC formation (Buganim, Y. et al. Cell 150, 1209-1222, 2012). While the study of intermediate populations (Hanna, J. et al. Nature 462, 595-601, 2009) has provided important insights into mechanisms of pluripotency reprogramming, such cells overly great molecular heterogeneity and retain randomness in progressing towards pluripotency (Polo, J. M. et al. Cell 151, 1617-1632, 2012). The deterministic reprogramming strategy reported herein may allow dissection of authentic molecular events accompanying a more synchronized and non-saltatory progression pattern towards iPSCs, which is critical for biochemical and functional deciphering of the black box of reprogramming.

Example 5

Chemically Defined Growth Conditions for Deriving Transgene Independent and Indefinitely Stable Human Naive Pluripotent Cells The recent isolation of naive pluripotent stem cells from non-obese diabetic (NOD) mouse strains and rats (Hanna et al., 2009a), previously considered "non-permissive" for ESC derivation, has been achieved by supplementation with small molecules or growth factors that alleviate inhibitory differentiation cues and/or reinforce key signaling pathways that stabilize core transcriptional circuitry of naive pluripotency (Hanna et al., 2010b).

Defining Human Naive Pluripotency Growth Conditions

To define conditions for expanding human naive pluripotent cells that are independent of ERK1/2 signaling, the present inventors first utilized a previously described "secondary" human female C1.2 iPSC line containing Doxycycline (DOX) inducible lentiviral transgenes encoding OCT4 (SEQ ID NO:54 protein), SOX2 (SEQ ID NO:56 protein) and KLF4 (SEQ ID NO:58 protein) reprogramming factors (Hanna, J. et al. Proc. Natl. Acad. Sci. U.S.A. 107, 9222-9227, 2010; Chia, N.-Y. et al. Nature 468, 316-320 (2010); Lengner, C. J. et al. Cell 141, 872-883 (2010); Tomoda, K. et al. Cell Stem Cell 11, 91-99 (2012); Bernstein, B. E. et al. Cell 125, 315-326 (2006); Guenther, M. G. et al. Cell Stem Cell 7, 249-257 (2010)], and a constitutively active lentivirus encoding the reverse tetracycline transactivator (FUW-M2rtTA) (FIGS. 12A-C). This clone was targeted with an OCT4-GFP-2A-PURO knock-in reporter construct [Takahashi, K. & Yamanaka, S. *Cell* 126, 663-676 (2006); Hockemeyer, D. et al. *Nat Biotechnol* 29, 731-734 (2011)] to track their pluripotency maintenance (FIGS. 12A-C). As previously established [Nichols, J. & Smith, A. *Cell Stem Cell* 4, 487-492 (2009); Hanna, J. et al. *Proc. Natl. Acad. Sci. U.S.A.* 107, 9222-9227, 2010] exogenous expression of reprogramming factors transgenes by DOX supplementation, allows maintaining cells that are morphologically similar to mESCs, while retaining approximately 60% OCT4-GFP+ cell fraction in 2i/LIF conditions (FIG. 12D). Notably, SOX1 neural marker was highly expressed, indicating that these previously described cells are aberrantly stabilized and retain a propensity for differentiation in 2i/LIF+DOX (FIG. 72A). The DOX-dependent C1.2 hiPSC line was utilized to screen for additional compounds and/or growth factors [Ying, Q.-L. et al. Nature 453, 519-523 (2008); Hanna, J. et al. Proc. Natl. Acad. Sci. U.S.A. 107, 9222-9227, 2010; Tiwari, V K. et al. Nat Genet. 2011, 44(1):94-100; De Los Angeles A., et al. Curr. Opin. Genet. Dev. 22, 272-282 (2012); L1, W. et al. Cell Stem Cell 4, 16-19 (2009)] that, upon DOX withdrawal, could stabilize C1.2 hiPSCs in 2i/LIF indefinitely with homogenous OCT4-GFP expression (in nearly 100% of the cells) (FIGS. 12A-C).

While C1.2 cells rapidly differentiated in 2i/LIF only conditions, the combined action of 16 factor conditions (16F—divided into Pool 1 and Pool 2 subgroups) attenuated the differentiation propensity and allowed retaining 32% of OCT4-GFP+ cells as measured at day 14 after DOX withdrawal (FIG. 12D). This indicated that the 16F combination contains factors that cooperatively promote human pluripotency maintenance in 2i/LIF conditions. When Pool 2 components were removed (FIG. 12D), OCT4-GFP+ cell fraction significantly increased relative to 16F combination, suggesting that Pool 2 contained factors that were negatively influencing GFP+ cell maintenance (FIG. 12D). Without being bound by any theory, the present inventors hypothesized that FGF and TGFβ pathway inhibition was detrimental to growing human pluripotent cells in 2i/LIF conditions. FGF2 and TGFβ have an evolutionary divergent function in promoting pluripotency in humans by inducing KLF4 and NANOG expression in hESCs [Hanna, J. et al. *Proc. Natl. Acad. Sci. U.S.A.* 107, 9222-9227, 2010; De Los Angeles, A., et al. Dev. 22, 272-282 (2012); L1, W. et al. Cell Stem Cell 4, 16-19 (2009); Pribluda, A. et al. Nat Biotechnol 30, 247-249 (2012); Nichols, J. & Smith, A. Pluripotency in the embryo and in culture. Cold Spring Harb Perspect Biol 4, a008128 (2012); Roode, M. et al. Dev. Biol. 361, 358-363 (2012); Rad, R., et al., Proc Natl Acad Sci USA. 2011, 108(45):18283-8; Xu, Y. et al. Proc. Natl. Acad. Sci. U.S.A. 107, 8129-8134 (2010); Buecker, C. et al. Cell Stem Cell 6, 535-546 (2010)], but not in mEpiSCs, where they play an opposite role and promote murine pluripotency priming. Further, applying FGF receptor inhibition on human developing blastocysts did not prevent ICM differentiation, further suggesting a divergent role for FGF signaling in influencing pluripotency in humans (Roode, M. et al. *Dev. Biol.* 361, 358-363 (2012); Hanna, J. et al. *Proc. Natl. Acad. Sci. U.S.A.* 107, 9222-9227, 2010). Indeed, removing both TGFβ and FGF receptor inhibitors recapitulated the phenotype obtained when removing DOX and Pool 2 components (FIG. 12D), and further suggesting that Pool 2 components were not required to promote the maintenance of GFP+ cells in 2i/LIF containing conditions. Moreover, Pool 1 components supplemented with exogenous FGF2 and TGFβ cytokines resulted in homogenous OCT4-GFP in >95% of cells independent of DOX in 2i/LIF containing conditions (FIG. 12D). The present inventors then tested which of the Pool 1 components were essential to maintain OCT4-GFP+ DOX independent C1.2 hiPSCs, and found that 2i/LIF, p38i, JNKi together with FGF2 and TGFβ1 cytokine supplementation were essential to maintain exogenous transgene-independent GFP+ C1.2 clones on feeder free gelatin/vitronectin coated plates (FIG. 12S). Secondary optimization identified Rho-associated coiled-coil kinases (ROCK) Watanabe, K. et al. A ROCK inhibitor permits survival of dissociated human embryonic stem cells. *Nat Biotechnol* 25, 681-686 (2007)) and Protein Kinase C (PKC) (Rajendran, G. et al. Inhibition of protein kinase C signaling maintains rat embryonic stem cell pluripotency. *Journal of Biological Chemistry* 288, 24351-24362 (2013)) inhibitors as optional boosters of cell viability, and resulted in optimized chemically defined conditions termed WIS-NHSM (Weizmann Institute of Science—Naïve Human Stem cell Medium) (FIG. 12U). This optimized chemically defined conditions, termed "WIS-NHSM" (FIGS. 12G, 12T, 72B, 72C and 72D), enabled expansion of karyotypically normal and GFP+ C1.2 hiPSCs for over 50 passages (FIGS. 12J-K, 12V). Remarkably, human pluripotent cells grown in WIS-NHSM medium have domed-shaped colonies resembling murine naive cells, thus the present inventors refer to the selected cells as naive human iPSCs and ESCs, as the present inventors systematically validate below the molecular evidence for this claim.

Example 6

Derivation of Ground State Naive Human ESCs

New human embryo derived naive ESCs—The present inventors next examined whether WIS-NHSM conditions allow derivation of new hESC lines from the ICM of human blastocysts [Lengner, C. J. et al. *Cell* 141, 872-883 (2010); Roode, M. et al. *Dev. Biol.* 361, 358-363 (2012)]. In contrast to the lack of derivation of any cell lines from blastocysts explanted in 2i/LIF/FGF2 conditions (0% efficiency, n=82), human blastocysts plated on mouse embryonic fibroblast (MEF) coated plates and WIS-NHSM medium successfully generated domed cell outgrowths following only 6-8 days of plating (FIGS. 13N-O). ICM derived outgrowths were then trypsinized and passaged and the present inventors were able to establish and characterize 4 newly derived stem cell lines termed LIS1, LIS2, WIS1 and WIS2 hESCs in naive condition at 36% efficiency (n=11 embryos) versus 9.5% efficiency in conventional/primed conditions as previously published [Hanna, J. et al. Cell Stem Cell 4, 513-524 (2009); Nichols, J. & Smith, A. Cell Stem Cell 4, 487-492 (2009); Ben-Yosef, D. et al. Stem Cells and Development 21, 363-372 (2012)] (FIGS. 13N-O 14A-B). The outcome of growing already established conventional hESC lines in WIS-NHSM conditions was also evaluated. Multiple primed/conventional hESC lines (H1, H9, BGO1, WIBR1, WIBR3) and hiPSC lines (C1 and C2) were plated on gelatin/vitronectin-coated dishes in WIS-NHSM medium (FIGS. 13A-E). After 4-8 days of applying this protocol, dome-shaped colonies with packed round cell morphology, typical of mESCs, could be readily isolated and further expanded (FIGS. 13A-E and 68A-B). Human BJ fibroblast cells were reprogrammed to hiPSCs in WIS-NHSM conditions following either lentiviral transduction with DOX inducible OKSM factors or by transient transfection with OSKM and Lin28 mRNA (FIGS. 13V-W). Domed iPSC colonies appeared 10 days following reprogramming factor transductions in WIS-NHSM medium (FIG. 13V), which were subsequently picked, trypsinized and expanded for further follow up and characterization (FIGS. 14A-D). All polyclonal and subcloned hESC and iPSC lines expanded in WIS-NHSM conditions were uniformly positive for pluripotent markers (representative images in FIGS. 68A-B, 15N-O, 18A-F, 16A-H, and 73A-F), adequately differentiated in vitro upon cultivation as embryonic bodies (FIGS. 19A-I, and 19J-O) and formed mature teratomas in vivo (FIGS. 68C-H, 20A-L and 20M-T).

Naive hESCs and hiPSC lines were expanded in defined growth conditions independent of feeders or fetal bovine serum on vitronectin/gelatin coated plates, and passaged following trypsinization into single cells. Human naive pluripotent lines maintained normal karyotype after extended passaging (FIGS. 15H-M). The average doubling time for naive hESCs in WIS-NHSM was significantly reduced from 26 hours for primed hESCs to 14 hours for naive hESCs/hiPSCs (FIG. 74A). Human naive iPSCs/ESCs displayed 35% single cell cloning efficiency after trypsinization and sorting (without the use of ROCK inhibitors), while conventional genetically matched primed hESCs and hiPSCs did not survive single cell cloning (FIG. 74B) (Hanna, J. et al. *Proc. Natl. Acad. Sci. U.S.A.* 107, 9222-9227, 2010). In the presence of ROCK inhibitor, naive hPSCs had single cell cloning efficient up to 88%, while primed cell single cell cloning increased only up to 22% (FIG. 74B). However, the relative reduced single cell cloning efficiency in human naive PSCs is not attributed to limitation of WIS-NHSM conditions, but rather due to the fact that humans, unlike rodents, do not express mouse naive pluripotency specific protein ERAS as a result of an upstream premature poly-adenylation signal that results in a truncated non-coding transcript [Kameda, T. & Thomson, J. *Stem Cells* 23, 1535-1540 (2005)]. Remarkably, naive $Eras^{-/Y}$ mESCs had single cell plating levels nearing 45%, similarly to those obtained in naive hESCs and hiPSCs without the use of ROCK inhibitor (FIG. 74C). Transgenic reconstitution of ERAS in naive hESC/hiPSC conditions enabled single cell cloning efficiency comparable to those seen in mESCs (FIG. 74C). The present inventors note that Eras null mESC derivation efficiency is also reduced in comparison to wild type (WT) embryos in 2i/LIF (FIG. 74D). Collectively, these results indicate that naive hESCs have distinct growth properties from primed hESCs, and are comparable to mESCs, particularly when taking into account the divergence in functional ERAS gene presence between the two species.

The naive hESC/hiPSCs described herein are stably pluripotent in vitro—All cell lines stained uniformly positive for Oct4, Sox2, Nanog, SSEA3, SSEA4, TRA1-60 and TRA1-81 pluripotency markers (representative images in FIGS. 13F-H, FIGS. 16A-H, FIGS. 17A-H and FIGS. 18A-F). To determine the differentiation ability of naive hiPSCs and hESCs in vitro, the present inventors used floating cultivation to form embryoid bodies (EBs). After 6 days in suspension culture, ball-shaped structures were readily formed from all cell lines tested (FIGS. 19A-F).

The naive hESC/hiPSCs described herein are stably pluripotent in vivo—To test pluripotency in vivo, the present inventors transplanted naive hESC/hiPSCs subcutaneously into immunodeficient (SCID) mice and 3-5 weeks after injection, teratomas were extracted for histological examination that showed that the tumor contained various tissues, including gut-like epithelial tissues (endoderm), striated muscle (mesoderm), cartilage (mesoderm), neural tissues (ectoderm) (FIGS. 20A-U).

Together these results indicate that naive hESC/hiPSC lines established from previously isolated primed hESCs/iPSCs have the functional properties and developmental potency of pluripotent ESCs and iPSCs.

The WIS-NHSM medium can be used to generate naive PSC from a human inner cell mass (ICM)—The present inventors examined the ability to expand human ICM derived cells (Lengner et al., 2010) in WIS-NHSM conditions. A human blastocyst was plated on mouse embryonic fibroblast (MEF) cells in WIS-NHSM medium (FIGS. 13N-O). Outgrowth was evident at day 8, and was trypsinized and passaged. A pluripotent cell line was established and termed WIS1 hESC line (FIG. 13O). The line exhibited a normal karyotype 46XX, stained positive for all pluripotent markers tested, and differentiated in vivo into teratomas (FIGS. 13P-U). This indicates that WIS-NHSM supports derivation of human ESC lines directly from human embryos.

Example 7

Epigenetic Features of Human Naive Pluripotency

The present inventors next moved to characterize epigenetic features in naive hiPSCs and genetically unmodified hESCs established in WIS-NHSM conditions. The evolutionary conserved distal (DE) and proximal enhancer (PE) regions of Oct4 gene are reciprocally regulated in the pre- and post-implantation mouse embryo, and thus the Oct4 distal enhancer is predominantly utilized in naive mESCs (Hanna, J. et al. *Proc. Natl. Acad. Sci. U.S.A.* 107, 9222-9227, 2010), while the proximal enhancer element is preferentially active in primed mEpiSCs. Primed and naive hESC/hiPSCs were transfected with a luciferase reporter construct under the control of either the human distal or the proximal enhancer sequences that control expression of the OCT4 gene (FIG. 25A). Consistent with previous reports, primed hESCs showed preferential activation of the proximal OCT4 enhancer element as typically seen in mEpiSCs [Hanna, J. et al. *Proc. Natl. Acad. Sci. U.S.A.* 107, 9222-9227, 2010; Chia, N.-Y. et al. A genome-wide RNAi screen reveals determinants of human embryonic stem cell identity. Nature 468, 316-320 (2010)]. Remarkably, predominant utilization of the OCT4 distal enhancer was detected in naive hESCs and hiPSCs, indicating that the gene expression program active in naive hESCs favors utilization of the distal OCT4 enhancer as typically observed in mESCs (FIG. 25A). To further substantiate the latter findings, WIBR3 hESCs were stably transfected with full-length OCT4-GFP-2A-PURO, ΔPE-OCT4-GFP-2A-PURO or ΔDE-OCT4-GFP-2A-PURO engineered BAC reporter constructs (FIG. 75A). The wild-type OCT4-GFP reporter was specifically active in both naive and primed conditions, and not detected upon differentiation (FIG. 25A). ΔPE-OCT4-GFP reporter was predominantly active in naive growth conditions while the ΔDE-OCT4-GFP reporter was more active in primed pluripotent cells (FIG. 25A and FIGS. 75A-I). Collectively these finding indicate that hESCs/hiPSCs captured in WIS-NHSM conditions utilize a distinct epigenetic regulation of OCT4 expression from conventional/primed hESCs and hiPSCs.

As a minority of human primed PSC lines can maintain a pre-X inactivation state [Mekhoubad, S. et al. Cell Stem Cell 10, 595-609 (2012); Papp, B. & Plath, K. Cell 152, 1324-1343 (2013)], X chromosome epigenetic status may not be a single reliable marker to unequivocally distinguish between naive and primed state. However, the present inventors aimed to analyze the frequency and properties of X inactivation state in multiple naive hESC/hiPSC lines.

Human ICM (inner cell mass) cells of late stage blastocysts display a unique pre-X inactivation state in females, where despite XIST gene is weakly transcribed (even in male embryos), both X chromosomes are in a pre X-inactivation state and do not demonstrate H3K27me3 and XIST chromosome coating until differentiation [Okamoto, I. et al. Nature. 2011; 472(7343):370-4].

The present inventors characterized X-chromosome inactivation state in naive-hESCs/hiPSCs. Primed/conventional WIBR3 hESCs demonstrate X inactivation as evident by ~50% methylation of XIST gene, very high transcription of XIST transcript consistent with initiation of X chromosome inactivation (FIGS. 23A-D). Remarkably, all naive hESC and IPSC clones expanded in WIS-NHSM and tested demonstrated a unique pre-X inactivation status similar to that described in human ICM. The cells displayed the near complete absence of H3K27me3/polycomb foci on the X-chromosome alleles (FIG. 23C), which was upregulated upon EB differentiation (FIG. 23D).

Close monitoring of X chromosome dynamics in primed female hESC lines during in vitro derivation in conventional bFGF/TGFβ only conditions, demonstrated that the cells have a great tendency to undergo X chromosome inactivation as a part of an in vitro adaptation process [Lengner, C. J. et al. Cell 141, 872-883 (2010); Papp, B. & Plath, K. Cell 152, 1324-1343 (2013); O'Leary, T. et al. Nat Biotechnol 30, 278-282 (2012)]. Indeed, naive pluripotent cells captured in WIS-NHSM uniformly maintain a pre-inactivated X chromosome as evident by nearly complete lack of H3K27me3 nuclear foci and down regulation of XIST expression (FIGS. 68I-K and FIGS. 76A-B). The majority of primed/conventional hESCs and hiPSCs demonstrate X inactivation as evident by the presence of H3K27me3 nuclear foci, methylation of one of the XIST gene alleles and very high transcription of XIST transcript consistent with initiation of X chromosome inactivation (FIGS. 68I-K and 76A-B). Consistently, genome wide mapping of H3K9me3 by Chromatin Immuno-precipitation followed by deep sequencing (ChIP-Seq) in female and male naive and primed human pluripotent cells, indicated a significant increase (p<$2.1^{-10}$) in this mark in female cell lines on X chromosome, but not on autosomal chromosome 1, and only in female primed pluripotent cells (FIG. 76C). Importantly, as observed in human ICM cells, XIST is transcribed at low levels in human naive pluripotency, even in male cell lines (FIG. 76B). XIST promoter alleles are entirely demethylated in male and female naive ESCs (FIG. 23A). Upon EB differentiation of female naive hESCs/hiPSCs, inactivation of one of the X chromosomes alleles becomes evident and the cells demonstrate H3K27me3 clouds, upregulation of XIST transcription simultaneously with methylation of one of the XIST promoter regions (FIGS. 68I-K, FIG. 76B and FIG. 23A). Collectively, these results indicate that hESCs/hiPSCs expanded in WIS-NHSM uniformly maintain a unique pre-X inactivation state akin to that described in human and primate ICMs [Okamoto, I. et al. Nature, 2011, 472(7343): 370-4; Masterson, K R., et al. Dev Biol. 2012, 371(2):146-55], and can adequately initiate X chromosome inactivation upon differentiation.

Example 8

Transcriptional and Chromatin State of Human Naive Pluripotency

The present inventors compared global gene expression patterns between naive and primed hESCs and hiPSCs, many of which were genetically matched. Unbiased clustering of genome-wide expression profiles demonstrated that naive hESC and hiPSCs possess a distinct gene expression pattern and clustered separately from conventional/primed hESCs and hiPSCs (FIG. 69A and FIG. 24A). Gene expression analysis indicated that while OCT4 and KLF4 were similarly transcribed in naive and primed cells, other transcripts associated with naive pluripotency were significantly upregulated in naive cells. The later included NANOG and DUSP family member genes, that has been shown to maintain ERK de-phosphorylation in rodent naive ESCs (FIGS. 77A-B) [Chappell, J., et al. Genes Dev. 27, 725-733 (2013)]. Importantly, naive pluripotent cells had profoundly down regulated transcripts associated with lineage commitment genes including ZIC1, SOX6 and SOX11 that are expressed at low, but appreciable, levels in primed hESCs (FIGS. 77A-B). Functional annotation analysis of differentially expressed genes with Gene Ontology (GO) revealed that genes down regulated genes in naive pluripotency were significantly enriched for GO terms linked to developmental processes, particularly ectoderm and neural germ cell specification (FIG. 69A, and FIG. 78). Furthermore, hierarchical clustering and Principal Component Analysis (PCA) showed that human ICM samples are transcriptionally more similar to Naïve hESCs, than to primed cells (FIGS. 69H-I). Nearly all of these terms were also found to be significantly down regulated in mouse naive pluripotent cells, in comparison to mEpiSCs (FIG. 69A), and are consistent with transcriptional changes associate with pluripotency priming reported in mice [Marks, H. et al. The transcriptional and epigenomic foundations of ground state pluripotency. Cell 149, 590-604 (2012)]. Furthermore, while ICM cells are known to undergo major transcriptional changes after in vitro derivation [Chu, L.-F., et al. Curr. Biol. 21, 1759-1765 (2011)], hierarchical clustering and Principal Component Analysis (PCA) showed that human ICM samples transcriptionally cluster closer to Naive hESCs, than to primed cells (FIG. 79). Analogous to expression pattern differences between mouse naive and primed stem cells, primed hESCs demonstrate intermediate expression levels of MHC class I antigen in comparison to somatic cells, while naive hESC/hiPSC express trace levels of MHC class I surface antigen (FIGS. 24B-C). Moreover, while E-CADHERIN is expressed in primed hESCs, the surface expression pattern becomes more prominent and evenly distributed on the cell surface membrane of naive hESC colonies (FIGS. 81A-D). The present inventors next conducted an unbiased cross-species hierarchical clustering of globally measured transcriptome to evaluate whether the human primed/conventional and naive pluripotent cells described herein globally correspond to those established in mice (Hanna, J. et al. Proc. Natl. Acad. Sci. U.S.A. 107, 9222-9227, 2010). Using a previously established method for cross-species gene expression analysis on all 9,803 mouse-human orthologous genes found in our gene expression datasets (Hanna, J. et al. Proc. Natl. Acad. Sci. U.S.A. 107, 9222-9227, 2010; Hanna, J. et al. Cell Stem Cell 4, 513-524 (2009)], the present inventors found that while primed/conventional hESCs and hiPSC clustered with mEpiSCs, all naive hESCs/hiPSCs clustered with mESCs and miPSCs independent of the genetic background or naive growth conditions used (FIGS. 69B and 82A). Further, primed mouse and human pluripotent cells expression patterns were significantly more heterogeneous in comparison to naive counterparts, as reflected by the noise distribution of the two groups in both species (FIGS. 69C-D). The latter conclusions are consistent with findings reported in serum primed mESCs [Marks, H. et al. Cell 149, 590-604 (2012)] and apply when looking at transcriptional heterogeneity of previously highlighted [Oakley, D. H., Cell 144, 439-452 (2011)] markers know to highly vary between human iPSCs/ESCs (FIG. 82B). Finally, nuclear localization of the transcription factor TFE3 was recently shown to be enhanced in naive mESCs, and compromised upon pluripotency priming [Betschinger, J. et al. Cell 153, 335-347 (2013)]. Remarkably, a similar nuclear enrichment pattern for TFE3 was evident in naive hESCs, and relative enrichment was compromised in primed/conventional hESCs (FIGS. 69E, 69F and 69G, and FIGS. 80A-D). Collectively, these data demonstrates that WIS-NHSM endows human pluripotent cells with defining features of pluripotency gene expression patterns typically seen in ground state naive mESCs [Marks, H. et al. Cell 149, 590-604 (2012)].

The present inventors next tested whether a difference between human naive and primed cells is also apparent at the chromatin level, as priming of murine naive ESCs induced by 2i withdrawal and providing serum is associated with accumulation of H3K27me3 mark and formation of bivalent domains (gene promoter marked by H3K27me3 and H3K4me3) on developmental regulatory genes [Marks, H. et al. Cell 149, 590-604 (2012)]. The present inventors mapped H3K4me3 and H3K27me3 chromatin marks by using ChIP-Seq in mouse and human naive ESCs and primed EpiSCs (both expanded in serum free conditions). Indeed, while distribution of both epigenetic markers over all genes showed a significant ($p<2e^{-37}$) decrease in H3K27me3 (FIGS. 83A-D), an even more dramatic decrease of both marks in developmental genes was observed in mESCs in 2i/LIF conditions in comparison to mEpiSCs ($p<2.5e^{-50}$, FIG. 70B). Remarkably, while total levels of H3K27me3 were not altered, there was a dramatic ($p<8.6e^{-61}$) redistribution and reduction of H3K27me3 in promoter and gene body region over developmental genes (n=5922) in human naive cells compared to primed (FIGS. 70A-B and 70E-F), equivalent to that observed in rodent cells. Notably, together with the reduction of H3K27me3 in naive cells, there is a mild ($p<1.4e^{-9}$) reduction of H3K4me3 in the promoters of developmental genes in naive cells (FIGS. 70A-B). The reduction of H3K27me3 mark to nearly background levels in human naive cells is also reflected in the number of bivalent genes, which is more than 13-fold higher in primed (3013) compared to naive cells (226). Pluripotent genes (e.g. OCT4, SOX2, SALL4) showed consistent active chromatin in both naive and primed conditions in human and mouse, while TBX3 pluripotency regulator acquired repressive H3K27me3 marks in primed human and mouse samples (FIGS. 70C-D).

The present inventors tested whether the WIS-NHSM naive human conditions have an effect also in other genomic components such as enhancers. For this, the present inventors first measured the distribution of H3K27me3 in three genomic components: promoters, genes body and intergenic regions. Consistent with what was observed in mouse cells [Marks, H. et al. Cell 149, 590-604 (2012)], the present inventors found that in naive cell state, H3K27me3 peaks are depleted more from promoters and gene-bodies, than from intergenic regions (FIGS. 84A-B). The present inventors then globally mapped enhancers of class I and class II in the two-pluripotency states. Class I enhancers [Rada-Iglesias, A. et al. Nature 470, 279-283 (2011)] are characterized by the presence of H3K4me1 and H3K27ac, and the absence of H3K4me3 and H3K27me3 marks, and are associated with active expression of nearby genes. Class II enhancers on the other hand, are characterized by the presence of H3K4me1 and H3K27me3, and the absence of H3K27ac mark, and are associated with being poised for activation [Rada-Iglesias, A. et al. Nature 470, 279-283 (2011)]. Consistent with the reduction of lineage priming molecular features in naive pluripotency, the present inventors observed (FIGS. 84D-E) a major reduction in the annotated Class II enhancers in naive cell state, in both human (5.8-fold) and mouse (62.5-fold). Although Class II associated genes lose their H3K27me3 mark in naive state, they do not become more actively transcribed (FIGS. 84F-G) (as was observed previously in mouse [Marks, H. et al. Cell 149, 590-604 (2012)]. Collectively, these findings indicate the naive ground state of pluripotency largely lacks features associated with pre-marking of repressed developmental genes and rendering them poised for activation.

Rodent ground state naive pluripotency is associated with global DNA hypomethylation, while maintaining epigenetic imprinting signatures. This effect is mediated by 2i-mediated down regulation of de novo methyltransferase enzymes, and maintaining expression of TET hydroxylases and Dnmt1 enzyme. Remarkably, human naive ESC sand IPSCs expanded in WIS-NHSM conditions demonstrated a dramatic down-regulation of DNMT3a, DNMT3b and DNMT3L methyl-transferase enzymes, but not of DNMT1 and TET1/2 enzymes (FIG. 71D). The present inventors then analyzed human naive and primed pluripotent cells for global levels of 5-methylcytosine (5mC) by LC-MS) [Leitch, H. G. et al. Embryonic germ cells from mice and rats exhibit properties consistent with a generic pluripotent ground state. Development 137, 2279-2287 (2010); Meissner, A. et al. Genome-scale DNA methylation maps of pluripotent and differentiated cells. Nature 454, 766-770 (2008)]. A striking drop in global 5mC content was observed in under WIS-NHSM conditions, equivalent to those measured in naive mESC in 2i/LIF conditions or mouse ICM (FIG. 71E). Collectively, these results highlight that human naive pluripotent cells captured herein, recapitulate defining epigenetic characteristics of rodent naive pluripotency: global reduction of DNA methylation and H3K27me3 modification on lineage commitment affiliated gene promoter and enhancers.

ICM-Like Pre-x Inactivation State in Naive Human PSCs

The highly conserved distal and proximal enhancer regions of Oct4 genes are reciprocally regulated in the pre and post implantation mouse embryo, and thus the Oct4 distal enhancer is predominantly utilized in mouse naive ESCs (Hanna et al., 2010b). Primed and naive hESC/hiPSCs were transfected with a luciferase reporter construct under the control of either the human distal or the proximal enhancers sequences that control expression of the Oct4 gene (FIG. 25A). Predominant utilization of the Oct4 distal enhancer was observed in rev-hESCs and human-iPSCs indicating that the gene expression program active in rev-hESCs favors utilization of the distal Oct4 enhancer as typically observed in mouse ESCs (FIG. 25A). To further substantiate the latter findings, WIBR3 hESCs were targeted with Oct4-GFP-2A-PURO or deltaPE-Oct4-GFP-2A-PURO (FIGS. 25B-M). The complete Oct4 GFP reporter was specifically active in both naive and primed conditions (and lost upon differentiation). DeltaPE-Oct4-GFp-2A-PURO reporter was specifically active in naive, but not conventional/primed, pluripotent growth conditions (FIGS. 25B-M). Collectively these finding indicate that ESCs/iPSCs expanded in WIS-NHSM conditions carry a distinct molecular and epigenetic state.

Naive human iPSCs can contribute to mouse development in vivo—Human naive C2 iPSCs were constitutively labeled with GFP and BCL-2 overexpression vector. Cells were aggregated with developing mouse embryo morulas, and 24 hours GFP cells were viable in developing early mouse embryos (FIGS. 26A-C). These results indicate that human naive cells grown in WIS-NHSM conditions can contribute to cross-species chimeric organisms.

Example 9

Functional and Signaling Properties of Human Naive PSCs

The above results indicate that while both human naive and primed growth conditions that contain bFGF and TGFβ cytokines, the supplementation of the naive conditions with 2i/LIF, p38 and JNK inhibitors reconfigures the molecular and epigenetic properties of human pluripotent cells. Thus, the present inventors next characterized the signaling dependence and response patterns of naive and primed human pluripotent cells to different signaling stimuli or inhibitors, in comparison to their rodent counterparts. The pluripotency of mESCs is stabilized upon inhibition of RAF-ERK1/2 pathway, while in hESCs and mEpiSCs (Hanna, J. et al. *Proc. Natl. Acad. Sci. U.S.A.* 107, 9222-9227, 2010), ERK and RAF inhibition with either one out of four different small molecules leads to their differentiation (FIGS. 21A-F, and FIGS. 15A-M). However, as similarly observed with naive mESCs, the stability of naive hESCs/iPSCs was dependent on the continuous presence of ERK1/2 inhibition (FIGS. 12S, 86A-C, 87A). Supplementation of TGFβ is necessary to inhibit the pro-neural differentiation effect of ERK inhibition in naive WIS-NHSM conditions (FIG. 86B). When testing p38 and JNK pathways signaling requirements, primed hESCs and mEpiSC tend to differentiate upon inhibition of these pathways (FIGS. 21A-D, 15A-M, and 86C). Murine ESCs maintain their naive pluripotent state identity as measure by ΔPE-Oct4-GFP expression and "all-ESC" mouse formation ability by tetraploid embryo complementation assay, upon inhibition of either one of p38, JNK or ERK pathways (FIGS. 88A-J and 89A-D). In human naive cells, simultaneous inhibition of these pathways is essentially required to maintain naive pluripotency, and their withdrawal resulted in differentiation and upregulation of lineage commitment genes (FIGS. 21A-L, 15A-M, 86A-C, and 87A-B). Supplementation of TGFβ is necessary to inhibit the pro-neural differentiation effect of ERK inhibition in naive WIS-NHSM conditions. Naïve hESCs stably transfected with a dominant-negative Stat3 encoding transgenes rapidly differentiated and could not be maintained in vitro with WIS-NHSM conditions, while cells transgenic for a constitutively active Stat3 mutant (Stat3-CA) could be propagated in vitro in the absence of exogenous LIF (FIG. 108B). These findings highlight that several signaling pathways distinctly regulate the two human pluripotent states, in a manner similar to that observed in mice (Marks, H. et al. The transcriptional and epigenomic foundations of ground state pluripotency. Cell 149, 590-604 (2012); Hanna, J. et al. Human embryonic stem cells with biological and epigenetic characteristics similar to those of mouse ESCs. Proc. Natl. Acad. Sci. U.S.A. 107, 9222-9227 (2010)].

LIF/Stat3 signaling is an important pathway in promoting the rodent ground state of naive pluripotency, and in 2i/LIF conditions, mESCs are dependent on LIF signaling and readily differentiate when exposed to JAK inhibitor (JAKi) that blocks Stat3 phosphorylation (FIGS. 21A-D) [Niwa, H., et al. *Nature* 460, 118-122 (2009)]. Traditional hESCs maintained low levels of phosphorylated STAT3 (pSTAT3), which was increased in response to LIF addition, however the cells were resistant to addition of JAK1 inhibitor (FIGS. 15A-M and 90). Alternatively, naive hESCs/hiPSCs had high levels of pSTAT3 (FIGS. 15A-M) and differentiated upon pharmacological inhibition of JAK/STAT3, as similarly observed with mESCs (FIGS. 21A-D). Naive hESCs stably transfected with a dominant-negative Stat3 encoding transgenes rapidly differentiated and could not be maintained in vitro with WIS-NHSM conditions, while cells transgenic for a constitutively active Stat3 mutant (Stat3-CA) could be propagated in vitro in the absence of exogenous recombinant LIF and generated teratomas (FIG. 71A, FIGS. 22G-L). Finally, BMP4 cytokine and Forskolin, a PKA agonist, led to differentiation of primed but not naive human or mouse pluripotent cells (FIGS. 21A-D, FIGS. 22A-F and FIGS. 91A-C), indicating that several pathways are differentially regulated between the two human pluripotent cell states in a similar manner to that observed between mESCs and mEpiSCs.

The present inventors next characterized functional difference between human naive and primed pluripotent cells. Naive human pluripotent cells were reproducibly more amenable to gene targeting by homologous recombination with isogenic targeting vectors directed at the endogenous OCT4 and COL1A loci, in comparison to their genetically matched primed cells (FIGS. 71B, C). Further, given that naive pluripotency promoting conditions have been shown to be important for deterministic induction of pluripotency by OSKM upon Mbd3 depletion in mice, WIS-NHSM are analogously critical for obtaining near 100% naive ground state iPSC formation levels from Mbd3 depleted human fibroblasts following OSKM induction (FIG. 71D). Consistent with global reduction of DNA methylation levels in naive human pluripotency conditions, iPSC from fragile X patient specific fibroblasts [Urbach, A., Bar-Nur, O., Daley, G. Q. & Benvenisty, N. Brief Report. Stem Cell 6, 407-411 (2010)] are able to undergo FMR1 gene reactivation and demethylation following reprogramming under naive, but not primed, pluripotency conditions (FIGS. 71E-G). Finally, consistent with robust E-cadherin expression and enhanced single cell survival, microinjection of human naive iPSCs into mouse morulas shows robust integration in mouse ICM at E3.5 (FIGS. 26D-K) and microinjection of human GFP labeled naïve iPSCs into mouse E2.5 morulas showed robust integration in mouse in vitro developed ICMs at E3.5, and higher than that of primed pluripotent cells (FIGS. 109A-C). The latter results (with respect to primed iPSCs in FIG. 109B) are consistent with previously reported near absence of integration and chimerism following embryo microinjection of primate primed ESCs (James, D., Noggle, S. A., Swigut, T. & Brivanlou, A. H. Contribution of human embryonic stem cells to mouse blastocysts. *Dev. Biol.* 295, 90-102 (2006); Tachibana, M., Sparman, M., Ramsey, C., Ma, H. & Lee, H. S. Generation of Chimeric Rhesus Monkeys. *Cell* 148, 285-295 (2012)]. Mouse blastocysts obtained after microinjection with human naïve iPSCs were implanted in pseudo-pregnant female mice and allowed to develop for 7 additional days in vivo, after which they were dissected and imaged in toto under confocal microscopy for GFP+ cell detection. Remarkably, the present inventors were able to obtain multiple mouse embryos (n=4), corresponding to E8.5-E10.5 developmental stages, that showed chimerism with naïve human iPSC derived GFP+ cells integrated at different locations, including craniofacial tissues and embryonic neural folds (FIG. 108C; FIG. 109D). In depth functional and developmental analysis of the in vivo integrating human naïve iPSC derived cells is of great future scientific interest. Collectively, the above indicate that the altered biological features of human naive PSCs directly endows them with unique functional properties.

Notably however, naive human ESC/iPSCs generated herein are distinct from murine naive cells, in the way that they are still dependent on bFGF and TGF signaling, and inhibition of these pathways leads to their naive cells state loss and differentiation.

Collectively these findings indicate that the naive ground state of pluripotency requires a unique combination of growth factors and cytokines. Human cells are more stringent from mouse, thus they need simultaneous inhibition of different MAPK pathways (ERK and JNK and p38 simultaneous inhibition) together with LIF and WNT stimulation (by CHIR99021). Also, bFGF and TGF have diverged between mouse and humans, and in humans they are also essential to promote naive pluripotency and contribute to the unique molecular and epigenetic configuration of naive pluripotency described herein.

These findings substantiate the concept of naive ground state in human pluripotent cells, and indicate that its maintenance requires a unique combination of growth factors and cytokines. Human pluripotent cells are more stringent relative to their mouse counterparts, as they need simultaneous inhibition of different MAPK pathways (ERK, JNK and P38 MAPK simultaneous inhibition) together with LIF and WNT stimulation (by CHIR99021). FGF2 and TGFβ signaling are divergent between mice and humans [Greber, B. et al. Cell Stem Cell 6, 215-226 (2010); Roode, M. et al. Dev. Biol. 361, 358-363 (2012)], as in humans they are also essential to promote naive pluripotency and contribute to the unique molecular and epigenetic configuration of naive pluripotency described herein. These results suggest that epigenetic priming of human pluripotent cells is predominantly caused by withdrawal of LIF and inhibitors of MAPK signaling [Pribluda, A. & Hanna, J. H. Nat Biotechnol 30, 247-249 (2012)]. These findings are consistent with the notion that different genetic backgrounds assume distinct states of pluripotency in vitro, the stability of which is regulated by endogenous genetic determinants and can be modified by defined exogenous factors that support the naive ground state of pluripotency. The stringency in requirement for these factors appears to be different among distinct species, as exemplified by the requirement for simultaneous inhibition of multiple MAPK kinase pathways in human naive cells [Hanna, J. et al. Cell Stem Cell 4, 513-524 (2009); Hanna, J. H., et al., Cell 143, 508-525 (2010); Hanna, J. et al. Proc. Natl. Acad. Sci. U.S.A. 107, 9222-9227, 2010]. It would be of interest to explore whether the naive ground state of pluripotency in humans could be captured merely by signaling pathway inhibition [Ying, Q.-L. et al. *Nature* 453, 519-523 (2008)]. The epigenetic changes induced by naive pluripotency conditions indicate that naive conditions might influence previously described phenotypes of epigenetic memory and aberrant reprogramming in human iPSCs.

Without being bound by any theory, these data do not claim that naive and primed pluripotent states are identical between humans and mice, and in fact differences may still exist between naive mESCs and the naive human pluripotent cells described in this work. Without being bound by any theory, the present inventors cannot exclude that alternative growth conditions may be devised to capture human naive pluripotent cells with features similar to those described herein, or that WIS-NHSM conditions might be modified for improving the extent of naive features in human pluripotent cells. Further molecular characterization of human ICM cells will help improve and understand the relevance of naive pluripotency in vitro characteristics described herein [Smith, Z. D. et al. Nature 484, 339-344 (2012); Okamoto, I. et al. Nature. 2011, 472(7343):370-4; Niakan K K, et al. Dev. Biol. 375, 54-64 (2013)]. Finally, defining a novel naive pluripotent state in humans that is stable and does not require any genetic modifications might be relevant for the molecular study of early lineage commitment in vitro, and for expanding the capabilities for utilizing hESCs and hiPSCs in regenerative medicine research and disease modeling in vitro and in vivo [Dimos J T, et al. Science 321, 1218-1221 (2008); Sandoe, J. et al. Nature Publishing Group 16, 780-789 (2013)].

The results described herein demonstrate that naive hESC/iPSCs grown in WIS-NHSM are distinct from previously isolated hESCs/hiPSCs and extensively recapitulate growth characteristics, signaling dependence, epigenetic and transcriptional properties that define naive mouse ESCs, rather than the mouse post-implantation epiblast and EpiSCs. Further, they capture molecular features of human ICM that are not present in rodent/mouse ICM. These findings supports the notion that different genetic backgrounds assume distinct states of pluripotency in vitro, the stability of which is regulated by endogenous genetic determinants and can be modified by defined exogenous factors that support the naive pluripotent state. The threshold and requirement for these factors is different among different species where in the "permissive" 129 mouse strain LIF/Stat3 signaling can stabilize mouse ESCs, while on the NOD genetic background promotion of Wnt signaling and inhibition of ERK1 or providing small molecules that promote Klf2/4 expression (KP or FK) stabilize NOD ESCs. The human genetic background seems to be further non-permissive, as it required modulation of additional signaling pathways to stabilize the naive state in vitro. Evolutionary divergence has contributed to the findings that in humans, and possibly other species, as bFGF and TGF signaling contribute to human naive pluripotency maintenance. Finally, defining a novel naive pluripotent state in humans that is indefinitely stable and does not require any genetic modifications might be relevant for the molecular study of early lineage commitment in vitro and for expanding the capabilities for utilizing human ESCs and iPSCs in regenerative medicine research and disease modeling in vitro and in vivo.

Framing these challenges by WIS-NHSM conditions and/or Mbd3 inhibition, may prove to be key not only for understanding early human development, but also for dissecting the core-transcriptional circuitry in human naive pluripotent cells in the absence of exogenous transgenes, as it allows more authentic analysis of this state. Most importantly, Human primed ESCs display great level of heterogeneity in gene expression, including differential expression of lineage commitment genes and X chromosome activation status. Moreover, substantial differences among cell lines in gene expression are not evident in the undifferentiated state but appear when cells differentiate in same growth conditions. Careful comparative analysis for directed differentiation into specific lineages uncovered dramatic heterogeneity that was evident by marked differences in differentiation propensity among human embryonic stem cell line. It is possible that this properties are direct result of the cells used correspond to EpiSC stage, where the cells become highly sensitive to exogenous differentiating cues and initiate lineage commitment. Naive human ESCs/iPSCs are homogenous functionally and molecularly when expanded in WIS-NHSM conditions. Without being bound by any theory is seems that the naive pluripotent cells are inherently resistant to differentiation signals by the presence that promote naive pluripotency, and thus may prove to display reduced heterogeneity upon differentiation.

In addition to heterogeneity in differentiation propensity, naive human pluripotent state might facilitate adaptation of differentiation protocols that have been only been successful with naive mouse ESCs. A prominent example is the generation of engraftment competent hematopoietic progenitors with mouse ESC capable of long-term in vivo re-population and secondary engraftment, while the success with conventional human ESC has been rudimentary. It remains to be seen whether human naive pluripotent cells will be more useful and more efficient in generating Disease-Relevant Phenotypes with Human-Animal Chimeras (as shown here in FIGS. 26A-C). Lastly, achieving homologous recombination has been highly inefficient in primed/conventional human embryonic stem cells. The use of zinc finger exonuclease has been very successful however this method is complex, expensive, and could introduce non-specific genetic alterations in the manipulated cells that are hard to identify. Comparative analysis for susceptibility to homologous recombination between WIS-NHSM naive and primed pluripotent states in mice and humans might provide conclusive answer to whether the naive cells are significantly more amenable to homologous recombination.

Example 10

P66 Alpha Coiled-Coil Domain as a Dominant Negative Inhibitor of Mbd3/Nurd and as a Facilitator for Deterministic IPSC Reprogramming Following the studies described hereinabove concerning the effect of Mbd3 upon the reprogramming process, the present inventors aimed to screen for an Mbd3 inhibitor, in order to neutralize the function of the MBD3\NuRD complex.

Since the inhibitory effect of Mbd3 is probably mediated by the recruitment of the NuRD complex, one of the approaches that were taken by the present inventors was to try and prevent the binding of MBD3 to the complex.

Gnanapragasam et al. (Gnanapragasam et al. 2011. "p66α-MBD2 coiled-coil interaction and recruitment of Mi-2 are critical for globin gene silencing by the MBD2-NuRD complex". Proc. Natl. Acad. Sci. 108:7487-7492) describe a unique coiled-coil interaction between MBD2 and p66α, another component of the NuRD complex, mediated by two coiled-coil regions in these proteins.

The MBD2 coiled coil region is highly conserved between the MBD2 homologs (including MBD3), and inter-species.

Gnanapragasam et al. 2011 (Supra) show that overexpression of p66α coiled-coil region competes with the wild type p66α, and inhibits the binding of MBD2 to Mi-2(α or β). Moreover, they show that the p66α-CC also binds to MBD3 in the same region, and creates a similar structure [Nuclear magnetic resonance (NMR) structure of MBD2 binding to the p66α-CC is found under the Protein Data Bank (PDB) ID 2L2L; An Information Portal to Biological Macromolecular Structures]. This interaction between the p66α-CC and the MBD2 inhibits the ability of MBD2 to repress its downstream target gene expression, probably mediated through the binding to CHD4 (chromodomain helicase DNA binding protein 4).

Another paper that was recently published by Walavalkar et al. (Walavalkar et el. 2013. "Unique features of the anti-parallel, heterodimeric coiled-coil interaction between methyl-cytosine-binding domain 2 (MBD2) homologues and GATA zinc finger domain containing 2A (GATAD2A\P66α)". J. Biol. Chem. 288: 3419-3427) shows that the p66α coiled-coil domain interacts with Mbd3, mbd311, mbd312 in different efficiency; MBD2 and MBD3 binds approximately in the same efficiency to p66α. Therefore, without being bound by any theory, the present inventors envisage that the p66α coiled-coil domain can interfere with the NuRD complex assembly, and inhibit the recruitment of Chd4, a critical component.

As mentioned, p66α is a component of the NuRD complex. It has been shown that P66α null (loss of function) mice die during early development (day 10), and that p66 is not required for blastocyst formation (Marino et al. 2007. "Mutants in the mouse NuRD/Mi2 component p66 are embryonic lethal". PLoS ONE 2(6): e519. doi: 10.1371/journal.pone.0000519).

As a proof of concept the present inventors cloned p66α coiled-coil domain into the pCAG-HA vector, in order to check its effect upon the NuRD complex assembly.

The present inventors overexpressed MBD3-WT (SEQ ID NO: 112) and the HA-tagged p66α-CC in 293T cells, and further show in a co-immunoprecipitation for anti-Mbd3 pulldown, that the presence of p66α inhibits MBD3 binding and recruitment to CHD4 (FIG. 93).

In addition, FIGS. 92A-C show that knockdown of Mbd3 or Chd4 increases the efficiency of reprogramming efficiency of MEFs (FIGS. 92A-D).

Following are the MBD3 and CHD4 siRNAs used by the present inventors:

For mouse:
Mbd3 Stealth siRNA mix that includes MSS-237238, MSS-275658 and MSS-275659 components (Invitrogen);
Chd4 Stealth siRNA mix that includes MSS-200894, MSS-200895 and MSS-200896 (Invitrogen), were used for efficient knockdown in mouse cells.

For human:
MBD3 Stealth siRNAs that include HSS147580 and HSS147581 components (catalogue number 1299003) were used for efficient MBD3 knockdown in human cells.
Human CHD4 stealth siRNA—Life technologies HSS101850 was used to efficiently knockdown CHD4 in human.

Since the present inventors have proved in previous experiments that MBD3 inhibitory effect is probably mediated mainly by Chd4, without being bound by any theory it is assumed that a peptide which can inhibit Chd4 binding to Mbd3 can serve as a potent inhibitor to MBD3.

Further biochemical investigation of MBD3 loss of function as a result of P66aCC over expression (examining the interactions with the OSKM and the NuRD complex other members Mta2, Hdac 1, 2) are ongoing. The coding sequence of the P66 alpha coiled-coil domain was amplified using the primers depicted in SEQ ID NOs: 115 and 116. The resulting P66 alpha coiled-coil domain coding sequence is set forth in SEQ ID NO: 113, and the encoded P66 alpha coiled-coil domain amino acid sequence is set forth in SEQ ID NO: 114. The P66 alpha coiled-coil domain (SEQ ID NO:114) can be used as an inhibitor of MBD3.

Functional assays, including reprogramming (following chip-seq with and without p66aCC treatment) are ongoing.

Deep structural analysis of the predicted NMR in order to find or design compounds which can bind this region of MBD3 is ongoing.

Synthesizing a peptide of the p66alpha CC region (with TAT-NLS-signal) for functional test is ongoing.

Example 11

IPSC Reprogramming from Human Adult Somatic Cells Via OKSM and Eras Over Expression, Together with Mbd3 Depletion Human BJ fibroblasts were infected with TRIPZ MBD3 shRNA lentiviruses (3.1, 3.2, 3.3 indicate three different hairpin constructs targeting MBD3). Real time PCR expression for MBD3 was conducted after 72 hours with or without DOX induction. The results presented in FIG. 99A validate down-regulation of MBD3 in human fibroblasts in a DOX dependent manner. ShRNA hairpin numbers 1 and 3 were used for further analysis as a combination.

Human primary fibroblast cell lines #13 and 14# (obtained from adult healthy dermal biopsy) were infected with lentiviruses encoding OKSM, RtTa, ERAS (SEQ ID NO:109) (for overexpression of OKSM, RtTa, and ERAS) and with a lentivirus encoding MBD3 shRNAs (for down-regulation of MBD3).

RtTa (also known as M2rtTA) is the element that allows responding to Doxyccycline. Any DOX inducible system requires introducing RtTA element, so the present inventors used a Lentiviral plasmid expressing the reverse tetracycline transactivator (M2rtTA) [vector from addgene, Catalogue Number: 20342; SEQ ID NO:110).

The following DOX inducible MBD3 knockdown lentiviral clones were used: TRIPZ Human MBD3 shRNA Clone ID: V3THS_392206 (#1) and V3THS_392210 (#3)—Thermo Scientific). Clonal populations with ES-like morphology appeared 6-10 days after DOX induction (FIGS. 99B-C). Red fluorescent protein (RFP) fluorescence is driven by TetO promoter (DOX responsive) of the TRIPZ-MBD3 shRNA constructs. More examples of colonies observed at day 5 or 11 are shown in FIGS. 99D-G.

FIGS. 100A-I show staining for OCT4 and SSEA4 pluripotency markers on cells reprogramming in NHSM conditions following 10 days of OKSM, RtTa, ERAS and MBD3 shRNA DOX induction. It is noted that the MBD3-shRNA induction reporter (ShMBD3, FIG. 100I) co-localizes with OCT4 expression and SSEA4 pluripotency markers.

FIGS. 100J-N show staining for OCT4 and TRA1-60 staining pluripotency markers on cells reprogramming in NHSM conditions following 10 days of OKSM, RtTa, ERAS and MBD3 shRNA DOX induction. It is noted that the MBD3-shRNA induction reporter (ShMBD3, FIG. 100I) co-localizes with OCT4 expression and TRA1-60 pluripotency markers.

FIGS. 100O-S show staining for OCT4 and TRA1-81 staining pluripotency markers on cells reprogramming in NHSM conditions following 10 days of OKSM, RtTa, ERAS and MBD3 shRNA DOX induction. It is noted that the MBD3-shRNA induction reporter (ShMBD3, FIG. 100I) co-localizes with OCT4 expression and TRA1-81 pluripotency markers.

Primary females adult dermal fibroblast cells (line #13) were transduced with RtTa, OSKM and ERAS vectors in WIS-NHSM conditions, with or without TRIPZ-MBD3 shRNAs 1+3 mix (to knockdown human MBD3). iPSC colony numbers were counted at day 10 by staining for NANOG and TRA1-60 markers (FIG. 100T). Note the dramatic increase in iPSC formation from primary human somatic cells when MBD3 inhibition is introduced.

Example 12

Human Naive IPSCS and ESCS can Differentiate into Primordial Germ Cells Precursors Primordial germ cell (PGC)-like cells (PGCLC) derived from human naive iPSCs/ESCs can be injected in human/primate or mouse testis and give rise to functional sperm. Alternatively, they may be used for oocyte generation.

Materials and Media:

N2-KSR medium—250 ml Neurobasal medium (Invitrogen—#21103-049), 250 ml DMEM-F12, N2 supplement (Invitrogen, #17502-048), 1% KSR (knockout serum replacement, Invitrogen, #10828028) medium] with 8 ng/ml bFGF (Peprotech), 1 ng/ml TGF-β1 (Peprotech) and ROCKi (10 µM).

PGC medium is comprised of GMEM (Invitrogen, #21710082), 15% KSR, 1% NNEA (Biological industries, 01-340-1B), Penicillin-Streptomycin, 1 mM L-Glutamine, 5 µM ROCKi (Y-27632, Axon Medchem) and the following cytokines: 500 ng/ml BMP4 (bone morphogenetic protein 4; R&D Systems Inc.), 20 ng/ml LIF (leukemia inhibitory factor; PeproTech), 100 ng/ml SCF (Stem Cell Factor; PeproTech), 50 ng/ml EGF (Epidermal Growth Factor; Peprotech).

Experimental Methods:

Generation of mCherry knock in reporter allele in NANOS3 locus—In order to create mCherry reporter expression driven by endogenous human NANOS3 locus, the present inventors have chosen to knock in p2a-mCherry coding sequence in frame with the last exon of the NANOS3 gene. The present inventors have generated plasmids encoding TALEN molecules specific to the region covering NANOS3 stop codon. TALEN constructs were generated using GoldenGate TALEN kit2.0 (addgene cat #1000000024).

Targeting construct for 2A-mCherry knock in was designed as shown in FIG. 94A. WIS1 naive human ESCs (carrying also deltaPE-OCT4-GFP reporter) were electroporated with pair of TALEN coding plasmids and donor targeting construct. After selection with G418 (150 µg/ml) and ganciclovir (2 µM), the present inventors used PCR to analyze 96 of surviving individual clones. One of the correctly targeted clones (based on PCR and Southern Blot analysis) was transfected with a plasmid encoding flippase enzyme with subsequent subcloning. Neo cassette deletion was confirmed by PCR. In addition to this the whole targeted locus was sequenced, and karyotype analysis was performed for one of correctly targeted clones. Both sequencing and karyotyping did not revealed any abnormalities, and thus the cells were used for further functional validation.

Inducement of epiblast state—Naive human ESCs, either genetically modified cells with the NANOS3-mCherry construct or unmodified cells, were grown on irradiated mouse embryonic fibroblasts (MEFs) or 0.2% Gelatin or vitronectin\gelatin coated plates, in WIS-NHSM medium supplemented with 5 µM ROCKi (Y-27632, Axon Medchem). The cells were trypsinized with 0.05% Trypsin+EDTA, and 50,000 cells/6-well were plated on 1 ng/ml Fibronectin (F1141, Sigma) covered plates in N2-KSR medium, which induces epiblast like (EpiLC) state.

After two days in the N2-KSR medium the EpiLC cells were trypsinized and moved to low-cell-binding 96-well plates (145399, NUNC), at a density of 2500 cells/well, in 120 μl PGC medium.

Fifty microliters (50 μl) of fresh PGC medium were added to each well after two days. Four or six days after the cells were moved to the PGC medium, they were separated using TripLE select (10×) (Invitrogen) for flow-cytometry or molecular analysis.

Experimental Results

Generation of mCherry knock in reporter allele in Nanos3 locus—As shown in FIGS. 94A-B, human naive cells (WIS1) were targeted to a genetic engineering process via the TALENs in order to prepare cells in which expression of NANOS3 is visible by expression of the reporter gene mCherry. NANOS3 is a gene specifically expressed in PGCs already from early stages of their development (Julaton et al. Hum Mol. Genet. 2011 Jun. 1; 20(11):2238-50.)

Naive ESCs were induced to the epiblasts state by plating the cells on fibronectin covered plates and incubation in the presence of N2-KSR medium for 2 days. Following, the cells were removed by trypsinization from the plates and were transferred to low-cell binding plates in the presence of the PGC medium. Four to six days later, the cells were separated from the plates using TripLE select agent and were subjected to flow cytometry and molecular analysis. FIG. 95 shows representative images of the cells during the differentiation process.

BMP4 induces expression of NANOS3-m Cherry reporter gene—Cells that were subjected to the differentiation process described herein, using the N2-KSR and PGC media were examined by FACS for the expression of the NANOS3-mCherry reporter gene which indicates that the cells are in the PGC-like state. Thus, as shown in FIGS. 96A and 96B, while naive ESCs (FIG. 96BA) and primed EpiLC (FIG. 96C) cells did not express the NANOS3-mCherry reporter, following 4 days in the PGC medium (after being for 2 days in the N2-KSR medium), and in the presence of BMP4 in the PGC medium, a significant fraction of the cells expressed the mCherry reporter gene, indicating expression of NANOS3 (17.7%; FIG. 96E). On the other hand, under the same conditions but without the BMP4 in the PGC medium, only minimal expression of mCherry reporter was seen (0.45% of the cells; FIG. 96H), suggesting that BMP4 is important for differentiation of the human naive cells into PGC-like cells (PGCLCs).

Evaluation of PGC markers in the PGCLC cells induced from the naive ESCs demonstrates generation of PGC from naive pluripotent stem cells—The PGCLC cells generated by the method described herein were further evaluated for expression of PGC makers. Thus, as shown in FIGS. 97A-H, PGCLC markers are induced in protocol applied on human naive ESCs, including STELLA (FIG. 97D), INTEGRINB3 (FIG. 97G), BLIMP1 (FIG. 97B) and VASA (FIG. 97H).

Primed ESCs, that were genetically modified with the NANOS3-mCherry knock in vector, were subjected to the same differentiation protocol described herein. However, they failed to form PGCLC. Thus, as shown in FIGS. 98A-B, FACS analyses of conventional/primed human ESCs that were subjected to either incubation in the PGC medium alone (FIG. 98A) or in the EpiLC medium followed by the PGC medium (FIG. 98B) did not result in expression of the NANOS3-mCherry reporter gene, thus demonstrating lack of differentiation into the primordial germ cells. These results show that conventional/primed human ESCs subjected to BMP4 including PGCLC induction protocol do not successfully turn on NANOS3 mCherry reporter.

Further FACS analyses (FIGS. 106A-D) show that NANOS3 mcherry+ cells specifically upregulate CD61 surface marker (IntergrinB3). The NANOS3-mCherry+ cells also express SSEA4 surface markers (FIGS. 107A-B). This analysis indicates that CD61+ cells marker or CD61+/SSEA4+ cell surface combination can be used to sort out and isolate human PGCLCs derived from human naive pluripotent cells (without the need for NANOs3 knockin reporter genetic engineering). Results indicate the importance of using human naive pluripotent cells as a starting material for human PGCLC induction.

Example 13

Inhibition of Protein Kinase C Results in Reduced Mbd3 Protein Levels of Embryonic Stem Cells The present inventors tested various factors, small molecules and agents for the ability to reduce MBD3 protein expression levels in embryonic stem cells.

V6.5 mouse ES cells were expanded for 4 days in various conditions in order to identify combination of factors which result in reduced MBD3 protein levels. As shown in FIGS. 101A-B, while treatment with the "2i/LIF" conditions with or without DMSO, or addition of a TGFβ inhibitor did not affect MBD3 levels, the use of the "2i/LIF" conditions with a PKC inhibitor resulted in a significant reduction in MBD3 protein levels. The results show that inhibition of PKC leads to down regulation in MBD3 expression in mouse embryonic stem cells. These results suggest the use of PKC inhibitors as agents which deplete or downregulate MBD3 expression and as boosters of deterministic iPSC reprogramming.

Example 14

Adjustment of the WIS-NHSM Media

The present inventors have devised various modifications of the basic WIS-NHSM medium in order to test the effect of inhibitors and growth factors on naive pluripotent stem cells. Table 3 hereinbelow and FIGS. 102-105 describe the effect of various factors and inhibitors on maintenance of naive pluripotent state.

TABLE 3

| | WIS-NHSM media | | | | | |
|---|---|---|---|---|---|---|
| | Condition No. | | | | | |
| agents | 1 | 2 | 3 | 4 | 5 | 6 |
| LIF | 20 ng/ml | 20 ng/ml | 20 ng/ml | 20 ng/ml | 20 ng/ml | 20 ng/ml |
| ERK1/2i (PD0325901) | 1 μM | 1 μM | 1 μM | 1 μM | 1 μM | 1 μM |
| GSK3βi (CHIR99021) | 3 μM | 3 μM | 3 μM | 3 μM | 3 μM | 3 μM |
| JNKi (SP600125) | 5 μM | 5 μM | 5 μM | 5 μM | 5 μM | 5 μM |
| P38i (BIRB796) | 2 μM | 2 μM | 2 μM | 2 μM | 2 μM | — |
| FGF2 | 16 ng/ml | 16 ng/ml | 16 ng/ml | 16 ng/ml | 16 ng/ml | 16 ng/ml |
| TGFβ1 | 2 ng/ml | 2 ng/ml | 2 ng/ml | 2 ng/ml | 2 ng/ml | 2 ng/ml |
| ROCKi (Y27632) | 5 μM | 5 μM | 5 μM | 5 μM | 5 μM | 5 μM |
| IGFII | — | 20 ng/ml | 20 ng/ml | 20 ng/ml | — | — |

TABLE 3-continued

WIS-NHSM media

| agents | Condition No. | | | | | |
|---|---|---|---|---|---|---|
| | 1 | 2 | 3 | 4 | 5 | 6 |
| SCF | — | — | 10 ng/ml | 10 ng/ml | — | — |
| BMPi (LDN-193189) | — | — | — | 0.5 µM | 0.5 µM | 0.5 µM |

Table 3: Provided are the agents (factors, inhibitors) included in various modifications of the basic WIS-NHSM medium. LIF—leukemia inhibitory factor; FGF2 = fibroblast growth factor 2 (also termed "basic FGF"); TGFβ1 = transforming growth factor beta 1; SCF = stem cell factor; BMPi = bone morphogenetic protein inhibitor; IGFII = insulin-like growth factor 2 (somatomedin A). Note that condition No. 6 is devoid of the p38i.

FIGS. 102-105 show the effect of the various modifications of the WIS-NHSM media on methylation of DNA (% of total methylated cytosine levels (5 mdC) normalized to dG; FIG. 102), relative DNMT3L mRNA expression (normalized to primed cells; FIG. 103), relative DNMT3B mRNA expression (normalized to primed cells; FIG. 104), and percentage (%) of OCT4+ WIBR3 cells after 9 passages on 0.2% gelatin plates (FIG. 105). These experiments show that inclusion of p38i is essential to maintain naive pluripotency features associated with downregulation of de novo DNA methyltransferase genes DNMT3b and DNMT3L and leads to loss in global DNA methylation levels. Omission of p38i and addition of BMPi instead (combination 6, Table 3 above), did not result in such effect which is the hallmark of human naive pluripotency. BMPi can be added together with p38i, and does not compromise naive pluripotency when used in combination (combinations 4 or 5, Table 3 above).

Similarly, Tables 4 and 5 below and FIGS. 85A-C show the effect of the various compositions of the medium on the naive state of pluripotent stem cells. WIBR3 hESCs were cultured in the WIS-NHSM conditions 1 and 7-17 and the cells were tested for percentage of pluripotent stem cells (by OCT4 positive cells; FIG. 85B) and percentage of total methylated cytosine (5mdC; FIG. 85C).

TABLE 4

| | WIS-NHSM media (Conditions 1 and 7-11) | | | | | |
|---|---|---|---|---|---|---|
| | Condition No. | | | | | |
| agents | 1 | 7 | 8 | 9 | 10 | 11 |
| LIF | 20 ng/ml | 20 ng/ml | 20 ng/ml | 20 ng/ml | 20 ng/ml | 20 ng/ml |
| ERK1/2i (PD0325901) | 1 µM | 1 µM | 1 µM | 1 µM | 1 µM | 1 µM |
| GSK3βi (CHIR99021) | 3 µM | 3 µM | 3 µM | 3 µM | 3 µM | 3 µM |
| JNKi (SP600125) | 5 µM | 5 µM | 5 µM | 5 µM | 5 µM | 5 µM |
| P38i (BIRB796) | 2 µM | 2 µM | 2 µM | 2 µM | 2 µM | 2 |
| FGF2 | 16 ng/ml | 16 ng/ml | 16 ng/ml | 16 ng/ml | 16 ng/ml | 16 ng/ml |
| TGFβ1 | 2 ng/ml | 2 ng/ml | 2 ng/ml | 2 ng/ml | 2 ng/ml | 2 ng/ml |
| ROCKi (Y27632) | 5 µM | 5 µM | 5 µM | 5 µM | 5 µM | 5 µM |
| IGFII | — | — | — | — | 20 ng/ml | — |
| SCF | — | — | — | — | — | — |
| BMPi (LDN-193189) | — | 0.5 µM | — | 0.5 µM | 0.5 µM | 0.5 µM |
| NOTCHi (DBZ) | — | — | 2 µM | 2 µM | 2 µM | 2 µM |
| SHHi (RU-SKI-43) | — | — | — | — | — | 5 µM |

Table 4: Provided are the agents (factors, inhibitors) included in the WIS-NHSM medium. LIF—leukemia inhibitory factor; FGF2 = fibroblast growth factor 2 (also termed "basic FGF"); TGFβ1 = transforming growth factor bet 1; SCF = stem cell factor; BMPi = bone morphogenetic protein inhibitor; IGFII = insulin-like growth factor 2 (somatomedin A). NOTCHi = NOTCH inhibitor; SHHi = Sonic Hedgehog pathway (SHH) inhibitor; TGFRi = transforming growth factor receptor inhibitor; FGFRi = fibroblast growth factor receptor inhibitor.

TABLE 5

| | WIS-NHSM media (Conditions 12-17) | | | | | |
|---|---|---|---|---|---|---|
| | Condition No. | | | | | |
| agents | 12 | 13 | 14 | 15 | 16 | 17 |
| LIF | 20 ng/ml | 20 ng/ml | 20 ng/ml | 20 ng/ml | 20 ng/ml | 20 ng/ml |
| ERK1/2i (PD0325901) | 1 µM | 1 µM | 1 µM | 1 µM | 1 µM | 1 µM |
| GSK3βi (CHIR99021) | 3 µM | 3 µM | 3 µM | 3 µM | 3 µM | 3 µM |

TABLE 5-continued

WIS-NHSM media (Conditions 12-17)

| agents | 12 | 13 | 14 | 15 | 16 | 17 |
|---|---|---|---|---|---|---|
| JNKi (SP600125) | 5 µM | 5 µM | 5 µM | 5 µM | 5 µM | 5 µM |
| P38i (BIRB796) | 2 µM | 2 µM | 2 µM | 2 µM | 2 µM | 2 |
| FGF2 | 16 ng/ml | 16 ng/ml | — | 16 ng/ml | — | — |
| TGFβ1 | — | 2 ng/ml | — | — | 2 ng/ml | — |
| ROCKi (Y27632) | 5 µM | 5 µM | 5 µM | 5 µM | 5 µM | 5 µM |
| IGFII | — | 20 ng/ml | 20 ng/ml | — | 20 ng/ml | 20 ng/ml |
| SCF | — | 10 ng/ml | 10 ng/ml | — | 10 ng/ml | 10 ng/ml |
| BMPi (LDN-193189) | 0.5 µM | 0.5 µM | 0.5 µM | 0.5 µM | 0.5 µM | 0.5 µM |
| NOTCHi (DBZ) | 2 µM | 2 µM | 2 µM | 2 µM | 2 µM | 2 µM |
| SHHi (RU-SKI-43) | — | — | — | 5 µM | 5 µM | 5 µM |
| TGFRi (SB432541) | 2 µM | — | 2 µM | 2 µM | — | 2 µM |
| FGFRi (PD173471) | — | — | 0.1 µM | — | 0.1 µM | 0.1 µM |

Table 5: Provided are the agents (factors, inhibitors) included in the WIS-NHSM medium. LIF—leukemia inhibitory factor; FGF2 = fibroblast growth factor 2 (also termed "basic FGF"; TGFβ1 = transforming growth factor bet 1; SCF = stem cell factor; BMPi = bone morphogenetic protein inhibitor; IGFII = insulin-like growth factor 2 (somatomedin A). NOTCHi = NOTCH inhibitor; SHHi = Sonic Hedgehog pathway (SHH) inhibitor; TGFRi = transforming growth factor receptor inhibitor; FGFRi = fibroblast growth factor receptor inhibitor.

As shown in FIGS. 85A-C, all of conditions 1 and 7-17 were capable of maintaining the naive state of the pluripotent stem cells, with the notable reduced percentage of total methylated cytosine.

It is noted that in conditions 12 and 15 (Table 5 above), when NOTCHi is used, TGFRi can then be used (and recombinant TGFB1 can be omitted) to maintain naive pluripotency with reduced DNA methylation levels.

In addition, in condition 16, when NOTCHi is used, FGFRi can then be used (and recombinant FGF2 can be omitted) to maintain naive pluripotency with reduced DNA methylation levels. Recombinant IGFII and SCF are used in these conditions to boost human naive cells proliferation in the absence of FGF2 signaling.

In addition, in conditions 14 and 17, when NOTCHi is used, FGFRi and TGRFi can then be used (and recombinant FGF2 and TGFB1 can be omitted) to maintain naive pluripotency with reduced DNA methylation levels. Recombinant IGFII and SCF are used in these conditions to boost human naive cells proliferation in the absence of FGF2 signaling.

It should be noted that WIS-NHSM condition 15 medium (Table 5 above) is excellent for culturing human pluripotent stem cells in the naive state as is evidenced by the domed colony morphology and lack of defined borders between individual cells in each colony (data not shown).

It should be noted that the above WIS-NHSM conditions can be used to maintain the naive state of non-human primates pluripotent stem cells.

In summary, the following modifications of the medium for establishing a naive pluripotent state can be used:

P38i: Inhibitors for P38 include upstream blockers for pathways that activate p38 signaling: including BMP signaling inhibitors/

STAT3 activation: Activators for STAT3 signaling can be used to replace LIF including IL-6.

TGFB1—Activators of TGF/ACTIVIN pathway including ACTIVIN A (also known as Inhibin beta A, Gene ID: 3624 can be sued to replace TGFB1).

BMPi: protein inhibitors of BMP pathway like recombinant NOGGIN protein, can be used to replace small molecule inhibitors of BMP signaling.

A non-limiting example of a culture medium which can be used to maintain (and induce to naive state) pluripotent stem cells in a naive state include: A culture medium comprising leukemia inhibitor factor (LIF), an ERK1/2 inhibitor, a GSK3b inhibitor, a p38 inhibitor, a JNK inhibitor, basic fibroblast growth factor (bFGF) and transforming growth factor-beta 1 (TGFβ1), and one or more of the following components:

a) IGFII (range 0.1-100 ng/ml final concentration);

b) IGF1 [insulin-like growth factor 1 (somatomedin C)] (range 0.1-100 ng/ml final concentration);

c) SCF (range 0.1-100 ng/ml final concentration);

d) BMP signaling inhibitor [examples include, but are not limited to: LDN193189 (AXON 1509—0.01-20 microM final concentration), K02288 (Axon 2189; 0.1-20 microM final concentration), Dorsomorphin hydrochloride (AXON 2150 0.1-20 microM final concentration);

e) NOTCH signaling inhibitors [examples include, but are not limited to the following gamma secretase inhibitors: DAPT (Axon Medchem 1484—0.05—50 microM final concentration), LY2886721 hydrochloride (Axon Medchem 1964—0.05-50 microM final concentration)], DBZ (Axon Medchem—Axon 1488—0.05-50 microM final concentration).

f) Sonic Hedgehog pathway (SHH) inhibitors [examples include, but are not limited to the following: GANT61 (SigmaAldrich 0.05-50 microM final concentration), RU-SKI 43 (Axon Medchem—Axon 2035—0.05-50 microM final concentration)].

g) ERK5 inhibitors (BIX02189 Axon 1809; range 0.1-100 microM final concentration)

h) ROCK inhibitor [Y27632 (AXON 1683)—0.05-100 microM final].

i) FGF signaling inhibitor: Non-limiting examples of FGFR inhibitors include PD173074 and SU5401.

j) TGF pathway inhibitor: Non-limiting examples of TGFR inhibitors include SB431542 and A 83-01 small molecule compound (As used herein the term "TGFR inhibitor (or TGFRi)" refers to a molecule capable of inhibiting TGFR expression and/or activity level as determined by phosphorylated ALK4, 5 and 7).

Example 15

Activation of Eras for Inducing and Maintenance of Naive Pluripotent State

Human ES Ras (ERAS) gene (Gene ID: 3266) has an upstream premature polyadenylation signal that results in a truncated, noncoding transcript (Kameda T, and Thomson J A, Stem Cells 2005, 23:1535-40).

The present inventors have further envisaged that overexpression of ERas or activation of endogenous human ERas in pluripotent stem cells can be used to induce a naive state in pluripotent stem cells. Thus, genetically modified pluripotent stem cells in which ERas is either over expressed or endogenously activated exhibit a naive state of the pluripotent stem cells.

Overexpression of ERas in pluripotent stem cells—human pluripotent stem cells are transformed with a nucleic acid construct designed for constitutive or transient expression of ERas (SEQ ID NO: 109).

Activation of endogenous ERAS expression in human pluripotent stem cells—In human cells, the ERAS gene is not expressed due to the presence of viral sequences that integrated into the human genome and block ERAS expression. Activation of endogenous human ERAS expression is achieved by removing the combinations of polyadenylation sites (Marked as "pre-mature polyadenylation sites" in SEQ ID NO: 108 in the sequence listing; also defined as "poly-A signal" in A-1, A2 or A-3 boxed sequences in FIG. 3 by Kameda et al. Stem Cells 2005; 23:1535-1540; which is fully incorporated herein by reference in its entirety). The latter modification can be either achieved with homologous recombination, CRISPR [as described in Ryan M. Walsh and Konrad Hochedlinger, Proc Natl Acad Sci USA. 2013 Sep. 24; 110(39):15514-5; and Yang Hui et al., Cell 154: 1370-1379, Sep. 12, 2013; each of which is fully incorporated herein by reference in its entirety], or TALENs [Hockemeyer D, et al., Nat. Biotechnol. 2011 Jul. 7; 29(8):731-4, which is fully incorporated herein by reference in its entirety], either alone or in combination.

Human ERAS gene expression/reactivation may be used in combination with any of the media described herein for naive pluripotent stem cells to boost human naive pluripotent cells proliferation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

Ang, Y.-S., Tsai, S.-Y., Lee, D.-F., Monk, J., Su, J., Ratnakumar, K., Ding, J., Ge, Y., Darr, H., Chang, B., et al. (2011). Wdr5 mediates self-renewal and reprogramming via the embryonic stem cell core transcriptional network. Cell 145, 183-197.

De Los Angeles, A., Loh, Y.-H., Tesar, P. J., and Daley, G. Q. (2012). Accessing naive human pluripotency. Curr. Opin. Genet. Dev. 22, 272-282.

Durcova-Hills, G., Tang, F., Doody, G., Tooze, R., and Surani, M. A. (2008). Reprogramming primordial germ cells into pluripotent stem cells. PLoS ONE 3, e3531.

Fidalgo, M., Faiola, F., Pereira, C.-F., Ding, J., Saunders, A., Gingold, J., Schaniel, C., Lemischka, I. R., Silva, J. C. R., and Wang, J. (2012). Zfp281 mediates Nanog autorepression through recruitment of the NuRD complex and inhibits somatic cell reprogramming. Proc. Natl. Acad. Sci. U.S.a. 109, 16202-16207.

Hanna, J. H. (2010). The STATs on naive iPSC reprogramming. Cell Stem Cell 7, 274-276.

Hanna, J. H., Saha, K., and Jaenisch, R. (2010a). Pluripotency and cellular reprogramming: facts, hypotheses, unresolved issues. Cell 143, 508-525.

Hanna, J., Cheng, A. W., Saha, K., Kim, J., Lengner, C. J., Soldner, F., Cassady, J. P., Muffat, J., Carey, B. W., and Jaenisch, R. (2010b). Human embryonic stem cells with biological and epigenetic characteristics similar to those of mouse ESCs. Proc. Natl. Acad. Sci. U.S.a. 107, 9222-9227.

Hanna, J., Markoulaki, S., Mitalipova, M., Cheng, A. W., Cassady, J. P., Staerk, J., Carey, B. W., Lengner, C. J., Foreman, R., Love, J., et al. (2009a). Metastable pluripotent states in NOD-mouse-derived ESCs. Cell Stem Cell 4, 513-524.

Hanna, J., Saha, K., Pando, B., van Zon, J., Lengner, C. J., Creyghton, M. P., van Oudenaarden, A., and Jaenisch, R. (2009b). Direct cell reprogramming is a stochastic process amenable to acceleration. Nature 462, 595-601.

Hockemeyer, D., Wang, H., Kiani, S., Lai, C. S., Gao, Q., Cassady, J. P., Cost, G. J., Zhang, L., Santiago, Y., Miller, J. C., et al. (2011). Genetic engineering of human pluripotent cells using TALE nucleases. Nat Biotechnol 29, 731-734.

Kaji, K., Caballero, I. M., MacLeod, R., Nichols, J., Wilson, V. A., and Hendrich, B. (2006). The NuRD component Mbd3 is required for pluripotency of embryonic stem cells. Nat Cell Biol 8, 285-292.

Kaji, K., Nichols, J., and Hendrich, B. (2007). Mbd3, a component of the NuRD co-repressor complex, is required for development of pluripotent cells. Development 134, 1123-1132.

Lengner, C. J., Gimelbrant, A. A., Erwin, J. A., Cheng, A. W., Guenther, M. G., Welstead, G. G., Alagappan, R., Frampton, G. M., Xu, P., Muffat, J., et al. (2010). Derivation of pre-X inactivation human embryonic stem cells under physiological oxygen concentrations. Cell 141, 872-883.

Li, W., Wei, W., Zhu, S., Zhu, J., Shi, Y., Lin, T., Hao, E., Hayek, A., Deng, H., and Ding, S. (2009). Generation of rat and human induced pluripotent stem cells by combining genetic reprogramming and chemical inhibitors. Cell Stem Cell 4, 16-19.

Mansour, A. A., Gafni, O., Weinberger, L., Zviran, A., Ayyash, M., Rais, Y., Krupalnik, V., Zerbib, M., Amann-Zalcenstein, D., Maza, I., et al. (2012). The H3K27 demethylase Utx regulates somatic and germ cell epigenetic reprogramming. Nature 488, 409-413.

Marks, H., Kalkan, T., Menafra, R., Denissov, S., Jones, K., Hofemeister, H., Nichols, J., Kranz, A., Francis Stewart, A., Smith, A., et al. (2012). The transcriptional and epigenomic foundations of ground state pluripotency. Cell 149, 590-604.

Mikkelsen, T. S., Hanna, J., Zhang, X., Ku, M., Wernig, M., Schorderet, P., Bernstein, B. E., Jaenisch, R., Lander, E. S., and Meissner, A. (2008). Dissecting direct reprogramming through integrative genomic analysis. Nature 454, 49-55.

Nichols, J., and Smith, A. (2012). Pluripotency in the embryo and in culture. Cold Spring Harb Perspect Biol 4, a008128.

Okamoto, I., Patrat, C., Thepot, D., Peynot, N., Fauque, P., Daniel, N., Diabangouaya, P., Wolf, J.-P., Renard, J.-P., Duranthon, V., et al. (2011). Eutherian mammals use diverse strategies to initiate X-chromosome inactivation during development. Nature 1-7.

Onder, T. T., Kara, N., Cherry, A., Sinha, A. U., Zhu, N., Bernt, K. M., Cahan, P., Marcarci, B. O., Unternaehrer, J., Gupta, P. B., et al. (2012). Chromatin-modifying enzymes as modulators of reprogramming. Nature 483, 598-602.

Orkin, S. H., and Hochedlinger, K. (2011). Chromatin Connections to Pluripotency and Cellular Reprogramming. Cell 145, 835-850.

Polo, J. M., Anderssen, E., Walsh, R. M., Schwarz, B. A., Nefzger, C. M., Lim, S. M., Borkent, M., Apostolou, E., Alaei, S., Cloutier, J., et al. (2012). A Molecular Roadmap of Reprogramming Somatic Cells into iPS Cells. Cell 151, 1617-1632.

Pribluda, A., and Hanna, J. H. (2012). Tracing the genesis of human embryonic stem cells. Nat Biotechnol 30, 247-249.

Roode, M., Blair, K., Snell, P., Elder, K., Marchant, S., Smith, A., and Nichols, J. (2012). Human hypoblast formation is not dependent on FGF signalling. Dev. Biol. 361, 358-363.

Silva, J., Nichols, J., Theunissen, T. W., Guo, G., van Oosten, A. L., Barrandon, O., Wray, J., Yamanaka, S., Chambers, I., and Smith, A. (2009). Nanog is the gateway to the pluripotent ground state. Cell 138, 722-737.

Smith, Z. D., Nachman, I., Regev, A., and Meissner, A. (2010). Dynamic single-cell imaging of direct reprogramming reveals an early specifying event. Nat Biotechnol 28, 521-526.

Soufi, A., Donahue, G., and Zaret, K. S. (2012). Facilitators and Impediments of the Pluripotency Reprogramming Factors' Initial Engagement with the Genome. Cell 1-11.

Sridharan, R., Tchieu, J., Mason, M. J., and Yachechko, R. (2009). ScienceDirect.com—Cell—Role of the Murine Reprogramming Factors in the Induction of Pluripotency. Cell.

Takahashi, K., and Yamanaka, S. (2006). Induction of pluripotent stem cells from mouse embryonic and adult fibroblast cultures by defined factors. Cell 126, 663-676.

Tesar, P. J., Chenoweth, J. G., Brook, F. A., Davies, T. J., Evans, E. P., Mack, D. L., Gardner, R. L., and McKay, R. D. G. (2007). New cell lines from mouse epiblast share defining features with human embryonic stem cells. Nature 448, 196-199.

Tiwari, V. K., Stadler, M. B., Wirbelauer, C., Paro, R., Schübeler, D., and Beisel, C. (2011). A chromatin-modifying function of JNK during stem cell differentiation. Nat. Genet.

Tomoda, K., Takahashi, K., Leung, K., Okada, A., Narita, M., Yamada, N. A., Eilertson, K. E., Tsang, P., Baba, S., White, M. P., et al. (2012). Derivation conditions impact x-inactivation status in female human induced pluripotent stem cells. Cell Stem Cell 11, 91-99.

Warren, L., Ebina, W., Mandal, P. K., Smith, Z. D., Meissner, A., and Daley, G. Q. (2010). ScienceDirect.com—Cell Stem Cell—Highly Efficient Reprogramming to Pluripotency and Directed Differentiation of Human Cells with Synthetic Modified mRNA. Cell Stem Cell.

Wernig, M., Lengner, C. J., Hanna, J., Lodato, M. A., Steine, E., Foreman, R., Staerk, J., Markoulaki, S., and Jaenisch, R. (2008). A drug-inducible transgenic system for direct reprogramming of multiple somatic cell types. Nat Biotechnol 26, 916-924.

Ying, Q.-L., Wray, J., Nichols, J., Batlle-Morera, L., Doble, B., Woodgett, J., Cohen, P., and Smith, A. (2008). The ground state of embryonic stem cell self-renewal. Nature 453, 519-523.

Zhu, D., Fang, J., Li, Y., and Zhang, J. (2009). Mbd3, a Component of NuRD/Mi-2 Complex, Helps Maintain Pluripotency of Mouse Embryonic Stem Cells by Repressing Trophectoderm Differentiation. PLoS ONE 4, e7684.

---

What is claimed is:

1. A method of generating a naive human or monkey pluripotent stem cell (PSC), comprising:
    (a) obtaining a non-naive human or rhesus monkey PSC;
    (b) incubating said non-naive human or said non-naive rhesus monkey PSC in a culture medium comprising an ERK1/2 inhibitor at a concentration of 0.8-3 µM, a GSK3 beta inhibitor at a concentration of 0.2-3 µM, a p38 inhibitor at a concentration of 0.05-10 µM, a JNK inhibitor at a concentration of 1-20 µM, leukemia inhibitory factor (LIF) at a concentration of 0.5-1000 ng/ml, basic fibroblast growth factor (bFGF) at a concentration of 1-100 ng/ml, and at least one agent selected from the group consisting of: transforming growth factor beta 1 (TGFβ1) at a concentration of 0.1-100 ng/ml or an activator thereof, a protein kinase C (PKC) inhibitor at a concentration of 0.5-100 µM, a ROCK inhibitor at a concentration of 0.1-50 µM and a NOTCH inhibitor at a concentration of 0.05-50 µM; under conditions which allow generation of the naive human or the naive rhesus monkey PSC from said non-naive human or said non-naive rhesus monkey PSC,
    (c) identifying a naive human or a naive rhesus monkey PSC which comprises:
        (1) an unmethylated promoter of the X-inactive specific transcript (XIST) gene, wherein:
        (i) when said naive human or rhesus monkey PSC is a female PSC, then said naïve female human or rhesus monkey PSC has two unmethylated alleles of said promoter of said XIST gene; and
        (ii) when said naive human or rhesus monkey PSC is a male PSC, then said naïve male human or rhesus monkey PSC has an unmethylated allele of said promoter of said XIST gene, and
        (2) an expression level of transcription factor E3 (TFE3) in said naive human or rhesus monkey PSC is characterized by a nucleus to cytoplasm expression ratio which is equal to or higher than 1 as determined by an immunostaining assay,
    thereby generating the naive human or a naive rhesus monkey PSC.

2. The method of claim 1, wherein said conditions comprise hypoxia.

3. The method of claim 1, wherein said culture medium further comprises an MBD3 inhibitor.

4. The method of claim 1, wherein said culture medium further comprises a chromodomain helicase DNA binding protein 4 (CHD4) inhibitor.

5. The method of claim 1, wherein said culture medium further comprises P66 alpha coiled-coil domain.

6. The method of claim 1, wherein said non-naive PSC is selected from the group consisting of a primed PSC, a blastocyst, and an induced pluripotent stem cell (iPSC).

7. The method of claim 6, wherein said induced pluripotent stem cell (iPSC) is generated by subjecting a somatic cell to de-differentiation conditions, to thereby obtain an induced pluripotent stem cell.

8. The method of claim 7, wherein said de-differentiation conditions comprise expressing within said somatic cell at least two growth factors selected from the group consisting of Oct4, Sox2, Klf4 and c-Myc.

9. A method of generating a naive human pluripotent stem cell (PSC), comprising:
    incubating a non-naive human PSC cell in a cell culture medium under conditions which allow generation of the naive human PSC comprising an unmethylated promoter of the XIST gene from said non-naive human PSC, wherein the cell culture medium is selected from the group consisting of:

(a) a culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, leukemia inhibitory factor (LIF) at a concentration of 0.5-1000 ng/ml, basic fibroblast growth factor (bFGF) at a concentration of 1-100 ng/ml, and at least one agent selected from the group consisting of: transforming growth factor beta 1 (TGF 1) at a concentration of 0.1-100 ng/ml or an activator thereof, a protein kinase C (PKC) inhibitor at a concentration of 0.5-100 µM, a ROCK inhibitor at a concentration of 0.1-50 µM and a NOTCH inhibitor at a concentration of 0.05-50 µM; and (b) a culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, LIF at a concentration of 0.5-1000 ng/ml, a transforming growth factor receptor (TGFR) inhibitor at a concentration of 0.1-30 µM, a fibroblast growth factor receptor (FGFR) inhibitor at a concentration of 0.01-40 µM, a PKC inhibitor at a concentration of 0.5-100 µM, a ROCK inhibitor at a concentration of 0.1-50 µM and a NOTCH inhibitor at a concentration of 0.05-50 µM;

wherein: (i) when said naive human PSC is a female PSC, then said naïve female human PSC has two unmethylated alleles of the promoter of the XIST gene; and (ii) when said naive human PSC is a male PSC, then said naïve male human PSC has an unmethylated allele of the promoter of the XIST gene, and an expression level of transcription factor E3 (TFE3) in said naive human PSC is characterized by a nucleus to cytoplasm expression ratio which is equal to or higher than 1 as determined by an immunostaining assay, thereby generating the naive human PSC.

10. The method of claim 1, wherein said at least one agent comprises said TGF beta 1, said PKC inhibitor and said ROCK inhibitor.

11. The method of claim 1, wherein said at least one agent comprises said TGF beta 1 activator, said PKC inhibitor and said ROCK inhibitor.

12. The method of claim 11, wherein said TGF beta 1 activator is Activin A.

13. The method of claim 1, wherein said at least one agent comprises said TGF beta 1 and said ROCK inhibitor.

14. The method of claim 1, wherein said TGFβ1 activator is activin A.

15. The method of claim 9, wherein said at least one agent in said culture medium (a) comprises said TGF beta 1, said PKC inhibitor and said ROCK inhibitor.

16. The method of claim 9, wherein said at least one agent in said culture medium (a) comprises said TGF beta 1 activator, said PKC inhibitor and said ROCK inhibitor.

17. The method of claim 16, wherein said TGFβ1 activator is activin A.

18. The method of claim 9, wherein said at least one agent in said culture medium (a) comprises said TGF beta 1 and said ROCK inhibitor.

19. The method of claim 9, wherein said TGFβ1 activator is activin A.

20. The method of claim 9, wherein said conditions comprise hypoxia.

21. The method of claim 9, wherein said culture medium further comprises a chromodomain helicase DNA binding protein 4 (CHD4) inhibitor.

22. The method of claim 9, wherein said non-naive PSC is selected from the group consisting of a primed PSC, a blastocyst, and an induced pluripotent stem cell (iPSC).

23. The method of claim 9, further comprising identifying said naive human PSC following said incubating, wherein said naive human PSC is characterized by said unmethylated allele(s) of said XIST promoter and by said expression level of said TFE3.

24. A method of generating a naive human pluripotent stem cell (PSC), comprising:

incubating a non-naive human PSC cell in a cell culture medium under conditions which allow generation of the naive human PSC comprising an unmethylated promoter of the XIST gene from said non-naive human PSC, wherein the cell culture medium is selected from the group consisting of:

(a) a culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, leukemia inhibitory factor (LIF) at a concentration of 0.5-1000 ng/ml, P66 alpha coiled-coil domain, basic fibroblast growth factor (bFGF) at a concentration of 1-100 ng/ml, and at least one agent selected from the group consisting of: transforming growth factor beta 1 (TGF31) at a concentration of 0.1-100 ng/ml or an activator thereof, a protein kinase C (PKC) inhibitor at a concentration of 0.5-100 µM, a ROCK inhibitor at a concentration of 0.1-50 µM and a NOTCH inhibitor at a concentration of 0.05-50 µM; and (b) a culture medium comprising an ERK1/2 inhibitor at a concentration of 0.8-3 µM, a GSK3beta inhibitor at a concentration of 0.2-3 µM, a p38 inhibitor a at a concentration of 0.05-10 µM, a JNK inhibitor at a concentration of 1-20 µM, LIF at a concentration of 0.5-1000 ng/ml, P66 alpha coiled-coil domain, a transforming growth factor receptor (TGFR) inhibitor at a concentration of 0.1-30 µM, a fibroblast growth factor receptor (FGFR) inhibitor at a concentration of 0.01-40 µM, a PKC inhibitor at a concentration of 0.5-100 µM, a ROCK inhibitor at a concentration of 0.1-50 µM and a NOTCH inhibitor at a concentration of 0.05-50 µM;

wherein: (i) when said naive human PSC is a female PSC, then said naïve female human PSC has two unmethylated alleles of the promoter of the XIST gene; and (ii) when said naive human PSC is a male PSC, then said naïve male human PSC has an unmethylated allele of the promoter of the XIST gene, and an expression level of transcription factor E3 (TFE3) in said naive human PSC is characterized by a nucleus to cytoplasm expression ratio which is equal to or higher than 1 as determined by an immunostaining assay, thereby generating the naive human PSC.

25. The method of claim 24, further comprising identifying said naive human PSC following said incubating, wherein said naive human PSC is characterized by said unmethylated allele(s) of said XIST promoter and by said expression level of said TFE3.

26. The method of claim 9, wherein said culture medium in (a) and (b) does not include the Oct4, Sox2, Klf4 and/or c-Myc factors.

27. The method of claim 24, wherein said culture medium in (a) and (b) does not include the Oct4, Sox2, Klf4 and/or c-Myc factors.

28. The method of claim 24, wherein said non-naive PSC is selected from the group consisting of a primed PSC, a blastocyst, and an induced pluripotent stem cell (iPSC).

29. A method of generating a naive human pluripotent stem cell (PSC), comprising:

incubating a non-naive human PSC cell in a cell culture medium under conditions which allow generation of the naive human PSC comprising an unmethylated promoter of the XIST gene from said non-naive human PSC, wherein said non-naive human PSC is not genetically modified to express Oct4, Sox2, Klf4 and/or c-Myc protein(s), wherein said non-naive PSC is selected from the group consisting of a primed PSC, a blastocyst, and an induced pluripotent stem cell (iPSC), and wherein the culture medium is selected from the group consisting of:

(a) a culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, leukemia inhibitory factor (LIF) at a concentration of 0.5-1000 ng/ml, basic fibroblast growth factor (bFGF) at a concentration of 1-100 ng/ml, and at least one agent selected from the group consisting of: transforming growth factor beta 1 (TGF1) at a concentration of 0.1-100 ng/ml or an activator thereof, a protein kinase C (PKC) inhibitor at a concentration of 0.5-100 µM, a ROCK inhibitor at a concentration of 0.1-50 µM and a NOTCH inhibitor at a concentration of 0.05-50 µM; and (b) a culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, LIF at a concentration of 0.5-1000 ng/ml, a transforming growth factor receptor (TGFR) inhibitor at a concentration of 0.1-30 µM, a fibroblast growth factor receptor (FGFR) inhibitor at a concentration of 0.01-40 µM, a PKC inhibitor at a concentration of 0.5-100 µM, a ROCK inhibitor at a concentration of 0.1-50 µM and a NOTCH inhibitor at a concentration of 0.05-50 µM;

wherein: (i) when said naive human PSC is a female PSC, then said naïve female human PSC has two unmethylated alleles of the promoter of the XIST gene; and (ii) when said naive human PSC is a male PSC, then said naïve male human PSC has an unmethylated allele of the promoter of the XIST gene, and an expression level of transcription factor E3 (TFE3) in said naive human PSC is characterized by a nucleus to cytoplasm expression ratio which is equal to or higher than 1 as determined by an immunostaining assay, thereby generating the naive human PSC.

30. The method of claim 9, wherein said non-naive human PSC is not genetically modified to express Oct4, Sox2, Klf4 and/or c-Myc protein(s).

31. The method of claim 24, wherein said non-naive human PSC is not genetically modified to express Oct4, Sox2, Klf4 and/or c-Myc protein(s).

32. A method of generating a naive human pluripotent stem cell (PSC), comprising:

incubating a non-naive human PSC cell in a cell culture medium comprising an ERK1/2 inhibitor at a concentration of 0.8-3 µM, a GSK3beta inhibitor at a concentration of 0.2-3 µM, a p38 inhibitor at a concentration of 0.05-10 µM, a JNK inhibitor at a concentration of 1-20 µM, LIF at a concentration of 0.5-1000 ng/ml, a fibroblast growth factor receptor (FGFR) inhibitor at a concentration of 0.01-40 µM, a NOTCH inhibitor at a concentration of 0.05-50 µM, insulin-like growth factor II (IGFII) at a concentration of 0.1-100 ng/ml, and stem cell factor (SCF) at a concentration of 0.1-100 ng/ml; under condition which allow generation of the naive human PSC comprising an unmethylated promoter of the XIST gene from said non-naive human PSC;

wherein: (i) when said naive human PSC is a female PSC, then said naïve female human PSC has two unmethylated alleles of the promoter of the XIST gene; and (ii) when said naive human PSC is a male PSC, then said naïve male human PSC has an unmethylated allele of the promoter of the XIST gene, and an expression level of transcription factor E3 (TFE3) in said naive human PSC is characterized by a nucleus to cytoplasm expression ratio which is equal to or higher than 1 as determined by an immunostaining assay, thereby generating the naive human PSC.

* * * * *